United States Patent
Grammenos et al.

(10) Patent No.: US 9,670,192 B2
(45) Date of Patent: Jun. 6, 2017

(54) SUBSTITUTED ISOXAZOLE DERIVATIVES

(71) Applicant: BASF SE, Ludwigshafen (DE)

(72) Inventors: Wassilios Grammenos, Ludwigshafen (DE); Ian Robert Craig, Ludwigshafen (DE); Nadege Boudet, Hirschberg (DE); Bernd Mueller, Frankenthal (DE); Erica May Wilson Lauterwasser, Wachenheim (DE); Jan Klaas Lohmann, Loxstedt (DE); Thomas Grote, Wachenheim (DE); Egon Haden, Speyer (DE); Ana Escribano Cuesta, Mannheim (DE)

(73) Assignee: BASF SE, Ludwigshafen (DE)

( * ) Notice: Subject to any disclaimer, the term of this patent is extended or adjusted under 35 U.S.C. 154(b) by 15 days.

(21) Appl. No.: 14/890,704

(22) PCT Filed: May 14, 2014

(86) PCT No.: PCT/EP2014/059835
§ 371 (c)(1),
(2) Date: Nov. 12, 2015

(87) PCT Pub. No.: WO2014/184236
PCT Pub. Date: Nov. 20, 2014

(65) Prior Publication Data
US 2016/0096829 A1    Apr. 7, 2016

(30) Foreign Application Priority Data
May 16, 2013    (EP) ..................... 13168091

(51) Int. Cl.
| | |
|---|---|
| *C07D 413/06* | (2006.01) |
| *C07D 413/14* | (2006.01) |
| *C07D 417/14* | (2006.01) |
| *A01N 43/80* | (2006.01) |

(52) U.S. Cl.
CPC ........... *C07D 413/06* (2013.01); *A01N 43/80* (2013.01); *C07D 413/14* (2013.01); *C07D 417/14* (2013.01)

(58) Field of Classification Search
None
See application file for complete search history.

(56) References Cited

FOREIGN PATENT DOCUMENTS

WO    2012143395 A1    10/2012

OTHER PUBLICATIONS

International Search Report, issued in PCT/EP2014/059835, dated Jun. 24, 2014.
International Preliminary Report on Patentability, issued in PCT/EP2014/059835, dated Nov. 17, 2015.

*Primary Examiner* — Alicia L Otton
(74) *Attorney, Agent, or Firm* — Brinks Gilson & Lione

(57) ABSTRACT

The present invention relates to compounds of the formula I

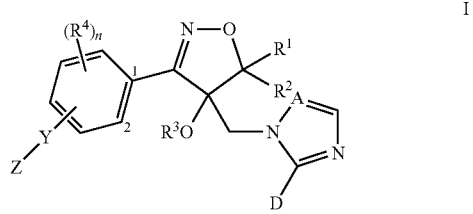

wherein the substituents are defined in the claims and the specification.

16 Claims, No Drawings

SUBSTITUTED ISOXAZOLE DERIVATIVES

This application is a National Stage application of International Application No. PCT/EP2014/059835, filed May 14, 2014. This application also claims priority under 35 U.S.C. §119 to European Patent Application No. 13168091.0, filed May 16, 2013.

The present invention relates to substituted isoxazole derivatives and the N-oxides and the salts thereof for combating phytopathogenic fungi, and to the use and methods for combating phytopathogenic fungi and to seeds coated with at least one such compound. The invention also relates to processes for preparing these compounds, intermediates, processes for preparing such intermediates, and to compositions comprising at least one inventive compound.

WO 2012/143395 relates to certain 4,5-dihydro-isoxazole derivatives and their use as fungicides. The compounds specifically described are substituted by halogen-substituted phenyls.

Using the known pesticidal compounds, in many cases, in particular at low application rates, the fungicidal activity of the known fungicidal compounds is unsatisfactory. Based on this, it was an object of the present invention to provide compounds having improved activity and/or a broader activity spectrum against phytopathogenic fungi.

Surprisingly, this object is achieved by the use of the inventive substituted isoxazole derivatives having favorable fungicidal activity against phytopathogenic fungi.

Accordingly, the present invention relates to compounds of the formula I

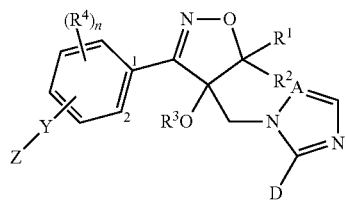

wherein

A is CH or N;

D is H, halogen or $SR^D$, wherein $R^D$ is hydrogen, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl or CN;

$R^1$ is hydrogen, $C_1$-$C_8$-alkyl, $C_1$-$C_8$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, $C_1$-$C_6$-alkoxy, $C_1$-$C_6$-haloalkoxy, $C_1$-$C_6$-alkoxy-$C_1$-$C_6$-alkyl, $C_1$-$C_6$-alkylthio, $C_1$-$C_6$-haloalkylthio;

wherein the aliphatic and/or alicyclic moieties of $R^1$ are not further substituted or carry one, two, three, four or five identical or different groups $R^{1a}$; wherein each $R^{1a}$ is independently selected from halogen, OH, CN, nitro, $C_1$-$C_8$-alkoxy, $C_1$-$C_8$-haloalkoxy, $C_1$-$C_8$-alkylthio, $C_1$-$C_8$-haloalkylthio, $C_1$-$C_8$-alkylsulfinyl, $C_1$-$C_8$-haloalkylsulfinyl, $C_1$-$C_8$-alkylsulfonyl, $C_1$-$C_8$-haloalkylsulfonyl, $C_1$-$C_8$-alkylcarbonyl, $C_1$-$C_8$-alkoxycarbonyl, unsubstituted aryl, aryl, that is substituted by one, two, three, four or five independently selected $R^{1b}$, unsubstituted saturated, partially unsaturated or aromatic heterocyclyl and saturated, partially unsaturated or aromatic heterocyclyl, that is substituted by one, two, three, four or five independently selected $R^{1b}$;

each $R^{1b}$ is independently selected from halogen, OH, CN, nitro, $NH_2$, $C_1$-$C_4$-alkyl, $C_1$-$C_4$-haloalkyl, $C_2$-$C_4$-alkenyl, $C_2$-$C_4$-haloalkenyl, $C_2$-$C_4$-alkynyl, $C_2$-$C_4$-haloalkynyl, $C_3$-$C_6$-cycloalkyl, $C_3$-$C_6$-halocycloalkyl, $C_1$-$C_3$-alkoxy, $C_1$-$C_3$-haloalkoxy, $C_1$-$C_3$-alkylthio, $C_1$-$C_3$-haloalkylthio, $C_1$-$C_3$-alkylsulfinyl, $C_1$-$C_3$-haloalkylsulfinyl, $C_1$-$C_3$-alkylsulfonyl, $C_1$-$C_3$-haloalkylsulfonyl, $C_1$-$C_4$-alkylamino, di-($C_1$-$C_4$-alkyl)-amino, $C_1$-$C_4$-alkylcarbonyl, $C_1$-$C_4$-alkylcarbonyloxy, $C_1$-$C_4$-alkoxycarbonyl, $C_1$-$C_4$-alkylcarbonylamino;

$R^2$ is independently selected from the substituents as given for $R^1$;

or $R^1$ and $R^2$ together with the carbon atom to which they are bound form a saturated or partially unsaturated three-, four-, five-, six-, seven-, eight-, nine-, ten-, eleven-, twelve-, thirteen- or fourteen-membered carbocycle, which may be monocyclic or polycyclic or spirocyclic, or saturated or partially unsaturated three-, four-, five-, six-, seven-, eight-, nine-, ten-, eleven-, twelve-, thirteen- or fourteen-membered heterocycle, which may be monocyclic or polycyclic or spirocyclic, wherein the heterocycle contains one, two, three or four heteroatoms selected from N, O and S, or wherein the heterocycle contains one of S=O and $SO_2$ as ring members, and wherein the carbo- or heterocycle is unsubstituted or carries one, two, three, four or five substituents $R^{12a}$ independently selected from halogen, CN, $NO_2$, OH, SH, $NH_2$, $C_1$-$C_6$-alkyl, $C_1$-$C_6$-haloalkyl, $C_1$-$C_4$-alkoxy-$C_1$-$C_4$-alkyl, $C_1$-$C_8$-alkoxy, $C_1$-$C_8$-haloalkoxy, $C_1$-$C_8$-alkylthio, $C_1$-$C_8$-haloalkylthio, $C_1$-$C_8$-alkylsulfinyl, $C_1$-$C_8$-haloalkylsulfinyl, $C_1$-$C_8$-alkylsulfonyl, $C_1$-$C_8$-haloalkylsulfonyl, $C_1$-$C_8$-alkylcarbonyl, $C_1$-$C_8$-alkoxycarbonyl, phenyl and phenyl that is substituted by one, two, three, four or five independently selected $R^{1b}$; and wherein one or two $CH_2$ groups of the carbo- or heterocycle may be replaced by a group independently selected from C=$CH_2$, C(=O) and C(=S);

$R^3$ is hydrogen, $C_1$-$C_6$-alkyl, $C_2$-$C_6$-alkenyl, $C_2$-$C_6$-alkynyl, $C_3$-$C_8$-cycloalkyl, $C_3$-$C_8$-cycloalkyl-$C_1$-$C_6$-alkyl, phenyl, phenyl-$C_1$-$C_4$-alkyl, phenyl-$C_2$-$C_4$-alkenyl or phenyl-$C_2$-$C_4$-alkynyl;

wherein the aliphatic moieties of $R^3$ are not further substituted or carry one, two, three or up to the maximum possible number of identical or different groups $R^{1a}$ which independently of one another are selected from:

$R^{3a}$ halogen, OH, CN, nitro, $C_1$-$C_4$-alkoxy, $C_3$-$C_8$-cycloalkyl, $C_3$-$C_8$-halocycloalkyl and $C_1$-$C_4$-haloalkoxy;

wherein the cycloalkyl and/or phenyl moieties of $R^3$ are not further substituted or carry one, two, three, four, five or up to the maximum number of identical or different groups $R^{3b}$ which independently of one another are selected from:

$R^{3b}$ halogen, OH, CN, nitro, $C_1$-$C_4$-alkyl, $C_1$-$C_4$-alkoxy, $C_1$-$C_4$-haloalkyl, $C_3$-$C_8$-cycloalkyl, $C_3$-$C_8$-halocycloalkyl and $C_1$-$C_4$-haloalkoxy;

n is 0, 1, 2, 3 or 4;

each $R^4$ is independently selected from halogen, CN, $NO_2$, OH, SH, $C_1$-$C_6$-alkyl, $C_1$-$C_6$-alkoxy, $C_2$-$C_6$-alkenyl, $C_2$-$C_6$-alkynyl, $C_3$-$C_8$-cycloalkyl, $C_3$-$C_8$-cycloalkyloxy, $NH_2$, $NH(C_1$-$C_4$-alkyl), $N(C_1$-$C_4$-alkyl)$_2$, $NH(C_3$-$C_6$-cycloalkyl), $N(C_3$-$C_6$-cycloalkyl)$_2$, $S(O)_p(C_1$-$C_4$-alkyl), C(=O)($C_1$-$C_4$-alkyl), C(=O)(OH), C(=O)(O—$C_1$-$C_4$-alkyl), C(=O)(NH($C_1$-$C_4$-alkyl)), C(=O)(N($C_1$-$C_4$-alkyl)$_2$), C(=O)(NH($C_3$-$C_6$-cycloalkyl)) and C(=O)—(N($C_3$-$C_6$-cycloalkyl)$_2$); wherein each of $R^4$ is unsubstituted or further substituted by one, two, three or four $R^{4a}$; wherein each $R^{4a}$ is independently selected from halogen, CN, $NO_2$, OH, $C_1$-$C_4$-alkyl, $C_1$-$C_4$-haloalkyl, $C_3$-$C_8$-cycloalkyl, $C_3$-$C_8$-halocycloalkyl, $C_1$-$C_4$-alkoxy and $C_1$-$C_4$-halogenalkoxy;

Y is a divalent group selected from the group consisting of —O—, —S—, SO—, —SO$_2$—, —NH—, —N(C$_1$-C$_4$-alkyl)-, CR$^6$R$^7$—, —CR$^8$R$^9$—CR$^{10}$R$^{11}$—, —CR$^{12}$=CR$^{13}$ and —C≡C—; wherein R$^6$, R$^7$, R$^8$, R$^9$, R$^{10}$, R$^{11}$, R$^{12}$, R$^{13}$ are independently selected from hydrogen, halogen, CN, nitro, OH, C$_1$-C$_4$-halogenalkyl, C$_1$-C$_4$-alkoxy and C$_1$-C$_4$-halogenalkoxy;

Z is phenyl or five or six-membered heteroaryl, wherein the heteroaryl contains 1, 2, 3 or 4 heteroatoms selected from the group consisting of O, N and S, wherein the phenyl and the heteroaryl is unsubstituted (m=0) or substituted by (R$^5$)$_m$; wherein m is 0, 1, 2, 3, 4 or 5; and each R$^5$ is independently selected from halogen, CN, NO$_2$, OH, SH, C$_1$-C$_6$-alkyl, C$_1$-C$_6$-alkoxy, C$_2$-C$_6$-alkenyl, C$_2$-C$_6$-alkynyl, C$_3$-C$_8$-cycloalkyl, C$_3$-C$_8$-cycloalkyloxy, NH$_2$, NH(C$_1$-C$_4$-alkyl), N(C$_1$-C$_4$-alkyl)$_2$, NH(C$_3$-C$_6$-cycloalkyl), N(C$_3$-C$_6$-cycloalkyl)$_2$, S(O)$_p$(C$_1$-C$_4$-alkyl), C(=O)(C$_1$-C$_4$-alkyl), C(=O)(OH), C(=O)(O—C$_1$-C$_4$-alkyl), C(=O)(NH(C$_1$-C$_4$-alkyl)), C(=O)(N(C$_1$-C$_4$-alkyl)$_2$), C(=O)(NH(C$_3$-C$_6$-cycloalkyl)) and C(=O)—(N (C$_3$-C$_6$-cycloalkyl)$_2$); wherein each of R$^5$ is unsubstituted or further substituted by one, two, three or four R$^{5a}$ wherein each R$^{5a}$ is independently selected from halogen, CN, NO$_2$, OH, C$_1$-C$_4$-alkyl, C$_1$-C$_4$-haloalkyl, C$_3$-C$_8$-cycloalkyl, C$_3$-C$_8$-halocycloalkyl, C$_1$-C$_4$-alkoxy and C$_1$-C$_4$-haloalkoxy;

p is 0, 1 or 2;

and the N-oxides and the agriculturally acceptable salts thereof.

A further aspect of the present invention are processes for the synthesis of compounds I and intermediates and the N-oxides and the salts thereof. The invention also relates to methods for combating phytopathogenic fungi, and to the use and methods for combating phytopathogenic fungi and to seeds coated with at least one such compound.

The inventive compounds can be obtained for example in analogy to prior art processes known (WO 2012/143395) and by the synthesis routes shown in the following schemes.

Compounds I, bearing D=halogen or SR$^D$, can be synthesized from compounds I, wherein D is H by simple deprotonation with a base (eg, LDA, BuLi, LHMDS, i-PrMgCl, EtMgI, NaH, KH, t-BuOK, t-BuOK, TMPLi, TMPZnCl, TMPMgCl, (TMP)$_2$Zn, (TMP)$_2$Mg, EtONa, EtOK) at low temperature and treatment with an electrophile (e.g. Iodine, ICl, Sulfur, alkyl-disulfide) in a suitable solvent such as Et$_2$O, MTBE or THF. These compounds can be synthesized for example in analogy with reported methods in: Tetrahedron Letters (2011), 52(36), 4590-4594, WO2006/102194, Journal of Organic Chemistry (2009), 74(21), 8309-8313, WO2011/113820. Alternatively, compounds I with D=SCN can be obtained by treating a compound I with D equals SH with cyanogen halide such as Br—CN or Cl—CN and a base (organic or inorganic base such as K$_2$CO$_3$, NaOH, KOH or NEt$_3$, DBU) in a suitable solvent such as acetone, MeCN or THF. These compounds can be synthesized for example in analogy with reported methods in: WO2009/077497, Chemical & Pharmaceutical Bulletin (1964), 12(2), 182-191. Alternatively, compounds I with D=SR$^D$ can be obtained by treating a compound I with D equals SH with an alkylation agent such as methyl iodide a base (organic or inorganic base such as K$_2$CO$_3$, NaOH, KOH or NEt$_3$, DBU) in a suitable solvent such as acetone, MeCN or THF. These compounds can be synthesized for example in analogy with reported methods in: WO2012/047762, Heteroatom Chemistry (2010), 20(7), 405-410, Khimiya Geterotsiklicheskikh Soedinenii (1977), (11), 1561-1563, Indian Journal of Heterocyclic Chemistry (1999), 8(4), 341-342, WO2011/113820.

Compounds I with D=H can be synthesized using various synthetic routes outlined in following schemes.

The compounds I, wherein R$^3$ is different from hydrogen can be prepared from the respective alcohol compounds I (wherein R$^3$ is hydrogen), by reacting the alcohol compound with R$^3$-LG (wherein R$^3$ is not H), wherein LG represents a nucleophilically replaceable leaving group, such as halogen, alkylsulfonyl, alkylsulfonyloxy and arylsulfonyloxy, preferably chloro, bromo or iodo, particularly preferably bromo or iodo, preferably in the presence of a base, such as, for example, NaH. A suitable solvent that may be used is for example THF.

Alcohol compounds I, wherein R$^3$ is hydrogen, are obtainable from epoxides II by reaction with with 1H-1,2,4-triazole or imidazole, respectively, preferably in the presence of a base such as potassium carbonate and preferably in the presence of a suitable organic solvent such as dimethylformamide (DMF) according to the following scheme:

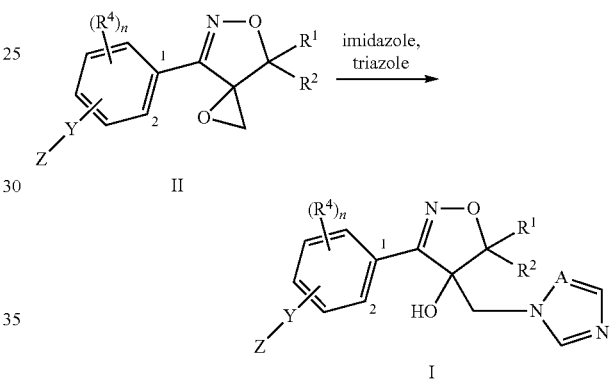

It may be appropriate if the reaction temperature is 0° C. to 50° C. See for example DE 94-44259, WO 2007/107556, WO 2008/124922.

The epoxides II may be prepared from compounds III by means of an epoxidation reaction by using for example peracids such as meta-chloroperoxybenzoic acid (m-CPBA) in a suitable solvent such as dichloromethane:

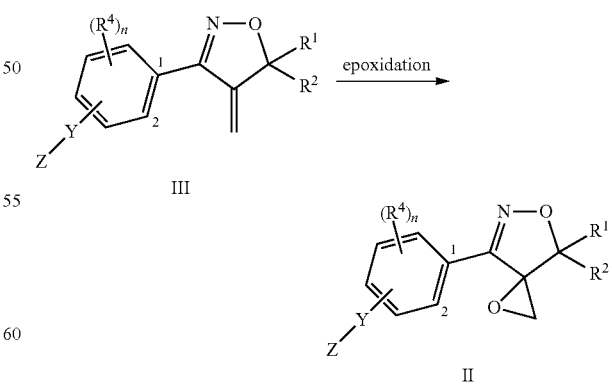

Preferably, the temperature is from 0° C. to 100° C. See for example D. Swern, Org. React. 1953, 7, 378; D. Swern, Organic Peroxides, 2, 355, Interscience Publishers, NY, 1971; D. I. Metelitsa, Russ. Chem. Rev. 1972, 41, 807.

The compounds II are at least partly novel. Consequently, one object of the present invention are also the novel compounds of formula II, wherein $R^1$, $R^2$, $R^4$, n, Y and Z are as defined and preferably defined as given herein for compounds I.

The compounds III may be obtained by reaction of compounds IV, wherein LG is a suitable nucleophilically replaceable leaving group such as halogen, alkylsulfonyl, alkylsulfonyloxy and arylsulfonyloxy, preferably chloro, bromo or iodo, particularly preferably bromo or alkylsulfonyl, in particular mesylate, with an appropriate base such as 1,8-diazabicyclo[5.4.0]undec-7-ene (DBU) to form the double bond:

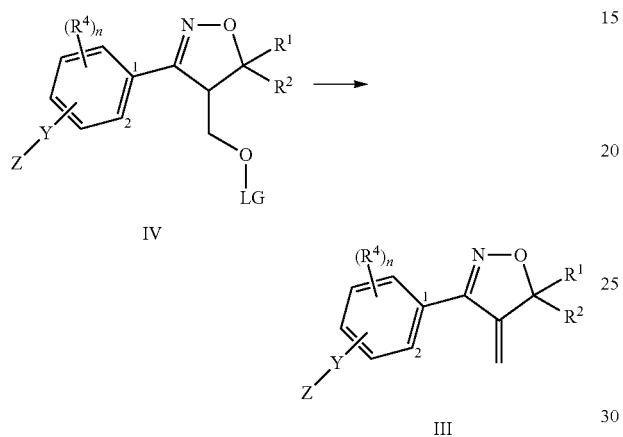

A suitable solvent that may be used is for example dichloromethane. Preferably, the reaction temperature is from 0° C. to 100° C.

The compounds III are at least partly novel. Consequently, one object of the present invention are also the novel compounds of formula III, wherein $R^1$, $R^2$, $R^4$, n, Y and Z are as defined and preferably defined as given herein for compounds I.

Compounds IV can be synthesized from the respective alcohol compounds V by introduction of the leaving group LG as generally known to the skilled artisan and using known methods.

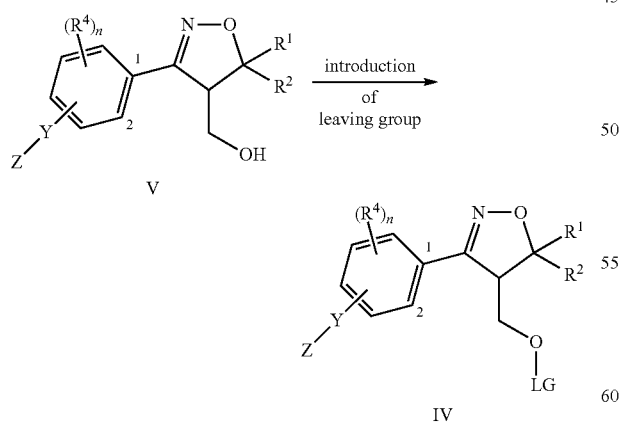

The compounds IV are at least partly novel. Consequently, one object of the present invention are also the novel compounds of formula IV, wherein $R^1$, $R^2$, $R^4$, n, Y and Z are as defined and preferably defined as given herein for compounds I.

The alcohol compounds V may be obtained by reduction of the ester group in compounds VI, wherein RE stands for a $C_1$-$C_4$-alkyl group such as methyl or ethyl, in particular ethyl:

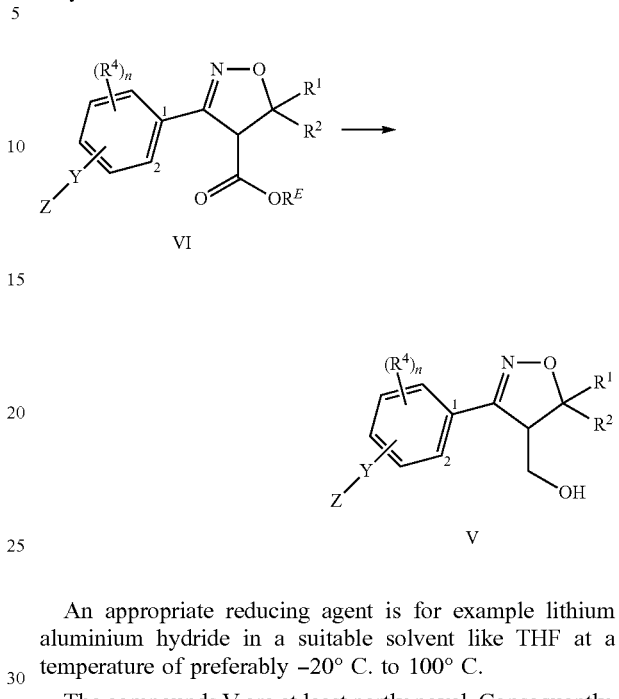

An appropriate reducing agent is for example lithium aluminium hydride in a suitable solvent like THF at a temperature of preferably −20° C. to 100° C.

The compounds V are at least partly novel. Consequently, one object of the present invention are also the novel compounds of formula V, wherein $R^1$, $R^2$, $R^4$, n, Y and Z are as defined and preferably defined as given herein for compounds I.

The ester VI may be obtained from halo oxime VII and alkene VIII via cycloaddition:

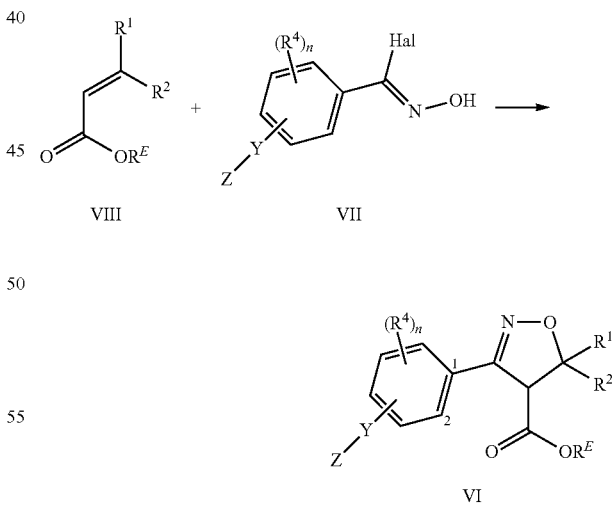

The compounds VI are at least partly novel. Consequently, one object of the present invention are also the novel compounds of formula VI, wherein $R^1$, $R^2$, $R^4$, n, Y and Z are as defined and preferably defined as given herein for compounds I.

Halo oxime VII may be prepared from aldehyde IX as depicted in the following scheme:

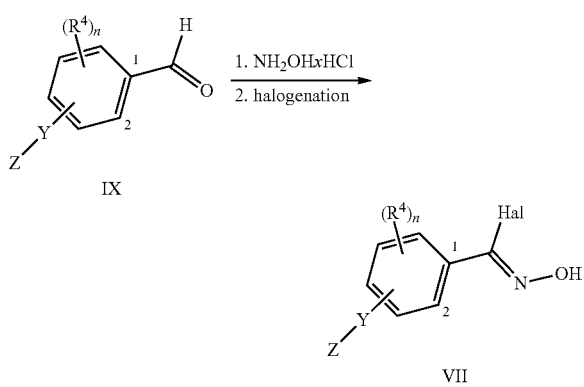

The compounds VII are at least partly novel. Consequently, one object of the present invention are also the novel compounds of formula VII, wherein $R^4$, n, Y and Z are as defined and preferably defined as given herein for compounds I.

A skilled person can provide compounds IX in analogy to known syntheses.

A skilled person will readily understand that the preferences for the substituents given herein in connection with compounds I apply for the intermediates accordingly. Thereby, the substituents in each case have independently of each other or more preferably in combination the meanings as defined herein. Some of the intermediates occurring in the synthesis of the inventive compounds are novel and therefore are also an object of the present invention.

If individual inventive compounds cannot be directly obtained by the routes described above, they may be prepared by derivatization of other inventive compounds.

The N-oxides may be prepared from the inventive compounds according to conventional oxidation methods, e. g. by treating compounds I with an organic peracid such as metachloroperbenzoic acid (cf. WO 03/64572 or J. Med. Chem. 38(11), 1892-903, 1995); or with inorganic oxidizing agents such as hydrogen peroxide (cf. J. Heterocyc. Chem. 18(7), 1305-8, 1981) or oxone (cf. J. Am. Chem. Soc. 123(25), 5962-5973, 2001). The oxidation may lead to pure mono-N-oxides or to a mixture of different N-oxides, which can be separated by conventional methods such as chromatography.

If the synthesis yields mixtures of isomers, a separation is generally not necessarily required since in some cases the individual isomers can be interconverted during work-up for use or during application (e. g. under the action of light, acids or bases). Such conversions may also take place after use, e. g. in the treatment of plants in the treated plant, or in the harmful fungus to be controlled.

In the definitions of the variables given above, collective terms are used which are generally representative for the substituents in question. The term "$C_n$-$C_m$" indicates the number of carbon atoms possible in each case in the substituent or substituent moiety in question.

The term "halogen" refers to fluorine, chlorine, bromine and iodine.

The term "$C_1$-$C_8$-alkyl" refers to a straight-chained or branched saturated hydrocarbon group having 1 to 8 carbon atoms, "$C_1$-$C_6$-alkyl" refers to a straight-chained or branched saturated hydrocarbon group having 1 to 6 carbon atoms, e.g. methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, 1,1-dimethylpropyl, 1,2-dimethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl. Likewise, the term "$C_2$-$C_4$-alkyl" refers to a straight-chained or branched alkyl group having 2 to 4 carbon atoms, such as ethyl, propyl (n-propyl), 1-methylethyl (isopropoyl), butyl, 1-methylpropyl (sec.-butyl), 2-methylpropyl (iso-butyl), 1,1-dimethylethyl (tert.butyl).

The term "$C_1$-$C_8$-haloalkyl" refers to an alkyl group having 1 or 8 carbon atoms as defined above, "$C_1$-$C_6$-haloalkyl" refers to an alkyl group having 1 or 6 carbon atoms as defined above, wherein some or all of the hydrogen atoms in these groups may be replaced by halogen atoms as mentioned above. Examples are "$C_1$-$C_2$-haloalkyl" groups such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl or pentafluoroethyl.

The term "$C_2$-$C_6$-alkenyl" refers to a straight-chain or branched unsaturated hydrocarbon radical having 2 to 6 carbon atoms and a double bond in an position. Examples are "$C_2$-$C_4$-alkenyl" groups, such as ethenyl, 1-propenyl, 2-propenyl (allyl), 1-methylethenyl, 1-butenyl, 2-butenyl, 3-butenyl, 1-methyl-1-propenyl, 2-methyl-1-propenyl, 1-methyl-2-propenyl, 2-methyl-2-propenyl.

The term "$C_2$-$C_6$-alkynyl" refers to a straight-chain or branched unsaturated hydrocarbon radical having 2 to 6 carbon atoms and containing at least one triple bond. Examples are "$C_2$-$C_4$-alkynyl" groups, such as ethynyl, prop-1-ynyl, prop-2-ynyl (propargyl), but-1-ynyl, but-2-ynyl, but-3-ynyl, 1-methyl-prop-2-ynyl.

The term "$C_3$-$C_8$-cycloalkyl" refers to monocyclic saturated hydrocarbon radicals having 3 to 8 carbon ring members, such as cyclopropyl, cyclobutyl, cyclopentyl, cyclohexyl, cycloheptyl or cyclooctyl.

The term "$C_3$-$C_8$-cycloalkyl-$C_1$-$C_4$-alkyl" refers to alkyl having 1 to 4 carbon atoms (as defined above), wherein one hydrogen atom of the alkyl radical is replaced by a cycloalkyl radical having 3 to 8 carbon atoms (as defined above).

The term "$C_1$-$C_6$-alkoxy" refers to a straight-chain or branched alkyl group having 1 to 6 carbon atoms which is bonded via an oxygen, at any position in the alkyl group. Examples are "$C_1$-$C_4$-alkoxy" groups, such as methoxy, ethoxy, n-propoxy, 1-methylethoxy, butoxy, 1-methylpropoxy, 2-methylpropoxy or 1,1-dimethylethoxy.

The term "$C_1$-$C_6$-haloalkoxy" refers to a $C_1$-$C_6$-alkoxy radical as defined above, wherein some or all of the hydrogen atoms in these groups may be replaced by halogen atoms as mentioned above. Examples are "$C_1$-$C_4$-haloalkoxy" groups, such as $OCH_2F$, $OCHF_2$, $OCF_3$, $OCH_2Cl$, $OCHCl_2$, $OCCl_3$, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, $OC_2F_5$, 2-fluoropropoxy, 3-fluoropropoxy, 2,2-difluoropropoxy, 2,3-difluoro-propoxy, 2 chloropropoxy, 3-chloropropoxy, 2,3-dichloropropoxy, 2-bromo-propoxy, 3 bromopropoxy, 3,3,3-trifluoropropoxy, 3,3,3-trichloropropoxy, OCH$_2$—C$_2$F$_5$, OCF$_2$-C$_2$F$_5$, 1-fluoromethyl-2-fluoroethoxy, 1-chloromethyl-2-chloroethoxy, 1-bromomethyl-2-bromo-ethoxy, 4-fluorobutoxy, 4-chlorobutoxy, 4-bromobutoxy or nonafluorobutoxy.

The term "phenyl-C$_1$-C$_6$-alkyl" refers to alkyl having 1 to 6 carbon atoms (as defined above), wherein one hydrogen atom of the alkyl radical is replaced by a phenyl radical. Likewise, the terms "phenyl-C$_2$-C$_6$-alkenyl" and "phenyl-C$_2$-C$_6$-alkynyl" refer to alkenyl and alkynyl, respectively, wherein one hydrogen atom of the aforementioned radicals is replaced by a phenyl radical.

The term "C$_1$-C$_4$-alkoxy-C$_1$-C$_4$-alkyl" refers to alkyl having 1 to 4 carbon atoms (as defined above), wherein one hydrogen atom of the alkyl radical is replaced by a C$_1$-C$_4$-alkoxy group (as defined above). Likewise, the term "C$_1$-C$_6$-alkoxy-C$_1$-C$_4$-alkyl" refers to alkyl having 1 to 4 carbon atoms (as defined above), wherein one hydrogen atom of the alkyl radical is replaced by a C$_1$-C$_6$-alkoxy group (as defined above).

The term "C$_1$-C$_6$-alkylthio" as used herein refers to straight-chain or branched alkyl groups having 1 to 6 carbon atoms (as defined above) bonded via a sulfur atom. Accordingly, the term "C$_1$-C$_6$-haloalkylthio" as used herein refers to straight-chain or branched haloalkyl group having 1 to 6 carbon atoms (as defined above) bonded through a sulfur atom, at any position in the haloalkyl group.

The term "C$_1$-C$_6$-alkylsulfinyl" refers to straight-chain or branched alkyl groups having 1 to 6 carbon atoms (as defined above) bonded through a —S(=O)— moiety, at any position in the alkyl group, for example methylsulfinyl and ethylsulfinyl, and the like. Accordingly, the term "C$_1$-C$_6$-haloalkylsulfinyl" refers to straight-chain or branched haloalkyl group having 1 to 6 carbon atoms (as defined above), bonded through a —S(=O)— moiety, at any position in the haloalkyl group.

The term "C$_1$-C$_6$-alkylsulfonyl" refers to straight-chain or branched alkyl groups having 1 to 6 carbon atoms (as defined above), bonded through a —S(=O)$_2$— moiety, at any position in the alkyl group, for example methylsulfonyl. Accordingly, the term "C$_1$-C$_6$-haloalkylsulfonyl" refers to straight-chain or branched haloalkyl group having 1 to 6 carbon atoms (as defined above), bonded through a —S(=O)$_2$— moiety, at any position in the haloalkyl group.

The term "C$_3$-C$_8$-cycloalkyl-C$_3$-C$_8$-cycloalkyl" refers to a cycloalkyl radical having 3 to 8 carbon atoms (as defined above), which is substituted by a further cycloalkyl radical having 3 to 8 carbon atoms.

The term "C$_3$-C$_8$-cycloalkoxy" refers to a cycloalkyl radical having 3 to 8 carbon atoms (as defined above), which is bonded via an oxygen.

The term "C(=O)—C$_1$-C$_4$-alkyl" refers to a radical which is attached through the carbon atom of the group C(=O) as indicated by the number valence of the carbon atom. The number of valence of carbon is 4, that of nitrogen is 3. Likewise the following terms are to be construed: NH(C$_1$-C$_4$-alkyl), N(C$_1$-C$_4$-alkyl)$_2$, NH(C$_3$-C$_6$-cycloalkyl), N(C$_3$-C$_6$-cycloalkyl)$_2$, C(=O)OH, C(=O)O—O—C$_1$-C$_4$-alkyl, C(=O)—NH(C$_1$-C$_4$-alkyl), C(=O)—N(C$_1$-C$_4$-alkyl)$_2$, C(=O)—NH(C$_3$-C$_6$-cycloalkyl), C(=O)—N(C$_3$-C$_6$-cycloalkyl)$_2$.

The term "saturated or partially unsaturated 3-, 4-5-, 6-, 7-, 8-, 9-, 10-, 11-, 12-, 13- or 14-membered carbocycle" is to be understood as meaning both saturated and partially unsaturated carbocycles having 3, 4, 5, 6, 7, 8, 9, 10, 11, 12, 13 or 14 ring members. The carbocycles may be monocyclic or polycyclic or spirocyclic. Examples include cyclopropyl, cyclopentyl, cyclopentenyl, cyclopentadienyl, cyclohexyl, cyclohexenyl, cyclohexadienyl, cycloheptyl, cycloheptenyl, cycloheptadienyl, and the like.

The term "saturated or partially unsaturated 3-, 4-, 5-, 6-, 7-, 8-, 9-, 10-, 11-, 12-, 13- or 14-membered heterocycle, wherein the ring member atoms of the heterocycle include besides carbon atoms 1, 2, 3 or 4 heteroatoms independently selected from the group of N, O and S", is to be understood as meaning both saturated and partially unsaturated heterocycles. The heterocycles may be monocyclic or polycyclic or spirocyclic.

Examples are a 3- or 4-membered saturated heterocycle which contains 1 or 2 heteroatoms from the group consisting of N, O and S as ring members such as oxirane, aziridine, thiirane, oxetane, azetidine, thiethane, [1,2]dioxetane, [1,2]dithietane, [1,2]diazetidine; and a 5- or 6-membered saturated or partially unsaturated heterocycle which contains 1, 2 or 3 heteroatoms from the group consisting of N, O and S as ring members such as 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-piperidinyl, 3-piperidinyl, 4-piperidinyl, 1,3-dioxan-5-yl, 2-tetrahydropyranyl, 4-tetrahydropyranyl, 2-tetrahydrothienyl, 3-hexahydropyridazinyl, 4-hexahydropyridazinyl, 2-hexahydropyrimidinyl, 4-hexahydropyrimidinyl, 5-hexahydropyrimidinyl, 2-piperazinyl, 1,3,5-hexahydrotriazin-2-yl and 1,2,4-hexahydrotriazin-3-yl and also the corresponding -ylidene radicals; and a 7-membered saturated or partially unsaturated heterocycle such as tetra- and hexahydroazepinyl, such as 2,3,4,5-tetrahydro[1H]azepin-1-,-2-, -3-, -4-, -5-, -6- or -7-yl, 3,4,5,6-tetrahydro[2H]azepin-2-,-3-, -4-, -5-, -6- or -7-yl, 2,3,4,7-tetrahydro[1H]azepin-1-,-2-, -3-, -4-, -5-, -6- or -7-yl, 2,3,6,7-tetrahydro[1H]azepin-1-,-2-, -3-, -4-, -5-, -6- or -7-yl, hexahydroazepin-1-,-2-, -3- or -4-yl, tetra- and hexahydrooxepinyl such as 2,3,4,5-tetrahydro[1H]oxepin-2-, -3-, -4-, -5-, -6- or -7-yl, 2,3,4,7-tetrahydro[1H]oxepin-2-, -3-, -4-, -5-, -6- or -7-yl, 2,3,6,7-tetrahydro[1H]oxepin-2-, -3-, -4-, -5-, -6- or -7-yl, hexahydrooxepin-1-,-2-, -3- or -4-yl, tetra- and hexahydro-1,3-diazepinyl, tetra- and hexahydro-1,4-diazepinyl, tetra- and hexahydro-1,3-oxazepinyl, tetra- and hexahydro-1,4-oxazepinyl, tetra- and hexahydro-1,3-dioxepinyl, tetra- and hexahydro-1,4-dioxepinyl and the corresponding -ylidene radicals.

The term "aromatic heterocycle (or heterocyclyl)" refers to heteroaryl as defined herein.

The term "heteroaryl" refers to aromatic ring systems including besides carbon atoms, 1, 2, 3 or 4 heteroatoms independently selected from the group consisting of N, O and S. Examples are in particular "5- or 6-membered heteroaryl" referring to aromatic ring systems including besides carbon atoms, 1, 2, 3 or 4 heteroatoms independently selected from the group consisting of N, O and S, for example, a 5-membered heteroaryl such as pyrrol-1-yl, pyrrol-2-yl, pyrrol-3-yl, thien-2-yl, thien-3-yl, furan-2-yl, furan-3-yl, pyrazol-1-yl, pyrazol-3-yl, pyrazol-4-yl, pyrazol-5-yl, imidazol-1-yl, imidazol-2-yl, imidazol-4-yl, imidazol-5-yl, oxazol-2-yl, oxazol-4-yl, oxazol-5-yl, isoxazol-3-yl, isoxazol-4-yl, isoxazol-5-yl, thiazol-2-yl, thiazol-4-yl, thiazol-5-yl, isothiazol-3-yl, isothiazol-4-yl, isothiazol-5-yl, 1,2,4-triazolyl-1-yl, 1,2,4-triazol-3-yl 1,2,4-triazol-5-yl, 1,2,4-oxadiazol-3-yl, 1,2,4-oxadiazol-5-yl and 1,2,4-thiadiazol-3-yl, 1,2,4-thiadiazol-5-yl; or a 6-membered heteroaryl, such as pyridin-2-yl, pyridin-3-yl, pyridin-4-yl, pyridazin-3-yl, pyridazin-4-yl, pyrimidin-2-yl, pyrimidin-4-yl, pyrimidin-5-yl, pyrazin-2-yl and 1,3,5-triazin-2-yl and 1,2,4-triazin-3-yl.

"Aryl" or "aromatic ring moiety" refers to an aromatic system which may be a single ring or multiple rings which are fused together, linked covalently or linked to a common group such as an ethylene or methylene moiety and does not contain heteroatoms. In particular, the aryl is 6- to 14-membered. Representative examples of aryl include naphthyl and phenyl.

Agriculturally acceptable salts of the inventive compounds encompass especially the salts of those cations or the acid addition salts of those acids whose cations and anions, respectively, have no adverse effect on the fungicidal action of said compounds. Suitable cations are thus in particular the ions of the alkali metals, preferably sodium and potassium, of the alkaline earth metals, preferably calcium, magnesium and barium, of the transition metals, preferably manganese, copper, zinc and iron, and also the ammonium ion which, if desired, may carry one to four $C_1$-$C_4$-alkyl substituents and/or one phenyl or benzyl substituent, preferably diisopropylammonium, tetramethylammonium, tetrabutylammonium, trimethylbenzylammonium, furthermore phosphonium ions, sulfonium ions, preferably tri($C_1$-$C_4$-alkyl)sulfonium, and sulfoxonium ions, preferably tri($C_1$-$C_4$-alkyl)sulfoxonium. Anions of useful acid addition salts are primarily chloride, bromide, fluoride, hydrogensulfate, sulfate, dihydrogenphosphate, hydrogenphosphate, phosphate, nitrate, bicarbonate, carbonate, hexafluorosilicate, hexafluorophosphate, benzoate, and the anions of $C_1$-$C_4$-alkanoic acids, preferably formate, acetate, propionate and butyrate. They can be formed by reacting such inventive compound with an acid of the corresponding anion, preferably of hydrochloric acid, hydrobromic acid, sulfuric acid, phosphoric acid or nitric acid.

The inventive compounds can be present in atropisomers arising from restricted rotation about a single bond of asymmetric groups. They also form part of the subject matter of the present invention.

Depending on the substitution pattern, the compounds of formula I, and their N-oxides and salts may have one or more centers of chirality, in which case they are present as pure enantiomers or pure diastereomers or as enantiomer or diastereomer mixtures. Both, the pure enantiomers or diastereomers and their mixtures are subject matter of the present invention.

In the following, particular embodiments of the inventive compounds are described. Therein, specific meanings of the respective substituents are further detailed, wherein the meanings are in each case on their own but also in any combination with one another, particular embodiments of the present invention.

Furthermore, in respect of the variables, generally, the embodiments of the compounds I also apply to the intermediates.

A according to the invention is N or CH. According to one embodiment A is N. According to a further embodiment A is CH.

D according to the present invention is hydrogen, halogen or $SR^D$, wherein $R^D$ is hydrogen, CN, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl or $C_2$-$C_6$-haloalkynyl.

In a preferred embodiment D is hydrogen, halogen, SH, SCN or S—$CH_2$—CH=$CH_2$ (5-allyl). According to one embodiment D is hydrogen. According to a further embodiment, D is halogen, in particular iodine. According to another preferred embodiment D is $SR^D$. According to a particular embodiment, $R^D$ is H. In yet another preferred embodiment $R^D$ is CN. In a further preferred embodiment $R^D$ is —$CH_2$—CH=$CH_2$.

$R^1$ according to the invention is hydrogen, $C_1$-$C_8$-alkyl, $C_1$-$C_8$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, $C_1$-$C_6$-alkoxy, $C_1$-$C_6$-haloalkoxy, $C_1$-$C_6$-alkoxy-$C_1$-$C_6$-alkyl, $C_1$-$C_6$-alkylthio, $C_1$-$C_6$-haloalkylthio; wherein the aliphatic and/or alicyclic moieties of $R^1$ are not further substituted or carry one, two, three, four or five identical or different groups $R^{1a}$; wherein each $R^{1a}$ is independently selected from halogen, OH, CN, nitro, $C_1$-$C_8$-alkoxy, $C_1$-$C_8$-haloalkoxy, $C_1$-$C_8$-alkylthio, $C_1$-$C_8$-haloalkylthio, $C_1$-$C_8$-alkylsulfinyl, $C_1$-$C_8$-haloalkylsulfinyl, $C_1$-$C_8$-alkylsulfonyl, $C_1$-$C_8$-haloalkylsulfonyl, $C_1$-$C_8$-alkylcarbonyl, $C_1$-$C_8$-alkoxycarbonyl, unsubstituted aryl, aryl, that is substituted by one, two, three, four or five independently selected $R^{1b}$, unsubstituted saturated, partially unsaturated or aromatic heterocyclyl and saturated, partially unsaturated or aromatic heterocyclyl, that is substituted by one, two, three, four or five independently selected $R^{1b}$; wherein each $R^{1b}$ is independently selected from halogen, OH, CN, nitro, $NH_2$, $C_1$-$C_4$-alkyl, $C_1$-$C_4$-haloalkyl, $C_2$-$C_4$-alkenyl, $C_2$-$C_4$-haloalkenyl, $C_2$-$C_4$-alkynyl, $C_2$-$C_4$-haloalkynyl, $C_3$-$C_6$-cycloalkyl, $C_3$-$C_6$-halocycloalkyl, $C_1$-$C_3$-alkoxy, $C_1$-$C_3$-haloalkoxy, $C_1$-$C_3$-alkylthio, $C_1$-$C_3$-haloalkylthio, $C_1$-$C_3$-alkylsulfinyl, $C_1$-$C_3$-haloalkylsulfinyl, $C_1$-$C_3$-alkylsulfonyl, $C_1$-$C_3$-haloalkylsulfonyl, $C_1$-$C_4$-alkylcarbonyl, $C_1$-$C_4$-alkylcarbonyloxy, $C_1$-$C_4$-alkoxycarbonyl and $C_1$-$C_4$-alkylcarbonylamino.

$R^2$ is independently selected from the substitutents as defined for $R^1$; or $R^1$ and $R^2$ together with the carbon atom to which they are bound form a saturated or partially unsaturated three-, four-, five-, six-, seven-, eight-, nine-, ten-, eleven-, twelve-, thirteen- or fourteen-membered carbocycle, which may be monocyclic or polycyclic, or saturated or partially unsaturated three-, four-, five-, six-, seven-, eight-, nine-, ten-, eleven-, twelve-, thirteen- or fourteen-membered heterocycle, which may be monocyclic or polycyclic or spirocyclic, wherein the heterocycle contains one, two, three or four heteroatoms selected from N, O and S, or wherein the heterocycle contains one of S=O and SO$_2$ as ring members, and wherein the carbo- or heterocycle is unsubstituted or carries one, two, three, four or five substituents R$^{12a}$ independently selected from halogen, CN, NO$_2$, OH, SH, NH$_2$, C$_1$-C$_6$-alkyl, C$_1$-C$_6$-haloalkyl, C$_1$-C$_4$-alkoxy-C$_1$-C$_4$-alkyl, C$_1$-C$_8$-alkoxy, C$_1$-C$_8$-haloalkoxy, C$_1$-C$_8$-alkylthio, C$_1$-C$_8$-haloalkylthio, C$_1$-C$_8$-alkylsulfinyl, C$_1$-C$_8$-haloalkylsulfinyl, C$_1$-C$_8$-alkylsulfonyl, C$_1$-C$_8$-haloalkylsulfonyl, C$_1$-C$_8$-alkylcarbonyl, C$_1$-C$_8$-alkoxycarbonyl, phenyl and phenyl that is substituted by one, two, three, four or five independently selected R$^{1b}$; wherein each R$^{1b}$ is independently selected from halogen, OH, CN, nitro, NH$_2$, C$_1$-C$_4$-alkyl, C$_1$-C$_4$-haloalkyl, C$_2$-C$_4$-alkenyl, C$_2$-C$_4$-haloalkenyl, C$_2$-C$_4$-alkynyl, C$_2$-C$_4$-haloalkynyl, C$_3$-C$_6$-cycloalkyl, C$_3$-C$_6$-halocycloalkyl, C$_1$-C$_3$-alkoxy, C$_1$-C$_3$-haloalkoxy, C$_1$-C$_3$-alkylthio, C$_1$-C$_3$-haloalkylthio, C$_1$-C$_3$-alkylsulfinyl, C$_1$-C$_3$-haloalkylsulfinyl, C$_1$-C$_3$-alkylsulfonyl, C$_1$-C$_3$-haloalkylsulfonyl, C$_1$-C$_4$-alkylamino, C$_1$-C$_4$-alkylcarbonyl, C$_1$-C$_4$-alkylcarbonyloxy, C$_1$-C$_4$-alkoxycarbonyl and C$_1$-C$_4$-alkylcarbonylamino; and wherein one or two CH$_2$ groups of the carbo- or heterocycle may be replaced by a group independently selected from C=CH$_2$ (exocyclic double bond), C(=O) and C(=S).

According to one embodiment, R$^1$ is hydrogen.

According to a further embodiment, R$^1$ is selected from C$_1$-C$_8$-alkyl, C$_1$-C$_8$-haloalkyl, C$_2$-C$_6$-alkenyl, C$_2$-C$_6$-haloalkenyl, C$_2$-C$_6$-alkynyl, C$_2$-C$_6$-haloalkynyl, C$_3$-C$_8$-cycloalkyl, C$_3$-C$_8$-halocycloalkyl, C$_1$-C$_6$-alkoxy, C$_1$-C$_6$-haloalkoxy, C$_1$-C$_6$-alkoxy-C$_1$-C$_6$-alkyl, C$_1$-C$_6$-alkylthio and C$_1$-C$_6$-haloalkylthio; wherein the aliphatic and/or alicyclic moieties of R$^1$ are not further substituted or carry one, two, three, four or five identical or different groups R$^{1a}$ as defined and preferably defined herein.

According to a further embodiment, R$^1$ is selected from hydrogen, C$_1$-C$_8$-alkyl, C$_1$-C$_8$-haloalkyl, C$_2$-C$_6$-alkenyl, C$_2$-C$_6$-haloalkenyl, C$_2$-C$_6$-alkynyl and C$_2$-C$_6$-haloalkynyl. According to one specific embodiment thereof, the respective substituent is not further substituted. According to another specific embodiment thereof, the respective substituent contains one, two, three, four or five R$^{1a}$ independently selected from the R$^{1a}$ as defined and preferably defined herein. In particular, if substituted, each R$^{1a}$ is independently selected from halogen, OH, CN, C$_1$-C$_2$-alkoxy, C$_1$-C$_2$-haloalkoxy, C$_1$-C$_2$-alkylthio, C$_1$-C$_2$-haloalkylthio, C$_1$-C$_2$-alkylcarbonyl and C$_1$-C$_2$-alkoxycarbonyl. According to one specific embodiment thereof, R$^1$ is selected from hydrogen, C$_1$-C$_6$-alkyl, C$_1$-C$_6$-haloalkyl and C$_1$-C$_4$-alkoxy-C$_1$-C$_6$-alkyl.

According to a further embodiment, R$^1$ is selected from C$_1$-C$_8$-alkyl, C$_1$-C$_8$-haloalkyl, C$_2$-C$_6$-alkenyl, C$_2$-C$_6$-haloalkenyl, C$_2$-C$_6$-alkynyl and C$_2$-C$_6$-haloalkynyl. According to one specific embodiment thereof, the respective substituent is not further substituted. According to another specific embodiment thereof, the respective substituent contains one, two, three, four or five R$^{1a}$ independently selected from the R$^{1a}$ as defined and preferably defined herein. In particular, if substituted, each R$^{1a}$ is independently selected from halogen, OH, CN, C$_1$-C$_2$-alkoxy, C$_1$-C$_2$-haloalkoxy, C$_1$-C$_2$-alkylthio, C$_1$-C$_2$-haloalkylthio, C$_1$-C$_2$-alkylcarbonyl and C$_1$-C$_2$-alkoxycarbonyl. According to one specific embodiment thereof, R$^1$ is selected from hydrogen, C$_1$-C$_6$-alkyl, C$_1$-C$_6$-haloalkyl, C$_1$-C$_6$-alkoxy-C$_1$-C$_6$-alkyl.

According to a further specific embodiment, R$^1$ is C$_1$-C$_8$-alkyl, in particular C$_1$-C$_6$-alkyl, more specifically C$_1$-C$_4$-alkyl, such as methyl, ethyl, n-propyl, iso-propyl, n-butyl, tert-butyl, iso-butyl.

According to a further specific embodiment, R$^1$ is C$_1$-C$_8$-haloalkyl, in particular C$_1$-C$_6$-haloalkyl, more specifically C$_1$-C$_4$-haloalkyl, containing one, two, three or four or up to the maximum possible number of independently selected Br, Cl, I and F, such as CF$_3$ or CHF$_2$.

In still a further specific embodiment R$^1$ is C$_1$-C$_6$-alkoxy-C$_1$-C$_6$-alkyl, in particular C$_1$-C$_4$-alkoxy-C$_1$-C$_4$-alkyl, more specifically C$_1$-C$_2$-alkoxy-C$_1$-C$_2$-alkyl, such as methoxy-C$_1$-C$_2$-alkyl or ethoxy-C$_1$-C$_2$-alkyl.

In still a further specific embodiment R$^1$ is C$_1$-C$_6$-haloalkoxy-C$_1$-C$_6$-alkyl, C$_1$-C$_6$-alkoxy-C$_1$-C$_6$-haloalkyl or C$_1$-C$_6$-haloalkoxy-C$_1$-C$_6$-haloalkyl, in particular C$_1$-C$_4$-haloalkoxy-C$_1$-C$_3$-alkyl, alkoxy-C$_1$-C$_2$-haloalkyl or C$_1$-C$_4$-haloalkoxy-C$_1$-C$_2$-haloalkyl.

In another preferred embodiment R$^1$ is C$_2$-C$_6$-alkenyl, in particular C$_2$-C$_4$-alkenyl, more specifically C$_3$-C$_4$-alkenyl, such as 2-propenyl.

In another preferred embodiment R$^1$ is C$_2$-C$_6$-haloalkenyl, in particular C$_2$-C$_4$-haloalkenyl, more specifically C$_3$-C$_4$-haloalkenyl, containing one, two, three or four or up to the maximum possible number of independently selected Br, Cl, I and F, such as halo-2-propenyl.

In another preferred embodiment R$^1$ is C$_2$-C$_6$-alkynyl, in particular C$_2$-C$_4$-alkynyl, more specifically C$_3$-C$_4$-alkynyl, such as 2-propynyl or 2-butynyl.

In another preferred embodiment R$^1$ is C$_2$-C$_6$-haloalkynyl, in particular C$_2$-C$_4$-haloalkynyl, more specifically C$_3$-C$_4$-haloalkyenyl, containing one, two, three or four or up to the maximum possible number of independently selected Br, Cl, I and F, such as halo-2-propynyl or halo-2-butynyl.

According to a further embodiment, R$^1$ is selected from hydrogen, C$_1$-C$_6$-alkoxy, C$_1$-C$_6$-haloalkoxy, C$_1$-C$_6$-alkylthio and C$_1$-C$_6$-haloalkylthio. According to one specific embodiment thereof, the respective substituent is not further substituted. According to another specific embodiment thereof, the respective substituent contains one, two, three, four or five R$^{1a}$ independently selected from the R$^{1a}$ as defined and preferably defined herein. In particular, if substituted, each R$^{1a}$ is independently selected from halogen, OH, CN, C$_1$-C$_2$-alkoxy, C$_1$-C$_2$-haloalkoxy, C$_1$-C$_2$-alkylthio, C$_1$-C$_2$-haloalkylthio, C$_1$-C$_2$-alkylcarbonyl and C$_1$-C$_2$-alkoxycarbonyl.

According to a further embodiment, R$^1$ is selected from C$_1$-C$_6$-alkoxy, C$_1$-C$_6$-haloalkoxy, C$_1$-C$_6$-alkylthio and C$_1$-C$_6$-haloalkylthio. According to one specific embodiment thereof, the respective substituent is not further substituted. According to another specific embodiment thereof, the respective substituent contains one, two, three, four or five R$^{1a}$ independently selected from the R$^{1a}$ as defined and preferably defined herein. In particular, if substituted, each R$^{1a}$ is independently selected from halogen, OH, CN, C$_1$-C$_2$-alkoxy, C$_1$-C$_2$-haloalkoxy, C$_1$-C$_2$-alkylthio, C$_1$-C$_2$-haloalkylthio, C$_1$-C$_2$-alkylcarbonyl and C$_1$-C$_2$-alkoxycarbonyl.

In one further particular embodiment R$^1$ is C$_1$-C$_6$-alkoxy, in particular C$_1$-C$_4$-alkoxy, more particularly methoxy, ethoxy or 1-methylethoxy.

In a further specific embodiment R$^1$ is C$_1$-C$_6$-haloalkoxy, in particular C$_1$-C$_4$-haloalkoxy, containing one, two, three or four or up to the maximum possible number of independently selected Br, Cl, I and F. In a specific embodiment thereof R$^1$ is C$_1$-C$_2$-haloalkoxy, such as OCF$_3$ or OCHF$_2$.

In one further particular embodiment R$^1$ is C$_1$-C$_6$-alkylthio, in particular C$_1$-C$_4$-alkylthio, more specifically C$_1$-C$_2$-alkylthio.

In one further particular embodiment R$^1$ is C$_1$-C$_6$-haloalkylthio, in particular C$_1$-C$_4$-haloalkylthio, more specifically $C_1$-$C_2$-haloalkylthio, containing one, two, three or four or up to the maximum possible number of independently selected Br, Cl, I and F.

According to a further embodiment, $R^1$ is selected from hydrogen, $C_3$-$C_8$-cycloalkyl and $C_3$-$C_8$-halocycloalkyl. According to one specific embodiment thereof, the cycloalkyl moiety is not further substituted. According to another specific embodiment thereof, the cycloalkyl moiety contains one, two, three, four or five $R^{1a}$ independently selected from the $R^{1a}$ as defined and preferably defined herein. In particular, if substituted, each $R^{1a}$ is independently selected from halogen, OH, CN, $C_1$-$C_2$-alkoxy, $C_1$-$C_2$-haloalkoxy, $C_1$-$C_2$-alkylthio, $C_1$-$C_2$-haloalkylthio, $C_1$-$C_2$-alkylcarbonyl and $C_1$-$C_2$-alkoxycarbonyl.

According to a further embodiment, $R^1$ is selected from $C_3$-$C_8$-cycloalkyl and $C_3$-$C_8$-halocycloalkyl. According to one specific embodiment thereof, the cycloalkyl moiety is not further substituted. According to another specific embodiment thereof, the cycloalkyl moiety contains one, two, three, four or five $R^{1a}$ independently selected from the $R^{1a}$ as defined and preferably defined herein. In particular, if substituted, each $R^{1a}$ is independently selected from halogen, OH, CN, $C_1$-$C_2$-alkoxy, $C_1$-$C_2$-haloalkoxy, $C_1$-$C_2$-alkylthio, $C_1$-$C_2$-haloalkylthio, $C_1$-$C_2$-alkylcarbonyl and $C_1$-$C_2$-alkoxycarbonyl.

According to a further particular embodiment of the invention, $R^1$ is $C_3$-$C_8$-cycloalkyl, in particular $C_3$-$C_6$-cycloalkyl, more particularly cyclopropyl, cyclobutyl, cyclopentyl or cyclohexyl.

According to still a further particular embodiment $R^1$ is $C_3$-$C_8$-halocycloalkyl, in particular $C_3$-$C_6$-halocycloalkyl, containing one, two, three or four or up to the maximum possible number of independently selected Br, Cl, I and F, for example 1-Cl-cyclopropyl and 1-F-cyclopropyl.

According to one embodiment, $R^2$ is hydrogen.

According to a further embodiment, $R^2$ is selected from $C_1$-$C_8$-alkyl, $C_1$-$C_8$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, $C_1$-$C_6$-alkoxy, $C_1$-$C_6$-haloalkoxy, $C_1$-$C_6$-alkoxy-$C_1$-$C_6$-alkyl, $C_1$-$C_6$-alkylthio and $C_1$-$C_6$-haloalkylthio; wherein the aliphatic and/or alicyclic moieties of $R^2$ are not further substituted or carry one, two, three, four or five identical or different groups $R^{2a}$ as defined and preferably defined herein.

According to a further embodiment, $R^2$ is selected from hydrogen, $C_1$-$C_8$-alkyl, $C_1$-$C_8$-haloalkyl, $C_2$-$C_6$-alkenyl, $C_2$-$C_6$-haloalkenyl, $C_2$-$C_6$-alkynyl and $C_2$-$C_6$-haloalkynyl. According to one specific embodiment thereof, the respective substituent is not further substituted. According to another specific embodiment thereof, the respective substituent contains one, two, three, four or five $R^{2a}$ independently selected from the $R^{2a}$ as defined and preferably defined herein. In particular, if substituted, each $R^{2a}$ is independently selected from halogen, OH, CN, $C_1$-$C_2$-alkoxy, $C_1$-$C_2$-haloalkoxy, $C_1$-$C_2$-alkylthio, $C_1$-$C_2$-haloalkylthio, $C_1$-$C_2$-alkylcarbonyl and $C_1$-$C_2$-alkoxycarbonyl. According to one specific embodiment thereof, $R^2$ is selected from hydrogen, $C_1$-$C_6$-alkyl, $C_1$-$C_6$-haloalkyl and $C_1$-$C_4$-alkoxy-$C_1$-$C_6$-alkyl.

According to a further embodiment, $R^2$ is selected from $C_1$-$C_8$-alkyl, $C_1$-$C_8$-haloalkyl, $C_2$-$C_6$-alkenyl, $C_2$-$C_6$-haloalkenyl, $C_2$-$C_6$-alkynyl and $C_2$-$C_6$-haloalkynyl. According to one specific embodiment thereof, the respective substituent is not further substituted. According to another specific embodiment thereof, the respective substituent contains one, two, three, four or five $R^{2a}$ independently selected from the $R^{2a}$ as defined and preferably defined herein. In particular, if substituted, each $R^{2a}$ is independently selected from halogen, OH, CN, $C_1$-$C_2$-alkoxy, $C_1$-$C_2$-haloalkoxy, $C_1$-$C_2$-alkylthio, $C_1$-$C_2$-haloalkylthio, $C_1$-$C_2$-alkylcarbonyl and $C_1$-$C_2$-alkoxycarbonyl. According to one specific embodiment thereof, $R^2$ is selected from hydrogen, $C_1$-$C_6$-alkyl, $C_1$-$C_6$-haloalkyl, $C_1$-$C_6$-alkoxy-$C_1$-$C_6$-alkyl.

According to a further specific embodiment, $R^2$ is $C_1$-$C_8$-alkyl, in particular $C_1$-$C_6$-alkyl, more specifically $C_1$-$C_4$-alkyl, such as methyl, ethyl, n-propyl, iso-propyl, n-butyl, tert-butyl, iso-butyl.

According to a further specific embodiment, $R^2$ is $C_1$-$C_8$-haloalkyl, in particular $C_1$-$C_6$-haloalkyl, more specifically $C_1$-$C_4$-haloalkyl, containing one, two, three or four or up to the maximum possible number of independently selected Br, Cl, I and F, such as $CF_3$ or $CHF_2$.

In still a further specific embodiment $R^2$ is $C_1$-$C_6$-alkoxy-$C_1$-$C_6$-alkyl, in particular $C_1$-$C_4$-alkoxy-$C_1$-$C_4$-alkyl, more specifically $C_1$-$C_2$-alkoxy-$C_1$-$C_2$-alkyl, such as methoxy-$C_1$-$C_2$-alkyl or ethoxy-$C_1$-$C_2$-alkyl.

In still a further specific embodiment $R^2$ is $C_1$-$C_6$-haloalkoxy-$C_1$-$C_6$-alkyl, $C_1$-$C_6$-alkoxy-$C_1$-$C_6$-haloalkyl or $C_1$-$C_6$-haloalkoxy-$C_1$-$C_6$-haloalkyl, in particular $C_1$-$C_4$-haloalkoxy-$C_1$-$C_3$-alkyl, $C_1$-$C_4$-alkoxy-$C_1$-$C_2$-haloalkyl or $C_1$-$C_4$-haloalkoxy-$C_1$-$C_2$-haloalkyl.

In another preferred embodiment $R^2$ is $C_2$-$C_6$-alkenyl, in particular $C_2$-$C_4$-alkenyl, more specifically $C_3$-$C_4$-alkenyl, such as 2-propenyl.

In another preferred embodiment $R^2$ is $C_2$-$C_6$-haloalkenyl, in particular $C_2$-$C_4$-haloalkenyl, more specifically $C_3$-$C_4$-haloalkenyl, containing one, two, three or four or up to the maximum possible number of independently selected Br, Cl, I and F, such as halo-2-propenyl.

In another preferred embodiment $R^2$ is $C_2$-$C_6$-alkynyl, in particular $C_2$-$C_4$-alkynyl, more specifically $C_3$-$C_4$-alkynyl, such as 2-propynyl or 2-butynyl.

In another preferred embodiment $R^2$ is $C_2$-$C_6$-haloalkynyl, in particular $C_2$-$C_4$-haloalkynyl, more specifically $C_3$-$C_4$-haloalkyenyl, containing one, two, three or four or up to the maximum possible number of independently selected Br, Cl, I and F, such as halo-2-propynyl or halo-2-butynyl.

According to a further embodiment, $R^2$ is selected from hydrogen, $C_1$-$C_6$-alkoxy, $C_1$-$C_6$-haloalkoxy, $C_1$-$C_6$-alkylthio and $C_1$-$C_6$-haloalkylthio. According to one specific embodiment thereof, the respective substituent is not further substituted. According to another specific embodiment thereof, the respective substituent contains one, two, three, four or five $R^{2a}$ independently selected from the $R^{2a}$ as defined and preferably defined herein. In particular, if substituted, each $R^{2a}$ is independently selected from halogen, OH, CN, $C_1$-$C_2$-alkoxy, $C_1$-$C_2$-haloalkoxy, $C_1$-$C_2$-alkylthio, $C_1$-$C_2$-haloalkylthio, $C_1$-$C_2$-alkylcarbonyl and $C_1$-$C_2$-alkoxycarbonyl.

According to a further embodiment, $R^2$ is selected from $C_1$-$C_6$-alkoxy, $C_1$-$C_6$-haloalkoxy, $C_1$-$C_6$-alkylthio and $C_1$-$C_6$-haloalkylthio. According to one specific embodiment thereof, the respective substituent is not further substituted. According to another specific embodiment thereof, the respective substituent contains one, two, three, four or five $R^{2a}$ independently selected from the $R^{2a}$ as defined and preferably defined herein. In particular, if substituted, each $R^{2a}$ is independently selected from halogen, OH, CN, $C_1$-$C_2$-alkoxy, $C_1$-$C_2$-haloalkoxy, $C_1$-$C_2$-alkylthio, $C_1$-$C_2$-haloalkylthio, $C_1$-$C_2$-alkylcarbonyl and $C_1$-$C_2$-alkoxycarbonyl.

In one further particular embodiment $R^2$ is $C_1$-$C_6$-alkoxy, in particular $C_1$-$C_4$-alkoxy, more particularly methoxy, ethoxy or 1-methylethoxy.

In a further specific embodiment $R^2$ is $C_1$-$C_6$-haloalkoxy, in particular $C_1$-$C_4$-haloalkoxy, containing one, two, three or four or up to the maximum possible number of independently selected Br, Cl, I and F. In a specific embodiment thereof $R^2$ is $C_1$-$C_2$-haloalkoxy, such as $OCF_3$ or $OCHF_2$.

In one further particular embodiment $R^2$ is $C_1$-$C_6$-alkylthio, in particular $C_1$-$C_4$-alkylthio, more specifically $C_1$-$C_2$-alkylthio.

In one further particular embodiment $R^2$ is $C_1$-$C_6$-haloalkylthio, in particular $C_1$-$C_4$-haloalkylthio, more specifically $C_1$-$C_2$-haloalkylthio, containing one, two, three or four or up to the maximum possible number of independently selected Br, Cl, I and F.

According to a further embodiment, $R^2$ is selected from hydrogen, $C_3$-$C_8$-cycloalkyl and $C_3$-$C_8$-halocycloalkyl. According to one specific embodiment thereof, the cycloalkyl moiety is not further substituted. According to another specific embodiment thereof, the cycloalkyl moiety contains one, two, three, four or five $R^{2a}$ independently selected from the $R^{2a}$ as defined and preferably defined herein. In particular, if substituted, each $R^{2a}$ is independently selected from halogen, OH, CN, $C_1$-$C_2$-alkoxy, $C_1$-$C_2$-haloalkoxy, $C_1$-$C_2$-alkylthio, $C_1$-$C_2$-haloalkylthio, $C_1$-$C_2$-alkylcarbonyl and $C_1$-$C_2$-alkoxycarbonyl.

According to a further embodiment, $R^2$ is selected from $C_3$-$C_8$-cycloalkyl and $C_3$-$C_8$-halocycloalkyl. According to one specific embodiment thereof, the cycloalkyl moiety is not further substituted. According to another specific embodiment thereof, the cycloalkyl moiety contains one, two, three, four or five $R^{2a}$ independently selected from the $R^{2a}$ as defined and preferably defined herein. In particular, if substituted, each $R^{2a}$ is independently selected from halogen, OH, CN, $C_1$-$C_2$-alkoxy, $C_1$-$C_2$-haloalkoxy, $C_1$-$C_2$-alkylthio, $C_1$-$C_2$-haloalkylthio, $C_1$-$C_2$-alkylcarbonyl and $C_1$-$C_2$-alkoxycarbonyl.

According to a further particular embodiment of the invention, $R^2$ is $C_3$-$C_8$-cycloalkyl, in particular $C_3$-$C_6$-cycloalkyl, more particularly cyclopropyl, cyclobutyl, cyclopentyl or cyclohexyl.

According to still a further particular embodiment $R^2$ is $C_3$-$C_8$-halocycloalkyl, in particular $C_3$-$C_6$-halocycloalkyl, containing one, two, three or four or up to the maximum possible number of independently selected Br, Cl, I and F, for example 1-Cl-cyclopropyl and 1-F-cyclopropyl.

As detailed above, $R^1$ may contain one or more $R^{1a}$ as given above. If not defined otherwise, each $R^{1a}$ is preferably independently selected from halogen, OH, CN, $C_1$-$C_4$-alkoxy, haloalkoxy, $C_1$-$C_4$-alkylthio, $C_1$-$C_4$-haloalkylthio, $C_1$-$C_4$-haloalkylsulfinyl, $C_1$-$C_4$-alkylsulfonyl, $C_1$-$C_4$-haloalkylsulfonyl, $C_1$-$C_4$-alkylcarbonyl, $C_1$-$C_4$-alkoxycarbonyl, unsubstituted aryl, aryl, that is substituted by one, two, three, four or five independently selected $R^{1b}$, unsubstituted heterocyclyl and heterocyclyl, that is substituted by one, two, three, four or five independently selected $R^{1b}$; wherein each $R^{1b}$ is independently selected from halogen, OH, CN, nitro, $NH_2$, $C_1$-$C_4$-alkyl, $C_1$-$C_4$-haloalkyl, $C_2$-$C_4$-alkenyl, $C_2$-$C_4$-haloalkenyl, $C_2$-$C_4$-alkynyl, $C_2$-$C_4$-haloalkynyl, $C_3$-$C_6$-cycloalkyl, $C_3$-$C_6$-halocycloalkyl, $C_1$-$C_3$-alkoxy, $C_1$-$C_3$-haloalkoxy, $C_1$-$C_3$-alkylthio, $C_1$-$C_3$-haloalkylthio, $C_1$-$C_3$-alkylsulfinyl, $C_1$-$C_3$-haloalkylsulfinyl, $C_1$-$C_3$-alkylsulfonyl, $C_1$-$C_3$-haloalkylsulfonyl, $C_1$-$C_4$-alkylamino, $C_1$-$C_4$-alkylcarbonyl, $C_1$-$C_4$-alkylcarbonyloxy, $C_1$-$C_4$-alkoxycarbonyl and $C_1$-$C_4$-alkylcarbonylamino.

More specifically, each $R^{1a}$ is independently selected from F, Br, Cl, OH, CN, $C_1$-$C_2$-alkoxy, $C_1$-$C_2$-haloalkoxy, $C_1$-$C_2$-alkylcarbonyl and $C_1$-$C_4$-alkoxycarbonyl.

Accordingly, $R^2$ may contain one or more $R^{2a}$, wherein $R^{2a}$ is defined and preferably defined as $R^{1a}$ According to a further embodiment of the invention, $R^1$ and $R^2$ together with the carbon atom to which they are bound form a saturated or partially unsaturated three-, four-, five-, six-, seven-, eight-, nine-, ten-, eleven-, twelve-, thirteen- or fourteen-membered carbocycle, which may be monocyclic or polycyclic or spirocyclic, or saturated or partially unsaturated three-, four-, five-, six-, seven-, eight-, nine-, ten-, eleven-, twelve-, thirteen- or fourteen-membered heterocycle, which may be monocyclic or polycyclic or spirocyclic, wherein the heterocycle contains one, two, three or four heteroatoms selected from N, O and S, or wherein the heterocycle contains one of S=O and $SO_2$ as ring members, and wherein the carbo- or heterocycle is unsubstituted or carries one, two, three, four or five substituents $R^{12a}$ independently selected from halogen, CN, $NO_2$, OH, SH, $NH_2$, $C_1$-$C_6$-alkyl, $C_1$-$C_4$-alkoxy-$C_1$-$C_4$-alkyl, $C_1$-$C_8$-alkoxy, $C_1$-$C_8$-haloalkoxy, $C_1$-$C_8$-alkylthio, $C_1$-$C_8$-haloalkylthio, $C_1$-$C_8$-alkylsulfinyl, $C_1$-$C_8$-haloalkylsulfinyl, $C_1$-$C_8$-alkylsulfonyl, $C_1$-$C_8$-haloalkylsulfonyl, $C_1$-$C_8$-alkylcarbonyl, $C_1$-$C_8$-alkoxycarbonyl, phenyl and phenyl that is substituted by one, two, three, four or five independently selected $R^{1b}$ as defined herein; and wherein one or two $CH_2$ groups of the carbo- or heterocycle may be replaced by a group independently selected from $C=CH_2$, $C(=O)$ and $C(=S)$. Specific embodiments are listed in Table P12 below.

According to one particular embodiment thereof, $R^1$ and $R^2$ together with the carbon atom to which they are bound form a saturated or partially unsaturated three-, four-, five-, six- or seven-membered, in particular saturated or partially unsaturated three-, four-, five- or six-membered carbocycle, which is monocyclic and which is unsubstituted or carries one, two, three or four independently selected substituents $R^{12a}$ as defined and preferably defined herein. Specific embodiments are listed in Table P12 below.

In one preferred embodiment $R^1$ and $R^2$ together with the carbon atom to which they are bound form a saturated monocyclic carbocycle, in particular $C_3$-$C_7$-cycloalkyl, specifically selected from the group consisting of cyclopropyl, cyclobutyl, cyclopentyl, cyclohexyl and cycloheptyl, wherein the carbocycle in each case is unsubstituted or carries one, two, three or four independently selected substituents $R^{12a}$ as defined and preferably defined below, in particular independently selected from Cl, F, Br, CN, OH, $C_1$-$C_4$-alkyl, $C_1$-$C_4$-alkoxy, $C_1$-$C_4$-haloalkoxy and $C_1$-$C_4$-alkoxy-$C_1$-$C_4$-alkyl. Specific embodiments are listed in Table P12 below.

In a specific embodiment thereof, $R^1$ and $R^2$ together with the carbon atom to which they are bound form a cyclopropyl ring which is unsubstituted or carries one, two, three or four independently selected substituents $R^{12a}$ as defined and preferably defined herein.

According to a further specific embodiment $R^1$ and $R^2$ together with the carbon atom to which they are bound form a cyclobutyl ring which is unsubstituted or carries one, two, three or four independently selected substituents $R^{12a}$ as defined and preferably defined herein.

In still a further specific embodiment of the invention $R^1$ and $R^2$ together with the carbon atom to which they are bound form a cyclopentyl ring which is unsubstituted or carries one, two, three or four independently selected substituents $R^{12a}$ as defined and preferably defined herein.

In yet another preferred embodiment $R^1$ and $R^2$ together with the carbon atom to which they are bound form a cyclohexyl ring which is unsubstituted or carries one, two, three or four independently selected substituents $R^{12a}$ as defined and preferably defined herein.

In another preferred embodiment $R^1$ and $R^2$ together with the carbon atom to which they are bound form a partially unsaturated monocyclic carbocycle, in particular selected from the group consisting of cyclopentenyl, cyclopentadienyl and cyclohexenyl and wherein the carbocycle is unsubstituted or carries one, two, three or four independently selected substituents $R^{12a}$ as defined and preferably defined below. Specific embodiments are listed in Table P12 below.

According to still another embodiment of the invention $R^1$ and $R^2$ together with the carbon atom to which they are bound form a saturated or partially unsaturated monocyclic or polycyclic or spirocyclic three-, four-, five-, six-, seven-, eight-, nine-, ten-, eleven-, twelve-, thirteen- or fourteen-membered heterocycle, in particular a monocyclic three-, four- or six-membered or bicyclic or spirocyclic nine-, ten-, eleven-, twelve-, thirteen- or fourteen-membered heterocycle, wherein the heterocycle includes beside carbon atoms one, two, three or four, in particular one or two, heteroatoms independently selected from the group consisting of N, O and S, and wherein the heterocycle is unsubstituted or carries one, two, three or four independently selected substituents $R^{12a}$ as defined and preferably defined below. Specific embodiments are listed in Table P12 below.

In one specific embodiment thereof $R^1$ and $R^2$ form a heterocycle selected from the group consisting of oxetane, azetidine, thiethane, 2-tetrahydrofuranyl, 3-tetrahydrofuranyl, 2-tetrahydrothienyl and 3-tetrahydrothienyl, wherein the heterocycle is unsubstituted or carries one, two, three or four independently selected substituents $R^{12a}$ as defined and preferably defined below. Specific embodiments are listed in Table P12 below.

In still a further specific embodiment of the invention $R^1$ and $R^2$ together with the carbon atom to which they are bound form an oxetane which is unsubstituted or carries one, two, three or four independently selected substituents $R^{12a}$ as defined and preferably defined below.

$R^{12a}$ according to the invention is in each case independently selected from the group consisting of halogen, CN, $NO_2$, OH, SH, $NH_2$, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio and $C_1$-$C_4$-alkoxy-$C_1$-$C_4$-alkyl. In a preferred embodiment $R^{12}2$ is halogen, CN, $NO_2$, OH, SH, $NH_2$, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio or $C_1$-$C_2$-alkoxy-$C_1$-$C_2$-alkyl. In another preferred embodiment $R^{12a}$ is halogen, CN, $C_1$-$C_4$-haloalkyl, $C_1$-$C_4$-alkoxy or $C_1$-$C_4$-haloalkoxy. In another preferred embodiment $R^{12a}$ is halogen, CN or $C_1$-$C_6$-alkyl. In yet another preferred embodiment $R^{12a}$ is halogen, in particular fluorine. In a further preferred embodiment $R^{12a}$ is chlorine. In still another preferred aspect of the invention $R^{12a}$ is $C_1$-$C_6$-alkyl, in particular $C_1$-$C_4$-alkyl, even more specifically methyl or ethyl.

According to one further particular embodiment of the invention, $R^1$ and $R^2$ are independently selected from hydrogen, $C_1$-$C_6$-alkyl, $C_1$-$C_6$-haloalkyl, $C_3$-$C_8$-cycloalkyl, $C_3$-$C_8$-halocycloalkyl, or together with the carbon atom to which they are bound together form a saturated $C_3$-$C_7$-cycloalkyl, as defined and specifically defined above.

According to one further particular embodiment of the invention, $R^1$ and $R^2$ are independently selected from $C_1$-$C_6$-alkyl and $C_1$-$C_6$-haloalkyl, or together with the carbon atom to which they are bound together form a saturated $C_3$-$C_7$-cycloalkyl, as defined and specifically defined above, in particular form cyclopentyl or cyclohexyl, specifically selected from $C_1$-$C_6$-alkyl or together with the carbon atom to which they are bound together form a saturated $C_3$-$C_7$-cycloalkyl, as defined and specifically defined above, in particular form cyclopentyl or cyclohexyl.

According to one specific embodiment of the invention, one or both of $R^1$ and $R^2$ is/are not hydrogen.

According to a further specific embodiment of the invention, both, $R^1$ and $R^2$ are not hydrogen.

According to a further specific embodiment of the invention, exactly one of $R^1$ and $R^2$ is hydrogen.

According to a further specific embodiment of the invention, both $R^1$ and $R^2$ are hydrogen.

According to one particular embodiment of the invention, $R^1$ is hydrogen and $R^2$ is selected from hydrogen, $C_1$-$C_6$-alkyl, $C_1$-$C_6$-haloalkyl, $C_3$-$C_8$-cycloalkyl, $C_3$-$C_8$-halocycloalkyl, $C_1$-$C_6$-alkoxy and $C_1$-$C_6$-haloalkoxy, in particular $R^2$ is hydrogen, $C_1$-$C_6$-alkyl, $C_1$-$C_6$-haloalkyl, $C_3$-$C_8$-cycloalkyl or $C_3$-$C_8$-halocycloalkyl.

Particularly preferred embodiments of $R^1$ according to the invention are in Table P1 below, wherein each line of lines P1-1 to P1-15 corresponds to one particular embodiment of the invention, wherein P1-1 to P1-15 are also in any combination preferred embodiments of the present invention.

TABLE P1

| line | $R^1$ |
|---|---|
| P1-1 | H |
| P1-2 | $CH_3$ |
| P1-3 | $CH_2CH_3$ |
| P1-4 | $CH_2CH_2CH_3$ |
| P1-5 | $CH(CH_3)_2$ |
| P1-6 | $C(CH_3)_3$ |
| P1-7 | $CH(CH_3)CH_2CH_3$ |
| P1-8 | $CH_2CH(CH_3)_2$ |
| P1-9 | $CH_2CH_2CH_2CH_3$ |
| P1-10 | $CH_2CH_2CH(CH_3)_2$ |
| P1-11 | $CF_3$ |
| P1-12 | cyclopropyl |
| P1-13 | cyclobutyl |
| P1-14 | cyclopentyl |
| P1-15 | cyclohexyl |

Particularly preferred embodiments of $R^2$ according to the invention are in Table P2 below, wherein each line of lines P2-1 to P2-15 corresponds to one particular embodiment of the invention, wherein P2-1 to P2-15 are also in any combination preferred embodiments of the present invention.

TABLE P2

| line | $R^2$ |
|---|---|
| P2-1 | H |
| P2-2 | $CH_3$ |
| P2-3 | $CH_2CH_3$ |
| P2-4 | $CH_2CH_2CH_3$ |
| P2-5 | $CH(CH_3)_2$ |
| P2-6 | $C(CH_3)_3$ |
| P2-7 | $CH(CH_3)CH_2CH_3$ |
| P2-8 | $CH_2CH(CH_3)_2$ |
| P2-9 | $CH_2CH_2CH_2CH_3$ |
| P2-10 | $CH_2CH_2CH(CH_3)_2$ |
| P2-11 | $CF_3$ |
| P2-12 | cyclopropyl |
| P2-13 | cyclobutyl |
| P2-14 | cyclopentyl |
| P2-15 | cyclohexyl |

Particularly preferred embodiments of $R^1$ in combination with $R^2$ according to the invention are in Table P12 below, wherein each line of lines P12-1 to P12-71 corresponds to one particular embodiment of the invention, wherein P12-1 to P12-71 are also in any combination preferred embodiments of the present invention.

TABLE P12

| line | $R^1$ | $R^2$ |
|---|---|---|
| P12-1 | H | H |
| P12-2 | $CH_3$ | H |
| P12-3 | $CH_2CH_3$ | H |
| P12-4 | $CH_2CH_2CH_3$ | H |
| P12-5 | $CH(CH_3)_2$ | H |
| P12-6 | $C(CH_3)_3$ | H |
| P12-7 | $CH(CH_3)CH_2CH_3$ | H |
| P12-8 | $CH_2CH(CH_3)2$ | H |
| P12-9 | $CH_2CH_2CH_2CH_3$ | H |
| P12-10 | $CH_2CH_2CH(CH_3)_2$ | H |
| P12-11 | $CF_3$ | H |
| P12-12 | cyclopropyl | H |
| P12-13 | cyclobutyl | H |
| P12-14 | cyclopentyl | H |
| P12-15 | cyclohexyl | H |
| P12-16 | H | $CH_3$ |
| P12-17 | $CH_3$ | $CH_3$ |
| P12-18 | $CH_2CH_3$ | $CH_3$ |
| P12-19 | $CH_2CH_2CH_3$ | $CH_3$ |
| P12-20 | $CH(CH_3)_2$ | $CH_3$ |
| P12-21 | $C(CH_3)_3$ | $CH_3$ |
| P12-22 | $CH(CH_3)CH_2CH_3$ | $CH_3$ |
| P12-23 | $CH_2CH(CH_3)_2$ | $CH_3$ |
| P12-24 | $CH_2CH_2CH_2CH_3$ | $CH_3$ |
| P12-25 | $CH_2CH_2CH(CH_3)_2$ | $CH_3$ |
| P12-26 | $CF_3$ | $CH_3$ |
| P12-27 | cyclopropyl | $CH_3$ |
| P12-28 | cyclobutyl | $CH_3$ |
| P12-29 | cyclopentyl | $CH_3$ |
| P12-30 | cyclohexyl | $CH_3$ |
| P12-31 | H | $CH_2CH_3$ |
| P12-32 | $CH_3$ | $CH_2CH_3$ |
| P12-33 | $CH_2CH_3$ | $CH_2CH_3$ |
| P12-34 | $CH_2CH_2CH_3$ | $CH_2CH_3$ |
| P12-35 | $CH(CH_3)_2$ | $CH_2CH_3$ |
| P12-36 | $C(CH_3)_3$ | $CH_2CH_3$ |
| P12-37 | $CH(CH_3)CH_2CH_3$ | $CH_2CH_3$ |
| P12-38 | $CH_2CH(CH_3)_2$ | $CH_2CH_3$ |
| P12-39 | $CH_2CH_2CH_2CH_3$ | $CH_2CH_3$ |
| P12-40 | $CH_2CH_2CH(CH_3)_2$ | $CH_2CH_3$ |
| P12-41 | $CF_3$ | $CH_2CH_3$ |
| P12-42 | cyclopropyl | $CH_2CH_3$ |
| P12-43 | cyclobutyl | $CH_2CH_3$ |
| P12-44 | cyclopentyl | $CH_2CH_3$ |
| P12-45 | cyclohexyl | $CH_2CH_3$ |
| P12-46 | | cyclopropyl |
| P12-47 | | cyclobutyl |
| P12-48 | | cyclopentyl |
| P12-49 | | cyclohexyl |
| P12-50 | | C*—(oxiranyl, 3-membered ring with O) |
| P12-51 | | C*—(oxetanyl, 4-membered ring with O) |
| P12-52 | | C*—(thietanyl, 4-membered ring with S) |
| P12-53 | | C*—(thietanyl S-oxide, 4-membered ring with S=O) |
| P12-54 | | C*—(thietanyl S,S-dioxide, 4-membered ring with $SO_2$) |
| P12-55 | | C*—(N-methyl azetidinyl, 4-membered ring with N—$CH_3$) |
| P12-56 | | C*—(N-acetyl azetidinyl, 4-membered ring with N—C(=O)$CH_3$) |
| P12-57 | | C*—(tetrahydrothiopyranyl, 6-membered ring with S) |
| P12-58 | | C*—(tetrahydrothiopyranyl S-oxide, 6-membered ring with S=O) |
| P12-59 | | C*—(tetrahydrothiopyranyl S,S-dioxide, 6-membered ring with $SO_2$) |
| P12-60 | | C*—(tetrahydropyranyl, 6-membered ring with O at 4-position) |
| P12-61 | | C*—(tetrahydropyranyl, 6-membered ring with O at 3-position) |
| P12-62 | | C*—(tetrahydropyranyl, 6-membered ring with O at 2-position) |
| P12-63 | | C*—(1,3-dioxanyl, 6-membered ring with two O) |
| P12-64 | | C*—(1,4-dioxanyl, 6-membered ring with two O) |
| P12-65 | | C*—(N-methyl piperidinyl, 6-membered ring with N—$CH_3$) |
| P12-66 | | C*—(N-methoxy piperidinyl, 6-membered ring with N—$OCH_3$) |
| P12-67 | | C*—(N-acetyl piperidinyl, 6-membered ring with N—C(=O)$CH_3$) |
| P12-68 | | C*—(3,4-dihydro-2H-pyranyl, 6-membered ring with O and one double bond) |

TABLE P12-continued

| line | $R^1$ | $R^2$ |
|---|---|---|
| P12-69 | |  |
| P12-70 | |  |
| P12-71 | | 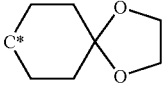 |

"C*" denotes the carbon atom to which $R^1$ and $R^2$ are bound.

According to the invention, $R^3$ is hydrogen, $C_1$-$C_6$-alkyl, $C_2$-$C_6$-alkenyl, $C_2$-$C_6$-alkynyl, $C_3$-$C_8$-cycloalkyl, $C_3$-$C_8$-cycloalkyl-$C_1$-$C_6$-alkyl, phenyl, phenyl-$C_1$-$C_4$-alkyl, phenyl-$C_2$-$C_4$-alkenyl or phenyl-$C_2$-$C_4$-alkynyl, wherein the aliphatic moieties of $R^3$ are not further substituted or carry one, two, three or up to the maximum possible number of identical or different groups $R^{1a}$ which independently of one another are selected from halogen, OH, CN, nitro, $C_1$-$C_4$-alkoxy, $C_3$-$C_8$-cycloalkyl, $C_3$-$C_8$-halocycloalkyl and $C_1$-$C_4$-halonalkoxy; and wherein the cycloalkyl and/or phenyl moieties of $R^3$ are not further substituted or carry one, two, three, four, five or up to the maximum number of identical or different groups $R^{3b}$ which independently of one another are selected from halogen, OH, CN, nitro, $C_1$-$C_4$-alkyl, $C_1$-$C_4$-alkoxy, $C_1$-$C_4$-halogenalkyl, $C_3$-$C_8$-cycloalkyl, $C_3$-$C_8$-halocycloalkyl and $C_1$-$C_4$-halonalkoxy.

According to one embodiment of the invention, $R^3$ is hydrogen.

According to a further embodiment of the invention, $R^3$ is selected from hydrogen, $C_1$-$C_6$-alkyl, $C_2$-$C_6$-alkenyl, $C_2$-$C_6$-alkynyl, wherein the $R^3$ are in each case unsubstituted or are substituted by $R^{3a}$ as defined and preferably defined herein, in particular wherein each $R^{3a}$ is independently selected from halogen, OH, CN, $C_1$-$C_4$-alkoxy and $C_1$-$C_4$-halogenalkoxy, more specifically selected from OH, CN, $C_1$-$C_4$-alkoxy and $C_1$-$C_4$-halogenalkoxy. Specific embodiments thereof can be found in the below Table P3.

In a further embodiment of the invention, $R^3$ is selected from $C_1$-$C_6$-alkyl, $C_2$-$C_6$-alkenyl and $C_2$-$C_6$-alkynyl, wherein the $R^3$ are in each case unsubstituted or are substituted by $R^{3a}$ as defined and preferably defined herein, in particular wherein each $R^{3a}$ is independently selected from halogen, OH, CN, $C_1$-$C_4$-alkoxy and $C_1$-$C_4$-halogenalkoxy, more specifically selected from OH, CN, $C_1$-$C_4$-alkoxy and $C_1$-$C_4$-halogenalkoxy. In a preferred embodiment, $R^3$ is selected from hydrogen, methyl, ethyl, $CH_2CH=CH_2$ and $CH_2C\equiv CH$. Further specific embodiments can be found in the below Table P3.

According to one particular embodiment, $R^3$ is hydrogen or $C_1$-$C_6$-alkyl, in particular hydrogen or $C_1$-$C_4$-alkyl, such as H, $CH_3$, $C_2H_5$, $CH(CH_3)_2$, $CH_2CH_2CH_3$, $CH_2CH_2CH_2CH_3$ or $CH_2CH(CH_3)_2$. A further embodiment relates to compounds, wherein $R^3$ is hydrogen or $C_1$-$C_6$-alkyl, in particular hydrogen or $C_1$-$C_4$-alkyl, that is substituted by one, two or three or up to the maximum possible number of identical or different groups $R^{3a}$, as defined and preferably defined herein. According to a specific embodiment thereof, $R^3$ is hydrogen or $C_1$-$C_6$-haloalkyl, in particular hydrogen or $C_1$-$C_4$-haloalkyl, more particularly hydrogen or $C_1$-$C_2$-haloalkyl. According to a further specific embodiment thereof, $R^3$ is hydrogen or $C_1$-$C_4$-alkoxy-$C_1$-$C_6$-alkyl, in particular hydrogen or $C_1$-$C_4$-alkoxy-$C_1$-$C_4$-alkyl, such as H, $CH_2OCH_3$ or $CH_2CH_2OCH_3$. According to still a further specific embodiment thereof, $R^3$ is hydrogen or hydroxy-$C_1$-$C_6$-alkyl, in particular hydrogen or hydroxyl-$C_1$-$C_4$-alkyl, such as H or $CH_2CH_2OH$. According to a further specific embodiment thereof, $R^3$ is hydrogen or cyano-$C_1$-$C_6$-alkyl, in particular hydrogen or $C_1$-$C_4$-cyano-$C_1$-$C_4$-alkyl, such as H, $CH_2CN$ or $CH_2CH_2CN$. Further specific embodiments thereof can be found in the below Table P3.

According to one particular embodiment, $R^3$ is $C_1$-$C_6$-alkyl, in particular $C_1$-$C_4$-alkyl, such as $CH_3$, $C_2H_5$, $CH(CH_3)_2$, $CH_2CH_2CH_3$, $CH_2CH_2CH_2CH_3$, $CH_2CH(CH_3)_2$. A further embodiment relates to compounds, wherein $R^3$ is $C_1$-$C_6$-alkyl, in particular $C_1$-$C_4$-alkyl, that is substituted by one, two or three or up to the maximum possible number of identical or different groups $R^{3a}$, as defined and preferably defined herein. According to a specific embodiment thereof, $R^3$ is $C_1$-$C_6$-haloalkyl, in particular $C_1$-$C_4$-haloalkyl, more particularly $C_1$-$C_2$-haloalkyl. According to a further specific embodiment thereof, $R^3$ is $C_1$-$C_4$-alkoxy-$C_1$-$C_6$-alkyl, in particular $C_1$-$C_4$-alkoxy-$C_1$-$C_4$-alkyl, such as $CH_2OCH_3$ or $CH_2CH_2OCH_3$. According to still a further specific embodiment thereof, $R^3$ is hydroxy-$C_1$-$C_6$-alkyl, in particular hydroxyl-$C_1$-$C_4$-alkyl, such as $CH_2CH_2OH$. According to a further specific embodiment thereof, $R^3$ is cyano-$C_1$-$C_6$-alkyl, in particular $C_1$-$C_4$-cyano-$C_1$-$C_4$-alkyl, such as $CH_2CN$ or $CH_2CH_2CN$. Further specific embodiments thereof can be found in the below Table P3.

According to still another embodiment, $R^3$ is hydrogen or $C_3$-$C_8$-cycloalkyl-$C_1$-$C_6$-alkyl, in particular hydrogen or $C_3$-$C_6$-cycloalkyl-$C_1$-$C_4$-alkyl. A further embodiment relates to compounds, wherein $R^3$ is hydrogen or $C_3$-$C_8$-cycloalkyl-$C_1$-$C_6$-alkyl, in particular H or $C_3$-$C_6$-cycloalkyl-$C_1$-$C_4$-alkyl, more particularly H or $C_3$-$C_6$-cycloalkyl-$C_1$-$C_2$-alkyl, that is substituted by one, two or three or up to the maximum possible number of identical or different groups $R^{3a}$ in the alkyl moiety and/or substituted by one, two, three four or five or up to the maximum possible number of identical or different groups $R^{3b}$ in the cycloalkyl moiety. $R^{3a}$ and $R^{3b}$ are in each case as defined and preferably defined herein. Specific embodiments thereof can be found in the below Table P3.

According to still another embodiment, $R^3$ is $C_3$-$C_8$-cycloalkyl-$C_1$-$C_6$-alkyl, in particular $C_3$-$C_6$-cycloalkyl-$C_1$-$C_4$-alkyl. A further embodiment relates to compounds, wherein $R^3$ is $C_3$-$C_8$-cycloalkyl-$C_1$-$C_6$-alkyl, in particular $C_3$-$C_6$-cycloalkyl-$C_1$-$C_4$-alkyl, more particularly $C_3$-$C_6$-cycloalkyl-$C_1$-$C_2$-alkyl, that is substituted by one, two or three or up to the maximum possible number of identical or different groups $R^{1a}$ in the alkyl moiety and/or substituted by one, two, three four or five or up to the maximum possible number of identical or different groups $R^{3b}$ in the cycloalkyl moiety. $R^{3a}$ and $R^{3b}$ are in each case as defined and preferably defined herein. Specific embodiments thereof can be found in the below Table P3.

According to another embodiment, $R^3$ is H or $C_2$-$C_6$-alkenyl, in particular H or $C_2$-$C_4$-alkenyl, such as H, $CH_2CH=CH_2$, $CH_2C(CH_3)=CH_2$ or $CH_2CH=CHCH_3$. A further embodiment relates to compounds, wherein $R^3$ is H or $C_2$-$C_6$-alkenyl, in particular H or $C_2$-$C_4$-alkenyl, that is substituted by one, two or three or up to the maximum possible number of identical or different groups $R^{3a}$ as defined and preferably defined herein. According to a specific embodiment thereof, $R^3$ is H or $C_2$-$C_6$-haloalkenyl, in particular H or $C_2$-$C_4$-haloalkenyl, such as H, $CH_2C(Cl)$=$CH_2$ and $CH_2C(H)$=$CHCl$. According to a further specific embodiment thereof, $R^3$ is H or $C_3$-$C_8$-cycloalkyl-$C_2$-$C_6$-alkenyl or $C_3$-$C_8$-halocycloalkyl-$C_2$-$C_6$-alkenyl, in particular H, $C_3$-$C_6$-cycloalkyl-$C_2$-$C_4$-alkenyl or $C_3$-$C_6$-halocycloalkyl-$C_2$-$C_4$-alkenyl. Further specific embodiments thereof can be found in the below Table P3.

According to another embodiment, $R^3$ is $C_2$-$C_6$-alkenyl, in particular $C_2$-$C_4$-alkenyl, such as $CH_2CH$=$CH_2$, $CH_2C(CH_3)$=$CH_2$ or $CH_2CH$=$CHCH_3$. A further embodiment relates to compounds, wherein $R^3$ is $C_2$-$C_6$-alkenyl, in particular $C_2$-$C_4$-alkenyl, that is substituted by one, two or three or up to the maximum possible number of identical or different groups $R^{3a}$ as defined and preferably defined herein. According to a specific embodiment thereof, $R^3$ is $C_2$-$C_6$-haloalkenyl, in particular $C_2$-$C_4$-haloalkenyl, such as $CH_2C(Cl)$=$CH_2$ and $CH_2C(H)$=$CHCl$. According to a further specific embodiment thereof, $R^3$ is $C_3$-$C_8$-cycloalkyl-$C_2$-$C_6$-alkenyl or $C_3$-$C_8$-halocycloalkyl-$C_2$-$C_6$-alkenyl, in particular $C_3$-$C_6$-cycloalkyl-$C_2$-$C_4$-alkenyl or $C_3$-$C_6$-halocycloalkyl-$C_2$-$C_4$-alkenyl. Further specific embodiments thereof can be found in the below Table P3.

According to still another embodiment, $R^3$ is H or $C_2$-$C_6$-alkynyl, in particular H or $C_2$-$C_4$-alkynyl, such as H, $CH_2C$≡$CH$ or $CH_2C$≡$CCH_3$. A further embodiment relates to compounds, wherein $R^3$ is H or $C_2$-$C_6$-alkynyl, in particular H or $C_2$-$C_4$-alkynyl, that is substituted by one, two or three or up to the maximum possible number of identical or different groups $R^{3a}$, as defined and preferably defined herein. According to a specific embodiment thereof, $R^3$ is H or $C_2$-$C_6$-haloalkynyl, in particular H or $C_2$-$C_4$-haloalkynyl. According to a further specific embodiment thereof, $R^3$ is H, $C_3$-$C_8$-cycloalkyl-$C_2$-$C_6$-alkynyl or $C_3$-$C_8$-halocycloalkyl-$C_2$-$C_6$-alkynyl, in particular H, $C_3$-$C_6$-cycloalkyl-$C_2$-$C_4$-alkynyl or $C_3$-$C_6$-halocycloalkyl-$C_2$-$C_4$-alkynyl. Specific embodiments thereof can be found in the below Table P3.

According to still another embodiment, $R^3$ is $C_2$-$C_6$-alkynyl, in particular $C_2$-$C_4$-alkynyl, such as $CH_2C$≡$CH$ or $CH_2C$≡$CCH_3$. A further embodiment relates to compounds, wherein $R^3$ is $C_2$-$C_6$-alkynyl, in particular $C_2$-$C_4$-alkynyl, that is substituted by one, two or three or up to the maximum possible number of identical or different groups $R^{3a}$, as defined and preferably defined herein.

According to a specific embodiment thereof, $R^3$ is $C_2$-$C_6$-haloalkynyl, in particular $C_2$-$C_4$-haloalkynyl. According to a further specific embodiment thereof, $R^3$ is $C_3$-$C_8$-cycloalkyl-$C_2$-$C_6$-alkynyl or $C_3$-$C_8$-halocycloalkyl-$C_2$-$C_6$-alkynyl, in particular $C_3$-$C_6$-cycloalkyl-$C_2$-$C_4$-alkynyl or $C_3$-$C_6$-halocycloalkyl-$C_2$-$C_4$-alkynyl. Specific embodiments thereof can be found in the below Table P3.

According to still another embodiment, $R^3$ is H or phenyl-$C_1$-$C_4$-alkyl, in particular H or phenyl-$C_1$-$C_2$-alkyl, such as H or benzyl, wherein the alkyl moiety in each case is unsubstituted or carries one, two or three $R^{3a}$ as defined and preferably defined herein, in particular selected from halogen, in particular F and Cl, $C_1$-$C_4$-alkoxy, in particular $OCH_3$, and CN, and wherein the phenyl in each case is unsubstituted or carries one, two or three $R^{3b}$ as defined and preferably defined herein, in particular selected from halogen, in particular Cl and F, $C_1$-$C_4$-alkoxy, in particular $OCH_3$, $C_1$-$C_4$-alkyl, in particular $CH_3$ or $C_2H_5$, and CN. Specific embodiments thereof can be found in the below Table P3.

According to still another embodiment, $R^3$ is phenyl-$C_1$-$C_4$-alkyl, in particular phenyl-$C_1$-$C_2$-alkyl, such as benzyl, wherein the alkyl moiety in each case is unsubstituted or carries one, two or three $R^{3a}$ as defined and preferably defined herein, in particular selected from halogen, in particular F and Cl, $C_1$-$C_4$-alkoxy, in particular $OCH_3$, and CN, and wherein the phenyl in each case is unsubstituted or carries one, two or three $R^{3b}$ as defined and preferably defined herein, in particular selected from halogen, in particular Cl and F, $C_1$-$C_4$-alkoxy, in particular $OCH_3$, alkyl, in particular $CH_3$ or $C_2H_5$, and CN. Specific embodiments thereof can be found in the below Table P3.

According to still another embodiment, $R^3$ is H or phenyl-$C_2$-$C_4$-alkenyl, in particular H or phenyl-$C_2$-$C_3$-alkenyl, such as H or phenylethenyl, wherein the alkenyl moiety in each case is unsubstituted or carries one, two or three $R^{3a}$ as defined and preferably defined herein, in particular selected from halogen, in particular F and Cl, $C_1$-$C_4$-alkoxy, in particular $OCH_3$, and CN, and wherein the phenyl in each case is unsubstituted or carries one, two or three $R^{3b}$ as defined and preferably defined herein, in particular selected from halogen, in particular Cl and F, $C_1$-$C_4$-alkoxy, in particular $OCH_3$, $C_1$-$C_4$-alkyl, in particular $CH_3$ or $C_2H_5$, and CN.

According to still another embodiment, $R^3$ is phenyl-$C_2$-$C_4$-alkenyl, in particular phenyl-$C_2$-$C_3$-alkenyl, such as phenylethenyl, wherein the alkenyl moiety in each case is unsubstituted or carries one, two or three $R^{3a}$ as defined and preferably defined herein, in particular selected from halogen, in particular F and Cl, $C_1$-$C_4$-alkoxy, in particular $OCH_3$, and CN, and wherein the phenyl in each case is unsubstituted or carries one, two or three $R^{3b}$ as defined and preferably defined herein, in particular selected from halogen, in particular Cl and F, $C_1$-$C_4$-alkoxy, in particular $OCH_3$, $C_1$-$C_4$-alkyl, in particular $CH_3$ or $C_2H_5$, and CN.

According to still another embodiment, $R^3$ is H or phenyl-$C_2$-$C_4$-alkynyl, in particular H or phenyl-$C_2$-$C_3$-alkynyl, such as H or phenylethinyl, wherein the alkynyl moiety in each case is unsubstituted or carries one, two or three $R^{3a}$, as defined and preferably defined herein, in particular selected from halogen, in particular F and Cl, $C_1$-$C_4$-alkoxy, in particular $OCH_3$, and CN, and wherein the phenyl in each case is unsubstituted or carries one, two or three $R^{3b}$ as defined and preferably defined herein, in particular selected from halogen, in particular Cl and F, $C_1$-$C_4$-alkoxy, in particular $OCH_3$, $C_1$-$C_4$-alkyl, in particular $CH_3$ or $C_2H_5$, and CN.

According to still another embodiment, $R^3$ is phenyl-$C_2$-$C_4$-alkynyl, in particular phenyl-$C_2$-$C_3$-alkynyl, such as phenylethinyl, wherein the alkynyl moiety in each case is unsubstituted or carries one, two or three $R^{3a}$, as defined and preferably defined herein, in particular selected from halogen, in particular F and Cl, $C_1$-$C_4$-alkoxy, in particular $OCH_3$, and CN, and wherein the phenyl in each case is unsubstituted or carries one, two or three $R^{3b}$ as defined and preferably defined herein, in particular selected from halogen, in particular Cl and F, $C_1$-$C_4$-alkoxy, in particular $OCH_3$, $C_1$-$C_4$-alkyl, in particular $CH_3$ or $C_2H_5$, and CN.

According to still another embodiment, $R^3$ is H or $C_3$-$C_8$-cycloalkyl, in particular H or $C_3$-$C_6$-cycloalkyl, such as H, $C_3H_5$ (cyclopropyl), $C_4H_7$ (cyclobutyl), cyclopentyl or cyclohexyl. A further embodiment relates to compounds, wherein $R^3$ is H or $C_3$-$C_8$-cycloalkyl, in particular H or $C_3$-$C_6$-cycloalkyl, such as H, $C_3H_5$ (cyclopropyl) or $C_4H_7$ (cyclobutyl), that is substituted by one, two, three four or five or up to the maximum possible number of identical or different groups $R^{3b}$ as defined and preferably defined herein. According to a specific embodiment thereof, $R^3$ is H or $C_3$-$C_8$-halocycloalkyl, in particular H or $C_3$-$C_6$-halocycloalkyl, such as H or halocyclopropyl, in particular H, 1-F-cyclopropyl or 1-Cl-cyclopropyl. According to a further specific embodiment thereof, $R^3$ is H or $C_3$-$C_8$-cycloalkyl-$C_3$-$C_8$-cycloalkyl, in particular H or $C_3$-$C_6$-cycloalkyl-$C_3$-$C_6$-cycloalkyl, wherein each of said cycloalkyl-cycloalkyl moieties is unsubstituted or carries one, two or three $R^{3b}$ as defined and preferably defined herein.

According to still another embodiment, $R^3$ is $C_3$-$C_8$-cycloalkyl, in particular $C_3$-$C_6$-cycloalkyl, such as $C_3H_5$ (cyclopropyl), $C_4H_7$ (cyclobutyl), cyclopentyl or cyclohexyl. A further embodiment relates to compounds, wherein $R^3$ is $C_3$-$C_8$-cycloalkyl, in particular $C_3$-$C_6$-cycloalkyl, such as $C_3H_5$ (cyclopropyl) or $C_4H_7$ (cyclobutyl), that is substituted by one, two, three four or five or up to the maximum possible number of identical or different groups $R^{3b}$ as defined and preferably defined herein. According to a specific embodiment thereof, $R^3$ is $C_3$-$C_8$-halocycloalkyl, in particular $C_3$-$C_6$-halocycloalkyl, such as halocycloalkyl, in particular 1-F-cyclopropyl or 1-Cl-cyclopropyl. According to a further specific embodiment thereof, $R^3$ is $C_3$-$C_8$-cycloalkyl-$C_3$-$C_8$-cycloalkyl, in particular $C_3$-$C_6$-cycloalkyl-$C_3$-$C_6$-cycloalkyl, wherein each of said cycloalkyl-cycloalkyl moieties is unsubstituted or carries one, two or three $R^{3b}$ as defined and preferably defined herein.

According to still another embodiment, $R^3$ is H or phenyl, wherein the phenyl is unsubstituted or carries one, two, three, four or five independently selected $R^{3b}$ as defined and preferably defined herein, in particular selected from halogen, in particular Cl and F, $C_1$-$C_4$-alkoxy, in particular $OCH_3$, $C_1$-$C_4$-alkyl, in particular $CH_3$ or $C_2H_5$, and CN.

According to still another embodiment, $R^3$ is phenyl, wherein the phenyl is unsubstituted or carries one, two, three, four or five independently selected $R^{3b}$ as defined and preferably defined herein, in particular selected from halogen, in particular Cl and F, $C_1$-$C_4$-alkoxy, in particular $OCH_3$, $C_1$-$C_4$-alkyl, in particular $CH_3$ or $C_2H_5$, and CN.

Particularly preferred embodiments of $R^3$ according to the invention are in Table P3 below, wherein each line of lines P3-1 to P3-88 corresponds to one particular embodiment of the invention, wherein P3-1 to P3-88 are also in any combination preferred embodiments of the present invention.

TABLE P3

| line | $R^3$ |
|---|---|
| P3-1 | H |
| P3-2 | $CH_3$ |
| P3-3 | $CH_2CH_3$ |
| P3-4 | $CH(CH_3)_2$ |
| P3-5 | $CH_2CH_2CH_3$ |
| P3-6 | $CH_2CH_2CH_2CH_3$ |
| P3-7 | $CH_2CH(CH_3)_2$ |
| P3-8 | $CF_3$ |
| P3-9 | $CHF_2$ |
| P3-10 | $CFH_2$ |
| P3-11 | $CCl_3$. |
| P3-12 | $CHCl_2$ |
| P3-13 | $CClH_2$ |
| P3-14 | $CH_2CF_3$ |
| P3-15 | $CH_2CHF_2$ |
| P3-16 | $CH_2CCl_3$ |
| P3-17 | $CH_2CHCl_2$ |
| P3-18 | $CH_2CH_2OCH_2CH_3$ |
| P3-19 | $CH(CH_3)OCH_2CH_3$ |
| P3-20 | $CH(CH_3)OCH_3$ |
| P3-21 | $CH_2OCH_3$ |
| P3-22 | $CH_2CH_2OCH_3$ |
| P3-23 | $CH_2OCF_3$ |
| P3-24 | $CH_2CH_2OCF_3$ |
| P3-25 | $CH_2OCCl_3$ |
| P3-26 | $CH_2CH_2OCCl_3$ |
| P3-27 | $CH_2CH_2OH$ |
| P3-28 | $CH_2OH$ |
| P3-29 | $CH_2CH_2CH_2OH$, |
| P3-30 | $CH(CH_3)CH_2OH$ |
| P3-31 | $CH_2CH(CH_3)OH$ |
| P3-32 | $CH_2CH_2CH_2CH_2OH$ |
| P3-33 | $CH_2CN$ |
| P3-34 | $CH_2CH_2CN$, |
| P3-35 | $CH_2CH_2CH_2CN$, |
| P3-36 | $CH(CH_3)CH_2CN$, |
| P3-37 | $CH_2CH(CH_3)CN$, |
| P3-38 | $CH_2CH_2CH_2CH_2CN$ |
| P3-39 | $CH=CH_2$ |
| P3-40 | $C(CH_3)=CH_2$ |
| P3-41 | $CH=CHCH_3$ |
| P3-42 | $CH_2CH=CH_2$ |
| P3-43 | $CH_2CH=CHCH_3$ |
| P3-44 | $CH_2C(CH_3)=CH_2$ |
| P3-45 | $C(CH_3)=CH(CH_3)$ |
| P3-46 | $C(CH_3)=C(CH_3)_2$ |
| P3-47 | $CH=C(CH_3)_2$ |
| P3-48 | $CH=C(Cl)_2$ |
| P3-49 | $C(CH_3)=CH_2$ |
| P3-50 | $CH_2C(Cl)=CH_2$ |
| P3-51 | $CH_2C(H)=CHCl$ |
| P3-52 | $CH=CHCH_2OH$ |
| P3-53 | $CH=C(CH_3)OH$ |
| P3-54 | $CH=CHOCH_3$ |
| P3-55 | $CH=CHCH_2OCH_3$ |
| P3-56 | $CH_2CH=CHCH_2OCH_3$ |
| P3-57 | $CH=CHOCF_3$ |
| P3-58 | $CH=CHCH_2OCF_3$ |
| P3-59 | $CH=CHOCCl_3$ |
| P3-60 | $CH=CHCH_2OCCl_3$ |
| P3-61 | $CH_2CH=CH(C_3H_5)$ |
| P3-62 | $CH_2CH=CH(C_4H_7)$ |
| P3-63 | $CH_2CH=CH(1\text{-}Cl\text{---}C_3H_4)$ |
| P3-64 | $CH_2CH=CH(1\text{-}F\text{---}C_3H_4)$ |
| P3-65 | $CH_2C\equiv CCH(CH_3)_2$ |
| P3-66 | $CH_2C\equiv CH$ |
| P3-67 | $CH_2C\equiv CCH_3$ |
| P3-68 | $CH_2C\equiv CCH_2CH_3$ |
| P3-69 | $CH_2C\equiv CCl$ |
| P3-70 | $CH_2C\equiv CF$ |
| P3-71 | $CH_2C\equiv C\text{---}I$ |
| P3-72 | $CH_2C\equiv CCH_2OH$ |
| P3-73 | $CH_2C\equiv CCH_2OCH_3$ |
| P3-74 | $CH_2C\equiv COCH_3$ |
| P3-75 | $CH_2C\equiv CCCH_2OCH_3$ |
| P3-76 | $C\equiv COCF_3$ |
| P3-77 | $CH_2C\equiv COCF_3$ |
| P3-78 | $C\equiv COCCl_3$ |
| P3-79 | $CH_2C\equiv COCCl_3$ |
| P3-80 | $CH_2\text{-}(\text{cyclopropyl})$ |
| P3-81 | $CH_2\text{-}(\text{cyclobutyl})$ |
| P3-82 | $CH_2\text{-}(1\text{-Cl-cyclopropyl})$ |
| P3-83 | $CH_2\text{-}(1\text{-F-cyclopropyl})$ |
| P3-84 | $CH_2C_6H_5$ |
| P3-85 | $CH_2\text{-}(4\text{-Cl})\text{---}C_6H_4$ |
| P3-86 | $CH_2\text{-}(4\text{-F})\text{---}C_6H_4$ |
| P3-87 | $CH_2\text{-}(4\text{-}CH_3)\text{---}C_6H_4$ |
| P3-88 | $CH_2\text{-}(4\text{-}OCH_3)\text{---}C_6H_4$ |

More specific embodiments of $R^3$ according to the invention are in Table P31 below, wherein each line of lines P31-1 to P31-14 corresponds to one particular embodiment of the invention, wherein P31-1 to P31-14 are also in any combination preferred embodiments of the present invention.

TABLE P31

| line | $R^3$ |
|---|---|
| P31-1 | H |
| P31-2 | $CH_3$ |
| P31-3 | $CH_2CH_3$ |
| P31-4 | $CH(CH_3)_2$ |

TABLE P31-continued

| line | $R^3$ |
|---|---|
| P31-5 | $CH_2CH_2CH_3$ |
| P31-6 | $CH_2OCH_3$ |
| P31-7 | $CH_2CH_2OCH_3$ |
| P31-8 | $CH_2CH_2OH$ |
| P31-9 | $CH_2CN$, |
| P31-10 | $CH_2CH_2CN$, |
| P31-11 | $CH_2CH=CH_2$ |
| P31-12 | $CH_2CH=CHCH_3$ |
| P31-13 | $CH_2C\equiv CH$ |
| P31-14 | $CH_2C\equiv CCH_3$ |

Each $R^4$ according to the present invention is independently selected from halogen, CN, $NO_2$, OH, SH, $C_1$-$C_6$-alkyl, $C_1$-$C_6$-alkoxy, $C_2$-$C_6$-alkenyl, $C_2$-$C_6$-alkynyl, $C_3$-$C_8$-cycloalkyl, $C_3$-$C_8$-cycloalkyloxy, $NH_2$, $NH(C_1$-$C_4$-alkyl), $N(C_1$-$C_4$-alkyl)$_2$, $NH(C_3$-$C_6$-cycloalkyl), $N(C_3$-$C_6$-cycloalkyl)$_2$, $S(O)_p(C_1$-$C_4$-alkyl), $C(=O)(C_1$-$C_4$-alkyl), $C(=O)(OH)$, $C(=O)(O-C_1$-$C_4$-alkyl), $C(=O)(NH(C_1$-$C_4$-alkyl))$, $C(=O)(N(C_1$-$C_4$-alkyl)$_2$), $C(=O)(NH(C_3$-$C_6$-cycloalkyl))$ and $C(=O)-(N(C_3$-$C_6$-cycloalkyl)$_2$); wherein each of $R^4$ is unsubstituted or further substituted by one, two, three or four $R^{4a}$; wherein $R^{4a}$ is independently selected from halogen, CN, $NO_2$, OH, $C_1$-$C_4$-alkyl, $C_1$-$C_4$-haloalkyl, $C_3$-$C_8$-cycloalkyl, $C_3$-$C_8$-halocycloalkyl, $C_1$-$C_4$-alkoxy and $C_1$-$C_4$-halogenalkoxy.

According to the invention, there can be zero, one, two, three or four $R^4$ present, namely for n is 0, 1, 2, 3 or 4.

According to one embodiment, n is 0.

According to a further embodiment, n is 1.

According to a further embodiment, n is 2 or 3. According to one specific embodiment thereof, n is 2, according to a further specific embodiment, n is 3.

According to one embodiment of the invention, one $R^4$ is attached to the 2-position (in relation to the attachment of the isoxazole unit; $R^{41}$). According to one specific embodiment thereof, n is 1, according to a further specific embodiment, n is 2.

According to one embodiment of the invention, one $R^4$ is attached to the 3-position (in relation to the attachment of the isoxazole unit; $R^{42}$), if Z—Y is attached in para (4-position). According to one specific embodiment thereof, n is 1, according to a further specific embodiment, n is 2.

According to one embodiment of the invention, one $R^4$ is attached to the 4-position (in relation to the attachment of the isoxazole unit; $R^{42}$), if Z—Y is attached in meta (3-position). According to one specific embodiment thereof, n is 1, according to a further specific embodiment, n is 2.

According to one embodiment of the invention, one $R^4$ is attached to the 5-position (in relation to the attachment of the isoxazole unit; $R^{43}$), if Z—Y is attached in meta (3-position). According to one specific embodiment thereof, n is 1, according to a further specific embodiment, n is 2.

According to one embodiment of the invention, one $R^4$ is attached to the 6-position (in relation to the attachment of the isoxazole unit; $R^{44}$), if Z—Y is attached in meta (3-position). According to one specific embodiment thereof, n is 1, according to a further specific embodiment, n is 2.

According to still a further embodiment, n is 1, 2 or 3 and one $R^4$ is in 2-position (in relation to the attachment of the isoxazole unit).

According to a further embodiment of the invention, two $R^4$ are attached in 2,3-position (in relation to the attachment of the isoxazole unit), if Z—Y is attached in para (4-position). According to one specific embodiment thereof, n is 2, according to a further specific embodiment, n is 3.

According to a further embodiment of the invention, two $R^4$ are attached in 2,4-position (in relation to the attachment of the isoxazole unit), if Z—Y is attached in meta (3-position). According to one specific embodiment thereof, n is 2, according to a further specific embodiment, n is 3.

According to a further embodiment of the invention, two $R^4$ are attached in 2,5-position (in relation to the attachment of the isoxazole unit). According to one specific embodiment thereof, n is 2, according to a further specific embodiment, n is 3.

According to a further embodiment of the invention, two $R^4$ are attached in 2,6-position (in relation to the attachment of the isoxazole unit). According to one specific embodiment thereof, n is 2, according to a further specific embodiment, n is 3.

According to a further embodiment of the invention, two $R^4$ are attached in 3,5-position (in relation to the attachment of the isoxazole unit), if Z—Y is attached in para (4-position). According to one specific embodiment thereof, n is 2, according to a further specific embodiment, n is 3.

For every $R^4$ (or $R^{41}$, $R^{42}$, $R^{43}$, $R^{44}$, respectively) that is present in the inventive compounds, the following embodiments and preferences apply independently of the meaning of any other $R^4$ (or $R^{41}$, $R^{42}$, $R^{44}$, $R^{44}$, respectively) that may be present in the phenyl ring. Furthermore, the particular embodiments and preferences given herein for $R^4$ (or $R^{41}$, $R^{42}$, $R^{44}$, $R^{44}$, respectively) apply independently for each of n=1, n=2, n=3 and n=4.

According to one embodiment, $R^4$ is independently selected from halogen, CN, $NO_2$, $C_1$-$C_4$-alkyl, $C_1$-$C_4$-haloalkyl, $C_1$-$C_4$-alkoxy, $C_1$-$C_4$-haloalkoxy, $C_2$-$C_4$-alkenyl, $C_2$-$C_4$-haloalkenyl, $C_2$-$C_4$-alkynyl, $C_2$-$C_4$-haloalkynyl, $C_3$-$C_6$-cycloalkyl, $C_3$-$C_6$-halocycloalkyl, $S(C_1$-$C_2$-alkyl), $S(O)(C_1$-$C_2$-alkyl), $S(O)_2(C_1$-$C_2$-alkyl), $C(=O)(C_1$-$C_2$-alkyl), $C(=O)(OH)$ and $C(=O)(O-C_1$-$C_2$-alkyl).

According to a further embodiment, $R^4$ is independently selected from halogen, CN, $NO_2$, OH, SH, $C_1$-$C_6$-alkyl, $C_1$-$C_6$-alkoxy, $C_2$-$C_6$-alkenyl, $C_2$-$C_6$-alkynyl, $C_3$-$C_8$-cycloalkyl, $C_3$-$C_8$-cycloalkyloxy, $NH_2$, $NH(C_1$-$C_4$-alkyl), $N(C_1$-$C_4$-alkyl)$_2$, $NH(C_3$-$C_6$-cycloalkyl), $N(C_3$-$C_6$-cycloalkyl)$_2$, $S(O)_p(C_1$-$C_4$-alkyl) (p=0, 1 or 2), $C(=O)(C_1$-$C_4$-alkyl), $C(=O)(OH)$, $C(=O)(O-C_1$-$C_4$-alkyl), $C(=O)(NH(C_1$-$C_4$-alkyl))$, $C(=O)(N(C_1$-$C_4$-alkyl)$_2$), $C(=O)(NH(C_3$-$C_6$-cycloalkyl))$ and $C(=O)(N(C_3$-$C_6$-cycloalkyl)$_2$); wherein each of $R^4$ is unsubstituted or further substituted by one, two, three or four $R^{4a}$, wherein $R^{4a}$ is as defined and preferably defined herein.

According to still a further embodiment, $R^4$ is independently selected from halogen, CN, $NO_2$, $C_1$-$C_4$-alkoxy, $C_1$-$C_4$-haloalkoxy, $C_2$-$C_4$-alkenyl, $C_2$-$C_4$-haloalkenyl, $C_2$-$C_4$-alkynyl, $C_2$-$C_4$-haloalkynyl, $C_3$-$C_6$-cycloalkyl, $C_3$-$C_6$-halocycloalkyl, $S(C_1$-$C_2$-alkyl), $S(O)(C_1$-$C_2$-alkyl), $S(O)_2(C_1$-$C_2$-alkyl), $C(=O)(C_1$-$C_2$-alkyl), $C(=O)(OH)$ and $C(=O)(O-C_1$-$C_2$-alkyl).

According to still a further embodiment, $R^4$ is independently selected from F, $C_1$, Br, CN, $C_1$-$C_4$-alkyl, $C_1$-$C_4$-haloalkyl, $C_1$-$C_4$-alkoxy, $C_1$-$C_4$-haloalkoxy, $S(C_1$-$C_4$-alkyl), $S(O)(C_1$-$C_4$-alkyl) and $S(O)_2(C_1$-$C_4$-alkyl).

According to one specific embodiment, $R^4$ is halogen, in particular Br, F or Cl, more specifically F or $C_1$.

According to a further specific embodiment, $R^4$ is CN.

According to a further specific embodiment, $R^4$ is $C_1$-$C_6$-alkyl, in particular $C_1$-$C_4$-alkyl, such as $CH_3$.

According to a further specific embodiment, $R^4$ is $C_1$-$C_6$-haloalkyl, in particular $C_1$-$C_4$-haloalkyl, such as $CF_3$, $CHF_2$, $CH_2F$, $CCl_3$, $CHCl_2$ or $CH_2Cl$.

According to a further specific embodiment, $R^4$ is $C_1$-$C_6$-alkoxy, in particular $C_1$-$C_4$-alkoxy, more specifically $C_1$-$C_2$-alkoxy such as $OCH_3$ or $OCH_2CH_3$.

According to a further specific embodiment, $R^4$ is $C_1$-$C_6$-haloalkoxy, in particular $C_1$-$C_4$-haloalkoxy, more specifically $C_1$-$C_2$-haloalkoxy such as $OCF_3$, $OCHF_2$, $OCH_2F$, $OCCl_3$, $OCHCl_2$ or $OCH_2Cl$, in particular $OCF_3$, $OCHF_2$, $OCCl_3$ or $OCHCl_2$.

According to still a further embodiment, $R^4$ is $C_2$-$C_6$-alkenyl or $C_2$-$C_6$-haloalkenyl, in particular $C_2$-$C_4$-alkenyl or $C_2$-$C_4$-haloalkenyl, such as $CH=CH_2$.

According to still a further embodiment, $R^4$ is $C_2$-$C_6$-alkynyl or $C_2$-$C_6$-haloalkynyl, in particular $C_2$-$C_4$-alkynyl or $C_2$-$C_4$-haloalkynyl, such as $C\equiv CH$.

According to still a further embodiment, $R^4$ is selected from $C(=O)(C_1$-$C_4$-alkyl), $C(=O)(OH)$, $C(=O)(O-C_1$-$C_4$-alkyl), $C(=O)(NH(C_1$-$C_4$-alkyl))$, $C(=O)(N(C_1$-$C_4$-alkyl)_2)$, $C(=O)(NH(C_3$-$C_6$-cycloalkyl))$ and $C(=O)(N(C_3$-$C_6$-cycloalkyl)_2)$, in particular selected from $C(=O)(C_1$-$C_2$-alkyl), $C(=O)(OH)$, $C(=O)(O-C_1$-$C_2$-alkyl), $C(=O)(NH(C_1$-$C_2$-alkyl))$, $C(=O)(N(C_1$-$C_2$-alkyl)_2)$, $C(=O)(NH(C_3$-$C_6$-cycloalkyl))$ and $C(=O)(N(C_3$-$C_6$-cycloalkyl)_2)$. According to one specific embodiment thereof, $R^4$ is $C(=O)(OH)$ or $C(=O)(O-C_1$-$C_4$-alkyl), in particular $C(=O)(OCH_3)$.

According to still a further embodiment, $R^4$ is selected from $S(C_1$-$C_2$-alkyl), $S(O)(C_1$-$C_2$-alkyl)$ and $S(O)_2(C_1$-$C_2$-alkyl), in particular $SCH_3$, $S(O)(CH_3)$ and $S(O)_2(CH_3)$.

According to still a further embodiment, $R^4$ is unsubstituted phenyl or phenyl that is substituted by one, two, three or four $R^{4a}$, as defined herein.

According to still a further embodiment, $R^4$ is unsubstituted phenoxy or phenoxy that is substituted by one, two, three or four $R^{4a}$, as defined herein.

According to still a further embodiment, $R^4$ is unsubstituted 5- or 6-membered heteroaryl. According to still a further embodiment, $R^4$ is 5- or 6-membered heteroaryl that is substituted by one, two or three $R^{4a}$, as defined herein. According to one specific embodiment, the heteroaryl in each case is 5-membered such as. According to a further specific embodiment, the heteroaryl in each case is 6-membered such as.

According to still a further embodiment, $R^4$ is unsubstituted 5- or 6-membered heteroaryloxy. According to still a further embodiment, $R^4$ is 5- or 6-membered heteroaryloxy that is substituted by one, two or three $R^{4a}$, as defined herein. According to one specific embodiment, the heteroaryloxy in each case is 5-membered. According to a further specific embodiment, the heteroaryloxy in each case is 6-membered.

$R^{4a}$ is independently selected from halogen, CN, $NO_2$, OH, $C_1$-$C_4$-alkyl, $C_1$-$C_4$-haloalkyl, $C_3$-$C_8$-cycloalkyl, $C_3$-$C_8$-halocycloalkyl, $C_1$-$C_4$-alkoxy and $C_1$-$C_4$halogenalkoxy, in particular selected from halogen, CN, $C_1$-$C_2$-haloalkyl, $C_3$-$C_6$-cycloalkyl, $C_3$-$C_6$-halocycloalkyl, $C_1$-$C_2$-alkoxy and $C_1$-$C_2$-halogenalkoxy. Specifically, $R^{4a}$ is independently selected from F, Cl, CN, OH, $CH_3$, halomethyl, cyclopropyl, halocyclopropyl, $OCH_3$ and halogenmethoxy.

Particularly preferred embodiments of $R^4$ according to the invention are in Table P4 below, wherein each line of lines P4-1 to P4-16 corresponds to one particular embodiment of the invention, wherein P4-1 to P4-16 are also in any combination with one another preferred embodiments of the present invention. Thereby, for every $R^4$ that is present in the inventive compounds, these specific embodiments and preferences apply independently of the meaning of any other $R^4$ that may be present in the phenyl ring:

TABLE P4

| No. | $R^4$ |
| --- | --- |
| P4-1 | Cl |
| P4-2 | F |
| P4-3 | CN |
| P4-4 | $NO_2$ |
| P4-5 | $CH_3$ |
| P4-6 | $CH_2CH_3$ |
| P4-7 | $CF_3$ |
| P4-8 | $CHF_2$ |
| P4-9 | $OCH_3$ |
| P4-10 | $OCH_2CH_3$ |
| P4-11 | $OCF_3$ |
| P4-12 | $OCHF_2$ |
| P4-13 | $SCH_3$ |
| P4-14 | $SOCH_3$ |
| P4-15 | $SO_2CH_3$ |
| P4-16 | $CO_2CH_3$ |

For compounds, wherein Z—Y is in para-position, particularly preferred embodiments of ($R^4$), according to the invention are in Table P41 below, wherein each line of lines P41-1 to P41-73 corresponds to one particular embodiment of the invention, wherein P41-1 to P41-73 are also in any combination preferred embodiments of the present invention. The position(s) of the substituent(s) is/are given in relation to the attachment of the isoxazole unit.

TABLE P41

| No. | $(R^4)_n$ |
| --- | --- |
| P41-1 | —* |
| P41-2 | 2-Cl |
| P41-3 | 3-Cl |
| P41-4 | 2-F |
| P41-5 | 3-F |
| P41-6 | 2-CN |
| P41-7 | 3-CN |
| P41-8 | $2$-$NO_2$ |
| P41-9 | $3$-$NO_2$ |
| P41-10 | $2$-$SCH_3$ |
| P41-11 | $3$-$SCH_3$ |
| P41-12 | $2$-$SOCH_3$ |
| P41-13 | $3$-$SOCH_3$ |
| P41-14 | $2$-$SO_2CH_3$ |
| P41-15 | $3$-$SO_2CH_3$ |
| P41-16 | $2$-$CO_2CH_3$ |
| P41-17 | $3$-$CO_2CH_3$ |
| P41-18 | $2,3$-$Cl_2$ |
| P41-19 | $2,5$-$Cl_2$ |
| P41-20 | $3,5$-$Cl_2$ |
| P41-21 | $2,6$-$Cl_2$ |
| P41-22 | $2,3$-$F_2$ |
| P41-23 | $2,5$-$F_2$ |
| P41-24 | $2,6$-$F_2$ |
| P41-25 | $3,5$-$F_2$ |
| P41-26 | $2,6$-$F_2$ |
| P41-27 | 2-F-3-Cl |
| P41-28 | 2-F-5-Cl |
| P41-29 | 2-F-6-Cl |
| P41-30 | 2-Cl-3-F |
| P41-31 | 2-Cl-5-F |
| P41-32 | $2$-$CH_3$ |
| P41-33 | $3$-$CH_3$ |
| P41-34 | $2$-$CH_2CH_3$ |
| P41-35 | $3$-$CH_2CH_3$ |
| P41-36 | $2$-$CF_3$ |
| P41-37 | $3$-$CF_3$ |
| P41-38 | $2$-$CHF_2$ |
| P41-39 | $3$-$CHF_2$ |
| P41-40 | $2$-$OCH_3$ |
| P41-41 | $3$-$OCH_3$ |
| P41-42 | $2$-$OCH_2CH_3$ |
| P41-43 | $3$-$OCH_2CH_3$ |
| P41-44 | $2$-$OCF_3$ |
| P41-45 | $3$-$OCF_3$ |

TABLE P41-continued

| No. | $(R^4)_n$ |
|---|---|
| P41-46 | 2-OCHF$_2$ |
| P41-47 | 3-OCHF$_2$ |
| P41-48 | 2,3-(CH$_3$)$_2$ |
| P41-49 | 2,6-(CH$_3$)$_2$ |
| P41-50 | 2,3-(CH$_2$CH$_3$)$_2$ |
| P41-51 | 2,6-(CH$_2$CH$_3$)$_2$ |
| P41-52 | 2,3-(CF$_3$)$_2$ |
| P41-53 | 2,5-(CF$_3$)$_2$ |
| P41-54 | 3,5-(CF$_3$)$_2$ |
| P41-55 | 2,6-(CF$_3$)$_2$ |
| P41-56 | 2,3-(CHF$_2$)$_2$ |
| P41-57 | 2,6-(CHF$_2$)$_2$ |
| P41-58 | 2,3-(OCH$_3$)$_2$ |
| P41-59 | 2,6-(OCH$_3$)$_2$ |
| P41-60 | 2,3-(OCH$_2$CH$_3$)$_2$ |
| P41-61 | 2,6-(OCH$_2$CH$_3$)$_2$ |
| P41-62 | 2,3-(OCF$_3$)$_2$ |
| P41-63 | 2,6-(OCF$_3$)$_2$ |
| P41-64 | 2,3-(OCHF$_2$)$_2$ |
| P41-65 | 2,6-(OCHF$_2$)$_2$ |
| P41-66 | 2-CF$_3$-5-Cl |
| P41-67 | 2-CF$_3$-5-F |
| P41-68 | 2-CF$_3$-3-Cl— |
| P41-69 | 2-CF$_3$-3-F |
| P41-70 | 3-CF$_3$-5-Cl |
| P41-71 | 3-CF$_3$-5-F |
| P41-72 | 3-CF$_3$-6-F |
| P41-73 | 3-CF$_3$-6-Cl |

—* means that n = 0

Even more specific embodiments of $(R^4)_n$ according to the invention, for compounds, wherein Z—Y is in para-position, are in Table P42 below, wherein each line of lines P42-1 to P42-40 corresponds to one particular embodiment of the invention, wherein P42-1 to P42-40 are also in any combination preferred embodiments of the present invention. The position(s) of the substituent(s) is/are given in relation to the attachment of the isoxazole unit.

TABLE P42

| No. | $(R^4)_n$ |
|---|---|
| P42-1 | —* |
| P42-2 | 2-Cl |
| P42-3 | 3-Cl |
| P42-4 | 2-F |
| P42-5 | 3-F |
| P42-6 | 2-CN |
| P42-7 | 3-CN |
| P42-8 | 2,3-Cl$_2$ |
| P42-9 | 2,5-Cl$_2$ |
| P42-10 | 3,5-Cl$_2$ |
| P42-11 | 2,6-Cl$_2$ |
| P42-12 | 2,3-F$_2$ |
| P42-13 | 2,5-F$_2$ |
| P42-14 | 3,5-F$_2$ |
| P42-15 | 2,6-F$_2$ |
| P42-16 | 2-F-3-Cl |
| P42-17 | 2-F-5-Cl |
| P42-18 | 2-F-6-Cl |
| P42-19 | 2-Cl-3-F |
| P42-20 | 2-Cl-5-F |
| P42-21 | 2-CH$_3$ |
| P42-22 | 3-CH$_3$ |
| P42-23 | 2-CF$_3$ |
| P42-24 | 3-CF$_3$ |
| P42-25 | 2-CHF$_2$ |
| P42-26 | 3-CHF$_2$ |
| P42-27 | 2-OCH$_3$ |
| P42-28 | 3-OCH$_3$ |
| P42-29 | 2,3-(CF$_3$)$_2$ |
| P42-30 | 2,5-(CF$_3$)$_2$ |
| P42-31 | 3,5-(CF$_3$)$_2$ |
| P42-32 | 2,6-(CF$_3$)$_2$ |

TABLE P42-continued

| No. | $(R^4)_n$ |
|---|---|
| P42-33 | 2-CF$_3$-5-Cl |
| P42-34 | 2-CF$_3$-5-F |
| P42-35 | 2-CF$_3$-3-Cl— |
| P42-36 | 2-CF$_3$-3-F |
| P42-37 | 3-CF$_3$-5-Cl |
| P42-38 | 3-CF$_3$-5-F |
| P42-39 | 3-CF$_3$-6-F |
| P42-40 | 3-CF$_3$-6-Cl |

—* means that n = 0

For compounds, wherein Z—Y is in meta-position, particularly preferred embodiments of $(R^4)$, according to the invention are in Table P43 below, wherein each line of lines P43-1 to P43-103 corresponds to one particular embodiment of the invention, wherein P43-1 to P43-103 are also in any combination preferred embodiments of the present invention. The position(s) of the substituent(s) is/are given in relation to the attachment of the isoxazole unit.

TABLE P43

| No. | $(R^4)_n$ |
|---|---|
| P43-1 | —* |
| P43-2 | 2-Cl |
| P43-3 | 4-Cl |
| P43-4 | 5-Cl |
| P43-5 | 6-Cl |
| P43-6 | 2-F |
| P43-7 | 4-F |
| P43-8 | 5-F |
| P43-9 | 6-F |
| P43-10 | 2-CN |
| P43-11 | 4-CN |
| P43-12 | 5-CN |
| P43-13 | 6-CN |
| P43-14 | 2-NO$_2$ |
| P43-15 | 4-NO$_2$ |
| P43-16 | 5-NO$_2$ |
| P43-17 | 6-NO$_2$ |
| P43-18 | 2-SCH$_3$ |
| P43-19 | 4-SCH$_3$ |
| P43-20 | 5-SCH$_3$ |
| P43-21 | 6-SCH$_3$ |
| P43-22 | 2-SOCH$_3$ |
| P43-23 | 4-SOCH$_3$ |
| P43-24 | 5-SOCH$_3$ |
| P43-25 | 6-SOCH$_3$ |
| P43-26 | 2-SO$_2$CH$_3$ |
| P43-27 | 4-SO$_2$CH$_3$ |
| P43-28 | 5-SO$_2$CH$_3$ |
| P43-29 | 6-SO$_2$CH$_3$ |
| P43-30 | 2-CO$_2$CH$_3$ |
| P43-31 | 4-CO$_2$CH$_3$ |
| P43-32 | 5-CO$_2$CH$_3$ |
| P43-33 | 6-CO$_2$CH$_3$ |
| P43-34 | 4,6-Cl$_2$ |
| P43-35 | 2,5-Cl$_2$ |
| P43-36 | 2,6-Cl$_2$ |
| P43-37 | 4,6-F$_2$ |
| P43-38 | 2,5-F$_2$ |
| P43-39 | 2,6-F$_2$ |
| P43-40 | 4-F-6-Cl |
| P43-41 | 4-Cl-6-F |
| P43-42 | 2-F-5-Cl |
| P43-43 | 2-F-6-Cl |
| P43-44 | 4-Cl-6-F |
| P43-45 | 4-F-6-Cl |
| P43-46 | 2-Cl-5-F |
| P43-47 | 2-CH$_3$ |
| P43-48 | 4-CH$_3$ |
| P43-49 | 5-CH$_3$ |
| P43-50 | 6-CH$_3$ |
| P43-51 | 2-CH$_2$CH$_3$ |
| P43-52 | 4-CH$_2$CH$_3$ |

TABLE P43-continued

| No. | $(R^4)_n$ |
|---|---|
| P43-53 | 5-CH$_2$CH$_3$ |
| P43-54 | 6-CH$_2$CH$_3$ |
| P43-55 | 2-CF$_3$ |
| P43-56 | 4-CF$_3$ |
| P43-57 | 5-CF$_3$ |
| P43-58 | 6-CF$_3$ |
| P43-59 | 2-CHF$_2$ |
| P43-60 | 4-CHF$_2$ |
| P43-61 | 5-CHF$_2$ |
| P43-62 | 6-CHF$_2$ |
| P43-63 | 2-OCH$_3$ |
| P43-64 | 4-OCH$_3$ |
| P43-65 | 5-OCH$_3$ |
| P43-66 | 6-OCH$_3$ |
| P43-67 | 2-OCH$_2$CH$_3$ |
| P43-68 | 4-OCH$_2$CH$_3$ |
| P43-69 | 5-OCH$_2$CH$_3$ |
| P43-70 | 6-OCH$_2$CH$_3$ |
| P43-71 | 2-OCF$_3$ |
| P43-72 | 4-OCF$_3$ |
| P43-73 | 5-OCF$_3$ |
| P43-74 | 6-OCF$_3$ |
| P43-75 | 2-OCHF$_2$ |
| P43-76 | 4-OCHF$_2$ |
| P43-77 | 5-OCHF$_2$ |
| P43-78 | 6-OCHF$_2$ |
| P43-79 | 4,6-(CH$_3$)$_2$ |
| P43-80 | 2,6-(CH$_3$)$_2$ |
| P43-81 | 4,6-(CH$_2$CH$_3$)$_2$ |
| P43-82 | 2,6-(CH$_2$CH$_3$)$_2$ |
| P43-83 | 4,6-(CF$_3$)$_2$ |
| P43-84 | 2,5-(CF$_3$)$_2$ |
| P43-85 | 2,6-(CF$_3$)$_2$ |
| P43-86 | 4,6-(CHF$_2$)$_2$ |
| P43-87 | 2,6-(CHF$_2$)$_2$ |
| P43-88 | 4,6-(OCH$_3$)$_2$ |
| P43-89 | 2,6-(OCH$_3$)$_2$ |
| P43-90 | 4,6-(OCH$_2$CH$_3$)$_2$ |
| P43-91 | 2,6-(OCH$_2$CH$_3$)$_2$ |
| P43-92 | 4,6-(OCF$_3$)$_2$ |
| P43-93 | 2,6-(OCF$_3$)$_2$ |
| P43-94 | 4,6-(OCHF$_2$)$_2$ |
| P43-95 | 2,6-(OCHF$_2$)$_2$ |
| P43-96 | 2-CF$_3$-5-Cl |
| P43-97 | 2-CF$_3$-5-F |
| P43-98 | 2-CF$_3$-4-Cl— |
| P43-99 | 2-CF$_3$-4-F |
| P43-100 | 4-CF$_3$-6-Cl |
| P43-101 | 4-CF$_3$-6-F |
| P43-102 | 6-CF$_3$-4-F |
| P43-103 | 6-CF$_3$-4-Cl |

—* means that n = 0

Even more specific embodiments of (R$^4$), according to the invention, for compounds, wherein Z—Y is in meta-position, are in Table P44 below, wherein each line of lines P44-1 to P44-47 corresponds to one particular embodiment of the invention, wherein P44-1 to P44-47 are also in any combination preferred embodiments of the present invention. The position(s) of the substituent(s) is/are given in relation to the attachment of the isoxazole unit.

TABLE P44

| No. | $(R^4)_n$ |
|---|---|
| P44-1 | —* |
| P44-2 | 2-Cl |
| P44-3 | 4-Cl |
| P44-4 | 5-Cl |
| P44-5 | 6-Cl |
| P44-6 | 2-F |
| P44-7 | 4-F |
| P44-8 | 5-F |
| P44-9 | 6-F |

TABLE P44-continued

| No. | $(R^4)_n$ |
|---|---|
| P44-10 | 2-CN |
| P44-11 | 4-CN |
| P44-12 | 5-CN |
| P44-13 | 6-CN |
| P44-14 | 4,6-Cl$_2$ |
| P44-15 | 2,5-Cl$_2$ |
| P44-16 | 2,6-Cl$_2$ |
| P44-17 | 4,6-F$_2$ |
| P44-18 | 2,5-F$_2$ |
| P44-19 | 2,6-F$_2$ |
| P44-20 | 4-F-6-Cl |
| P44-21 | 4-Cl-6-F |
| P44-22 | 2-F-6-Cl |
| P44-23 | 2-Cl-5-F |
| P44-24 | 2-CH$_3$ |
| P44-25 | 4-CH$_3$ |
| P44-26 | 5-CH$_3$ |
| P44-27 | 6-CH$_3$ |
| P44-28 | 2-CF$_3$ |
| P44-29 | 4-CF$_3$ |
| P44-30 | 5-CF$_3$ |
| P44-31 | 6-CF$_3$ |
| P44-32 | 2-CHF$_2$ |
| P44-33 | 4-CHF$_2$ |
| P44-34 | 5-CHF$_2$ |
| P44-35 | 6-CHF$_2$ |
| P44-36 | 2-OCH$_3$ |
| P44-37 | 4-OCH$_3$ |
| P44-38 | 5-OCH$_3$ |
| P44-39 | 6-OCH$_3$ |
| P44-40 | 4,6-(CF$_3$)$_2$ |
| P44-41 | 2,5-(CF$_3$)$_2$ |
| P44-42 | 2,4-(CF$_3$)$_2$ |
| P44-43 | 2,6-(CF$_3$)$_2$ |
| P44-44 | 4-CF$_3$-6-Cl |
| P44-45 | 4-CF$_3$-6-F |
| P44-46 | 4-Cl-6-CF$_3$ |
| P44-47 | 4-F-6-CF$_3$ |

—* means that n = 0

Y is a divalent group selected from the group consisting of —O—, —S—, —SO—, SO$_2$—, —NH—, —N(C$_1$-C$_4$-alkyl)-, —CR$^6$R$^7$—, —CR$^8$R$^9$—CR$^{10}$R$^{11}$—, —CR$^{12}$=CR$^{13}$— and —C≡C—; wherein R$^6$, R$^7$, R$^8$, R$^9$, R$^{10}$, R$^{11}$, R$^{12}$ and R$^{13}$ are independently selected from hydrogen, halogen, CN, nitro, OH, C$_1$-C$_4$-alkyl, C$_1$-C$_4$-halogenalkyl, C$_1$-C$_4$-alkoxy and C$_1$-C$_4$-halogenalkoxy.

According to an embodiment, Y is selected from —O—, —CR$^6$R$^7$—, —CR$^8$R$^9$—CR$^{10}$R$^{11}$—, —CR$^{12}$=CR$^{13}$— and —C≡C—; wherein R$^6$, R$^7$, R$^8$, R$^9$, R$^{10}$, R$^{11}$, R$^{12}$ and R$^{13}$ are independently selected from hydrogen, halogen, CN, nitro, OH, C$_1$-C$_4$-alkyl, C$_1$-C$_4$-halogenalkyl, C$_1$-C$_4$-alkoxy and C$_1$-C$_4$-halogenalkoxy.

According to one embodiment, Z—Y is attached to the ortho-position (2-position) in relation to the attachment of the isoxazole unit.

According to a further embodiment, Z—Y is attached to the meta-position (3-position) in relation to the attachment of the isoxazole unit.

According to one embodiment, Z—Y is attached to the para-position (4-position) in relation to the attachment of the isoxazole unit.

According to one particular embodiment, Y is —O—. In a specific embodiment thereof, Z—Y is attached to the meta-position (3-position) in relation to the attachment of the isoxazole unit. In a further specific embodiment thereof, Z—Y is attached to the para-position (4-position) in relation to the attachment of the isoxazole unit.

According to a further embodiment, Y is —S—. In a specific embodiment thereof, Z—Y is attached to the meta-position (3-position) in relation to the attachment of the isoxazole unit. In a further specific embodiment thereof, Z—Y is attached to the para-position (4-position) in relation to the attachment of the isoxazole unit.

According to still a further embodiment, Y is —SO—. In a specific embodiment thereof, Z—Y is attached to the meta-position (3-position) in relation to the attachment of the isoxazole unit. In a further specific embodiment thereof, Z—Y is attached to the para-position (4-position) in relation to the attachment of the isoxazole unit.

According to still a further embodiment, Y is —SO$_2$—. In a specific embodiment thereof, Z—Y is attached to the meta-position (3-position) in relation to the attachment of the isoxazole unit. In a further specific embodiment thereof, Z—Y is attached to the para-position (4-position) in relation to the attachment of the isoxazole unit.

According to still a further embodiment, Y is —NH—. In a specific embodiment thereof, Z—Y is attached to the meta-position (3-position) in relation to the attachment of the isoxazole unit. In a further specific embodiment thereof, Z—Y is attached to the para-position (4-position) in relation to the attachment of the isoxazole unit.

According to still a further embodiment, Y is —N($C_1$-$C_4$-alkyl). In a specific embodiment thereof, Z—Y is attached to the meta-position (3-position) in relation to the attachment of the isoxazole unit.

In a further specific embodiment thereof, Z—Y is attached to the para-position (4-position) in relation to the attachment of the isoxazole unit.

According to still a further embodiment, Y is —$CR^6R^7$—. In a specific embodiment thereof, Z—Y is attached to the meta-position (3-position) in relation to the attachment of the isoxazole unit. In a further specific embodiment thereof, Z—Y is attached to the para-position (4-position) in relation to the attachment of the isoxazole unit.

$R^6$ and $R^7$ are independently selected from hydrogen, halogen, CN, nitro, OH, $C_1$-$C_4$-alkyl, $C_1$-$C_4$-halogenalkyl, $C_1$-$C_4$-alkoxy and $C_1$-$C_4$-halogenalkoxy.

In one preferred embodiment $R^6$ and $R^7$ are independently selected from hydrogen and halogen, in particular hydrogen, fluorine and chlorine. In a further preferred embodiment $R^6$ and $R^7$ are independently selected from hydrogen and $C_1$-$C_4$-alkyl, in particular hydrogen, methyl and ethyl. In a preferred embodiment, $R^6$ and $R^7$ are independently selected from hydrogen and $C_1$-$C_4$-alkoxy, in particular hydrogen, methoxy and ethoxy. In another preferred embodiment, $R^6$ and $R^7$ are independently selected from hydrogen and CN. In yet another preferred embodiment $R^6$ and $R^7$ are independently selected from hydrogen and OH.

According to still a further embodiment, Y is —$CR^8R^9$—$CR^{10}R^{11}$—. In a specific embodiment thereof, Z—Y is attached to the meta-position (3-position) in relation to the attachment of the isoxazole unit. In a further specific embodiment thereof, Z—Y is attached to the para-position (4-position) in relation to the attachment of the isoxazole unit.

$R^8$, $R^9$, $R^{10}$ and $R^{11}$ are independently selected from hydrogen, halogen, CN, nitro, OH, $C_1$-$C_4$-alkyl, $C_1$-$C_4$-halogenalkyl, $C_1$-$C_4$-alkoxy and $C_1$-$C_4$-halogenalkoxy.

In one preferred embodiment $R^8$, $R^9$, $R^{10}$ and $R^{11}$ are independently selected from hydrogen and halogen, in particular hydrogen, fluorine and chlorine. In a further preferred embodiment $R^8$, $R^9$, $R^{10}$ and $R^{11}$ are independently selected from hydrogen and $C_1$-$C_4$-alkyl, in particular hydrogen, methyl and ethyl. In a preferred embodiment, $R^8$, $R^9$, $R^{10}$ and $R^{11}$ are independently selected from hydrogen and $C_1$-$C_4$-alkoxy, in particular hydrogen, methoxy and ethoxy.

In another preferred embodiment, $R^8$, $R^9$, $R^{10}$ and $R^{11}$ are independently selected from hydrogen and CN. In yet another preferred embodiment $R^8$, $R^9$, $R^{10}$ and $R^{11}$ are independently selected from hydrogen and OH.

According to still a further embodiment, Y is —$CR^{12}$=$CR^{13}$—. In a specific embodiment thereof, Z—Y is attached to the meta-position (3-position) in relation to the attachment of the isoxazole unit. In a further specific embodiment thereof, Z—Y is attached to the para-position (4-position) in relation to the attachment of the isoxazole unit. $R^{12}$ and $R^{13}$ are independently selected from hydrogen, halogen, CN, nitro, OH, $C_1$-$C_4$-alkyl, $C_1$-$C_4$-halogenalkyl, $C_1$-$C_4$-alkoxy and $C_1$-$C_4$-halogenalkoxy.

In one preferred embodiment $R^{12}$ and $R^{13}$ are independently selected from hydrogen and halogen, in particular hydrogen, fluorine and chlorine. In a further preferred embodiment $R^{12}$ and $R^{13}$ are independently selected from hydrogen and $C_1$-$C_4$-alkyl, in particular hydrogen, methyl and ethyl. In a preferred embodiment, $R^{12}$ and $R^{13}$ are independently selected from hydrogen and $C_1$-$C_4$-alkoxy, in particular hydrogen, methoxy and ethoxy. In another preferred embodiment, $R^{12}$ and $R^{13}$ are independently selected from hydrogen and CN. In yet another preferred embodiment $R^{12}$ and $R^{13}$ are independently selected from hydrogen and OH.

According to still a further embodiment, Y is —C≡C—. In a specific embodiment thereof, Z—Y is attached to the meta-position (3-position) in relation to the attachment of the isoxazole unit. In a further specific embodiment thereof, Z—Y is attached to the para-position (4-position) in relation to the attachment of the isoxazole unit.

In general, $R^6$, $R^7$, $R^8$, $R^9$, $R^{10}$, $R^{11}$, $R^{12}$ and $R^{13}$ are independently selected from hydrogen, halogen, CN, nitro, OH, $C_1$-$C_4$-alkyl, $C_1$-$C_4$-halogenalkyl, $C_1$-$C_4$-alkoxy and $C_1$-$C_4$-halogenalkoxy. In one preferred embodiment of the invention $R^6$, $R^7$, $R^8$, $R^9$, $R^{10}$, $R^{11}$, $R^{12}$ and $R^{13}$ are independently selected from hydrogen and halogen, in particular hydrogen, fluorine and chlorine. In a further preferred embodiment $R^6$, $R^7$, $R^8$, $R^9$, $R^{10}$, $R^{11}$, $R^{12}$ and $R^{13}$ are independently selected from hydrogen and $C_1$-$C_4$-alkyl, in particular hydrogen, methyl and ethyl. In a preferred embodiment, $R^6$, $R^7$, $R^8$, $R^9$, $R^{10}$, $R^{11}$, $R^{12}$ and $R^{13}$ are independently selected from hydrogen and $C_1$-$C_4$-alkoxy, in particular hydrogen, methoxy and ethoxy. In another preferred embodiment, $R^6$, $R^7$, $R^8$, $R^9$, $R^{10}$, $R^{11}$, $R^{12}$ and $R^{13}$ are independently selected from hydrogen and CN. In yet another preferred embodiment $R^6$, $R^7$, $R^8$, $R^9$, $R^{10}$, $R^{11}$, $R^{12}$ and $R^{13}$ are independently selected from hydrogen and OH.

According to one embodiment, Z is phenyl that is unsubstituted (m=0) or substituted by $(R^5)_m$.

According to the invention, there can be zero, one, two, three, four or five $R^5$ present, namely for m is 0, 1, 2, 3, 4 or 5. In particular, m is 0, 1, 2, 3 or 4.

According to one embodiment, m is 0.

According to a further embodiment, m is 1, 2, 3 or 4, in particular 1, 2 or 3, more specifically 1 or 2. According to one specific embodiment thereof, m is 1, according to a further specific embodiment, m is 2.

According to still a further embodiment, m is 2, 3 or 4.

According to still a further embodiment, m is 3.

According to one embodiment of the invention, one $R^5$ is attached to the para-position (4-position) in relation to the attachment of Y.

According to a further embodiment of the invention, one $R^5$ is attached to the meta-position (3-position) in relation to the attachment of Y.

According to a further embodiment of the invention, one $R^5$ is attached to the ortho-position (2-position) in relation to the attachment of Y.

According to a further embodiment of the invention, two $R^5$ are attached in 2,4-position in relation to the attachment of Y.

According to a further embodiment of the invention, two $R^5$ are attached in 2,3-position in relation to the attachment of Y.

According to a further embodiment of the invention, two $R^5$ are attached in 2,5-position in relation to the attachment of Y.

According to a further embodiment of the invention, two $R^5$ are attached in 2,6-position in relation to the attachment of Y.

According to a further embodiment of the invention, two $R^5$ are attached in 3,4-position in relation to the attachment of Y.

According to a further embodiment of the invention, two $R^5$ are attached in 3,5-position in relation to the attachment of Y.

According to a further embodiment of the invention, three $R^5$ are attached in 2,4,6-position in relation to the attachment of Y.

For every $R^5$ that is present in the inventive compounds, the following embodiments and preferences apply independently of the meaning of any other $R^5$ that may be present in the phenyl ring. Furthermore, the particular embodiments and preferences given herein for $R^5$ apply independently for each of m=1, m=2, m=3, m=4 and m=5.

Each $R^5$ is independently selected from halogen, CN, $NO_2$, OH, $C_1$-$C_6$-alkyl, $C_1$-$C_6$-alkoxy, $C_1$-$C_6$-alkylthio, $C_1$-$C_6$-alkylsulfinyl, $C_1$-$C_6$-alkylsulfonyl, $C_2$-$C_6$-alkenyl, $C_2$-$C_6$-alkynyl, $C_3$-$C_8$-cycloalkyl, $C_3$-$C_8$-cycloalkyl-$C_1$-$C_4$-alkyl, $C_3$-$C_8$-cycloalkyloxy, $NH_2$, $NH(C_1$-$C_4$-alkyl), $N(C_1$-$C_4$-alkyl)$_2$, $NH(C_3$-$C_6$-cycloalkyl), $N(C_3$-$C_6$-cycloalkyl)$_2$, $C(=O)$—$C_1$-$C_4$-alkyl, $C(=O)OH$, $C(=O)$—$O$—$C_1$-$C_4$-alkyl, $C(=O)$—$NH(C_1$-$C_4$-alkyl), $C(=O)$—$N(C_1$-$C_4$-alkyl)$_2$, $C(=O)$—$NH(C_3$-$C_6$-cycloalkyl), $C(=O)N(C_3$-$C_6$-cycloalkyl)$_2$, phenyl and phenyl-$C_1$-$C_4$-alkyl, wherein the aliphatic, alicyclic and aromatic moieties of $R^5$ are unsubstituted or substituted by one, two, three or four or up to the maximum possible number of $R^{5a}$; wherein $R^{5a}$ is independently selected from halogen, CN, $NO_2$, OH, SH, $NH_2$, $C_1$-$C_6$-alkyl, $C_1$-$C_6$-haloalkyl, $C_3$-$C_8$-cycloalkyl, $C_3$-$C_8$-halocycloalkyl, $C_1$-$C_6$-alkoxy, $C_1$-$C_6$-haloalkoxy, $C_1$-$C_6$-alkylthio and $C_1$-$C_6$-haloalkylthio.

According to one embodiment, $R^5$ is independently selected from halogen, CN, $NO_2$, OH, SH, $C_1$-$C_6$-alkyl, $C_1$-$C_6$-alkoxy, $C_2$-$C_6$-alkenyl, $C_2$-$C_6$-alkynyl, $C_3$-$C_8$-cycloalkyl, $C_3$-$C_8$-cycloalkyloxy, $NH_2$, $NH(C_1$-$C_4$-alkyl), $N(C_1$-$C_4$-alkyl)$_2$, $NH(C_3$-$C_6$-cycloalkyl), $N(C_3$-$C_6$-cycloalkyl)$_2$, $S(O)_p(C_1$-$C_4$-alkyl) (p=0, 1 or 2), $C(=O)(C_1$-$C_4$-alkyl), $C(=O)(OH)$, $C(=O)(O$—$C_1$-$C_4$-alkyl), $C(=O)(NH(C_1$-$C_4$-alkyl))$, $C(=O)(N(C_1$-$C_4$-alkyl)$_2$), $C(=O)(NH(C_3$-$C_6$-cycloalkyl))$ and $C(=O)$—$(N(C_3$-$C_6$-cycloalkyl)$_2$); wherein each of $R^5$ is unsubstituted or further substituted by one, two, three or four independently selected $R^{5a}$, wherein $R^{5a}$ is as defined and preferably defined herein.

According to a further embodiment, $R^5$ is independently selected from halogen, CN, $NO_2$, $C_1$-$C_4$-alkyl, $C_1$-$C_4$-alkoxy, $C_2$-$C_4$-alkenyl, $C_2$-$C_4$-alkynyl, $C_3$-$C_6$-cycloalkyl, $C_3$-$C_6$-cycloalkyloxy, $NH_2$, $NH(C_1$-$C_{42}$-alkyl), $N(C_1$-$C_2$-alkyl)$_2$, $S(C_1$-$C_2$-alkyl), $S(O)(C_1$-$C_2$-alkyl), $S(O)_2(C_1$-$C_2$-alkyl), $C(=O)(C_1$-$C_2$-alkyl), $C(=O)(OH)$ and $C(=O)(O$—$C_1$-$C_2$-alkyl), wherein each of $R^5$ is unsubstituted or further substituted by one, two, three or four independently selected $R^{5a}$, wherein $R^{5a}$ is as defined and preferably defined herein.

According to a further embodiment, $R^5$ is independently selected from halogen, CN, $NO_2$, $C_1$-$C_4$-alkyl, $C_1$-$C_4$-haloalkyl, $C_1$-$C_4$-alkoxy, $C_1$-$C_4$-haloalkoxy, $C_2$-$C_4$-alkenyl, $C_2$-$C_4$-haloalkenyl, $C_2$-$C_4$-alkynyl, $C_2$-$C_4$-haloalkynyl, $C_3$-$C_6$-cycloalkyl, $C_3$-$C_6$-halocycloalkyl, $S(C_1$-$C_2$-alkyl), $S(O)(C_1$-$C_2$-alkyl), $S(O)_2(C_1$-$C_2$-alkyl), $C(=O)(C_1$-$C_2$-alkyl), $C(=O)(OH)$ and $C(=O)(O$—$C_1$-$C_2$-alkyl).

According to a further embodiment, each $R^5$ is independently selected from halogen, CN, $NO_2$, $C_1$-$C_2$-alkyl, $C_1$-$C_2$-haloalkyl, $C_1$-$C_2$-alkoxy, $C_1$-$C_2$-haloalkoxy, $S(C_1$-$C_2$-alkyl), $S(O)(C_1$-$C_2$-alkyl), $S(O)_2(C_1$-$C_2$-alkyl), $C(=O)(OH)$ and $C(=O)(O$—$C_1$-$C_2$-alkyl).

According to a further embodiment, $R^5$ is independently selected from F, $C_1$, Br, CN, $C_1$-$C_4$-alkoxy, $C_1$-$C_4$-haloalkoxy, $S(C_1$-$C_4$-alkyl), $S(O)(C_1$-$C_4$-alkyl) and $S(O)_2(C_1$-$C_4$-alkyl).

According to still a further specific embodiment, $R^5$ is independently selected from halogen, in particular from Br, F and Cl, more specifically from F and Cl.

According to a further specific embodiment, $R^5$ is CN.

According to one further embodiment $R^5$ is $NO_2$.

According to one further embodiment $R^5$ is OH.

According to one further embodiment $R^5$ is SH.

According to a further specific embodiment, $R^5$ is $C_1$-$C_6$-alkyl, in particular $C_1$-$C_4$-alkyl, such as $CH_3$. Further appropriate alkyls are ethyl, n-propyl, i-propyl, n-butyl, i-butyl and t-butyl.

According to a further specific embodiment, $R^5$ is $C_1$-$C_6$-haloalkyl, in particular $C_1$-$C_4$-haloalkyl, such as $CF_3$, $CHF_2$, $CH_2F$, $CCl_3$, $CHCl_2$ or $CH_2Cl$.

According to a further specific embodiment $R^5$ is $C_1$-$C_6$-alkyl, preferably $C_1$-$C_4$-alkyl, substituted by OH, more preferably $CH_2OH$, $CH_2CH_2OH$, $CH_2CH_2CH_2OH$, $CH(CH_3)CH_2OH$, $CH_2CH(CH_3)OH$, $CH_2CH_2CH_2CH_2OH$. In a special embodiment $R^5$ is $CH_2OH$. According to a further specific embodiment $R^5$ is $C_1$-$C_6$-alkyl, preferably $C_1$-$C_4$-alkyl substituted by CN, more preferably $CH_2CN$, $CH_2CH_2CN$, $CH_2CH_2CH_2CN$, $CH(CH_3)CH_2CN$, $CH_2CH(CH_3)CN$, $CH_2CH_2CH_2CH_2CN$. In a special embodiment $R^5$ is $CH_2CH_2CN$. In a further special embodiment $R^4$ is $CH(CH_3)CN$. According to a further specific embodiment $R^5$ is $C_1$-$C_4$-alkoxy-$C_1$-$C_6$-alkyl, more preferably $C_1$-$C_4$-alkoxy-$C_1$-$C_4$-alkyl. In a special embodiment $R^5$ is $CH_2OCH_3$. In a further special embodiment $R^5$ is $CH_2CH_2OCH_3$. In a further special embodiment $R^5$ is $CH(CH_3)OCH_3$. In a further special embodiment $R^5$ is $CH(CH_3)OCH_2CH_3$. In a further special embodiment $R^5$ is $CH_2CH_2OCH_2CH_3$. According to a further specific embodiment $R^5$ is $C_1$-$C_4$-haloalkoxy-$C_1$-$C_6$-alkyl, more preferably $C_1$-$C_4$-alkoxy-$C_1$-$C_4$-alkyl. In a special embodiment $R^5$ is $CH_2OCF_3$. In a further special embodiment $R^5$ is $CH_2CH_2OCF_3$. In a further special embodiment $R^5$ is $CH_2OCCl_3$. In a further special embodiment $R^5$ is $CH_2CH_2OCCl_3$.

According to a further specific embodiment, $R^5$ is $C_1$-$C_6$-alkoxy, in particular $C_1$-$C_4$-alkoxy, more specifically $C_1$-$C_2$-alkoxy such as $OCH_3$ or $OCH_2CH_3$.

According to a further specific embodiment, $R^5$ is $C_1$-$C_6$-haloalkoxy, in particular $C_1$-$C_4$-haloalkoxy, more specifically $C_1$-$C_2$-haloalkoxy such as $OCF_3$, $OCHF_2$, $OCH_2F$, $OCCl_3$, $OCHCl_2$ or $OCH_2Cl$, in particular $OCF_3$, $OCHF_2$, $OCCl_3$ or $OCHCl_2$.

According to still a further embodiment, $R^5$ is $C_2$-$C_6$-alkenyl or $C_2$-$C_6$-haloalkenyl, in particular $C_2$-$C_4$-alkenyl or $C_2$-$C_4$-haloalkenyl, such as CH=CH$_2$, CH$_2$CH=CH$_2$, CH=CHCH$_3$ or C(CH$_3$)=CH$_2$.

According to a further specific embodiment $R^5$ is $C_2$-$C_6$-alkenyl, preferably $C_2$-$C_4$-alkenyl, substituted by OH, more preferably, CH=CHOH, CH=CHCH$_2$OH, C(CH$_3$)=CHOH, CH=C(CH$_3$)OH. In a special embodiment $R^5$ is CH=CHOH. In a further special embodiment $R^5$ is CH=CHCH$_2$OH.

According to a further specific embodiment $R^5$ is $C_1$-$C_4$-alkoxy-$C_2$-$C_6$-alkenyl, more preferably $C_1$-$C_4$-alkoxy-$C_2$-$C_4$-alkenyl. In a special embodiment $R^5$ is CH=CHOCH$_3$. In a further special embodiment $R^5$ is CH=CHCH$_2$OCH$_3$. According to a further specific embodiment $R^5$ is $C_1$-$C_4$-haloalkoxy-$C_2$-$C_6$-alkenyl, more preferably $C_1$-$C_4$-haloalkoxy-$C_2$-$C_4$-alkenyl. In a special embodiment $R^5$ is CH=CHOCF$_3$. In a further special embodiment $R^5$ is CH=CHCH$_2$OCF$_3$. In a further special embodiment $R^5$ is CH=CHOCCl$_3$. In a further special embodiment $R^5$ is CH=CHCH$_2$OCCl$_3$. According to a further specific embodiment $R^5$ is $C_3$-$C_8$-cycloalkyl-$C_2$-$C_6$-alkenyl, preferably $C_3$-$C_6$-cycloalkyl-$C_2$-$C_4$-alkenyl. According to a further specific embodiment $R^5$ is $C_3$-$C_6$-halocycloalkyl-$C_2$-$C_4$-alkenyl, preferably $C_3$-$C_8$-halocycloalkyl-$C_2$-$C_6$-alkenyl.

According to still a further embodiment, $R^5$ is $C_2$-$C_6$-alkynyl or $C_2$-$C_6$-haloalkynyl, in particular $C_2$-$C_4$-alkynyl or $C_2$-$C_4$-haloalkynyl, such as C≡CH, CH$_2$CCH or CH$_2$CCCH$_3$.

According to a further specific embodiment $R^5$ is $C_2$-$C_6$-alkynyl, preferably $C_2$-$C_4$-alkynyl, substituted by OH, more preferably, CCOH, CH$_2$CCOH. In a special embodiment $R^5$ is CCOH. In a further special embodiment $R^5$ is CH$_2$CCOH. According to a further specific embodiment $R^5$ is $C_1$-$C_4$-alkoxy-$C_2$-$C_6$-alkynyl, more preferably $C_1$-$C_4$-alkoxy-$C_2$-$C_4$-alkynyl. In a special embodiment $R^5$ is CCOCH$_3$. In a further special embodiment $R^5$ is CH$_2$CCOCH$_3$. According to a further specific embodiment $R^5$ is $C_1$-$C_4$-haloalkoxy-$C_2$-$C_6$-alkynyl, more preferably $C_1$-$C_4$-haloalkoxy-$C_2$-$C_4$-alkynyl. In a special embodiment $R^5$ is CCOCF$_3$. In a further special embodiment $R^5$ is CH$_2$CCOCF$_3$. In a further special embodiment $R^5$ is CCOCCl$_3$. In a further special embodiment $R^5$ is CH$_2$CCOCCl$_3$. According to a further specific embodiment $R^5$ is $C_3$-$C_8$-cycloalkyl-$C_2$-$C_6$-alkynyl, preferably $C_3$-$C_6$-cycloalkyl-$C_2$-$C_4$-alkynyl. According to a further specific embodiment $R^5$ is $C_3$-$C_6$-halocycloalkyl-$C_2$-$C_4$-alkynyl, preferably $C_3$-$C_8$-halocycloalkyl-$C_2$-$C_6$-alkynyl.

According to one another embodiment $R^5$ is $C_3$-$C_8$-cycloalkyl, preferably cyclopropyl, cyclobutyl, cyclopentyl or cyclohexyl, in particular cyclopropyl or cyclobutyl. In a special embodiment $R^5$ is cyclopropyl. In a further special embodiment $R^5$ is cyclobutyl. In a further special embodiment $R^4$ is cyclopentyl. In a further special embodiment $R^5$ is cyclohexyl.

According to one another embodiment $R^5$ is $C_3$-$C_8$-cycloalkoxy, preferably $C_3$-$C_6$-cycloalkoxy. In a special embodiment $R^5$ is O-cyclopropyl.

According to a specific embodiment $R^5$ is $C_3$-$C_8$-halocycloalkyl, more preferably fully or partially halogenated $C_3$-$C_6$-cycloalkyl. In a special embodiment $R^5$ is fully or partially halogenated cyclopropyl. In a further special embodiment $R^5$ is 1-Cl-cyclopropyl. In a further special embodiment $R^5$ is 2-Cl-cyclopropyl. In a further special embodiment $R^5$ is 1-F-cyclopropyl. In a further special embodiment $R^5$ is 2-F-cyclopropyl. In a further special embodiment $R^5$ is fully or partially halogenated cyclobutyl. In a further special embodiment $R^5$ is 1-Cl-cyclobutyl. In a further special embodiment $R^5$ is 1-F-cyclobutyl. In a further special embodiment $R^5$ is 3,3-$C_{12}$-cyclobutyl. In a further special embodiment $R^5$ is 3,3-$F_2$-cyclobutyl. According to a specific embodiment $R^5$ is $C_3$-$C_8$-cycloalkyl substituted by $C_1$-$C_4$-alkyl, more preferably is $C_3$-$C_6$-cycloalkyl substituted by $C_1$-$C_4$-alkyl. In a special embodiment $R^5$ is 1-CH$_3$-cyclopropyl. According to a specific embodiment $R^5$ is $C_3$-$C_8$-cycloalkyl substituted by CN, more preferably is $C_3$-$C_6$-cycloalkyl substituted by CN. In a special embodiment $R^5$ is 1-CN-cyclopropyl. According to a further specific embodiment $R^5$ is $C_3$-$C_8$-cycloalkyl-$C_3$-$C_8$-cycloalkyl, preferably $C_3$-$C_6$-cycloalkyl-$C_3$-$C_6$-cycloalkyl. In a special embodiment $R^5$ is cyclopropyl-cyclopropyl. In a special embodiment $R^5$ is 2-cyclopropyl-cyclopropyl. According to a further specific embodiment $R^5$ is $C_3$-$C_8$-cycloalkyl-$C_3$-$C_8$-halocycloalkyl, preferably $C_3$-$C_6$-cycloalkyl-$C_3$-$C_6$-halocycloalkyl.

According to one another embodiment $R^5$ is $C_3$-$C_8$-cycloalkyl-$C_1$-$C_4$-alkyl, preferably $C_3$-$C_6$-cycloalkyl-$C_1$-$C_4$-alkyl. In a special embodiment $R^5$ is CH(CH$_3$)(cyclopropyl). In a further special embodiment $R^5$ is CH$_2$-(cyclopropyl).

According to a further preferred embodiment $R^5$ is $C_3$-$C_8$-cycloalkyl-$C_1$-$C_4$-alkyl wherein the alkyl moiety can be substituted by one, two, three or up to the maximum possible number of identical or different groups $R^a$ as defined and preferably herein and the cycloalkyl moiety can be substituted by one, two, three or up to the maximum possible number of identical or different groups $R^b$ as defined and preferably herein.

According to a specific embodiment $R^5$ is $C_3$-$C_8$-cycloalkyl-$C_1$-$C_4$-haloalkyl, $C_3$-$C_6$-cycloalkyl-$C_1$-$C_4$-haloalkyl. According to a specific embodiment $R^5$ is $C_3$-$C_8$-halocycloalkyl-$C_1$-$C_4$-alkyl, $C_3$-$C_6$-halocycloalkyl-$C_1$-$C_4$-alkyl. In a special embodiment $R^5$ is fully or partially halogenated cyclopropyl-$C_1$-$C_4$-alkyl. In a further special embodiment $R^5$ is 1-Cl-cyclopropyl-$C_1$-$C_4$-alkyl. In a further special embodiment $R^5$ is 1-F-cyclopropyl-$C_1$-$C_4$-alkyl.

According to one another embodiment $R^5$ is NH$_2$.

According to one another embodiment $R^5$ is NH($C_1$-$C_4$-alkyl). According to a specific embodiment $R^5$ is NH(CH$_3$). According to a specific embodiment $R^5$ is NH(CH$_2$CH$_3$). According to a specific embodiment $R^5$ is NH(CH$_2$CH$_2$CH$_3$). According to a specific embodiment $R^5$ is NH(CH(CH$_3$)$_2$). According to a specific embodiment $R^5$ is NH(CH$_2$CH$_2$CH$_2$CH$_3$). According to a specific embodiment $R^5$ is NH(C(CH$_3$)$_3$).

According to one another embodiment $R^5$ is N($C_1$-$C_4$-alkyl)$_2$. According to a specific embodiment $R^5$ is N(CH$_3$)$_2$. According to a specific embodiment $R^5$ is N(CH$_2$CH$_3$)$_2$. According to a specific embodiment $R^5$ is N(CH$_2$CH$_2$CH$_3$)$_2$. According to a specific embodiment $R^5$ is N(CH(CH$_3$)$_2$)$_2$. According to a specific embodiment $R^5$ is N(CH$_2$CH$_2$CH$_2$CH$_3$)$_2$. According to a specific embodiment $R^5$ is NH(C(CH$_3$)$_3$)$_2$.

According to one another embodiment $R^5$ is NH($C_3$-$C_8$-cycloalkyl) preferably NH($C_3$-$C_6$-cycloalkyl). According to a specific embodiment $R^5$ is NH(cyclopropyl). According to a specific embodiment $R^5$ is NH(cyclobutyl). According to a specific embodiment $R^5$ is NH(cyclopentyl). According to a specific embodiment $R^5$ is NH(cyclohexyl).

According to one another embodiment $R^5$ is N($C_3$-$C_8$-cycloalkyl)$_2$ preferably N($C_3$-$C_6$-cycloalkyl)$_2$. According to a specific embodiment $R^5$ is N(cyclopropyl)$_2$. According to a specific embodiment $R^5$ is N(cyclobutyl)$_2$. According to a specific embodiment $R^5$ is N(cyclopentyl)$_2$. According to a specific embodiment $R^5$ is N(cyclohexyl)$_2$.

According to still a further embodiment, $R^5$ is selected from $C(=O)(C_1-C_4\text{-alkyl})$, $C(=O)(OH)$, $C(=O)(O-C_1-C_4\text{-alkyl})$, $C(=O)(NH(C_1-C_4\text{-alkyl}))$, $C(=O)(N(C_1-C_4\text{-alkyl})_2)$, $C(=O)(NH(C_3-C_6\text{-cycloalkyl}))$ and $C(=O)(N(C_3-C_6\text{-cycloalkyl})_2)$, in particular selected from $C(=O)(C_1-C_2\text{-alkyl})$, $C(=O)(OH)$, $C(=O)(O-C_1-C_2\text{-alkyl})$, $C(=O)(NH(C_1-C_2\text{-alkyl}))$, $C(=O)(N(C_1-C_2\text{-alkyl})_2)$, $C(=O)(NH(C_3-C_6\text{-cycloalkyl}))$ and $C(=O)(N(C_3-C_6\text{-cycloalkyl})_2)$. According to one specific embodiment thereof, $R^5$ is $C(=O)(OH)$ or $C(=O)(O-C_1-C_4\text{-alkyl})$, in particular $C(=O)(OCH_3)$.

According to one another embodiment $R^5$ is $C(=O)(C_1-C_4\text{-alkyl})$. According to a specific embodiment $R^5$ is $C(=O)CH_3$. According to a further specific embodiment $R^5$ is $C(=O)CH_2CH_3$. According to a further specific embodiment $R^5$ is $C(=O)CH_2CH_2CH_3$. According to a further specific embodiment $R^5$ is $C(=O)CH(CH_3)_2$. According to a further specific embodiment $R^5$ is $C(=O)C(CH_3)_3$.

According to one another embodiment $R^5$ is $C(=O)OH$.

According to one another embodiment $R^5$ is $C(=O)(O-C_1-C_4\text{-alkyl})$. According to a specific embodiment $R^5$ is $C(=O)OCH_3$. According to a further specific embodiment $R^5$ is $C(=O)OCH_2CH_3$. According to a further specific embodiment $R^5$ is $C(=O)OCH_2CH_2CH_3$. According to a further specific embodiment $R^5$ is $C(=O)OCH(CH_3)_2$. According to a further specific embodiment $R^5$ is $C(=O)OC(CH_3)_3$.

According to one another embodiment $R^5$ is $C(=O)-NH(C_1-C_4\text{-alkyl})$. According to a specific embodiment $R^5$ is $C(=O)NHCH_3$. According to a further specific embodiment $R^5$ is $C(=O)NHCH_2CH_3$. According to a further specific embodiment $R^5$ is $C(=O)NHCH_2CH_2CH_3$. According to a further specific embodiment $R^5$ is $C(=O)NHCH(CH_3)_2$. According to a further specific embodiment $R^5$ is $C(=O)NHC(CH_3)_3$.

According to one another embodiment $R^5$ is $C(=O)-N(C_1-C_4\text{-alkyl})_2$. According to a specific embodiment $R^5$ is $C(=O)N(CH_3)_2$. According to a further specific embodiment $R^5$ is $C(=O)N(CH_2CH_3)_2$. According to a further specific embodiment $R^5$ is $C(=O)N(CH_2CH_2CH_3)_2$. According to a further specific embodiment $R^5$ is $C(=O)N(CH(CH_3)_2)_2$. According to a further specific embodiment $R^5$ is $C(=O)N(C(CH_3)_3)_2$.

According to one another embodiment $R^5$ is $C(=O)-NH(C_3-C_6\text{-cycloalkyl})$. According to a specific embodiment $R^5$ is $C(=O)NH(\text{cyclopropyl})$. According to a further specific embodiment $R^5$ is $C(=O)NH(\text{cyclobutyl})$. According to a further specific embodiment $R^5$ is $C(=O)NH(\text{cyclopentyl})$. According to a further specific embodiment $R^5$ is $C(=O)NH(\text{cyclohexyl})$.

According to one another embodiment $R^5$ is $C(=O)-N(C_3-C_6\text{-cycloalkyl})_2$. According to a specific embodiment $R^5$ is $C(=O)N(\text{cyclopropyl})_2$. According to a further specific embodiment $R^5$ is $C(=O)N(\text{cyclobutyl})_2$. According to a further specific embodiment $R^5$ is $C(=O)N(\text{cyclopentyl})_2$. According to a further specific embodiment $R^5$ is $C(=O)N(\text{cyclohexyl})_2$.

According to still a further embodiment, $R^5$ is selected from $S(C_1-C_2\text{-alkyl})$, $S(O)(C_1-C_2\text{-alkyl})$ and $S(O)_2(C_1-C_2\text{-alkyl})$, in particular $SCH_3$, $S(O)(CH_3)$ and $S(O)_2(CH_3)$. According to a specific embodiment $R^5$ is selected from $S(C_1-C_2\text{-haloalkyl})$, $S(O)(C_1-C_2\text{-haloalkyl})$ and $S(O)_2(C_1-C_2\text{-haloalkyl})$, such as $SO_2CF_3$.

Particularly preferred embodiments of $R^5$ according to the invention are in Table P5 below, wherein each line of lines P5-1 to P5-16 corresponds to one particular embodiment of the invention, wherein P5-1 to P5-16 are also in any combination with one another preferred embodiments of the present invention. Thereby, for every $R^5$ that is present in the inventive compounds, these specific embodiments and preferences apply independently of the meaning of any other $R^5$ that may be present in the phenyl ring:

TABLE P5

| No. | $R^5$ |
|---|---|
| P5-1 | Cl |
| P5-2 | F |
| P5-3 | CN |
| P5-4 | $NO_2$ |
| P5-5 | $CH_3$ |
| P5-6 | $CH_2CH_3$ |
| P5-7 | $CF_3$ |
| P5-8 | $CHF_2$ |
| P5-9 | $OCH_3$ |
| P5-10 | $OCH_2CH_3$ |
| P5-11 | $OCF_3$ |
| P5-12 | $OCHF_2$ |
| P5-13 | $SCH_3$ |
| P5-14 | $SOCH_3$ |
| P5-15 | $SO_2CH_3$ |
| P5-16 | $CO_2CH_3$ |

Particularly preferred embodiments of $(R^5)_m$ if Z is phenyl according to the invention are in Table P51 below, wherein each line of lines P51-1 to P51-155 corresponds to one particular embodiment of the invention, wherein P51-1 to P51-155 are also in any combination preferred embodiments of the present invention. The position(s) of the substituent(s) is/are given in relation to the attachment of the phenyl to the Y unit.

TABLE P51

| No. | $(R^5)_m$ |
|---|---|
| P51-1 | —* |
| P51-2 | 2-Cl |
| P51-3 | 3-Cl |
| P51-4 | 4-Cl |
| P51-5 | 2-F |
| P51-6 | 3-F |
| P51-7 | 4-F |
| P51-8 | 2-CN |
| P51-9 | 3-CN |
| P51-10 | 4-CN |
| P51-11 | $2\text{-}NO_2$ |
| P51-12 | $3\text{-}NO_2$ |
| P51-13 | $4\text{-}NO_2$ |
| P51-14 | $2\text{-}SCH_3$ |
| P51-15 | $3\text{-}SCH_3$ |
| P51-16 | $4\text{-}SCH_3$ |
| P51-17 | $2\text{-}SOCH_3$ |
| P51-18 | $3\text{-}SOCH_3$ |
| P51-19 | $4\text{-}SOCH_3$ |
| P51-20 | $2\text{-}SO_2CH_3$ |
| P51-21 | $3\text{-}SO_2CH_3$ |
| P51-22 | $4\text{-}SO_2CH_3$ |
| P51-23 | $2\text{-}CO_2CH_3$ |
| P51-24 | $3\text{-}CO_2CH_3$ |
| P51-25 | $4\text{-}CO_2CH_3$ |
| P51-26 | $2,3\text{-}Cl_2$ |
| P51-27 | $2,4\text{-}Cl_2$ |
| P51-28 | $2,5\text{-}Cl_2$ |
| P51-29 | $3,4\text{-}Cl_2$ |
| P51-30 | $3,5\text{-}Cl_2$ |
| P51-31 | $2,6\text{-}Cl_2$ |
| P51-32 | $2,3\text{-}F_2$ |
| P51-33 | $2,4\text{-}F_2$ |
| P51-34 | $2,5\text{-}F_2$ |
| P51-35 | $3,4\text{-}F_2$ |
| P51-36 | $3,5\text{-}F_2$ |
| P51-37 | $2,6\text{-}F_2$ |

TABLE P51-continued

| No. | $(R^5)_m$ |
|---|---|
| P51-38 | 2-F-3-Cl |
| P51-39 | 2-F-4-Cl |
| P51-40 | 3-F-4-Cl |
| P51-41 | 2-F-6-Cl |
| P51-42 | 2-Cl-3-F |
| P51-43 | 2-Cl-4-F |
| P51-44 | 3-Cl-4-F |
| P51-45 | 2,3,4-Cl$_3$ |
| P51-46 | 2,4,5-Cl$_3$ |
| P51-47 | 3,4,5-Cl$_3$ |
| P51-48 | 2,4,6-Cl$_3$ |
| P51-49 | 2,3,4-F$_3$ |
| P51-50 | 2,4,5-F$_3$ |
| P51-51 | 3,4,5-F$_3$ |
| P51-52 | 2,4,6-F$_3$ |
| P51-53 | 2,3-4-F$_3$ |
| P51-54 | 2,4-F$_2$-3-Cl |
| P51-55 | 2,6-F$_2$-4-Cl |
| P51-56 | 2,5-F$_2$-4-Cl |
| P51-57 | 2,4-Cl$_2$-3-F |
| P51-58 | 2,6-Cl$_2$-4-F |
| P51-59 | 2,5-Cl$_2$-4-F |
| P51-60 | 2-CH$_3$ |
| P51-61 | 3-CH$_3$ |
| P51-62 | 4-CH$_3$ |
| P51-63 | 2-CH$_2$CH$_3$ |
| P51-64 | 3-CH$_2$CH$_3$ |
| P51-65 | 4-CH$_2$CH$_3$ |
| P51-66 | 2-CF$_3$ |
| P51-67 | 3-CF$_3$ |
| P51-68 | 4-CF$_3$ |
| P51-69 | 2-CHF$_2$ |
| P51-70 | 3-CHF$_2$ |
| P51-71 | 4-CHF$_2$ |
| P51-72 | 2-OCH$_3$ |
| P51-73 | 3-OCH$_3$ |
| P51-74 | 4-OCH$_3$ |
| P51-75 | 2-OCH$_2$CH$_3$ |
| P51-76 | 3-OCH$_2$CH$_3$ |
| P51-77 | 4-OCH$_2$CH$_3$ |
| P51-78 | 2-OCF$_3$ |
| P51-79 | 3-OCF$_3$ |
| P51-80 | 4-OCF$_3$ |
| P51-81 | 2-OCHF$_2$ |
| P51-82 | 3-OCHF$_2$ |
| P51-83 | 4-OCHF$_2$ |
| P51-84 | 2,3-(CH$_3$)$_2$ |
| P51-85 | 2,4-(CH$_3$)$_2$ |
| P51-86 | 3,4-(CH$_3$)$_2$ |
| P51-87 | 2,6-(CH$_3$)$_2$ |
| P51-88 | 2,3-(CH$_2$CH$_3$)$_2$ |
| P51-89 | 2,4-(CH$_2$CH$_3$)$_2$ |
| P51-90 | 3,4-(CH$_2$CH$_3$)$_2$ |
| P51-91 | 2,6-(CH$_2$CH$_3$)$_2$ |
| P51-92 | 2,3-(CF$_3$)$_2$ |
| P51-93 | 2,4-(CF$_3$)$_2$ |
| P51-94 | 3,4-(CF$_3$)$_2$ |
| P51-95 | 2,6-(CF$_3$)$_2$ |
| P51-96 | 2,3-(CHF$_2$)$_2$ |
| P51-97 | 2,4-(CHF$_2$)$_2$ |
| P51-98 | 3,4-(CHF$_2$)$_2$ |
| P51-99 | 2,6-(CHF$_2$)$_2$ |
| P51-100 | 2,3-(OCH$_3$)$_2$ |
| P51-101 | 2,4-(OCH$_3$)$_2$ |
| P51-102 | 3,4-(OCH$_3$)$_2$ |
| P51-103 | 2,6-(OCH$_3$)$_2$ |
| P51-104 | 2,3-(OCH$_2$CH$_3$)$_2$ |
| P51-105 | 2,4-(OCH$_2$CH$_3$)$_2$ |
| P51-106 | 3,4-(OCH$_2$CH$_3$)$_2$ |
| P51-107 | 2,6-(OCH$_2$CH$_3$)$_2$ |
| P51-108 | 2,3-(OCF$_3$)$_2$ |
| P51-109 | 2,4-(OCF$_3$)$_2$ |
| P51-110 | 3,4-(OCF$_3$)$_2$ |
| P51-111 | 2,6-(OCF$_3$)$_2$ |
| P51-112 | 2,3-(OCHF$_2$)$_2$ |
| P51-113 | 2,4-(OCHF$_2$)$_2$ |
| P51-114 | 3,4-(OCHF$_2$)$_2$ |
| P51-115 | 2,6-(OCHF$_2$)$_2$ |
| P51-116 | 2,3,4-(CH$_3$)$_3$ |
| P51-117 | 2,4,5-(CH$_3$)$_3$ |
| P51-118 | 3,4,5-(CH$_3$)$_3$ |
| P51-119 | 2,4,6-(CH$_3$)$_3$ |
| P51-120 | 2,3,4-(CH$_2$CH$_3$)$_3$ |
| P51-121 | 2,4,5-(CH$_2$CH$_3$)$_3$ |
| P51-122 | 3,4,5-(CH$_2$CH$_3$)$_3$ |
| P51-123 | 2,4,6-(CH$_2$CH$_3$)$_3$ |
| P51-124 | 2,3,4-(CF$_3$)$_3$ |
| P51-125 | 2,4,5-(CF$_3$)$_3$ |
| P51-126 | 3,4,5-(CF$_3$)$_3$ |
| P51-127 | 2,4,6-(CF$_3$)$_3$ |
| P51-128 | 2,3,4-(CHF$_2$)$_3$ |
| P51-129 | 2,4,5-(CHF$_2$)$_3$ |
| P51-130 | 3,4,5-(CHF$_2$)$_3$ |
| P51-131 | 2,4,6-(CHF$_2$)$_3$ |
| P51-132 | 2,3,4-(OCH$_3$)$_3$ |
| P51-133 | 2,4,5-(OCH$_3$)$_3$ |
| P51-134 | 3,4,5-(OCH$_3$)$_3$ |
| P51-135 | 2,4,6-(OCH$_3$)$_3$ |
| P51-136 | 2,3,4-(OCH$_2$CH$_3$)$_3$ |
| P51-137 | 2,4,5-(OCH$_2$CH$_3$)$_3$ |
| P51-138 | 3,4,5-(OCH$_2$CH$_3$)$_3$ |
| P51-139 | 2,4,6-(OCH$_2$CH$_3$)$_3$ |
| P51-140 | 2,3,4-(OCF$_3$)$_3$ |
| P51-141 | 2,4,5-(OCF$_3$)$_3$ |
| P51-142 | 3,4,5-(OCF$_3$)$_3$ |
| P51-143 | 2,4,6-(OCF$_3$)$_3$ |
| P51-144 | 2,3,4-(OCHF$_2$)$_3$ |
| P51-145 | 2,4,5-(OCHF$_2$)$_3$ |
| P51-146 | 3,4,5-(OCHF$_2$)$_3$ |
| P51-147 | 2,4,6-(OCHF$_2$)$_3$ |
| P51-148 | 2-CF$_3$-4-Cl |
| P51-149 | 2-CF$_3$-4-F |
| P51-150 | 2-Cl-4-CF$_3$ |
| P51-151 | 2-F-4-CF$_3$ |
| P51-152 | 2-CN-4-Cl |
| P51-153 | 2-CN-4-F |
| P51-154 | 2-Cl-4-CN |
| P51-155 | 2-F-4-CN |

*means that m = 0

In another embodiment Z is a five- or six-membered heteroaryl that is unsubstituted (m=0) or substituted by $(R^5)_m$. According to one embodiment thereof, Z is a five-membered heteroaryl which is unsubstituted or carries one, two or three independently selected radicals $R^5$ as defined or preferably defined below. According to a further embodiment thereof, Z is a six-membered heteroaryl which is unsubstituted or carries one, two or three independently selected radicals $R^5$ as defined or preferably defined below.

According to one embodiment thereof, Z is selected from the group consisting of pyrimidin-2-yl, pyrimidin-3-yl, pyrimidin-4-yl, pyridin-2-yl, pyridin-3-yl, pyridin-4-yl, thiazol-2-yl, thiazol-4-yl, thiazol-5-yl, isothiazol-3-yl, isothiazol-4-yl, isothiazol-5-yl, pyrazin-2-yl, pyridazin-3-yl, 1,3,5-triazin-2-yl and 1,2,4-triazin-3-yl; wherein said heteroaryl is unsubstituted or carry one, two, three or four independently selected radicals $R^5$ as defined or preferably defined below.

According to one specific embodiment of the invention Z is selected from the group consisting of pyrimidin-2-yl, pyrimidin-3-yl, pyrimidin-4-yl, pyridin-2-yl, pyridin-3-yl, pyridin-4-yl, thiazol-2-yl, pyrazin-2-yl, pyridazin-3-yl, 1,3,5-triazin-2-yl, and 1,2,4-triazin-3-yl; preferably Z is pyrimidin-2-yl, pyridin-2-yl, pyridin-3-yl, pyridin-4-yl and thiazol-2-yl, that are unsubstituted or carry one, two, three or four independently selected radicals $R^5$ as defined or preferably defined below.

According to the invention, there can be zero, one, two, three, four or five $R^5$ present, namely for m is 0, 1, 2, 3, 4 or 5. The number of m also depends on the kind of heteroaryl. In particular, m is 0, 1, 2 or 3. According to one embodiment, m is 0. According to a further embodiment, m is 1, 2 or 3, in particular 1 or 2. According to one specific embodiment thereof, m is 1, according to a further specific embodiment, m is 2.

For every $R^5$ that is present in the inventive compounds, the following embodiments and preferences apply independently of the meaning of any other $R^5$ that may be present in the heteroaryl ring. Furthermore, the particular embodiments and preferences given herein for $R^5$ apply independently for each of m=1, m=2, m=3, m=4 and m=5.

Each $R^5$ is independently selected from halogen, CN, $NO_2$, OH, $C_1$-$C_6$-alkyl, $C_1$-$C_6$-alkoxy, $C_1$-$C_6$-alkylthio, $C_1$-$C_6$-alkylsulfinyl, $C_1$-$C_6$-alkylsulfonyl, $C_2$-$C_6$-alkenyl, $C_2$-$C_6$-alkynyl, $C_3$-$C_8$-cycloalkyl, $C_3$-$C_8$-cycloalkyloxy, $NH_2$, $NH(C_1$-$C_4$-alkyl), $N(C_1$-$C_4$-alkyl)$_2$, $NH(C_3$-$C_6$-cycloalkyl), $N(C_3$-$C_6$-cycloalkyl)$_2$, C(=O)—$C_1$-$C_4$-alkyl, C(=O)OH, C(=O)—O—$C_1$-$C_4$-alkyl, C(=O)—$NH(C_1$-$C_4$-alkyl), C(=O)—$N(C_1$-$C_4$-alkyl)$_2$, C(=O)—$NH(C_3$-$C_6$-cycloalkyl), C(=O)$N(C_3$-$C_6$-cycloalkyl)$_2$, phenyl and phenyl-$C_1$-$C_4$-alkyl, wherein the aliphatic, alicyclic and aromatic moieties of $R^5$ are unsubstituted or substituted by one, two, three or four or up to the maximum possible number of $R^{5a}$; wherein $R^{5a}$ is independently selected from halogen, CN, $NO_2$, OH, SH, $NH_2$, $C_1$-$C_6$-alkyl, $C_1$-$C_6$-haloalkyl, $C_3$-$C_8$-cycloalkyl, $C_3$-$C_8$-halocycloalkyl, $C_1$-$C_6$-alkoxy, $C_1$-$C_6$-haloalkoxy, $C_1$-$C_6$-alkylthio and $C_1$-$C_6$-haloalkylthio.

According to one embodiment, $R^5$ is independently selected from halogen, CN, $NO_2$, OH, SH, $C_1$-$C_6$-alkyl, $C_1$-$C_6$-alkoxy, $C_2$-$C_6$-alkenyl, $C_2$-$C_6$-alkynyl, $C_3$-$C_8$-cycloalkyl, $C_3$-$C_8$-cycloalkyloxy, $NH_2$, $NH(C_1$-$C_4$-alkyl), $N(C_1$-$C_4$-alkyl)$_2$, $NH(C_3$-$C_6$-cycloalkyl), $N(C_3$-$C_6$-cycloalkyl)$_2$, $S(O)_p(C_1$-$C_4$-alkyl) (p=0, 1 or 2), C(=O)($C_1$-$C_4$-alkyl), C(=O)(OH), C(=O)(O—$C_1$-$C_4$-alkyl), C(=O)$(NH(C_1$-$C_4$-alkyl))$, C(=O)$(N(C_1$-$C_4$-alkyl)_2)$, C(=O)$(NH(C_3$-$C_6$-cycloalkyl))$ and C(=O)—$(N(C_3$-$C_6$-cycloalkyl)_2)$; wherein each of $R^5$ is unsubstituted or further substituted by one, two, three or four independently selected $R^{5a}$, wherein $R^{5a}$ is as defined and preferably defined herein.

According to a further embodiment, $R^5$ is independently selected from halogen, CN, $NO_2$, $C_1$-$C_4$-alkyl, $C_1$-$C_4$-alkoxy, $C_2$-$C_4$-alkenyl, $C_2$-$C_4$-alkynyl, $C_3$-$C_6$-cycloalkyl, $C_3$-$C_6$-cycloalkyloxy, $NH_2$, $NH(C_1$-$C_{42}$-alkyl), $N(C_1$-$C_2$-alkyl)$_2$, $S(C_1$-$C_2$-alkyl), $S(O)(C_1$-$C_2$-alkyl), $S(O)_2(C_1$-$C_2$-alkyl), C(=O)($C_1$-$C_2$-alkyl), C(=O)(OH) and C(=O)(O—$C_1$-$C_2$-alkyl), wherein each of $R^5$ is unsubstituted or further substituted by one, two, three or four independently selected $R^{5a}$, wherein $R^{5a}$ is as defined and preferably defined herein.

According to a further embodiment, $R^5$ is independently selected from halogen, CN, $NO_2$, $C_1$-$C_4$-alkyl, $C_1$-$C_4$-haloalkyl, $C_1$-$C_4$-alkoxy, $C_1$-$C_4$-haloalkoxy, $C_2$-$C_4$-alkenyl, $C_2$-$C_4$-haloalkenyl, $C_2$-$C_4$-alkynyl, $C_2$-$C_4$-haloalkynyl, $C_3$-$C_6$-cycloalkyl, $C_3$-$C_6$-halocycloalkyl, $S(C_1$-$C_2$-alkyl), $S(O)(C_1$-$C_2$-alkyl), $S(O)_2(C_1$-$C_2$-alkyl), C(=O)($C_1$-$C_2$-alkyl), C(=O)(OH) and C(=O)(O—$C_1$-$C_2$-alkyl).

According to a further embodiment, $R^5$ is independently selected from halogen, CN, $NO_2$, $C_1$-$C_2$-alkyl, $C_1$-$C_2$-haloalkyl, $C_1$-$C_2$-alkoxy, $C_1$-$C_2$-haloalkoxy, $S(C_1$-$C_2$-alkyl), $S(O)(C_1$-$C_2$-alkyl), $S(O)_2(C_1$-$C_2$-alkyl), C(=O)(OH) and C(=O)(O—$C_1$-$C_2$-alkyl).

According to a further embodiment, $R^5$ is independently selected from F, $C_1$, Br, CN, $C_1$-$C_4$-haloalkyl, $C_1$-$C_4$-alkoxy, $C_1$-$C_4$-haloalkoxy, $S(C_1$-$C_4$-alkyl), $S(O)(C_1$-$C_4$-alkyl) and $S(O)_2(C_1$-$C_4$-alkyl).

According to still a further specific embodiment, $R^5$ is independently selected from halogen, in particular from Br, F and Cl, more specifically from F and $C_1$.

According to a further specific embodiment, $R^5$ is CN.
According to one further embodiment $R^5$ is $NO_2$.
According to one further embodiment $R^5$ is OH.
According to one further embodiment $R^5$ is SH.
According to a further specific embodiment, $R^5$ is $C_1$-$C_6$-alkyl, in particular $C_1$-$C_4$-alkyl, such as $CH_3$. Further appropriate alkyls are ethyl, n-propyl, i-propyl, n-butyl, i-butyl and t-butyl.

According to a further specific embodiment, $R^5$ is $C_1$-$C_6$-haloalkyl, in particular $C_1$-$C_4$-haloalkyl, such as $CF_3$, $CHF_2$, $CH_2F$, $CCl_3$, $CHCl_2$ or $CH_2Cl$.

According to a further specific embodiment $R^5$ is $C_1$-$C_6$-alkyl, preferably $C_1$-$C_4$-alkyl, substituted by OH, more preferably $CH_2OH$, $CH_2CH_2OH$, $CH_2CH_2CH_2OH$, $CH(CH_3)CH_2OH$, $CH_2CH(CH_3)OH$, $CH_2CH_2CH_2CH_2OH$. In a special embodiment $R^5$ is $CH_2OH$. According to a further specific embodiment $R^5$ is $C_1$-$C_6$-alkyl, preferably $C_1$-$C_4$-alkyl substituted by CN, more preferably $CH_2CN$, $CH_2CH_2CN$, $CH_2CH_2CH_2CN$, $CH(CH_3)CH_2CN$, $CH_2CH(CH_3)CN$, $CH_2CH_2CH_2CH_2CN$. In a special embodiment $R^5$ is $CH_2CH_2CN$. In a further specific embodiment $R^4$ is $CH(CH_3)CN$. According to a further specific embodiment $R^5$ is $C_1$-$C_4$-alkoxy-$C_1$-$C_6$-alkyl, more preferably $C_1$-$C_4$-alkoxy-$C_1$-$C_4$-alkyl. In a special embodiment $R^5$ is $CH_2OCH_3$. In a further special embodiment $R^5$ is $CH_2CH_2OCH_3$. In a further special embodiment $R^5$ is $CH(CH_3)OCH_3$. In a further special embodiment $R^5$ is $CH(CH_3)OCH_2CH_3$. In a further special embodiment $R^5$ is $CH_2CH_2OCH_2CH_3$. According to a further specific embodiment $R^5$ is $C_1$-$C_4$-haloalkoxy-$C_1$-$C_6$-alkyl, more preferably $C_1$-$C_4$-alkoxy-$C_1$-$C_4$-alkyl. In a special embodiment $R^5$ is $CH_2OCF_3$. In a further special embodiment $R^5$ is $CH_2CH_2OCF_3$. In a further special embodiment $R^5$ is $CH_2OCCl_3$. In a further special embodiment $R^5$ is $CH_2CH_2OCCl_3$.

According to a further specific embodiment, $R^5$ is $C_1$-$C_6$-alkoxy, in particular $C_1$-$C_4$-alkoxy, more specifically $C_1$-$C_2$-alkoxy such as $OCH_3$ or $OCH_2CH_3$.

According to a further specific embodiment, $R^5$ is $C_1$-$C_6$-haloalkoxy, in particular $C_1$-$C_4$-haloalkoxy, more specifically $C_1$-$C_2$-haloalkoxy such as $OCF_3$, $OCHF_2$, $OCH_2F$, $OCCl_3$, $OCHCl_2$ or $OCH_2Cl$, in particular $OCF_3$, $OCHF_2$, $OCCl_3$ or $OCHCl_2$.

According to still a further embodiment, $R^5$ is $C_2$-$C_6$-alkenyl or $C_2$-$C_6$-haloalkenyl, in particular $C_2$-$C_4$-alkenyl or $C_2$-$C_4$-haloalkenyl, such as $CH=CH_2$, $CH_2CH=CH_2$, $CH=CHCH_3$ or $C(CH_3)=CH_2$.

According to a further specific embodiment $R^5$ is $C_2$-$C_6$-alkenyl, preferably $C_2$-$C_4$-alkenyl, substituted by OH, more preferably, $CH=CHOH$, $CH=CHCH_2OH$, $C(CH_3)=CHOH$, $CH=C(CH_3)OH$. In a special embodiment $R^5$ is $CH=CHOH$. In a further special embodiment $R^5$ is $CH=CHCH_2OH$. According to a further specific embodiment $R^5$ is $C_1$-$C_4$-alkoxy-$C_2$-$C_6$-alkenyl, more preferably $C_1$-$C_4$-alkoxy-$C_2$-$C_4$-alkenyl. In a special embodiment $R^5$ is $CH=CHOCH_3$. In a further special embodiment $R^5$ is $CH=CHCH_2OCH_3$. According to a further specific embodiment $R^5$ is $C_1$-$C_4$-haloalkoxy-$C_2$-$C_6$-alkenyl, more preferably $C_1$-$C_4$-haloalkoxy-$C_2$-$C_4$-alkenyl. In a special embodiment $R^5$ is $CH=CHOCF_3$. In a further special embodiment $R^5$ is $CH=CHCH_2OCF_3$. In a further special embodiment $R^5$ is $CH=CHOCCl_3$. In a further special embodiment $R^5$ is $CH=CHCH_2OCCl_3$. According to a further specific embodiment $R^5$ is $C_3$-$C_8$-cycloalkyl-$C_2$-$C_6$-alkenyl, preferably $C_3$-$C_6$-cycloalkyl-$C_2$-$C_4$-alkenyl. According to a further specific embodiment $R^5$ is $C_3$-$C_6$-halocycloalkyl-$C_2$-$C_4$-alkenyl, preferably $C_3$-$C_8$-halocycloalkyl-$C_2$-$C_6$-alkenyl.

According to still a further embodiment, $R^5$ is $C_2$-$C_6$-alkynyl or $C_2$-$C_6$-haloalkynyl, in particular $C_2$-$C_4$-alkynyl or $C_2$-$C_4$-haloalkynyl, such as C≡CH, $CH_2CCH$ or $CH_2CCCH_3$.

According to a further specific embodiment $R^5$ is $C_2$-$C_6$-alkynyl, preferably $C_2$-$C_4$-alkynyl, substituted by OH, more preferably, CCOH, $CH_2CCOH$. In a special embodiment $R^5$ is CCOH. In a further special embodiment $R^5$ is $CH_2CCOH$. According to a further specific embodiment $R^5$ is $C_1$-$C_4$-alkoxy-$C_2$-$C_6$-alkynyl, more preferably $C_1$-$C_4$-alkoxy-$C_2$-$C_4$-alkynyl. In a special embodiment $R^5$ is $CCOCH_3$. In a further special embodiment $R^5$ is $CH_2CCOCH_3$. According to a further specific embodiment $R^5$ is $C_1$-$C_4$-haloalkoxy-$C_2$-$C_6$-alkynyl, more preferably $C_1$-$C_4$-haloalkoxy-$C_2$-$C_4$-alkynyl. In a special embodiment $R^5$ is $CCOCF_3$. In a further special embodiment $R^5$ is $CH_2CCOCF_3$. In a further special embodiment $R^5$ is $CCOCCl_3$. In a further special embodiment $R^5$ is $CH_2CCOCCl_3$. According to a further specific embodiment $R^5$ is $C_3$-$C_8$-cycloalkyl-$C_2$-$C_6$-alkynyl, preferably $C_3$-$C_6$-cycloalkyl-$C_2$-$C_4$-alkynyl. According to a further specific embodiment $R^5$ is $C_3$-$C_6$-halocycloalkyl-$C_2$-$C_4$-alkynyl, preferably $C_3$-$C_8$-halocycloalkyl-$C_2$-$C_6$-alkynyl.

According to one another embodiment $R^5$ is $C_3$-$C_8$-cycloalkyl, preferably cyclopropyl, cyclobutyl, cyclopentyl or cyclohexyl, in particular cyclopropyl or cyclobutyl. In a special embodiment $R^5$ is cyclopropyl. In a further special embodiment $R^5$ is cyclobutyl. In a further special embodiment $R^4$ is cyclopentyl. In a further special embodiment $R^5$ is cyclohexyl.

According to one another embodiment $R^5$ is $C_3$-$C_8$-cycloalkoxy, preferably $C_3$-$C_6$-cycloalkoxy. In a special embodiment $R^5$ is O-cyclopropyl.

According to a specific embodiment $R^5$ is $C_3$-$C_8$-halocycloalkyl, more preferably fully or partially halogenated $C_3$-$C_6$-cycloalkyl. In a special embodiment $R^5$ is fully or partially halogenated cyclopropyl. In a further special embodiment $R^5$ is 1-Cl-cyclopropyl. In a further special embodiment $R^5$ is 2-Cl-cyclopropyl. In a further special embodiment $R^5$ is 1-F-cyclopropyl. In a further special embodiment $R^5$ is 2-F-cyclopropyl. In a further special embodiment $R^5$ is fully or partially halogenated cyclobutyl. In a further special embodiment $R^5$ is 1-Cl-cyclobutyl. In a further special embodiment $R^5$ is 1-F-cyclobutyl. In a further special embodiment $R^5$ is 3,3-$C_{12}$-cyclobutyl. In a further special embodiment $R^5$ is 3,3-$F_2$-cyclobutyl. According to a specific embodiment $R^5$ is $C_3$-$C_8$-cycloalkyl substituted by $C_1$-$C_4$-alkyl, more preferably is $C_3$-$C_6$-cycloalkyl substituted by $C_1$-$C_4$-alkyl. In a special embodiment $R^5$ is 1-$CH_3$-cyclopropyl. According to a specific embodiment $R^5$ is $C_3$-$C_8$-cycloalkyl substituted by CN, more preferably is $C_3$-$C_6$-cycloalkyl substituted by CN. In a special embodiment $R^5$ is 1-CN-cyclopropyl. According to a further specific embodiment $R^5$ is $C_3$-$C_8$-cycloalkyl-$C_3$-$C_8$-cycloalkyl, preferably $C_3$-$C_6$-cycloalkyl-$C_3$-$C_6$-cycloalkyl. In a special embodiment $R^5$ is cyclopropyl-cyclopropyl. In a special embodiment $R^5$ is 2-cyclopropyl-cyclopropyl. According to a further specific embodiment $R^5$ is $C_3$-$C_8$-cycloalkyl-$C_3$-$C_8$-halocycloalkyl, preferably $C_3$-$C_6$-cycloalkyl-$C_3$-$C_6$-halocycloalkyl.

According to one another embodiment $R^5$ is $C_3$-$C_8$-cycloalkyl-$C_1$-$C_4$-alkyl, preferably $C_3$-$C_6$-cycloalkyl-$C_1$-$C_4$-alkyl. In a special embodiment $R^5$ is $CH(CH_3)$(cyclopropyl). In a further special embodiment $R^5$ is $CH_2$-(cyclopropyl).

According to a further preferred embodiment $R^5$ is $C_3$-$C_8$-cycloalkyl-$C_1$-$C_4$-alkyl wherein the alkyl moiety can be substituted by one, two, three or up to the maximum possible number of identical or different groups $R^a$ as defined and preferably herein and the cycloalkyl moiety can be substituted by one, two, three or up to the maximum possible number of identical or different groups Rb as defined and preferably herein.

According to a specific embodiment $R^5$ is $C_3$-$C_8$-cycloalkyl-$C_1$-$C_4$-haloalkyl, $C_3$-$C_6$-cycloalkyl-$C_1$-$C_4$-haloalkyl. According to a specific embodiment $R^5$ is $C_3$-$C_8$-halocycloalkyl-$C_1$-$C_4$-alkyl, $C_3$-$C_6$-halocycloalkyl-$C_1$-$C_4$-alkyl. In a special embodiment $R^5$ is fully or partially halogenated cyclopropyl-$C_1$-$C_4$-alkyl. In a further special embodiment $R^5$ is 1-Cl-cyclopropyl-$C_1$-$C_4$-alkyl. In a further special embodiment $R^5$ is 1-F-cyclopropyl-$C_1$-$C_4$-alkyl.

According to one another embodiment $R^5$ is $NH_2$.

According to one another embodiment $R^5$ is $NH(C_1$-$C_4$-alkyl). According to a specific embodiment $R^5$ is $NH(CH_3)$. According to a specific embodiment $R^5$ is $NH(CH_2CH_3)$. According to a specific embodiment $R^5$ is $NH(CH_2CH_2CH_3)$. According to a specific embodiment $R^5$ is $NH(CH(CH_3)_2)$. According to a specific embodiment $R^5$ is $NH(CH_2CH_2CH_2CH_3)$. According to a specific embodiment $R^5$ is $NH(C(CH_3)_3)$.

According to one another embodiment $R^5$ is $N(C_1$-$C_4$-alkyl)$_2$. According to a specific embodiment $R^5$ is $N(CH_3)_2$. According to a specific embodiment $R^5$ is $N(CH_2CH_3)_2$. According to a specific embodiment $R^5$ is $N(CH_2CH_2CH_3)_2$. According to a specific embodiment $R^5$ is $N(CH(CH_3)_2)_2$. According to a specific embodiment $R^5$ is $N(CH_2CH_2CH_2CH_3)_2$. According to a specific embodiment $R^5$ is $NH(C(CH_3)_3)_2$.

According to one another embodiment $R^5$ is $NH(C_3$-$C_8$-cycloalkyl) preferably $NH(C_3$-$C_6$-cycloalkyl). According to a specific embodiment $R^5$ is NH(cyclopropyl). According to a specific embodiment $R^5$ is NH(cyclobutyl). According to a specific embodiment $R^5$ is NH(cyclopentyl). According to a specific embodiment $R^5$ is NH(cyclohexyl).

According to one another embodiment $R^5$ is $N(C_3$-$C_8$-cycloalkyl)$_2$ preferably $N(C_3$-$C_6$-cycloalkyl)$_2$. According to a specific embodiment $R^5$ is N(cyclopropyl)$_2$. According to a specific embodiment $R^5$ is N(cyclobutyl)$_2$. According to a specific embodiment $R^5$ is N(cyclopentyl)$_2$. According to a specific embodiment $R^5$ is N(cyclohexyl)$_2$.

According to still a further embodiment, $R^5$ is selected from C(=O)($C_1$-$C_4$-alkyl), C(=O)(OH), C(=O)(O—$C_1$-$C_4$-alkyl), C(=O)(NH($C_1$-$C_4$-alkyl)), C(=O)(N($C_1$-$C_4$-alkyl)$_2$), C(=O)(NH($C_3$-$C_6$-cycloalkyl)) and C(=O)(N($C_3$-$C_6$-cycloalkyl)$_2$), in particular selected from C(=O)($C_1$-$C_2$-alkyl), C(=O)(OH), C(=O)(O—$C_1$-$C_2$-alkyl), C(=O)(NH($C_1$-$C_2$-alkyl)), C(=O)(N($C_1$-$C_2$-alkyl)$_2$), C(=O)(NH($C_3$-$C_6$-cycloalkyl)) and C(=O)(N($C_3$-$C_6$-cycloalkyl)$_2$). According to one specific embodiment thereof, $R^5$ is C(=O)(OH) or C(=O)(O—$C_1$-$C_4$-alkyl), in particular C(=O)(OCH$_3$).

According to one another embodiment $R^5$ is C(=O)(—$C_1$-$C_4$-alkyl). According to a specific embodiment $R^5$ is C(=O)CH$_3$. According to a further specific embodiment $R^5$ is C(=O)CH$_2$CH$_3$. According to a further specific embodiment $R^5$ is C(=O)CH$_2$CH$_2$CH$_3$. According to a further specific embodiment R⁵ is C(=O)CH(CH₃)₂. According to a further specific embodiment R⁵ is C(=O)C(CH₃)₃.

According to one another embodiment R⁵ is C(=O)OH.

According to one another embodiment R⁵ is C(=O)(—O—C₁-C₄-alkyl). According to a specific embodiment R⁵ is C(=O)OCH₃. According to a further specific embodiment R⁵ is C(=O)OCH₂CH₃. According to a further specific embodiment R⁵ is C(=O)OCH₂CH₂CH₃. According to a further specific embodiment R⁵ is C(=O)OCH(CH₃)₂. According to a further specific embodiment R⁵ is C(=O)OC(CH₃)₃.

According to one another embodiment R⁵ is C(=O)—NH(C₁-C₄-alkyl). According to a specific embodiment R⁵ is C(=O)NHCH₃. According to a further specific embodiment R⁵ is C(=O)NHCH₂CH₃.

According to a further specific embodiment R⁵ is C(=O)NHCH₂CH₂CH₃. According to a further specific embodiment R⁵ is C(=O)NHCH(CH₃)₂. According to a further specific embodiment R⁵ is C(=O)NHC(CH₃)₃.

According to one another embodiment R⁵ is C(=O)—N(C₁-C₄-alkyl)₂. According to a specific embodiment R⁵ is C(=O)N(CH₃)₂. According to a further specific embodiment R⁵ is C(=O)N(CH₂CH₃)₂. According to a further specific embodiment R⁵ is C(=O)N(CH₂CH₂CH₃)₂. According to a further specific embodiment R⁵ is C(=O)N(CH(CH₃)₂)₂. According to a further specific embodiment R⁵ is C(=O)N(C(CH₃)₃)₂.

According to one another embodiment R⁵ is C(=O)—NH(C₃-C₆-cycloalkyl). According to a specific embodiment R⁵ is C(=O)NH(cyclopropyl). According to a further specific embodiment R⁵ is C(=O)NH(cyclobutyl). According to a further specific embodiment R⁵ is C(=O)NH(cyclopentyl). According to a further specific embodiment R⁵ is C(=O)NH(cyclohexyl).

According to one another embodiment R⁵ is C(=O)—N(C₃-C₆-cycloalkyl)₂. According to a specific embodiment R⁵ is C(=O)N(cyclopropyl)₂. According to a further specific embodiment R⁵ is C(=O)N(cyclobutyl)₂. According to a further specific embodiment R⁵ is C(=O)N(cyclopentyl)₂. According to a further specific embodiment R⁵ is C(=O)N(cyclohexyl)₂.

According to still a further embodiment, R⁵ is selected from S(C₁-C₂-alkyl), S(O)(C₁-C₂-alkyl) and S(O)₂(C₁-C₂-alkyl), in particular SCH₃, S(O)(CH₃) and S(O)₂(CH₃). According to a specific embodiment R⁵ is selected from S(C₁-C₂-haloalkyl), S(O)(C₁-C₂-haloalkyl) and S(O)₂(C₁-C₂-haloalkyl), such as SO₂CF₃.

Particularly preferred embodiments of R⁵ present in the heteroaryl according to the invention are in Table P5 above (as defined for Z=phenyl), wherein each line of lines P5-1 to P5-16 corresponds to one particular embodiment of the invention, wherein P5-1 to P5-16 are also in any combination with one another a preferred embodiment of the present invention. Thereby, for every R⁵ that is present in the inventive compounds, these specific embodiments and preferences apply independently of the meaning of any other R⁵ that may be present in the heteroaryl ring.

Particularly preferred embodiments of (R⁵)ₘ if Z is heteroaryl according to the invention are in Table H below, wherein each line of lines H-1 to H-103 corresponds to one particular embodiment of the invention, wherein H-1 to H-103 are also in any combination preferred embodiments of the present invention.

TABLE H

| line | Z |
|---|---|
| H-1 | 2-pyridyl |
| H-2 | 3-pyridyl |
| H-3 | 4-pyridyl |
| H-4 | 3-fluoro-2-pyridyl |
| H-5 | 4-fluoro-2-pyridyl |
| H-6 | 5-fluoro-2-pyridyl |
| H-7 | 6-fluoro-2-pyridyl |
| H-8 | 4-fluoro-3-pyridyl |
| H-9 | 5-fluoro-3-pyridyl |
| H-10 | 2-fluoro-4-pyridyl |

TABLE H-continued

| line | Z |
|---|---|
| H-11 | 5-fluoropyridin-3-yl (F at 5, # at 3) |
| H-12 | 3-fluoropyridin-4-yl |
| H-13 | 2-fluoropyridin-4-yl |
| H-14 | 3-chloropyridin-2-yl |
| H-15 | 4-chloropyridin-2-yl |
| H-16 | 5-chloropyridin-2-yl |
| H-17 | 6-chloropyridin-2-yl |
| H-18 | 4-chloropyridin-3-yl |
| H-19 | 5-chloropyridin-3-yl |
| H-20 | 6-chloropyridin-3-yl |
| H-21 | 2-chloropyridin-3-yl |
| H-22 | 3-chloropyridin-4-yl |
| H-23 | 2-chloropyridin-4-yl |
| H-24 | 3-cyanopyridin-2-yl |
| H-25 | 4-cyanopyridin-2-yl |
| H-26 | 5-cyanopyridin-2-yl |
| H-27 | 2-cyanopyridin-6-yl |
| H-28 | 4-cyanopyridin-3-yl |

TABLE H-continued
| line | Z |
|---|---|
| H-29 | 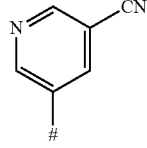 |
| H-30 | 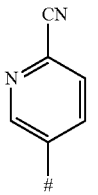 |
| H-31 | 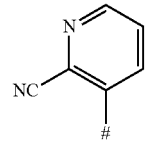 |
| H-32 | 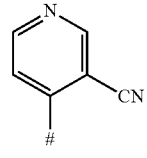 |
| H-33 | 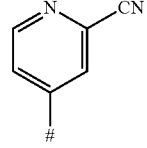 |
| H-34 | 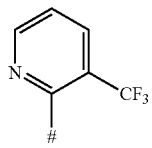 |
| H-35 | 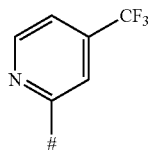 |
| H-36 | 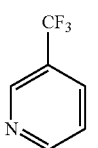 |
| H-37 | 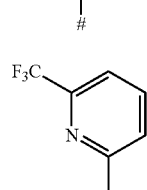 |
| H-38 | 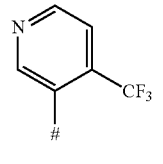 |
| H-39 | 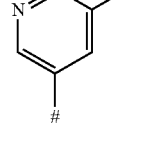 |
| H-40 | 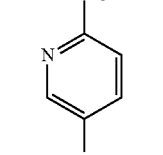 |
| H-41 |  |
| H-42 |  |
| H-43 |  |
| H-44 | 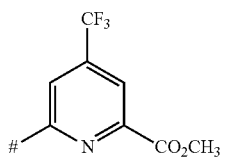 |
| H-45 | 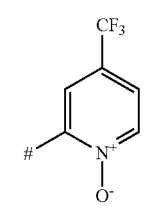 |
| H-46 | 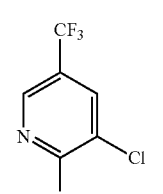 |

TABLE H-continued

| line | Z |
|---|---|
| H-47 | 2-Cl, 6-CF₃-pyridin-4-yl (#) |
| H-48 | 5-CF₃, 3-F-pyridin-2-yl (#) |
| H-49 | pyrimidin-4-yl (#) |
| H-50 | pyrimidin-2-yl (#) |
| H-51 | 2-CF₃-pyridin-4-yl (#) |
| H-52 | 4-CF₃-pyrimidin-6-yl (#) |
| H-53 | 2-Cl-pyrimidin-4-yl (#) |
| H-54 | 4-Cl-pyrimidin-6-yl (#) |
| H-55 | 2,6-diCl-pyrimidin-4-yl (#) |
| H-56 | 2,6-bis(CF₃)-pyrimidin-4-yl (#) |
| H-57 | 2-CF₃, 6-Cl-pyrimidin-4-yl (#) |
| H-58 | 5-OCH₃, 6-Cl-pyrimidin-4-yl (#) |
| H-59 | 2-CH₃, 6-Cl-pyrimidin-4-yl (#) |
| H-60 | 2-phenyl, 6-Cl-pyrimidin-4-yl (#) |
| H-61 | 5-C(O)OCH₃, 6-Cl-pyrimidin-4-yl (#) |
| H-62 | 4-CH₃, 2-Cl-pyrimidin-6-yl (#) |
| H-63 | 2,5-diCH₃, 6-Cl-pyrimidin-4-yl (#) |
| H-64 | 5-CH₃, 6-Cl-pyrimidin-4-yl (#) |

TABLE H-continued

| line | Z |
|---|---|
| H-65 | 4-chloro-2-(dimethylamino)pyrimidin-6-yl (# at 6-position) |
| H-66 | 4-chloro-2-methoxypyrimidin-6-yl (# at 6-position) |
| H-67 | 4-chloro-5-fluoropyrimidin-6-yl (# at 6-position) |
| H-68 | 6-chloro-5-cyanopyrimidin-4-yl (# at 4-position) |
| H-69 | 5,6-dichloropyrimidin-4-yl (# at 4-position) |
| H-70 | 6-chloro-2-(trifluoromethyl)pyrimidin-4-yl (# at 4-position) |
| H-71 | 4-methoxypyrimidin-6-yl (# at 6-position) |
| H-72 | 2-methoxypyrimidin-4-yl (# at 4-position) |
| H-73 | 4-(trifluoromethyl)pyrimidin-2-yl (# at 2-position) |

TABLE H-continued

| line | Z |
|---|---|
| H-74 | 4,6-dichloropyrimidin-2-yl (# at 2-position) |
| H-75 | 4,6-bis(trifluoromethyl)pyrimidin-2-yl (# at 2-position) |
| H-76 | 4-chloro-6-(trifluoromethyl)pyrimidin-2-yl (# at 2-position) |
| H-77 | 4-chloro-6-(trifluoromethyl)pyrimidin-2-yl (# at 2-position) |
| H-78 | pyridazin-3-yl (# at 3-position) |
| H-79 | 6-(trifluoromethyl)pyridazin-3-yl (# at 3-position) |
| H-80 | 6-chloropyridazin-3-yl (# at 3-position) |
| H-81 | 6-methoxypyridazin-3-yl (# at 3-position) |
| H-82 | 1-methyl-3-(trifluoromethyl)-1H-pyrazol-5-yl (# at 5-position) |

TABLE H-continued

| line | Z |
|---|---|
| H-83 | [4-Cl, 3-CF₃, 1-methyl pyrazole, # at 5] |
| H-84 | [3-methyl, 1-methyl pyrazole, # at 5] |
| H-85 | [4-Cl, 3-methyl, 1-methyl pyrazole, # at 5] |
| H-86 | [3-CF₃, 5-Cl, 1-# pyrazole] |
| H-87 | [4-Cl, 3-CF₃, 5-Cl, 1-# pyrazole] |
| H-88 | [3-CF₃, 5-CF₃, 1-# pyrazole] |
| H-89 | [4-Cl, 3-CF₃, 5-CF₃, 1-# pyrazole] |
| H-90 | [1-methyl pyrazole, # at 5] |
| H-91 | [1-methyl pyrazole, # at 4] |
| H-92 | [thiazole, # at 2] |
| H-93 | [thiazole, # at 5] |
| H-94 | [thiazole, # at 4] |
| H-95 | [4-CF₃ thiazole, # at 2] |
| H-96 | [5-CF₃ thiazole, # at 2] |
| H-97 | [4-CF₃ thiazole, # at 5] |
| H-98 | [2-CF₃ thiazole, # at 5] |
| H-99 | [2-CF₃ thiazole, # at 4] |
| H-100 | [5-CF₃ thiazole, # at 4] |
| H-101 | [4-CF₃, 5-Cl thiazole, # at 2] |
| H-102 | [4-Cl thiazole, # at 2] |
| H-103 | [4-CN, 5-Cl isothiazole, # at 3] | in which # indicates the point of attachment of the group Y.

According to one embodiment, A is N and D is H, corresponding to compounds I.A:

I.A

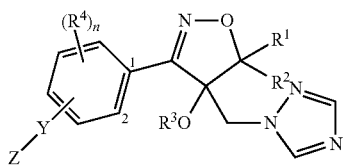

One specific embodiment thereof relates to compounds, wherein Z—Y is para-phenyl-O, corresponding to compounds I.A1:

I.A1

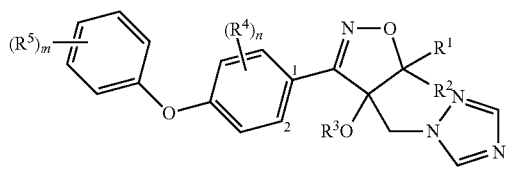

One further specific embodiment thereof relates to compounds, wherein Z—Y is meta-phenyl-O, corresponding to compounds I.A2:

I.A2

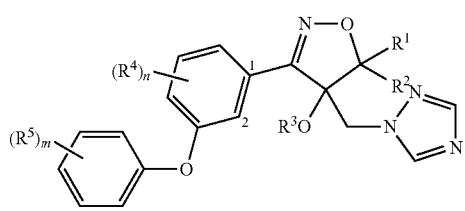

According to a further embodiment, A is N and D is SH, corresponding to compounds I.B:

I.B

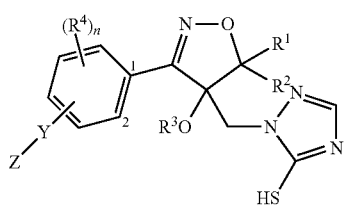

One specific embodiment thereof relates to compounds, wherein Z—Y is para-phenyl-O, corresponding to compounds I.B1:

I.B1

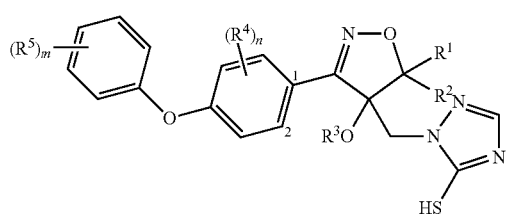

One further specific embodiment thereof relates to compounds, wherein Z—Y is meta-phenyl-O, corresponding to compounds I.B2:

I.B2

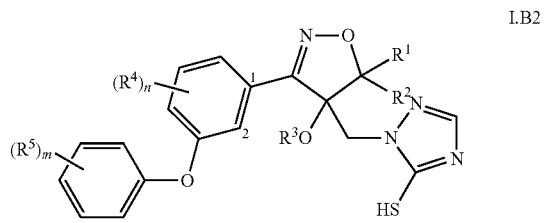

According to a further embodiment, A is CH and D is H, corresponding to compounds I.C:

I.C

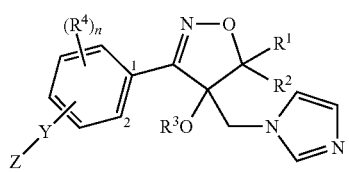

One specific embodiment thereof relates to compounds, wherein Z—Y is para-phenyl-O, corresponding to compounds I.C1:

I.C1

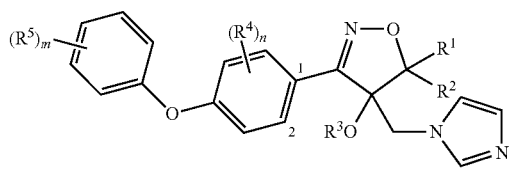

One further specific embodiment thereof relates to compounds, wherein Z—Y is meta-phenyl-O, corresponding to compounds I.C2:

I.C2

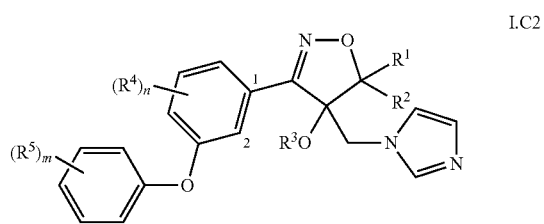

According to a further embodiment, A is CH and D is SH, corresponding to compounds I.D:

I.D

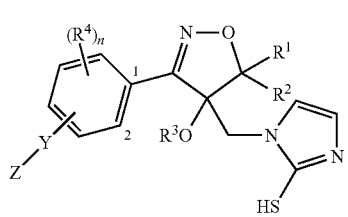

One specific embodiment thereof relates to compounds, wherein Z—Y is para-phenyl-O, corresponding to compounds I.D1:

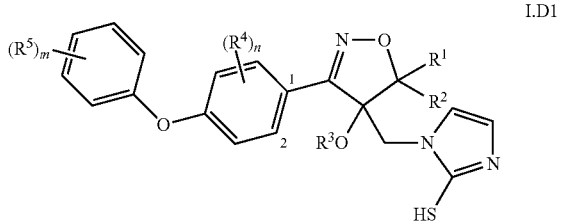

One further specific embodiment thereof relates to compounds, wherein Z—Y is meta-phenyl-O, corresponding to compounds I.D2:

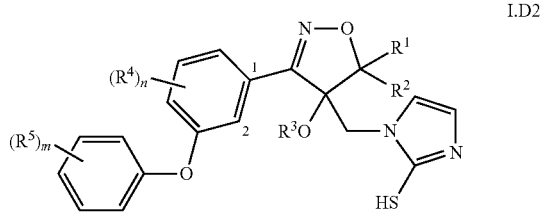

In particular with a view to their use, preference is given to the compounds of the formula I, such as I.A, I.B, I.C and I.D. more specifically I.A1, I.A2, I.B1, I.B2, I.C1, I.C2, I.D1 and I.D2, in particular I.A1, I.A2, I.C1 and I.C2, compiled in the Tables 1a to 142a, Tables 1b to 142b, Tables 1c to 142c and Tables 1d to 142d below. Each of the groups mentioned for a substituent in the tables is furthermore per se, independently of the combination in which it is mentioned, a particularly preferred aspect of the substituent in question.

Table 1a Compounds of the formula I.A1 in which the combination of $R^1$, $R^2$ and $R^3$ corresponds to line A-1 of Table A and the meaning for the combination of the combination of $(R^4)_n$ and $(R^5)_m$ for each individual compound corresponds in each case to one line of Table B (compounds I.A1.A1.B1 to I.A1.A1.B2496).

Table 2a Compounds of the formula I.A1 in which the combination of $R^1$, $R^2$ and $R^3$ corresponds to line A-2 of Table A and the meaning for the combination of $(R^4)_n$ and $(R^5)_m$ for each individual compound corresponds in each case to one line of Table B (compounds I.A1.A2.B1 to I.A1.A2.B2496).

Table 3a Compounds of the formula I.A1 in which the combination of $R^1$, $R^2$ and $R^3$ corresponds to line A-3 of Table A and the meaning for the combination of $(R^4)_n$ and $(R^5)_m$ for each individual compound corresponds in each case to one line of Table B (compounds I.A1.A3.B1 to I.A1.A3.B2496).

Table 4a Compounds of the formula I.A1 in which the combination of $R^1$, $R^2$ and $R^3$ corresponds to line A-4 of Table A and the meaning for the combination of $(R^4)_n$ and $(R^5)_m$ for each individual compound corresponds in each case to one line of Table B (compounds I.A1.A4.B1 to I.A1.A4.B2496).

Table 5a Compounds of the formula I.A1 in which the combination of $R^1$, $R^2$ and $R^3$ corresponds to line A-5 of Table A and the meaning for the combination of $(R^4)_n$ and $(R^5)_m$ for each individual compound corresponds in each case to one line of Table B (compounds I.A1.A5.B1 to I.A1.A5.B2496).

Table 6a Compounds of the formula I.A1 in which the combination of $R^1$, $R^2$ and $R^3$ corresponds to line A-6 of Table A and the meaning for the combination of $(R^4)_n$ and $(R^5)_m$ for each individual compound corresponds in each case to one line of Table B (compounds I.A1.A6.B1 to I.A1.A6.B2496).

Table 7a Compounds of the formula I.A1 in which the combination of $R^1$, $R^2$ and $R^3$ corresponds to line A-7 of Table A and the meaning for the combination of $(R^4)_n$ and $(R^5)_m$ for each individual compound corresponds in each case to one line of Table B (compounds I.A1.A7.B1 to I.A1.A7.B2496).

Table 8a Compounds of the formula I.A1 in which the combination of $R^1$, $R^2$ and $R^3$ corresponds to line A-8 of Table A and the meaning for the combination of $(R^4)_n$ and $(R^5)_m$ for each individual compound corresponds in each case to one line of Table B (compounds I.A1.A8.B1 to I.A1.A8.B2496).

Table 9a Compounds of the formula I.A1 in which the combination of $R^1$, $R^2$ and $R^3$ corresponds to line A-9 of Table A and the meaning for the combination of $(R^4)_n$ and $(R^5)_m$ for each individual compound corresponds in each case to one line of Table B (compounds I.A1.A9.B1 to I.A1.A9.B2496).

Table 10a Compounds of the formula I.A1 in which the combination of $R^1$, $R^2$ and $R^3$ corresponds to line A-10 of Table A and the meaning for the combination of $(R^4)_n$ and $(R^5)_m$ for each individual compound corresponds in each case to one line of Table B (compounds I.A1.A10.B1 to I.A1.A10.B2496).

Table 11a Compounds of the formula I.A1 in which the combination of $R^1$, $R^2$ and $R^3$ corresponds to line A-11 of Table A and the meaning for the combination of $(R^4)_n$ and $(R^5)_m$ for each individual compound corresponds in each case to one line of Table B (compounds I.A1.A11.B1 to I.A1.A11.B2496).

Table 12a Compounds of the formula I.A1 in which the combination of $R^1$, $R^2$ and $R^3$ corresponds to line A-12 of Table A and the meaning for the combination of $(R^4)_n$ and $(R^5)_m$ for each individual compound corresponds in each case to one line of Table B (compounds I.A1.A12.B1 to I.A1.A12.B2496).

Table 13a Compounds of the formula I.A1 in which the combination of $R^1$, $R^2$ and $R^3$ corresponds to line A-13 of Table A and the meaning for the combination of $(R^4)_n$ and $(R^5)_m$ for each individual compound corresponds in each case to one line of Table B (compounds I.A1.A13.B1 to I.A1.A13.B2496).

Table 14a Compounds of the formula I.A1 in which the combination of $R^1$, $R^2$ and $R^3$ corresponds to line A-14 of Table A and the meaning for the combination of $(R^4)_n$ and $(R^5)_m$ for each individual compound corresponds in each case to one line of Table B (compounds I.A1.A14.B1 to I.A1.A14.B2496).

Table 15a Compounds of the formula I.A1 in which the combination of $R^1$, $R^2$ and $R^3$ corresponds to line A-15 of Table A and the meaning for the combination of $(R^4)_n$ and $(R^5)_m$ for each individual compound corresponds in each case to one line of Table B (compounds I.A1.A15.B1 to I.A1.A15.B2496).

Table 16a Compounds of the formula I.A1 in which the combination of $R^1$, $R^2$ and $R^3$ corresponds to line A-16 of Table A and the meaning for the combination of $(R^4)_n$ and ($R^5$)$_m$ for each individual compound corresponds in each case to one line of Table B (compounds I.A1.A16.B1 to I.A1.A16.B2496).

Table 17a Compounds of the formula I.A1 in which the combination of $R^1$, $R^2$ and $R^3$ corresponds to line A-17 of Table A and the meaning for the combination of ($R^4$)$_n$ and ($R^5$)$_m$ for each individual compound corresponds in each case to one line of Table B (compounds I.A1.A17.B1 to I.A1.A17.B2496).

Table 18a Compounds of the formula I.A1 in which the combination of $R^1$, $R^2$ and $R^3$ corresponds to line A-18 of Table A and the meaning for the combination of ($R^4$)$_n$ and ($R^5$)$_m$ for each individual compound corresponds in each case to one line of Table B (compounds I.A1.A18.B1 to I.A1.A18.B2496).

Table 19a Compounds of the formula I.A1 in which the combination of $R^1$, $R^2$ and $R^3$ corresponds to line A-19 of Table A and the meaning for the combination of ($R^4$)$_n$ and ($R^5$)$_m$ for each individual compound corresponds in each case to one line of Table B (compounds I.A1.A19.B1 to I.A1.A19.B2496).

Table 20a Compounds of the formula I.A1 in which the combination of $R^1$, $R^2$ and $R^3$ corresponds to line A-20 of Table A and the meaning for the combination of ($R^4$)$_n$ and ($R^5$)$_m$ for each individual compound corresponds in each case to one line of Table B (compounds I.A1.A20.B1 to I.A1.A20.B2496).

Table 21a Compounds of the formula I.A1 in which the combination of $R^1$, $R^2$ and $R^3$ corresponds to line A-21 of Table A and the meaning for the combination of ($R^4$)$_n$ and ($R^5$)$_m$ for each individual compound corresponds in each case to one line of Table B (compounds I.A1.A21.B1 to I.A1.A21.B2496).

Table 22a Compounds of the formula I.A1 in which the combination of $R^1$, $R^2$ and $R^3$ corresponds to line A-22 of Table A and the meaning for the combination of ($R^4$)$_n$ and ($R^5$)$_m$ for each individual compound corresponds in each case to one line of Table B (compounds I.A1.A22.B1 to I.A1.A22.B2496).

Table 23a Compounds of the formula I.A1 in which the combination of $R^1$, $R^2$ and $R^3$ corresponds to line A-23 of Table A and the meaning for the combination of ($R^4$)$_n$ and ($R^5$)$_m$ for each individual compound corresponds in each case to one line of Table B (compounds I.A1.A23.B1 to I.A1.A23.B2496).

Table 24a Compounds of the formula I.A1 in which the combination of $R^1$, $R^2$ and $R^3$ corresponds to line A-24 of Table A and the meaning for the combination of ($R^4$)$_n$ and ($R^5$)$_m$ for each individual compound corresponds in each case to one line of Table B (compounds I.A1.A24.B1 to I.A1.A24.B2496).

Table 25a Compounds of the formula I.A1 in which the combination of $R^1$, $R^2$ and $R^3$ corresponds to line A-25 of Table A and the meaning for the combination of ($R^4$)$_n$ and ($R^5$)$_m$ for each individual compound corresponds in each case to one line of Table B (compounds I.A1.A25.B1 to I.A1.A25.B2496).

Table 26a Compounds of the formula I.A1 in which the combination of $R^1$, $R^2$ and $R^3$ corresponds to line A-26 of Table A and the meaning for the combination of ($R^4$)$_n$ and ($R^5$)$_m$ for each individual compound corresponds in each case to one line of Table B (compounds I.A1.A26.B1 to I.A1.A26.B2496).

Table 27a Compounds of the formula I.A1 in which the combination of $R^1$, $R^2$ and $R^3$ corresponds to line A-27 of Table A and the meaning for the combination of ($R^4$)$_n$ and ($R^5$)$_m$ for each individual compound corresponds in each case to one line of Table B (compounds I.A1.A27.B1 to I.A1.A27.B2496).

Table 28a Compounds of the formula I.A1 in which the combination of $R^1$, $R^2$ and $R^3$ corresponds to line A-28 of Table A and the meaning for the combination of ($R^4$)$_n$ and ($R^5$)$_m$ for each individual compound corresponds in each case to one line of Table B (compounds I.A1.A28.B1 to I.A1.A28.B2496).

Table 29a Compounds of the formula I.A1 in which the combination of $R^1$, $R^2$ and $R^3$ corresponds to line A-29 of Table A and the meaning for the combination of ($R^4$)$_n$ and ($R^5$)$_m$ for each individual compound corresponds in each case to one line of Table B (compounds I.A1.A29.B1 to I.A1.A29.B2496).

Table 30a Compounds of the formula I.A1 in which the combination of $R^1$, $R^2$ and $R^3$ corresponds to line A-30 of Table A and the meaning for the combination of ($R^4$)$_n$ and ($R^5$)$_m$ for each individual compound corresponds in each case to one line of Table B (compounds I.A1.A30.B1 to I.A1.A30.B2496).

Table 31a Compounds of the formula I.A1 in which the combination of $R^1$, $R^2$ and $R^3$ corresponds to line A-31 of Table A and the meaning for the combination of ($R^4$)$_n$ and ($R^5$)$_m$ for each individual compound corresponds in each case to one line of Table B (compounds I.A1.A31.B1 to I.A1.A31.B2496).

Table 32a Compounds of the formula I.A1 in which the combination of $R^1$, $R^2$ and $R^3$ corresponds to line A-32 of Table A and the meaning for the combination of ($R^4$)$_n$ and ($R^5$)$_m$ for each individual compound corresponds in each case to one line of Table B (compounds I.A1.A32.B1 to I.A1.A32.B2496).

Table 33a Compounds of the formula I.A1 in which the combination of $R^1$, $R^2$ and $R^3$ corresponds to line A-33 of Table A and the meaning for the combination of ($R^4$)$_n$ and ($R^5$)$_m$ for each individual compound corresponds in each case to one line of Table B (compounds I.A1.A33.B1 to I.A1.A33.B2496).

Table 34a Compounds of the formula I.A1 in which the combination of $R^1$, $R^2$ and $R^3$ corresponds to line A-34 of Table A and the meaning for the combination of ($R^4$)$_n$ and ($R^5$)$_m$ for each individual compound corresponds in each case to one line of Table B (compounds I.A1.A34.B1 to I.A1.A34.B2496).

Table 35a Compounds of the formula I.A1 in which the combination of $R^1$, $R^2$ and $R^3$ corresponds to line A-35 of Table A and the meaning for the combination of ($R^4$)$_n$ and ($R^5$)$_m$ for each individual compound corresponds in each case to one line of Table B (compounds I.A1.A35.B1 to I.A1.A35.B2496).

Table 36a Compounds of the formula I.A1 in which the combination of $R^1$, $R^2$ and $R^3$ corresponds to line A-36 of Table A and the meaning for the combination of ($R^4$)$_n$ and ($R^5$)$_m$ for each individual compound corresponds in each case to one line of Table B (compounds I.A1.A36.B1 to I.A1.A36.B2496).

Table 37a Compounds of the formula I.A1 in which the combination of $R^1$, $R^2$ and $R^3$ corresponds to line A-37 of Table A and the meaning for the combination of ($R^4$)$_n$ and ($R^5$)$_m$ for each individual compound corresponds in each case to one line of Table B (compounds I.A1.A37.B1 to I.A1.A37.B2496).

Table 38a Compounds of the formula I.A1 in which the combination of $R^1$, $R^2$ and $R^3$ corresponds to line A-38 of Table A and the meaning for the combination of ($R^4$)$_n$ and ($R^5$)$_m$ for each individual compound corresponds in each case to one line of Table B (compounds I.A1.A38.B1 to I.A1.A38.B2496).

Table 39a Compounds of the formula I.A1 in which the combination of $R^1$, $R^2$ and $R^3$ corresponds to line A-39 of Table A and the meaning for the combination of ($R^4$)$_n$ and ($R^5$)$_m$ for each individual compound corresponds in each case to one line of Table B (compounds I.A1.A39.B1 to I.A1.A39.B2496).

Table 40a Compounds of the formula I.A1 in which the combination of $R^1$, $R^2$ and $R^3$ corresponds to line A-40 of Table A and the meaning for the combination of ($R^4$)$_n$ and ($R^5$)$_m$ for each individual compound corresponds in each case to one line of Table B (compounds I.A1.A40.B1 to I.A1.A40.B2496).

Table 41a Compounds of the formula I.A1 in which the combination of $R^1$, $R^2$ and $R^3$ corresponds to line A-41 of Table A and the meaning for the combination of ($R^4$)$_n$ and ($R^5$)$_m$ for each individual compound corresponds in each case to one line of Table B (compounds I.A1.A41.B1 to I.A1.A41.B2496).

Table 42a Compounds of the formula I.A1 in which the combination of $R^1$, $R^2$ and $R^3$ corresponds to line A-42 of Table A and the meaning for the combination of ($R^4$)$_n$ and ($R^5$)$_m$ for each individual compound corresponds in each case to one line of Table B (compounds I.A1.A42.B1 to I.A1.A42.B2496).

Table 43a Compounds of the formula I.A1 in which the combination of $R^1$, $R^2$ and $R^3$ corresponds to line A-43 of Table A and the meaning for the combination of ($R^4$)$_n$ and ($R^5$)$_m$ for each individual compound corresponds in each case to one line of Table B (compounds I.A1.A43.B1 to I.A1.A43.B2496).

Table 44a Compounds of the formula I.A1 in which the combination of $R^1$, $R^2$ and $R^3$ corresponds to line A-44 of Table A and the meaning for the combination of ($R^4$)$_n$ and ($R^5$)$_m$ for each individual compound corresponds in each case to one line of Table B (compounds I.A1.A44.B1 to I.A1.A44.B2496).

Table 45a Compounds of the formula I.A1 in which the combination of $R^1$, $R^2$ and $R^3$ corresponds to line A-45 of Table A and the meaning for the combination of ($R^4$)$_n$ and ($R^5$)$_m$ for each individual compound corresponds in each case to one line of Table B (compounds I.A1.A45.B1 to I.A1.A45.B2496).

Table 46a Compounds of the formula I.A1 in which the combination of $R^1$, $R^2$ and $R^3$ corresponds to line A-46 of Table A and the meaning for the combination of ($R^4$)$_n$ and ($R^5$)$_m$ for each individual compound corresponds in each case to one line of Table B (compounds I.A1.A46.B1 to I.A1.A46.B2496).

Table 47a Compounds of the formula I.A1 in which the combination of $R^1$, $R^2$ and $R^3$ corresponds to line A-47 of Table A and the meaning for the combination of ($R^4$)$_n$ and ($R^5$)$_m$ for each individual compound corresponds in each case to one line of Table B (compounds I.A1.A47.B1 to I.A1.A47.B2496).

Table 48a Compounds of the formula I.A1 in which the combination of $R^1$, $R^2$ and $R^3$ corresponds to line A-48 of Table A and the meaning for the combination of ($R^4$)$_n$ and ($R^5$)$_m$ for each individual compound corresponds in each case to one line of Table B (compounds I.A1.A48.B1 to I.A1.A48.B2496).

Table 49a Compounds of the formula I.A1 in which the combination of $R^1$, $R^2$ and $R^3$ corresponds to line A-49 of Table A and the meaning for the combination of ($R^4$)$_n$ and ($R^5$)$_m$ for each individual compound corresponds in each case to one line of Table B (compounds I.A1.A49.B1 to I.A1.A49.B2496).

Table 50a Compounds of the formula I.A1 in which the combination of $R^1$, $R^2$ and $R^3$ corresponds to line A-50 of Table A and the meaning for the combination of ($R^4$)$_n$ and ($R^5$)$_m$ for each individual compound corresponds in each case to one line of Table B (compounds I.A1.A50.B1 to I.A1.A50.B2496).

Table 51a Compounds of the formula I.A1 in which the combination of $R^1$, $R^2$ and $R^3$ corresponds to line A-51 of Table A and the meaning for the combination of ($R^4$)$_n$ and ($R^5$)$_m$ for each individual compound corresponds in each case to one line of Table B (compounds I.A1.A51.B1 to I.A1.A51.B2496).

Table 52a Compounds of the formula I.A1 in which the combination of $R^1$, $R^2$ and $R^3$ corresponds to line A-52 of Table A and the meaning for the combination of ($R^4$)$_n$ and ($R^5$)$_m$ for each individual compound corresponds in each case to one line of Table B (compounds I.A1.A52.B1 to I.A1.A52.B2496).

Table 53a Compounds of the formula I.A1 in which the combination of $R^1$, $R^2$ and $R^3$ corresponds to line A-53 of Table A and the meaning for the combination of ($R^4$)$_n$ and ($R^5$)$_m$ for each individual compound corresponds in each case to one line of Table B (compounds I.A1.A53.B1 to I.A1.A53.B2496).

Table 54a Compounds of the formula I.A1 in which the combination of $R^1$, $R^2$ and $R^3$ corresponds to line A-54 of Table A and the meaning for the combination of ($R^4$)$_n$ and ($R^5$)$_m$ for each individual compound corresponds in each case to one line of Table B (compounds I.A1.A54.B1 to I.A1.A54.B2496).

Table 55a Compounds of the formula I.A1 in which the combination of $R^1$, $R^2$ and $R^3$ corresponds to line A-55 of Table A and the meaning for the combination of ($R^4$)$_n$ and ($R^5$)$_m$ for each individual compound corresponds in each case to one line of Table B (compounds I.A1.A55.B1 to I.A1.A55.B2496).

Table 56a Compounds of the formula I.A1 in which the combination of $R^1$, $R^2$ and $R^3$ corresponds to line A-56 of Table A and the meaning for the combination of ($R^4$)$_n$ and ($R^5$)$_m$ for each individual compound corresponds in each case to one line of Table B (compounds I.A1.A56.B1 to I.A1.A56.B2496).

Table 57a Compounds of the formula I.A1 in which the combination of $R^1$, $R^2$ and $R^3$ corresponds to line A-57 of Table A and the meaning for the combination of ($R^4$)$_n$ and ($R^5$)$_m$ for each individual compound corresponds in each case to one line of Table B (compounds I.A1.A57.B1 to I.A1.A57.B2496).

Table 58a Compounds of the formula I.A1 in which the combination of $R^1$, $R^2$ and $R^3$ corresponds to line A-58 of Table A and the meaning for the combination of ($R^4$)$_n$ and ($R^5$)$_m$ for each individual compound corresponds in each case to one line of Table B (compounds I.A1.A58.B1 to I.A1.A58.B2496).

Table 59a Compounds of the formula I.A1 in which the combination of $R^1$, $R^2$ and $R^3$ corresponds to line A-59 of Table A and the meaning for the combination of ($R^4$)$_n$ and ($R^5$)$_m$ for each individual compound corresponds in each case to one line of Table B (compounds I.A1.A59.B1 to I.A1.A59.B2496).

Table 60a Compounds of the formula I.A1 in which the combination of $R^1$, $R^2$ and $R^3$ corresponds to line A-60 of Table A and the meaning for the combination of ($R^4$)$_n$ and $(R^5)_m$ for each individual compound corresponds in each case to one line of Table B (compounds I.A1.A60.B1 to I.A1.A60.B2496).

Table 61a Compounds of the formula I.A1 in which the combination of $R^1$, $R^2$ and $R^3$ corresponds to line A-61 of Table A and the meaning for the combination of $(R^4)_n$ and $(R^5)_m$ for each individual compound corresponds in each case to one line of Table B (compounds I.A1.A61.B1 to I.A1.A61.B2496).

Table 62a Compounds of the formula I.A1 in which the combination of $R^1$, $R^2$ and $R^3$ corresponds to line A-62 of Table A and the meaning for the combination of $(R^4)_n$ and $(R^5)_m$ for each individual compound corresponds in each case to one line of Table B (compounds I.A1.A62.B1 to I.A1.A62.B2496).

Table 63a Compounds of the formula I.A1 in which the combination of $R^1$, $R^2$ and $R^3$ corresponds to line A-63 of Table A and the meaning for the combination of $(R^4)_n$ and $(R^5)_m$ for each individual compound corresponds in each case to one line of Table B (compounds I.A1.A63.B1 to I.A1.A63.B2496).

Table 64a Compounds of the formula I.A1 in which the combination of $R^1$, $R^2$ and $R^3$ corresponds to line A-64 of Table A and the meaning for the combination of $(R^4)_n$ and $(R^5)_m$ for each individual compound corresponds in each case to one line of Table B (compounds I.A1.A64.B1 to I.A1.A64.B2496).

Table 65a Compounds of the formula I.A1 in which the combination of $R^1$, $R^2$ and $R^3$ corresponds to line A-65 of Table A and the meaning for the combination of $(R^4)_n$ and $(R^5)_m$ for each individual compound corresponds in each case to one line of Table B (compounds I.A1.A65.B1 to I.A1.A65.B2496).

Table 66a Compounds of the formula I.A1 in which the combination of $R^1$, $R^2$ and $R^3$ corresponds to line A-66 of Table A and the meaning for the combination of $(R^4)_n$ and $(R^5)_m$ for each individual compound corresponds in each case to one line of Table B (compounds I.A1.A66.B1 to I.A1.A66.B2496).

Table 67a Compounds of the formula I.A1 in which the combination of $R^1$, $R^2$ and $R^3$ corresponds to line A-67 of Table A and the meaning for the combination of $(R^4)_n$ and $(R^5)_m$ for each individual compound corresponds in each case to one line of Table B (compounds I.A1.A67.B1 to I.A1.A67.B2496).

Table 68a Compounds of the formula I.A1 in which the combination of $R^1$, $R^2$ and $R^3$ corresponds to line A-68 of Table A and the meaning for the combination of $(R^4)_n$ and $(R^5)_m$ for each individual compound corresponds in each case to one line of Table B (compounds I.A1.A68.B1 to I.A1.A68.B2496).

Table 69a Compounds of the formula I.A1 in which the combination of $R^1$, $R^2$ and $R^3$ corresponds to line A-69 of Table A and the meaning for the combination of $(R^4)_n$ and $(R^5)_m$ for each individual compound corresponds in each case to one line of Table B (compounds I.A1.A69.B1 to I.A1.A69.B2496).

Table 70a Compounds of the formula I.A1 in which the combination of $R^1$, $R^2$ and $R^3$ corresponds to line A-70 of Table A and the meaning for the combination of $(R^4)_n$ and $(R^5)_m$ for each individual compound corresponds in each case to one line of Table B (compounds I.A1.A70.B1 to I.A1.A70.B2496).

Table 71a Compounds of the formula I.A1 in which the combination of $R^1$, $R^2$ and $R^3$ corresponds to line A-71 of Table A and the meaning for the combination of $(R^4)_n$ and $(R^5)_m$ for each individual compound corresponds in each case to one line of Table B (compounds I.A1.A71.B1 to I.A1.A71.B2496).

Table 72a Compounds of the formula I.A1 in which the combination of $R^1$, $R^2$ and $R^3$ corresponds to line A-72 of Table A and the meaning for the combination of $(R^4)_n$ and $(R^5)_m$ for each individual compound corresponds in each case to one line of Table B (compounds I.A1.A72.B1 to I.A1.A72.B2496).

Table 73a Compounds of the formula I.A1 in which the combination of $R^1$, $R^2$ and $R^3$ corresponds to line A-73 of Table A and the meaning for the combination of $(R^4)_n$ and $(R^5)_m$ for each individual compound corresponds in each case to one line of Table B (compounds I.A1.A73.B1 to I.A1.A73.B2496).

Table 74a Compounds of the formula I.A1 in which the combination of $R^1$, $R^2$ and $R^3$ corresponds to line A-74 of Table A and the meaning for the combination of $(R^4)_n$ and $(R^5)_m$ for each individual compound corresponds in each case to one line of Table B (compounds I.A1.A74.B1 to I.A1.A74.B2496).

Table 75a Compounds of the formula I.A1 in which the combination of $R^1$, $R^2$ and $R^3$ corresponds to line A-75 of Table A and the meaning for the combination of $(R^4)_n$ and $(R^5)_m$ for each individual compound corresponds in each case to one line of Table B (compounds I.A1.A75.B1 to I.A1.A75.B2496).

Table 76a Compounds of the formula I.A1 in which the combination of $R^1$, $R^2$ and $R^3$ corresponds to line A-76 of Table A and the meaning for the combination of $(R^4)_n$ and $(R^5)_m$ for each individual compound corresponds in each case to one line of Table B (compounds I.A1.A76.B1 to I.A1.A76.B2496).

Table 77a Compounds of the formula I.A1 in which the combination of $R^1$, $R^2$ and $R^3$ corresponds to line A-77 of Table A and the meaning for the combination of $(R^4)_n$ and $(R^5)_m$ for each individual compound corresponds in each case to one line of Table B (compounds I.A1.A77.B1 to I.A1.A77.B2496).

Table 78a Compounds of the formula I.A1 in which the combination of $R^1$, $R^2$ and $R^3$ corresponds to line A-78 of Table A and the meaning for the combination of $(R^4)_n$ and $(R^5)_m$ for each individual compound corresponds in each case to one line of Table B (compounds I.A1.A78.B1 to I.A1.A78.B2496).

Table 79a Compounds of the formula I.A1 in which the combination of $R^1$, $R^2$ and $R^3$ corresponds to line A-79 of Table A and the meaning for the combination of $(R^4)_n$ and $(R^5)_m$ for each individual compound corresponds in each case to one line of Table B (compounds I.A1.A79.B1 to I.A1.A79.B2496).

Table 80a Compounds of the formula I.A1 in which the combination of $R^1$, $R^2$ and $R^3$ corresponds to line A-80 of Table A and the meaning for the combination of $(R^4)_n$ and $(R^5)_m$ for each individual compound corresponds in each case to one line of Table B (compounds I.A1.A80.B1 to I.A1.A80.B2496).

Table 81a Compounds of the formula I.A1 in which the combination of $R^1$, $R^2$ and $R^3$ corresponds to line A-81 of Table A and the meaning for the combination of $(R^4)_n$ and $(R^5)_m$ for each individual compound corresponds in each case to one line of Table B (compounds I.A1.A81.B1 to I.A1.A81.B2496).

Table 82a Compounds of the formula I.A1 in which the combination of $R^1$, $R^2$ and $R^3$ corresponds to line A-82 of Table A and the meaning for the combination of $(R^4)_n$ and $(R^5)_m$ for each individual compound corresponds in each case to one line of Table B (compounds I.A1.A82.B1 to I.A1.A82.B2496).

Table 83a Compounds of the formula I.A1 in which the combination of $R^1$, $R^2$ and $R^3$ corresponds to line A-83 of Table A and the meaning for the combination of $(R^4)_n$ and $(R^5)_m$ for each individual compound corresponds in each case to one line of Table B (compounds I.A1.A83.B1 to I.A1.A83.B2496).

Table 84a Compounds of the formula I.A1 in which the combination of $R^1$, $R^2$ and $R^3$ corresponds to line A-84 of Table A and the meaning for the combination of $(R^4)_n$ and $(R^5)_m$ for each individual compound corresponds in each case to one line of Table B (compounds I.A1.A84.B1 to I.A1.A84.B2496).

Table 85a Compounds of the formula I.A1 in which the combination of $R^1$, $R^2$ and $R^3$ corresponds to line A-85 of Table A and the meaning for the combination of $(R^4)_n$ and $(R^5)_m$ for each individual compound corresponds in each case to one line of Table B (compounds I.A1.A85.B1 to I.A1.A85.B2496).

Table 86a Compounds of the formula I.A1 in which the combination of $R^1$, $R^2$ and $R^3$ corresponds to line A-86 of Table A and the meaning for the combination of $(R^4)_n$ and $(R^5)_m$ for each individual compound corresponds in each case to one line of Table B (compounds I.A1.A86.B1 to I.A1.A86.B2496).

Table 87a Compounds of the formula I.A1 in which the combination of $R^1$, $R^2$ and $R^3$ corresponds to line A-87 of Table A and the meaning for the combination of $(R^4)_n$ and $(R^5)_m$ for each individual compound corresponds in each case to one line of Table B (compounds I.A1.A87.B1 to I.A1.A87.B2496).

Table 88a Compounds of the formula I.A1 in which the combination of $R^1$, $R^2$ and $R^3$ corresponds to line A-88 of Table A and the meaning for the combination of $(R^4)_n$ and $(R^5)_m$ for each individual compound corresponds in each case to one line of Table B (compounds I.A1.A88.B1 to I.A1.A88.B2496).

Table 89a Compounds of the formula I.A1 in which the combination of $R^1$, $R^2$ and $R^3$ corresponds to line A-89 of Table A and the meaning for the combination of $(R^4)_n$ and $(R^5)_m$ for each individual compound corresponds in each case to one line of Table B (compounds I.A1.A89.B1 to I.A1.A89.B2496).

Table 90a Compounds of the formula I.A1 in which the combination of $R^1$, $R^2$ and $R^3$ corresponds to line A-90 of Table A and the meaning for the combination of $(R^4)_n$ and $(R^5)_m$ for each individual compound corresponds in each case to one line of Table B (compounds I.A1.A90.B1 to I.A1.A90.B2496).

Table 91a Compounds of the formula I.A1 in which the combination of $R^1$, $R^2$ and $R^3$ corresponds to line A-91 of Table A and the meaning for the combination of $(R^4)_n$ and $(R^5)_m$ for each individual compound corresponds in each case to one line of Table B (compounds I.A1.A91.B1 to I.A1.A91.B2496).

Table 92a Compounds of the formula I.A1 in which the combination of $R^1$, $R^2$ and $R^3$ corresponds to line A-92 of Table A and the meaning for the combination of $(R^4)_n$ and $(R^5)_m$ for each individual compound corresponds in each case to one line of Table B (compounds I.A1.A92.B1 to I.A1.A92.B2496).

Table 93a Compounds of the formula I.A1 in which the combination of $R^1$, $R^2$ and $R^3$ corresponds to line A-93 of Table A and the meaning for the combination of $(R^4)_n$ and $(R^5)_m$ for each individual compound corresponds in each case to one line of Table B (compounds I.A1.A93.B1 to I.A1.A93.B2496).

Table 94a Compounds of the formula I.A1 in which the combination of $R^1$, $R^2$ and $R^3$ corresponds to line A-94 of Table A and the meaning for the combination of $(R^4)_n$ and $(R^5)_m$ for each individual compound corresponds in each case to one line of Table B (compounds I.A1.A94.B1 to I.A1.A94.B2496).

Table 95a Compounds of the formula I.A1 in which the combination of $R^1$, $R^2$ and $R^3$ corresponds to line A-95 of Table A and the meaning for the combination of $(R^4)_n$ and $(R^5)_m$ for each individual compound corresponds in each case to one line of Table B (compounds I.A1.A95.B1 to I.A1.A95.B2496).

Table 96a Compounds of the formula I.A1 in which the combination of $R^1$, $R^2$ and $R^3$ corresponds to line A-96 of Table A and the meaning for the combination of $(R^4)_n$ and $(R^5)_m$ for each individual compound corresponds in each case to one line of Table B (compounds I.A1.A96.B1 to I.A1.A96.B2496).

Table 97a Compounds of the formula I.A1 in which the combination of $R^1$, $R^2$ and $R^3$ corresponds to line A-97 of Table A and the meaning for the combination of $(R^4)_n$ and $(R^5)_m$ for each individual compound corresponds in each case to one line of Table B (compounds I.A1.A97.B1 to I.A1.A97.B2496).

Table 98a Compounds of the formula I.A1 in which the combination of $R^1$, $R^2$ and $R^3$ corresponds to line A-98 of Table A and the meaning for the combination of $(R^4)_n$ and $(R^5)_m$ for each individual compound corresponds in each case to one line of Table B (compounds I.A1.A98.B1 to I.A1.A98.B2496).

Table 99a Compounds of the formula I.A1 in which the combination of $R^1$, $R^2$ and $R^3$ corresponds to line A-99 of Table A and the meaning for the combination of $(R^4)_n$ and $(R^5)_m$ for each individual compound corresponds in each case to one line of Table B (compounds I.A1.A99.B1 to I.A1.A99.B2496).

Table 100a Compounds of the formula I.A1 in which the combination of $R^1$, $R^2$ and $R^3$ corresponds to line A-100 of Table A and the meaning for the combination of $(R^4)_n$ and $(R^5)_m$ for each individual compound corresponds in each case to one line of Table B (compounds I.A1.A100.B1 to I.A1.A100.B2496).

Table 101a Compounds of the formula I.A1 in which the combination of $R^1$, $R^2$ and $R^3$ corresponds to line A-101 of Table A and the meaning for the combination of $(R^4)_n$ and $(R^5)_m$ for each individual compound corresponds in each case to one line of Table B (compounds I.A1.A101.B1 to I.A1.A101.B2496).

Table 102a Compounds of the formula I.A1 in which the combination of $R^1$, $R^2$ and $R^3$ corresponds to line A-102 of Table A and the meaning for the combination of $(R^4)_n$ and $(R^5)_m$ for each individual compound corresponds in each case to one line of Table B (compounds I.A1.A102.B1 to I.A1.A102.B2496).

Table 103a Compounds of the formula I.A1 in which the combination of $R^1$, $R^2$ and $R^3$ corresponds to line A-103 of Table A and the meaning for the combination of $(R^4)_n$ and $(R^5)_m$ for each individual compound corresponds in each case to one line of Table B (compounds I.A1.A103.B1 to I.A1.A103.B2496).

Table 104a Compounds of the formula I.A1 in which the combination of $R^1$, $R^2$ and $R^3$ corresponds to line A-104 of Table A and the meaning for the combination of $(R^4)_n$ and $(R^5)_m$ for each individual compound corresponds in each case to one line of Table B (compounds I.A1.A104.B1 to I.A1.A104.B2496).

Table 105a Compounds of the formula I.A1 in which the combination of $R^1$, $R^2$ and $R^3$ corresponds to line A-105 of Table A and the meaning for the combination of $(R^4)_n$ and $(R^5)_m$ for each individual compound corresponds in each case to one line of Table B (compounds I.A1.A105.B1 to I.A1.A105.B2496).

Table 106a Compounds of the formula I.A1 in which the combination of $R^1$, $R^2$ and $R^3$ corresponds to line A-106 of Table A and the meaning for the combination of $(R^4)_n$ and $(R^5)_m$ for each individual compound corresponds in each case to one line of Table B (compounds I.A1.A106.B1 to I.A1.A106.B2496).

Table 107a Compounds of the formula I.A1 in which the combination of $R^1$, $R^2$ and $R^3$ corresponds to line A-107 of Table A and the meaning for the combination of $(R^4)_n$ and $(R^5)_m$ for each individual compound corresponds in each case to one line of Table B (compounds I.A1.A107.B1 to I.A1.A107.B2496).

Table 108a Compounds of the formula I.A1 in which the combination of $R^1$, $R^2$ and $R^3$ corresponds to line A-108 of Table A and the meaning for the combination of $(R^4)_n$ and $(R^5)_m$ for each individual compound corresponds in each case to one line of Table B (compounds I.A1.A108.B1 to I.A1.A108.B2496).

Table 109a Compounds of the formula I.A1 in which the combination of $R^1$, $R^2$ and $R^3$ corresponds to line A-109 of Table A and the meaning for the combination of $(R^4)_n$ and $(R^5)_m$ for each individual compound corresponds in each case to one line of Table B (compounds I.A1.A109.B1 to I.A1.A109.B2496).

Table 110a Compounds of the formula I.A1 in which the combination of $R^1$, $R^2$ and $R^3$ corresponds to line A-110 of Table A and the meaning for the combination of $(R^4)_n$ and $(R^5)_m$ for each individual compound corresponds in each case to one line of Table B (compounds I.A1.A110.B1 to I.A1.A110.B2496).

Table 111a Compounds of the formula I.A1 in which the combination of $R^1$, $R^2$ and $R^3$ corresponds to line A-111 of Table A and the meaning for the combination of $(R^4)_n$ and $(R^5)_m$ for each individual compound corresponds in each case to one line of Table B (compounds I.A1.A111.B1 to I.A1.A111.B2496).

Table 112a Compounds of the formula I.A1 in which the combination of $R^1$, $R^2$ and $R^3$ corresponds to line A-112 of Table A and the meaning for the combination of $(R^4)_n$ and $(R^5)_m$ for each individual compound corresponds in each case to one line of Table B (compounds I.A1.A112.B1 to I.A1.A112.B2496).

Table 113a Compounds of the formula I.A1 in which the combination of $R^1$, $R^2$ and $R^3$ corresponds to line A-113 of Table A and the meaning for the combination of $(R^4)_n$ and $(R^5)_m$ for each individual compound corresponds in each case to one line of Table B (compounds I.A1.A113.B1 to I.A1.A113.B2496).

Table 114a Compounds of the formula I.A1 in which the combination of $R^1$, $R^2$ and $R^3$ corresponds to line A-114 of Table A and the meaning for the combination of $(R^4)_n$ and $(R^5)_m$ for each individual compound corresponds in each case to one line of Table B (compounds I.A1.A114.B1 to I.A1.A114.B2496).

Table 115a Compounds of the formula I.A1 in which the combination of $R^1$, $R^2$ and $R^3$ corresponds to line A-115 of Table A and the meaning for the combination of $(R^4)_n$ and $(R^5)_m$ for each individual compound corresponds in each case to one line of Table B (compounds I.A1.A115.B1 to I.A1.A115.B2496).

Table 116a Compounds of the formula I.A1 in which the combination of $R^1$, $R^2$ and $R^3$ corresponds to line A-116 of Table A and the meaning for the combination of $(R^4)_n$ and $(R^5)_m$ for each individual compound corresponds in each case to one line of Table B (compounds I.A1.A116.B1 to I.A1.A116.B2496).

Table 117a Compounds of the formula I.A1 in which the combination of $R^1$, $R^2$ and $R^3$ corresponds to line A-117 of Table A and the meaning for the combination of $(R^4)_n$ and $(R^5)_m$ for each individual compound corresponds in each case to one line of Table B (compounds I.A1.A117.B1 to I.A1.A117.B2496).

Table 118a Compounds of the formula I.A1 in which the combination of $R^1$, $R^2$ and $R^3$ corresponds to line A-118 of Table A and the meaning for the combination of $(R^4)_n$ and $(R^5)_m$ for each individual compound corresponds in each case to one line of Table B (compounds I.A1.A118.B1 to I.A1.A118.B2496).

Table 119a Compounds of the formula I.A1 in which the combination of $R^1$, $R^2$ and $R^3$ corresponds to line A-119 of Table A and the meaning for the combination of $(R^4)_n$ and $(R^5)_m$ for each individual compound corresponds in each case to one line of Table B (compounds I.A1.A119.B1 to I.A1.A119.B2496).

Table 120a Compounds of the formula I.A1 in which the combination of $R^1$, $R^2$ and $R^3$ corresponds to line A-120 of Table A and the meaning for the combination of $(R^4)_n$ and $(R^5)_m$ for each individual compound corresponds in each case to one line of Table B (compounds I.A1.A120.B1 to I.A1.A120.B2496).

Table 121a Compounds of the formula I.A1 in which the combination of $R^1$, $R^2$ and $R^3$ corresponds to line A-121 of Table A and the meaning for the combination of $(R^4)_n$ and $(R^5)_m$ for each individual compound corresponds in each case to one line of Table B (compounds I.A1.A121.B1 to I.A1.A121.B2496).

Table 122a Compounds of the formula I.A1 in which the combination of $R^1$, $R^2$ and $R^3$ corresponds to line A-122 of Table A and the meaning for the combination of $(R^4)_n$ and $(R^5)_m$ for each individual compound corresponds in each case to one line of Table B (compounds I.A1.A122.B1 to I.A1.A122.B2496).

Table 123a Compounds of the formula I.A1 in which the combination of $R^1$, $R^2$ and $R^3$ corresponds to line A-123 of Table A and the meaning for the combination of $(R^4)_n$ and $(R^5)_m$ for each individual compound corresponds in each case to one line of Table B (compounds I.A1.A123.B1 to I.A1.A123.B2496).

Table 124a Compounds of the formula I.A1 in which the combination of $R^1$, $R^2$ and $R^3$ corresponds to line A-124 of Table A and the meaning for the combination of $(R^4)_n$ and $(R^5)_m$ for each individual compound corresponds in each case to one line of Table B (compounds I.A1.A124.B1 to I.A1.A124.B2496).

Table 125a Compounds of the formula I.A1 in which the combination of $R^1$, $R^2$ and $R^3$ corresponds to line A-125 of Table A and the meaning for the combination of $(R^4)_n$ and $(R^5)_m$ for each individual compound corresponds in each case to one line of Table B (compounds I.A1.A125.B1 to I.A1.A125.B2496).

Table 126a Compounds of the formula I.A1 in which the combination of $R^1$, $R^2$ and $R^3$ corresponds to line A-126 of Table A and the meaning for the combination of $(R^4)_n$ and $(R^5)_m$ for each individual compound corresponds in each case to one line of Table B (compounds I.A1.A126.B1 to I.A1.A126.B2496).

Table 127a Compounds of the formula I.A1 in which the combination of $R^1$, $R^2$ and $R^3$ corresponds to line A-127 of Table A and the meaning for the combination of $(R^4)_n$ and $(R^5)_m$ for each individual compound corresponds in each case to one line of Table B (compounds I.A1.A127.B1 to I.A1.A127.B2496).

Table 128a Compounds of the formula I.A1 in which the combination of $R^1$, $R^2$ and $R^3$ corresponds to line A-128 of Table A and the meaning for the combination of $(R^4)_n$ and $(R^5)_m$ for each individual compound corresponds in each case to one line of Table B (compounds I.A1.A128.B1 to I.A1.A128.B2496).

Table 129a Compounds of the formula I.A1 in which the combination of $R^1$, $R^2$ and $R^3$ corresponds to line A-129 of Table A and the meaning for the combination of $(R^4)_n$ and $(R^5)_m$ for each individual compound corresponds in each case to one line of Table B (compounds I.A1.A129.B1 to I.A1.A129.B2496).

Table 130a Compounds of the formula I.A1 in which the combination of $R^1$, $R^2$ and $R^3$ corresponds to line A-130 of Table A and the meaning for the combination of $(R^4)_n$ and $(R^5)_m$ for each individual compound corresponds in each case to one line of Table B (compounds I.A1.A130.B1 to I.A1.A130.B2496).

Table 131a Compounds of the formula I.A1 in which the combination of $R^1$, $R^2$ and $R^3$ corresponds to line A-131 of Table A and the meaning for the combination of $(R^4)_n$ and $(R^5)_m$ for each individual compound corresponds in each case to one line of Table B (compounds I.A1.A131.B1 to I.A1.A131.B2496).

Table 132a Compounds of the formula I.A1 in which the combination of $R^1$, $R^2$ and $R^3$ corresponds to line A-132 of Table A and the meaning for the combination of $(R^4)_n$ and $(R^5)_m$ for each individual compound corresponds in each case to one line of Table B (compounds I.A1.A132.B1 to I.A1.A132.B2496).

Table 133a Compounds of the formula I.A1 in which the combination of $R^1$, $R^2$ and $R^3$ corresponds to line A-133 of Table A and the meaning for the combination of $(R^4)_n$ and $(R^5)_m$ for each individual compound corresponds in each case to one line of Table B (compounds I.A1.A133.B1 to I.A1.A133.B2496).

Table 134a Compounds of the formula I.A1 in which the combination of $R^1$, $R^2$ and $R^3$ corresponds to line A-134 of Table A and the meaning for the combination of $(R^4)_n$ and $(R^5)_m$ for each individual compound corresponds in each case to one line of Table B (compounds I.A1.A134.B1 to I.A1.A134.B2496).

Table 135a Compounds of the formula I.A1 in which the combination of $R^1$, $R^2$ and $R^3$ corresponds to line A-135 of Table A and the meaning for the combination of $(R^4)_n$ and $(R^5)_m$ for each individual compound corresponds in each case to one line of Table B (compounds I.A1.A135.B1 to I.A1.A135.B2496).

Table 136a Compounds of the formula I.A1 in which the combination of $R^1$, $R^2$ and $R^3$ corresponds to line A-136 of Table A and the meaning for the combination of $(R^4)_n$ and $(R^5)_m$ for each individual compound corresponds in each case to one line of Table B (compounds I.A1.A136.B1 to I.A1.A136.B2496).

Table 137a Compounds of the formula I.A1 in which the combination of $R^1$, $R^2$ and $R^3$ corresponds to line A-137 of Table A and the meaning for the combination of $(R^4)_n$ and $(R^5)_m$ for each individual compound corresponds in each case to one line of Table B (compounds I.A1.A137.B1 to I.A1.A137.B2496).

Table 138a Compounds of the formula I.A1 in which the combination of $R^1$, $R^2$ and $R^3$ corresponds to line A-138 of Table A and the meaning for the combination of $(R^4)_n$ and $(R^5)_m$ for each individual compound corresponds in each case to one line of Table B (compounds I.A1.A138.B1 to I.A1.A138.B2496).

Table 139a Compounds of the formula I.A1 in which the combination of $R^1$, $R^2$ and $R^3$ corresponds to line A-139 of Table A and the meaning for the combination of $(R^4)_n$ and $(R^5)_m$ for each individual compound corresponds in each case to one line of Table B (compounds I.A1.A139.B1 to I.A1.A139.B2496).

Table 140a Compounds of the formula I.A1 in which the combination of $R^1$, $R^2$ and $R^3$ corresponds to line A-140 of Table A and the meaning for the combination of $(R^4)_n$ and $(R^5)_m$ for each individual compound corresponds in each case to one line of Table B (compounds I.A1.A140.B1 to I.A1.A140.B2496).

Table 141a Compounds of the formula I.A1 in which the combination of $R^1$, $R^2$ and $R^3$ corresponds to line A-141 of Table A and the meaning for the combination of $(R^4)_n$ and $(R^5)_m$ for each individual compound corresponds in each case to one line of Table B (compounds I.A1.A141.B1 to I.A1.A141.B2496).

Table 142a Compounds of the formula I.A1 in which the combination of $R^1$, $R^2$ and $R^3$ corresponds to line A-142 of Table A and the meaning for the combination of $(R^4)_n$ and $(R^5)_m$ for each individual compound corresponds in each case to one line of Table B (compounds I.A1.A142.B1 to I.A1.A142.B2496).

Table 1b Compounds of the formula I.A2 in which the combination of $R^1$, $R^2$ and $R^3$ corresponds to line A-1 of Table A and the meaning for the combination of the combination of $(R^4)_n$ and $(R^5)_m$ for each individual compound corresponds in each case to one line of Table B1 (compounds I.A2.A1.B1-1 to I.A2.A1.B1-2112).

Table 2b Compounds of the formula I.A2 in which the combination of $R^1$, $R^2$ and $R^3$ corresponds to line A-2 of Table A and the meaning for the combination of $(R^4)_n$ and $(R^5)_m$ for each individual compound corresponds in each case to one line of Table B1 (compounds I.A2.A2.B1-1 to I.A2.A2. B1-2112).

Table 3b Compounds of the formula I.A2 in which the combination of $R^1$, $R^2$ and $R^3$ corresponds to line A-3 of Table A and the meaning for the combination of $(R^4)_n$ and $(R^5)_m$ for each individual compound corresponds in each case to one line of Table B1 (compounds I.A2.A3.B1-1 to I.A2.A3.B1-2112).

Table 4b Compounds of the formula I.A2 in which the combination of $R^1$, $R^2$ and $R^3$ corresponds to line A-4 of Table A and the meaning for the combination of $(R^4)_n$ and $(R^5)_m$ for each individual compound corresponds in each case to one line of Table B1 (compounds I.A2.A4.B1-1 to I.A2.A4. B1-2112).

Table 5b Compounds of the formula I.A2 in which the combination of $R^1$, $R^2$ and $R^3$ corresponds to line A-5 of Table A and the meaning for the combination of $(R^4)_n$ and $(R^5)_m$ for each individual compound corresponds in each case to one line of Table B1 (compounds I.A2.A5.B1-1 to I.A2.A5. B1-2112).

Table 6b Compounds of the formula I.A2 in which the combination of $R^1$, $R^2$ and $R^3$ corresponds to line A-6 of Table A and the meaning for the combination of $(R^4)_n$ and ($R^5)_m$ for each individual compound corresponds in each case to one line of Table B1 (compounds I.A2.A6.B1-1 to I.A2.A6. B1-2112).

Table 7b Compounds of the formula I.A2 in which the combination of $R^1$, $R^2$ and $R^3$ corresponds to line A-7 of Table A and the meaning for the combination of $(R^4)_n$ and $(R^5)_m$ for each individual compound corresponds in each case to one line of Table B1 (compounds I.A2.A7.B1-1 to I.A2.A7. B1-2112).

Table 8b Compounds of the formula I.A2 in which the combination of $R^1$, $R^2$ and $R^3$ corresponds to line A-8 of Table A and the meaning for the combination of $(R^4)_n$ and $(R^5)_m$ for each individual compound corresponds in each case to one line of Table B1 (compounds I.A2.A8.B1-1 to I.A2.A8.B1-2112).

Table 9b Compounds of the formula I.A2 in which the combination of $R^1$, $R^2$ and $R^3$ corresponds to line A-9 of Table A and the meaning for the combination of $(R^4)_n$ and $(R^5)_m$ for each individual compound corresponds in each case to one line of Table B1 (compounds I.A2.A9.B1-1 to I.A2.A9.B1-2112).

Table 10b Compounds of the formula I.A2 in which the combination of $R^1$, $R^2$ and $R^3$ corresponds to line A-10 of Table A and the meaning for the combination of $(R^4)_n$ and $(R^5)_m$ for each individual compound corresponds in each case to one line of Table B1 (compounds I.A2.A10.B1-1 to I.A2.A10.B1-2112).

Table 11b Compounds of the formula I.A2 in which the combination of $R^1$, $R^2$ and $R^3$ corresponds to line A-11 of Table A and the meaning for the combination of $(R^4)_n$ and $(R^5)_m$ for each individual compound corresponds in each case to one line of Table B1 (compounds I.A2.A11.B1-1 to I.A2.A11.B1-2112).

Table 12b Compounds of the formula I.A2 in which the combination of $R^1$, $R^2$ and $R^3$ corresponds to line A-12 of Table A and the meaning for the combination of $(R^4)_n$ and $(R^5)_m$ for each individual compound corresponds in each case to one line of Table B1 (compounds I.A2.A12.B1-1 to I.A2.A12.B1-2112).

Table 13b Compounds of the formula I.A2 in which the combination of $R^1$, $R^2$ and $R^3$ corresponds to line A-13 of Table A and the meaning for the combination of $(R^4)_n$ and $(R^5)_m$ for each individual compound corresponds in each case to one line of Table B1 (compounds I.A2.A13.B1-1 to I.A2.A13.B1-2112).

Table 14b Compounds of the formula I.A2 in which the combination of $R^1$, $R^2$ and $R^3$ corresponds to line A-14 of Table A and the meaning for the combination of $(R^4)_n$ and $(R^5)_m$ for each individual compound corresponds in each case to one line of Table B1 (compounds I.A2.A14.B1-1 to I.A2.A14.B1-2112).

Table 15b Compounds of the formula I.A2 in which the combination of $R^1$, $R^2$ and $R^3$ corresponds to line A-15 of Table A and the meaning for the combination of $(R^4)_n$ and $(R^5)_m$ for each individual compound corresponds in each case to one line of Table B1 (compounds I.A2.A15.B1-1 to I.A2.A15.B1-2112).

Table 16b Compounds of the formula I.A2 in which the combination of $R^1$, $R^2$ and $R^3$ corresponds to line A-16 of Table A and the meaning for the combination of $(R^4)_n$ and $(R^5)_m$ for each individual compound corresponds in each case to one line of Table B1 (compounds I.A2.A16.B1-1 to I.A2.A16.B1-2112).

Table 17b Compounds of the formula I.A2 in which the combination of $R^1$, $R^2$ and $R^3$ corresponds to line A-17 of Table A and the meaning for the combination of $(R^4)_n$ and $(R^5)_m$ for each individual compound corresponds in each case to one line of Table B1 (compounds I.A2.A17.B1-1 to I.A2.A17.B1-2112).

Table 18b Compounds of the formula I.A2 in which the combination of $R^1$, $R^2$ and $R^3$ corresponds to line A-18 of Table A and the meaning for the combination of $(R^4)_n$ and $(R^5)_m$ for each individual compound corresponds in each case to one line of Table B1 (compounds I.A2.A18.B1-1 to I.A2.A18.B1-2112).

Table 19b Compounds of the formula I.A2 in which the combination of $R^1$, $R^2$ and $R^3$ corresponds to line A-19 of Table A and the meaning for the combination of $(R^4)_n$ and $(R^5)_m$ for each individual compound corresponds in each case to one line of Table B1 (compounds I.A2.A19.B1-1 to I.A2.A19.B1-2112).

Table 20b Compounds of the formula I.A2 in which the combination of $R^1$, $R^2$ and $R^3$ corresponds to line A-20 of Table A and the meaning for the combination of $(R^4)_n$ and $(R^5)_m$ for each individual compound corresponds in each case to one line of Table B1 (compounds I.A2.A20.B1-1 to I.A2.A20.B1-2112).

Table 21b Compounds of the formula I.A2 in which the combination of $R^1$, $R^2$ and $R^3$ corresponds to line A-21 of Table A and the meaning for the combination of $(R^4)_n$ and $(R^5)_m$ for each individual compound corresponds in each case to one line of Table B1 (compounds I.A2.A21.B1-1 to I.A2.A21.B1-2112).

Table 22b Compounds of the formula I.A2 in which the combination of $R^1$, $R^2$ and $R^3$ corresponds to line A-22 of Table A and the meaning for the combination of $(R^4)_n$ and $(R^5)_m$ for each individual compound corresponds in each case to one line of Table B1 (compounds I.A2.A22.B1-1 to I.A2.A22.B1-2112).

Table 23b Compounds of the formula I.A2 in which the combination of $R^1$, $R^2$ and $R^3$ corresponds to line A-23 of Table A and the meaning for the combination of $(R^4)_n$ and $(R^5)_m$ for each individual compound corresponds in each case to one line of Table B1 (compounds I.A2.A23.B1-1 to I.A2.A23.B1-2112).

Table 24b Compounds of the formula I.A2 in which the combination of $R^1$, $R^2$ and $R^3$ corresponds to line A-24 of Table A and the meaning for the combination of $(R^4)_n$ and $(R^5)_m$ for each individual compound corresponds in each case to one line of Table B1 (compounds I.A2.A24.B1-1 to I.A2.A24.B1-2112).

Table 25b Compounds of the formula I.A2 in which the combination of $R^1$, $R^2$ and $R^3$ corresponds to line A-25 of Table A and the meaning for the combination of $(R^4)_n$ and $(R^5)_m$ for each individual compound corresponds in each case to one line of Table B1 (compounds I.A2.A25.B1-1 to I.A2.A25.B1-2112).

Table 26b Compounds of the formula I.A2 in which the combination of $R^1$, $R^2$ and $R^3$ corresponds to line A-26 of Table A and the meaning for the combination of $(R^4)_n$ and $(R^5)_m$ for each individual compound corresponds in each case to one line of Table B1 (compounds I.A2.A26.B1-1 to I.A2.A26.B1-2112).

Table 27b Compounds of the formula I.A2 in which the combination of $R^1$, $R^2$ and $R^3$ corresponds to line A-27 of Table A and the meaning for the combination of $(R^4)_n$ and $(R^5)_m$ for each individual compound corresponds in each case to one line of Table B1 (compounds I.A2.A27.B1-1 to I.A2.A27.B1-2112).

Table 28b Compounds of the formula I.A2 in which the combination of $R^1$, $R^2$ and $R^3$ corresponds to line A-28 of Table A and the meaning for the combination of $(R^4)_n$ and $(R^5)_m$ for each individual compound corresponds in each case to one line of Table B1 (compounds I.A2.A28.B1-1 to I.A2.A28.B1-2112).

Table 29b Compounds of the formula I.A2 in which the combination of $R^1$, $R^2$ and $R^3$ corresponds to line A-29 of Table A and the meaning for the combination of $(R^4)_n$ and $(R^5)_m$ for each individual compound corresponds in each case to one line of Table B1 (compounds I.A2.A29.B1-1 to I.A2.A29.B1-2112).

Table 30b Compounds of the formula I.A2 in which the combination of $R^1$, $R^2$ and $R^3$ corresponds to line A-30 of Table A and the meaning for the combination of $(R^4)_n$ and $(R^5)_m$ for each individual compound corresponds in each case to one line of Table B1 (compounds I.A2.A30.B1-1 to I.A2.A30.B1-2112).

Table 31b Compounds of the formula I.A2 in which the combination of $R^1$, $R^2$ and $R^3$ corresponds to line A-31 of Table A and the meaning for the combination of $(R^4)_n$ and $(R^5)_m$ for each individual compound corresponds in each case to one line of Table B1 (compounds I.A2.A31.B1-1 to I.A2.A31.B1-2112).

Table 32b Compounds of the formula I.A2 in which the combination of $R^1$, $R^2$ and $R^3$ corresponds to line A-32 of Table A and the meaning for the combination of $(R^4)_n$ and $(R^5)_m$ for each individual compound corresponds in each case to one line of Table B1 (compounds I.A2.A32.B1-1 to I.A2.A32.B1-2112).

Table 33b Compounds of the formula I.A2 in which the combination of $R^1$, $R^2$ and $R^3$ corresponds to line A-33 of Table A and the meaning for the combination of $(R^4)_n$ and $(R^5)_m$ for each individual compound corresponds in each case to one line of Table B1 (compounds I.A2.A33.B1-1 to I.A2.A33.B1-2112).

Table 34b Compounds of the formula I.A2 in which the combination of $R^1$, $R^2$ and $R^3$ corresponds to line A-34 of Table A and the meaning for the combination of $(R^4)_n$ and $(R^5)_m$ for each individual compound corresponds in each case to one line of Table B1 (compounds I.A2.A34.B1-1 to I.A2.A34.B1-2112).

Table 35b Compounds of the formula I.A2 in which the combination of $R^1$, $R^2$ and $R^3$ corresponds to line A-35 of Table A and the meaning for the combination of $(R^4)_n$ and $(R^5)_m$ for each individual compound corresponds in each case to one line of Table B1 (compounds I.A2.A35.B1-1 to I.A2.A35.B1-2112).

Table 36b Compounds of the formula I.A2 in which the combination of $R^1$, $R^2$ and $R^3$ corresponds to line A-36 of Table A and the meaning for the combination of $(R^4)_n$ and $(R^5)_m$ for each individual compound corresponds in each case to one line of Table B1 (compounds I.A2.A36.B1-1 to I.A2.A36.B1-2112).

Table 37b Compounds of the formula I.A2 in which the combination of $R^1$, $R^2$ and $R^3$ corresponds to line A-37 of Table A and the meaning for the combination of $(R^4)_n$ and $(R^5)_m$ for each individual compound corresponds in each case to one line of Table B1 (compounds I.A2.A37.B1-1 to I.A2.A37.B1-2112).

Table 38b Compounds of the formula I.A2 in which the combination of $R^1$, $R^2$ and $R^3$ corresponds to line A-38 of Table A and the meaning for the combination of $(R^4)_n$ and $(R^5)_m$ for each individual compound corresponds in each case to one line of Table B1 (compounds I.A2.A38.B1-1 to I.A2.A38.B1-2112).

Table 39b Compounds of the formula I.A2 in which the combination of $R^1$, $R^2$ and $R^3$ corresponds to line A-39 of Table A and the meaning for the combination of $(R^4)_n$ and $(R^5)_m$ for each individual compound corresponds in each case to one line of Table B1 (compounds I.A2.A39.B1-1 to I.A2.A39.B1-2112).

Table 40b Compounds of the formula I.A2 in which the combination of $R^1$, $R^2$ and $R^3$ corresponds to line A-40 of Table A and the meaning for the combination of $(R^4)_n$ and $(R^5)_m$ for each individual compound corresponds in each case to one line of Table B1 (compounds I.A2.A40.B1-1 to I.A2.A40.B1-2112).

Table 41b Compounds of the formula I.A2 in which the combination of $R^1$, $R^2$ and $R^3$ corresponds to line A-41 of Table A and the meaning for the combination of $(R^4)_n$ and $(R^5)_m$ for each individual compound corresponds in each case to one line of Table B1 (compounds I.A2.A41.B1-1 to I.A2.A41.B1-2112).

Table 42b Compounds of the formula I.A2 in which the combination of $R^1$, $R^2$ and $R^3$ corresponds to line A-42 of Table A and the meaning for the combination of $(R^4)_n$ and $(R^5)_m$ for each individual compound corresponds in each case to one line of Table B1 (compounds I.A2.A42.B1-1 to I.A2.A42.B1-2112).

Table 43b Compounds of the formula I.A2 in which the combination of $R^1$, $R^2$ and $R^3$ corresponds to line A-43 of Table A and the meaning for the combination of $(R^4)_n$ and $(R^5)_m$ for each individual compound corresponds in each case to one line of Table B1 (compounds I.A2.A43.B1-1 to I.A2.A43.B1-2112).

Table 44b Compounds of the formula I.A2 in which the combination of $R^1$, $R^2$ and $R^3$ corresponds to line A-44 of Table A and the meaning for the combination of $(R^4)_n$ and $(R^5)_m$ for each individual compound corresponds in each case to one line of Table B1 (compounds I.A2.A44.B1-1 to I.A2.A44.B1-2112).

Table 45b Compounds of the formula I.A2 in which the combination of $R^1$, $R^2$ and $R^3$ corresponds to line A-45 of Table A and the meaning for the combination of $(R^4)_n$ and $(R^5)_m$ for each individual compound corresponds in each case to one line of Table B1 (compounds I.A2.A45.B1-1 to I.A2.A45.B1-2112).

Table 46b Compounds of the formula I.A2 in which the combination of $R^1$, $R^2$ and $R^3$ corresponds to line A-46 of Table A and the meaning for the combination of $(R^4)_n$ and $(R^5)_m$ for each individual compound corresponds in each case to one line of Table B1 (compounds I.A2.A46.B1-1 to I.A2.A46.B1-2112).

Table 47b Compounds of the formula I.A2 in which the combination of $R^1$, $R^2$ and $R^3$ corresponds to line A-47 of Table A and the meaning for the combination of $(R^4)_n$ and $(R^5)_m$ for each individual compound corresponds in each case to one line of Table B1 (compounds I.A2.A47.B1-1 to I.A2.A47.B1-2112).

Table 48b Compounds of the formula I.A2 in which the combination of $R^1$, $R^2$ and $R^3$ corresponds to line A-48 of Table A and the meaning for the combination of $(R^4)_n$ and $(R^5)_m$ for each individual compound corresponds in each case to one line of Table B1 (compounds I.A2.A48.B1-1 to I.A2.A48.B1-2112).

Table 49b Compounds of the formula I.A2 in which the combination of $R^1$, $R^2$ and $R^3$ corresponds to line A-49 of Table A and the meaning for the combination of $(R^4)_n$ and $(R^5)_m$ for each individual compound corresponds in each case to one line of Table B1 (compounds I.A2.A49.B1-1 to I.A2.A49.B1-2112).

Table 50b Compounds of the formula I.A2 in which the combination of $R^1$, $R^2$ and $R^3$ corresponds to line A-50 of Table A and the meaning for the combination of $(R^4)_n$ and $(R^5)_m$ for each individual compound corresponds in each case to one line of Table B1 (compounds I.A2.A50.B1-1 to I.A2.A50.B1-2112).

Table 51b Compounds of the formula I.A2 in which the combination of $R^1$, $R^2$ and $R^3$ corresponds to line A-51 of Table A and the meaning for the combination of $(R^4)_n$ and $(R^5)_m$ for each individual compound corresponds in each case to one line of Table B1 (compounds I.A2.A51.B1-1 to I.A2.A51.B1-2112).

Table 52b Compounds of the formula I.A2 in which the combination of $R^1$, $R^2$ and $R^3$ corresponds to line A-52 of Table A and the meaning for the combination of $(R^4)_n$ and $(R^5)_m$ for each individual compound corresponds in each case to one line of Table B1 (compounds I.A2.A52.B1-1 to I.A2.A52.B1-2112).

Table 53b Compounds of the formula I.A2 in which the combination of $R^1$, $R^2$ and $R^3$ corresponds to line A-53 of Table A and the meaning for the combination of $(R^4)_n$ and $(R^5)_m$ for each individual compound corresponds in each case to one line of Table B1 (compounds I.A2.A53.B1-1 to I.A2.A53.B1-2112).

Table 54b Compounds of the formula I.A2 in which the combination of $R^1$, $R^2$ and $R^3$ corresponds to line A-54 of Table A and the meaning for the combination of $(R^4)_n$ and $(R^5)_m$ for each individual compound corresponds in each case to one line of Table B1 (compounds I.A2.A54.B1-1 to I.A2.A54.B1-2112).

Table 55b Compounds of the formula I.A2 in which the combination of $R^1$, $R^2$ and $R^3$ corresponds to line A-55 of Table A and the meaning for the combination of $(R^4)_n$ and $(R^5)_m$ for each individual compound corresponds in each case to one line of Table B1 (compounds I.A2.A55.B1-1 to I.A2.A55.B1-2112).

Table 56b Compounds of the formula I.A2 in which the combination of $R^1$, $R^2$ and $R^3$ corresponds to line A-56 of Table A and the meaning for the combination of $(R^4)_n$ and $(R^5)_m$ for each individual compound corresponds in each case to one line of Table B1 (compounds I.A2.A56.B1-1 to I.A2.A56.B1-2112).

Table 57b Compounds of the formula I.A2 in which the combination of $R^1$, $R^2$ and $R^3$ corresponds to line A-57 of Table A and the meaning for the combination of $(R^4)_n$ and $(R^5)_m$ for each individual compound corresponds in each case to one line of Table B1 (compounds I.A2.A57.B1-1 to I.A2.A57.B1-2112).

Table 58b Compounds of the formula I.A2 in which the combination of $R^1$, $R^2$ and $R^3$ corresponds to line A-58 of Table A and the meaning for the combination of $(R^4)_n$ and $(R^5)_m$ for each individual compound corresponds in each case to one line of Table B1 (compounds I.A2.A58.B1-1 to I.A2.A58.B1-2112).

Table 59b Compounds of the formula I.A2 in which the combination of $R^1$, $R^2$ and $R^3$ corresponds to line A-59 of Table A and the meaning for the combination of $(R^4)_n$ and $(R^5)_m$ for each individual compound corresponds in each case to one line of Table B1 (compounds I.A2.A59.B1-1 to I.A2.A59.B1-2112).

Table 60b Compounds of the formula I.A2 in which the combination of $R^1$, $R^2$ and $R^3$ corresponds to line A-60 of Table A and the meaning for the combination of $(R^4)_n$ and $(R^5)_m$ for each individual compound corresponds in each case to one line of Table B1 (compounds I.A2.A60.B1-1 to I.A2.A60.B1-2112).

Table 61b Compounds of the formula I.A2 in which the combination of $R^1$, $R^2$ and $R^3$ corresponds to line A-61 of Table A and the meaning for the combination of $(R^4)_n$ and $(R^5)_m$ for each individual compound corresponds in each case to one line of Table B1 (compounds I.A2.A61.B1-1 to I.A2.A61.B1-2112).

Table 62b Compounds of the formula I.A2 in which the combination of $R^1$, $R^2$ and $R^3$ corresponds to line A-62 of Table A and the meaning for the combination of $(R^4)_n$ and $(R^5)_m$ for each individual compound corresponds in each case to one line of Table B1 (compounds I.A2.A62.B1-1 to I.A2.A62.B1-2112).

Table 63b Compounds of the formula I.A2 in which the combination of $R^1$, $R^2$ and $R^3$ corresponds to line A-63 of Table A and the meaning for the combination of $(R^4)_n$ and $(R^5)_m$ for each individual compound corresponds in each case to one line of Table B1 (compounds I.A2.A63.B1-1 to I.A2.A63.B1-2112).

Table 64b Compounds of the formula I.A2 in which the combination of $R^1$, $R^2$ and $R^3$ corresponds to line A-64 of Table A and the meaning for the combination of $(R^4)_n$ and $(R^5)_m$ for each individual compound corresponds in each case to one line of Table B1 (compounds I.A2.A64.B1-1 to I.A2.A64.B1-2112).

Table 65b Compounds of the formula I.A2 in which the combination of $R^1$, $R^2$ and $R^3$ corresponds to line A-65 of Table A and the meaning for the combination of $(R^4)_n$ and $(R^5)_m$ for each individual compound corresponds in each case to one line of Table B1 (compounds I.A2.A65.B1-1 to I.A2.A65.B1-2112).

Table 66b Compounds of the formula I.A2 in which the combination of $R^1$, $R^2$ and $R^3$ corresponds to line A-66 of Table A and the meaning for the combination of $(R^4)_n$ and $(R^5)_m$ for each individual compound corresponds in each case to one line of Table B1 (compounds I.A2.A66.B1-1 to I.A2.A66.B1-2112).

Table 67b Compounds of the formula I.A2 in which the combination of $R^1$, $R^2$ and $R^3$ corresponds to line A-67 of Table A and the meaning for the combination of $(R^4)_n$ and $(R^5)_m$ for each individual compound corresponds in each case to one line of Table B1 (compounds I.A2.A67.B1-1 to I.A2.A67.B1-2112).

Table 68b Compounds of the formula I.A2 in which the combination of $R^1$, $R^2$ and $R^3$ corresponds to line A-68 of Table A and the meaning for the combination of $(R^4)_n$ and $(R^5)_m$ for each individual compound corresponds in each case to one line of Table B1 (compounds I.A2.A68.B1-1 to I.A2.A68.B1-2112).

Table 69b Compounds of the formula I.A2 in which the combination of $R^1$, $R^2$ and $R^3$ corresponds to line A-69 of Table A and the meaning for the combination of $(R^4)_n$ and $(R^5)_m$ for each individual compound corresponds in each case to one line of Table B1 (compounds I.A2.A69.B1-1 to I.A2.A69.B1-2112).

Table 70b Compounds of the formula I.A2 in which the combination of $R^1$, $R^2$ and $R^3$ corresponds to line A-70 of Table A and the meaning for the combination of $(R^4)_n$ and $(R^5)_m$ for each individual compound corresponds in each case to one line of Table B1 (compounds I.A2.A70.B1-1 to I.A2.A70.B1-2112).

Table 71b Compounds of the formula I.A2 in which the combination of $R^1$, $R^2$ and $R^3$ corresponds to line A-71 of Table A and the meaning for the combination of $(R^4)_n$ and $(R^5)_m$ for each individual compound corresponds in each case to one line of Table B1 (compounds I.A2.A71.B1-1 to I.A2.A71.B1-2112).

Table 72b Compounds of the formula I.A2 in which the combination of $R^1$, $R^2$ and $R^3$ corresponds to line A-72 of Table A and the meaning for the combination of $(R^4)_n$ and $(R^5)_m$ for each individual compound corresponds in each case to one line of Table B1 (compounds I.A2.A72.B1-1 to I.A2.A72.B1-2112).

Table 73b Compounds of the formula I.A2 in which the combination of $R^1$, $R^2$ and $R^3$ corresponds to line A-73 of Table A and the meaning for the combination of $(R^4)_n$ and $(R^5)_m$ for each individual compound corresponds in each case to one line of Table B1 (compounds I.A2.A73.B1-1 to I.A2.A73.B1-2112).

Table 74b Compounds of the formula I.A2 in which the combination of $R^1$, $R^2$ and $R^3$ corresponds to line A-74 of Table A and the meaning for the combination of $(R^4)_n$ and $(R^5)_m$ for each individual compound corresponds in each case to one line of Table B1 (compounds I.A2.A74.B1-1 to I.A2.A74.B1-2112).

Table 75b Compounds of the formula I.A2 in which the combination of $R^1$, $R^2$ and $R^3$ corresponds to line A-75 of Table A and the meaning for the combination of $(R^4)_n$ and $(R^5)_m$ for each individual compound corresponds in each case to one line of Table B1 (compounds I.A2.A75.B1-1 to I.A2.A75.B1-2112).

Table 76b Compounds of the formula I.A2 in which the combination of $R^1$, $R^2$ and $R^3$ corresponds to line A-76 of Table A and the meaning for the combination of $(R^4)_n$ and $(R^5)_m$ for each individual compound corresponds in each case to one line of Table B1 (compounds I.A2.A76.B1-1 to I.A2.A76.B1-2112).

Table 77b Compounds of the formula I.A2 in which the combination of $R^1$, $R^2$ and $R^3$ corresponds to line A-77 of Table A and the meaning for the combination of $(R^4)_n$ and $(R^5)_m$ for each individual compound corresponds in each case to one line of Table B1 (compounds I.A2.A77.B1-1 to I.A2.A77.B1-2112).

Table 78b Compounds of the formula I.A2 in which the combination of $R^1$, $R^2$ and $R^3$ corresponds to line A-78 of Table A and the meaning for the combination of $(R^4)_n$ and $(R^5)_m$ for each individual compound corresponds in each case to one line of Table B1 (compounds I.A2.A78.B1-1 to I.A2.A78.B1-2112).

Table 79b Compounds of the formula I.A2 in which the combination of $R^1$, $R^2$ and $R^3$ corresponds to line A-79 of Table A and the meaning for the combination of $(R^4)_n$ and $(R^5)_m$ for each individual compound corresponds in each case to one line of Table B1 (compounds I.A2.A79.B1-1 to I.A2.A79.B1-2112).

Table 80b Compounds of the formula I.A2 in which the combination of $R^1$, $R^2$ and $R^3$ corresponds to line A-80 of Table A and the meaning for the combination of $(R^4)_n$ and $(R^5)_m$ for each individual compound corresponds in each case to one line of Table B1 (compounds I.A2.A80.B1-1 to I.A2.A80.B1-2112).

Table 81b Compounds of the formula I.A2 in which the combination of $R^1$, $R^2$ and $R^3$ corresponds to line A-81 of Table A and the meaning for the combination of $(R^4)_n$ and $(R^5)_m$ for each individual compound corresponds in each case to one line of Table B1 (compounds I.A2.A81.B1-1 to I.A2.A81.B1-2112).

Table 82b Compounds of the formula I.A2 in which the combination of $R^1$, $R^2$ and $R^3$ corresponds to line A-82 of Table A and the meaning for the combination of $(R^4)_n$ and $(R^5)_m$ for each individual compound corresponds in each case to one line of Table B1 (compounds I.A2.A82.B1-1 to I.A2.A82.B1-2112).

Table 83b Compounds of the formula I.A2 in which the combination of $R^1$, $R^2$ and $R^3$ corresponds to line A-83 of Table A and the meaning for the combination of $(R^4)_n$ and $(R^5)_m$ for each individual compound corresponds in each case to one line of Table B1 (compounds I.A2.A83.B1-1 to I.A2.A83.B1-2112).

Table 84b Compounds of the formula I.A2 in which the combination of $R^1$, $R^2$ and $R^3$ corresponds to line A-84 of Table A and the meaning for the combination of $(R^4)_n$ and $(R^5)_m$ for each individual compound corresponds in each case to one line of Table B1 (compounds I.A2.A84.B1-1 to I.A2.A84.B1-2112).

Table 85b Compounds of the formula I.A2 in which the combination of $R^1$, $R^2$ and $R^3$ corresponds to line A-85 of Table A and the meaning for the combination of $(R^4)_n$ and $(R^5)_m$ for each individual compound corresponds in each case to one line of Table B1 (compounds I.A2.A85.B1-1 to I.A2.A85.B1-2112).

Table 86b Compounds of the formula I.A2 in which the combination of $R^1$, $R^2$ and $R^3$ corresponds to line A-86 of Table A and the meaning for the combination of $(R^4)_n$ and $(R^5)_m$ for each individual compound corresponds in each case to one line of Table B1 (compounds I.A2.A86.B1-1 to I.A2.A86.B1-2112).

Table 87b Compounds of the formula I.A2 in which the combination of $R^1$, $R^2$ and $R^3$ corresponds to line A-87 of Table A and the meaning for the combination of $(R^4)_n$ and $(R^5)_m$ for each individual compound corresponds in each case to one line of Table B1 (compounds I.A2.A87.B1-1 to I.A2.A87.B1-2112).

Table 88b Compounds of the formula I.A2 in which the combination of $R^1$, $R^2$ and $R^3$ corresponds to line A-88 of Table A and the meaning for the combination of $(R^4)_n$ and $(R^5)_m$ for each individual compound corresponds in each case to one line of Table B1 (compounds I.A2.A88.B1-1 to I.A2.A88.B1-2112).

Table 89b Compounds of the formula I.A2 in which the combination of $R^1$, $R^2$ and $R^3$ corresponds to line A-89 of Table A and the meaning for the combination of $(R^4)_n$ and $(R^5)_m$ for each individual compound corresponds in each case to one line of Table B1 (compounds I.A2.A89.B1-1 to I.A2.A89.B1-2112).

Table 90b Compounds of the formula I.A2 in which the combination of $R^1$, $R^2$ and $R^3$ corresponds to line A-90 of Table A and the meaning for the combination of $(R^4)_n$ and $(R^5)_m$ for each individual compound corresponds in each case to one line of Table B1 (compounds I.A2.A90.B1-1 to I.A2.A90.B1-2112).

Table 91b Compounds of the formula I.A2 in which the combination of $R^1$, $R^2$ and $R^3$ corresponds to line A-91 of Table A and the meaning for the combination of $(R^4)_n$ and $(R^5)_m$ for each individual compound corresponds in each case to one line of Table B1 (compounds I.A2.A91.B1-1 to I.A2.A91.B1-2112).

Table 92b Compounds of the formula I.A2 in which the combination of $R^1$, $R^2$ and $R^3$ corresponds to line A-92 of Table A and the meaning for the combination of $(R^4)_n$ and $(R^5)_m$ for each individual compound corresponds in each case to one line of Table B1 (compounds I.A2.A92.B1-1 to I.A2.A92.B1-2112).

Table 93b Compounds of the formula I.A2 in which the combination of $R^1$, $R^2$ and $R^3$ corresponds to line A-93 of Table A and the meaning for the combination of $(R^4)_n$ and $(R^5)_m$ for each individual compound corresponds in each case to one line of Table B1 (compounds I.A2.A93.B1-1 to I.A2.A93.B1-2112).

Table 94b Compounds of the formula I.A2 in which the combination of $R^1$, $R^2$ and $R^3$ corresponds to line A-94 of Table A and the meaning for the combination of $(R^4)_n$ and ($R^5)_m$ for each individual compound corresponds in each case to one line of Table B1 (compounds I.A2.A94.B1-1 to I.A2.A94.B1-2112).

Table 95b Compounds of the formula I.A2 in which the combination of $R^1$, $R^2$ and $R^3$ corresponds to line A-95 of Table A and the meaning for the combination of $(R^4)_n$ and $(R^5)_m$ for each individual compound corresponds in each case to one line of Table B1 (compounds I.A2.A95.B1-1 to I.A2.A95.B1-2112).

Table 96b Compounds of the formula I.A2 in which the combination of $R^1$, $R^2$ and $R^3$ corresponds to line A-96 of Table A and the meaning for the combination of $(R^4)_n$ and $(R^5)_m$ for each individual compound corresponds in each case to one line of Table B1 (compounds I.A2.A96.B1-1 to I.A2.A96.B1-2112).

Table 97b Compounds of the formula I.A2 in which the combination of $R^1$, $R^2$ and $R^3$ corresponds to line A-97 of Table A and the meaning for the combination of $(R^4)_n$ and $(R^5)_m$ for each individual compound corresponds in each case to one line of Table B1 (compounds I.A2.A97.B1-1 to I.A2.A97.B1-2112).

Table 98b Compounds of the formula I.A2 in which the combination of $R^1$, $R^2$ and $R^3$ corresponds to line A-98 of Table A and the meaning for the combination of $(R^4)_n$ and $(R^5)_m$ for each individual compound corresponds in each case to one line of Table B1 (compounds I.A2.A98.B1-1 to I.A2.A98.B1-2112).

Table 99b Compounds of the formula I.A2 in which the combination of $R^1$, $R^2$ and $R^3$ corresponds to line A-99 of Table A and the meaning for the combination of $(R^4)_n$ and $(R^5)_m$ for each individual compound corresponds in each case to one line of Table B1 (compounds I.A2.A99.B1-1 to I.A2.A99.B1-2112).

Table 100b Compounds of the formula I.A2 in which the combination of $R^1$, $R^2$ and $R^3$ corresponds to line A-100 of Table A and the meaning for the combination of $(R^4)_n$ and $(R^5)_m$ for each individual compound corresponds in each case to one line of Table B1 (compounds I.A2.A100.B1-1 to I.A2.A100.B1-2112).

Table 101b Compounds of the formula I.A2 in which the combination of $R^1$, $R^2$ and $R^3$ corresponds to line A-101 of Table A and the meaning for the combination of $(R^4)_n$ and $(R^5)_m$ for each individual compound corresponds in each case to one line of Table B1 (compounds I.A2.A101.B1-1 to I.A2.A101.B1-2112).

Table 102b Compounds of the formula I.A2 in which the combination of $R^1$, $R^2$ and $R^3$ corresponds to line A-102 of Table A and the meaning for the combination of $(R^4)_n$ and $(R^5)_m$ for each individual compound corresponds in each case to one line of Table B1 (compounds I.A2.A102.B1-1 to I.A2.A102.B1-2112).

Table 103b Compounds of the formula I.A2 in which the combination of $R^1$, $R^2$ and $R^3$ corresponds to line A-103 of Table A and the meaning for the combination of $(R^4)_n$ and $(R^5)_m$ for each individual compound corresponds in each case to one line of Table B1 (compounds I.A2.A103.B1-1 to I.A2.A103.B1-2112).

Table 104b Compounds of the formula I.A2 in which the combination of $R^1$, $R^2$ and $R^3$ corresponds to line A-104 of Table A and the meaning for the combination of $(R^4)_n$ and $(R^5)_m$ for each individual compound corresponds in each case to one line of Table B1 (compounds I.A2.A104.B1-1 to I.A2.A104.B1-2112).

Table 105b Compounds of the formula I.A2 in which the combination of $R^1$, $R^2$ and $R^3$ corresponds to line A-105 of Table A and the meaning for the combination of $(R^4)_n$ and $(R^5)_m$ for each individual compound corresponds in each case to one line of Table B1 (compounds I.A2.A105.B1-1 to I.A2.A105.B1-2112).

Table 106b Compounds of the formula I.A2 in which the combination of $R^1$, $R^2$ and $R^3$ corresponds to line A-106 of Table A and the meaning for the combination of $(R^4)_n$ and $(R^5)_m$ for each individual compound corresponds in each case to one line of Table B1 (compounds I.A2.A106.B1-1 to I.A2.A106.B1-2112).

Table 107b Compounds of the formula I.A2 in which the combination of $R^1$, $R^2$ and $R^3$ corresponds to line A-107 of Table A and the meaning for the combination of $(R^4)_n$ and $(R^5)_m$ for each individual compound corresponds in each case to one line of Table B1 (compounds I.A2.A107.B1-1 to I.A2.A107.B1-2112).

Table 108b Compounds of the formula I.A2 in which the combination of $R^1$, $R^2$ and $R^3$ corresponds to line A-108 of Table A and the meaning for the combination of $(R^4)_n$ and $(R^5)_m$ for each individual compound corresponds in each case to one line of Table B1 (compounds I.A2.A108.B1-1 to I.A2.A108.B1-2112).

Table 109b Compounds of the formula I.A2 in which the combination of $R^1$, $R^2$ and $R^3$ corresponds to line A-109 of Table A and the meaning for the combination of $(R^4)_n$ and $(R^5)_m$ for each individual compound corresponds in each case to one line of Table B1 (compounds I.A2.A109.B1-1 to I.A2.A109.B1-2112).

Table 110b Compounds of the formula I.A2 in which the combination of $R^1$, $R^2$ and $R^3$ corresponds to line A-110 of Table A and the meaning for the combination of $(R^4)_n$ and $(R^5)_m$ for each individual compound corresponds in each case to one line of Table B1 (compounds I.A2.A110.B1-1 to I.A2.A110.B1-2112).

Table 111 b Compounds of the formula I.A2 in which the combination of $R^1$, $R^2$ and $R^3$ corresponds to line A-111 of Table A and the meaning for the combination of $(R^4)_n$ and $(R^5)_m$ for each individual compound corresponds in each case to one line of Table B1 (compounds I.A2.A111.B1-1 to I.A2.A111.B1-2112).

Table 112b Compounds of the formula I.A2 in which the combination of $R^1$, $R^2$ and $R^3$ corresponds to line A-112 of Table A and the meaning for the combination of $(R^4)_n$ and $(R^5)_m$ for each individual compound corresponds in each case to one line of Table B1 (compounds I.A2.A112.B1-1 to I.A2.A112.B1-2112).

Table 113b Compounds of the formula I.A2 in which the combination of $R^1$, $R^2$ and $R^3$ corresponds to line A-113 of Table A and the meaning for the combination of $(R^4)_n$ and $(R^5)_m$ for each individual compound corresponds in each case to one line of Table B1 (compounds I.A2.A113.B1-1 to I.A2.A113.B1-2112).

Table 114b Compounds of the formula I.A2 in which the combination of $R^1$, $R^2$ and $R^3$ corresponds to line A-114 of Table A and the meaning for the combination of $(R^4)_n$ and $(R^5)_m$ for each individual compound corresponds in each case to one line of Table B1 (compounds I.A2.A114.B1-1 to I.A2.A114.B1-2112).

Table 115b Compounds of the formula I.A2 in which the combination of $R^1$, $R^2$ and $R^3$ corresponds to line A-115 of Table A and the meaning for the combination of $(R^4)_n$ and $(R^5)_m$ for each individual compound corresponds in each case to one line of Table B1 (compounds I.A2.A115.B1-1 to I.A2.A115.B1-2112).

Table 116b Compounds of the formula I.A2 in which the combination of $R^1$, $R^2$ and $R^3$ corresponds to line A-116 of Table A and the meaning for the combination of $(R^4)_n$ and Table 117b Compounds of the formula I.A2 in which the combination of $R^1$, $R^2$ and $R^3$ corresponds to line A-117 of Table A and the meaning for the combination of $(R^4)_n$ and $(R^5)_m$ for each individual compound corresponds in each case to one line of Table B1 (compounds I.A2.A117.B1-1 to I.A2.A117.B1-2112).

Table 118b Compounds of the formula I.A2 in which the combination of $R^1$, $R^2$ and $R^3$ corresponds to line A-118 of Table A and the meaning for the combination of $(R^4)_n$ and $(R^5)_m$ for each individual compound corresponds in each case to one line of Table B1 (compounds I.A2.A118.B1-1 to I.A2.A118.B1-2112).

Table 119b Compounds of the formula I.A2 in which the combination of $R^1$, $R^2$ and $R^3$ corresponds to line A-119 of Table A and the meaning for the combination of $(R^4)_n$ and $(R^5)_m$ for each individual compound corresponds in each case to one line of Table B1 (compounds I.A2.A119.B1-1 to I.A2.A119.B1-2112).

Table 120b Compounds of the formula I.A2 in which the combination of $R^1$, $R^2$ and $R^3$ corresponds to line A-120 of Table A and the meaning for the combination of $(R^4)_n$ and $(R^5)_m$ for each individual compound corresponds in each case to one line of Table B1 (compounds I.A2.A120.B1-1 to I.A2.A120.B1-2112).

Table 121b Compounds of the formula I.A2 in which the combination of $R^1$, $R^2$ and $R^3$ corresponds to line A-121 of Table A and the meaning for the combination of $(R^4)_n$ and $(R^5)_m$ for each individual compound corresponds in each case to one line of Table B1 (compounds I.A2.A121.B1-1 to I.A2.A121.B1-2112).

Table 122b Compounds of the formula I.A2 in which the combination of $R^1$, $R^2$ and $R^3$ corresponds to line A-122 of Table A and the meaning for the combination of $(R^4)_n$ and $(R^5)_m$ for each individual compound corresponds in each case to one line of Table B1 (compounds I.A2.A122.B1-1 to I.A2.A122.B1-2112).

Table 123b Compounds of the formula I.A2 in which the combination of $R^1$, $R^2$ and $R^3$ corresponds to line A-123 of Table A and the meaning for the combination of $(R^4)_n$ and $(R^5)_m$ for each individual compound corresponds in each case to one line of Table B1 (compounds I.A2.A123.B1-1 to I.A2.A123.B1-2112).

Table 124b Compounds of the formula I.A2 in which the combination of $R^1$, $R^2$ and $R^3$ corresponds to line A-124 of Table A and the meaning for the combination of $(R^4)_n$ and $(R^5)_m$ for each individual compound corresponds in each case to one line of Table B1 (compounds I.A2.A124.B1-1 to I.A2.A124.B1-2112).

Table 125b Compounds of the formula I.A2 in which the combination of $R^1$, $R^2$ and $R^3$ corresponds to line A-125 of Table A and the meaning for the combination of $(R^4)_n$ and $(R^5)_m$ for each individual compound corresponds in each case to one line of Table B1 (compounds I.A2.A125.B1-1 to I.A2.A125.B1-2112).

Table 126b Compounds of the formula I.A2 in which the combination of $R^1$, $R^2$ and $R^3$ corresponds to line A-126 of Table A and the meaning for the combination of $(R^4)_n$ and $(R^5)_m$ for each individual compound corresponds in each case to one line of Table B1 (compounds I.A2.A126.B1-1 to I.A2.A126.B1-2112).

Table 127b Compounds of the formula I.A2 in which the combination of $R^1$, $R^2$ and $R^3$ corresponds to line A-127 of Table A and the meaning for the combination of $(R^4)_n$ and $(R^5)_m$ for each individual compound corresponds in each case to one line of Table B1 (compounds I.A2.A127.B1-1 to I.A2.A127.B1-2112).

Table 128b Compounds of the formula I.A2 in which the combination of $R^1$, $R^2$ and $R^3$ corresponds to line A-128 of Table A and the meaning for the combination of $(R^4)_n$ and $(R^5)_m$ for each individual compound corresponds in each case to one line of Table B1 (compounds I.A2.A128.B1-1 to I.A2.A128.B1-2112).

Table 129b Compounds of the formula I.A2 in which the combination of $R^1$, $R^2$ and $R^3$ corresponds to line A-129 of Table A and the meaning for the combination of $(R^4)_n$ and $(R^5)_m$ for each individual compound corresponds in each case to one line of Table B1 (compounds I.A2.A129.B1-1 to I.A2.A129.B1-2112).

Table 130b Compounds of the formula I.A2 in which the combination of $R^1$, $R^2$ and $R^3$ corresponds to line A-130 of Table A and the meaning for the combination of $(R^4)_n$ and $(R^5)_m$ for each individual compound corresponds in each case to one line of Table B1 (compounds I.A2.A130.B1-1 to I.A2.A130.B1-2112).

Table 131b Compounds of the formula I.A2 in which the combination of $R^1$, $R^2$ and $R^3$ corresponds to line A-131 of Table A and the meaning for the combination of $(R^4)_n$ and $(R^5)_m$ for each individual compound corresponds in each case to one line of Table B1 (compounds I.A2.A131.B1-1 to I.A2.A131.B1-2112).

Table 132b Compounds of the formula I.A2 in which the combination of $R^1$, $R^2$ and $R^3$ corresponds to line A-132 of Table A and the meaning for the combination of $(R^4)_n$ and $(R^5)_m$ for each individual compound corresponds in each case to one line of Table B1 (compounds I.A2.A132.B1-1 to I.A2.A132.B1-2112).

Table 133b Compounds of the formula I.A2 in which the combination of $R^1$, $R^2$ and $R^3$ corresponds to line A-133 of Table A and the meaning for the combination of $(R^4)_n$ and $(R^5)_m$ for each individual compound corresponds in each case to one line of Table B1 (compounds I.A2.A133.B1-1 to I.A2.A133.B1-2112).

Table 134b Compounds of the formula I.A2 in which the combination of $R^1$, $R^2$ and $R^3$ corresponds to line A-134 of Table A and the meaning for the combination of $(R^4)_n$ and $(R^5)_m$ for each individual compound corresponds in each case to one line of Table B1 (compounds I.A2.A134.B1-1 to I.A2.A134.B1-2112).

Table 135b Compounds of the formula I.A2 in which the combination of $R^1$, $R^2$ and $R^3$ corresponds to line A-135 of Table A and the meaning for the combination of $(R^4)_n$ and $(R^5)_m$ for each individual compound corresponds in each case to one line of Table B1 (compounds I.A2.A135.B1-1 to I.A2.A135.B1-2112).

Table 136b Compounds of the formula I.A2 in which the combination of $R^1$, $R^2$ and $R^3$ corresponds to line A-136 of Table A and the meaning for the combination of $(R^4)_n$ and $(R^5)_m$ for each individual compound corresponds in each case to one line of Table B1 (compounds I.A2.A136.B1-1 to I.A2.A136.B1-2112).

Table 137b Compounds of the formula I.A2 in which the combination of $R^1$, $R^2$ and $R^3$ corresponds to line A-137 of Table A and the meaning for the combination of $(R^4)_n$ and $(R^5)_m$ for each individual compound corresponds in each case to one line of Table B1 (compounds I.A2.A137.B1-1 to I.A2.A137.B1-2112).

Table 138b Compounds of the formula I.A2 in which the combination of $R^1$, $R^2$ and $R^3$ corresponds to line A-138 of Table A and the meaning for the combination of $(R^4)_n$ and ($R^5$)$_m$ for each individual compound corresponds in each case to one line of Table B1 (compounds I.A2.A138.B1-1 to I.A2.A138.B1-2112).

Table 139b Compounds of the formula I.A2 in which the combination of $R^1$, $R^2$ and $R^3$ corresponds to line A-139 of Table A and the meaning for the combination of ($R^4$)$_n$ and ($R^5$)$_m$ for each individual compound corresponds in each case to one line of Table B1 (compounds I.A2.A139.B1-1 to I.A2.A139.B1-2112).

Table 140b Compounds of the formula I.A2 in which the combination of $R^1$, $R^2$ and $R^3$ corresponds to line A-140 of Table A and the meaning for the combination of ($R^4$)$_n$ and ($R^5$)$_m$ for each individual compound corresponds in each case to one line of Table B1 (compounds I.A2.A140.B1-1 to I.A2.A140.B1-2112).

Table 141b Compounds of the formula I.A2 in which the combination of $R^1$, $R^2$ and $R^3$ corresponds to line A-141 of Table A and the meaning for the combination of ($R^4$)$_n$ and ($R^5$)$_m$ for each individual compound corresponds in each case to one line of Table B1 (compounds I.A2.A141.B1-1 to I.A2.A141.B1-2112).

Table 142b Compounds of the formula I.A2 in which the combination of $R^1$, $R^2$ and $R^3$ corresponds to line A-142 of Table A and the meaning for the combination of ($R^4$)$_n$ and ($R^5$)$_m$ for each individual compound corresponds in each case to one line of Table B1 (compounds I.A2.A142.B1-1 to I.A2.A142.B1-2112).

Table 1c Compounds of the formula I.C1 in which the combination of $R^1$, $R^2$ and $R^3$ corresponds to line A-1 of Table A and the meaning for the combination of the combination of ($R^4$)$_n$ and ($R^5$)$_m$ for each individual compound corresponds in each case to one line of Table B (compounds I.C1.A1.B1 to I.C1.A1.B2496).

Table 2c Compounds of the formula I.C1 in which the combination of $R^1$, $R^2$ and $R^3$ corresponds to line A-2 of Table A and the meaning for the combination of ($R^4$)$_n$ and ($R^5$)$_m$ for each individual compound corresponds in each case to one line of Table B (compounds I.C1.A2.B1 to I.C1.A2.B2496).

Table 3c Compounds of the formula I.C1 in which the combination of $R^1$, $R^2$ and $R^3$ corresponds to line A-3 of Table A and the meaning for the combination of ($R^4$)$_n$ and ($R^5$)$_m$ for each individual compound corresponds in each case to one line of Table B (compounds I.C1.A3.B1 to I.C1.A3.B2496).

Table 4c Compounds of the formula I.C1 in which the combination of $R^1$, $R^2$ and $R^3$ corresponds to line A-4 of Table A and the meaning for the combination of ($R^4$)$_n$ and ($R^5$)$_m$ for each individual compound corresponds in each case to one line of Table B (compounds I.C1.A4.B1 to I.C1.A4.B2496).

Table 5c Compounds of the formula I.C1 in which the combination of $R^1$, $R^2$ and $R^3$ corresponds to line A-5 of Table A and the meaning for the combination of ($R^4$)$_n$ and ($R^5$)$_m$ for each individual compound corresponds in each case to one line of Table B (compounds I.C1.A5.B1 to I.C1.A5.B2496).

Table 6c Compounds of the formula I.C1 in which the combination of $R^1$, $R^2$ and $R^3$ corresponds to line A-6 of Table A and the meaning for the combination of ($R^4$)$_n$ and ($R^5$)$_m$ for each individual compound corresponds in each case to one line of Table B (compounds I.C1.A6.B1 to I.C1.A6.B2496).

Table 7c Compounds of the formula I.C1 in which the combination of $R^1$, $R^2$ and $R^3$ corresponds to line A-7 of Table A and the meaning for the combination of ($R^4$)$_n$ and ($R^5$)$_m$ for each individual compound corresponds in each case to one line of Table B (compounds I.C1.A7.B1 to I.C1.A7.B2496).

Table 8c Compounds of the formula I.C1 in which the combination of $R^1$, $R^2$ and $R^3$ corresponds to line A-8 of Table A and the meaning for the combination of ($R^4$)$_n$ and ($R^5$)$_m$ for each individual compound corresponds in each case to one line of Table B (compounds I.C1.A8.B1 to I.C1.A8.B2496).

Table 9c Compounds of the formula I.C1 in which the combination of $R^1$, $R^2$ and $R^3$ corresponds to line A-9 of Table A and the meaning for the combination of ($R^4$)$_n$ and ($R^5$)$_m$ for each individual compound corresponds in each case to one line of Table B (compounds I.C1.A9.B1 to I.C1.A9.B2496).

Table 10c Compounds of the formula I.C1 in which the combination of $R^1$, $R^2$ and $R^3$ corresponds to line A-10 of Table A and the meaning for the combination of ($R^4$)$_n$ and ($R^5$)$_m$ for each individual compound corresponds in each case to one line of Table B (compounds I.C1.A10.B1 to I.C1.A10.B2496).

Table 11c Compounds of the formula I.C1 in which the combination of $R^1$, $R^2$ and $R^3$ corresponds to line A-11 of Table A and the meaning for the combination of ($R^4$)$_n$ and ($R^5$)$_m$ for each individual compound corresponds in each case to one line of Table B (compounds I.C1.A11.B1 to I.C1.A11.B2496).

Table 12c Compounds of the formula I.C1 in which the combination of $R^1$, $R^2$ and $R^3$ corresponds to line A-12 of Table A and the meaning for the combination of ($R^4$)$_n$ and ($R^5$)$_m$ for each individual compound corresponds in each case to one line of Table B (compounds I.C1.A12.B1 to I.C1.A12.B2496).

Table 13c Compounds of the formula I.C1 in which the combination of $R^1$, $R^2$ and $R^3$ corresponds to line A-13 of Table A and the meaning for the combination of ($R^4$)$_n$ and ($R^5$)$_m$ for each individual compound corresponds in each case to one line of Table B (compounds I.C1.A13.B1 to I.C1.A13.B2496).

Table 14c Compounds of the formula I.C1 in which the combination of $R^1$, $R^2$ and $R^3$ corresponds to line A-14 of Table A and the meaning for the combination of ($R^4$)$_n$ and ($R^5$)$_m$ for each individual compound corresponds in each case to one line of Table B (compounds I.C1.A14.B1 to I.C1.A14.B2496).

Table 15c Compounds of the formula I.C1 in which the combination of $R^1$, $R^2$ and $R^3$ corresponds to line A-15 of Table A and the meaning for the combination of ($R^4$)$_n$ and ($R^5$)$_m$ for each individual compound corresponds in each case to one line of Table B (compounds I.C1.A15.B1 to I.C1.A15.B2496).

Table 16c Compounds of the formula I.C1 in which the combination of $R^1$, $R^2$ and $R^3$ corresponds to line A-16 of Table A and the meaning for the combination of ($R^4$)$_n$ and ($R^5$)$_m$ for each individual compound corresponds in each case to one line of Table B (compounds I.C1.A16.B1 to I.C1.A16.B2496).

Table 17c Compounds of the formula I.C1 in which the combination of $R^1$, $R^2$ and $R^3$ corresponds to line A-17 of Table A and the meaning for the combination of ($R^4$)$_n$ and ($R^5$)$_m$ for each individual compound corresponds in each case to one line of Table B (compounds I.C1.A17.B1 to I.C1.A17.B2496).

Table 18c Compounds of the formula I.C1 in which the combination of $R^1$, $R^2$ and $R^3$ corresponds to line A-18 of Table A and the meaning for the combination of ($R^4$)$_n$ and ($R^5$)$_m$ for each individual compound corresponds in each case to one line of Table B (compounds I.C1.A18.B1 to I.C1.A18.B2496).

Table 19c Compounds of the formula I.C1 in which the combination of $R^1$, $R^2$ and $R^3$ corresponds to line A-19 of Table A and the meaning for the combination of ($R^4$)$_n$ and ($R^5$)$_m$ for each individual compound corresponds in each case to one line of Table B (compounds I.C1.A19.B1 to I.C1.A19.B2496).

Table 20c Compounds of the formula I.C1 in which the combination of $R^1$, $R^2$ and $R^3$ corresponds to line A-20 of Table A and the meaning for the combination of ($R^4$)$_n$ and ($R^5$)$_m$ for each individual compound corresponds in each case to one line of Table B (compounds I.C1.A20.B1 to I.C1.A20.B2496).

Table 21c Compounds of the formula I.C1 in which the combination of $R^1$, $R^2$ and $R^3$ corresponds to line A-21 of Table A and the meaning for the combination of ($R^4$)$_n$ and ($R^5$)$_m$ for each individual compound corresponds in each case to one line of Table B (compounds I.C1.A21.B1 to I.C1.A21.B2496).

Table 22c Compounds of the formula I.C1 in which the combination of $R^1$, $R^2$ and $R^3$ corresponds to line A-22 of Table A and the meaning for the combination of ($R^4$)$_n$ and ($R^5$)$_m$ for each individual compound corresponds in each case to one line of Table B (compounds I.C1.A22.B1 to I.C1.A22.B2496).

Table 23c Compounds of the formula I.C1 in which the combination of $R^1$, $R^2$ and $R^3$ corresponds to line A-23 of Table A and the meaning for the combination of ($R^4$)$_n$ and ($R^5$)$_m$ for each individual compound corresponds in each case to one line of Table B (compounds I.C1.A23.B1 to I.C1.A23.B2496).

Table 24c Compounds of the formula I.C1 in which the combination of $R^1$, $R^2$ and $R^3$ corresponds to line A-24 of Table A and the meaning for the combination of ($R^4$)$_n$ and ($R^5$)$_m$ for each individual compound corresponds in each case to one line of Table B (compounds I.C1.A24.B1 to I.C1.A24.B2496).

Table 25c Compounds of the formula I.C1 in which the combination of $R^1$, $R^2$ and $R^3$ corresponds to line A-25 of Table A and the meaning for the combination of ($R^4$)$_n$ and ($R^5$)$_m$ for each individual compound corresponds in each case to one line of Table B (compounds I.C1.A25.B1 to I.C1.A25.B2496).

Table 26c Compounds of the formula I.C1 in which the combination of $R^1$, $R^2$ and $R^3$ corresponds to line A-26 of Table A and the meaning for the combination of ($R^4$)$_n$ and ($R^5$)$_m$ for each individual compound corresponds in each case to one line of Table B (compounds I.C1.A26.B1 to I.C1.A26.B2496).

Table 27c Compounds of the formula I.C1 in which the combination of $R^1$, $R^2$ and $R^3$ corresponds to line A-27 of Table A and the meaning for the combination of ($R^4$)$_n$ and ($R^5$)$_m$ for each individual compound corresponds in each case to one line of Table B (compounds I.C1.A27.B1 to I.C1.A27.B2496).

Table 28c Compounds of the formula I.C1 in which the combination of $R^1$, $R^2$ and $R^3$ corresponds to line A-28 of Table A and the meaning for the combination of ($R^4$)$_n$ and ($R^5$)$_m$ for each individual compound corresponds in each case to one line of Table B (compounds I.C1.A28.B1 to I.C1.A28.B2496).

Table 29c Compounds of the formula I.C1 in which the combination of $R^1$, $R^2$ and $R^3$ corresponds to line A-29 of Table A and the meaning for the combination of ($R^4$)$_n$ and ($R^5$)$_m$ for each individual compound corresponds in each case to one line of Table B (compounds I.C1.A29.B1 to I.C1.A29.B2496).

Table 30c Compounds of the formula I.C1 in which the combination of $R^1$, $R^2$ and $R^3$ corresponds to line A-30 of Table A and the meaning for the combination of ($R^4$)$_n$ and ($R^5$)$_m$ for each individual compound corresponds in each case to one line of Table B (compounds I.C1.A30.B1 to I.C1.A30.B2496).

Table 31c Compounds of the formula I.C1 in which the combination of $R^1$, $R^2$ and $R^3$ corresponds to line A-31 of Table A and the meaning for the combination of ($R^4$)$_n$ and ($R^5$)$_m$ for each individual compound corresponds in each case to one line of Table B (compounds I.C1.A31.B1 to I.C1.A31.B2496).

Table 32c Compounds of the formula I.C1 in which the combination of $R^1$, $R^2$ and $R^3$ corresponds to line A-32 of Table A and the meaning for the combination of ($R^4$)$_n$ and ($R^5$)$_m$ for each individual compound corresponds in each case to one line of Table B (compounds I.C1.A32.B1 to I.C1.A32.B2496).

Table 33c Compounds of the formula I.C1 in which the combination of $R^1$, $R^2$ and $R^3$ corresponds to line A-33 of Table A and the meaning for the combination of ($R^4$)$_n$ and ($R^5$)$_m$ for each individual compound corresponds in each case to one line of Table B (compounds I.C1.A33.B1 to I.C1.A33.B2496).

Table 34c Compounds of the formula I.C1 in which the combination of $R^1$, $R^2$ and $R^3$ corresponds to line A-34 of Table A and the meaning for the combination of ($R^4$)$_n$ and ($R^5$)$_m$ for each individual compound corresponds in each case to one line of Table B (compounds I.C1.A34.B1 to I.C1.A34.B2496).

Table 35c Compounds of the formula I.C1 in which the combination of $R^1$, $R^2$ and $R^3$ corresponds to line A-35 of Table A and the meaning for the combination of ($R^4$)$_n$ and ($R^5$)$_m$ for each individual compound corresponds in each case to one line of Table B (compounds I.C1.A35.B1 to I.C1.A35.B2496).

Table 36c Compounds of the formula I.C1 in which the combination of $R^1$, $R^2$ and $R^3$ corresponds to line A-36 of Table A and the meaning for the combination of ($R^4$)$_n$ and ($R^5$)$_m$ for each individual compound corresponds in each case to one line of Table B (compounds I.C1.A36.B1 to I.C1.A36.B2496).

Table 37c Compounds of the formula I.C1 in which the combination of $R^1$, $R^2$ and $R^3$ corresponds to line A-37 of Table A and the meaning for the combination of ($R^4$)$_n$ and ($R^5$)$_m$ for each individual compound corresponds in each case to one line of Table B (compounds I.C1.A37.B1 to I.C1.A37.B2496).

Table 38c Compounds of the formula I.C1 in which the combination of $R^1$, $R^2$ and $R^3$ corresponds to line A-38 of Table A and the meaning for the combination of ($R^4$)$_n$ and ($R^5$)$_m$ for each individual compound corresponds in each case to one line of Table B (compounds I.C1.A38.B1 to I.C1.A38.B2496).

Table 39c Compounds of the formula I.C1 in which the combination of $R^1$, $R^2$ and $R^3$ corresponds to line A-39 of Table A and the meaning for the combination of ($R^4$)$_n$ and ($R^5$)$_m$ for each individual compound corresponds in each case to one line of Table B (compounds I.C1.A39.B1 to I.C1.A39.B2496).

Table 40c Compounds of the formula I.C1 in which the combination of $R^1$, $R^2$ and $R^3$ corresponds to line A-40 of Table A and the meaning for the combination of ($R^4$)$_n$ and $(R^5)_m$ for each individual compound corresponds in each case to one line of Table B (compounds I.C1.A40.B1 to I.C1.A40.B2496).

Table 41c Compounds of the formula I.C1 in which the combination of $R^1$, $R^2$ and $R^3$ corresponds to line A-41 of Table A and the meaning for the combination of $(R^4)_n$ and $(R^5)_m$ for each individual compound corresponds in each case to one line of Table B (compounds I.C1.A41.B1 to I.C1.A41.B2496).

Table 42c Compounds of the formula I.C1 in which the combination of $R^1$, $R^2$ and $R^3$ corresponds to line A-42 of Table A and the meaning for the combination of $(R^4)_n$ and $(R^5)_m$ for each individual compound corresponds in each case to one line of Table B (compounds I.C1.A42.B1 to I.C1.A42.B2496).

Table 43c Compounds of the formula I.C1 in which the combination of $R^1$, $R^2$ and $R^3$ corresponds to line A-43 of Table A and the meaning for the combination of $(R^4)_n$ and $(R^5)_m$ for each individual compound corresponds in each case to one line of Table B (compounds I.C1.A43.B1 to I.C1.A43.B2496).

Table 44c Compounds of the formula I.C1 in which the combination of $R^1$, $R^2$ and $R^3$ corresponds to line A-44 of Table A and the meaning for the combination of $(R^4)_n$ and $(R^5)_m$ for each individual compound corresponds in each case to one line of Table B (compounds I.C1.A44.B1 to I.C1.A44.B2496).

Table 45c Compounds of the formula I.C1 in which the combination of $R^1$, $R^2$ and $R^3$ corresponds to line A-45 of Table A and the meaning for the combination of $(R^4)_n$ and $(R^5)_m$ for each individual compound corresponds in each case to one line of Table B (compounds I.C1.A45.B1 to I.C1.A45.B2496).

Table 46c Compounds of the formula I.C1 in which the combination of $R^1$, $R^2$ and $R^3$ corresponds to line A-46 of Table A and the meaning for the combination of $(R^4)_n$ and $(R^5)_m$ for each individual compound corresponds in each case to one line of Table B (compounds I.C1.A46.B1 to I.C1.A46.B2496).

Table 47c Compounds of the formula I.C1 in which the combination of $R^1$, $R^2$ and $R^3$ corresponds to line A-47 of Table A and the meaning for the combination of $(R^4)_n$ and $(R^5)_m$ for each individual compound corresponds in each case to one line of Table B (compounds I.C1.A47.B1 to I.C1.A47.B2496).

Table 48c Compounds of the formula I.C1 in which the combination of $R^1$, $R^2$ and $R^3$ corresponds to line A-48 of Table A and the meaning for the combination of $(R^4)_n$ and $(R^5)_m$ for each individual compound corresponds in each case to one line of Table B (compounds I.C1.A48.B1 to I.C1.A48.B2496).

Table 49c Compounds of the formula I.C1 in which the combination of $R^1$, $R^2$ and $R^3$ corresponds to line A-49 of Table A and the meaning for the combination of $(R^4)_n$ and $(R^5)_m$ for each individual compound corresponds in each case to one line of Table B (compounds I.C1.A49.B1 to I.C1.A49.B2496).

Table 50c Compounds of the formula I.C1 in which the combination of $R^1$, $R^2$ and $R^3$ corresponds to line A-50 of Table A and the meaning for the combination of $(R^4)_n$ and $(R^5)_m$ for each individual compound corresponds in each case to one line of Table B (compounds I.C1.A50.B1 to I.C1.A50.B2496).

Table 51c Compounds of the formula I.C1 in which the combination of $R^1$, $R^2$ and $R^3$ corresponds to line A-51 of Table A and the meaning for the combination of $(R^4)_n$ and $(R^5)_m$ for each individual compound corresponds in each case to one line of Table B (compounds I.C1.A51.B1 to I.C1.A51.B2496).

Table 52c Compounds of the formula I.C1 in which the combination of $R^1$, $R^2$ and $R^3$ corresponds to line A-52 of Table A and the meaning for the combination of $(R^4)_n$ and $(R^5)_m$ for each individual compound corresponds in each case to one line of Table B (compounds I.C1.A52.B1 to I.C1.A52.B2496).

Table 53c Compounds of the formula I.C1 in which the combination of $R^1$, $R^2$ and $R^3$ corresponds to line A-53 of Table A and the meaning for the combination of $(R^4)_n$ and $(R^5)_m$ for each individual compound corresponds in each case to one line of Table B (compounds I.C1.A53.B1 to I.C1.A53.B2496).

Table 54c Compounds of the formula I.C1 in which the combination of $R^1$, $R^2$ and $R^3$ corresponds to line A-54 of Table A and the meaning for the combination of $(R^4)_n$ and $(R^5)_m$ for each individual compound corresponds in each case to one line of Table B (compounds I.C1.A54.B1 to I.C1.A54.B2496).

Table 55c Compounds of the formula I.C1 in which the combination of $R^1$, $R^2$ and $R^3$ corresponds to line A-55 of Table A and the meaning for the combination of $(R^4)_n$ and $(R^5)_m$ for each individual compound corresponds in each case to one line of Table B (compounds I.C1.A55.B1 to I.C1.A55.B2496).

Table 56c Compounds of the formula I.C1 in which the combination of $R^1$, $R^2$ and $R^3$ corresponds to line A-56 of Table A and the meaning for the combination of $(R^4)_n$ and $(R^5)_m$ for each individual compound corresponds in each case to one line of Table B (compounds I.C1.A56.B1 to I.C1.A56.B2496).

Table 57c Compounds of the formula I.C1 in which the combination of $R^1$, $R^2$ and $R^3$ corresponds to line A-57 of Table A and the meaning for the combination of $(R^4)_n$ and $(R^5)_m$ for each individual compound corresponds in each case to one line of Table B (compounds I.C1.A57.B1 to I.C1.A57.B2496).

Table 58c Compounds of the formula I.C1 in which the combination of $R^1$, $R^2$ and $R^3$ corresponds to line A-58 of Table A and the meaning for the combination of $(R^4)_n$ and $(R^5)_m$ for each individual compound corresponds in each case to one line of Table B (compounds I.C1.A58.B1 to I.C1.A58.B2496).

Table 59c Compounds of the formula I.C1 in which the combination of $R^1$, $R^2$ and $R^3$ corresponds to line A-59 of Table A and the meaning for the combination of $(R^4)_n$ and $(R^5)_m$ for each individual compound corresponds in each case to one line of Table B (compounds I.C1.A59.B1 to I.C1.A59.B2496).

Table 60c Compounds of the formula I.C1 in which the combination of $R^1$, $R^2$ and $R^3$ corresponds to line A-60 of Table A and the meaning for the combination of $(R^4)_n$ and $(R^5)_m$ for each individual compound corresponds in each case to one line of Table B (compounds I.C1.A60.B1 to I.C1.A60.B2496).

Table 61c Compounds of the formula I.C1 in which the combination of $R^1$, $R^2$ and $R^3$ corresponds to line A-61 of Table A and the meaning for the combination of $(R^4)_n$ and $(R^5)_m$ for each individual compound corresponds in each case to one line of Table B (compounds I.C1.A61.B1 to I.C1.A61.B2496).

Table 62c Compounds of the formula I.C1 in which the combination of $R^1$, $R^2$ and $R^3$ corresponds to line A-62 of Table A and the meaning for the combination of $(R^4)_n$ and ($R^5$)$_m$ for each individual compound corresponds in each case to one line of Table B (compounds I.C1.A62.B1 to I.C1.A62.B2496).

Table 63c Compounds of the formula I.C1 in which the combination of $R^1$, $R^2$ and $R^3$ corresponds to line A-63 of Table A and the meaning for the combination of ($R^4$)$_n$ and ($R^5$)$_m$ for each individual compound corresponds in each case to one line of Table B (compounds I.C1.A63.B1 to I.C1.A63.B2496).

Table 64c Compounds of the formula I.C1 in which the combination of $R^1$, $R^2$ and $R^3$ corresponds to line A-64 of Table A and the meaning for the combination of ($R^4$)$_n$ and ($R^5$)$_m$ for each individual compound corresponds in each case to one line of Table B (compounds I.C1.A64.B1 to I.C1.A64.B2496).

Table 65c Compounds of the formula I.C1 in which the combination of $R^1$, $R^2$ and $R^3$ corresponds to line A-65 of Table A and the meaning for the combination of ($R^4$)$_n$ and ($R^5$)$_m$ for each individual compound corresponds in each case to one line of Table B (compounds I.C1.A65.B1 to I.C1.A65.B2496).

Table 66c Compounds of the formula I.C1 in which the combination of $R^1$, $R^2$ and $R^3$ corresponds to line A-66 of Table A and the meaning for the combination of ($R^4$)$_n$ and ($R^5$)$_m$ for each individual compound corresponds in each case to one line of Table B (compounds I.C1.A66.B1 to I.C1.A66.B2496).

Table 67c Compounds of the formula I.C1 in which the combination of $R^1$, $R^2$ and $R^3$ corresponds to line A-67 of Table A and the meaning for the combination of ($R^4$)$_n$ and ($R^5$)$_m$ for each individual compound corresponds in each case to one line of Table B (compounds I.C1.A67.B1 to I.C1.A67.B2496).

Table 68c Compounds of the formula I.C1 in which the combination of $R^1$, $R^2$ and $R^3$ corresponds to line A-68 of Table A and the meaning for the combination of ($R^4$)$_n$ and ($R^5$)$_m$ for each individual compound corresponds in each case to one line of Table B (compounds I.C1.A68.B1 to I.C1.A68.B2496).

Table 69c Compounds of the formula I.C1 in which the combination of $R^1$, $R^2$ and $R^3$ corresponds to line A-69 of Table A and the meaning for the combination of ($R^4$)$_n$ and ($R^5$)$_m$ for each individual compound corresponds in each case to one line of Table B (compounds I.C1.A69.B1 to I.C1.A69.B2496).

Table 70c Compounds of the formula I.C1 in which the combination of $R^1$, $R^2$ and $R^3$ corresponds to line A-70 of Table A and the meaning for the combination of ($R^4$)$_n$ and ($R^5$)$_m$ for each individual compound corresponds in each case to one line of Table B (compounds I.C1.A70.B1 to I.C1.A70.B2496).

Table 71c Compounds of the formula I.C1 in which the combination of $R^1$, $R^2$ and $R^3$ corresponds to line A-71 of Table A and the meaning for the combination of ($R^4$)$_n$ and ($R^5$)$_m$ for each individual compound corresponds in each case to one line of Table B (compounds I.C1.A71.B1 to I.C1.A71.B2496).

Table 72c Compounds of the formula I.C1 in which the combination of $R^1$, $R^2$ and $R^3$ corresponds to line A-72 of Table A and the meaning for the combination of ($R^4$)$_n$ and ($R^5$)$_m$ for each individual compound corresponds in each case to one line of Table B (compounds I.C1.A72.B1 to I.C1.A72.B2496).

Table 73c Compounds of the formula I.C1 in which the combination of $R^1$, $R^2$ and $R^3$ corresponds to line A-73 of Table A and the meaning for the combination of ($R^4$)$_n$ and ($R^5$)$_m$ for each individual compound corresponds in each case to one line of Table B (compounds I.C1.A73.B1 to I.C1.A73.B2496).

Table 74c Compounds of the formula I.C1 in which the combination of $R^1$, $R^2$ and $R^3$ corresponds to line A-74 of Table A and the meaning for the combination of ($R^4$)$_n$ and ($R^5$)$_m$ for each individual compound corresponds in each case to one line of Table B (compounds I.C1.A74.B1 to I.C1.A74.B2496).

Table 75c Compounds of the formula I.C1 in which the combination of $R^1$, $R^2$ and $R^3$ corresponds to line A-75 of Table A and the meaning for the combination of ($R^4$)$_n$ and ($R^5$)$_m$ for each individual compound corresponds in each case to one line of Table B (compounds I.C1.A75.B1 to I.C1.A75.B2496).

Table 76c Compounds of the formula I.C1 in which the combination of $R^1$, $R^2$ and $R^3$ corresponds to line A-76 of Table A and the meaning for the combination of ($R^4$)$_n$ and ($R^5$)$_m$ for each individual compound corresponds in each case to one line of Table B (compounds I.C1.A76.B1 to I.C1.A76.B2496).

Table 77c Compounds of the formula I.C1 in which the combination of $R^1$, $R^2$ and $R^3$ corresponds to line A-77 of Table A and the meaning for the combination of ($R^4$)$_n$ and ($R^5$)$_m$ for each individual compound corresponds in each case to one line of Table B (compounds I.C1.A77.B1 to I.C1.A77.B2496).

Table 78c Compounds of the formula I.C1 in which the combination of $R^1$, $R^2$ and $R^3$ corresponds to line A-78 of Table A and the meaning for the combination of ($R^4$)$_n$ and ($R^5$)$_m$ for each individual compound corresponds in each case to one line of Table B (compounds I.C1.A78.B1 to I.C1.A78.B2496).

Table 79c Compounds of the formula I.C1 in which the combination of $R^1$, $R^2$ and $R^3$ corresponds to line A-79 of Table A and the meaning for the combination of ($R^4$)$_n$ and ($R^5$)$_m$ for each individual compound corresponds in each case to one line of Table B (compounds I.C1.A79.B1 to I.C1.A79.B2496).

Table 80c Compounds of the formula I.C1 in which the combination of $R^1$, $R^2$ and $R^3$ corresponds to line A-80 of Table A and the meaning for the combination of ($R^4$)$_n$ and ($R^5$)$_m$ for each individual compound corresponds in each case to one line of Table B (compounds I.C1.A80.B1 to I.C1.A80.B2496).

Table 81c Compounds of the formula I.C1 in which the combination of $R^1$, $R^2$ and $R^3$ corresponds to line A-81 of Table A and the meaning for the combination of ($R^4$)$_n$ and ($R^5$)$_m$ for each individual compound corresponds in each case to one line of Table B (compounds I.C1.A81.B1 to I.C1.A81.B2496).

Table 82c Compounds of the formula I.C1 in which the combination of $R^1$, $R^2$ and $R^3$ corresponds to line A-82 of Table A and the meaning for the combination of ($R^4$)$_n$ and ($R^5$)$_m$ for each individual compound corresponds in each case to one line of Table B (compounds I.C1.A82.B1 to I.C1.A82.B2496).

Table 83c Compounds of the formula I.C1 in which the combination of $R^1$, $R^2$ and $R^3$ corresponds to line A-83 of Table A and the meaning for the combination of ($R^4$)$_n$ and ($R^5$)$_m$ for each individual compound corresponds in each case to one line of Table B (compounds I.C1.A83.B1 to I.C1.A83.B2496).

Table 84c Compounds of the formula I.C1 in which the combination of $R^1$, $R^2$ and $R^3$ corresponds to line A-84 of Table A and the meaning for the combination of ($R^4$)$_n$ and Table 85c Compounds of the formula I.C1 in which the combination of $R^1$, $R^2$ and $R^3$ corresponds to line A-85 of Table A and the meaning for the combination of $(R^4)_n$ and $(R^5)_m$ for each individual compound corresponds in each case to one line of Table B (compounds I.C1.A85.B1 to I.C1.A85.B2496).

Table 86c Compounds of the formula I.C1 in which the combination of $R^1$, $R^2$ and $R^3$ corresponds to line A-86 of Table A and the meaning for the combination of $(R^4)_n$ and $(R^5)_m$ for each individual compound corresponds in each case to one line of Table B (compounds I.C1.A86.B1 to I.C1.A86.B2496).

Table 87c Compounds of the formula I.C1 in which the combination of $R^1$, $R^2$ and $R^3$ corresponds to line A-87 of Table A and the meaning for the combination of $(R^4)_n$ and $(R^5)_m$ for each individual compound corresponds in each case to one line of Table B (compounds I.C1.A87.B1 to I.C1.A87.B2496).

Table 88c Compounds of the formula I.C1 in which the combination of $R^1$, $R^2$ and $R^3$ corresponds to line A-88 of Table A and the meaning for the combination of $(R^4)_n$ and $(R^5)_m$ for each individual compound corresponds in each case to one line of Table B (compounds I.C1.A88.B1 to I.C1.A88.B2496).

Table 89c Compounds of the formula I.C1 in which the combination of $R^1$, $R^2$ and $R^3$ corresponds to line A-89 of Table A and the meaning for the combination of $(R^4)_n$ and $(R^5)_m$ for each individual compound corresponds in each case to one line of Table B (compounds I.C1.A89.B1 to I.C1.A89.B2496).

Table 90c Compounds of the formula I.C1 in which the combination of $R^1$, $R^2$ and $R^3$ corresponds to line A-90 of Table A and the meaning for the combination of $(R^4)_n$ and $(R^5)_m$ for each individual compound corresponds in each case to one line of Table B (compounds I.C1.A90.B1 to I.C1.A90.B2496).

Table 91c Compounds of the formula I.C1 in which the combination of $R^1$, $R^2$ and $R^3$ corresponds to line A-91 of Table A and the meaning for the combination of $(R^4)_n$ and $(R^5)_m$ for each individual compound corresponds in each case to one line of Table B (compounds I.C1.A91.B1 to I.C1.A91.B2496).

Table 92c Compounds of the formula I.C1 in which the combination of $R^1$, $R^2$ and $R^3$ corresponds to line A-92 of Table A and the meaning for the combination of $(R^4)_n$ and $(R^5)_m$ for each individual compound corresponds in each case to one line of Table B (compounds I.C1.A92.B1 to I.C1.A92.B2496).

Table 93c Compounds of the formula I.C1 in which the combination of $R^1$, $R^2$ and $R^3$ corresponds to line A-93 of Table A and the meaning for the combination of $(R^4)_n$ and $(R^5)_m$ for each individual compound corresponds in each case to one line of Table B (compounds I.C1.A93.B1 to I.C1.A93.B2496).

Table 94c Compounds of the formula I.C1 in which the combination of $R^1$, $R^2$ and $R^3$ corresponds to line A-94 of Table A and the meaning for the combination of $(R^4)_n$ and $(R^5)_m$ for each individual compound corresponds in each case to one line of Table B (compounds I.C1.A94.B1 to I.C1.A94.B2496).

Table 95c Compounds of the formula I.C1 in which the combination of $R^1$, $R^2$ and $R^3$ corresponds to line A-95 of Table A and the meaning for the combination of $(R^4)_n$ and $(R^5)_m$ for each individual compound corresponds in each case to one line of Table B (compounds I.C1.A95.B1 to I.C1.A95.B2496).

Table 96c Compounds of the formula I.C1 in which the combination of $R^1$, $R^2$ and $R^3$ corresponds to line A-96 of Table A and the meaning for the combination of $(R^4)_n$ and $(R^5)_m$ for each individual compound corresponds in each case to one line of Table B (compounds I.C1.A96.B1 to I.C1.A96.B2496).

Table 97c Compounds of the formula I.C1 in which the combination of $R^1$, $R^2$ and $R^3$ corresponds to line A-97 of Table A and the meaning for the combination of $(R^4)_n$ and $(R^5)_m$ for each individual compound corresponds in each case to one line of Table B (compounds I.C1.A97.B1 to I.C1.A97.B2496).

Table 98c Compounds of the formula I.C1 in which the combination of $R^1$, $R^2$ and $R^3$ corresponds to line A-98 of Table A and the meaning for the combination of $(R^4)_n$ and $(R^5)_m$ for each individual compound corresponds in each case to one line of Table B (compounds I.C1.A98.B1 to I.C1.A98.B2496).

Table 99c Compounds of the formula I.C1 in which the combination of $R^1$, $R^2$ and $R^3$ corresponds to line A-99 of Table A and the meaning for the combination of $(R^4)_n$ and $(R^5)_m$ for each individual compound corresponds in each case to one line of Table B (compounds I.C1.A99.B1 to I.C1.A99.B2496).

Table 100c Compounds of the formula I.C1 in which the combination of $R^1$, $R^2$ and $R^3$ corresponds to line A-100 of Table A and the meaning for the combination of $(R^4)_n$ and $(R^5)_m$ for each individual compound corresponds in each case to one line of Table B (compounds I.C1.A100.B1 to I.C1.A100.B2496).

Table 101c Compounds of the formula I.C1 in which the combination of $R^1$, $R^2$ and $R^3$ corresponds to line A-101 of Table A and the meaning for the combination of $(R^4)_n$ and $(R^5)_m$ for each individual compound corresponds in each case to one line of Table B (compounds I.C1.A101.B1 to I.C1.A101.B2496).

Table 102c Compounds of the formula I.C1 in which the combination of $R^1$, $R^2$ and $R^3$ corresponds to line A-102 of Table A and the meaning for the combination of $(R^4)_n$ and $(R^5)_m$ for each individual compound corresponds in each case to one line of Table B (compounds I.C1.A102.B1 to I.C1.A102.B2496).

Table 103c Compounds of the formula I.C1 in which the combination of $R^1$, $R^2$ and $R^3$ corresponds to line A-103 of Table A and the meaning for the combination of $(R^4)_n$ and $(R^5)_m$ for each individual compound corresponds in each case to one line of Table B (compounds I.C1.A103.B1 to I.C1.A103.B2496).

Table 104c Compounds of the formula I.C1 in which the combination of $R^1$, $R^2$ and $R^3$ corresponds to line A-104 of Table A and the meaning for the combination of $(R^4)_n$ and $(R^5)_m$ for each individual compound corresponds in each case to one line of Table B (compounds I.C1.A104.B1 to I.C1.A104.B2496).

Table 105c Compounds of the formula I.C1 in which the combination of $R^1$, $R^2$ and $R^3$ corresponds to line A-105 of Table A and the meaning for the combination of $(R^4)_n$ and $(R^5)_m$ for each individual compound corresponds in each case to one line of Table B (compounds I.C1.A105.B1 to I.C1.A105.B2496).

Table 106c Compounds of the formula I.C1 in which the combination of $R^1$, $R^2$ and $R^3$ corresponds to line A-106 of Table A and the meaning for the combination of $(R^4)_n$ and (R$^5$)$_m$ for each individual compound corresponds in each case to one line of Table B (compounds I.C1.A106.B1 to I.C1.A106.B2496).

Table 107c Compounds of the formula I.C1 in which the combination of R$^1$, R$^2$ and R$^3$ corresponds to line A-107 of Table A and the meaning for the combination of (R$^4$)$_n$ and (R$^5$)$_m$ for each individual compound corresponds in each case to one line of Table B (compounds I.C1.A107.B1 to I.C1.A107.B2496).

Table 108c Compounds of the formula I.C1 in which the combination of R$^1$, R$^2$ and R$^3$ corresponds to line A-108 of Table A and the meaning for the combination of (R$^4$)$_n$ and (R$^5$)$_m$ for each individual compound corresponds in each case to one line of Table B (compounds I.C1.A108.B1 to I.C1.A108.B2496).

Table 109c Compounds of the formula I.C1 in which the combination of R$^1$, R$^2$ and R$^3$ corresponds to line A-109 of Table A and the meaning for the combination of (R$^4$)$_n$ and (R$^5$)$_m$ for each individual compound corresponds in each case to one line of Table B (compounds I.C1.A109.B1 to I.C1.A109.B2496).

Table 110c Compounds of the formula I.C1 in which the combination of R$^1$, R$^2$ and R$^3$ corresponds to line A-110 of Table A and the meaning for the combination of (R$^4$)$_n$ and (R$^5$)$_m$ for each individual compound corresponds in each case to one line of Table B (compounds I.C1.A110.B1 to I.C1.A110.B2496).

Table 111c Compounds of the formula I.C1 in which the combination of R$^1$, R$^2$ and R$^3$ corresponds to line A-111 of Table A and the meaning for the combination of (R$^4$)$_n$ and (R$^5$)$_m$ for each individual compound corresponds in each case to one line of Table B (compounds I.C1.A111.B1 to I.C1.A111.B2496).

Table 112c Compounds of the formula I.C1 in which the combination of R$^1$, R$^2$ and R$^3$ corresponds to line A-112 of Table A and the meaning for the combination of (R$^4$)$_n$ and (R$^5$)$_m$ for each individual compound corresponds in each case to one line of Table B (compounds I.C1.A112.B1 to I.C1.A112.B2496).

Table 113c Compounds of the formula I.C1 in which the combination of R$^1$, R$^2$ and R$^3$ corresponds to line A-113 of Table A and the meaning for the combination of (R$^4$)$_n$ and (R$^5$)$_m$ for each individual compound corresponds in each case to one line of Table B (compounds I.C1.A113.B1 to I.C1.A113.B2496).

Table 114c Compounds of the formula I.C1 in which the combination of R$^1$, R$^2$ and R$^3$ corresponds to line A-114 of Table A and the meaning for the combination of (R$^4$)$_n$ and (R$^5$)$_m$ for each individual compound corresponds in each case to one line of Table B (compounds I.C1.A114.B1 to I.C1.A114.B2496).

Table 115c Compounds of the formula I.C1 in which the combination of R$^1$, R$^2$ and R$^3$ corresponds to line A-115 of Table A and the meaning for the combination of (R$^4$)$_n$ and (R$^5$)$_m$ for each individual compound corresponds in each case to one line of Table B (compounds I.C1.A115.B1 to I.C1.A115.B2496).

Table 116c Compounds of the formula I.C1 in which the combination of R$^1$, R$^2$ and R$^3$ corresponds to line A-116 of Table A and the meaning for the combination of (R$^4$)$_n$ and (R$^5$)$_m$ for each individual compound corresponds in each case to one line of Table B (compounds I.C1.A116.B1 to I.C1.A116.B2496).

Table 117c Compounds of the formula I.C1 in which the combination of R$^1$, R$^2$ and R$^3$ corresponds to line A-117 of Table A and the meaning for the combination of (R$^4$)$_n$ and (R$^5$)$_m$ for each individual compound corresponds in each case to one line of Table B (compounds I.C1.A117.B1 to I.C1.A117.B2496).

Table 118c Compounds of the formula I.C1 in which the combination of R$^1$, R$^2$ and R$^3$ corresponds to line A-118 of Table A and the meaning for the combination of (R$^4$)$_n$ and (R$^5$)$_m$ for each individual compound corresponds in each case to one line of Table B (compounds I.C1.A118.B1 to I.C1.A118.B2496).

Table 119c Compounds of the formula I.C1 in which the combination of R$^1$, R$^2$ and R$^3$ corresponds to line A-119 of Table A and the meaning for the combination of (R$^4$)$_n$ and (R$^5$)$_m$ for each individual compound corresponds in each case to one line of Table B (compounds I.C1.A119.B1 to I.C1.A119.B2496).

Table 120c Compounds of the formula I.C1 in which the combination of R$^1$, R$^2$ and R$^3$ corresponds to line A-120 of Table A and the meaning for the combination of (R$^4$)$_n$ and (R$^5$)$_m$ for each individual compound corresponds in each case to one line of Table B (compounds I.C1.A120.B1 to I.C1.A120.B2496).

Table 121c Compounds of the formula I.C1 in which the combination of R$^1$, R$^2$ and R$^3$ corresponds to line A-121 of Table A and the meaning for the combination of (R$^4$)$_n$ and (R$^5$)$_m$ for each individual compound corresponds in each case to one line of Table B (compounds I.C1.A121.B1 to I.C1.A121.B2496).

Table 122c Compounds of the formula I.C1 in which the combination of R$^1$, R$^2$ and R$^3$ corresponds to line A-122 of Table A and the meaning for the combination of (R$^4$)$_n$ and (R$^5$)$_m$ for each individual compound corresponds in each case to one line of Table B (compounds I.C1.A122.B1 to I.C1.A122.B2496).

Table 123c Compounds of the formula I.C1 in which the combination of R$^1$, R$^2$ and R$^3$ corresponds to line A-123 of Table A and the meaning for the combination of (R$^4$)$_n$ and (R$^5$)$_m$ for each individual compound corresponds in each case to one line of Table B (compounds I.C1.A123.B1 to I.C1.A123.B2496).

Table 124c Compounds of the formula I.C1 in which the combination of R$^1$, R$^2$ and R$^3$ corresponds to line A-124 of Table A and the meaning for the combination of (R$^4$)$_n$ and (R$^5$)$_m$ for each individual compound corresponds in each case to one line of Table B (compounds I.C1.A124.B1 to I.C1.A124.B2496).

Table 125c Compounds of the formula I.C1 in which the combination of R$^1$, R$^2$ and R$^3$ corresponds to line A-125 of Table A and the meaning for the combination of (R$^4$)$_n$ and (R$^5$)$_m$ for each individual compound corresponds in each case to one line of Table B (compounds I.C1.A125.B1 to I.C1.A125.B2496).

Table 126c Compounds of the formula I.C1 in which the combination of R$^1$, R$^2$ and R$^3$ corresponds to line A-126 of Table A and the meaning for the combination of (R$^4$)$_n$ and (R$^5$)$_m$ for each individual compound corresponds in each case to one line of Table B (compounds I.C1.A126.B1 to I.C1.A126.B2496).

Table 127c Compounds of the formula I.C1 in which the combination of R$^1$, R$^2$ and R$^3$ corresponds to line A-127 of Table A and the meaning for the combination of (R$^4$)$_n$ and (R$^5$)$_m$ for each individual compound corresponds in each case to one line of Table B (compounds I.C1.A127.B1 to I.C1.A127.B2496).

Table 128c Compounds of the formula I.C1 in which the combination of R$^1$, R$^2$ and R$^3$ corresponds to line A-128 of Table A and the meaning for the combination of (R$^4$)$_n$ and $(R^5)_m$ for each individual compound corresponds in each case to one line of Table B (compounds I.C1.A128.B1 to I.C1.A128.B2496).

Table 129c Compounds of the formula I.C1 in which the combination of $R^1$, $R^2$ and $R^3$ corresponds to line A-129 of Table A and the meaning for the combination of $(R^4)_n$ and $(R^5)_m$ for each individual compound corresponds in each case to one line of Table B (compounds I.C1.A129.B1 to I.C1.A129.B2496).

Table 130c Compounds of the formula I.C1 in which the combination of $R^1$, $R^2$ and $R^3$ corresponds to line A-130 of Table A and the meaning for the combination of $(R^4)_n$ and $(R^5)_m$ for each individual compound corresponds in each case to one line of Table B (compounds I.C1.A130.B1 to I.C1.A130.B2496).

Table 131c Compounds of the formula I.C1 in which the combination of $R^1$, $R^2$ and $R^3$ corresponds to line A-131 of Table A and the meaning for the combination of $(R^4)_n$ and $(R^5)_m$ for each individual compound corresponds in each case to one line of Table B (compounds I.C1.A131.B1 to I.C1.A131.B2496).

Table 132c Compounds of the formula I.C1 in which the combination of $R^1$, $R^2$ and $R^3$ corresponds to line A-132 of Table A and the meaning for the combination of $(R^4)_n$ and $(R^5)_m$ for each individual compound corresponds in each case to one line of Table B (compounds I.C1.A132.B1 to I.C1.A132.B2496).

Table 133c Compounds of the formula I.C1 in which the combination of $R^1$, $R^2$ and $R^3$ corresponds to line A-133 of Table A and the meaning for the combination of $(R^4)_n$ and $(R^5)_m$ for each individual compound corresponds in each case to one line of Table B (compounds I.C1.A133.B1 to I.C1.A133.B2496).

Table 134c Compounds of the formula I.C1 in which the combination of $R^1$, $R^2$ and $R^3$ corresponds to line A-134 of Table A and the meaning for the combination of $(R^4)_n$ and $(R^5)_m$ for each individual compound corresponds in each case to one line of Table B (compounds I.C1.A134.B1 to I.C1.A134.B2496).

Table 135c Compounds of the formula I.C1 in which the combination of $R^1$, $R^2$ and $R^3$ corresponds to line A-135 of Table A and the meaning for the combination of $(R^4)_n$ and $(R^5)_m$ for each individual compound corresponds in each case to one line of Table B (compounds I.C1.A135.B1 to I.C1.A135.B2496).

Table 136c Compounds of the formula I.C1 in which the combination of $R^1$, $R^2$ and $R^3$ corresponds to line A-136 of Table A and the meaning for the combination of $(R^4)_n$ and $(R^5)_m$ for each individual compound corresponds in each case to one line of Table B (compounds I.C1.A136.B1 to I.C1.A136.B2496).

Table 137c Compounds of the formula I.C1 in which the combination of $R^1$, $R^2$ and $R^3$ corresponds to line A-137 of Table A and the meaning for the combination of $(R^4)_n$ and $(R^5)_m$ for each individual compound corresponds in each case to one line of Table B (compounds I.C1.A137.B1 to I.C1.A137.B2496).

Table 138c Compounds of the formula I.C1 in which the combination of $R^1$, $R^2$ and $R^3$ corresponds to line A-138 of Table A and the meaning for the combination of $(R^4)_n$ and $(R^5)_m$ for each individual compound corresponds in each case to one line of Table B (compounds I.C1.A138.B1 to I.C1.A138.B2496).

Table 139c Compounds of the formula I.C1 in which the combination of $R^1$, $R^2$ and $R^3$ corresponds to line A-139 of Table A and the meaning for the combination of $(R^4)_n$ and $(R^5)_m$ for each individual compound corresponds in each case to one line of Table B (compounds I.C1.A139.B1 to I.C1.A139.B2496).

Table 140c Compounds of the formula I.C1 in which the combination of $R^1$, $R^2$ and $R^3$ corresponds to line A-140 of Table A and the meaning for the combination of $(R^4)_n$ and $(R^5)_m$ for each individual compound corresponds in each case to one line of Table B (compounds I.C1.A140.B1 to I.C1.A140.B2496).

Table 141c Compounds of the formula I.C1 in which the combination of $R^1$, $R^2$ and $R^3$ corresponds to line A-141 of Table A and the meaning for the combination of $(R^4)_n$ and $(R^5)_m$ for each individual compound corresponds in each case to one line of Table B (compounds I.C1.A141.B1 to I.C1.A141.B2496).

Table 142c Compounds of the formula I.C1 in which the combination of $R^1$, $R^2$ and $R^3$ corresponds to line A-142 of Table A and the meaning for the combination of $(R^4)_n$ and $(R^5)_m$ for each individual compound corresponds in each case to one line of Table B (compounds I.C1.A142.B1 to I.C1.A142.B2496).

Table 1d Compounds of the formula I.C2 in which the combination of $R^1$, $R^2$ and $R^3$ corresponds to line A-1 of Table A and the meaning for the combination of the combination of $(R^4)_n$ and $(R^5)_m$ for each individual compound corresponds in each case to one line of Table B1 (compounds I.C2.A1.B1-1 to I.C2.A1.B1-2112).

Table 2d Compounds of the formula I.C2 in which the combination of $R^1$, $R^2$ and $R^3$ corresponds to line A-2 of Table A and the meaning for the combination of $(R^4)_n$ and $(R^5)_m$ for each individual compound corresponds in each case to one line of Table B1 (compounds I.C2.A2.B1-1 to I.C2.A2.B1-2112).

Table 3d Compounds of the formula I.C2 in which the combination of $R^1$, $R^2$ and $R^3$ corresponds to line A-3 of Table A and the meaning for the combination of $(R^4)_n$ and $(R^5)_m$ for each individual compound corresponds in each case to one line of Table B1 (compounds I.C2.A3.B1-1 to I.C2.A3.B1-2112).

Table 4d Compounds of the formula I.C2 in which the combination of $R^1$, $R^2$ and $R^3$ corresponds to line A-4 of Table A and the meaning for the combination of $(R^4)_n$ and $(R^5)_m$ for each individual compound corresponds in each case to one line of Table B1 (compounds I.C2.A4.B1-1 to I.C2.A4.B1-2112).

Table 5d Compounds of the formula I.C2 in which the combination of $R^1$, $R^2$ and $R^3$ corresponds to line A-5 of Table A and the meaning for the combination of $(R^4)_n$ and $(R^5)_m$ for each individual compound corresponds in each case to one line of Table B1 (compounds I.C2.A5.B1-1 to I.C2.A5.B1-2112).

Table 6d Compounds of the formula I.C2 in which the combination of $R^1$, $R^2$ and $R^3$ corresponds to line A-6 of Table A and the meaning for the combination of $(R^4)_n$ and $(R^5)_m$ for each individual compound corresponds in each case to one line of Table B1 (compounds I.C2.A6.B1-1 to I.C2.A6.B1-2112).

Table 7d Compounds of the formula I.C2 in which the combination of $R^1$, $R^2$ and $R^3$ corresponds to line A-7 of Table A and the meaning for the combination of $(R^4)_n$ and $(R^5)_m$ for each individual compound corresponds in each case to one line of Table B1 (compounds I.C2.A7.B1-1 to I.C2.A7.B1-2112).

Table 8d Compounds of the formula I.C2 in which the combination of $R^1$, $R^2$ and $R^3$ corresponds to line A-8 of Table A and the meaning for the combination of $(R^4)_n$ and ($R^5$)$_m$ for each individual compound corresponds in each case to one line of Table B1 (compounds I.C2.A8.B1-1 to I.C2.A8.B1-2112).

Table 9d Compounds of the formula I.C2 in which the combination of $R^1$, $R^2$ and $R^3$ corresponds to line A-9 of Table A and the meaning for the combination of ($R^4$)$_n$ and ($R^5$)$_m$ for each individual compound corresponds in each case to one line of Table B1 (compounds I.C2.A9.B1-1 to I.C2.A9.B1-2112).

Table 10d Compounds of the formula I.C2 in which the combination of $R^1$, $R^2$ and $R^3$ corresponds to line A-10 of Table A and the meaning for the combination of ($R^4$)$_n$ and ($R^5$)$_m$ for each individual compound corresponds in each case to one line of Table B1 (compounds I.C2.A10.B1-1 to I.C2.A10.B1-2112).

Table 11d Compounds of the formula I.C2 in which the combination of $R^1$, $R^2$ and $R^3$ corresponds to line A-11 of Table A and the meaning for the combination of ($R^4$)$_n$ and ($R^5$)$_m$ for each individual compound corresponds in each case to one line of Table B1 (compounds I.C2.A11.B1-1 to I.C2.A11.B1-2112).

Table 12d Compounds of the formula I.C2 in which the combination of $R^1$, $R^2$ and $R^3$ corresponds to line A-12 of Table A and the meaning for the combination of ($R^4$)$_n$ and ($R^5$)$_m$ for each individual compound corresponds in each case to one line of Table B1 (compounds I.C2.A12.B1-1 to I.C2.A12.B1-2112).

Table 13d Compounds of the formula I.C2 in which the combination of $R^1$, $R^2$ and $R^3$ corresponds to line A-13 of Table A and the meaning for the combination of ($R^4$)$_n$ and ($R^5$)$_m$ for each individual compound corresponds in each case to one line of Table B1 (compounds I.C2.A13.B1-1 to I.C2.A13.B1-2112).

Table 14d Compounds of the formula I.C2 in which the combination of $R^1$, $R^2$ and $R^3$ corresponds to line A-14 of Table A and the meaning for the combination of ($R^4$)$_n$ and ($R^5$)$_m$ for each individual compound corresponds in each case to one line of Table B1 (compounds I.C2.A14.B1-1 to I.C2.A14.B1-2112).

Table 15d Compounds of the formula I.C2 in which the combination of $R^1$, $R^2$ and $R^3$ corresponds to line A-15 of Table A and the meaning for the combination of ($R^4$)$_n$ and ($R^5$)$_m$ for each individual compound corresponds in each case to one line of Table B1 (compounds I.C2.A15.B1-1 to I.C2.A15.B1-2112).

Table 16d Compounds of the formula I.C2 in which the combination of $R^1$, $R^2$ and $R^3$ corresponds to line A-16 of Table A and the meaning for the combination of ($R^4$)$_n$ and ($R^5$)$_m$ for each individual compound corresponds in each case to one line of Table B1 (compounds I.C2.A16.B1-1 to I.C2.A16.B1-2112).

Table 17d Compounds of the formula I.C2 in which the combination of $R^1$, $R^2$ and $R^3$ corresponds to line A-17 of Table A and the meaning for the combination of ($R^4$)$_n$ and ($R^5$)$_m$ for each individual compound corresponds in each case to one line of Table B1 (compounds I.C2.A17.B1-1 to I.C2.A17.B1-2112).

Table 18d Compounds of the formula I.C2 in which the combination of $R^1$, $R^2$ and $R^3$ corresponds to line A-18 of Table A and the meaning for the combination of ($R^4$)$_n$ and ($R^5$)$_m$ for each individual compound corresponds in each case to one line of Table B1 (compounds I.C2.A18.B1-1 to I.C2.A18.B1-2112).

Table 19d Compounds of the formula I.C2 in which the combination of $R^1$, $R^2$ and $R^3$ corresponds to line A-19 of Table A and the meaning for the combination of ($R^4$)$_n$ and ($R^5$)$_m$ for each individual compound corresponds in each case to one line of Table B1 (compounds I.C2.A19.B1-1 to I.C2.A19.B1-2112).

Table 20d Compounds of the formula I.C2 in which the combination of $R^1$, $R^2$ and $R^3$ corresponds to line A-20 of Table A and the meaning for the combination of ($R^4$)$_n$ and ($R^5$)$_m$ for each individual compound corresponds in each case to one line of Table B1 (compounds I.C2.A20.B1-1 to I.C2.A20.B1-2112).

Table 21d Compounds of the formula I.C2 in which the combination of $R^1$, $R^2$ and $R^3$ corresponds to line A-21 of Table A and the meaning for the combination of ($R^4$)$_n$ and ($R^5$)$_m$ for each individual compound corresponds in each case to one line of Table B1 (compounds I.C2.A21.B1-1 to I.C2.A21.B1-2112).

Table 22d Compounds of the formula I.C2 in which the combination of $R^1$, $R^2$ and $R^3$ corresponds to line A-22 of Table A and the meaning for the combination of ($R^4$)$_n$ and ($R^5$)$_m$ for each individual compound corresponds in each case to one line of Table B1 (compounds I.C2.A22.B1-1 to I.C2.A22.B1-2112).

Table 23d Compounds of the formula I.C2 in which the combination of $R^1$, $R^2$ and $R^3$ corresponds to line A-23 of Table A and the meaning for the combination of ($R^4$)$_n$ and ($R^5$)$_m$ for each individual compound corresponds in each case to one line of Table B1 (compounds I.C2.A23.B1-1 to I.C2.A23.B1-2112).

Table 24d Compounds of the formula I.C2 in which the combination of $R^1$, $R^2$ and $R^3$ corresponds to line A-24 of Table A and the meaning for the combination of ($R^4$)$_n$ and ($R^5$)$_m$ for each individual compound corresponds in each case to one line of Table B1 (compounds I.C2.A24.B1-1 to I.C2.A24.B1-2112).

Table 25d Compounds of the formula I.C2 in which the combination of $R^1$, $R^2$ and $R^3$ corresponds to line A-25 of Table A and the meaning for the combination of ($R^4$)$_n$ and ($R^5$)$_m$ for each individual compound corresponds in each case to one line of Table B1 (compounds I.C2.A25.B1-1 to I.C2.A25.B1-2112).

Table 26d Compounds of the formula I.C2 in which the combination of $R^1$, $R^2$ and $R^3$ corresponds to line A-26 of Table A and the meaning for the combination of ($R^4$)$_n$ and ($R^5$)$_m$ for each individual compound corresponds in each case to one line of Table B1 (compounds I.C2.A26.B1-1 to I.C2.A26.B1-2112).

Table 27d Compounds of the formula I.C2 in which the combination of $R^1$, $R^2$ and $R^3$ corresponds to line A-27 of Table A and the meaning for the combination of ($R^4$)$_n$ and ($R^5$)$_m$ for each individual compound corresponds in each case to one line of Table B1 (compounds I.C2.A27.B1-1 to I.C2.A27.B1-2112).

Table 28d Compounds of the formula I.C2 in which the combination of $R^1$, $R^2$ and $R^3$ corresponds to line A-28 of Table A and the meaning for the combination of ($R^4$)$_n$ and ($R^5$)$_m$ for each individual compound corresponds in each case to one line of Table B1 (compounds I.C2.A28.B1-1 to I.C2.A28.B1-2112).

Table 29d Compounds of the formula I.C2 in which the combination of $R^1$, $R^2$ and $R^3$ corresponds to line A-29 of Table A and the meaning for the combination of ($R^4$)$_n$ and ($R^5$)$_m$ for each individual compound corresponds in each case to one line of Table B1 (compounds I.C2.A29.B1-1 to I.C2.A29.B1-2112).

Table 30d Compounds of the formula I.C2 in which the combination of $R^1$, $R^2$ and $R^3$ corresponds to line A-30 of Table A and the meaning for the combination of ($R^4$)$_n$ and $(R^5)_m$ for each individual compound corresponds in each case to one line of Table B1 (compounds I.C2.A30.B1-1 to I.C2.A30.B1-2112).

Table 31d Compounds of the formula I.C2 in which the combination of $R^1$, $R^2$ and $R^3$ corresponds to line A-31 of Table A and the meaning for the combination of $(R^4)_n$ and $(R^5)_m$ for each individual compound corresponds in each case to one line of Table B1 (compounds I.C2.A31.B1-1 to I.C2.A31.B1-2112).

Table 32d Compounds of the formula I.C2 in which the combination of $R^1$, $R^2$ and $R^3$ corresponds to line A-32 of Table A and the meaning for the combination of $(R^4)_n$ and $(R^5)_m$ for each individual compound corresponds in each case to one line of Table B1 (compounds I.C2.A32.B1-1 to I.C2.A32.B1-2112).

Table 33d Compounds of the formula I.C2 in which the combination of $R^1$, $R^2$ and $R^3$ corresponds to line A-33 of Table A and the meaning for the combination of $(R^4)_n$ and $(R^5)_m$ for each individual compound corresponds in each case to one line of Table B1 (compounds I.C2.A33.B1-1 to I.C2.A33.B1-2112).

Table 34d Compounds of the formula I.C2 in which the combination of $R^1$, $R^2$ and $R^3$ corresponds to line A-34 of Table A and the meaning for the combination of $(R^4)_n$ and $(R^5)_m$ for each individual compound corresponds in each case to one line of Table B1 (compounds I.C2.A34.B1-1 to I.C2.A34.B1-2112).

Table 35d Compounds of the formula I.C2 in which the combination of $R^1$, $R^2$ and $R^3$ corresponds to line A-35 of Table A and the meaning for the combination of $(R^4)_n$ and $(R^5)_m$ for each individual compound corresponds in each case to one line of Table B1 (compounds I.C2.A35.B1-1 to I.C2.A35.B1-2112).

Table 36d Compounds of the formula I.C2 in which the combination of $R^1$, $R^2$ and $R^3$ corresponds to line A-36 of Table A and the meaning for the combination of $(R^4)_n$ and $(R^5)_m$ for each individual compound corresponds in each case to one line of Table B1 (compounds I.C2.A36.B1-1 to I.C2.A36.B1-2112).

Table 37d Compounds of the formula I.C2 in which the combination of $R^1$, $R^2$ and $R^3$ corresponds to line A-37 of Table A and the meaning for the combination of $(R^4)_n$ and $(R^5)_m$ for each individual compound corresponds in each case to one line of Table B1 (compounds I.C2.A37.B1-1 to I.C2.A37.B1-2112).

Table 38d Compounds of the formula I.C2 in which the combination of $R^1$, $R^2$ and $R^3$ corresponds to line A-38 of Table A and the meaning for the combination of $(R^4)_n$ and $(R^5)_m$ for each individual compound corresponds in each case to one line of Table B1 (compounds I.C2.A38.B1-1 to I.C2.A38.B1-2112).

Table 39d Compounds of the formula I.C2 in which the combination of $R^1$, $R^2$ and $R^3$ corresponds to line A-39 of Table A and the meaning for the combination of $(R^4)_n$ and $(R^5)_m$ for each individual compound corresponds in each case to one line of Table B1 (compounds I.C2.A39.B1-1 to I.C2.A39.B1-2112).

Table 40d Compounds of the formula I.C2 in which the combination of $R^1$, $R^2$ and $R^3$ corresponds to line A-40 of Table A and the meaning for the combination of $(R^4)_n$ and $(R^5)_m$ for each individual compound corresponds in each case to one line of Table B1 (compounds I.C2.A40.B1-1 to I.C2.A40.B1-2112).

Table 41d Compounds of the formula I.C2 in which the combination of $R^1$, $R^2$ and $R^3$ corresponds to line A-41 of Table A and the meaning for the combination of $(R^4)_n$ and $(R^5)_m$ for each individual compound corresponds in each case to one line of Table B1 (compounds I.C2.A41.B1-1 to I.C2.A41.B1-2112).

Table 42d Compounds of the formula I.C2 in which the combination of $R^1$, $R^2$ and $R^3$ corresponds to line A-42 of Table A and the meaning for the combination of $(R^4)_n$ and $(R^5)_m$ for each individual compound corresponds in each case to one line of Table B1 (compounds I.C2.A42.B1-1 to I.C2.A42.B1-2112).

Table 43d Compounds of the formula I.C2 in which the combination of $R^1$, $R^2$ and $R^3$ corresponds to line A-43 of Table A and the meaning for the combination of $(R^4)_n$ and $(R^5)_m$ for each individual compound corresponds in each case to one line of Table B1 (compounds I.C2.A43.B1-1 to I.C2.A43.B1-2112).

Table 44d Compounds of the formula I.C2 in which the combination of $R^1$, $R^2$ and $R^3$ corresponds to line A-44 of Table A and the meaning for the combination of $(R^4)_n$ and $(R^5)_m$ for each individual compound corresponds in each case to one line of Table B1 (compounds I.C2.A44.B1-1 to I.C2.A44.B1-2112).

Table 45d Compounds of the formula I.C2 in which the combination of $R^1$, $R^2$ and $R^3$ corresponds to line A-45 of Table A and the meaning for the combination of $(R^4)_n$ and $(R^5)_m$ for each individual compound corresponds in each case to one line of Table B1 (compounds I.C2.A45.B1-1 to I.C2.A45.B1-2112).

Table 46d Compounds of the formula I.C2 in which the combination of $R^1$, $R^2$ and $R^3$ corresponds to line A-46 of Table A and the meaning for the combination of $(R^4)_n$ and $(R^5)_m$ for each individual compound corresponds in each case to one line of Table B1 (compounds I.C2.A46.B1-1 to I.C2.A46.B1-2112).

Table 47d Compounds of the formula I.C2 in which the combination of $R^1$, $R^2$ and $R^3$ corresponds to line A-47 of Table A and the meaning for the combination of $(R^4)_n$ and $(R^5)_m$ for each individual compound corresponds in each case to one line of Table B1 (compounds I.C2.A47.B1-1 to I.C2.A47.B1-2112).

Table 48d Compounds of the formula I.C2 in which the combination of $R^1$, $R^2$ and $R^3$ corresponds to line A-48 of Table A and the meaning for the combination of $(R^4)_n$ and $(R^5)_m$ for each individual compound corresponds in each case to one line of Table B1 (compounds I.C2.A48.B1-1 to I.C2.A48.B1-2112).

Table 49d Compounds of the formula I.C2 in which the combination of $R^1$, $R^2$ and $R^3$ corresponds to line A-49 of Table A and the meaning for the combination of $(R^4)_n$ and $(R^5)_m$ for each individual compound corresponds in each case to one line of Table B1 (compounds I.C2.A49.B1-1 to I.C2.A49.B1-2112).

Table 50d Compounds of the formula I.C2 in which the combination of $R^1$, $R^2$ and $R^3$ corresponds to line A-50 of Table A and the meaning for the combination of $(R^4)_n$ and $(R^5)_m$ for each individual compound corresponds in each case to one line of Table B1 (compounds I.C2.A50.B1-1 to I.C2.A50.B1-2112).

Table 51d Compounds of the formula I.C2 in which the combination of $R^1$, $R^2$ and $R^3$ corresponds to line A-51 of Table A and the meaning for the combination of $(R^4)_n$ and $(R^5)_m$ for each individual compound corresponds in each case to one line of Table B1 (compounds I.C2.A51.B1-1 to I.C2.A51.B1-2112).

Table 52d Compounds of the formula I.C2 in which the combination of $R^1$, $R^2$ and $R^3$ corresponds to line A-52 of Table A and the meaning for the combination of $(R^4)_n$ and $(R^5)_m$ for each individual compound corresponds in each case to one line of Table B1 (compounds I.C2.A52.B1-1 to I.C2.A52.B1-2112).

Table 53d Compounds of the formula I.C2 in which the combination of $R^1$, $R^2$ and $R^3$ corresponds to line A-53 of Table A and the meaning for the combination of $(R^4)_n$ and $(R^5)_m$ for each individual compound corresponds in each case to one line of Table B1 (compounds I.C2.A53.B1-1 to I.C2.A53.B1-2112).

Table 54d Compounds of the formula I.C2 in which the combination of $R^1$, $R^2$ and $R^3$ corresponds to line A-54 of Table A and the meaning for the combination of $(R^4)_n$ and $(R^5)_m$ for each individual compound corresponds in each case to one line of Table B1 (compounds I.C2.A54.B1-1 to I.C2.A54.B1-2112).

Table 55d Compounds of the formula I.C2 in which the combination of $R^1$, $R^2$ and $R^3$ corresponds to line A-55 of Table A and the meaning for the combination of $(R^4)_n$ and $(R^5)_m$ for each individual compound corresponds in each case to one line of Table B1 (compounds I.C2.A55.B1-1 to I.C2.A55.B1-2112).

Table 56d Compounds of the formula I.C2 in which the combination of $R^1$, $R^2$ and $R^3$ corresponds to line A-56 of Table A and the meaning for the combination of $(R^4)_n$ and $(R^5)_m$ for each individual compound corresponds in each case to one line of Table B1 (compounds I.C2.A56.B1-1 to I.C2.A56.B1-2112).

Table 57d Compounds of the formula I.C2 in which the combination of $R^1$, $R^2$ and $R^3$ corresponds to line A-57 of Table A and the meaning for the combination of $(R^4)_n$ and $(R^5)_m$ for each individual compound corresponds in each case to one line of Table B1 (compounds I.C2.A57.B1-1 to I.C2.A57.B1-2112).

Table 58d Compounds of the formula I.C2 in which the combination of $R^1$, $R^2$ and $R^3$ corresponds to line A-58 of Table A and the meaning for the combination of $(R^4)_n$ and $(R^5)_m$ for each individual compound corresponds in each case to one line of Table B1 (compounds I.C2.A58.B1-1 to I.C2.A58.B1-2112).

Table 59d Compounds of the formula I.C2 in which the combination of $R^1$, $R^2$ and $R^3$ corresponds to line A-59 of Table A and the meaning for the combination of $(R^4)_n$ and $(R^5)_m$ for each individual compound corresponds in each case to one line of Table B1 (compounds I.C2.A59.B1-1 to I.C2.A59.B1-2112).

Table 60d Compounds of the formula I.C2 in which the combination of $R^1$, $R^2$ and $R^3$ corresponds to line A-60 of Table A and the meaning for the combination of $(R^4)_n$ and $(R^5)_m$ for each individual compound corresponds in each case to one line of Table B1 (compounds I.C2.A60.B1-1 to I.C2.A60.B1-2112).

Table 61d Compounds of the formula I.C2 in which the combination of $R^1$, $R^2$ and $R^3$ corresponds to line A-61 of Table A and the meaning for the combination of $(R^4)_n$ and $(R^5)_m$ for each individual compound corresponds in each case to one line of Table B1 (compounds I.C2.A61.B1-1 to I.C2.A61.B1-2112).

Table 62d Compounds of the formula I.C2 in which the combination of $R^1$, $R^2$ and $R^3$ corresponds to line A-62 of Table A and the meaning for the combination of $(R^4)_n$ and $(R^5)_m$ for each individual compound corresponds in each case to one line of Table B1 (compounds I.C2.A62.B1-1 to I.C2.A62.B1-2112).

Table 63d Compounds of the formula I.C2 in which the combination of $R^1$, $R^2$ and $R^3$ corresponds to line A-63 of Table A and the meaning for the combination of $(R^4)_n$ and $(R^5)_m$ for each individual compound corresponds in each case to one line of Table B1 (compounds I.C2.A63.B1-1 to I.C2.A63.B1-2112).

Table 64d Compounds of the formula I.C2 in which the combination of $R^1$, $R^2$ and $R^3$ corresponds to line A-64 of Table A and the meaning for the combination of $(R^4)_n$ and $(R^5)_m$ for each individual compound corresponds in each case to one line of Table B1 (compounds I.C2.A64.B1-1 to I.C2.A64.B1-2112).

Table 65d Compounds of the formula I.C2 in which the combination of $R^1$, $R^2$ and $R^3$ corresponds to line A-65 of Table A and the meaning for the combination of $(R^4)_n$ and $(R^5)_m$ for each individual compound corresponds in each case to one line of Table B1 (compounds I.C2.A65.B1-1 to I.C2.A65.B1-2112).

Table 66d Compounds of the formula I.C2 in which the combination of $R^1$, $R^2$ and $R^3$ corresponds to line A-66 of Table A and the meaning for the combination of $(R^4)_n$ and $(R^5)_m$ for each individual compound corresponds in each case to one line of Table B1 (compounds I.C2.A66.B1-1 to I.C2.A66.B1-2112).

Table 67d Compounds of the formula I.C2 in which the combination of $R^1$, $R^2$ and $R^3$ corresponds to line A-67 of Table A and the meaning for the combination of $(R^4)_n$ and $(R^5)_m$ for each individual compound corresponds in each case to one line of Table B1 (compounds I.C2.A67.B1-1 to I.C2.A67.B1-2112).

Table 68d Compounds of the formula I.C2 in which the combination of $R^1$, $R^2$ and $R^3$ corresponds to line A-68 of Table A and the meaning for the combination of $(R^4)_n$ and $(R^5)_m$ for each individual compound corresponds in each case to one line of Table B1 (compounds I.C2.A68.B1-1 to I.C2.A68.B1-2112).

Table 69d Compounds of the formula I.C2 in which the combination of $R^1$, $R^2$ and $R^3$ corresponds to line A-69 of Table A and the meaning for the combination of $(R^4)_n$ and $(R^5)_m$ for each individual compound corresponds in each case to one line of Table B1 (compounds I.C2.A69.B1-1 to I.C2.A69.B1-2112).

Table 70d Compounds of the formula I.C2 in which the combination of $R^1$, $R^2$ and $R^3$ corresponds to line A-70 of Table A and the meaning for the combination of $(R^4)_n$ and $(R^5)_m$ for each individual compound corresponds in each case to one line of Table B1 (compounds I.C2.A70.B1-1 to I.C2.A70.B1-2112).

Table 71d Compounds of the formula I.C2 in which the combination of $R^1$, $R^2$ and $R^3$ corresponds to line A-71 of Table A and the meaning for the combination of $(R^4)_n$ and $(R^5)_m$ for each individual compound corresponds in each case to one line of Table B1 (compounds I.C2.A71.B1-1 to I.C2.A71.B1-2112).

Table 72d Compounds of the formula I.C2 in which the combination of $R^1$, $R^2$ and $R^3$ corresponds to line A-72 of Table A and the meaning for the combination of $(R^4)_n$ and $(R^5)_m$ for each individual compound corresponds in each case to one line of Table B1 (compounds I.C2.A72.B1-1 to I.C2.A72.B1-2112).

Table 73d Compounds of the formula I.C2 in which the combination of $R^1$, $R^2$ and $R^3$ corresponds to line A-73 of Table A and the meaning for the combination of $(R^4)_n$ and $(R^5)_m$ for each individual compound corresponds in each case to one line of Table B1 (compounds I.C2.A73.B1-1 to I.C2.A73.B1-2112).

Table 74d Compounds of the formula I.C2 in which the combination of $R^1$, $R^2$ and $R^3$ corresponds to line A-74 of Table A and the meaning for the combination of $(R^4)_n$ and ($R^5)_m$ for each individual compound corresponds in each case to one line of Table B1 (compounds I.C2.A74.B1-1 to I.C2.A74.B1-2112).

Table 75d Compounds of the formula I.C2 in which the combination of $R^1$, $R^2$ and $R^3$ corresponds to line A-75 of Table A and the meaning for the combination of $(R^4)_n$ and $(R^5)_m$ for each individual compound corresponds in each case to one line of Table B1 (compounds I.C2.A75.B1-1 to I.C2.A75.B1-2112).

Table 76d Compounds of the formula I.C2 in which the combination of $R^1$, $R^2$ and $R^3$ corresponds to line A-76 of Table A and the meaning for the combination of $(R^4)_n$ and $(R^5)_m$ for each individual compound corresponds in each case to one line of Table B1 (compounds I.C2.A76.B1-1 to I.C2.A76.B1-2112).

Table 77d Compounds of the formula I.C2 in which the combination of $R^1$, $R^2$ and $R^3$ corresponds to line A-77 of Table A and the meaning for the combination of $(R^4)_n$ and $(R^5)_m$ for each individual compound corresponds in each case to one line of Table B1 (compounds I.C2.A77.B1-1 to I.C2.A77.B1-2112).

Table 78d Compounds of the formula I.C2 in which the combination of $R^1$, $R^2$ and $R^3$ corresponds to line A-78 of Table A and the meaning for the combination of $(R^4)_n$ and $(R^5)_m$ for each individual compound corresponds in each case to one line of Table B1 (compounds I.C2.A78.B1-1 to I.C2.A78.B1-2112).

Table 79d Compounds of the formula I.C2 in which the combination of $R^1$, $R^2$ and $R^3$ corresponds to line A-79 of Table A and the meaning for the combination of $(R^4)_n$ and $(R^5)_m$ for each individual compound corresponds in each case to one line of Table B1 (compounds I.C2.A79.B1-1 to I.C2.A79.B1-2112).

Table 80d Compounds of the formula I.C2 in which the combination of $R^1$, $R^2$ and $R^3$ corresponds to line A-80 of Table A and the meaning for the combination of $(R^4)_n$ and $(R^5)_m$ for each individual compound corresponds in each case to one line of Table B1 (compounds I.C2.A80.B1-1 to I.C2.A80.B1-2112).

Table 81d Compounds of the formula I.C2 in which the combination of $R^1$, $R^2$ and $R^3$ corresponds to line A-81 of Table A and the meaning for the combination of $(R^4)_n$ and $(R^5)_m$ for each individual compound corresponds in each case to one line of Table B1 (compounds I.C2.A81.B1-1 to I.C2.A81.B1-2112).

Table 82d Compounds of the formula I.C2 in which the combination of $R^1$, $R^2$ and $R^3$ corresponds to line A-82 of Table A and the meaning for the combination of $(R^4)_n$ and $(R^5)_m$ for each individual compound corresponds in each case to one line of Table B1 (compounds I.C2.A82.B1-1 to I.C2.A82.B1-2112).

Table 83d Compounds of the formula I.C2 in which the combination of $R^1$, $R^2$ and $R^3$ corresponds to line A-83 of Table A and the meaning for the combination of $(R^4)_n$ and $(R^5)_m$ for each individual compound corresponds in each case to one line of Table B1 (compounds I.C2.A83.B1-1 to I.C2.A83.B1-2112).

Table 84d Compounds of the formula I.C2 in which the combination of $R^1$, $R^2$ and $R^3$ corresponds to line A-84 of Table A and the meaning for the combination of $(R^4)_n$ and $(R^5)_m$ for each individual compound corresponds in each case to one line of Table B1 (compounds I.C2.A84.B1-1 to I.C2.A84.B1-2112).

Table 85d Compounds of the formula I.C2 in which the combination of $R^1$, $R^2$ and $R^3$ corresponds to line A-85 of Table A and the meaning for the combination of $(R^4)_n$ and $(R^5)_m$ for each individual compound corresponds in each case to one line of Table B1 (compounds I.C2.A85.B1-1 to I.C2.A85.B1-2112).

Table 86d Compounds of the formula I.C2 in which the combination of $R^1$, $R^2$ and $R^3$ corresponds to line A-86 of Table A and the meaning for the combination of $(R^4)_n$ and $(R^5)_m$ for each individual compound corresponds in each case to one line of Table B1 (compounds I.C2.A86.B1-1 to I.C2.A86.B1-2112).

Table 87d Compounds of the formula I.C2 in which the combination of $R^1$, $R^2$ and $R^3$ corresponds to line A-87 of Table A and the meaning for the combination of $(R^4)_n$ and $(R^5)_m$ for each individual compound corresponds in each case to one line of Table B1 (compounds I.C2.A87.B1-1 to I.C2.A87.B1-2112).

Table 88d Compounds of the formula I.C2 in which the combination of $R^1$, $R^2$ and $R^3$ corresponds to line A-88 of Table A and the meaning for the combination of $(R^4)_n$ and $(R^5)_m$ for each individual compound corresponds in each case to one line of Table B1 (compounds I.C2.A88.B1-1 to I.C2.A88.B1-2112).

Table 89d Compounds of the formula I.C2 in which the combination of $R^1$, $R^2$ and $R^3$ corresponds to line A-89 of Table A and the meaning for the combination of $(R^4)_n$ and $(R^5)_m$ for each individual compound corresponds in each case to one line of Table B1 (compounds I.C2.A89.B1-1 to I.C2.A89.B1-2112).

Table 90d Compounds of the formula I.C2 in which the combination of $R^1$, $R^2$ and $R^3$ corresponds to line A-90 of Table A and the meaning for the combination of $(R^4)_n$ and $(R^5)_m$ for each individual compound corresponds in each case to one line of Table B1 (compounds I.C2.A90.B1-1 to I.C2.A90.B1-2112).

Table 91d Compounds of the formula I.C2 in which the combination of $R^1$, $R^2$ and $R^3$ corresponds to line A-91 of Table A and the meaning for the combination of $(R^4)_n$ and $(R^5)_m$ for each individual compound corresponds in each case to one line of Table B1 (compounds I.C2.A91.B1-1 to I.C2.A91.B1-2112).

Table 92d Compounds of the formula I.C2 in which the combination of $R^1$, $R^2$ and $R^3$ corresponds to line A-92 of Table A and the meaning for the combination of $(R^4)_n$ and $(R^5)_m$ for each individual compound corresponds in each case to one line of Table B1 (compounds I.C2.A92.B1-1 to I.C2.A92.B1-2112).

Table 93d Compounds of the formula I.C2 in which the combination of $R^1$, $R^2$ and $R^3$ corresponds to line A-93 of Table A and the meaning for the combination of $(R^4)_n$ and $(R^5)_m$ for each individual compound corresponds in each case to one line of Table B1 (compounds I.C2.A93.B1-1 to I.C2.A93.B1-2112).

Table 94d Compounds of the formula I.C2 in which the combination of $R^1$, $R^2$ and $R^3$ corresponds to line A-94 of Table A and the meaning for the combination of $(R^4)_n$ and $(R^5)_m$ for each individual compound corresponds in each case to one line of Table B1 (compounds I.C2.A94.B1-1 to I.C2.A94.B1-2112).

Table 95d Compounds of the formula I.C2 in which the combination of $R^1$, $R^2$ and $R^3$ corresponds to line A-95 of Table A and the meaning for the combination of $(R^4)_n$ and $(R^5)_m$ for each individual compound corresponds in each case to one line of Table B1 (compounds I.C2.A95.B1-1 to I.C2.A95.B1-2112).

Table 96d Compounds of the formula I.C2 in which the combination of $R^1$, $R^2$ and $R^3$ corresponds to line A-96 of Table A and the meaning for the combination of $(R^4)_n$ and (R$^5$)$_m$ for each individual compound corresponds in each case to one line of Table B1 (compounds I.C2.A96.B1-1 to I.C2.A96.B1-2112).

Table 97d Compounds of the formula I.C2 in which the combination of R$^1$, R$^2$ and R$^3$ corresponds to line A-97 of Table A and the meaning for the combination of (R$^4$)$_n$ and (R$^5$)$_m$ for each individual compound corresponds in each case to one line of Table B1 (compounds I.C2.A97.B1-1 to I.C2.A97.B1-2112).

Table 98d Compounds of the formula I.C2 in which the combination of R$^1$, R$^2$ and R$^3$ corresponds to line A-98 of Table A and the meaning for the combination of (R$^4$)$_n$ and (R$^5$)$_m$ for each individual compound corresponds in each case to one line of Table B1 (compounds I.C2.A98.B1-1 to I.C2.A98.B1-2112).

Table 99d Compounds of the formula I.C2 in which the combination of R$^1$, R$^2$ and R$^3$ corresponds to line A-99 of Table A and the meaning for the combination of (R$^4$)$_n$ and (R$^5$)$_m$ for each individual compound corresponds in each case to one line of Table B1 (compounds I.C2.A99.B1-1 to I.C2.A99.B1-2112).

Table 100d Compounds of the formula I.C2 in which the combination of R$^1$, R$^2$ and R$^3$ corresponds to line A-100 of Table A and the meaning for the combination of (R$^4$)$_n$ and (R$^5$)$_m$ for each individual compound corresponds in each case to one line of Table B1 (compounds I.C2.A100.B1-1 to I.C2.A100.B1-2112).

Table 101d Compounds of the formula I.C2 in which the combination of R$^1$, R$^2$ and R$^3$ corresponds to line A-101 of Table A and the meaning for the combination of (R$^4$)$_n$ and (R$^5$)$_m$ for each individual compound corresponds in each case to one line of Table B1 (compounds I.C2.A101.B1-1 to I.C2.A101.B1-2112).

Table 102d Compounds of the formula I.C2 in which the combination of R$^1$, R$^2$ and R$^3$ corresponds to line A-102 of Table A and the meaning for the combination of (R$^4$)$_n$ and (R$^5$)$_m$ for each individual compound corresponds in each case to one line of Table B1 (compounds I.C2.A102.B1-1 to I.C2.A102.B1-2112).

Table 103d Compounds of the formula I.C2 in which the combination of R$^1$, R$^2$ and R$^3$ corresponds to line A-103 of Table A and the meaning for the combination of (R$^4$)$_n$ and (R$^5$)$_m$ for each individual compound corresponds in each case to one line of Table B1 (compounds I.C2.A103.B1-1 to I.C2.A103.B1-2112).

Table 104d Compounds of the formula I.C2 in which the combination of R$^1$, R$^2$ and R$^3$ corresponds to line A-104 of Table A and the meaning for the combination of (R$^4$)$_n$ and (R$^5$)$_m$ for each individual compound corresponds in each case to one line of Table B1 (compounds I.C2.A104.B1-1 to I.C2.A104.B1-2112).

Table 105d Compounds of the formula I.C2 in which the combination of R$^1$, R$^2$ and R$^3$ corresponds to line A-105 of Table A and the meaning for the combination of (R$^4$)$_n$ and (R$^5$)$_m$ for each individual compound corresponds in each case to one line of Table B1 (compounds I.C2.A105.B1-1 to I.C2.A105.B1-2112).

Table 106d Compounds of the formula I.C2 in which the combination of R$^1$, R$^2$ and R$^3$ corresponds to line A-106 of Table A and the meaning for the combination of (R$^4$)$_n$ and (R$^5$)$_m$ for each individual compound corresponds in each case to one line of Table B1 (compounds I.C2.A106.B1-1 to I.C2.A106.B1-2112).

Table 107d Compounds of the formula I.C2 in which the combination of R$^1$, R$^2$ and R$^3$ corresponds to line A-107 of Table A and the meaning for the combination of (R$^4$)$_n$ and (R$^5$)$_m$ for each individual compound corresponds in each case to one line of Table B1 (compounds I.C2.A107.B1-1 to I.C2.A107.B1-2112).

Table 108d Compounds of the formula I.C2 in which the combination of R$^1$, R$^2$ and R$^3$ corresponds to line A-108 of Table A and the meaning for the combination of (R$^4$)$_n$ and (R$^5$)$_m$ for each individual compound corresponds in each case to one line of Table B1 (compounds I.C2.A108.B1-1 to I.C2.A108.B1-2112).

Table 109d Compounds of the formula I.C2 in which the combination of R$^1$, R$^2$ and R$^3$ corresponds to line A-109 of Table A and the meaning for the combination of (R$^4$)$_n$ and (R$^5$)$_m$ for each individual compound corresponds in each case to one line of Table B1 (compounds I.C2.A109.B1-1 to I.C2.A109.B1-2112).

Table 110d Compounds of the formula I.C2 in which the combination of R$^1$, R$^2$ and R$^3$ corresponds to line A-110 of Table A and the meaning for the combination of (R$^4$)$_n$ and (R$^5$)$_m$ for each individual compound corresponds in each case to one line of Table B1 (compounds I.C2.A110.B1-1 to I.C2.A110.B1-2112).

Table 111d Compounds of the formula I.C2 in which the combination of R$^1$, R$^2$ and R$^3$ corresponds to line A-111 of Table A and the meaning for the combination of (R$^4$)$_n$ and (R$^5$)$_m$ for each individual compound corresponds in each case to one line of Table B1 (compounds I.C2.A111.B1-1 to I.C2.A111.B1-2112).

Table 112d Compounds of the formula I.C2 in which the combination of R$^1$, R$^2$ and R$^3$ corresponds to line A-112 of Table A and the meaning for the combination of (R$^4$)$_n$ and (R$^5$)$_m$ for each individual compound corresponds in each case to one line of Table B1 (compounds I.C2.A112.B1-1 to I.C2.A112.B1-2112).

Table 113d Compounds of the formula I.C2 in which the combination of R$^1$, R$^2$ and R$^3$ corresponds to line A-113 of Table A and the meaning for the combination of (R$^4$)$_n$ and (R$^5$)$_m$ for each individual compound corresponds in each case to one line of Table B1 (compounds I.C2.A113.B1-1 to I.C2.A113.B1-2112).

Table 114d Compounds of the formula I.C2 in which the combination of R$^1$, R$^2$ and R$^3$ corresponds to line A-114 of Table A and the meaning for the combination of (R$^4$)$_n$ and (R$^5$)$_m$ for each individual compound corresponds in each case to one line of Table B1 (compounds I.C2.A114.B1-1 to I.C2.A114.B1-2112).

Table 115d Compounds of the formula I.C2 in which the combination of R$^1$, R$^2$ and R$^3$ corresponds to line A-115 of Table A and the meaning for the combination of (R$^4$)$_n$ and (R$^5$)$_m$ for each individual compound corresponds in each case to one line of Table B1 (compounds I.C2.A115.B1-1 to I.C2.A115.B1-2112).

Table 116d Compounds of the formula I.C2 in which the combination of R$^1$, R$^2$ and R$^3$ corresponds to line A-116 of Table A and the meaning for the combination of (R$^4$)$_n$ and (R$^5$)$_m$ for each individual compound corresponds in each case to one line of Table B1 (compounds I.C2.A116.B1-1 to I.C2.A116.B1-2112).

Table 117d Compounds of the formula I.C2 in which the combination of R$^1$, R$^2$ and R$^3$ corresponds to line A-117 of Table A and the meaning for the combination of (R$^4$)$_n$ and (R$^5$)$_m$ for each individual compound corresponds in each case to one line of Table B1 (compounds I.C2.A117.B1-1 to I.C2.A117.B1-2112).

Table 118d Compounds of the formula I.C2 in which the combination of R$^1$, R$^2$ and R$^3$ corresponds to line A-118 of Table A and the meaning for the combination of (R$^4$)$_n$ and $(R^5)_m$ for each individual compound corresponds in each case to one line of Table B1 (compounds I.C2.A118.B1-1 to I.C2.A118.B1-2112).

Table 119d Compounds of the formula I.C2 in which the combination of $R^1$, $R^2$ and $R^3$ corresponds to line A-119 of Table A and the meaning for the combination of $(R^4)_n$ and $(R^5)_m$ for each individual compound corresponds in each case to one line of Table B1 (compounds I.C2.A119.B1-1 to I.C2.A119.B1-2112).

Table 120d Compounds of the formula I.C2 in which the combination of $R^1$, $R^2$ and $R^3$ corresponds to line A-120 of Table A and the meaning for the combination of $(R^4)_n$ and $(R^5)_m$ for each individual compound corresponds in each case to one line of Table B1 (compounds I.C2.A120.B1-1 to I.C2.A120.B1-2112).

Table 121d Compounds of the formula I.C2 in which the combination of $R^1$, $R^2$ and $R^3$ corresponds to line A-121 of Table A and the meaning for the combination of $(R^4)_n$ and $(R^5)_m$ for each individual compound corresponds in each case to one line of Table B1 (compounds I.C2.A121.B1-1 to I.C2.A121.B1-2112).

Table 122d Compounds of the formula I.C2 in which the combination of $R^1$, $R^2$ and $R^3$ corresponds to line A-122 of Table A and the meaning for the combination of $(R^4)_n$ and $(R^5)_m$ for each individual compound corresponds in each case to one line of Table B1 (compounds I.C2.A122.B1-1 to I.C2.A122.B1-2112).

Table 123d Compounds of the formula I.C2 in which the combination of $R^1$, $R^2$ and $R^3$ corresponds to line A-123 of Table A and the meaning for the combination of $(R^4)_n$ and $(R^5)_m$ for each individual compound corresponds in each case to one line of Table B1 (compounds I.C2.A123.B1-1 to I.C2.A123.B1-2112).

Table 124d Compounds of the formula I.C2 in which the combination of $R^1$, $R^2$ and $R^3$ corresponds to line A-124 of Table A and the meaning for the combination of $(R^4)_n$ and $(R^5)_m$ for each individual compound corresponds in each case to one line of Table B1 (compounds I.C2.A124.B1-1 to I.C2.A124.B1-2112).

Table 125d Compounds of the formula I.C2 in which the combination of $R^1$, $R^2$ and $R^3$ corresponds to line A-125 of Table A and the meaning for the combination of $(R^4)_n$ and $(R^5)_m$ for each individual compound corresponds in each case to one line of Table B1 (compounds I.C2.A125.B1-1 to I.C2.A125.B1-2112).

Table 126d Compounds of the formula I.C2 in which the combination of $R^1$, $R^2$ and $R^3$ corresponds to line A-126 of Table A and the meaning for the combination of $(R^4)_n$ and $(R^5)_m$ for each individual compound corresponds in each case to one line of Table B1 (compounds I.C2.A126.B1-1 to I.C2.A126.B1-2112).

Table 127d Compounds of the formula I.C2 in which the combination of $R^1$, $R^2$ and $R^3$ corresponds to line A-127 of Table A and the meaning for the combination of $(R^4)_n$ and $(R^5)_m$ for each individual compound corresponds in each case to one line of Table B1 (compounds I.C2.A127.B1-1 to I.C2.A127.B1-2112).

Table 128d Compounds of the formula I.C2 in which the combination of $R^1$, $R^2$ and $R^3$ corresponds to line A-128 of Table A and the meaning for the combination of $(R^4)_n$ and $(R^5)_m$ for each individual compound corresponds in each case to one line of Table B1 (compounds I.C2.A128.B1-1 to I.C2.A128.B1-2112).

Table 129d Compounds of the formula I.C2 in which the combination of $R^1$, $R^2$ and $R^3$ corresponds to line A-129 of Table A and the meaning for the combination of $(R^4)_n$ and $(R^5)_m$ for each individual compound corresponds in each case to one line of Table B1 (compounds I.C2.A129.B1-1 to I.C2.A129.B1-2112).

Table 130d Compounds of the formula I.C2 in which the combination of $R^1$, $R^2$ and $R^3$ corresponds to line A-130 of Table A and the meaning for the combination of $(R^4)_n$ and $(R^5)_m$ for each individual compound corresponds in each case to one line of Table B1 (compounds I.C2.A130.B1-1 to I.C2.A130.B1-2112).

Table 131d Compounds of the formula I.C2 in which the combination of $R^1$, $R^2$ and $R^3$ corresponds to line A-131 of Table A and the meaning for the combination of $(R^4)_n$ and $(R^5)_m$ for each individual compound corresponds in each case to one line of Table B1 (compounds I.C2.A131.B1-1 to I.C2.A131.B1-2112).

Table 132d Compounds of the formula I.C2 in which the combination of $R^1$, $R^2$ and $R^3$ corresponds to line A-132 of Table A and the meaning for the combination of $(R^4)_n$ and $(R^5)_m$ for each individual compound corresponds in each case to one line of Table B1 (compounds I.C2.A132.B1-1 to I.C2.A132.B1-2112).

Table 133d Compounds of the formula I.C2 in which the combination of $R^1$, $R^2$ and $R^3$ corresponds to line A-133 of Table A and the meaning for the combination of $(R^4)_n$ and $(R^5)_m$ for each individual compound corresponds in each case to one line of Table B1 (compounds I.C2.A133.B1-1 to I.C2.A133.B1-2112).

Table 134d Compounds of the formula I.C2 in which the combination of $R^1$, $R^2$ and $R^3$ corresponds to line A-134 of Table A and the meaning for the combination of $(R^4)_n$ and $(R^5)_m$ for each individual compound corresponds in each case to one line of Table B1 (compounds I.C2.A134.B1-1 to I.C2.A134.B1-2112).

Table 135d Compounds of the formula I.C2 in which the combination of $R^1$, $R^2$ and $R^3$ corresponds to line A-135 of Table A and the meaning for the combination of $(R^4)_n$ and $(R^5)_m$ for each individual compound corresponds in each case to one line of Table B1 (compounds I.C2.A135.B1-1 to I.C2.A135.B1-2112).

Table 136d Compounds of the formula I.C2 in which the combination of $R^1$, $R^2$ and $R^3$ corresponds to line A-136 of Table A and the meaning for the combination of $(R^4)_n$ and $(R^5)_m$ for each individual compound corresponds in each case to one line of Table B1 (compounds I.C2.A136.B1-1 to I.C2.A136.B1-2112).

Table 137d Compounds of the formula I.C2 in which the combination of $R^1$, $R^2$ and $R^3$ corresponds to line A-137 of Table A and the meaning for the combination of $(R^4)_n$ and $(R^5)_m$ for each individual compound corresponds in each case to one line of Table B1 (compounds I.C2.A137.B1-1 to I.C2.A137.B1-2112).

Table 138d Compounds of the formula I.C2 in which the combination of $R^1$, $R^2$ and $R^3$ corresponds to line A-138 of Table A and the meaning for the combination of $(R^4)_n$ and $(R^5)_m$ for each individual compound corresponds in each case to one line of Table B1 (compounds I.C2.A138.B1-1 to I.C2.A138.B1-2112).

Table 139d Compounds of the formula I.C2 in which the combination of $R^1$, $R^2$ and $R^3$ corresponds to line A-139 of Table A and the meaning for the combination of $(R^4)_n$ and $(R^5)_m$ for each individual compound corresponds in each case to one line of Table B1 (compounds I.C2.A139.B1-1 to I.C2.A139.B1-2112).

Table 140d Compounds of the formula I.C2 in which the combination of $R^1$, $R^2$ and $R^3$ corresponds to line A-140 of Table A and the meaning for the combination of $(R^4)_n$ and $(R^5)_m$ for each individual compound corresponds in each case to one line of Table B1 (compounds I.C2.A140.B1-1 to I.C2.A140.B1-2112).

Table 141d Compounds of the formula I.C2 in which the combination of $R^1$, $R^2$ and $R^3$ corresponds to line A-141 of Table A and the meaning for the combination of $(R^4)_n$ and $(R^5)_m$ for each individual compound corresponds in each case to one line of Table B1 (compounds I.C2.A141.B1-1 to I.C2.A141.B1-2112).

Table 142d Compounds of the formula I.C2 in which the combination of $R^1$, $R^2$ and $R^3$ corresponds to line A-142 of Table A and the meaning for the combination of $(R^4)_n$ and $(R^5)_m$ for each individual compound corresponds in each case to one line of Table B1 (compounds I.C2.A142.B1-1 to I.C2.A142.B1-2112).

TABLE A

| line | $R^1$ | $R^2$ | $R^3$ |
| --- | --- | --- | --- |
| A-1 | H | H | H |
| A-2 | $CH_3$ | H | H |
| A-3 | $CH_2CH_3$ | H | H |
| A-4 | $CH_2CH_2CH_3$ | H | H |
| A-5 | $CH(CH_3)_2$ | H | H |
| A-6 | $C(CH_3)_3$ | H | H |
| A-7 | $CH(CH_3)CH_2CH_3$ | H | H |
| A-8 | $CH_2CH(CH_3)_2$ | H | H |
| A-9 | $CH_2CH_2CH_2CH_3$ | H | H |
| A-10 | $CH_2CH_2CH(CH_3)_2$ | H | H |
| A-11 | $CF_3$ | H | H |
| A-12 | cyclopropyl | H | H |
| A-13 | cyclobutyl | H | H |
| A-14 | cyclopentyl | H | H |
| A-15 | cyclohexyl | H | H |
| A-16 | H | $CH_3$ | H |
| A-17 | $CH_3$ | $CH_3$ | H |
| A-18 | $CH_2CH_3$ | $CH_3$ | H |
| A-19 | $CH_2CH_2CH_3$ | $CH_3$ | H |
| A-20 | $CH(CH_3)_2$ | $CH_3$ | H |
| A-21 | $C(CH_3)_3$ | $CH_3$ | H |
| A-22 | $CH(CH_3)CH_2CH_3$ | $CH_3$ | H |
| A-23 | $CH_2CH(CH_3)_2$ | $CH_3$ | H |
| A-24 | $CH_2CH_2CH_2CH_3$ | $CH_3$ | H |
| A-25 | $CH_2CH_2CH(CH_3)_2$ | $CH_3$ | H |
| A-26 | $CF_3$ | $CH_3$ | H |
| A-27 | cyclopropyl | $CH_3$ | H |
| A-28 | cyclobutyl | $CH_3$ | H |
| A-29 | cyclopentyl | $CH_3$ | H |
| A-30 | cyclohexyl | $CH_3$ | H |
| A-31 | H | $CH_2CH_3$ | H |
| A-32 | $CH_3$ | $CH_2CH_3$ | H |
| A-33 | $CH_2CH_3$ | $CH_2CH_3$ | H |
| A-34 | $CH_2CH_2CH_3$ | $CH_2CH_3$ | H |
| A-35 | $CH(CH_3)_2$ | $CH_2CH_3$ | H |
| A-36 | $C(CH_3)_3$ | $CH_2CH_3$ | H |
| A-37 | $CH(CH_3)CH_2CH_3$ | $CH_2CH_3$ | H |
| A-38 | $CH_2CH(CH_3)_2$ | $CH_2CH_3$ | H |
| A-39 | $CH_2CH_2CH_2CH_3$ | $CH_2CH_3$ | H |
| A-40 | $CH_2CH_2CH(CH_3)_2$ | $CH_2CH_3$ | H |
| A-41 | $CF_3$ | $CH_2CH_3$ | H |
| A-42 | cyclopropyl | $CH_2CH_3$ | H |
| A-43 | cyclobutyl | $CH_2CH_3$ | H |
| A-44 | cyclopentyl | $CH_2CH_3$ | H |
| A-45 | cyclohexyl | $CH_2CH_3$ | H |
| A-46 | H | H | $CH_3$ |
| A-47 | $CH_3$ | H | $CH_3$ |
| A-48 | $CH_2CH_3$ | H | $CH_3$ |
| A-49 | $CH_2CH_2CH_3$ | H | $CH_3$ |
| A-50 | $CH(CH_3)_2$ | H | $CH_3$ |
| A-51 | $C(CH_3)_3$ | H | $CH_3$ |
| A-52 | $CH(CH_3)CH_2CH_3$ | H | $CH_3$ |
| A-53 | $CH_2CH(CH_3)_2$ | H | $CH_3$ |
| A-54 | $CH_2CH_2CH_2CH_3$ | H | $CH_3$ |
| A-55 | $CH_2CH_2CH(CH_3)_2$ | H | $CH_3$ |
| A-56 | $CF_3$ | H | $CH_3$ |
| A-57 | cyclopropyl | H | $CH_3$ |
| A-58 | cyclobutyl | H | $CH_3$ |
| A-59 | cyclopentyl | H | $CH_3$ |
| A-60 | cyclohexyl | H | $CH_3$ |
| A-61 | H | $CH_3$ | $CH_3$ |
| A-62 | $CH_3$ | $CH_3$ | $CH_3$ |
| A-63 | $CH_2CH_3$ | $CH_3$ | $CH_3$ |
| A-64 | $CH_2CH_2CH_3$ | $CH_3$ | $CH_3$ |
| A-65 | $CH(CH_3)_2$ | $CH_3$ | $CH_3$ |
| A-66 | $C(CH_3)_3$ | $CH_3$ | $CH_3$ |
| A-67 | $CH(CH_3)CH_2CH_3$ | $CH_3$ | $CH_3$ |
| A-68 | $CH_2CH(CH_3)_2$ | $CH_3$ | $CH_3$ |
| A-69 | $CH_2CH_2CH_2CH_3$ | $CH_3$ | $CH_3$ |
| A-70 | $CH_2CH_2CH(CH_3)_2$ | $CH_3$ | $CH_3$ |
| A-71 | $CF_3$ | $CH_3$ | $CH_3$ |
| A-72 | cyclopropyl | $CH_3$ | $CH_3$ |
| A-73 | cyclobutyl | $CH_3$ | $CH_3$ |
| A-74 | cyclopentyl | $CH_3$ | $CH_3$ |
| A-75 | cyclohexyl | $CH_3$ | $CH_3$ |
| A-76 | H | $CH_2CH_3$ | $CH_3$ |
| A-77 | $CH_3$ | $CH_2CH_3$ | $CH_3$ |
| A-78 | $CH_2CH_3$ | $CH_2CH_3$ | $CH_3$ |
| A-79 | $CH_2CH_2CH_3$ | $CH_2CH_3$ | $CH_3$ |
| A-80 | $CH(CH_3)_2$ | $CH_2CH_3$ | $CH_3$ |
| A-81 | $C(CH_3)_3$ | $CH_2CH_3$ | $CH_3$ |
| A-82 | $CH(CH_3)CH_2CH_3$ | $CH_2CH_3$ | $CH_3$ |
| A-83 | $CH_2CH(CH_3)_2$ | $CH_2CH_3$ | $CH_3$ |
| A-84 | $CH_2CH_2CH_2CH_3$ | $CH_2CH_3$ | $CH_3$ |
| A-85 | $CH_2CH_2CH(CH_3)_2$ | $CH_2CH_3$ | $CH_3$ |
| A-86 | $CF_3$ | $CH_2CH_3$ | $CH_3$ |
| A-87 | cyclopropyl | $CH_2CH_3$ | $CH_3$ |
| A-88 | cyclobutyl | $CH_2CH_3$ | $CH_3$ |
| A-89 | cyclopentyl | $CH_2CH_3$ | $CH_3$ |
| A-90 | cyclohexyl | $CH_2CH_3$ | $CH_3$ |
| A-91 | | cyclopropyl | H |
| A-92 | | cyclobutyl | H |
| A-93 | | cyclopentyl | H |
| A-94 | | cyclohexyl | H |
| A-95 | | oxiranyl (C*) | H |
| A-96 | | oxetanyl (C*) | H |
| A-97 | | thietanyl (C*) | H |
| A-98 | | 1-oxo-thietanyl (C*) | H |
| A-99 | | 1,1-dioxo-thietanyl (C*) | H |
| A-100 | | 1-methyl-azetidinyl (C*) | H |
| A-101 | | 1-acetyl-azetidinyl (C*) | H |
| A-102 | | thianyl (C*) | H |

TABLE A-continued

| line | R¹ | R² | R³ |
|---|---|---|---|
| A-103 | | (tetrahydrothiopyran S-oxide, C*) | H |
| A-104 | | (tetrahydrothiopyran S,S-dioxide, C*) | H |
| A-105 | | (tetrahydropyran, C* adjacent to O) | H |
| A-106 | | (tetrahydropyran, C*) | H |
| A-107 | | (tetrahydropyran, C*) | H |
| A-108 | | (1,3-dioxane, C*) | H |
| A-109 | | (1,3-dioxane, C*) | H |
| A-110 | | (N-methylpiperidine, C*) | H |
| A-111 | | (N-methoxypiperidine, C*) | H |
| A-112 | | (N-acetylpiperidine, C*) | H |
| A-113 | | (dihydropyran, C*) | H |
| A-114 | | (1,3-dioxine, C*) | H |
| A-115 | | (cyclohexenyl, C*) | CH₃ |
| A-116 | | (cyclohexene-dioxolane spiro, C*) | CH₃ |
| A-117 | cyclopropyl | | CH₃ |
| A-118 | cyclobutyl | | CH₃ |
| A-119 | cyclopentyl | | CH₃ |
| A-120 | cyclohexyl | | CH₃ |

TABLE A-continued

| line | R¹ | R² | R³ |
|---|---|---|---|
| A-121 | | (oxiranyl, C*) | CH₃ |
| A-122 | | (oxetanyl, C*) | CH₃ |
| A-123 | | (thietanyl, C*) | CH₃ |
| A-124 | | (thietane S-oxide, C*) | CH₃ |
| A-125 | | (thietane S,S-dioxide, C*) | CH₃ |
| A-126 | | (N-methylazetidine, C*) | CH₃ |
| A-127 | | (N-acetylazetidine, C*) | CH₃ |
| A-128 | | (tetrahydrothiopyran, C*) | CH₃ |
| A-129 | | (tetrahydrothiopyran S-oxide, C*) | CH₃ |
| A-130 | | (tetrahydrothiopyran S,S-dioxide, C*) | CH₃ |
| A-131 | | (tetrahydropyran, C*) | CH₃ |
| A-132 | | (tetrahydropyran, C*) | CH₃ |
| A-133 | | (tetrahydropyran, C*) | CH₃ |
| A-134 | | (1,3-dioxane, C*) | CH₃ |
| A-135 | | (1,3-dioxane, C*) | CH₃ |

TABLE A-continued

| line | R$^1$ | R$^2$ | R$^3$ |
|---|---|---|---|
| A-136 | | C*-(piperidinyl)N—CH$_3$ | CH$_3$ |
| A-137 | | C*-(piperidinyl)N—OCH$_3$ | CH$_3$ |
| A-138 | | C*-(piperidinyl)N—C(=O)CH$_3$ | CH$_3$ |
| A-139 | | C*-(dihydropyran) | CH$_3$ |
| A-140 | | C*-(dioxine) | CH$_3$ |
| A-141 | | C*-(cyclohexenyl) | CH$_3$ |
| A-142 | | C*-(spiro dioxolane cyclohexene) | CH$_3$ |

TABLE B

For compounds where ZY is in para-position. The position(s) of the substituent(s) (R$^4$)$_n$ is/are given in relation to the attachment of the isoxazole-unit. The position(s) of the substituent(s) (R$^5$)$_m$ is/are given in relation to the attachment of the phenyl to the O-phenyl-unit.

| line | (R$^4$)$_n$ | (R$^5$)$_m$ |
|---|---|---|
| B-1 | —* | —* |
| B-2 | —* | 2-Cl |
| B-3 | —* | 3-Cl |
| B-4 | —* | 4-Cl |
| B-5 | —* | 2-F |
| B-6 | —* | 3-F |
| B-7 | —* | 4-F |
| B-8 | —* | 2-CN |
| B-9 | —* | 3-CN |
| B-10 | —* | 4-CN |
| B-11 | —* | 2-NO$_2$ |
| B-12 | —* | 3-NO$_2$ |
| B-13 | —* | 4-NO$_2$ |
| B-14 | —* | 2-SCH$_3$ |
| B-15 | —* | 3-SCH$_3$ |
| B-16 | —* | 4-SCH$_3$ |
| B-17 | —* | 2-SOCH$_3$ |
| B-18 | —* | 3-SOCH$_3$ |
| B-19 | —* | 4-SOCH$_3$ |
| B-20 | —* | 2-SO$_2$CH$_3$ |
| B-21 | —* | 3-SO$_2$CH$_3$ |
| B-22 | —* | 4-SO$_2$CH$_3$ |
| B-23 | —* | 2-CO$_2$CH$_3$ |
| B-24 | —* | 3-CO$_2$CH$_3$ |
| B-25 | —* | 4-CO$_2$CH$_3$ |
| B-26 | —* | 2-CH$_3$ |
| B-27 | —* | 3-CH$_3$ |
| B-28 | —* | 4-CH$_3$ |
| B-29 | —* | 2-CF$_3$ |
| B-30 | —* | 3-CF$_3$ |
| B-31 | —* | 4-CF$_3$ |
| B-32 | —* | 2-CHF$_2$ |
| B-33 | —* | 3-CHF$_2$ |
| B-34 | —* | 4-CHF$_2$ |
| B-35 | —* | 2-OCH$_3$ |
| B-36 | —* | 3-OCH$_3$ |
| B-37 | —* | 4-OCH$_3$ |
| B-38 | —* | 2-OCF$_3$ |
| B-39 | —* | 3-OCF$_3$ |
| B-40 | —* | 4-OCF$_3$ |
| B-41 | —* | 2-OCHF$_2$ |
| B-42 | —* | 3-OCHF$_2$ |
| B-43 | —* | 4-OCHF$_2$ |
| B-44 | —* | 2,4,6-(CH$_3$)$_3$ |
| B-45 | —* | 2,3-Cl$_2$ |
| B-46 | —* | 2,4-Cl$_2$ |
| B-47 | —* | 2,5-Cl$_2$ |
| B-48 | —* | 3,4-Cl$_2$ |
| B-49 | —* | 3,5-Cl$_2$ |
| B-50 | —* | 2,6-Cl$_2$ |
| B-51 | —* | 2,3-F$_2$ |
| B-52 | —* | 2,4-F$_2$ |
| B-53 | —* | 2,5-F$_2$ |
| B-54 | —* | 3,4-F$_2$ |
| B-55 | —* | 3,5-F$_2$ |
| B-56 | —* | 2,6-F$_2$ |
| B-57 | —* | 2-CF$_3$-4-Cl |
| B-58 | —* | 2-CF$_3$-4-F |
| B-59 | —* | 2-Cl-4-CF$_3$ |
| B-60 | —* | 2-F-4-CF$_3$ |
| B-61 | —* | 2-CN-4-Cl |
| B-62 | —* | 2-CN-4-F |
| B-63 | —* | 2-Cl-4-CN |
| B-64 | —* | 2-F-4-CN |
| B-65 | 2-Cl | —* |
| B-66 | 2-Cl | 2-Cl |
| B-67 | 2-Cl | 3-Cl |
| B-68 | 2-Cl | 4-Cl |
| B-69 | 2-Cl | 2-F |
| B-70 | 2-Cl | 3-F |
| B-71 | 2-Cl | 4-F |
| B-72 | 2-Cl | 2-CN |
| B-73 | 2-Cl | 3-CN |
| B-74 | 2-Cl | 4-CN |
| B-75 | 2-Cl | 2-NO$_2$ |
| B-76 | 2-Cl | 3-NO$_2$ |
| B-77 | 2-Cl | 4-NO$_2$ |
| B-78 | 2-Cl | 2-SCH$_3$ |
| B-79 | 2-Cl | 3-SCH$_3$ |
| B-80 | 2-Cl | 4-SCH$_3$ |
| B-81 | 2-Cl | 2-SOCH$_3$ |
| B-82 | 2-Cl | 3-SOCH$_3$ |
| B-83 | 2-Cl | 4-SOCH$_3$ |
| B-84 | 2-Cl | 2-SO$_2$CH$_3$ |
| B-85 | 2-Cl | 3-SO$_2$CH$_3$ |
| B-86 | 2-Cl | 4-SO$_2$CH$_3$ |
| B-87 | 2-Cl | 2-CO$_2$CH$_3$ |
| B-88 | 2-Cl | 3-CO$_2$CH$_3$ |
| B-89 | 2-Cl | 4-CO$_2$CH$_3$ |
| B-90 | 2-Cl | 2-CH$_3$ |
| B-91 | 2-Cl | 3-CH$_3$ |
| B-92 | 2-Cl | 4-CH$_3$ |
| B-93 | 2-Cl | 2-CF$_3$ |
| B-94 | 2-Cl | 3-CF$_3$ |
| B-95 | 2-Cl | 4-CF$_3$ |
| B-96 | 2-Cl | 2-CHF$_2$ |
| B-97 | 2-Cl | 3-CHF$_2$ |
| B-98 | 2-Cl | 4-CHF$_2$ |
| B-99 | 2-Cl | 2-OCH$_3$ |
| B-100 | 2-Cl | 3-OCH$_3$ |
| B-101 | 2-Cl | 4-OCH$_3$ |
| B-102 | 2-Cl | 2-OCF$_3$ |
| B-103 | 2-Cl | 3-OCF$_3$ |

TABLE B-continued

For compounds where ZY is in para-position. The position(s) of the substituent(s) $(R^4)_n$ is/are given in relation to the attachment of the isoxazole-unit. The position(s) of the substituent(s) $(R^5)_m$ is/are given in relation to the attachment of the phenyl to the O-phenyl-unit.

| line | $(R^4)_n$ | $(R^5)_m$ |
|---|---|---|
| B-104 | 2-Cl | 4-OCF$_3$ |
| B-105 | 2-Cl | 2-OCHF$_2$ |
| B-106 | 2-Cl | 3-OCHF$_2$ |
| B-107 | 2-Cl | 4-OCHF$_2$ |
| B-108 | 2-Cl | 2,4,6-(CH$_3$)$_3$ |
| B-109 | 2-Cl | 2,3-Cl$_2$ |
| B-110 | 2-Cl | 2,4-Cl$_2$ |
| B-111 | 2-Cl | 2,5-Cl$_2$ |
| B-112 | 2-Cl | 3,4-Cl$_2$ |
| B-113 | 2-Cl | 3,5-Cl$_2$ |
| B-114 | 2-Cl | 2,6-Cl$_2$ |
| B-115 | 2-Cl | 2,3-F$_2$ |
| B-116 | 2-Cl | 2,4-F$_2$ |
| B-117 | 2-Cl | 2,5-F$_2$ |
| B-118 | 2-Cl | 3,4-F$_2$ |
| B-119 | 2-Cl | 3,5-F$_2$ |
| B-120 | 2-Cl | 2,6-F$_2$ |
| B-121 | 2-Cl | 2-CF$_3$-4-Cl |
| B-122 | 2-Cl | 2-CF$_3$-4-F |
| B-123 | 2-Cl | 2-Cl-4-CF$_3$ |
| B-124 | 2-Cl | 2-F-4-CF$_3$ |
| B-125 | 2-Cl | 2-CN-4-Cl |
| B-126 | 2-Cl | 2-CN-4-F |
| B-127 | 2-Cl | 2-Cl-4-CN |
| B-128 | 2-Cl | 2-F-4-CN |
| B-129 | 3-Cl | —* |
| B-130 | 3-Cl | 2-Cl |
| B-131 | 3-Cl | 3-Cl |
| B-132 | 3-Cl | 4-Cl |
| B-133 | 3-Cl | 2-F |
| B-134 | 3-Cl | 3-F |
| B-135 | 3-Cl | 4-F |
| B-136 | 3-Cl | 2-CN |
| B-137 | 3-Cl | 3-CN |
| B-138 | 3-Cl | 4-CN |
| B-139 | 3-Cl | 2-NO$_2$ |
| B-140 | 3-Cl | 3-NO$_2$ |
| B-141 | 3-Cl | 4-NO$_2$ |
| B-142 | 3-Cl | 2-SCH$_3$ |
| B-143 | 3-Cl | 3-SCH$_3$ |
| B-144 | 3-Cl | 4-SCH$_3$ |
| B-145 | 3-Cl | 2-SOCH$_3$ |
| B-146 | 3-Cl | 3-SOCH$_3$ |
| B-147 | 3-Cl | 4-SOCH$_3$ |
| B-148 | 3-Cl | 2-SO$_2$CH$_3$ |
| B-149 | 3-Cl | 3-SO$_2$CH$_3$ |
| B-150 | 3-Cl | 4-SO$_2$CH$_3$ |
| B-151 | 3-Cl | 2-CO$_2$CH$_3$ |
| B-152 | 3-Cl | 3-CO$_2$CH$_3$ |
| B-153 | 3-Cl | 4-CO$_2$CH$_3$ |
| B-154 | 3-Cl | 2-CH$_3$ |
| B-155 | 3-Cl | 3-CH$_3$ |
| B-156 | 3-Cl | 4-CH$_3$ |
| B-157 | 3-Cl | 2-CF$_3$ |
| B-158 | 3-Cl | 3-CF$_3$ |
| B-159 | 3-Cl | 4-CF$_3$ |
| B-160 | 3-Cl | 2-CHF$_2$ |
| B-161 | 3-Cl | 3-CHF$_2$ |
| B-162 | 3-Cl | 4-CHF$_2$ |
| B-163 | 3-Cl | 2-OCH$_3$ |
| B-164 | 3-Cl | 3-OCH$_3$ |
| B-165 | 3-Cl | 4-OCH$_3$ |
| B-166 | 3-Cl | 2-OCF$_3$ |
| B-167 | 3-Cl | 3-OCF$_3$ |
| B-168 | 3-Cl | 4-OCF$_3$ |
| B-169 | 3-Cl | 2-OCHF$_2$ |
| B-170 | 3-Cl | 3-OCHF$_2$ |
| B-171 | 3-Cl | 4-OCHF$_2$ |
| B-172 | 3-Cl | 2,4,6-(CH$_3$)$_3$ |
| B-173 | 3-Cl | 2,3-Cl$_2$ |
| B-174 | 3-Cl | 2,4-Cl$_2$ |
| B-175 | 3-Cl | 2,5-Cl$_2$ |
| B-176 | 3-Cl | 3,4-Cl$_2$ |
| B-177 | 3-Cl | 3,5-Cl$_2$ |
| B-178 | 3-Cl | 2,6-Cl$_2$ |
| B-179 | 3-Cl | 2,3-F$_2$ |
| B-180 | 3-Cl | 2,4-F$_2$ |
| B-181 | 3-Cl | 2,5-F$_2$ |
| B-182 | 3-Cl | 3,4-F$_2$ |
| B-183 | 3-Cl | 3,5-F$_2$ |
| B-184 | 3-Cl | 2,6-F$_2$ |
| B-185 | 3-Cl | 2-CF$_3$-4-Cl |
| B-186 | 3-Cl | 2-CF$_3$-4-F |
| B-187 | 3-Cl | 2-Cl-4-CF$_3$ |
| B-188 | 3-Cl | 2-F-4-CF$_3$ |
| B-189 | 3-Cl | 2-CN-4-Cl |
| B-190 | 3-Cl | 2-CN-4-F |
| B-191 | 3-Cl | 2-Cl-4-CN |
| B-192 | 3-Cl | 2-F-4-CN |
| B-193 | 2-F | —* |
| B-194 | 2-F | 2-Cl |
| B-195 | 2-F | 3-Cl |
| B-196 | 2-F | 4-Cl |
| B-197 | 2-F | 2-F |
| B-198 | 2-F | 3-F |
| B-199 | 2-F | 4-F |
| B-200 | 2-F | 2-CN |
| B-201 | 2-F | 3-CN |
| B-202 | 2-F | 4-CN |
| B-203 | 2-F | 2-NO$_2$ |
| B-204 | 2-F | 3-NO$_2$ |
| B-205 | 2-F | 4-NO$_2$ |
| B-206 | 2-F | 2-SCH$_3$ |
| B-207 | 2-F | 3-SCH$_3$ |
| B-208 | 2-F | 4-SCH$_3$ |
| B-209 | 2-F | 2-SOCH$_3$ |
| B-210 | 2-F | 3-SOCH$_3$ |
| B-211 | 2-F | 4-SOCH$_3$ |
| B-212 | 2-F | 2-SO$_2$CH$_3$ |
| B-213 | 2-F | 3-SO$_2$CH$_3$ |
| B-214 | 2-F | 4-SO$_2$CH$_3$ |
| B-215 | 2-F | 2-CO$_2$CH$_3$ |
| B-216 | 2-F | 3-CO$_2$CH$_3$ |
| B-217 | 2-F | 4-CO$_2$CH$_3$ |
| B-218 | 2-F | 2-CH$_3$ |
| B-219 | 2-F | 3-CH$_3$ |
| B-220 | 2-F | 4-CH$_3$ |
| B-221 | 2-F | 2-CF$_3$ |
| B-222 | 2-F | 3-CF$_3$ |
| B-223 | 2-F | 4-CF$_3$ |
| B-224 | 2-F | 2-CHF$_2$ |
| B-225 | 2-F | 3-CHF$_2$ |
| B-226 | 2-F | 4-CHF$_2$ |
| B-227 | 2-F | 2-OCH$_3$ |
| B-228 | 2-F | 3-OCH$_3$ |
| B-229 | 2-F | 4-OCH$_3$ |
| B-230 | 2-F | 2-OCF$_3$ |
| B-231 | 2-F | 3-OCF$_3$ |
| B-232 | 2-F | 4-OCF$_3$ |
| B-233 | 2-F | 2-OCHF$_2$ |
| B-234 | 2-F | 3-OCHF$_2$ |
| B-235 | 2-F | 4-OCHF$_2$ |
| B-236 | 2-F | 2,4,6-(CH$_3$)$_3$ |
| B-237 | 2-F | 2,3-Cl$_2$ |
| B-238 | 2-F | 2,4-Cl$_2$ |
| B-239 | 2-F | 2,5-Cl$_2$ |
| B-240 | 2-F | 3,4-Cl$_2$ |
| B-241 | 2-F | 3,5-Cl$_2$ |
| B-242 | 2-F | 2,6-Cl$_2$ |
| B-243 | 2-F | 2,3-F$_2$ |
| B-244 | 2-F | 2,4-F$_2$ |
| B-245 | 2-F | 2,5-F$_2$ |
| B-246 | 2-F | 3,4-F$_2$ |
| B-247 | 2-F | 3,5-F$_2$ |
| B-248 | 2-F | 2,6-F$_2$ |
| B-249 | 2-F | 2-CF$_3$-4-Cl |

TABLE B-continued

For compounds where ZY is in para-position. The position(s) of the substituent(s) $(R^4)_n$ is/are given in relation to the attachment of the isoxazole-unit. The position(s) of the substituent(s) $(R^5)_m$ is/are given in relation to the attachment of the phenyl to the O-phenyl-unit.

| line | $(R^4)_n$ | $(R^5)_m$ |
|---|---|---|
| B-250 | 2-F | 2-CF$_3$-4-F |
| B-251 | 2-F | 2-Cl-4-CF$_3$ |
| B-252 | 2-F | 2-F-4-CF$_3$ |
| B-253 | 2-F | 2-CN-4-Cl |
| B-254 | 2-F | 2-CN-4-F |
| B-255 | 2-F | 2-Cl-4-CN |
| B-256 | 2-F | 2-F-4-CN |
| B-257 | 3-F | —* |
| B-258 | 3-F | 2-Cl |
| B-259 | 3-F | 3-Cl |
| B-260 | 3-F | 4-Cl |
| B-261 | 3-F | 2-F |
| B-262 | 3-F | 3-F |
| B-263 | 3-F | 4-F |
| B-264 | 3-F | 2-CN |
| B-265 | 3-F | 3-CN |
| B-266 | 3-F | 4-CN |
| B-267 | 3-F | 2-NO$_2$ |
| B-268 | 3-F | 3-NO$_2$ |
| B-269 | 3-F | 4-NO$_2$ |
| B-270 | 3-F | 2-SCH$_3$ |
| B-271 | 3-F | 3-SCH$_3$ |
| B-272 | 3-F | 4-SCH$_3$ |
| B-273 | 3-F | 2-SOCH$_3$ |
| B-274 | 3-F | 3-SOCH$_3$ |
| B-275 | 3-F | 4-SOCH$_3$ |
| B-276 | 3-F | 2-SO$_2$CH$_3$ |
| B-277 | 3-F | 3-SO$_2$CH$_3$ |
| B-278 | 3-F | 4-SO$_2$CH$_3$ |
| B-279 | 3-F | 2-CO$_2$CH$_3$ |
| B-280 | 3-F | 3-CO$_2$CH$_3$ |
| B-281 | 3-F | 4-CO$_2$CH$_3$ |
| B-282 | 3-F | 2-CH$_3$ |
| B-283 | 3-F | 3-CH$_3$ |
| B-284 | 3-F | 4-CH$_3$ |
| B-285 | 3-F | 2-CF$_3$ |
| B-286 | 3-F | 3-CF$_3$ |
| B-287 | 3-F | 4-CF$_3$ |
| B-288 | 3-F | 2-CHF$_2$ |
| B-289 | 3-F | 3-CHF$_2$ |
| B-290 | 3-F | 4-CHF$_2$ |
| B-291 | 3-F | 2-OCH$_3$ |
| B-292 | 3-F | 3-OCH$_3$ |
| B-293 | 3-F | 4-OCH$_3$ |
| B-294 | 3-F | 2-OCF$_3$ |
| B-295 | 3-F | 3-OCF$_3$ |
| B-296 | 3-F | 4-OCF$_3$ |
| B-297 | 3-F | 2-OCHF$_2$ |
| B-298 | 3-F | 3-OCHF$_2$ |
| B-299 | 3-F | 4-OCHF$_2$ |
| B-300 | 3-F | 2,4,6-(CH$_3$)$_3$ |
| B-301 | 3-F | 2,3-Cl$_2$ |
| B-302 | 3-F | 2,4-Cl$_2$ |
| B-303 | 3-F | 2,5-Cl$_2$ |
| B-304 | 3-F | 3,4-Cl$_2$ |
| B-305 | 3-F | 3,5-Cl$_2$ |
| B-306 | 3-F | 2,6-Cl$_2$ |
| B-307 | 3-F | 2,3-F$_2$ |
| B-308 | 3-F | 2,4-F$_2$ |
| B-309 | 3-F | 2,5-F$_2$ |
| B-310 | 3-F | 3,4-F$_2$ |
| B-311 | 3-F | 3,5-F$_2$ |
| B-312 | 3-F | 2,6-F$_2$ |
| B-313 | 3-F | 2-CF$_3$-4-Cl |
| B-314 | 3-F | 2-CF$_3$-4-F |
| B-315 | 3-F | 2-Cl-4-CF$_3$ |
| B-316 | 3-F | 2-F-4-CF$_3$ |
| B-317 | 3-F | 2-CN-4-Cl |
| B-318 | 3-F | 2-CN-4-F |
| B-319 | 3-F | 2-Cl-4-CN |
| B-320 | 3-F | 2-F-4-CN |
| B-321 | 2-CN | —* |
| B-322 | 2-CN | 2-Cl |
| B-323 | 2-CN | 3-Cl |
| B-324 | 2-CN | 4-Cl |
| B-325 | 2-CN | 2-F |
| B-326 | 2-CN | 3-F |
| B-327 | 2-CN | 4-F |
| B-328 | 2-CN | 2-CN |
| B-329 | 2-CN | 3-CN |
| B-330 | 2-CN | 4-CN |
| B-331 | 2-CN | 2-NO$_2$ |
| B-332 | 2-CN | 3-NO$_2$ |
| B-333 | 2-CN | 4-NO$_2$ |
| B-334 | 2-CN | 2-SCH$_3$ |
| B-335 | 2-CN | 3-SCH$_3$ |
| B-336 | 2-CN | 4-SCH$_3$ |
| B-337 | 2-CN | 2-SOCH$_3$ |
| B-338 | 2-CN | 3-SOCH$_3$ |
| B-339 | 2-CN | 4-SOCH$_3$ |
| B-340 | 2-CN | 2-SO$_2$CH$_3$ |
| B-341 | 2-CN | 3-SO$_2$CH$_3$ |
| B-342 | 2-CN | 4-SO$_2$CH$_3$ |
| B-343 | 2-CN | 2-CO$_2$CH$_3$ |
| B-344 | 2-CN | 3-CO$_2$CH$_3$ |
| B-345 | 2-CN | 4-CO$_2$CH$_3$ |
| B-346 | 2-CN | 2-CH$_3$ |
| B-347 | 2-CN | 3-CH$_3$ |
| B-348 | 2-CN | 4-CH$_3$ |
| B-349 | 2-CN | 2-CF$_3$ |
| B-350 | 2-CN | 3-CF$_3$ |
| B-351 | 2-CN | 4-CF$_3$ |
| B-352 | 2-CN | 2-CHF$_2$ |
| B-353 | 2-CN | 3-CHF$_2$ |
| B-354 | 2-CN | 4-CHF$_2$ |
| B-355 | 2-CN | 2-OCH$_3$ |
| B-356 | 2-CN | 3-OCH$_3$ |
| B-357 | 2-CN | 4-OCH$_3$ |
| B-358 | 2-CN | 2-OCF$_3$ |
| B-359 | 2-CN | 3-OCF$_3$ |
| B-360 | 2-CN | 4-OCF$_3$ |
| B-361 | 2-CN | 2-OCHF$_2$ |
| B-362 | 2-CN | 3-OCHF$_2$ |
| B-363 | 2-CN | 4-OCHF$_2$ |
| B-364 | 2-CN | 2,4,6-(CH$_3$)$_3$ |
| B-365 | 2-CN | 2,3-Cl$_2$ |
| B-366 | 2-CN | 2,4-Cl$_2$ |
| B-367 | 2-CN | 2,5-Cl$_2$ |
| B-368 | 2-CN | 3,4-Cl$_2$ |
| B-369 | 2-CN | 3,5-Cl$_2$ |
| B-370 | 2-CN | 2,6-Cl$_2$ |
| B-371 | 2-CN | 2,3-F$_2$ |
| B-372 | 2-CN | 2,4-F$_2$ |
| B-373 | 2-CN | 2,5-F$_2$ |
| B-374 | 2-CN | 3,4-F$_2$ |
| B-375 | 2-CN | 3,5-F$_2$ |
| B-376 | 2-CN | 2,6-F$_2$ |
| B-377 | 2-CN | 2-CF$_3$-4-Cl |
| B-378 | 2-CN | 2-CF$_3$-4-F |
| B-379 | 2-CN | 2-Cl-4-CF$_3$ |
| B-380 | 2-CN | 2-F-4-CF$_3$ |
| B-381 | 2-CN | 2-CN-4-Cl |
| B-382 | 2-CN | 2-CN-4-F |
| B-383 | 2-CN | 2-Cl-4-CN |
| B-384 | 2-CN | 2-F-4-CN |
| B-385 | 3-CN | —* |
| B-386 | 3-CN | 2-Cl |
| B-387 | 3-CN | 3-Cl |
| B-388 | 3-CN | 4-Cl |
| B-389 | 3-CN | 2-F |
| B-390 | 3-CN | 3-F |
| B-391 | 3-CN | 4-F |
| B-392 | 3-CN | 2-CN |
| B-393 | 3-CN | 3-CN |
| B-394 | 3-CN | 4-CN |
| B-395 | 3-CN | 2-NO$_2$ |

TABLE B-continued

For compounds where ZY is in para-position. The position(s) of the substituent(s) $(R^4)_n$ is/are given in relation to the attachment of the isoxazole-unit. The position(s) of the substituent(s) $(R^5)_m$ is/are given in relation to the attachment of the phenyl to the O-phenyl-unit.

| line | $(R^4)_n$ | $(R^5)_m$ |
|---|---|---|
| B-396 | 3-CN | 3-NO$_2$ |
| B-397 | 3-CN | 4-NO$_2$ |
| B-398 | 3-CN | 2-SCH$_3$ |
| B-399 | 3-CN | 3-SCH$_3$ |
| B-400 | 3-CN | 4-SCH$_3$ |
| B-401 | 3-CN | 2-SOCH$_3$ |
| B-402 | 3-CN | 3-SOCH$_3$ |
| B-403 | 3-CN | 4-SOCH$_3$ |
| B-404 | 3-CN | 2-SO$_2$CH$_3$ |
| B-405 | 3-CN | 3-SO$_2$CH$_3$ |
| B-406 | 3-CN | 4-SO$_2$CH$_3$ |
| B-407 | 3-CN | 2-CO$_2$CH$_3$ |
| B-408 | 3-CN | 3-CO$_2$CH$_3$ |
| B-409 | 3-CN | 4-CO$_2$CH$_3$ |
| B-410 | 3-CN | 2-CH$_3$ |
| B-411 | 3-CN | 3-CH$_3$ |
| B-412 | 3-CN | 4-CH$_3$ |
| B-413 | 3-CN | 2-CF$_3$ |
| B-414 | 3-CN | 3-CF$_3$ |
| B-415 | 3-CN | 4-CF$_3$ |
| B-416 | 3-CN | 2-CHF$_2$ |
| B-417 | 3-CN | 3-CHF$_2$ |
| B-418 | 3-CN | 4-CHF$_2$ |
| B-419 | 3-CN | 2-OCH$_3$ |
| B-420 | 3-CN | 3-OCH$_3$ |
| B-421 | 3-CN | 4-OCH$_3$ |
| B-422 | 3-CN | 2-OCF$_3$ |
| B-423 | 3-CN | 3-OCF$_3$ |
| B-424 | 3-CN | 4-OCF$_3$ |
| B-425 | 3-CN | 2-OCHF$_2$ |
| B-426 | 3-CN | 3-OCHF$_2$ |
| B-427 | 3-CN | 4-OCHF$_2$ |
| B-428 | 3-CN | 2,4,6-(CH$_3$)$_3$ |
| B-429 | 3-CN | 2,3-Cl$_2$ |
| B-430 | 3-CN | 2,4-Cl$_2$ |
| B-431 | 3-CN | 2,5-Cl$_2$ |
| B-432 | 3-CN | 3,4-Cl$_2$ |
| B-433 | 3-CN | 3,5-Cl$_2$ |
| B-434 | 3-CN | 2,6-Cl$_2$ |
| B-435 | 3-CN | 2,3-F$_2$ |
| B-436 | 3-CN | 2,4-F$_2$ |
| B-437 | 3-CN | 2,5-F$_2$ |
| B-438 | 3-CN | 3,4-F$_2$ |
| B-439 | 3-CN | 3,5-F$_2$ |
| B-440 | 3-CN | 2,6-F$_2$ |
| B-441 | 3-CN | 2-CF$_3$-4-Cl |
| B-442 | 3-CN | 2-CF$_3$-4-F |
| B-443 | 3-CN | 2-Cl-4-CF$_3$ |
| B-444 | 3-CN | 2-F-4-CF$_3$ |
| B-445 | 3-CN | 2-CN-4-Cl |
| B-446 | 3-CN | 2-CN-4-F |
| B-447 | 3-CN | 2-Cl-4-CN |
| B-448 | 3-CN | 2-F-4-CN |
| B-449 | 2,3-Cl$_2$ | —* |
| B-450 | 2,3-Cl$_2$ | 2-Cl |
| B-451 | 2,3-Cl$_2$ | 3-Cl |
| B-452 | 2,3-Cl$_2$ | 4-Cl |
| B-453 | 2,3-Cl$_2$ | 2-F |
| B-454 | 2,3-Cl$_2$ | 3-F |
| B-455 | 2,3-Cl$_2$ | 4-F |
| B-456 | 2,3-Cl$_2$ | 2-CN |
| B-457 | 2,3-Cl$_2$ | 3-CN |
| B-458 | 2,3-Cl$_2$ | 4-CN |
| B-459 | 2,3-Cl$_2$ | 2-NO$_2$ |
| B-460 | 2,3-Cl$_2$ | 3-NO$_2$ |
| B-461 | 2,3-Cl$_2$ | 4-NO$_2$ |
| B-462 | 2,3-Cl$_2$ | 2-SCH$_3$ |
| B-463 | 2,3-Cl$_2$ | 3-SCH$_3$ |
| B-464 | 2,3-Cl$_2$ | 4-SCH$_3$ |
| B-465 | 2,3-Cl$_2$ | 2-SOCH$_3$ |
| B-466 | 2,3-Cl$_2$ | 3-SOCH$_3$ |
| B-467 | 2,3-Cl$_2$ | 4-SOCH$_3$ |
| B-468 | 2,3-Cl$_2$ | 2-SO$_2$CH$_3$ |
| B-469 | 2,3-Cl$_2$ | 3-SO$_2$CH$_3$ |
| B-470 | 2,3-Cl$_2$ | 4-SO$_2$CH$_3$ |
| B-471 | 2,3-Cl$_2$ | 2-CO$_2$CH$_3$ |
| B-472 | 2,3-Cl$_2$ | 3-CO$_2$CH$_3$ |
| B-473 | 2,3-Cl$_2$ | 4-CO$_2$CH$_3$ |
| B-474 | 2,3-Cl$_2$ | 2-CH$_3$ |
| B-475 | 2,3-Cl$_2$ | 3-CH$_3$ |
| B-476 | 2,3-Cl$_2$ | 4-CH$_3$ |
| B-477 | 2,3-Cl$_2$ | 2-CF$_3$ |
| B-478 | 2,3-Cl$_2$ | 3-CF$_3$ |
| B-479 | 2,3-Cl$_2$ | 4-CF$_3$ |
| B-480 | 2,3-Cl$_2$ | 2-CHF$_2$ |
| B-481 | 2,3-Cl$_2$ | 3-CHF$_2$ |
| B-482 | 2,3-Cl$_2$ | 4-CHF$_2$ |
| B-483 | 2,3-Cl$_2$ | 2-OCH$_3$ |
| B-484 | 2,3-Cl$_2$ | 3-OCH$_3$ |
| B-485 | 2,3-Cl$_2$ | 4-OCH$_3$ |
| B-486 | 2,3-Cl$_2$ | 2-OCF$_3$ |
| B-487 | 2,3-Cl$_2$ | 3-OCF$_3$ |
| B-488 | 2,3-Cl$_2$ | 4-OCF$_3$ |
| B-489 | 2,3-Cl$_2$ | 2-OCHF$_2$ |
| B-490 | 2,3-Cl$_2$ | 3-OCHF$_2$ |
| B-491 | 2,3-Cl$_2$ | 4-OCHF$_2$ |
| B-492 | 2,3-Cl$_2$ | 2,4,6-(CH$_3$)$_3$ |
| B-493 | 2,3-Cl$_2$ | 2,3-Cl$_2$ |
| B-494 | 2,3-Cl$_2$ | 2,4-Cl$_2$ |
| B-495 | 2,3-Cl$_2$ | 2,5-Cl$_2$ |
| B-496 | 2,3-Cl$_2$ | 3,4-Cl$_2$ |
| B-497 | 2,3-Cl$_2$ | 3,5-Cl$_2$ |
| B-498 | 2,3-Cl$_2$ | 2,6-Cl$_2$ |
| B-499 | 2,3-Cl$_2$ | 2,3-F$_2$ |
| B-500 | 2,3-Cl$_2$ | 2,4-F$_2$ |
| B-501 | 2,3-Cl$_2$ | 2,5-F$_2$ |
| B-502 | 2,3-Cl$_2$ | 3,4-F$_2$ |
| B-503 | 2,3-Cl$_2$ | 3,5-F$_2$ |
| B-504 | 2,3-Cl$_2$ | 2,6-F$_2$ |
| B-505 | 2,3-Cl$_2$ | 2-CF$_3$-4-Cl |
| B-506 | 2,3-Cl$_2$ | 2-CF$_3$-4-F |
| B-507 | 2,3-Cl$_2$ | 2-Cl-4-CF$_3$ |
| B-508 | 2,3-Cl$_2$ | 2-F-4-CF$_3$ |
| B-509 | 2,3-Cl$_2$ | 2-CN-4-Cl |
| B-510 | 2,3-Cl$_2$ | 2-CN-4-F |
| B-511 | 2,3-Cl$_2$ | 2-Cl-4-CN |
| B-512 | 2,3-Cl$_2$ | 2-F-4-CN |
| B-513 | 2,5-Cl$_2$ | —* |
| B-514 | 2,5-Cl$_2$ | 2-Cl |
| B-515 | 2,5-Cl$_2$ | 3-Cl |
| B-516 | 2,5-Cl$_2$ | 4-Cl |
| B-517 | 2,5-Cl$_2$ | 2-F |
| B-518 | 2,5-Cl$_2$ | 3-F |
| B-519 | 2,5-Cl$_2$ | 4-F |
| B-520 | 2,5-Cl$_2$ | 2-CN |
| B-521 | 2,5-Cl$_2$ | 3-CN |
| B-522 | 2,5-Cl$_2$ | 4-CN |
| B-523 | 2,5-Cl$_2$ | 2-NO$_2$ |
| B-524 | 2,5-Cl$_2$ | 3-NO$_2$ |
| B-525 | 2,5-Cl$_2$ | 4-NO$_2$ |
| B-526 | 2,5-Cl$_2$ | 2-SCH$_3$ |
| B-527 | 2,5-Cl$_2$ | 3-SCH$_3$ |
| B-528 | 2,5-Cl$_2$ | 4-SCH$_3$ |
| B-529 | 2,5-Cl$_2$ | 2-SOCH$_3$ |
| B-530 | 2,5-Cl$_2$ | 3-SOCH$_3$ |
| B-531 | 2,5-Cl$_2$ | 4-SOCH$_3$ |
| B-532 | 2,5-Cl$_2$ | 2-SO$_2$CH$_3$ |
| B-533 | 2,5-Cl$_2$ | 3-SO$_2$CH$_3$ |
| B-534 | 2,5-Cl$_2$ | 4-SO$_2$CH$_3$ |
| B-535 | 2,5-Cl$_2$ | 2-CO$_2$CH$_3$ |
| B-536 | 2,5-Cl$_2$ | 3-CO$_2$CH$_3$ |
| B-537 | 2,5-Cl$_2$ | 4-CO$_2$CH$_3$ |
| B-538 | 2,5-Cl$_2$ | 2-CH$_3$ |
| B-539 | 2,5-Cl$_2$ | 3-CH$_3$ |
| B-540 | 2,5-Cl$_2$ | 4-CH$_3$ |
| B-541 | 2,5-Cl$_2$ | 2-CF$_3$ |

TABLE B-continued

For compounds where ZY is in para-position. The position(s) of the substituent(s) $(R^4)_n$ is/are given in relation to the attachment of the isoxazole-unit. The position(s) of the substituent(s) $(R^5)_m$ is/are given in relation to the attachment of the phenyl to the O-phenyl-unit.

| line | $(R^4)_n$ | $(R^5)_m$ |
|---|---|---|
| B-542 | 2,5-Cl$_2$ | 3-CF$_3$ |
| B-543 | 2,5-Cl$_2$ | 4-CF$_3$ |
| B-544 | 2,5-Cl$_2$ | 2-CHF$_2$ |
| B-545 | 2,5-Cl$_2$ | 3-CHF$_2$ |
| B-546 | 2,5-Cl$_2$ | 4-CHF$_2$ |
| B-547 | 2,5-Cl$_2$ | 2-OCH$_3$ |
| B-548 | 2,5-Cl$_2$ | 3-OCH$_3$ |
| B-549 | 2,5-Cl$_2$ | 4-OCH$_3$ |
| B-550 | 2,5-Cl$_2$ | 2-OCF$_3$ |
| B-551 | 2,5-Cl$_2$ | 3-OCF$_3$ |
| B-552 | 2,5-Cl$_2$ | 4-OCF$_3$ |
| B-553 | 2,5-Cl$_2$ | 2-OCHF$_2$ |
| B-554 | 2,5-Cl$_2$ | 3-OCHF$_2$ |
| B-555 | 2,5-Cl$_2$ | 4-OCHF$_2$ |
| B-556 | 2,5-Cl$_2$ | 2,4,6-(CH$_3$)$_3$ |
| B-557 | 2,5-Cl$_2$ | 2,3-Cl$_2$ |
| B-558 | 2,5-Cl$_2$ | 2,4-Cl$_2$ |
| B-559 | 2,5-Cl$_2$ | 2,5-Cl$_2$ |
| B-560 | 2,5-Cl$_2$ | 3,4-Cl$_2$ |
| B-561 | 2,5-Cl$_2$ | 3,5-Cl$_2$ |
| B-562 | 2,5-Cl$_2$ | 2,6-Cl$_2$ |
| B-563 | 2,5-Cl$_2$ | 2,3-F$_2$ |
| B-564 | 2,5-Cl$_2$ | 2,4-F$_2$ |
| B-565 | 2,5-Cl$_2$ | 2,5-F$_2$ |
| B-566 | 2,5-Cl$_2$ | 3,4-F$_2$ |
| B-567 | 2,5-Cl$_2$ | 3,5-F$_2$ |
| B-568 | 2,5-Cl$_2$ | 2,6-F$_2$ |
| B-569 | 2,5-Cl$_2$ | 2-CF$_3$-4-Cl |
| B-570 | 2,5-Cl$_2$ | 2-CF$_3$-4-F |
| B-571 | 2,5-Cl$_2$ | 2-Cl-4-CF$_3$ |
| B-572 | 2,5-Cl$_2$ | 2-F-4-CF$_3$ |
| B-573 | 2,5-Cl$_2$ | 2-CN-4-Cl |
| B-574 | 2,5-Cl$_2$ | 2-CN-4-F |
| B-575 | 2,5-Cl$_2$ | 2-Cl-4-CN |
| B-576 | 2,5-Cl$_2$ | 2-F-4-CN |
| B-577 | 3,5-Cl$_2$ | —* |
| B-578 | 3,5-Cl$_2$ | 2-Cl |
| B-579 | 3,5-Cl$_2$ | 3-Cl |
| B-580 | 3,5-Cl$_2$ | 4-Cl |
| B-581 | 3,5-Cl$_2$ | 2-F |
| B-582 | 3,5-Cl$_2$ | 3-F |
| B-583 | 3,5-Cl$_2$ | 4-F |
| B-584 | 3,5-Cl$_2$ | 2-CN |
| B-585 | 3,5-Cl$_2$ | 3-CN |
| B-586 | 3,5-Cl$_2$ | 4-CN |
| B-587 | 3,5-Cl$_2$ | 2-NO$_2$ |
| B-588 | 3,5-Cl$_2$ | 3-NO$_2$ |
| B-589 | 3,5-Cl$_2$ | 4-NO$_2$ |
| B-590 | 3,5-Cl$_2$ | 2-SCH$_3$ |
| B-591 | 3,5-Cl$_2$ | 3-SCH$_3$ |
| B-592 | 3,5-Cl$_2$ | 4-SCH$_3$ |
| B-593 | 3,5-Cl$_2$ | 2-SOCH$_3$ |
| B-594 | 3,5-Cl$_2$ | 3-SOCH$_3$ |
| B-595 | 3,5-Cl$_2$ | 4-SOCH$_3$ |
| B-596 | 3,5-Cl$_2$ | 2-SO$_2$CH$_3$ |
| B-597 | 3,5-Cl$_2$ | 3-SO$_2$CH$_3$ |
| B-598 | 3,5-Cl$_2$ | 4-SO$_2$CH$_3$ |
| B-599 | 3,5-Cl$_2$ | 2-CO$_2$CH$_3$ |
| B-600 | 3,5-Cl$_2$ | 3-CO$_2$CH$_3$ |
| B-601 | 3,5-Cl$_2$ | 4-CO$_2$CH$_3$ |
| B-602 | 3,5-Cl$_2$ | 2-CH$_3$ |
| B-603 | 3,5-Cl$_2$ | 3-CH$_3$ |
| B-604 | 3,5-Cl$_2$ | 4-CH$_3$ |
| B-605 | 3,5-Cl$_2$ | 2-CF$_3$ |
| B-606 | 3,5-Cl$_2$ | 3-CF$_3$ |
| B-607 | 3,5-Cl$_2$ | 4-CF$_3$ |
| B-608 | 3,5-Cl$_2$ | 2-CHF$_2$ |
| B-609 | 3,5-Cl$_2$ | 3-CHF$_2$ |
| B-610 | 3,5-Cl$_2$ | 4-CHF$_2$ |
| B-611 | 3,5-Cl$_2$ | 2-OCH$_3$ |
| B-612 | 3,5-Cl$_2$ | 3-OCH$_3$ |
| B-613 | 3,5-Cl$_2$ | 4-OCH$_3$ |
| B-614 | 3,5-Cl$_2$ | 2-OCF$_3$ |
| B-615 | 3,5-Cl$_2$ | 3-OCF$_3$ |
| B-616 | 3,5-Cl$_2$ | 4-OCF$_3$ |
| B-617 | 3,5-Cl$_2$ | 2-OCHF$_2$ |
| B-618 | 3,5-Cl$_2$ | 3-OCHF$_2$ |
| B-619 | 3,5-Cl$_2$ | 4-OCHF$_2$ |
| B-620 | 3,5-Cl$_2$ | 2,4,6-(CH$_3$)$_3$ |
| B-621 | 3,5-Cl$_2$ | 2,3-Cl$_2$ |
| B-622 | 3,5-Cl$_2$ | 2,4-Cl$_2$ |
| B-623 | 3,5-Cl$_2$ | 2,5-Cl$_2$ |
| B-624 | 3,5-Cl$_2$ | 3,4-Cl$_2$ |
| B-625 | 3,5-Cl$_2$ | 3,5-Cl$_2$ |
| B-626 | 3,5-Cl$_2$ | 2,6-Cl$_2$ |
| B-627 | 3,5-Cl$_2$ | 2,3-F$_2$ |
| B-628 | 3,5-Cl$_2$ | 2,4-F$_2$ |
| B-629 | 3,5-Cl$_2$ | 2,5-F$_2$ |
| B-630 | 3,5-Cl$_2$ | 3,4-F$_2$ |
| B-631 | 3,5-Cl$_2$ | 3,5-F$_2$ |
| B-632 | 3,5-Cl$_2$ | 2,6-F$_2$ |
| B-633 | 3,5-Cl$_2$ | 2-CF$_3$-4-Cl |
| B-634 | 3,5-Cl$_2$ | 2-CF$_3$-4-F |
| B-635 | 3,5-Cl$_2$ | 2-Cl-4-CF$_3$ |
| B-636 | 3,5-Cl$_2$ | 2-F-4-CF$_3$ |
| B-637 | 3,5-Cl$_2$ | 2-CN-4-Cl |
| B-638 | 3,5-Cl$_2$ | 2-CN-4-F |
| B-639 | 3,5-Cl$_2$ | 2-Cl-4-CN |
| B-640 | 3,5-Cl$_2$ | 2-F-4-CN |
| B-641 | 2,6-Cl$_2$ | —* |
| B-642 | 2,6-Cl$_2$ | 2-Cl |
| B-643 | 2,6-Cl$_2$ | 3-Cl |
| B-644 | 2,6-Cl$_2$ | 4-Cl |
| B-645 | 2,6-Cl$_2$ | 2-F |
| B-646 | 2,6-Cl$_2$ | 3-F |
| B-647 | 2,6-Cl$_2$ | 4-F |
| B-648 | 2,6-Cl$_2$ | 2-CN |
| B-649 | 2,6-Cl$_2$ | 3-CN |
| B-650 | 2,6-Cl$_2$ | 4-CN |
| B-651 | 2,6-Cl$_2$ | 2-NO$_2$ |
| B-652 | 2,6-Cl$_2$ | 3-NO$_2$ |
| B-653 | 2,6-Cl$_2$ | 4-NO$_2$ |
| B-654 | 2,6-Cl$_2$ | 2-SCH$_3$ |
| B-655 | 2,6-Cl$_2$ | 3-SCH$_3$ |
| B-656 | 2,6-Cl$_2$ | 4-SCH$_3$ |
| B-657 | 2,6-Cl$_2$ | 2-SOCH$_3$ |
| B-658 | 2,6-Cl$_2$ | 3-SOCH$_3$ |
| B-659 | 2,6-Cl$_2$ | 4-SOCH$_3$ |
| B-660 | 2,6-Cl$_2$ | 2-SO$_2$CH$_3$ |
| B-661 | 2,6-Cl$_2$ | 3-SO$_2$CH$_3$ |
| B-662 | 2,6-Cl$_2$ | 4-SO$_2$CH$_3$ |
| B-663 | 2,6-Cl$_2$ | 2-CO$_2$CH$_3$ |
| B-664 | 2,6-Cl$_2$ | 3-CO$_2$CH$_3$ |
| B-665 | 2,6-Cl$_2$ | 4-CO$_2$CH$_3$ |
| B-666 | 2,6-Cl$_2$ | 2-CH$_3$ |
| B-667 | 2,6-Cl$_2$ | 3-CH$_3$ |
| B-668 | 2,6-Cl$_2$ | 4-CH$_3$ |
| B-669 | 2,6-Cl$_2$ | 2-CF$_3$ |
| B-670 | 2,6-Cl$_2$ | 3-CF$_3$ |
| B-671 | 2,6-Cl$_2$ | 4-CF$_3$ |
| B-672 | 2,6-Cl$_2$ | 2-CHF$_2$ |
| B-673 | 2,6-Cl$_2$ | 3-CHF$_2$ |
| B-674 | 2,6-Cl$_2$ | 4-CHF$_2$ |
| B-675 | 2,6-Cl$_2$ | 2-OCH$_3$ |
| B-676 | 2,6-Cl$_2$ | 3-OCH$_3$ |
| B-677 | 2,6-Cl$_2$ | 4-OCH$_3$ |
| B-678 | 2,6-Cl$_2$ | 2-OCF$_3$ |
| B-679 | 2,6-Cl$_2$ | 3-OCF$_3$ |
| B-680 | 2,6-Cl$_2$ | 4-OCF$_3$ |
| B-681 | 2,6-Cl$_2$ | 2-OCHF$_2$ |
| B-682 | 2,6-Cl$_2$ | 3-OCHF$_2$ |
| B-683 | 2,6-Cl$_2$ | 4-OCHF$_2$ |
| B-684 | 2,6-Cl$_2$ | 2,4,6-(CH$_3$)$_3$ |
| B-685 | 2,6-Cl$_2$ | 2,3-Cl$_2$ |
| B-686 | 2,6-Cl$_2$ | 2,4-Cl$_2$ |
| B-687 | 2,6-Cl$_2$ | 2,5-Cl$_2$ |

TABLE B-continued

For compounds where ZY is in para-position. The position(s) of the substituent(s) $(R^4)_n$ is/are given in relation to the attachment of the isoxazole-unit. The position(s) of the substituent(s) $(R^5)_m$ is/are given in relation to the attachment of the phenyl to the O-phenyl-unit.

| line | $(R^4)_n$ | $(R^5)_m$ |
|---|---|---|
| B-688 | 2,6-Cl$_2$ | 3,4-Cl$_2$ |
| B-689 | 2,6-Cl$_2$ | 3,5-Cl$_2$ |
| B-690 | 2,6-Cl$_2$ | 2,6-Cl$_2$ |
| B-691 | 2,6-Cl$_2$ | 2,3-F$_2$ |
| B-692 | 2,6-Cl$_2$ | 2,4-F$_2$ |
| B-693 | 2,6-Cl$_2$ | 2,5-F$_2$ |
| B-694 | 2,6-Cl$_2$ | 3,4-F$_2$ |
| B-695 | 2,6-Cl$_2$ | 3,5-F$_2$ |
| B-696 | 2,6-Cl$_2$ | 2,6-F$_2$ |
| B-697 | 2,6-Cl$_2$ | 2-CF$_3$-4-Cl |
| B-698 | 2,6-Cl$_2$ | 2-CF$_3$-4-F |
| B-699 | 2,6-Cl$_2$ | 2-Cl-4-CF$_3$ |
| B-700 | 2,6-Cl$_2$ | 2-F-4-CF$_3$ |
| B-701 | 2,6-Cl$_2$ | 2-CN-4-Cl |
| B-702 | 2,6-Cl$_2$ | 2-CN-4-F |
| B-703 | 2,6-Cl$_2$ | 2-Cl-4-CN |
| B-704 | 2,6-Cl$_2$ | 2-F-4-CN |
| B-705 | 2,3-F$_2$ | —* |
| B-706 | 2,3-F$_2$ | 2-Cl |
| B-707 | 2,3-F$_2$ | 3-Cl |
| B-708 | 2,3-F$_2$ | 4-Cl |
| B-709 | 2,3-F$_2$ | 2-F |
| B-710 | 2,3-F$_2$ | 3-F |
| B-711 | 2,3-F$_2$ | 4-F |
| B-712 | 2,3-F$_2$ | 2-CN |
| B-713 | 2,3-F$_2$ | 3-CN |
| B-714 | 2,3-F$_2$ | 4-CN |
| B-715 | 2,3-F$_2$ | 2-NO$_2$ |
| B-716 | 2,3-F$_2$ | 3-NO$_2$ |
| B-717 | 2,3-F$_2$ | 4-NO$_2$ |
| B-718 | 2,3-F$_2$ | 2-SCH$_3$ |
| B-719 | 2,3-F$_2$ | 3-SCH$_3$ |
| B-720 | 2,3-F$_2$ | 4-SCH$_3$ |
| B-721 | 2,3-F$_2$ | 2-SOCH$_3$ |
| B-722 | 2,3-F$_2$ | 3-SOCH$_3$ |
| B-723 | 2,3-F$_2$ | 4-SOCH$_3$ |
| B-724 | 2,3-F$_2$ | 2-SO$_2$CH$_3$ |
| B-725 | 2,3-F$_2$ | 3-SO$_2$CH$_3$ |
| B-726 | 2,3-F$_2$ | 4-SO$_2$CH$_3$ |
| B-727 | 2,3-F$_2$ | 2-CO$_2$CH$_3$ |
| B-728 | 2,3-F$_2$ | 3-CO$_2$CH$_3$ |
| B-729 | 2,3-F$_2$ | 4-CO$_2$CH$_3$ |
| B-730 | 2,3-F$_2$ | 2-CH$_3$ |
| B-731 | 2,3-F$_2$ | 3-CH$_3$ |
| B-732 | 2,3-F$_2$ | 4-CH$_3$ |
| B-733 | 2,3-F$_2$ | 2-CF$_3$ |
| B-734 | 2,3-F$_2$ | 3-CF$_3$ |
| B-735 | 2,3-F$_2$ | 4-CF$_3$ |
| B-736 | 2,3-F$_2$ | 2-CHF$_2$ |
| B-737 | 2,3-F$_2$ | 3-CHF$_2$ |
| B-738 | 2,3-F$_2$ | 4-CHF$_2$ |
| B-739 | 2,3-F$_2$ | 2-OCH$_3$ |
| B-740 | 2,3-F$_2$ | 3-OCH$_3$ |
| B-741 | 2,3-F$_2$ | 4-OCH$_3$ |
| B-742 | 2,3-F$_2$ | 2-OCF$_3$ |
| B-743 | 2,3-F$_2$ | 3-OCF$_3$ |
| B-744 | 2,3-F$_2$ | 4-OCF$_3$ |
| B-745 | 2,3-F$_2$ | 2-OCHF$_2$ |
| B-746 | 2,3-F$_2$ | 3-OCHF$_2$ |
| B-747 | 2,3-F$_2$ | 4-OCHF$_2$ |
| B-748 | 2,3-F$_2$ | 2,4,6-(CH$_3$)$_3$ |
| B-749 | 2,3-F$_2$ | 2,3-Cl$_2$ |
| B-750 | 2,3-F$_2$ | 2,4-Cl$_2$ |
| B-751 | 2,3-F$_2$ | 2,5-Cl$_2$ |
| B-752 | 2,3-F$_2$ | 3,4-Cl$_2$ |
| B-753 | 2,3-F$_2$ | 3,5-Cl$_2$ |
| B-754 | 2,3-F$_2$ | 2,6-Cl$_2$ |
| B-755 | 2,3-F$_2$ | 2,3-F$_2$ |
| B-756 | 2,3-F$_2$ | 2,4-F$_2$ |
| B-757 | 2,3-F$_2$ | 2,5-F$_2$ |
| B-758 | 2,3-F$_2$ | 3,4-F$_2$ |
| B-759 | 2,3-F$_2$ | 3,5-F$_2$ |
| B-760 | 2,3-F$_2$ | 2,6-F$_2$ |
| B-761 | 2,3-F$_2$ | 2-CF$_3$-4-Cl |
| B-762 | 2,3-F$_2$ | 2-CF$_3$-4-F |
| B-763 | 2,3-F$_2$ | 2-Cl-4-CF$_3$ |
| B-764 | 2,3-F$_2$ | 2-F-4-CF$_3$ |
| B-765 | 2,3-F$_2$ | 2-CN-4-Cl |
| B-766 | 2,3-F$_2$ | 2-CN-4-F |
| B-767 | 2,3-F$_2$ | 2-Cl-4-CN |
| B-768 | 2,3-F$_2$ | 2-F-4-CN |
| B-769 | 2,5-F$_2$ | —* |
| B-770 | 2,5-F$_2$ | 2-Cl |
| B-771 | 2,5-F$_2$ | 3-Cl |
| B-772 | 2,5-F$_2$ | 4-Cl |
| B-773 | 2,5-F$_2$ | 2-F |
| B-774 | 2,5-F$_2$ | 3-F |
| B-775 | 2,5-F$_2$ | 4-F |
| B-776 | 2,5-F$_2$ | 2-CN |
| B-777 | 2,5-F$_2$ | 3-CN |
| B-778 | 2,5-F$_2$ | 4-CN |
| B-779 | 2,5-F$_2$ | 2-NO$_2$ |
| B-780 | 2,5-F$_2$ | 3-NO$_2$ |
| B-781 | 2,5-F$_2$ | 4-NO$_2$ |
| B-782 | 2,5-F$_2$ | 2-SCH$_3$ |
| B-783 | 2,5-F$_2$ | 3-SCH$_3$ |
| B-784 | 2,5-F$_2$ | 4-SCH$_3$ |
| B-785 | 2,5-F$_2$ | 2-SOCH$_3$ |
| B-786 | 2,5-F$_2$ | 3-SOCH$_3$ |
| B-787 | 2,5-F$_2$ | 4-SOCH$_3$ |
| B-788 | 2,5-F$_2$ | 2-SO$_2$CH$_3$ |
| B-789 | 2,5-F$_2$ | 3-SO$_2$CH$_3$ |
| B-790 | 2,5-F$_2$ | 4-SO$_2$CH$_3$ |
| B-791 | 2,5-F$_2$ | 2-CO$_2$CH$_3$ |
| B-792 | 2,5-F$_2$ | 3-CO$_2$CH$_3$ |
| B-793 | 2,5-F$_2$ | 4-CO$_2$CH$_3$ |
| B-794 | 2,5-F$_2$ | 2-CH$_3$ |
| B-795 | 2,5-F$_2$ | 3-CH$_3$ |
| B-796 | 2,5-F$_2$ | 4-CH$_3$ |
| B-797 | 2,5-F$_2$ | 2-CF$_3$ |
| B-798 | 2,5-F$_2$ | 3-CF$_3$ |
| B-799 | 2,5-F$_2$ | 4-CF$_3$ |
| B-800 | 2,5-F$_2$ | 2-CHF$_2$ |
| B-801 | 2,5-F$_2$ | 3-CHF$_2$ |
| B-802 | 2,5-F$_2$ | 4-CHF$_2$ |
| B-803 | 2,5-F$_2$ | 2-OCH$_3$ |
| B-804 | 2,5-F$_2$ | 3-OCH$_3$ |
| B-805 | 2,5-F$_2$ | 4-OCH$_3$ |
| B-806 | 2,5-F$_2$ | 2-OCF$_3$ |
| B-807 | 2,5-F$_2$ | 3-OCF$_3$ |
| B-808 | 2,5-F$_2$ | 4-OCF$_3$ |
| B-809 | 2,5-F$_2$ | 2-OCHF$_2$ |
| B-810 | 2,5-F$_2$ | 3-OCHF$_2$ |
| B-811 | 2,5-F$_2$ | 4-OCHF$_2$ |
| B-812 | 2,5-F$_2$ | 2,4,6-(CH$_3$)$_3$ |
| B-813 | 2,5-F$_2$ | 2,3-Cl$_2$ |
| B-814 | 2,5-F$_2$ | 2,4-Cl$_2$ |
| B-815 | 2,5-F$_2$ | 2,5-Cl$_2$ |
| B-816 | 2,5-F$_2$ | 3,4-Cl$_2$ |
| B-817 | 2,5-F$_2$ | 3,5-Cl$_2$ |
| B-818 | 2,5-F$_2$ | 2,6-Cl$_2$ |
| B-819 | 2,5-F$_2$ | 2,3-F$_2$ |
| B-820 | 2,5-F$_2$ | 2,4-F$_2$ |
| B-821 | 2,5-F$_2$ | 2,5-F$_2$ |
| B-822 | 2,5-F$_2$ | 3,4-F$_2$ |
| B-823 | 2,5-F$_2$ | 3,5-F$_2$ |
| B-824 | 2,5-F$_2$ | 2,6-F$_2$ |
| B-825 | 2,5-F$_2$ | 2-CF$_3$-4-Cl |
| B-826 | 2,5-F$_2$ | 2-CF$_3$-4-F |
| B-827 | 2,5-F$_2$ | 2-Cl-4-CF$_3$ |
| B-828 | 2,5-F$_2$ | 2-F-4-CF$_3$ |
| B-829 | 2,5-F$_2$ | 2-CN-4-Cl |
| B-830 | 2,5-F$_2$ | 2-CN-4-F |
| B-831 | 2,5-F$_2$ | 2-Cl-4-CN |
| B-832 | 2,5-F$_2$ | 2-F-4-CN |
| B-833 | 3,5-F$_2$ | —* |

TABLE B-continued

For compounds where ZY is in para-position. The position(s) of the substituent(s) $(R^4)_n$ is/are given in relation to the attachment of the isoxazole-unit. The position(s) of the substituent(s) $(R^5)_m$ is/are given in relation to the attachment of the phenyl to the O-phenyl-unit.

| line | $(R^4)_n$ | $(R^5)_m$ |
| --- | --- | --- |
| B-834 | 3,5-F$_2$ | 2-Cl |
| B-835 | 3,5-F$_2$ | 3-Cl |
| B-836 | 3,5-F$_2$ | 4-Cl |
| B-837 | 3,5-F$_2$ | 2-F |
| B-838 | 3,5-F$_2$ | 3-F |
| B-839 | 3,5-F$_2$ | 4-F |
| B-840 | 3,5-F$_2$ | 2-CN |
| B-841 | 3,5-F$_2$ | 3-CN |
| B-842 | 3,5-F$_2$ | 4-CN |
| B-843 | 3,5-F$_2$ | 2-NO$_2$ |
| B-844 | 3,5-F$_2$ | 3-NO$_2$ |
| B-845 | 3,5-F$_2$ | 4-NO$_2$ |
| B-846 | 3,5-F$_2$ | 2-SCH$_3$ |
| B-847 | 3,5-F$_2$ | 3-SCH$_3$ |
| B-848 | 3,5-F$_2$ | 4-SCH$_3$ |
| B-849 | 3,5-F$_2$ | 2-SOCH$_3$ |
| B-850 | 3,5-F$_2$ | 3-SOCH$_3$ |
| B-851 | 3,5-F$_2$ | 4-SOCH$_3$ |
| B-852 | 3,5-F$_2$ | 2-SO$_2$CH$_3$ |
| B-853 | 3,5-F$_2$ | 3-SO$_2$CH$_3$ |
| B-854 | 3,5-F$_2$ | 4-SO$_2$CH$_3$ |
| B-855 | 3,5-F$_2$ | 2-CO$_2$CH$_3$ |
| B-856 | 3,5-F$_2$ | 3-CO$_2$CH$_3$ |
| B-857 | 3,5-F$_2$ | 4-CO$_2$CH$_3$ |
| B-858 | 3,5-F$_2$ | 2-CH$_3$ |
| B-859 | 3,5-F$_2$ | 3-CH$_3$ |
| B-860 | 3,5-F$_2$ | 4-CH$_3$ |
| B-861 | 3,5-F$_2$ | 2-CF$_3$ |
| B-862 | 3,5-F$_2$ | 3-CF$_3$ |
| B-863 | 3,5-F$_2$ | 4-CF$_3$ |
| B-864 | 3,5-F$_2$ | 2-CHF$_2$ |
| B-865 | 3,5-F$_2$ | 3-CHF$_2$ |
| B-866 | 3,5-F$_2$ | 4-CHF$_2$ |
| B-867 | 3,5-F$_2$ | 2-OCH$_3$ |
| B-868 | 3,5-F$_2$ | 3-OCH$_3$ |
| B-869 | 3,5-F$_2$ | 4-OCH$_3$ |
| B-870 | 3,5-F$_2$ | 2-OCF$_3$ |
| B-871 | 3,5-F$_2$ | 3-OCF$_3$ |
| B-872 | 3,5-F$_2$ | 4-OCF$_3$ |
| B-873 | 3,5-F$_2$ | 2-OCHF$_2$ |
| B-874 | 3,5-F$_2$ | 3-OCHF$_2$ |
| B-875 | 3,5-F$_2$ | 4-OCHF$_2$ |
| B-876 | 3,5-F$_2$ | 2,4,6-(CH$_3$)$_3$ |
| B-877 | 3,5-F$_2$ | 2,3-Cl$_2$ |
| B-878 | 3,5-F$_2$ | 2,4-Cl$_2$ |
| B-879 | 3,5-F$_2$ | 2,5-Cl$_2$ |
| B-880 | 3,5-F$_2$ | 3,4-Cl$_2$ |
| B-881 | 3,5-F$_2$ | 3,5-Cl$_2$ |
| B-882 | 3,5-F$_2$ | 2,6-Cl$_2$ |
| B-883 | 3,5-F$_2$ | 2,3-F$_2$ |
| B-884 | 3,5-F$_2$ | 2,4-F$_2$ |
| B-885 | 3,5-F$_2$ | 2,5-F$_2$ |
| B-886 | 3,5-F$_2$ | 3,4-F$_2$ |
| B-887 | 3,5-F$_2$ | 3,5-F$_2$ |
| B-888 | 3,5-F$_2$ | 2,6-F$_2$ |
| B-889 | 3,5-F$_2$ | 2-CF$_3$-4-Cl |
| B-890 | 3,5-F$_2$ | 2-CF$_3$-4-F |
| B-891 | 3,5-F$_2$ | 2-Cl-4-CF$_3$ |
| B-892 | 3,5-F$_2$ | 2-F-4-CF$_3$ |
| B-893 | 3,5-F$_2$ | 2-CN-4-Cl |
| B-894 | 3,5-F$_2$ | 2-CN-4-F |
| B-895 | 3,5-F$_2$ | 2-Cl-4-CN |
| B-896 | 3,5-F$_2$ | 2-F-4-CN |
| B-897 | 2-F-3-Cl | —* |
| B-898 | 2-F-3-Cl | 2-Cl |
| B-899 | 2-F-3-Cl | 3-Cl |
| B-900 | 2-F-3-Cl | 4-Cl |
| B-901 | 2-F-3-Cl | 2-F |
| B-902 | 2-F-3-Cl | 3-F |
| B-903 | 2-F-3-Cl | 4-F |
| B-904 | 2-F-3-Cl | 2-CN |
| B-905 | 2-F-3-Cl | 3-CN |
| B-906 | 2-F-3-Cl | 4-CN |
| B-907 | 2-F-3-Cl | 2-NO$_2$ |
| B-908 | 2-F-3-Cl | 3-NO$_2$ |
| B-909 | 2-F-3-Cl | 4-NO$_2$ |
| B-910 | 2-F-3-Cl | 2-SCH$_3$ |
| B-911 | 2-F-3-Cl | 3-SCH$_3$ |
| B-912 | 2-F-3-Cl | 4-SCH$_3$ |
| B-913 | 2-F-3-Cl | 2-SOCH$_3$ |
| B-914 | 2-F-3-Cl | 3-SOCH$_3$ |
| B-915 | 2-F-3-Cl | 4-SOCH$_3$ |
| B-916 | 2-F-3-Cl | 2-SO$_2$CH$_3$ |
| B-917 | 2-F-3-Cl | 3-SO$_2$CH$_3$ |
| B-918 | 2-F-3-Cl | 4-SO$_2$CH$_3$ |
| B-919 | 2-F-3-Cl | 2-CO$_2$CH$_3$ |
| B-920 | 2-F-3-Cl | 3-CO$_2$CH$_3$ |
| B-921 | 2-F-3-Cl | 4-CO$_2$CH$_3$ |
| B-922 | 2-F-3-Cl | 2-CH$_3$ |
| B-923 | 2-F-3-Cl | 3-CH$_3$ |
| B-924 | 2-F-3-Cl | 4-CH$_3$ |
| B-925 | 2-F-3-Cl | 2-CF$_3$ |
| B-926 | 2-F-3-Cl | 3-CF$_3$ |
| B-927 | 2-F-3-Cl | 4-CF$_3$ |
| B-928 | 2-F-3-Cl | 2-CHF$_2$ |
| B-929 | 2-F-3-Cl | 3-CHF$_2$ |
| B-930 | 2-F-3-Cl | 4-CHF$_2$ |
| B-931 | 2-F-3-Cl | 2-OCH$_3$ |
| B-932 | 2-F-3-Cl | 3-OCH$_3$ |
| B-933 | 2-F-3-Cl | 4-OCH$_3$ |
| B-934 | 2-F-3-Cl | 2-OCF$_3$ |
| B-935 | 2-F-3-Cl | 3-OCF$_3$ |
| B-936 | 2-F-3-Cl | 4-OCF$_3$ |
| B-937 | 2-F-3-Cl | 2-OCHF$_2$ |
| B-938 | 2-F-3-Cl | 3-OCHF$_2$ |
| B-939 | 2-F-3-Cl | 4-OCHF$_2$ |
| B-940 | 2-F-3-Cl | 2,4,6-(CH$_3$)$_3$ |
| B-941 | 2-F-3-Cl | 2,3-Cl$_2$ |
| B-942 | 2-F-3-Cl | 2,4-Cl$_2$ |
| B-943 | 2-F-3-Cl | 2,5-Cl$_2$ |
| B-944 | 2-F-3-Cl | 3,4-Cl$_2$ |
| B-945 | 2-F-3-Cl | 3,5-Cl$_2$ |
| B-946 | 2-F-3-Cl | 2,6-Cl$_2$ |
| B-947 | 2-F-3-Cl | 2,3-F$_2$ |
| B-948 | 2-F-3-Cl | 2,4-F$_2$ |
| B-949 | 2-F-3-Cl | 2,5-F$_2$ |
| B-950 | 2-F-3-Cl | 3,4-F$_2$ |
| B-951 | 2-F-3-Cl | 3,5-F$_2$ |
| B-952 | 2-F-3-Cl | 2,6-F$_2$ |
| B-953 | 2-F-3-Cl | 2-CF$_3$-4-Cl |
| B-954 | 2-F-3-Cl | 2-CF$_3$-4-F |
| B-955 | 2-F-3-Cl | 2-Cl-4-CF$_3$ |
| B-956 | 2-F-3-Cl | 2-F-4-CF$_3$ |
| B-957 | 2-F-3-Cl | 2-CN-4-Cl |
| B-958 | 2-F-3-Cl | 2-CN-4-F |
| B-959 | 2-F-3-Cl | 2-Cl-4-CN |
| B-960 | 2-F-3-Cl | 2-F-4-CN |
| B-961 | 2-F-5-Cl | —* |
| B-962 | 2-F-5-Cl | 2-Cl |
| B-963 | 2-F-5-Cl | 3-Cl |
| B-964 | 2-F-5-Cl | 4-Cl |
| B-965 | 2-F-5-Cl | 2-F |
| B-966 | 2-F-5-Cl | 3-F |
| B-967 | 2-F-5-Cl | 4-F |
| B-968 | 2-F-5-Cl | 2-CN |
| B-969 | 2-F-5-Cl | 3-CN |
| B-970 | 2-F-5-Cl | 4-CN |
| B-971 | 2-F-5-Cl | 2-NO$_2$ |
| B-972 | 2-F-5-Cl | 3-NO$_2$ |
| B-973 | 2-F-5-Cl | 4-NO$_2$ |
| B-974 | 2-F-5-Cl | 2-SCH$_3$ |
| B-975 | 2-F-5-Cl | 3-SCH$_3$ |
| B-976 | 2-F-5-Cl | 4-SCH$_3$ |
| B-977 | 2-F-5-Cl | 2-SOCH$_3$ |
| B-978 | 2-F-5-Cl | 3-SOCH$_3$ |
| B-979 | 2-F-5-Cl | 4-SOCH$_3$ |

TABLE B-continued

For compounds where ZY is in para-position. The position(s) of the substituent(s) $(R^4)_n$ is/are given in relation to the attachment of the isoxazole-unit. The position(s) of the substituent(s) $(R^5)_m$ is/are given in relation to the attachment of the phenyl to the O-phenyl-unit.

| line | $(R^4)_n$ | $(R^5)_m$ |
|---|---|---|
| B-980 | 2-F-5-Cl | 2-SO$_2$CH$_3$ |
| B-981 | 2-F-5-Cl | 3-SO$_2$CH$_3$ |
| B-982 | 2-F-5-Cl | 4-SO$_2$CH$_3$ |
| B-983 | 2-F-5-Cl | 2-CO$_2$CH$_3$ |
| B-984 | 2-F-5-Cl | 3-CO$_2$CH$_3$ |
| B-985 | 2-F-5-Cl | 4-CO$_2$CH$_3$ |
| B-986 | 2-F-5-Cl | 2-CH$_3$ |
| B-987 | 2-F-5-Cl | 3-CH$_3$ |
| B-988 | 2-F-5-Cl | 4-CH$_3$ |
| B-989 | 2-F-5-Cl | 2-CF$_3$ |
| B-990 | 2-F-5-Cl | 3-CF$_3$ |
| B-991 | 2-F-5-Cl | 4-CF$_3$ |
| B-992 | 2-F-5-Cl | 2-CHF$_2$ |
| B-993 | 2-F-5-Cl | 3-CHF$_2$ |
| B-994 | 2-F-5-Cl | 4-CHF$_2$ |
| B-995 | 2-F-5-Cl | 2-OCH$_3$ |
| B-996 | 2-F-5-Cl | 3-OCH$_3$ |
| B-997 | 2-F-5-Cl | 4-OCH$_3$ |
| B-998 | 2-F-5-Cl | 2-OCF$_3$ |
| B-999 | 2-F-5-Cl | 3-OCF$_3$ |
| B-1000 | 2-F-5-Cl | 4-OCF$_3$ |
| B-1001 | 2-F-5-Cl | 2-OCHF$_2$ |
| B-1002 | 2-F-5-Cl | 3-OCHF$_2$ |
| B-1003 | 2-F-5-Cl | 4-OCHF$_2$ |
| B-1004 | 2-F-5-Cl | 2,4,6-(CH$_3$)$_3$ |
| B-1005 | 2-F-5-Cl | 2,3-Cl$_2$ |
| B-1006 | 2-F-5-Cl | 2,4-Cl$_2$ |
| B-1007 | 2-F-5-Cl | 2,5-Cl$_2$ |
| B-1008 | 2-F-5-Cl | 3,4-Cl$_2$ |
| B-1009 | 2-F-5-Cl | 3,5-Cl$_2$ |
| B-1010 | 2-F-5-Cl | 2,6-Cl$_2$ |
| B-1011 | 2-F-5-Cl | 2,3-F$_2$ |
| B-1012 | 2-F-5-Cl | 2,4-F$_2$ |
| B-1013 | 2-F-5-Cl | 2,5-F$_2$ |
| B-1014 | 2-F-5-Cl | 3,4-F$_2$ |
| B-1015 | 2-F-5-Cl | 3,5-F$_2$ |
| B-1016 | 2-F-5-Cl | 2,6-F$_2$ |
| B-1017 | 2-F-5-Cl | 2-CF$_3$-4-Cl |
| B-1018 | 2-F-5-Cl | 2-CF$_3$-4-F |
| B-1019 | 2-F-5-Cl | 2-Cl-4-CF$_3$ |
| B-1020 | 2-F-5-Cl | 2-F-4-CF$_3$ |
| B-1021 | 2-F-5-Cl | 2-CN-4-Cl |
| B-1022 | 2-F-5-Cl | 2-CN-4-F |
| B-1023 | 2-F-5-Cl | 2-Cl-4-CN |
| B-1024 | 2-F-5-Cl | 2-F-4-CN |
| B-1025 | 2-F-6-Cl | —* |
| B-1026 | 2-F-6-Cl | 2-Cl |
| B-1027 | 2-F-6-Cl | 3-Cl |
| B-1028 | 2-F-6-Cl | 4-Cl |
| B-1029 | 2-F-6-Cl | 2-F |
| B-1030 | 2-F-6-Cl | 3-F |
| B-1031 | 2-F-6-Cl | 4-F |
| B-1032 | 2-F-6-Cl | 2-CN |
| B-1033 | 2-F-6-Cl | 3-CN |
| B-1034 | 2-F-6-Cl | 4-CN |
| B-1035 | 2-F-6-Cl | 2-NO$_2$ |
| B-1036 | 2-F-6-Cl | 3-NO$_2$ |
| B-1037 | 2-F-6-Cl | 4-NO$_2$ |
| B-1038 | 2-F-6-Cl | 2-SCH$_3$ |
| B-1039 | 2-F-6-Cl | 3-SCH$_3$ |
| B-1040 | 2-F-6-Cl | 4-SCH$_3$ |
| B-1041 | 2-F-6-Cl | 2-SOCH$_3$ |
| B-1042 | 2-F-6-Cl | 3-SOCH$_3$ |
| B-1043 | 2-F-6-Cl | 4-SOCH$_3$ |
| B-1044 | 2-F-6-Cl | 2-SO$_2$CH$_3$ |
| B-1045 | 2-F-6-Cl | 3-SO$_2$CH$_3$ |
| B-1046 | 2-F-6-Cl | 4-SO$_2$CH$_3$ |
| B-1047 | 2-F-6-Cl | 2-CO$_2$CH$_3$ |
| B-1048 | 2-F-6-Cl | 3-CO$_2$CH$_3$ |
| B-1049 | 2-F-6-Cl | 4-CO$_2$CH$_3$ |
| B-1050 | 2-F-6-Cl | 2-CH$_3$ |
| B-1051 | 2-F-6-Cl | 3-CH$_3$ |
| B-1052 | 2-F-6-Cl | 4-CH$_3$ |
| B-1053 | 2-F-6-Cl | 2-CF$_3$ |
| B-1054 | 2-F-6-Cl | 3-CF$_3$ |
| B-1055 | 2-F-6-Cl | 4-CF$_3$ |
| B-1056 | 2-F-6-Cl | 2-CHF$_2$ |
| B-1057 | 2-F-6-Cl | 3-CHF$_2$ |
| B-1058 | 2-F-6-Cl | 4-CHF$_2$ |
| B-1059 | 2-F-6-Cl | 2-OCH$_3$ |
| B-1060 | 2-F-6-Cl | 3-OCH$_3$ |
| B-1061 | 2-F-6-Cl | 4-OCH$_3$ |
| B-1062 | 2-F-6-Cl | 2-OCF$_3$ |
| B-1063 | 2-F-6-Cl | 3-OCF$_3$ |
| B-1064 | 2-F-6-Cl | 4-OCF$_3$ |
| B-1065 | 2-F-6-Cl | 2-OCHF$_2$ |
| B-1066 | 2-F-6-Cl | 3-OCHF$_2$ |
| B-1067 | 2-F-6-Cl | 4-OCHF$_2$ |
| B-1068 | 2-F-6-Cl | 2,4,6-(CH$_3$)$_3$ |
| B-1069 | 2-F-6-Cl | 2,3-Cl$_2$ |
| B-1070 | 2-F-6-Cl | 2,4-Cl$_2$ |
| B-1071 | 2-F-6-Cl | 2,5-Cl$_2$ |
| B-1072 | 2-F-6-Cl | 3,4-Cl$_2$ |
| B-1073 | 2-F-6-Cl | 3,5-Cl$_2$ |
| B-1074 | 2-F-6-Cl | 2,6-Cl$_2$ |
| B-1075 | 2-F-6-Cl | 2,3-F$_2$ |
| B-1076 | 2-F-6-Cl | 2,4-F$_2$ |
| B-1077 | 2-F-6-Cl | 2,5-F$_2$ |
| B-1078 | 2-F-6-Cl | 3,4-F$_2$ |
| B-1079 | 2-F-6-Cl | 3,5-F$_2$ |
| B-1080 | 2-F-6-Cl | 2,6-F$_2$ |
| B-1081 | 2-F-6-Cl | 2-CF$_3$-4-Cl |
| B-1082 | 2-F-6-Cl | 2-CF$_3$-4-F |
| B-1083 | 2-F-6-Cl | 2-Cl-4-CF$_3$ |
| B-1084 | 2-F-6-Cl | 2-F-4-CF$_3$ |
| B-1085 | 2-F-6-Cl | 2-CN-4-Cl |
| B-1086 | 2-F-6-Cl | 2-CN-4-F |
| B-1087 | 2-F-6-Cl | 2-Cl-4-CN |
| B-1088 | 2-F-6-Cl | 2-F-4-CN |
| B-1089 | 2-Cl-3-F | —* |
| B-1090 | 2-Cl-3-F | 2-Cl |
| B-1091 | 2-Cl-3-F | 3-Cl |
| B-1092 | 2-Cl-3-F | 4-Cl |
| B-1093 | 2-Cl-3-F | 2-F |
| B-1094 | 2-Cl-3-F | 3-F |
| B-1095 | 2-Cl-3-F | 4-F |
| B-1096 | 2-Cl-3-F | 2-CN |
| B-1097 | 2-Cl-3-F | 3-CN |
| B-1098 | 2-Cl-3-F | 4-CN |
| B-1099 | 2-Cl-3-F | 2-NO$_2$ |
| B-1100 | 2-Cl-3-F | 3-NO$_2$ |
| B-1101 | 2-Cl-3-F | 4-NO$_2$ |
| B-1102 | 2-Cl-3-F | 2-SCH$_3$ |
| B-1103 | 2-Cl-3-F | 3-SCH$_3$ |
| B-1104 | 2-Cl-3-F | 4-SCH$_3$ |
| B-1105 | 2-Cl-3-F | 2-SOCH$_3$ |
| B-1106 | 2-Cl-3-F | 3-SOCH$_3$ |
| B-1107 | 2-Cl-3-F | 4-SOCH$_3$ |
| B-1108 | 2-Cl-3-F | 2-SO$_2$CH$_3$ |
| B-1109 | 2-Cl-3-F | 3-SO$_2$CH$_3$ |
| B-1110 | 2-Cl-3-F | 4-SO$_2$CH$_3$ |
| B-1111 | 2-Cl-3-F | 2-CO$_2$CH$_3$ |
| B-1112 | 2-Cl-3-F | 3-CO$_2$CH$_3$ |
| B-1113 | 2-Cl-3-F | 4-CO$_2$CH$_3$ |
| B-1114 | 2-Cl-3-F | 2-CH$_3$ |
| B-1115 | 2-Cl-3-F | 3-CH$_3$ |
| B-1116 | 2-Cl-3-F | 4-CH$_3$ |
| B-1117 | 2-Cl-3-F | 2-CF$_3$ |
| B-1118 | 2-Cl-3-F | 3-CF$_3$ |
| B-1119 | 2-Cl-3-F | 4-CF$_3$ |
| B-1120 | 2-Cl-3-F | 2-CHF$_2$ |
| B-1121 | 2-Cl-3-F | 3-CHF$_2$ |
| B-1122 | 2-Cl-3-F | 4-CHF$_2$ |
| B-1123 | 2-Cl-3-F | 2-OCH$_3$ |
| B-1124 | 2-Cl-3-F | 3-OCH$_3$ |
| B-1125 | 2-Cl-3-F | 4-OCH$_3$ |

TABLE B-continued

For compounds where ZY is in para-position. The position(s) of the substituent(s) $(R^4)_n$ is/are given in relation to the attachment of the isoxazole-unit. The position(s) of the substituent(s) $(R^5)_m$ is/are given in relation to the attachment of the phenyl to the O-phenyl-unit.

| line | $(R^4)_n$ | $(R^5)_m$ |
|---|---|---|
| B-1126 | 2-Cl-3-F | 2-OCF$_3$ |
| B-1127 | 2-Cl-3-F | 3-OCF$_3$ |
| B-1128 | 2-Cl-3-F | 4-OCF$_3$ |
| B-1129 | 2-Cl-3-F | 2-OCHF$_2$ |
| B-1130 | 2-Cl-3-F | 3-OCHF$_2$ |
| B-1131 | 2-Cl-3-F | 4-OCHF$_2$ |
| B-1132 | 2-Cl-3-F | 2,4,6-(CH$_3$)$_3$ |
| B-1133 | 2-Cl-3-F | 2,3-Cl$_2$ |
| B-1134 | 2-Cl-3-F | 2,4-Cl$_2$ |
| B-1135 | 2-Cl-3-F | 2,5-Cl$_2$ |
| B-1136 | 2-Cl-3-F | 3,4-Cl$_2$ |
| B-1137 | 2-Cl-3-F | 3,5-Cl$_2$ |
| B-1138 | 2-Cl-3-F | 2,6-Cl$_2$ |
| B-1139 | 2-Cl-3-F | 2,3-F$_2$ |
| B-1140 | 2-Cl-3-F | 2,4-F$_2$ |
| B-1141 | 2-Cl-3-F | 2,5-F$_2$ |
| B-1142 | 2-Cl-3-F | 3,4-F$_2$ |
| B-1143 | 2-Cl-3-F | 3,5-F$_2$ |
| B-1144 | 2-Cl-3-F | 2,6-F$_2$ |
| B-1145 | 2-Cl-3-F | 2-CF$_3$-4-Cl |
| B-1146 | 2-Cl-3-F | 2-CF$_3$-4-F |
| B-1147 | 2-Cl-3-F | 2-Cl-4-CF$_3$ |
| B-1148 | 2-Cl-3-F | 2-F-4-CF$_3$ |
| B-1149 | 2-Cl-3-F | 2-CN-4-Cl |
| B-1150 | 2-Cl-3-F | 2-CN-4-F |
| B-1151 | 2-Cl-3-F | 2-Cl-4-CN |
| B-1152 | 2-Cl-3-F | 2-F-4-CN |
| B-1153 | 2-Cl-5-F | —* |
| B-1154 | 2-Cl-5-F | 2-Cl |
| B-1155 | 2-Cl-5-F | 3-Cl |
| B-1156 | 2-Cl-5-F | 4-Cl |
| B-1157 | 2-Cl-5-F | 2-F |
| B-1158 | 2-Cl-5-F | 3-F |
| B-1159 | 2-Cl-5-F | 4-F |
| B-1160 | 2-Cl-5-F | 2-CN |
| B-1161 | 2-Cl-5-F | 3-CN |
| B-1162 | 2-Cl-5-F | 4-CN |
| B-1163 | 2-Cl-5-F | 2-NO$_2$ |
| B-1164 | 2-Cl-5-F | 3-NO$_2$ |
| B-1165 | 2-Cl-5-F | 4-NO$_2$ |
| B-1166 | 2-Cl-5-F | 2-SCH$_3$ |
| B-1167 | 2-Cl-5-F | 3-SCH$_3$ |
| B-1168 | 2-Cl-5-F | 4-SCH$_3$ |
| B-1169 | 2-Cl-5-F | 2-SOCH$_3$ |
| B-1170 | 2-Cl-5-F | 3-SOCH$_3$ |
| B-1171 | 2-Cl-5-F | 4-SOCH$_3$ |
| B-1172 | 2-Cl-5-F | 2-SO$_2$CH$_3$ |
| B-1173 | 2-Cl-5-F | 3-SO$_2$CH$_3$ |
| B-1174 | 2-Cl-5-F | 4-SO$_2$CH$_3$ |
| B-1175 | 2-Cl-5-F | 2-CO$_2$CH$_3$ |
| B-1176 | 2-Cl-5-F | 3-CO$_2$CH$_3$ |
| B-1177 | 2-Cl-5-F | 4-CO$_2$CH$_3$ |
| B-1178 | 2-Cl-5-F | 2-CH$_3$ |
| B-1179 | 2-Cl-5-F | 3-CH$_3$ |
| B-1180 | 2-Cl-5-F | 4-CH$_3$ |
| B-1181 | 2-Cl-5-F | 2-CF$_3$ |
| B-1182 | 2-Cl-5-F | 3-CF$_3$ |
| B-1183 | 2-Cl-5-F | 4-CF$_3$ |
| B-1184 | 2-Cl-5-F | 2-CHF$_2$ |
| B-1185 | 2-Cl-5-F | 3-CHF$_2$ |
| B-1186 | 2-Cl-5-F | 4-CHF$_2$ |
| B-1187 | 2-Cl-5-F | 2-OCH$_3$ |
| B-1188 | 2-Cl-5-F | 3-OCH$_3$ |
| B-1189 | 2-Cl-5-F | 4-OCH$_3$ |
| B-1190 | 2-Cl-5-F | 2-OCF$_3$ |
| B-1191 | 2-Cl-5-F | 3-OCF$_3$ |
| B-1192 | 2-Cl-5-F | 4-OCF$_3$ |
| B-1193 | 2-Cl-5-F | 2-OCHF$_2$ |
| B-1194 | 2-Cl-5-F | 3-OCHF$_2$ |
| B-1195 | 2-Cl-5-F | 4-OCHF$_2$ |
| B-1196 | 2-Cl-5-F | 2,4,6-(CH$_3$)$_3$ |
| B-1197 | 2-Cl-5-F | 2,3-Cl$_2$ |
| B-1198 | 2-Cl-5-F | 2,4-Cl$_2$ |
| B-1199 | 2-Cl-5-F | 2,5-Cl$_2$ |
| B-1200 | 2-Cl-5-F | 3,4-Cl$_2$ |
| B-1201 | 2-Cl-5-F | 3,5-Cl$_2$ |
| B-1202 | 2-Cl-5-F | 2,6-Cl$_2$ |
| B-1203 | 2-Cl-5-F | 2,3-F$_2$ |
| B-1204 | 2-Cl-5-F | 2,4-F$_2$ |
| B-1205 | 2-Cl-5-F | 2,5-F$_2$ |
| B-1206 | 2-Cl-5-F | 3,4-F$_2$ |
| B-1207 | 2-Cl-5-F | 3,5-F$_2$ |
| B-1208 | 2-Cl-5-F | 2,6-F$_2$ |
| B-1209 | 2-Cl-5-F | 2-CF$_3$-4-Cl |
| B-1210 | 2-Cl-5-F | 2-CF$_3$-4-F |
| B-1211 | 2-Cl-5-F | 2-Cl-4-CF$_3$ |
| B-1212 | 2-Cl-5-F | 2-F-4-CF$_3$ |
| B-1213 | 2-Cl-5-F | 2-CN-4-Cl |
| B-1214 | 2-Cl-5-F | 2-CN-4-F |
| B-1215 | 2-Cl-5-F | 2-Cl-4-CN |
| B-1216 | 2-Cl-5-F | 2-F-4-CN |
| B-1217 | 2-CH$_3$ | —* |
| B-1218 | 2-CH$_3$ | 2-Cl |
| B-1219 | 2-CH$_3$ | 3-Cl |
| B-1220 | 2-CH$_3$ | 4-Cl |
| B-1221 | 2-CH$_3$ | 2-F |
| B-1222 | 2-CH$_3$ | 3-F |
| B-1223 | 2-CH$_3$ | 4-F |
| B-1224 | 2-CH$_3$ | 2-CN |
| B-1225 | 2-CH$_3$ | 3-CN |
| B-1226 | 2-CH$_3$ | 4-CN |
| B-1227 | 2-CH$_3$ | 2-NO$_2$ |
| B-1228 | 2-CH$_3$ | 3-NO$_2$ |
| B-1229 | 2-CH$_3$ | 4-NO$_2$ |
| B-1230 | 2-CH$_3$ | 2-SCH$_3$ |
| B-1231 | 2-CH$_3$ | 3-SCH$_3$ |
| B-1232 | 2-CH$_3$ | 4-SCH$_3$ |
| B-1233 | 2-CH$_3$ | 2-SOCH$_3$ |
| B-1234 | 2-CH$_3$ | 3-SOCH$_3$ |
| B-1235 | 2-CH$_3$ | 4-SOCH$_3$ |
| B-1236 | 2-CH$_3$ | 2-SO$_2$CH$_3$ |
| B-1237 | 2-CH$_3$ | 3-SO$_2$CH$_3$ |
| B-1238 | 2-CH$_3$ | 4-SO$_2$CH$_3$ |
| B-1239 | 2-CH$_3$ | 2-CO$_2$CH$_3$ |
| B-1240 | 2-CH$_3$ | 3-CO$_2$CH$_3$ |
| B-1241 | 2-CH$_3$ | 4-CO$_2$CH$_3$ |
| B-1242 | 2-CH$_3$ | 2-CH$_3$ |
| B-1243 | 2-CH$_3$ | 3-CH$_3$ |
| B-1244 | 2-CH$_3$ | 4-CH$_3$ |
| B-1245 | 2-CH$_3$ | 2-CF$_3$ |
| B-1246 | 2-CH$_3$ | 3-CF$_3$ |
| B-1247 | 2-CH$_3$ | 4-CF$_3$ |
| B-1248 | 2-CH$_3$ | 2-CHF$_2$ |
| B-1249 | 2-CH$_3$ | 3-CHF$_2$ |
| B-1250 | 2-CH$_3$ | 4-CHF$_2$ |
| B-1251 | 2-CH$_3$ | 2-OCH$_3$ |
| B-1252 | 2-CH$_3$ | 3-OCH$_3$ |
| B-1253 | 2-CH$_3$ | 4-OCH$_3$ |
| B-1254 | 2-CH$_3$ | 2-OCF$_3$ |
| B-1255 | 2-CH$_3$ | 3-OCF$_3$ |
| B-1256 | 2-CH$_3$ | 4-OCF$_3$ |
| B-1257 | 2-CH$_3$ | 2-OCHF$_2$ |
| B-1258 | 2-CH$_3$ | 3-OCHF$_2$ |
| B-1259 | 2-CH$_3$ | 4-OCHF$_2$ |
| B-1260 | 2-CH$_3$ | 2,4,6-(CH$_3$)$_3$ |
| B-1261 | 2-CH$_3$ | 2,3-Cl$_2$ |
| B-1262 | 2-CH$_3$ | 2,4-Cl$_2$ |
| B-1263 | 2-CH$_3$ | 2,5-Cl$_2$ |
| B-1264 | 2-CH$_3$ | 3,4-Cl$_2$ |
| B-1265 | 2-CH$_3$ | 3,5-Cl$_2$ |
| B-1266 | 2-CH$_3$ | 2,6-Cl$_2$ |
| B-1267 | 2-CH$_3$ | 2,3-F$_2$ |
| B-1268 | 2-CH$_3$ | 2,4-F$_2$ |
| B-1269 | 2-CH$_3$ | 2,5-F$_2$ |
| B-1270 | 2-CH$_3$ | 3,4-F$_2$ |
| B-1271 | 2-CH$_3$ | 3,5-F$_2$ |

TABLE B-continued

For compounds where ZY is in para-position. The position(s) of the substituent(s) $(R^4)_n$ is/are given in relation to the attachment of the isoxazole-unit. The position(s) of the substituent(s) $(R^5)_m$ is/are given in relation to the attachment of the phenyl to the O-phenyl-unit.

| line | $(R^4)_n$ | $(R^5)_m$ |
|---|---|---|
| B-1272 | 2-CH₃ | 2,6-F₂ |
| B-1273 | 2-CH₃ | 2-CF₃-4-Cl |
| B-1274 | 2-CH₃ | 2-CF₃-4-F |
| B-1275 | 2-CH₃ | 2-Cl-4-CF₃ |
| B-1276 | 2-CH₃ | 2-F-4-CF₃ |
| B-1277 | 2-CH₃ | 2-CN-4-Cl |
| B-1278 | 2-CH₃ | 2-CN-4-F |
| B-1279 | 2-CH₃ | 2-Cl-4-CN |
| B-1280 | 2-CH₃ | 2-F-4-CN |
| B-1281 | 3-CH₃ | —* |
| B-1282 | 3-CH₃ | 2-Cl |
| B-1283 | 3-CH₃ | 3-Cl |
| B-1284 | 3-CH₃ | 4-Cl |
| B-1285 | 3-CH₃ | 2-F |
| B-1286 | 3-CH₃ | 3-F |
| B-1287 | 3-CH₃ | 4-F |
| B-1288 | 3-CH₃ | 2-CN |
| B-1289 | 3-CH₃ | 3-CN |
| B-1290 | 3-CH₃ | 4-CN |
| B-1291 | 3-CH₃ | 2-NO₂ |
| B-1292 | 3-CH₃ | 3-NO₂ |
| B-1293 | 3-CH₃ | 4-NO₂ |
| B-1294 | 3-CH₃ | 2-SCH₃ |
| B-1295 | 3-CH₃ | 3-SCH₃ |
| B-1296 | 3-CH₃ | 4-SCH₃ |
| B-1297 | 3-CH₃ | 2-SOCH₃ |
| B-1298 | 3-CH₃ | 3-SOCH₃ |
| B-1299 | 3-CH₃ | 4-SOCH₃ |
| B-1300 | 3-CH₃ | 2-SO₂CH₃ |
| B-1301 | 3-CH₃ | 3-SO₂CH₃ |
| B-1302 | 3-CH₃ | 4-SO₂CH₃ |
| B-1303 | 3-CH₃ | 2-CO₂CH₃ |
| B-1304 | 3-CH₃ | 3-CO₂CH₃ |
| B-1305 | 3-CH₃ | 4-CO₂CH₃ |
| B-1306 | 3-CH₃ | 2-CH₃ |
| B-1307 | 3-CH₃ | 3-CH₃ |
| B-1308 | 3-CH₃ | 4-CH₃ |
| B-1309 | 3-CH₃ | 2-CF₃ |
| B-1310 | 3-CH₃ | 3-CF₃ |
| B-1311 | 3-CH₃ | 4-CF₃ |
| B-1312 | 3-CH₃ | 2-CHF₂ |
| B-1313 | 3-CH₃ | 3-CHF₂ |
| B-1314 | 3-CH₃ | 4-CHF₂ |
| B-1315 | 3-CH₃ | 2-OCH₃ |
| B-1316 | 3-CH₃ | 3-OCH₃ |
| B-1317 | 3-CH₃ | 4-OCH₃ |
| B-1318 | 3-CH₃ | 2-OCF₃ |
| B-1319 | 3-CH₃ | 3-OCF₃ |
| B-1320 | 3-CH₃ | 4-OCF₃ |
| B-1321 | 3-CH₃ | 2-OCHF₂ |
| B-1322 | 3-CH₃ | 3-OCHF₂ |
| B-1323 | 3-CH₃ | 4-OCHF₂ |
| B-1324 | 3-CH₃ | 2,4,6-(CH₃)₃ |
| B-1325 | 3-CH₃ | 2,3-Cl₂ |
| B-1326 | 3-CH₃ | 2,4-Cl₂ |
| B-1327 | 3-CH₃ | 2,5-Cl₂ |
| B-1328 | 3-CH₃ | 3,4-Cl₂ |
| B-1329 | 3-CH₃ | 3,5-Cl₂ |
| B-1330 | 3-CH₃ | 2,6-Cl₂ |
| B-1331 | 3-CH₃ | 2,3-F₂ |
| B-1332 | 3-CH₃ | 2,4-F₂ |
| B-1333 | 3-CH₃ | 2,5-F₂ |
| B-1334 | 3-CH₃ | 3,4-F₂ |
| B-1335 | 3-CH₃ | 3,5-F₂ |
| B-1336 | 3-CH₃ | 2,6-F₂ |
| B-1337 | 3-CH₃ | 2-CF₃-4-Cl |
| B-1338 | 3-CH₃ | 2-CF₃-4-F |
| B-1339 | 3-CH₃ | 2-Cl-4-CF₃ |
| B-1340 | 3-CH₃ | 2-F-4-CF₃ |
| B-1341 | 3-CH₃ | 2-CN-4-Cl |
| B-1342 | 3-CH₃ | 2-CN-4-F |
| B-1343 | 3-CH₃ | 2-Cl-4-CN |
| B-1344 | 3-CH₃ | 2-F-4-CN |
| B-1345 | 2-CF₃ | —* |
| B-1346 | 2-CF₃ | 2-Cl |
| B-1347 | 2-CF₃ | 3-Cl |
| B-1348 | 2-CF₃ | 4-Cl |
| B-1349 | 2-CF₃ | 2-F |
| B-1350 | 2-CF₃ | 3-F |
| B-1351 | 2-CF₃ | 4-F |
| B-1352 | 2-CF₃ | 2-CN |
| B-1353 | 2-CF₃ | 3-CN |
| B-1354 | 2-CF₃ | 4-CN |
| B-1355 | 2-CF₃ | 2-NO₂ |
| B-1356 | 2-CF₃ | 3-NO₂ |
| B-1357 | 2-CF₃ | 4-NO₂ |
| B-1358 | 2-CF₃ | 2-SCH₃ |
| B-1359 | 2-CF₃ | 3-SCH₃ |
| B-1360 | 2-CF₃ | 4-SCH₃ |
| B-1361 | 2-CF₃ | 2-SOCH₃ |
| B-1362 | 2-CF₃ | 3-SOCH₃ |
| B-1363 | 2-CF₃ | 4-SOCH₃ |
| B-1364 | 2-CF₃ | 2-SO₂CH₃ |
| B-1365 | 2-CF₃ | 3-SO₂CH₃ |
| B-1366 | 2-CF₃ | 4-SO₂CH₃ |
| B-1367 | 2-CF₃ | 2-CO₂CH₃ |
| B-1368 | 2-CF₃ | 3-CO₂CH₃ |
| B-1369 | 2-CF₃ | 4-CO₂CH₃ |
| B-1370 | 2-CF₃ | 2-CH₃ |
| B-1371 | 2-CF₃ | 3-CH₃ |
| B-1372 | 2-CF₃ | 4-CH₃ |
| B-1373 | 2-CF₃ | 2-CF₃ |
| B-1374 | 2-CF₃ | 3-CF₃ |
| B-1375 | 2-CF₃ | 4-CF₃ |
| B-1376 | 2-CF₃ | 2-CHF₂ |
| B-1377 | 2-CF₃ | 3-CHF₂ |
| B-1378 | 2-CF₃ | 4-CHF₂ |
| B-1379 | 2-CF₃ | 2-OCH₃ |
| B-1380 | 2-CF₃ | 3-OCH₃ |
| B-1381 | 2-CF₃ | 4-OCH₃ |
| B-1382 | 2-CF₃ | 2-OCF₃ |
| B-1383 | 2-CF₃ | 3-OCF₃ |
| B-1384 | 2-CF₃ | 4-OCF₃ |
| B-1385 | 2-CF₃ | 2-OCHF₂ |
| B-1386 | 2-CF₃ | 3-OCHF₂ |
| B-1387 | 2-CF₃ | 4-OCHF₂ |
| B-1388 | 2-CF₃ | 2,4,6-(CH₃)₃ |
| B-1389 | 2-CF₃ | 2,3-Cl₂ |
| B-1390 | 2-CF₃ | 2,4-Cl₂ |
| B-1391 | 2-CF₃ | 2,5-Cl₂ |
| B-1392 | 2-CF₃ | 3,4-Cl₂ |
| B-1393 | 2-CF₃ | 3,5-Cl₂ |
| B-1394 | 2-CF₃ | 2,6-Cl₂ |
| B-1395 | 2-CF₃ | 2,3-F₂ |
| B-1396 | 2-CF₃ | 2,4-F₂ |
| B-1397 | 2-CF₃ | 2,5-F₂ |
| B-1398 | 2-CF₃ | 3,4-F₂ |
| B-1399 | 2-CF₃ | 3,5-F₂ |
| B-1400 | 2-CF₃ | 2,6-F₂ |
| B-1401 | 2-CF₃ | 2-CF₃-4-Cl |
| B-1402 | 2-CF₃ | 2-CF₃-4-F |
| B-1403 | 2-CF₃ | 2-Cl-4-CF₃ |
| B-1404 | 2-CF₃ | 2-F-4-CF₃ |
| B-1405 | 2-CF₃ | 2-CN-4-Cl |
| B-1406 | 2-CF₃ | 2-CN-4-F |
| B-1407 | 2-CF₃ | 2-Cl-4-CN |
| B-1408 | 2-CF₃ | 2-F-4-CN |
| B-1409 | 3-CF₃ | —* |
| B-1410 | 3-CF₃ | 2-Cl |
| B-1411 | 3-CF₃ | 3-Cl |
| B-1412 | 3-CF₃ | 4-Cl |
| B-1413 | 3-CF₃ | 2-F |
| B-1414 | 3-CF₃ | 3-F |
| B-1415 | 3-CF₃ | 4-F |
| B-1416 | 3-CF₃ | 2-CN |
| B-1417 | 3-CF₃ | 3-CN |

TABLE B-continued

For compounds where ZY is in para-position. The position(s) of the substituent(s) $(R^4)_n$ is/are given in relation to the attachment of the isoxazole-unit. The position(s) of the substituent(s) $(R^5)_m$ is/are given in relation to the attachment of the phenyl to the O-phenyl-unit.

| line | $(R^4)_n$ | $(R^5)_m$ |
|---|---|---|
| B-1418 | 3-CF$_3$ | 4-CN |
| B-1419 | 3-CF$_3$ | 2-NO$_2$ |
| B-1420 | 3-CF$_3$ | 3-NO$_2$ |
| B-1421 | 3-CF$_3$ | 4-NO$_2$ |
| B-1422 | 3-CF$_3$ | 2-SCH$_3$ |
| B-1423 | 3-CF$_3$ | 3-SCH$_3$ |
| B-1424 | 3-CF$_3$ | 4-SCH$_3$ |
| B-1425 | 3-CF$_3$ | 2-SOCH$_3$ |
| B-1426 | 3-CF$_3$ | 3-SOCH$_3$ |
| B-1427 | 3-CF$_3$ | 4-SOCH$_3$ |
| B-1428 | 3-CF$_3$ | 2-SO$_2$CH$_3$ |
| B-1429 | 3-CF$_3$ | 3-SO$_2$CH$_3$ |
| B-1430 | 3-CF$_3$ | 4-SO$_2$CH$_3$ |
| B-1431 | 3-CF$_3$ | 2-CO$_2$CH$_3$ |
| B-1432 | 3-CF$_3$ | 3-CO$_2$CH$_3$ |
| B-1433 | 3-CF$_3$ | 4-CO$_2$CH$_3$ |
| B-1434 | 3-CF$_3$ | 2-CH$_3$ |
| B-1435 | 3-CF$_3$ | 3-CH$_3$ |
| B-1436 | 3-CF$_3$ | 4-CH$_3$ |
| B-1437 | 3-CF$_3$ | 2-CF$_3$ |
| B-1438 | 3-CF$_3$ | 3-CF$_3$ |
| B-1439 | 3-CF$_3$ | 4-CF$_3$ |
| B-1440 | 3-CF$_3$ | 2-CHF$_2$ |
| B-1441 | 3-CF$_3$ | 3-CHF$_2$ |
| B-1442 | 3-CF$_3$ | 4-CHF$_2$ |
| B-1443 | 3-CF$_3$ | 2-OCH$_3$ |
| B-1444 | 3-CF$_3$ | 3-OCH$_3$ |
| B-1445 | 3-CF$_3$ | 4-OCH$_3$ |
| B-1446 | 3-CF$_3$ | 2-OCF$_3$ |
| B-1447 | 3-CF$_3$ | 3-OCF$_3$ |
| B-1448 | 3-CF$_3$ | 4-OCF$_3$ |
| B-1449 | 3-CF$_3$ | 2-OCHF$_2$ |
| B-1450 | 3-CF$_3$ | 3-OCHF$_2$ |
| B-1451 | 3-CF$_3$ | 4-OCHF$_2$ |
| B-1452 | 3-CF$_3$ | 2,4,6-(CH$_3$)$_3$ |
| B-1453 | 3-CF$_3$ | 2,3-Cl$_2$ |
| B-1454 | 3-CF$_3$ | 2,4-Cl$_2$ |
| B-1455 | 3-CF$_3$ | 2,5-Cl$_2$ |
| B-1456 | 3-CF$_3$ | 3,4-Cl$_2$ |
| B-1457 | 3-CF$_3$ | 3,5-Cl$_2$ |
| B-1458 | 3-CF$_3$ | 2,6-Cl$_2$ |
| B-1459 | 3-CF$_3$ | 2,3-F$_2$ |
| B-1460 | 3-CF$_3$ | 2,4-F$_2$ |
| B-1461 | 3-CF$_3$ | 2,5-F$_2$ |
| B-1462 | 3-CF$_3$ | 3,4-F$_2$ |
| B-1463 | 3-CF$_3$ | 3,5-F$_2$ |
| B-1464 | 3-CF$_3$ | 2,6-F$_2$ |
| B-1465 | 3-CF$_3$ | 2-CF$_3$-4-Cl |
| B-1466 | 3-CF$_3$ | 2-CF$_3$-4-F |
| B-1467 | 3-CF$_3$ | 2-Cl-4-CF$_3$ |
| B-1468 | 3-CF$_3$ | 2-F-4-CF$_3$ |
| B-1469 | 3-CF$_3$ | 2-CN-4-Cl |
| B-1470 | 3-CF$_3$ | 2-CN-4-F |
| B-1471 | 3-CF$_3$ | 2-Cl-4-CN |
| B-1472 | 3-CF$_3$ | 2-F-4-CN |
| B-1473 | 2-CHF$_2$ | —* |
| B-1474 | 2-CHF$_2$ | 2-Cl |
| B-1475 | 2-CHF$_2$ | 3-Cl |
| B-1476 | 2-CHF$_2$ | 4-Cl |
| B-1477 | 2-CHF$_2$ | 2-F |
| B-1478 | 2-CHF$_2$ | 3-F |
| B-1479 | 2-CHF$_2$ | 4-F |
| B-1480 | 2-CHF$_2$ | 2-CN |
| B-1481 | 2-CHF$_2$ | 3-CN |
| B-1482 | 2-CHF$_2$ | 4-CN |
| B-1483 | 2-CHF$_2$ | 2-NO$_2$ |
| B-1484 | 2-CHF$_2$ | 3-NO$_2$ |
| B-1485 | 2-CHF$_2$ | 4-NO$_2$ |
| B-1486 | 2-CHF$_2$ | 2-SCH$_3$ |
| B-1487 | 2-CHF$_2$ | 3-SCH$_3$ |
| B-1488 | 2-CHF$_2$ | 4-SCH$_3$ |
| B-1489 | 2-CHF$_2$ | 2-SOCH$_3$ |
| B-1490 | 2-CHF$_2$ | 3-SOCH$_3$ |
| B-1491 | 2-CHF$_2$ | 4-SOCH$_3$ |
| B-1492 | 2-CHF$_2$ | 2-SO$_2$CH$_3$ |
| B-1493 | 2-CHF$_2$ | 3-SO$_2$CH$_3$ |
| B-1494 | 2-CHF$_2$ | 4-SO$_2$CH$_3$ |
| B-1495 | 2-CHF$_2$ | 2-CO$_2$CH$_3$ |
| B-1496 | 2-CHF$_2$ | 3-CO$_2$CH$_3$ |
| B-1497 | 2-CHF$_2$ | 4-CO$_2$CH$_3$ |
| B-1498 | 2-CHF$_2$ | 2-CH$_3$ |
| B-1499 | 2-CHF$_2$ | 3-CH$_3$ |
| B-1500 | 2-CHF$_2$ | 4-CH$_3$ |
| B-1501 | 2-CHF$_2$ | 2-CF$_3$ |
| B-1502 | 2-CHF$_2$ | 3-CF$_3$ |
| B-1503 | 2-CHF$_2$ | 4-CF$_3$ |
| B-1504 | 2-CHF$_2$ | 2-CHF$_2$ |
| B-1505 | 2-CHF$_2$ | 3-CHF$_2$ |
| B-1506 | 2-CHF$_2$ | 4-CHF$_2$ |
| B-1507 | 2-CHF$_2$ | 2-OCH$_3$ |
| B-1508 | 2-CHF$_2$ | 3-OCH$_3$ |
| B-1509 | 2-CHF$_2$ | 4-OCH$_3$ |
| B-1510 | 2-CHF$_2$ | 2-OCF$_3$ |
| B-1511 | 2-CHF$_2$ | 3-OCF$_3$ |
| B-1512 | 2-CHF$_2$ | 4-OCF$_3$ |
| B-1513 | 2-CHF$_2$ | 2-OCHF$_2$ |
| B-1514 | 2-CHF$_2$ | 3-OCHF$_2$ |
| B-1515 | 2-CHF$_2$ | 4-OCHF$_2$ |
| B-1516 | 2-CHF$_2$ | 2,4,6-(CH$_3$)$_3$ |
| B-1517 | 2-CHF$_2$ | 2,3-Cl$_2$ |
| B-1518 | 2-CHF$_2$ | 2,4-Cl$_2$ |
| B-1519 | 2-CHF$_2$ | 2,5-Cl$_2$ |
| B-1520 | 2-CHF$_2$ | 3,4-Cl$_2$ |
| B-1521 | 2-CHF$_2$ | 3,5-Cl$_2$ |
| B-1522 | 2-CHF$_2$ | 2,6-Cl$_2$ |
| B-1523 | 2-CHF$_2$ | 2,3-F$_2$ |
| B-1524 | 2-CHF$_2$ | 2,4-F$_2$ |
| B-1525 | 2-CHF$_2$ | 2,5-F$_2$ |
| B-1526 | 2-CHF$_2$ | 3,4-F$_2$ |
| B-1527 | 2-CHF$_2$ | 3,5-F$_2$ |
| B-1528 | 2-CHF$_2$ | 2,6-F$_2$ |
| B-1529 | 2-CHF$_2$ | 2-CF$_3$-4-Cl |
| B-1530 | 2-CHF$_2$ | 2-CF$_3$-4-F |
| B-1531 | 2-CHF$_2$ | 2-Cl-4-CF$_3$ |
| B-1532 | 2-CHF$_2$ | 2-F-4-CF$_3$ |
| B-1533 | 2-CHF$_2$ | 2-CN-4-Cl |
| B-1534 | 2-CHF$_2$ | 2-CN-4-F |
| B-1535 | 2-CHF$_2$ | 2-Cl-4-CN |
| B-1536 | 2-CHF$_2$ | 2-F-4-CN |
| B-1537 | 3-CHF$_2$ | —* |
| B-1538 | 3-CHF$_2$ | 2-Cl |
| B-1539 | 3-CHF$_2$ | 3-Cl |
| B-1540 | 3-CHF$_2$ | 4-Cl |
| B-1541 | 3-CHF$_2$ | 2-F |
| B-1542 | 3-CHF$_2$ | 3-F |
| B-1543 | 3-CHF$_2$ | 4-F |
| B-1544 | 3-CHF$_2$ | 2-CN |
| B-1545 | 3-CHF$_2$ | 3-CN |
| B-1546 | 3-CHF$_2$ | 4-CN |
| B-1547 | 3-CHF$_2$ | 2-NO$_2$ |
| B-1548 | 3-CHF$_2$ | 3-NO$_2$ |
| B-1549 | 3-CHF$_2$ | 4-NO$_2$ |
| B-1550 | 3-CHF$_2$ | 2-SCH$_3$ |
| B-1551 | 3-CHF$_2$ | 3-SCH$_3$ |
| B-1552 | 3-CHF$_2$ | 4-SCH$_3$ |
| B-1553 | 3-CHF$_2$ | 2-SOCH$_3$ |
| B-1554 | 3-CHF$_2$ | 3-SOCH$_3$ |
| B-1555 | 3-CHF$_2$ | 4-SOCH$_3$ |
| B-1556 | 3-CHF$_2$ | 2-SO$_2$CH$_3$ |
| B-1557 | 3-CHF$_2$ | 3-SO$_2$CH$_3$ |
| B-1558 | 3-CHF$_2$ | 4-SO$_2$CH$_3$ |
| B-1559 | 3-CHF$_2$ | 2-CO$_2$CH$_3$ |
| B-1560 | 3-CHF$_2$ | 3-CO$_2$CH$_3$ |
| B-1561 | 3-CHF$_2$ | 4-CO$_2$CH$_3$ |
| B-1562 | 3-CHF$_2$ | 2-CH$_3$ |
| B-1563 | 3-CHF$_2$ | 3-CH$_3$ |

TABLE B-continued

For compounds where ZY is in para-position. The position(s) of the substituent(s) $(R^4)_n$ is/are given in relation to the attachment of the isoxazole-unit. The position(s) of the substituent(s) $(R^5)_m$ is/are given in relation to the attachment of the phenyl to the O-phenyl-unit.

| line | $(R^4)_n$ | $(R^5)_m$ |
|---|---|---|
| B-1564 | 3-CHF$_2$ | 4-CH$_3$ |
| B-1565 | 3-CHF$_2$ | 2-CF$_3$ |
| B-1566 | 3-CHF$_2$ | 3-CF$_3$ |
| B-1567 | 3-CHF$_2$ | 4-CF$_3$ |
| B-1568 | 3-CHF$_2$ | 2-CHF$_2$ |
| B-1569 | 3-CHF$_2$ | 3-CHF$_2$ |
| B-1570 | 3-CHF$_2$ | 4-CHF$_2$ |
| B-1571 | 3-CHF$_2$ | 2-OCH$_3$ |
| B-1572 | 3-CHF$_2$ | 3-OCH$_3$ |
| B-1573 | 3-CHF$_2$ | 4-OCH$_3$ |
| B-1574 | 3-CHF$_2$ | 2-OCF$_3$ |
| B-1575 | 3-CHF$_2$ | 3-OCF$_3$ |
| B-1576 | 3-CHF$_2$ | 4-OCF$_3$ |
| B-1577 | 3-CHF$_2$ | 2-OCHF$_2$ |
| B-1578 | 3-CHF$_2$ | 3-OCHF$_2$ |
| B-1579 | 3-CHF$_2$ | 4-OCHF$_2$ |
| B-1580 | 3-CHF$_2$ | 2,4,6-(CH$_3$)$_3$ |
| B-1581 | 3-CHF$_2$ | 2,3-Cl$_2$ |
| B-1582 | 3-CHF$_2$ | 2,4-Cl$_2$ |
| B-1583 | 3-CHF$_2$ | 2,5-Cl$_2$ |
| B-1584 | 3-CHF$_2$ | 3,4-Cl$_2$ |
| B-1585 | 3-CHF$_2$ | 3,5-Cl$_2$ |
| B-1586 | 3-CHF$_2$ | 2,6-Cl$_2$ |
| B-1587 | 3-CHF$_2$ | 2,3-F$_2$ |
| B-1588 | 3-CHF$_2$ | 2,4-F$_2$ |
| B-1589 | 3-CHF$_2$ | 2,5-F$_2$ |
| B-1590 | 3-CHF$_2$ | 3,4-F$_2$ |
| B-1591 | 3-CHF$_2$ | 3,5-F$_2$ |
| B-1592 | 3-CHF$_2$ | 2,6-F$_2$ |
| B-1593 | 3-CHF$_2$ | 2-CF$_3$-4-Cl |
| B-1594 | 3-CHF$_2$ | 2-CF$_3$-4-F |
| B-1595 | 3-CHF$_2$ | 2-Cl-4-CF$_3$ |
| B-1596 | 3-CHF$_2$ | 2-F-4-CF$_3$ |
| B-1597 | 3-CHF$_2$ | 2-CN-4-Cl |
| B-1598 | 3-CHF$_2$ | 2-CN-4-F |
| B-1599 | 3-CHF$_2$ | 2-Cl-4-CN |
| B-1600 | 3-CHF$_2$ | 2-F-4-CN |
| B-1601 | 2-OCH$_3$ | —* |
| B-1602 | 2-OCH$_3$ | 2-Cl |
| B-1603 | 2-OCH$_3$ | 3-Cl |
| B-1604 | 2-OCH$_3$ | 4-Cl |
| B-1605 | 2-OCH$_3$ | 2-F |
| B-1606 | 2-OCH$_3$ | 3-F |
| B-1607 | 2-OCH$_3$ | 4-F |
| B-1608 | 2-OCH$_3$ | 2-CN |
| B-1609 | 2-OCH$_3$ | 3-CN |
| B-1610 | 2-OCH$_3$ | 4-CN |
| B-1611 | 2-OCH$_3$ | 2-NO$_2$ |
| B-1612 | 2-OCH$_3$ | 3-NO$_2$ |
| B-1613 | 2-OCH$_3$ | 4-NO$_2$ |
| B-1614 | 2-OCH$_3$ | 2-SCH$_3$ |
| B-1615 | 2-OCH$_3$ | 3-SCH$_3$ |
| B-1616 | 2-OCH$_3$ | 4-SCH$_3$ |
| B-1617 | 2-OCH$_3$ | 2-SOCH$_3$ |
| B-1618 | 2-OCH$_3$ | 3-SOCH$_3$ |
| B-1619 | 2-OCH$_3$ | 4-SOCH$_3$ |
| B-1620 | 2-OCH$_3$ | 2-SO$_2$CH$_3$ |
| B-1621 | 2-OCH$_3$ | 3-SO$_2$CH$_3$ |
| B-1622 | 2-OCH$_3$ | 4-SO$_2$CH$_3$ |
| B-1623 | 2-OCH$_3$ | 2-CO$_2$CH$_3$ |
| B-1624 | 2-OCH$_3$ | 3-CO$_2$CH$_3$ |
| B-1625 | 2-OCH$_3$ | 4-CO$_2$CH$_3$ |
| B-1626 | 2-OCH$_3$ | 2-CH$_3$ |
| B-1627 | 2-OCH$_3$ | 3-CH$_3$ |
| B-1628 | 2-OCH$_3$ | 4-CH$_3$ |
| B-1629 | 2-OCH$_3$ | 2-CF$_3$ |
| B-1630 | 2-OCH$_3$ | 3-CF$_3$ |
| B-1631 | 2-OCH$_3$ | 4-CF$_3$ |
| B-1632 | 2-OCH$_3$ | 2-CHF$_2$ |
| B-1633 | 2-OCH$_3$ | 3-CHF$_2$ |
| B-1634 | 2-OCH$_3$ | 4-CHF$_2$ |
| B-1635 | 2-OCH$_3$ | 2-OCH$_3$ |
| B-1636 | 2-OCH$_3$ | 3-OCH$_3$ |
| B-1637 | 2-OCH$_3$ | 4-OCH$_3$ |
| B-1638 | 2-OCH$_3$ | 2-OCF$_3$ |
| B-1639 | 2-OCH$_3$ | 3-OCF$_3$ |
| B-1640 | 2-OCH$_3$ | 4-OCF$_3$ |
| B-1641 | 2-OCH$_3$ | 2-OCHF$_2$ |
| B-1642 | 2-OCH$_3$ | 3-OCHF$_2$ |
| B-1643 | 2-OCH$_3$ | 4-OCHF$_2$ |
| B-1644 | 2-OCH$_3$ | 2,4,6-(CH$_3$)$_3$ |
| B-1645 | 2-OCH$_3$ | 2,3-Cl$_2$ |
| B-1646 | 2-OCH$_3$ | 2,4-Cl$_2$ |
| B-1647 | 2-OCH$_3$ | 2,5-Cl$_2$ |
| B-1648 | 2-OCH$_3$ | 3,4-Cl$_2$ |
| B-1649 | 2-OCH$_3$ | 3,5-Cl$_2$ |
| B-1650 | 2-OCH$_3$ | 2,6-Cl$_2$ |
| B-1651 | 2-OCH$_3$ | 2,3-F$_2$ |
| B-1652 | 2-OCH$_3$ | 2,4-F$_2$ |
| B-1653 | 2-OCH$_3$ | 2,5-F$_2$ |
| B-1654 | 2-OCH$_3$ | 3,4-F$_2$ |
| B-1655 | 2-OCH$_3$ | 3,5-F$_2$ |
| B-1656 | 2-OCH$_3$ | 2,6-F$_2$ |
| B-1657 | 2-OCH$_3$ | 2-CF$_3$-4-Cl |
| B-1658 | 2-OCH$_3$ | 2-CF$_3$-4-F |
| B-1659 | 2-OCH$_3$ | 2-Cl-4-CF$_3$ |
| B-1660 | 2-OCH$_3$ | 2-F-4-CF$_3$ |
| B-1661 | 2-OCH$_3$ | 2-CN-4-Cl |
| B-1662 | 2-OCH$_3$ | 2-CN-4-F |
| B-1663 | 2-OCH$_3$ | 2-Cl-4-CN |
| B-1664 | 2-OCH$_3$ | 2-F-4-CN |
| B-1665 | 3-OCH$_3$ | —* |
| B-1666 | 3-OCH$_3$ | 2-Cl |
| B-1667 | 3-OCH$_3$ | 3-Cl |
| B-1668 | 3-OCH$_3$ | 4-Cl |
| B-1669 | 3-OCH$_3$ | 2-F |
| B-1670 | 3-OCH$_3$ | 3-F |
| B-1671 | 3-OCH$_3$ | 4-F |
| B-1672 | 3-OCH$_3$ | 2-CN |
| B-1673 | 3-OCH$_3$ | 3-CN |
| B-1674 | 3-OCH$_3$ | 4-CN |
| B-1675 | 3-OCH$_3$ | 2-NO$_2$ |
| B-1676 | 3-OCH$_3$ | 3-NO$_2$ |
| B-1677 | 3-OCH$_3$ | 4-NO$_2$ |
| B-1678 | 3-OCH$_3$ | 2-SCH$_3$ |
| B-1679 | 3-OCH$_3$ | 3-SCH$_3$ |
| B-1680 | 3-OCH$_3$ | 4-SCH$_3$ |
| B-1681 | 3-OCH$_3$ | 2-SOCH$_3$ |
| B-1682 | 3-OCH$_3$ | 3-SOCH$_3$ |
| B-1683 | 3-OCH$_3$ | 4-SOCH$_3$ |
| B-1684 | 3-OCH$_3$ | 2-SO$_2$CH$_3$ |
| B-1685 | 3-OCH$_3$ | 3-SO$_2$CH$_3$ |
| B-1686 | 3-OCH$_3$ | 4-SO$_2$CH$_3$ |
| B-1687 | 3-OCH$_3$ | 2-CO$_2$CH$_3$ |
| B-1688 | 3-OCH$_3$ | 3-CO$_2$CH$_3$ |
| B-1689 | 3-OCH$_3$ | 4-CO$_2$CH$_3$ |
| B-1690 | 3-OCH$_3$ | 2-CH$_3$ |
| B-1691 | 3-OCH$_3$ | 3-CH$_3$ |
| B-1692 | 3-OCH$_3$ | 4-CH$_3$ |
| B-1693 | 3-OCH$_3$ | 2-CF$_3$ |
| B-1694 | 3-OCH$_3$ | 3-CF$_3$ |
| B-1695 | 3-OCH$_3$ | 4-CF$_3$ |
| B-1696 | 3-OCH$_3$ | 2-CHF$_2$ |
| B-1697 | 3-OCH$_3$ | 3-CHF$_2$ |
| B-1698 | 3-OCH$_3$ | 4-CHF$_2$ |
| B-1699 | 3-OCH$_3$ | 2-OCH$_3$ |
| B-1700 | 3-OCH$_3$ | 3-OCH$_3$ |
| B-1701 | 3-OCH$_3$ | 4-OCH$_3$ |
| B-1702 | 3-OCH$_3$ | 2-OCF$_3$ |
| B-1703 | 3-OCH$_3$ | 3-OCF$_3$ |
| B-1704 | 3-OCH$_3$ | 4-OCF$_3$ |
| B-1705 | 3-OCH$_3$ | 2-OCHF$_2$ |
| B-1706 | 3-OCH$_3$ | 3-OCHF$_2$ |
| B-1707 | 3-OCH$_3$ | 4-OCHF$_2$ |
| B-1708 | 3-OCH$_3$ | 2,4,6-(CH$_3$)$_3$ |
| B-1709 | 3-OCH$_3$ | 2,3-Cl$_2$ |

TABLE B-continued

For compounds where ZY is in para-position. The position(s) of the substituent(s) $(R^4)_n$ is/are given in relation to the attachment of the isoxazole-unit. The position(s) of the substituent(s) $(R^5)_m$ is/are given in relation to the attachment of the phenyl to the O-phenyl-unit.

| line | $(R^4)_n$ | $(R^5)_m$ |
|---|---|---|
| B-1710 | 3-OCH$_3$ | 2,4-Cl$_2$ |
| B-1711 | 3-OCH$_3$ | 2,5-Cl$_2$ |
| B-1712 | 3-OCH$_3$ | 3,4-Cl$_2$ |
| B-1713 | 3-OCH$_3$ | 3,5-Cl$_2$ |
| B-1714 | 3-OCH$_3$ | 2,6-Cl$_2$ |
| B-1715 | 3-OCH$_3$ | 2,3-F$_2$ |
| B-1716 | 3-OCH$_3$ | 2,4-F$_2$ |
| B-1717 | 3-OCH$_3$ | 2,5-F$_2$ |
| B-1718 | 3-OCH$_3$ | 3,4-F$_2$ |
| B-1719 | 3-OCH$_3$ | 3,5-F$_2$ |
| B-1720 | 3-OCH$_3$ | 2,6-F$_2$ |
| B-1721 | 3-OCH$_3$ | 2-CF$_3$-4-Cl |
| B-1722 | 3-OCH$_3$ | 2-CF$_3$-4-F |
| B-1723 | 3-OCH$_3$ | 2-Cl-4-CF$_3$ |
| B-1724 | 3-OCH$_3$ | 2-F-4-CF$_3$ |
| B-1725 | 3-OCH$_3$ | 2-CN-4-Cl |
| B-1726 | 3-OCH$_3$ | 2-CN-4-F |
| B-1727 | 3-OCH$_3$ | 2-Cl-4-CN |
| B-1728 | 3-OCH$_3$ | 2-F-4-CN |
| B-1729 | 2,3-(CF$_3$)$_2$ | —* |
| B-1730 | 2,3-(CF$_3$)$_2$ | 2-Cl |
| B-1731 | 2,3-(CF$_3$)$_2$ | 3-Cl |
| B-1732 | 2,3-(CF$_3$)$_2$ | 4-Cl |
| B-1733 | 2,3-(CF$_3$)$_2$ | 2-F |
| B-1734 | 2,3-(CF$_3$)$_2$ | 3-F |
| B-1735 | 2,3-(CF$_3$)$_2$ | 4-F |
| B-1736 | 2,3-(CF$_3$)$_2$ | 2-CN |
| B-1737 | 2,3-(CF$_3$)$_2$ | 3-CN |
| B-1738 | 2,3-(CF$_3$)$_2$ | 4-CN |
| B-1739 | 2,3-(CF$_3$)$_2$ | 2-NO$_2$ |
| B-1740 | 2,3-(CF$_3$)$_2$ | 3-NO$_2$ |
| B-1741 | 2,3-(CF$_3$)$_2$ | 4-NO$_2$ |
| B-1742 | 2,3-(CF$_3$)$_2$ | 2-SCH$_3$ |
| B-1743 | 2,3-(CF$_3$)$_2$ | 3-SCH$_3$ |
| B-1744 | 2,3-(CF$_3$)$_2$ | 4-SCH$_3$ |
| B-1745 | 2,3-(CF$_3$)$_2$ | 2-SOCH$_3$ |
| B-1746 | 2,3-(CF$_3$)$_2$ | 3-SOCH$_3$ |
| B-1747 | 2,3-(CF$_3$)$_2$ | 4-SOCH$_3$ |
| B-1748 | 2,3-(CF$_3$)$_2$ | 2-SO$_2$CH$_3$ |
| B-1749 | 2,3-(CF$_3$)$_2$ | 3-SO$_2$CH$_3$ |
| B-1750 | 2,3-(CF$_3$)$_2$ | 4-SO$_2$CH$_3$ |
| B-1751 | 2,3-(CF$_3$)$_2$ | 2-CO$_2$CH$_3$ |
| B-1752 | 2,3-(CF$_3$)$_2$ | 3-CO$_2$CH$_3$ |
| B-1753 | 2,3-(CF$_3$)$_2$ | 4-CO$_2$CH$_3$ |
| B-1754 | 2,3-(CF$_3$)$_2$ | 2-CH$_3$ |
| B-1755 | 2,3-(CF$_3$)$_2$ | 3-CH$_3$ |
| B-1756 | 2,3-(CF$_3$)$_2$ | 4-CH$_3$ |
| B-1757 | 2,3-(CF$_3$)$_2$ | 2-CF$_3$ |
| B-1758 | 2,3-(CF$_3$)$_2$ | 3-CF$_3$ |
| B-1759 | 2,3-(CF$_3$)$_2$ | 4-CF$_3$ |
| B-1760 | 2,3-(CF$_3$)$_2$ | 2-CHF$_2$ |
| B-1761 | 2,3-(CF$_3$)$_2$ | 3-CHF$_2$ |
| B-1762 | 2,3-(CF$_3$)$_2$ | 4-CHF$_2$ |
| B-1763 | 2,3-(CF$_3$)$_2$ | 2-OCH$_3$ |
| B-1764 | 2,3-(CF$_3$)$_2$ | 3-OCH$_3$ |
| B-1765 | 2,3-(CF$_3$)$_2$ | 4-OCH$_3$ |
| B-1766 | 2,3-(CF$_3$)$_2$ | 2-OCF$_3$ |
| B-1767 | 2,3-(CF$_3$)$_2$ | 3-OCF$_3$ |
| B-1768 | 2,3-(CF$_3$)$_2$ | 4-OCF$_3$ |
| B-1769 | 2,3-(CF$_3$)$_2$ | 2-OCHF$_2$ |
| B-1770 | 2,3-(CF$_3$)$_2$ | 3-OCHF$_2$ |
| B-1771 | 2,3-(CF$_3$)$_2$ | 4-OCHF$_2$ |
| B-1772 | 2,3-(CF$_3$)$_2$ | 2,4,6-(CH$_3$)$_3$ |
| B-1773 | 2,3-(CF$_3$)$_2$ | 2,3-Cl$_2$ |
| B-1774 | 2,3-(CF$_3$)$_2$ | 2,4-Cl$_2$ |
| B-1775 | 2,3-(CF$_3$)$_2$ | 2,5-Cl$_2$ |
| B-1776 | 2,3-(CF$_3$)$_2$ | 3,4-Cl$_2$ |
| B-1777 | 2,3-(CF$_3$)$_2$ | 3,5-Cl$_2$ |
| B-1778 | 2,3-(CF$_3$)$_2$ | 2,6-Cl$_2$ |
| B-1779 | 2,3-(CF$_3$)$_2$ | 2,3-F$_2$ |
| B-1780 | 2,3-(CF$_3$)$_2$ | 2,4-F$_2$ |
| B-1781 | 2,3-(CF$_3$)$_2$ | 2,5-F$_2$ |
| B-1782 | 2,3-(CF$_3$)$_2$ | 3,4-F$_2$ |
| B-1783 | 2,3-(CF$_3$)$_2$ | 3,5-F$_2$ |
| B-1784 | 2,3-(CF$_3$)$_2$ | 2,6-F$_2$ |
| B-1785 | 2,3-(CF$_3$)$_2$ | 2-CF$_3$-4-Cl |
| B-1786 | 2,3-(CF$_3$)$_2$ | 2-CF$_3$-4-F |
| B-1787 | 2,3-(CF$_3$)$_2$ | 2-Cl-4-CF$_3$ |
| B-1788 | 2,3-(CF$_3$)$_2$ | 2-F-4-CF$_3$ |
| B-1789 | 2,3-(CF$_3$)$_2$ | 2-CN-4-Cl |
| B-1790 | 2,3-(CF$_3$)$_2$ | 2-CN-4-F |
| B-1791 | 2,3-(CF$_3$)$_2$ | 2-Cl-4-CN |
| B-1792 | 2,3-(CF$_3$)$_2$ | 2-F-4-CN |
| B-1793 | 2,5-(CF$_3$)$_2$ | —* |
| B-1794 | 2,5-(CF$_3$)$_2$ | 2-Cl |
| B-1795 | 2,5-(CF$_3$)$_2$ | 3-Cl |
| B-1796 | 2,5-(CF$_3$)$_2$ | 4-Cl |
| B-1797 | 2,5-(CF$_3$)$_2$ | 2-F |
| B-1798 | 2,5-(CF$_3$)$_2$ | 3-F |
| B-1799 | 2,5-(CF$_3$)$_2$ | 4-F |
| B-1800 | 2,5-(CF$_3$)$_2$ | 2-CN |
| B-1801 | 2,5-(CF$_3$)$_2$ | 3-CN |
| B-1802 | 2,5-(CF$_3$)$_2$ | 4-CN |
| B-1803 | 2,5-(CF$_3$)$_2$ | 2-NO$_2$ |
| B-1804 | 2,5-(CF$_3$)$_2$ | 3-NO$_2$ |
| B-1805 | 2,5-(CF$_3$)$_2$ | 4-NO$_2$ |
| B-1806 | 2,5-(CF$_3$)$_2$ | 2-SCH$_3$ |
| B-1807 | 2,5-(CF$_3$)$_2$ | 3-SCH$_3$ |
| B-1808 | 2,5-(CF$_3$)$_2$ | 4-SCH$_3$ |
| B-1809 | 2,5-(CF$_3$)$_2$ | 2-SOCH$_3$ |
| B-1810 | 2,5-(CF$_3$)$_2$ | 3-SOCH$_3$ |
| B-1811 | 2,5-(CF$_3$)$_2$ | 4-SOCH$_3$ |
| B-1812 | 2,5-(CF$_3$)$_2$ | 2-SO$_2$CH$_3$ |
| B-1813 | 2,5-(CF$_3$)$_2$ | 3-SO$_2$CH$_3$ |
| B-1814 | 2,5-(CF$_3$)$_2$ | 4-SO$_2$CH$_3$ |
| B-1815 | 2,5-(CF$_3$)$_2$ | 2-CO$_2$CH$_3$ |
| B-1816 | 2,5-(CF$_3$)$_2$ | 3-CO$_2$CH$_3$ |
| B-1817 | 2,5-(CF$_3$)$_2$ | 4-CO$_2$CH$_3$ |
| B-1818 | 2,5-(CF$_3$)$_2$ | 2-CH$_3$ |
| B-1819 | 2,5-(CF$_3$)$_2$ | 3-CH$_3$ |
| B-1820 | 2,5-(CF$_3$)$_2$ | 4-CH$_3$ |
| B-1821 | 2,5-(CF$_3$)$_2$ | 2-CF$_3$ |
| B-1822 | 2,5-(CF$_3$)$_2$ | 3-CF$_3$ |
| B-1823 | 2,5-(CF$_3$)$_2$ | 4-CF$_3$ |
| B-1824 | 2,5-(CF$_3$)$_2$ | 2-CHF$_2$ |
| B-1825 | 2,5-(CF$_3$)$_2$ | 3-CHF$_2$ |
| B-1826 | 2,5-(CF$_3$)$_2$ | 4-CHF$_2$ |
| B-1827 | 2,5-(CF$_3$)$_2$ | 2-OCH$_3$ |
| B-1828 | 2,5-(CF$_3$)$_2$ | 3-OCH$_3$ |
| B-1829 | 2,5-(CF$_3$)$_2$ | 4-OCH$_3$ |
| B-1830 | 2,5-(CF$_3$)$_2$ | 2-OCF$_3$ |
| B-1831 | 2,5-(CF$_3$)$_2$ | 3-OCF$_3$ |
| B-1832 | 2,5-(CF$_3$)$_2$ | 4-OCF$_3$ |
| B-1833 | 2,5-(CF$_3$)$_2$ | 2-OCHF$_2$ |
| B-1834 | 2,5-(CF$_3$)$_2$ | 3-OCHF$_2$ |
| B-1835 | 2,5-(CF$_3$)$_2$ | 4-OCHF$_2$ |
| B-1836 | 2,5-(CF$_3$)$_2$ | 2,4,6-(CH$_3$)$_3$ |
| B-1837 | 2,5-(CF$_3$)$_2$ | 2,3-Cl$_2$ |
| B-1838 | 2,5-(CF$_3$)$_2$ | 2,4-Cl$_2$ |
| B-1839 | 2,5-(CF$_3$)$_2$ | 2,5-Cl$_2$ |
| B-1840 | 2,5-(CF$_3$)$_2$ | 3,4-Cl$_2$ |
| B-1841 | 2,5-(CF$_3$)$_2$ | 3,5-Cl$_2$ |
| B-1842 | 2,5-(CF$_3$)$_2$ | 2,6-Cl$_2$ |
| B-1843 | 2,5-(CF$_3$)$_2$ | 2,3-F$_2$ |
| B-1844 | 2,5-(CF$_3$)$_2$ | 2,4-F$_2$ |
| B-1845 | 2,5-(CF$_3$)$_2$ | 2,5-F$_2$ |
| B-1846 | 2,5-(CF$_3$)$_2$ | 3,4-F$_2$ |
| B-1847 | 2,5-(CF$_3$)$_2$ | 3,5-F$_2$ |
| B-1848 | 2,5-(CF$_3$)$_2$ | 2,6-F$_2$ |
| B-1849 | 2,5-(CF$_3$)$_2$ | 2-CF$_3$-4-Cl |
| B-1850 | 2,5-(CF$_3$)$_2$ | 2-CF$_3$-4-F |
| B-1851 | 2,5-(CF$_3$)$_2$ | 2-Cl-4-CF$_3$ |
| B-1852 | 2,5-(CF$_3$)$_2$ | 2-F-4-CF$_3$ |
| B-1853 | 2,5-(CF$_3$)$_2$ | 2-CN-4-Cl |
| B-1854 | 2,5-(CF$_3$)$_2$ | 2-CN-4-F |
| B-1855 | 2,5-(CF$_3$)$_2$ | 2-Cl-4-CN |

TABLE B-continued

For compounds where ZY is in para-position. The position(s) of the substituent(s) $(R^4)_n$ is/are given in relation to the attachment of the isoxazole-unit. The position(s) of the substituent(s) $(R^5)_m$ is/are given in relation to the attachment of the phenyl to the O-phenyl-unit.

| line | $(R^4)_n$ | $(R^5)_m$ |
|---|---|---|
| B-1856 | 2,5-$(CF_3)_2$ | 2-F-4-CN |
| B-1857 | 3,5-$(CF_3)_2$ | —* |
| B-1858 | 3,5-$(CF_3)_2$ | 2-Cl |
| B-1859 | 3,5-$(CF_3)_2$ | 3-Cl |
| B-1860 | 3,5-$(CF_3)_2$ | 4-Cl |
| B-1861 | 3,5-$(CF_3)_2$ | 2-F |
| B-1862 | 3,5-$(CF_3)_2$ | 3-F |
| B-1863 | 3,5-$(CF_3)_2$ | 4-F |
| B-1864 | 3,5-$(CF_3)_2$ | 2-CN |
| B-1865 | 3,5-$(CF_3)_2$ | 3-CN |
| B-1866 | 3,5-$(CF_3)_2$ | 4-CN |
| B-1867 | 3,5-$(CF_3)_2$ | 2-$NO_2$ |
| B-1868 | 3,5-$(CF_3)_2$ | 3-$NO_2$ |
| B-1869 | 3,5-$(CF_3)_2$ | 4-$NO_2$ |
| B-1870 | 3,5-$(CF_3)_2$ | 2-$SCH_3$ |
| B-1871 | 3,5-$(CF_3)_2$ | 3-$SCH_3$ |
| B-1872 | 3,5-$(CF_3)_2$ | 4-$SCH_3$ |
| B-1873 | 3,5-$(CF_3)_2$ | 2-$SOCH_3$ |
| B-1874 | 3,5-$(CF_3)_2$ | 3-$SOCH_3$ |
| B-1875 | 3,5-$(CF_3)_2$ | 4-$SOCH_3$ |
| B-1876 | 3,5-$(CF_3)_2$ | 2-$SO_2CH_3$ |
| B-1877 | 3,5-$(CF_3)_2$ | 3-$SO_2CH_3$ |
| B-1878 | 3,5-$(CF_3)_2$ | 4-$SO_2CH_3$ |
| B-1879 | 3,5-$(CF_3)_2$ | 2-$CO_2CH_3$ |
| B-1880 | 3,5-$(CF_3)_2$ | 3-$CO_2CH_3$ |
| B-1881 | 3,5-$(CF_3)_2$ | 4-$CO_2CH_3$ |
| B-1882 | 3,5-$(CF_3)_2$ | 2-$CH_3$ |
| B-1883 | 3,5-$(CF_3)_2$ | 3-$CH_3$ |
| B-1884 | 3,5-$(CF_3)_2$ | 4-$CH_3$ |
| B-1885 | 3,5-$(CF_3)_2$ | 2-$CF_3$ |
| B-1886 | 3,5-$(CF_3)_2$ | 3-$CF_3$ |
| B-1887 | 3,5-$(CF_3)_2$ | 4-$CF_3$ |
| B-1888 | 3,5-$(CF_3)_2$ | 2-$CHF_2$ |
| B-1889 | 3,5-$(CF_3)_2$ | 3-$CHF_2$ |
| B-1890 | 3,5-$(CF_3)_2$ | 4-$CHF_2$ |
| B-1891 | 3,5-$(CF_3)_2$ | 2-$OCH_3$ |
| B-1892 | 3,5-$(CF_3)_2$ | 3-$OCH_3$ |
| B-1893 | 3,5-$(CF_3)_2$ | 4-$OCH_3$ |
| B-1894 | 3,5-$(CF_3)_2$ | 2-$OCF_3$ |
| B-1895 | 3,5-$(CF_3)_2$ | 3-$OCF_3$ |
| B-1896 | 3,5-$(CF_3)_2$ | 4-$OCF_3$ |
| B-1897 | 3,5-$(CF_3)_2$ | 2-$OCHF_2$ |
| B-1898 | 3,5-$(CF_3)_2$ | 3-$OCHF_2$ |
| B-1899 | 3,5-$(CF_3)_2$ | 4-$OCHF_2$ |
| B-1900 | 3,5-$(CF_3)_2$ | 2,4,6-$(CH_3)_3$ |
| B-1901 | 3,5-$(CF_3)_2$ | 2,3-$Cl_2$ |
| B-1902 | 3,5-$(CF_3)_2$ | 2,4-$Cl_2$ |
| B-1903 | 3,5-$(CF_3)_2$ | 2,5-$Cl_2$ |
| B-1904 | 3,5-$(CF_3)_2$ | 3,4-$Cl_2$ |
| B-1905 | 3,5-$(CF_3)_2$ | 3,5-$Cl_2$ |
| B-1906 | 3,5-$(CF_3)_2$ | 2,6-$Cl_2$ |
| B-1907 | 3,5-$(CF_3)_2$ | 2,3-$F_2$ |
| B-1908 | 3,5-$(CF_3)_2$ | 2,4-$F_2$ |
| B-1909 | 3,5-$(CF_3)_2$ | 2,5-$F_2$ |
| B-1910 | 3,5-$(CF_3)_2$ | 3,4-$F_2$ |
| B-1911 | 3,5-$(CF_3)_2$ | 3,5-$F_2$ |
| B-1912 | 3,5-$(CF_3)_2$ | 2,6-$F_2$ |
| B-1913 | 3,5-$(CF_3)_2$ | 2-$CF_3$-4-Cl |
| B-1914 | 3,5-$(CF_3)_2$ | 2-$CF_3$-4-F |
| B-1915 | 3,5-$(CF_3)_2$ | 2-Cl-4-$CF_3$ |
| B-1916 | 3,5-$(CF_3)_2$ | 2-F-4-$CF_3$ |
| B-1917 | 3,5-$(CF_3)_2$ | 2-CN-4-Cl |
| B-1918 | 3,5-$(CF_3)_2$ | 2-CN-4-F |
| B-1919 | 3,5-$(CF_3)_2$ | 2-Cl-4-CN |
| B-1920 | 3,5-$(CF_3)_2$ | 2-F-4-CN |
| B-1921 | 2,6-$(CF_3)_2$ | —* |
| B-1922 | 2,6-$(CF_3)_2$ | 2-Cl |
| B-1923 | 2,6-$(CF_3)_2$ | 3-Cl |
| B-1924 | 2,6-$(CF_3)_2$ | 4-Cl |
| B-1925 | 2,6-$(CF_3)_2$ | 2-F |
| B-1926 | 2,6-$(CF_3)_2$ | 3-F |
| B-1927 | 2,6-$(CF_3)_2$ | 4-F |
| B-1928 | 2,6-$(CF_3)_2$ | 2-CN |
| B-1929 | 2,6-$(CF_3)_2$ | 3-CN |
| B-1930 | 2,6-$(CF_3)_2$ | 4-CN |
| B-1931 | 2,6-$(CF_3)_2$ | 2-$NO_2$ |
| B-1932 | 2,6-$(CF_3)_2$ | 3-$NO_2$ |
| B-1933 | 2,6-$(CF_3)_2$ | 4-$NO_2$ |
| B-1934 | 2,6-$(CF_3)_2$ | 2-$SCH_3$ |
| B-1935 | 2,6-$(CF_3)_2$ | 3-$SCH_3$ |
| B-1936 | 2,6-$(CF_3)_2$ | 4-$SCH_3$ |
| B-1937 | 2,6-$(CF_3)_2$ | 2-$SOCH_3$ |
| B-1938 | 2,6-$(CF_3)_2$ | 3-$SOCH_3$ |
| B-1939 | 2,6-$(CF_3)_2$ | 4-$SOCH_3$ |
| B-1940 | 2,6-$(CF_3)_2$ | 2-$SO_2CH_3$ |
| B-1941 | 2,6-$(CF_3)_2$ | 3-$SO_2CH_3$ |
| B-1942 | 2,6-$(CF_3)_2$ | 4-$SO_2CH_3$ |
| B-1943 | 2,6-$(CF_3)_2$ | 2-$CO_2CH_3$ |
| B-1944 | 2,6-$(CF_3)_2$ | 3-$CO_2CH_3$ |
| B-1945 | 2,6-$(CF_3)_2$ | 4-$CO_2CH_3$ |
| B-1946 | 2,6-$(CF_3)_2$ | 2-$CH_3$ |
| B-1947 | 2,6-$(CF_3)_2$ | 3-$CH_3$ |
| B-1948 | 2,6-$(CF_3)_2$ | 4-$CH_3$ |
| B-1949 | 2,6-$(CF_3)_2$ | 2-$CF_3$ |
| B-1950 | 2,6-$(CF_3)_2$ | 3-$CF_3$ |
| B-1951 | 2,6-$(CF_3)_2$ | 4-$CF_3$ |
| B-1952 | 2,6-$(CF_3)_2$ | 2-$CHF_2$ |
| B-1953 | 2,6-$(CF_3)_2$ | 3-$CHF_2$ |
| B-1954 | 2,6-$(CF_3)_2$ | 4-$CHF_2$ |
| B-1955 | 2,6-$(CF_3)_2$ | 2-$OCH_3$ |
| B-1956 | 2,6-$(CF_3)_2$ | 3-$OCH_3$ |
| B-1957 | 2,6-$(CF_3)_2$ | 4-$OCH_3$ |
| B-1958 | 2,6-$(CF_3)_2$ | 2-$OCF_3$ |
| B-1959 | 2,6-$(CF_3)_2$ | 3-$OCF_3$ |
| B-1960 | 2,6-$(CF_3)_2$ | 4-$OCF_3$ |
| B-1961 | 2,6-$(CF_3)_2$ | 2-$OCHF_2$ |
| B-1962 | 2,6-$(CF_3)_2$ | 3-$OCHF_2$ |
| B-1963 | 2,6-$(CF_3)_2$ | 4-$OCHF_2$ |
| B-1964 | 2,6-$(CF_3)_2$ | 2,4,6-$(CH_3)_3$ |
| B-1965 | 2,6-$(CF_3)_2$ | 2,3-$Cl_2$ |
| B-1966 | 2,6-$(CF_3)_2$ | 2,4-$Cl_2$ |
| B-1967 | 2,6-$(CF_3)_2$ | 2,5-$Cl_2$ |
| B-1968 | 2,6-$(CF_3)_2$ | 3,4-$Cl_2$ |
| B-1969 | 2,6-$(CF_3)_2$ | 3,5-$Cl_2$ |
| B-1970 | 2,6-$(CF_3)_2$ | 2,6-$Cl_2$ |
| B-1971 | 2,6-$(CF_3)_2$ | 2,3-$F_2$ |
| B-1972 | 2,6-$(CF_3)_2$ | 2,4-$F_2$ |
| B-1973 | 2,6-$(CF_3)_2$ | 2,5-$F_2$ |
| B-1974 | 2,6-$(CF_3)_2$ | 3,4-$F_2$ |
| B-1975 | 2,6-$(CF_3)_2$ | 3,5-$F_2$ |
| B-1976 | 2,6-$(CF_3)_2$ | 2,6-$F_2$ |
| B-1977 | 2,6-$(CF_3)_2$ | 2-$CF_3$-4-Cl |
| B-1978 | 2,6-$(CF_3)_2$ | 2-$CF_3$-4-F |
| B-1979 | 2,6-$(CF_3)_2$ | 2-Cl-4-$CF_3$ |
| B-1980 | 2,6-$(CF_3)_2$ | 2-F-4-$CF_3$ |
| B-1981 | 2,6-$(CF_3)_2$ | 2-CN-4-Cl |
| B-1982 | 2,6-$(CF_3)_2$ | 2-CN-4-F |
| B-1983 | 2,6-$(CF_3)_2$ | 2-Cl-4-CN |
| B-1984 | 2,6-$(CF_3)_2$ | 2-F-4-CN |
| B-1985 | 2-$CF_3$-5-Cl | —* |
| B-1986 | 2-$CF_3$-5-Cl | 2-Cl |
| B-1987 | 2-$CF_3$-5-Cl | 3-Cl |
| B-1988 | 2-$CF_3$-5-Cl | 4-Cl |
| B-1989 | 2-$CF_3$-5-Cl | 2-F |
| B-1990 | 2-$CF_3$-5-Cl | 3-F |
| B-1991 | 2-$CF_3$-5-Cl | 4-F |
| B-1992 | 2-$CF_3$-5-Cl | 2-CN |
| B-1993 | 2-$CF_3$-5-Cl | 3-CN |
| B-1994 | 2-$CF_3$-5-Cl | 4-CN |
| B-1995 | 2-$CF_3$-5-Cl | 2-$NO_2$ |
| B-1996 | 2-$CF_3$-5-Cl | 3-$NO_2$ |
| B-1997 | 2-$CF_3$-5-Cl | 4-$NO_2$ |
| B-1998 | 2-$CF_3$-5-Cl | 2-$SCH_3$ |
| B-1999 | 2-$CF_3$-5-Cl | 3-$SCH_3$ |
| B-2000 | 2-$CF_3$-5-Cl | 4-$SCH_3$ |
| B-2001 | 2-$CF_3$-5-Cl | 2-$SOCH_3$ |

TABLE B-continued

For compounds where ZY is in para-position. The position(s) of the substituent(s) $(R^4)_n$ is/are given in relation to the attachment of the isoxazole-unit. The position(s) of the substituent(s) $(R^5)_m$ is/are given in relation to the attachment of the phenyl to the O-phenyl-unit.

| line | $(R^4)_n$ | $(R^5)_m$ |
|---|---|---|
| B-2002 | 2-CF$_3$-5-Cl | 3-SOCH$_3$ |
| B-2003 | 2-CF$_3$-5-Cl | 4-SOCH$_3$ |
| B-2004 | 2-CF$_3$-5-Cl | 2-SO$_2$CH$_3$ |
| B-2005 | 2-CF$_3$-5-Cl | 3-SO$_2$CH$_3$ |
| B-2006 | 2-CF$_3$-5-Cl | 4-SO$_2$CH$_3$ |
| B-2007 | 2-CF$_3$-5-Cl | 2-CO$_2$CH$_3$ |
| B-2008 | 2-CF$_3$-5-Cl | 3-CO$_2$CH$_3$ |
| B-2009 | 2-CF$_3$-5-Cl | 4-CO$_2$CH$_3$ |
| B-2010 | 2-CF$_3$-5-Cl | 2-CH$_3$ |
| B-2011 | 2-CF$_3$-5-Cl | 3-CH$_3$ |
| B-2012 | 2-CF$_3$-5-Cl | 4-CH$_3$ |
| B-2013 | 2-CF$_3$-5-Cl | 2-CF$_3$ |
| B-2014 | 2-CF$_3$-5-Cl | 3-CF$_3$ |
| B-2015 | 2-CF$_3$-5-Cl | 4-CF$_3$ |
| B-2016 | 2-CF$_3$-5-Cl | 2-CHF$_2$ |
| B-2017 | 2-CF$_3$-5-Cl | 3-CHF$_2$ |
| B-2018 | 2-CF$_3$-5-Cl | 4-CHF$_2$ |
| B-2019 | 2-CF$_3$-5-Cl | 2-OCH$_3$ |
| B-2020 | 2-CF$_3$-5-Cl | 3-OCH$_3$ |
| B-2021 | 2-CF$_3$-5-Cl | 4-OCH$_3$ |
| B-2022 | 2-CF$_3$-5-Cl | 2-OCF$_3$ |
| B-2023 | 2-CF$_3$-5-Cl | 3-OCF$_3$ |
| B-2024 | 2-CF$_3$-5-Cl | 4-OCF$_3$ |
| B-2025 | 2-CF$_3$-5-Cl | 2-OCHF$_2$ |
| B-2026 | 2-CF$_3$-5-Cl | 3-OCHF$_2$ |
| B-2027 | 2-CF$_3$-5-Cl | 4-OCHF$_2$ |
| B-2028 | 2-CF$_3$-5-Cl | 2,4,6-(CH$_3$)$_3$ |
| B-2029 | 2-CF$_3$-5-Cl | 2,3-Cl$_2$ |
| B-2030 | 2-CF$_3$-5-Cl | 2,4-Cl$_2$ |
| B-2031 | 2-CF$_3$-5-Cl | 2,5-Cl$_2$ |
| B-2032 | 2-CF$_3$-5-Cl | 3,4-Cl$_2$ |
| B-2033 | 2-CF$_3$-5-Cl | 3,5-Cl$_2$ |
| B-2034 | 2-CF$_3$-5-Cl | 2,6-Cl$_2$ |
| B-2035 | 2-CF$_3$-5-Cl | 2,3-F$_2$ |
| B-2036 | 2-CF$_3$-5-Cl | 2,4-F$_2$ |
| B-2037 | 2-CF$_3$-5-Cl | 2,5-F$_2$ |
| B-2038 | 2-CF$_3$-5-Cl | 3,4-F$_2$ |
| B-2039 | 2-CF$_3$-5-Cl | 3,5-F$_2$ |
| B-2040 | 2-CF$_3$-5-Cl | 2,6-F$_2$ |
| B-2041 | 2-CF$_3$-5-Cl | 2-CF$_3$-4-Cl |
| B-2042 | 2-CF$_3$-5-Cl | 2-CF$_3$-4-F |
| B-2043 | 2-CF$_3$-5-Cl | 2-Cl-4-CF$_3$ |
| B-2044 | 2-CF$_3$-5-Cl | 2-F-4-CF$_3$ |
| B-2045 | 2-CF$_3$-5-Cl | 2-CN-4-Cl |
| B-2046 | 2-CF$_3$-5-Cl | 2-CN-4-F |
| B-2047 | 2-CF$_3$-5-Cl | 2-Cl-4-CN |
| B-2048 | 2-CF$_3$-5-Cl | 2-F-4-CN |
| B-2049 | 2-CF$_3$-5-F | —* |
| B-2050 | 2-CF$_3$-5-F | 2-Cl |
| B-2051 | 2-CF$_3$-5-F | 3-Cl |
| B-2052 | 2-CF$_3$-5-F | 4-Cl |
| B-2053 | 2-CF$_3$-5-F | 2-F |
| B-2054 | 2-CF$_3$-5-F | 3-F |
| B-2055 | 2-CF$_3$-5-F | 4-F |
| B-2056 | 2-CF$_3$-5-F | 2-CN |
| B-2057 | 2-CF$_3$-5-F | 3-CN |
| B-2058 | 2-CF$_3$-5-F | 4-CN |
| B-2059 | 2-CF$_3$-5-F | 2-NO$_2$ |
| B-2060 | 2-CF$_3$-5-F | 3-NO$_2$ |
| B-2061 | 2-CF$_3$-5-F | 4-NO$_2$ |
| B-2062 | 2-CF$_3$-5-F | 2-SCH$_3$ |
| B-2063 | 2-CF$_3$-5-F | 3-SCH$_3$ |
| B-2064 | 2-CF$_3$-5-F | 4-SCH$_3$ |
| B-2065 | 2-CF$_3$-5-F | 2-SOCH$_3$ |
| B-2066 | 2-CF$_3$-5-F | 3-SOCH$_3$ |
| B-2067 | 2-CF$_3$-5-F | 4-SOCH$_3$ |
| B-2068 | 2-CF$_3$-5-F | 2-SO$_2$CH$_3$ |
| B-2069 | 2-CF$_3$-5-F | 3-SO$_2$CH$_3$ |
| B-2070 | 2-CF$_3$-5-F | 4-SO$_2$CH$_3$ |
| B-2071 | 2-CF$_3$-5-F | 2-CO$_2$CH$_3$ |
| B-2072 | 2-CF$_3$-5-F | 3-CO$_2$CH$_3$ |
| B-2073 | 2-CF$_3$-5-F | 4-CO$_2$CH$_3$ |
| B-2074 | 2-CF$_3$-5-F | 2-CH$_3$ |
| B-2075 | 2-CF$_3$-5-F | 3-CH$_3$ |
| B-2076 | 2-CF$_3$-5-F | 4-CH$_3$ |
| B-2077 | 2-CF$_3$-5-F | 2-CF$_3$ |
| B-2078 | 2-CF$_3$-5-F | 3-CF$_3$ |
| B-2079 | 2-CF$_3$-5-F | 4-CF$_3$ |
| B-2080 | 2-CF$_3$-5-F | 2-CHF$_2$ |
| B-2081 | 2-CF$_3$-5-F | 3-CHF$_2$ |
| B-2082 | 2-CF$_3$-5-F | 4-CHF$_2$ |
| B-2083 | 2-CF$_3$-5-F | 2-OCH$_3$ |
| B-2084 | 2-CF$_3$-5-F | 3-OCH$_3$ |
| B-2085 | 2-CF$_3$-5-F | 4-OCH$_3$ |
| B-2086 | 2-CF$_3$-5-F | 2-OCF$_3$ |
| B-2087 | 2-CF$_3$-5-F | 3-OCF$_3$ |
| B-2088 | 2-CF$_3$-5-F | 4-OCF$_3$ |
| B-2089 | 2-CF$_3$-5-F | 2-OCHF$_2$ |
| B-2090 | 2-CF$_3$-5-F | 3-OCHF$_2$ |
| B-2091 | 2-CF$_3$-5-F | 4-OCHF$_2$ |
| B-2092 | 2-CF$_3$-5-F | 2,4,6-(CH$_3$)$_3$ |
| B-2093 | 2-CF$_3$-5-F | 2,3-Cl$_2$ |
| B-2094 | 2-CF$_3$-5-F | 2,4-Cl$_2$ |
| B-2095 | 2-CF$_3$-5-F | 2,5-Cl$_2$ |
| B-2096 | 2-CF$_3$-5-F | 3,4-Cl$_2$ |
| B-2097 | 2-CF$_3$-5-F | 3,5-Cl$_2$ |
| B-2098 | 2-CF$_3$-5-F | 2,6-Cl$_2$ |
| B-2099 | 2-CF$_3$-5-F | 2,3-F$_2$ |
| B-2100 | 2-CF$_3$-5-F | 2,4-F$_2$ |
| B-2101 | 2-CF$_3$-5-F | 2,5-F$_2$ |
| B-2102 | 2-CF$_3$-5-F | 3,4-F$_2$ |
| B-2103 | 2-CF$_3$-5-F | 3,5-F$_2$ |
| B-2104 | 2-CF$_3$-5-F | 2,6-F$_2$ |
| B-2105 | 2-CF$_3$-5-F | 2-CF$_3$-4-Cl |
| B-2106 | 2-CF$_3$-5-F | 2-CF$_3$-4-F |
| B-2107 | 2-CF$_3$-5-F | 2-Cl-4-CF$_3$ |
| B-2108 | 2-CF$_3$-5-F | 2-F-4-CF$_3$ |
| B-2109 | 2-CF$_3$-5-F | 2-CN-4-Cl |
| B-2110 | 2-CF$_3$-5-F | 2-CN-4-F |
| B-2111 | 2-CF$_3$-5-F | 2-Cl-4-CN |
| B-2112 | 2-CF$_3$-5-F | 2-F-4-CN |
| B-2113 | 2-CF$_3$-3-Cl | —* |
| B-2114 | 2-CF$_3$-3-Cl | 2-Cl |
| B-2115 | 2-CF$_3$-3-Cl | 3-Cl |
| B-2116 | 2-CF$_3$-3-Cl | 4-Cl |
| B-2117 | 2-CF$_3$-3-Cl | 2-F |
| B-2118 | 2-CF$_3$-3-Cl | 3-F |
| B-2119 | 2-CF$_3$-3-Cl | 4-F |
| B-2120 | 2-CF$_3$-3-Cl | 2-CN |
| B-2121 | 2-CF$_3$-3-Cl | 3-CN |
| B-2122 | 2-CF$_3$-3-Cl | 4-CN |
| B-2123 | 2-CF$_3$-3-Cl | 2-NO$_2$ |
| B-2124 | 2-CF$_3$-3-Cl | 3-NO$_2$ |
| B-2125 | 2-CF$_3$-3-Cl | 4-NO$_2$ |
| B-2126 | 2-CF$_3$-3-Cl | 2-SCH$_3$ |
| B-2127 | 2-CF$_3$-3-Cl | 3-SCH$_3$ |
| B-2128 | 2-CF$_3$-3-Cl | 4-SCH$_3$ |
| B-2129 | 2-CF$_3$-3-Cl | 2-SOCH$_3$ |
| B-2130 | 2-CF$_3$-3-Cl | 3-SOCH$_3$ |
| B-2131 | 2-CF$_3$-3-Cl | 4-SOCH$_3$ |
| B-2132 | 2-CF$_3$-3-Cl | 2-SO$_2$CH$_3$ |
| B-2133 | 2-CF$_3$-3-Cl | 3-SO$_2$CH$_3$ |
| B-2134 | 2-CF$_3$-3-Cl | 4-SO$_2$CH$_3$ |
| B-2135 | 2-CF$_3$-3-Cl | 2-CO$_2$CH$_3$ |
| B-2136 | 2-CF$_3$-3-Cl | 3-CO$_2$CH$_3$ |
| B-2137 | 2-CF$_3$-3-Cl | 4-CO$_2$CH$_3$ |
| B-2138 | 2-CF$_3$-3-Cl | 2-CH$_3$ |
| B-2139 | 2-CF$_3$-3-Cl | 3-CH$_3$ |
| B-2140 | 2-CF$_3$-3-Cl | 4-CH$_3$ |
| B-2141 | 2-CF$_3$-3-Cl | 2-CF$_3$ |
| B-2142 | 2-CF$_3$-3-Cl | 3-CF$_3$ |
| B-2143 | 2-CF$_3$-3-Cl | 4-CF$_3$ |
| B-2144 | 2-CF$_3$-3-Cl | 2-CHF$_2$ |
| B-2145 | 2-CF$_3$-3-Cl | 3-CHF$_2$ |
| B-2146 | 2-CF$_3$-3-Cl | 4-CHF$_2$ |
| B-2147 | 2-CF$_3$-3-Cl | 2-OCH$_3$ |

TABLE B-continued

For compounds where ZY is in para-position. The position(s) of the substituent(s) $(R^4)_n$ is/are given in relation to the attachment of the isoxazole-unit. The position(s) of the substituent(s) $(R^5)_m$ is/are given in relation to the attachment of the phenyl to the O-phenyl-unit.

| line | $(R^4)_n$ | $(R^5)_m$ |
|---|---|---|
| B-2148 | 2-CF$_3$-3-Cl | 3-OCH$_3$ |
| B-2149 | 2-CF$_3$-3-Cl | 4-OCH$_3$ |
| B-2150 | 2-CF$_3$-3-Cl | 2-OCF$_3$ |
| B-2151 | 2-CF$_3$-3-Cl | 3-OCF$_3$ |
| B-2152 | 2-CF$_3$-3-Cl | 4-OCF$_3$ |
| B-2153 | 2-CF$_3$-3-Cl | 2-OCHF$_2$ |
| B-2154 | 2-CF$_3$-3-Cl | 3-OCHF$_2$ |
| B-2155 | 2-CF$_3$-3-Cl | 4-OCHF$_2$ |
| B-2156 | 2-CF$_3$-3-Cl | 2,4,6-(CH$_3$)$_3$ |
| B-2157 | 2-CF$_3$-3-Cl | 2,3-Cl$_2$ |
| B-2158 | 2-CF$_3$-3-Cl | 2,4-Cl$_2$ |
| B-2159 | 2-CF$_3$-3-Cl | 2,5-Cl$_2$ |
| B-2160 | 2-CF$_3$-3-Cl | 3,4-Cl$_2$ |
| B-2161 | 2-CF$_3$-3-Cl | 3,5-Cl$_2$ |
| B-2162 | 2-CF$_3$-3-Cl | 2,6-Cl$_2$ |
| B-2163 | 2-CF$_3$-3-Cl | 2,3-F$_2$ |
| B-2164 | 2-CF$_3$-3-Cl | 2,4-F$_2$ |
| B-2165 | 2-CF$_3$-3-Cl | 2,5-F$_2$ |
| B-2166 | 2-CF$_3$-3-Cl | 3,4-F$_2$ |
| B-2167 | 2-CF$_3$-3-Cl | 3,5-F$_2$ |
| B-2168 | 2-CF$_3$-3-Cl | 2,6-F$_2$ |
| B-2169 | 2-CF$_3$-3-Cl | 2-CF$_3$-4-Cl |
| B-2170 | 2-CF$_3$-3-Cl | 2-CF$_3$-4-F |
| B-2171 | 2-CF$_3$-3-Cl | 2-Cl-4-CF$_3$ |
| B-2172 | 2-CF$_3$-3-Cl | 2-F-4-CF$_3$ |
| B-2173 | 2-CF$_3$-3-Cl | 2-CN-4-Cl |
| B-2174 | 2-CF$_3$-3-Cl | 2-CN-4-F |
| B-2175 | 2-CF$_3$-3-Cl | 2-Cl-4-CN |
| B-2176 | 2-CF$_3$-3-Cl | 2-F-4-CN |
| B-2177 | 2-CF$_3$-3-F | —* |
| B-2178 | 2-CF$_3$-3-F | 2-Cl |
| B-2179 | 2-CF$_3$-3-F | 3-Cl |
| B-2180 | 2-CF$_3$-3-F | 4-Cl |
| B-2181 | 2-CF$_3$-3-F | 2-F |
| B-2182 | 2-CF$_3$-3-F | 3-F |
| B-2183 | 2-CF$_3$-3-F | 4-F |
| B-2184 | 2-CF$_3$-3-F | 2-CN |
| B-2185 | 2-CF$_3$-3-F | 3-CN |
| B-2186 | 2-CF$_3$-3-F | 4-CN |
| B-2187 | 2-CF$_3$-3-F | 2-NO$_2$ |
| B-2188 | 2-CF$_3$-3-F | 3-NO$_2$ |
| B-2189 | 2-CF$_3$-3-F | 4-NO$_2$ |
| B-2190 | 2-CF$_3$-3-F | 2-SCH$_3$ |
| B-2191 | 2-CF$_3$-3-F | 3-SCH$_3$ |
| B-2192 | 2-CF$_3$-3-F | 4-SCH$_3$ |
| B-2193 | 2-CF$_3$-3-F | 2-SOCH$_3$ |
| B-2194 | 2-CF$_3$-3-F | 3-SOCH$_3$ |
| B-2195 | 2-CF$_3$-3-F | 4-SOCH$_3$ |
| B-2196 | 2-CF$_3$-3-F | 2-SO$_2$CH$_3$ |
| B-2197 | 2-CF$_3$-3-F | 3-SO$_2$CH$_3$ |
| B-2198 | 2-CF$_3$-3-F | 4-SO$_2$CH$_3$ |
| B-2199 | 2-CF$_3$-3-F | 2-CO$_2$CH$_3$ |
| B-2200 | 2-CF$_3$-3-F | 3-CO$_2$CH$_3$ |
| B-2201 | 2-CF$_3$-3-F | 4-CO$_2$CH$_3$ |
| B-2202 | 2-CF$_3$-3-F | 2-CH$_3$ |
| B-2203 | 2-CF$_3$-3-F | 3-CH$_3$ |
| B-2204 | 2-CF$_3$-3-F | 4-CH$_3$ |
| B-2205 | 2-CF$_3$-3-F | 2-CF$_3$ |
| B-2206 | 2-CF$_3$-3-F | 3-CF$_3$ |
| B-2207 | 2-CF$_3$-3-F | 4-CF$_3$ |
| B-2208 | 2-CF$_3$-3-F | 2-CHF$_2$ |
| B-2209 | 2-CF$_3$-3-F | 3-CHF$_2$ |
| B-2210 | 2-CF$_3$-3-F | 4-CHF$_2$ |
| B-2211 | 2-CF$_3$-3-F | 2-OCH$_3$ |
| B-2212 | 2-CF$_3$-3-F | 3-OCH$_3$ |
| B-2213 | 2-CF$_3$-3-F | 4-OCH$_3$ |
| B-2214 | 2-CF$_3$-3-F | 2-OCF$_3$ |
| B-2215 | 2-CF$_3$-3-F | 3-OCF$_3$ |
| B-2216 | 2-CF$_3$-3-F | 4-OCF$_3$ |
| B-2217 | 2-CF$_3$-3-F | 2-OCHF$_2$ |
| B-2218 | 2-CF$_3$-3-F | 3-OCHF$_2$ |
| B-2219 | 2-CF$_3$-3-F | 4-OCHF$_2$ |
| B-2220 | 2-CF$_3$-3-F | 2,4,6-(CH$_3$)$_3$ |
| B-2221 | 2-CF$_3$-3-F | 2,3-Cl$_2$ |
| B-2222 | 2-CF$_3$-3-F | 2,4-Cl$_2$ |
| B-2223 | 2-CF$_3$-3-F | 2,5-Cl$_2$ |
| B-2224 | 2-CF$_3$-3-F | 3,4-Cl$_2$ |
| B-2225 | 2-CF$_3$-3-F | 3,5-Cl$_2$ |
| B-2226 | 2-CF$_3$-3-F | 2,6-Cl$_2$ |
| B-2227 | 2-CF$_3$-3-F | 2,3-F$_2$ |
| B-2228 | 2-CF$_3$-3-F | 2,4-F$_2$ |
| B-2229 | 2-CF$_3$-3-F | 2,5-F$_2$ |
| B-2230 | 2-CF$_3$-3-F | 3,4-F$_2$ |
| B-2231 | 2-CF$_3$-3-F | 3,5-F$_2$ |
| B-2232 | 2-CF$_3$-3-F | 2,6-F$_2$ |
| B-2233 | 2-CF$_3$-3-F | 2-CF$_3$-4-Cl |
| B-2234 | 2-CF$_3$-3-F | 2-CF$_3$-4-F |
| B-2235 | 2-CF$_3$-3-F | 2-Cl-4-CF$_3$ |
| B-2236 | 2-CF$_3$-3-F | 2-F-4-CF$_3$ |
| B-2237 | 2-CF$_3$-3-F | 2-CN-4-Cl |
| B-2238 | 2-CF$_3$-3-F | 2-CN-4-F |
| B-2239 | 2-CF$_3$-3-F | 2-Cl-4-CN |
| B-2240 | 2-CF$_3$-3-F | 2-F-4-CN |
| B-2241 | 3-CF$_3$-5-Cl | —* |
| B-2242 | 3-CF$_3$-5-Cl | 2-Cl |
| B-2243 | 3-CF$_3$-5-Cl | 3-Cl |
| B-2244 | 3-CF$_3$-5-Cl | 4-Cl |
| B-2245 | 3-CF$_3$-5-Cl | 2-F |
| B-2246 | 3-CF$_3$-5-Cl | 3-F |
| B-2247 | 3-CF$_3$-5-Cl | 4-F |
| B-2248 | 3-CF$_3$-5-Cl | 2-CN |
| B-2249 | 3-CF$_3$-5-Cl | 3-CN |
| B-2250 | 3-CF$_3$-5-Cl | 4-CN |
| B-2251 | 3-CF$_3$-5-Cl | 2-NO$_2$ |
| B-2252 | 3-CF$_3$-5-Cl | 3-NO$_2$ |
| B-2253 | 3-CF$_3$-5-Cl | 4-NO$_2$ |
| B-2254 | 3-CF$_3$-5-Cl | 2-SCH$_3$ |
| B-2255 | 3-CF$_3$-5-Cl | 3-SCH$_3$ |
| B-2256 | 3-CF$_3$-5-Cl | 4-SCH$_3$ |
| B-2257 | 3-CF$_3$-5-Cl | 2-SOCH$_3$ |
| B-2258 | 3-CF$_3$-5-Cl | 3-SOCH$_3$ |
| B-2259 | 3-CF$_3$-5-Cl | 4-SOCH$_3$ |
| B-2260 | 3-CF$_3$-5-Cl | 2-SO$_2$CH$_3$ |
| B-2261 | 3-CF$_3$-5-Cl | 3-SO$_2$CH$_3$ |
| B-2262 | 3-CF$_3$-5-Cl | 4-SO$_2$CH$_3$ |
| B-2263 | 3-CF$_3$-5-Cl | 2-CO$_2$CH$_3$ |
| B-2264 | 3-CF$_3$-5-Cl | 3-CO$_2$CH$_3$ |
| B-2265 | 3-CF$_3$-5-Cl | 4-CO$_2$CH$_3$ |
| B-2266 | 3-CF$_3$-5-Cl | 2-CH$_3$ |
| B-2267 | 3-CF$_3$-5-Cl | 3-CH$_3$ |
| B-2268 | 3-CF$_3$-5-Cl | 4-CH$_3$ |
| B-2269 | 3-CF$_3$-5-Cl | 2-CF$_3$ |
| B-2270 | 3-CF$_3$-5-Cl | 3-CF$_3$ |
| B-2271 | 3-CF$_3$-5-Cl | 4-CF$_3$ |
| B-2272 | 3-CF$_3$-5-Cl | 2-CHF$_2$ |
| B-2273 | 3-CF$_3$-5-Cl | 3-CHF$_2$ |
| B-2274 | 3-CF$_3$-5-Cl | 4-CHF$_2$ |
| B-2275 | 3-CF$_3$-5-Cl | 2-OCH$_3$ |
| B-2276 | 3-CF$_3$-5-Cl | 3-OCH$_3$ |
| B-2277 | 3-CF$_3$-5-Cl | 4-OCH$_3$ |
| B-2278 | 3-CF$_3$-5-Cl | 2-OCF$_3$ |
| B-2279 | 3-CF$_3$-5-Cl | 3-OCF$_3$ |
| B-2280 | 3-CF$_3$-5-Cl | 4-OCF$_3$ |
| B-2281 | 3-CF$_3$-5-Cl | 2-OCHF$_2$ |
| B-2282 | 3-CF$_3$-5-Cl | 3-OCHF$_2$ |
| B-2283 | 3-CF$_3$-5-Cl | 4-OCHF$_2$ |
| B-2284 | 3-CF$_3$-5-Cl | 2,4,6-(CH$_3$)$_3$ |
| B-2285 | 3-CF$_3$-5-Cl | 2,3-Cl$_2$ |
| B-2286 | 3-CF$_3$-5-Cl | 2,4-Cl$_2$ |
| B-2287 | 3-CF$_3$-5-Cl | 2,5-Cl$_2$ |
| B-2288 | 3-CF$_3$-5-Cl | 3,4-Cl$_2$ |
| B-2289 | 3-CF$_3$-5-Cl | 3,5-Cl$_2$ |
| B-2290 | 3-CF$_3$-5-Cl | 2,6-Cl$_2$ |
| B-2291 | 3-CF$_3$-5-Cl | 2,3-F$_2$ |
| B-2292 | 3-CF$_3$-5-Cl | 2,4-F$_2$ |
| B-2293 | 3-CF$_3$-5-Cl | 2,5-F$_2$ |

TABLE B-continued

For compounds where ZY is in para-position. The position(s) of the substituent(s) $(R^4)_n$ is/are given in relation to the attachment of the isoxazole-unit. The position(s) of the substituent(s) $(R^5)_m$ is/are given in relation to the attachment of the phenyl to the O-phenyl-unit.

| line | $(R^4)_n$ | $(R^5)_m$ |
|---|---|---|
| B-2294 | 3-CF$_3$-5-Cl | 3,4-F$_2$ |
| B-2295 | 3-CF$_3$-5-Cl | 3,5-F$_2$ |
| B-2296 | 3-CF$_3$-5-Cl | 2,6-F$_2$ |
| B-2297 | 3-CF$_3$-5-Cl | 2-CF$_3$-4-Cl |
| B-2298 | 3-CF$_3$-5-Cl | 2-CF$_3$-4-F |
| B-2299 | 3-CF$_3$-5-Cl | 2-Cl-4-CF$_3$ |
| B-2300 | 3-CF$_3$-5-Cl | 2-F-4-CF$_3$ |
| B-2301 | 3-CF$_3$-5-Cl | 2-CN-4-Cl |
| B-2302 | 3-CF$_3$-5-Cl | 2-CN-4-F |
| B-2303 | 3-CF$_3$-5-Cl | 2-Cl-4-CN |
| B-2304 | 3-CF$_3$-5-Cl | 2-F-4-CN |
| B-2305 | 3-CF$_3$-5-F | —* |
| B-2306 | 3-CF$_3$-5-F | 2-Cl |
| B-2307 | 3-CF$_3$-5-F | 3-Cl |
| B-2308 | 3-CF$_3$-5-F | 4-Cl |
| B-2309 | 3-CF$_3$-5-F | 2-F |
| B-2310 | 3-CF$_3$-5-F | 3-F |
| B-2311 | 3-CF$_3$-5-F | 4-F |
| B-2312 | 3-CF$_3$-5-F | 2-CN |
| B-2313 | 3-CF$_3$-5-F | 3-CN |
| B-2314 | 3-CF$_3$-5-F | 4-CN |
| B-2315 | 3-CF$_3$-5-F | 2-NO$_2$ |
| B-2316 | 3-CF$_3$-5-F | 3-NO$_2$ |
| B-2317 | 3-CF$_3$-5-F | 4-NO$_2$ |
| B-2318 | 3-CF$_3$-5-F | 2-SCH$_3$ |
| B-2319 | 3-CF$_3$-5-F | 3-SCH$_3$ |
| B-2320 | 3-CF$_3$-5-F | 4-SCH$_3$ |
| B-2321 | 3-CF$_3$-5-F | 2-SOCH$_3$ |
| B-2322 | 3-CF$_3$-5-F | 3-SOCH$_3$ |
| B-2323 | 3-CF$_3$-5-F | 4-SOCH$_3$ |
| B-2324 | 3-CF$_3$-5-F | 2-SO$_2$CH$_3$ |
| B-2325 | 3-CF$_3$-5-F | 3-SO$_2$CH$_3$ |
| B-2326 | 3-CF$_3$-5-F | 4-SO$_2$CH$_3$ |
| B-2327 | 3-CF$_3$-5-F | 2-CO$_2$CH$_3$ |
| B-2328 | 3-CF$_3$-5-F | 3-CO$_2$CH$_3$ |
| B-2329 | 3-CF$_3$-5-F | 4-CO$_2$CH$_3$ |
| B-2330 | 3-CF$_3$-5-F | 2-CH$_3$ |
| B-2331 | 3-CF$_3$-5-F | 3-CH$_3$ |
| B-2332 | 3-CF$_3$-5-F | 4-CH$_3$ |
| B-2333 | 3-CF$_3$-5-F | 2-CF$_3$ |
| B-2334 | 3-CF$_3$-5-F | 3-CF$_3$ |
| B-2335 | 3-CF$_3$-5-F | 4-CF$_3$ |
| B-2336 | 3-CF$_3$-5-F | 2-CHF$_2$ |
| B-2337 | 3-CF$_3$-5-F | 3-CHF$_2$ |
| B-2338 | 3-CF$_3$-5-F | 4-CHF$_2$ |
| B-2339 | 3-CF$_3$-5-F | 2-OCH$_3$ |
| B-2340 | 3-CF$_3$-5-F | 3-OCH$_3$ |
| B-2341 | 3-CF$_3$-5-F | 4-OCH$_3$ |
| B-2342 | 3-CF$_3$-5-F | 2-OCF$_3$ |
| B-2343 | 3-CF$_3$-5-F | 3-OCF$_3$ |
| B-2344 | 3-CF$_3$-5-F | 4-OCF$_3$ |
| B-2345 | 3-CF$_3$-5-F | 2-OCHF$_2$ |
| B-2346 | 3-CF$_3$-5-F | 3-OCHF$_2$ |
| B-2347 | 3-CF$_3$-5-F | 4-OCHF$_2$ |
| B-2348 | 3-CF$_3$-5-F | 2,4,6-(CH$_3$)$_3$ |
| B-2349 | 3-CF$_3$-5-F | 2,3-Cl$_2$ |
| B-2350 | 3-CF$_3$-5-F | 2,4-Cl$_2$ |
| B-2351 | 3-CF$_3$-5-F | 2,5-Cl$_2$ |
| B-2352 | 3-CF$_3$-5-F | 3,4-Cl$_2$ |
| B-2353 | 3-CF$_3$-5-F | 3,5-Cl$_2$ |
| B-2354 | 3-CF$_3$-5-F | 2,6-Cl$_2$ |
| B-2355 | 3-CF$_3$-5-F | 2,3-F$_2$ |
| B-2356 | 3-CF$_3$-5-F | 2,4-F$_2$ |
| B-2357 | 3-CF$_3$-5-F | 2,5-F$_2$ |
| B-2358 | 3-CF$_3$-5-F | 3,4-F$_2$ |
| B-2359 | 3-CF$_3$-5-F | 3,5-F$_2$ |
| B-2360 | 3-CF$_3$-5-F | 2,6-F$_2$ |
| B-2361 | 3-CF$_3$-5-F | 2-CF$_3$-4-Cl |
| B-2362 | 3-CF$_3$-5-F | 2-CF$_3$-4-F |
| B-2363 | 3-CF$_3$-5-F | 2-Cl-4-CF$_3$ |
| B-2364 | 3-CF$_3$-5-F | 2-F-4-CF$_3$ |
| B-2365 | 3-CF$_3$-5-F | 2-CN-4-Cl |
| B-2366 | 3-CF$_3$-5-F | 2-CN-4-F |
| B-2367 | 3-CF$_3$-5-F | 2-Cl-4-CN |
| B-2368 | 3-CF$_3$-5-F | 2-F-4-CN |
| B-2369 | 3-CF$_3$-6-F | —* |
| B-2370 | 3-CF$_3$-6-F | 2-Cl |
| B-2371 | 3-CF$_3$-6-F | 3-Cl |
| B-2372 | 3-CF$_3$-6-F | 4-Cl |
| B-2373 | 3-CF$_3$-6-F | 2-F |
| B-2374 | 3-CF$_3$-6-F | 3-F |
| B-2375 | 3-CF$_3$-6-F | 4-F |
| B-2376 | 3-CF$_3$-6-F | 2-CN |
| B-2377 | 3-CF$_3$-6-F | 3-CN |
| B-2378 | 3-CF$_3$-6-F | 4-CN |
| B-2379 | 3-CF$_3$-6-F | 2-NO$_2$ |
| B-2380 | 3-CF$_3$-6-F | 3-NO$_2$ |
| B-2381 | 3-CF$_3$-6-F | 4-NO$_2$ |
| B-2382 | 3-CF$_3$-6-F | 2-SCH$_3$ |
| B-2383 | 3-CF$_3$-6-F | 3-SCH$_3$ |
| B-2384 | 3-CF$_3$-6-F | 4-SCH$_3$ |
| B-2385 | 3-CF$_3$-6-F | 2-SOCH$_3$ |
| B-2386 | 3-CF$_3$-6-F | 3-SOCH$_3$ |
| B-2387 | 3-CF$_3$-6-F | 4-SOCH$_3$ |
| B-2388 | 3-CF$_3$-6-F | 2-SO$_2$CH$_3$ |
| B-2389 | 3-CF$_3$-6-F | 3-SO$_2$CH$_3$ |
| B-2390 | 3-CF$_3$-6-F | 4-SO$_2$CH$_3$ |
| B-2391 | 3-CF$_3$-6-F | 2-CO$_2$CH$_3$ |
| B-2392 | 3-CF$_3$-6-F | 3-CO$_2$CH$_3$ |
| B-2393 | 3-CF$_3$-6-F | 4-CO$_2$CH$_3$ |
| B-2394 | 3-CF$_3$-6-F | 2-CH$_3$ |
| B-2395 | 3-CF$_3$-6-F | 3-CH$_3$ |
| B-2396 | 3-CF$_3$-6-F | 4-CH$_3$ |
| B-2397 | 3-CF$_3$-6-F | 2-CF$_3$ |
| B-2398 | 3-CF$_3$-6-F | 3-CF$_3$ |
| B-2399 | 3-CF$_3$-6-F | 4-CF$_3$ |
| B-2400 | 3-CF$_3$-6-F | 2-CHF$_2$ |
| B-2401 | 3-CF$_3$-6-F | 3-CHF$_2$ |
| B-2402 | 3-CF$_3$-6-F | 4-CHF$_2$ |
| B-2403 | 3-CF$_3$-6-F | 2-OCH$_3$ |
| B-2404 | 3-CF$_3$-6-F | 3-OCH$_3$ |
| B-2405 | 3-CF$_3$-6-F | 4-OCH$_3$ |
| B-2406 | 3-CF$_3$-6-F | 2-OCF$_3$ |
| B-2407 | 3-CF$_3$-6-F | 3-OCF$_3$ |
| B-2408 | 3-CF$_3$-6-F | 4-OCF$_3$ |
| B-2409 | 3-CF$_3$-6-F | 2-OCHF$_2$ |
| B-2410 | 3-CF$_3$-6-F | 3-OCHF$_2$ |
| B-2411 | 3-CF$_3$-6-F | 4-OCHF$_2$ |
| B-2412 | 3-CF$_3$-6-F | 2,4,6-(CH$_3$)$_3$ |
| B-2413 | 3-CF$_3$-6-F | 2,3-Cl$_2$ |
| B-2414 | 3-CF$_3$-6-F | 2,4-Cl$_2$ |
| B-2415 | 3-CF$_3$-6-F | 2,5-Cl$_2$ |
| B-2416 | 3-CF$_3$-6-F | 3,4-Cl$_2$ |
| B-2417 | 3-CF$_3$-6-F | 3,5-Cl$_2$ |
| B-2418 | 3-CF$_3$-6-F | 2,6-Cl$_2$ |
| B-2419 | 3-CF$_3$-6-F | 2,3-F$_2$ |
| B-2420 | 3-CF$_3$-6-F | 2,4-F$_2$ |
| B-2421 | 3-CF$_3$-6-F | 2,5-F$_2$ |
| B-2422 | 3-CF$_3$-6-F | 3,4-F$_2$ |
| B-2423 | 3-CF$_3$-6-F | 3,5-F$_2$ |
| B-2424 | 3-CF$_3$-6-F | 2,6-F$_2$ |
| B-2425 | 3-CF$_3$-6-F | 2-CF$_3$-4-Cl |
| B-2426 | 3-CF$_3$-6-F | 2-CF$_3$-4-F |
| B-2427 | 3-CF$_3$-6-F | 2-Cl-4-CF$_3$ |
| B-2428 | 3-CF$_3$-6-F | 2-F-4-CF$_3$ |
| B-2429 | 3-CF$_3$-6-F | 2-CN-4-Cl |
| B-2430 | 3-CF$_3$-6-F | 2-CN-4-F |
| B-2431 | 3-CF$_3$-6-F | 2-Cl-4-CN |
| B-2432 | 3-CF$_3$-6-F | 2-F-4-CN |
| B-2433 | 3-CF$_3$-6-Cl | —* |
| B-2434 | 3-CF$_3$-6-Cl | 2-Cl |
| B-2435 | 3-CF$_3$-6-Cl | 3-Cl |
| B-2436 | 3-CF$_3$-6-Cl | 4-Cl |
| B-2437 | 3-CF$_3$-6-Cl | 2-F |
| B-2438 | 3-CF$_3$-6-Cl | 3-F |
| B-2439 | 3-CF$_3$-6-Cl | 4-F |

TABLE B-continued

For compounds where ZY is in para-position. The position(s) of the substituent(s) $(R^4)_n$ is/are given in relation to the attachment of the isoxazole-unit. The position(s) of the substituent(s) $(R^5)_m$ is/are given in relation to the attachment of the phenyl to the O-phenyl-unit.

| line | $(R^4)_n$ | $(R^5)_m$ |
|---|---|---|
| B-2440 | 3-CF$_3$-6-Cl | 2-CN |
| B-2441 | 3-CF$_3$-6-Cl | 3-CN |
| B-2442 | 3-CF$_3$-6-Cl | 4-CN |
| B-2443 | 3-CF$_3$-6-Cl | 2-NO$_2$ |
| B-2444 | 3-CF$_3$-6-Cl | 3-NO$_2$ |
| B-2445 | 3-CF$_3$-6-Cl | 4-NO$_2$ |
| B-2446 | 3-CF$_3$-6-Cl | 2-SCH$_3$ |
| B-2447 | 3-CF$_3$-6-Cl | 3-SCH$_3$ |
| B-2448 | 3-CF$_3$-6-Cl | 4-SCH$_3$ |
| B-2449 | 3-CF$_3$-6-Cl | 2-SOCH$_3$ |
| B-2450 | 3-CF$_3$-6-Cl | 3-SOCH$_3$ |
| B-2451 | 3-CF$_3$-6-Cl | 4-SOCH$_3$ |
| B-2452 | 3-CF$_3$-6-Cl | 2-SO$_2$CH$_3$ |
| B-2453 | 3-CF$_3$-6-Cl | 3-SO$_2$CH$_3$ |
| B-2454 | 3-CF$_3$-6-Cl | 4-SO$_2$CH$_3$ |
| B-2455 | 3-CF$_3$-6-Cl | 2-CO$_2$CH$_3$ |
| B-2456 | 3-CF$_3$-6-Cl | 3-CO$_2$CH$_3$ |
| B-2457 | 3-CF$_3$-6-Cl | 4-CO$_2$CH$_3$ |
| B-2458 | 3-CF$_3$-6-Cl | 2-CH$_3$ |
| B-2459 | 3-CF$_3$-6-Cl | 3-CH$_3$ |
| B-2460 | 3-CF$_3$-6-Cl | 4-CH$_3$ |
| B-2461 | 3-CF$_3$-6-Cl | 2-CF$_3$ |
| B-2462 | 3-CF$_3$-6-Cl | 3-CF$_3$ |
| B-2463 | 3-CF$_3$-6-Cl | 4-CF$_3$ |
| B-2464 | 3-CF$_3$-6-Cl | 2-CHF$_2$ |
| B-2465 | 3-CF$_3$-6-Cl | 3-CHF$_2$ |
| B-2466 | 3-CF$_3$-6-Cl | 4-CHF$_2$ |
| B-2467 | 3-CF$_3$-6-Cl | 2-OCH$_3$ |
| B-2468 | 3-CF$_3$-6-Cl | 3-OCH$_3$ |
| B-2469 | 3-CF$_3$-6-Cl | 4-OCH$_3$ |
| B-2470 | 3-CF$_3$-6-Cl | 2-OCF$_3$ |
| B-2471 | 3-CF$_3$-6-Cl | 3-OCF$_3$ |
| B-2472 | 3-CF$_3$-6-Cl | 4-OCF$_3$ |
| B-2473 | 3-CF$_3$-6-Cl | 2-OCHF$_2$ |
| B-2474 | 3-CF$_3$-6-Cl | 3-OCHF$_2$ |
| B-2475 | 3-CF$_3$-6-Cl | 4-OCHF$_2$ |
| B-2476 | 3-CF$_3$-6-Cl | 2,4,6-(CH$_3$)$_3$ |
| B-2477 | 3-CF$_3$-6-Cl | 2,3-Cl$_2$ |
| B-2478 | 3-CF$_3$-6-Cl | 2,4-Cl$_2$ |
| B-2479 | 3-CF$_3$-6-Cl | 2,5-Cl$_2$ |
| B-2480 | 3-CF$_3$-6-Cl | 3,4-Cl$_2$ |
| B-2481 | 3-CF$_3$-6-Cl | 3,5-Cl$_2$ |
| B-2482 | 3-CF$_3$-6-Cl | 2,6-Cl$_2$ |
| B-2483 | 3-CF$_3$-6-Cl | 2,3-F$_2$ |
| B-2484 | 3-CF$_3$-6-Cl | 2,4-F$_2$ |
| B-2485 | 3-CF$_3$-6-Cl | 2,5-F$_2$ |
| B-2486 | 3-CF$_3$-6-Cl | 3,4-F$_2$ |
| B-2487 | 3-CF$_3$-6-Cl | 3,5-F$_2$ |
| B-2488 | 3-CF$_3$-6-Cl | 2,6-F$_2$ |
| B-2489 | 3-CF$_3$-6-Cl | 2-CF$_3$-4-Cl |
| B-2490 | 3-CF$_3$-6-Cl | 2-CF$_3$-4-F |
| B-2491 | 3-CF$_3$-6-Cl | 2-Cl-4-CF$_3$ |
| B-2492 | 3-CF$_3$-6-Cl | 2-F-4-CF$_3$ |
| B-2493 | 3-CF$_3$-6-Cl | 2-CN-4-Cl |
| B-2494 | 3-CF$_3$-6-Cl | 2-CN-4-F |
| B-2495 | 3-CF$_3$-6-Cl | 2-Cl-4-CN |
| B-2496 | 3-CF$_3$-6-Cl | 2-F-4-CN |

*means that m = 0

TABLE B1

For compounds where ZY is in meta-position. The position(s) of the substituent(s) $(R^4)_n$ is/are given in relation to the attachment of the isoxazole-unit. The position(s) of the substituent(s) $(R^5)_m$ is/are given in relation to the attachment of the phenyl to the O-phenyl-unit.

| line | $(R^4)_n$ | $(R^5)_m$ |
|---|---|---|
| B1-1 | —* | —* |
| B1-2 | —* | 2-Cl |
| B1-3 | —* | 3-Cl |
| B1-4 | —* | 4-Cl |
| B1-5 | —* | 2-F |
| B1-6 | —* | 3-F |
| B1-7 | —* | 4-F |
| B1-8 | —* | 2-CN |
| B1-9 | —* | 3-CN |
| B1-10 | —* | 4-CN |
| B1-11 | —* | 2-NO$_2$ |
| B1-12 | —* | 3-NO$_2$ |
| B1-13 | —* | 4-NO$_2$ |
| B1-14 | —* | 2-SCH$_3$ |
| B1-15 | —* | 3-SCH$_3$ |
| B1-16 | —* | 4-SCH$_3$ |
| B1-17 | —* | 2-SOCH$_3$ |
| B1-18 | —* | 3-SOCH$_3$ |
| B1-19 | —* | 4-SOCH$_3$ |
| B1-20 | —* | 2-SO$_2$CH$_3$ |
| B1-21 | —* | 3-SO$_2$CH$_3$ |
| B1-22 | —* | 4-SO$_2$CH$_3$ |
| B1-23 | —* | 2-CO$_2$CH$_3$ |
| B1-24 | —* | 3-CO$_2$CH$_3$ |
| B1-25 | —* | 4-CO$_2$CH$_3$ |
| B1-26 | —* | 2-CH$_3$ |
| B1-27 | —* | 3-CH$_3$ |
| B1-28 | —* | 4-CH$_3$ |
| B1-29 | —* | 2-CF$_3$ |
| B1-30 | —* | 3-CF$_3$ |
| B1-31 | —* | 4-CF$_3$ |
| B1-32 | —* | 2-CHF$_2$ |
| B1-33 | —* | 3-CHF$_2$ |
| B1-34 | —* | 4-CHF$_2$ |
| B1-35 | —* | 2-OCH$_3$ |
| B1-36 | —* | 3-OCH$_3$ |
| B1-37 | —* | 4-OCH$_3$ |
| B1-38 | —* | 2-OCF$_3$ |
| B1-39 | —* | 3-OCF$_3$ |
| B1-40 | —* | 4-OCF$_3$ |
| B1-41 | —* | 2-OCHF$_2$ |
| B1-42 | —* | 3-OCHF$_2$ |
| B1-43 | —* | 4-OCHF$_2$ |
| B1-44 | —* | 2,4,6-(CH$_3$)$_3$ |
| B1-45 | —* | 2,3-Cl$_2$ |
| B1-46 | —* | 2,4-Cl$_2$ |
| B1-47 | —* | 2,5-Cl$_2$ |
| B1-48 | —* | 3,4-Cl$_2$ |
| B1-49 | —* | 3,5-Cl$_2$ |
| B1-50 | —* | 2,6-Cl$_2$ |
| B1-51 | —* | 2,3-F$_2$ |
| B1-52 | —* | 2,4-F$_2$ |
| B1-53 | —* | 2,5-F$_2$ |
| B1-54 | —* | 3,4-F$_2$ |
| B1-55 | —* | 3,5-F$_2$ |
| B1-56 | —* | 2,6-F$_2$ |
| B1-57 | —* | 2-CF$_3$-4-Cl |
| B1-58 | —* | 2-CF$_3$-4-F |
| B1-59 | —* | 2-Cl-4-CF$_3$ |
| B1-60 | —* | 2-F-4-CF$_3$ |
| B1-61 | —* | 2-CN-4-Cl |
| B1-62 | —* | 2-CN-4-F |
| B1-63 | —* | 2-Cl-4-CN |
| B1-64 | —* | 2-F-4-CN |
| B1-65 | 2-Cl | —* |
| B1-66 | 2-Cl | 2-Cl |
| B1-67 | 2-Cl | 3-Cl |
| B1-68 | 2-Cl | 4-Cl |
| B1-69 | 2-Cl | 2-F |
| B1-70 | 2-Cl | 3-F |
| B1-71 | 2-Cl | 4-F |
| B1-72 | 2-Cl | 2-CN |

TABLE B1-continued

For compounds where ZY is in meta-position. The position(s) of the substituent(s) $(R^4)_n$ is/are given in relation to the attachment of the isoxazole-unit. The position(s) of the substituent(s) $(R^5)_m$ is/are given in relation to the attachment of the phenyl to the O-phenyl-unit.

| line | $(R^4)_n$ | $(R^5)_m$ |
|---|---|---|
| B1-73 | 2-Cl | 3-CN |
| B1-74 | 2-Cl | 4-CN |
| B1-75 | 2-Cl | 2-NO$_2$ |
| B1-76 | 2-Cl | 3-NO$_2$ |
| B1-77 | 2-Cl | 4-NO$_2$ |
| B1-78 | 2-Cl | 2-SCH$_3$ |
| B1-79 | 2-Cl | 3-SCH$_3$ |
| B1-80 | 2-Cl | 4-SCH$_3$ |
| B1-81 | 2-Cl | 2-SOCH$_3$ |
| B1-82 | 2-Cl | 3-SOCH$_3$ |
| B1-83 | 2-Cl | 4-SOCH$_3$ |
| B1-84 | 2-Cl | 2-SO$_2$CH$_3$ |
| B1-85 | 2-Cl | 3-SO$_2$CH$_3$ |
| B1-86 | 2-Cl | 4-SO$_2$CH$_3$ |
| B1-87 | 2-Cl | 2-CO$_2$CH$_3$ |
| B1-88 | 2-Cl | 3-CO$_2$CH$_3$ |
| B1-89 | 2-Cl | 4-CO$_2$CH$_3$ |
| B1-90 | 2-Cl | 2-CH$_3$ |
| B1-91 | 2-Cl | 3-CH$_3$ |
| B1-92 | 2-Cl | 4-CH$_3$ |
| B1-93 | 2-Cl | 2-CF$_3$ |
| B1-94 | 2-Cl | 3-CF$_3$ |
| B1-95 | 2-Cl | 4-CF$_3$ |
| B1-96 | 2-Cl | 2-CHF$_2$ |
| B1-97 | 2-Cl | 3-CHF$_2$ |
| B1-98 | 2-Cl | 4-CHF$_2$ |
| B1-99 | 2-Cl | 2-OCH$_3$ |
| B1-100 | 2-Cl | 3-OCH$_3$ |
| B1-101 | 2-Cl | 4-OCH$_3$ |
| B1-102 | 2-Cl | 2-OCF$_3$ |
| B1-103 | 2-Cl | 3-OCF$_3$ |
| B1-104 | 2-Cl | 4-OCF$_3$ |
| B1-105 | 2-Cl | 2-OCHF$_2$ |
| B1-106 | 2-Cl | 3-OCHF$_2$ |
| B1-107 | 2-Cl | 4-OCHF$_2$ |
| B1-108 | 2-Cl | 2,4,6-(CH$_3$)$_3$ |
| B1-109 | 2-Cl | 2,3-Cl$_2$ |
| B1-110 | 2-Cl | 2,4-Cl$_2$ |
| B1-111 | 2-Cl | 2,5-Cl$_2$ |
| B1-112 | 2-Cl | 3,4-Cl$_2$ |
| B1-113 | 2-Cl | 3,5-Cl$_2$ |
| B1-114 | 2-Cl | 2,6-Cl$_2$ |
| B1-115 | 2-Cl | 2,3-F$_2$ |
| B1-116 | 2-Cl | 2,4-F$_2$ |
| B1-117 | 2-Cl | 2,5-F$_2$ |
| B1-118 | 2-Cl | 3,4-F$_2$ |
| B1-119 | 2-Cl | 3,5-F$_2$ |
| B1-120 | 2-Cl | 2,6-F$_2$ |
| B1-121 | 2-Cl | 2-CF$_3$-4-Cl |
| B1-122 | 2-Cl | 2-CF$_3$-4-F |
| B1-123 | 2-Cl | 2-Cl-4-CF$_3$ |
| B1-124 | 2-Cl | 2-F-4-CF$_3$ |
| B1-125 | 2-Cl | 2-CN-4-Cl |
| B1-126 | 2-Cl | 2-CN-4-F |
| B1-127 | 2-Cl | 2-Cl-4-CN |
| B1-128 | 2-Cl | 2-F-4-CN |
| B1-129 | 4-Cl | —* |
| B1-130 | 4-Cl | 2-Cl |
| B1-131 | 4-Cl | 3-Cl |
| B1-132 | 4-Cl | 4-Cl |
| B1-133 | 4-Cl | 2-F |
| B1-134 | 4-Cl | 3-F |
| B1-135 | 4-Cl | 4-F |
| B1-136 | 4-Cl | 2-CN |
| B1-137 | 4-Cl | 3-CN |
| B1-138 | 4-Cl | 4-CN |
| B1-139 | 4-Cl | 2-NO$_2$ |
| B1-140 | 4-Cl | 3-NO$_2$ |
| B1-141 | 4-Cl | 4-NO$_2$ |
| B1-142 | 4-Cl | 2-SCH$_3$ |
| B1-143 | 4-Cl | 3-SCH$_3$ |
| B1-144 | 4-Cl | 4-SCH$_3$ |
| B1-145 | 4-Cl | 2-SOCH$_3$ |
| B1-146 | 4-Cl | 3-SOCH$_3$ |
| B1-147 | 4-Cl | 4-SOCH$_3$ |
| B1-148 | 4-Cl | 2-SO$_2$CH$_3$ |
| B1-149 | 4-Cl | 3-SO$_2$CH$_3$ |
| B1-150 | 4-Cl | 4-SO$_2$CH$_3$ |
| B1-151 | 4-Cl | 2-CO$_2$CH$_3$ |
| B1-152 | 4-Cl | 3-CO$_2$CH$_3$ |
| B1-153 | 4-Cl | 4-CO$_2$CH$_3$ |
| B1-154 | 4-Cl | 2-CH$_3$ |
| B1-155 | 4-Cl | 3-CH$_3$ |
| B1-156 | 4-Cl | 4-CH$_3$ |
| B1-157 | 4-Cl | 2-CF$_3$ |
| B1-158 | 4-Cl | 3-CF$_3$ |
| B1-159 | 4-Cl | 4-CF$_3$ |
| B1-160 | 4-Cl | 2-CHF$_2$ |
| B1-161 | 4-Cl | 3-CHF$_2$ |
| B1-162 | 4-Cl | 4-CHF$_2$ |
| B1-163 | 4-Cl | 2-OCH$_3$ |
| B1-164 | 4-Cl | 3-OCH$_3$ |
| B1-165 | 4-Cl | 4-OCH$_3$ |
| B1-166 | 4-Cl | 2-OCF$_3$ |
| B1-167 | 4-Cl | 3-OCF$_3$ |
| B1-168 | 4-Cl | 4-OCF$_3$ |
| B1-169 | 4-Cl | 2-OCHF$_2$ |
| B1-170 | 4-Cl | 3-OCHF$_2$ |
| B1-171 | 4-Cl | 4-OCHF$_2$ |
| B1-172 | 4-Cl | 2,4,6-(CH$_3$)$_3$ |
| B1-173 | 4-Cl | 2,3-Cl$_2$ |
| B1-174 | 4-Cl | 2,4-Cl$_2$ |
| B1-175 | 4-Cl | 2,5-Cl$_2$ |
| B1-176 | 4-Cl | 3,4-Cl$_2$ |
| B1-177 | 4-Cl | 3,5-Cl$_2$ |
| B1-178 | 4-Cl | 2,6-Cl$_2$ |
| B1-179 | 4-Cl | 2,3-F$_2$ |
| B1-180 | 4-Cl | 2,4-F$_2$ |
| B1-181 | 4-Cl | 2,5-F$_2$ |
| B1-182 | 4-Cl | 3,4-F$_2$ |
| B1-183 | 4-Cl | 3,5-F$_2$ |
| B1-184 | 4-Cl | 2,6-F$_2$ |
| B1-185 | 4-Cl | 2-CF$_3$-4-Cl |
| B1-186 | 4-Cl | 2-CF$_3$-4-F |
| B1-187 | 4-Cl | 2-Cl-4-CF$_3$ |
| B1-188 | 4-Cl | 2-F-4-CF$_3$ |
| B1-189 | 4-Cl | 2-CN-4-Cl |
| B1-190 | 4-Cl | 2-CN-4-F |
| B1-191 | 4-Cl | 2-Cl-4-CN |
| B1-192 | 4-Cl | 2-F-4-CN |
| B1-193 | 5-Cl | —* |
| B1-194 | 5-Cl | 2-Cl |
| B1-195 | 5-Cl | 3-Cl |
| B1-196 | 5-Cl | 4-Cl |
| B1-197 | 5-Cl | 2-F |
| B1-198 | 5-Cl | 3-F |
| B1-199 | 5-Cl | 4-F |
| B1-200 | 5-Cl | 2-CN |
| B1-201 | 5-Cl | 3-CN |
| B1-202 | 5-Cl | 4-CN |
| B1-203 | 5-Cl | 2-NO$_2$ |
| B1-204 | 5-Cl | 3-NO$_2$ |
| B1-205 | 5-Cl | 4-NO$_2$ |
| B1-206 | 5-Cl | 2-SCH$_3$ |
| B1-207 | 5-Cl | 3-SCH$_3$ |
| B1-208 | 5-Cl | 4-SCH$_3$ |
| B1-209 | 5-Cl | 2-SOCH$_3$ |
| B1-210 | 5-Cl | 3-SOCH$_3$ |
| B1-211 | 5-Cl | 4-SOCH$_3$ |
| B1-212 | 5-Cl | 2-SO$_2$CH$_3$ |
| B1-213 | 5-Cl | 3-SO$_2$CH$_3$ |
| B1-214 | 5-Cl | 4-SO$_2$CH$_3$ |
| B1-215 | 5-Cl | 2-CO$_2$CH$_3$ |
| B1-216 | 5-Cl | 3-CO$_2$CH$_3$ |

TABLE B1-continued

For compounds where ZY is in meta-position. The position(s) of the substituent(s) $(R^4)_n$ is/are given in relation to the attachment of the isoxazole-unit. The position(s) of the substituent(s) $(R^5)_m$ is/are given in relation to the attachment of the phenyl to the O-phenyl-unit.

| line | $(R^4)_n$ | $(R^5)_m$ |
|---|---|---|
| B1-217 | 5-Cl | 4-CO$_2$CH$_3$ |
| B1-218 | 5-Cl | 2-CH$_3$ |
| B1-219 | 5-Cl | 3-CH$_3$ |
| B1-220 | 5-Cl | 4-CH$_3$ |
| B1-221 | 5-Cl | 2-CF$_3$ |
| B1-222 | 5-Cl | 3-CF$_3$ |
| B1-223 | 5-Cl | 4-CF$_3$ |
| B1-224 | 5-Cl | 2-CHF$_2$ |
| B1-225 | 5-Cl | 3-CHF$_2$ |
| B1-226 | 5-Cl | 4-CHF$_2$ |
| B1-227 | 5-Cl | 2-OCH$_3$ |
| B1-228 | 5-Cl | 3-OCH$_3$ |
| B1-229 | 5-Cl | 4-OCH$_3$ |
| B1-230 | 5-Cl | 2-OCF$_3$ |
| B1-231 | 5-Cl | 3-OCF$_3$ |
| B1-232 | 5-Cl | 4-OCF$_3$ |
| B1-233 | 5-Cl | 2-OCHF$_2$ |
| B1-234 | 5-Cl | 3-OCHF$_2$ |
| B1-235 | 5-Cl | 4-OCHF$_2$ |
| B1-236 | 5-Cl | 2,4,6-(CH$_3$)$_3$ |
| B1-237 | 5-Cl | 2,3-Cl$_2$ |
| B1-238 | 5-Cl | 2,4-Cl$_2$ |
| B1-239 | 5-Cl | 2,5-Cl$_2$ |
| B1-240 | 5-Cl | 3,4-Cl$_2$ |
| B1-241 | 5-Cl | 3,5-Cl$_2$ |
| B1-242 | 5-Cl | 2,6-Cl$_2$ |
| B1-243 | 5-Cl | 2,3-F$_2$ |
| B1-244 | 5-Cl | 2,4-F$_2$ |
| B1-245 | 5-Cl | 2,5-F$_2$ |
| B1-246 | 5-Cl | 3,4-F$_2$ |
| B1-247 | 5-Cl | 3,5-F$_2$ |
| B1-248 | 5-Cl | 2,6-F$_2$ |
| B1-249 | 5-Cl | 2-CF$_3$-4-Cl |
| B1-250 | 5-Cl | 2-CF$_3$-4-F |
| B1-251 | 5-Cl | 2-Cl-4-CF$_3$ |
| B1-252 | 5-Cl | 2-F-4-CF$_3$ |
| B1-253 | 5-Cl | 2-CN-4-Cl |
| B1-254 | 5-Cl | 2-CN-4-F |
| B1-255 | 5-Cl | 2-Cl-4-CN |
| B1-256 | 5-Cl | 2-F-4-CN |
| B1-257 | 6-Cl | —* |
| B1-258 | 6-Cl | 2-Cl |
| B1-259 | 6-Cl | 3-Cl |
| B1-260 | 6-Cl | 4-Cl |
| B1-261 | 6-Cl | 2-F |
| B1-262 | 6-Cl | 3-F |
| B1-263 | 6-Cl | 4-F |
| B1-264 | 6-Cl | 2-CN |
| B1-265 | 6-Cl | 3-CN |
| B1-266 | 6-Cl | 4-CN |
| B1-267 | 6-Cl | 2-NO$_2$ |
| B1-268 | 6-Cl | 3-NO$_2$ |
| B1-269 | 6-Cl | 4-NO$_2$ |
| B1-270 | 6-Cl | 2-SCH$_3$ |
| B1-271 | 6-Cl | 3-SCH$_3$ |
| B1-272 | 6-Cl | 4-SCH$_3$ |
| B1-273 | 6-Cl | 2-SOCH$_3$ |
| B1-274 | 6-Cl | 3-SOCH$_3$ |
| B1-275 | 6-Cl | 4-SOCH$_3$ |
| B1-276 | 6-Cl | 2-SO$_2$CH$_3$ |
| B1-277 | 6-Cl | 3-SO$_2$CH$_3$ |
| B1-278 | 6-Cl | 4-SO$_2$CH$_3$ |
| B1-279 | 6-Cl | 2-CO$_2$CH$_3$ |
| B1-280 | 6-Cl | 3-CO$_2$CH$_3$ |
| B1-281 | 6-Cl | 4-CO$_2$CH$_3$ |
| B1-282 | 6-Cl | 2-CH$_3$ |
| B1-283 | 6-Cl | 3-CH$_3$ |
| B1-284 | 6-Cl | 4-CH$_3$ |
| B1-285 | 6-Cl | 2-CF$_3$ |
| B1-286 | 6-Cl | 3-CF$_3$ |
| B1-287 | 6-Cl | 4-CF$_3$ |
| B1-288 | 6-Cl | 2-CHF$_2$ |
| B1-289 | 6-Cl | 3-CHF$_2$ |
| B1-290 | 6-Cl | 4-CHF$_2$ |
| B1-291 | 6-Cl | 2-OCH$_3$ |
| B1-292 | 6-Cl | 3-OCH$_3$ |
| B1-293 | 6-Cl | 4-OCH$_3$ |
| B1-294 | 6-Cl | 2-OCF$_3$ |
| B1-295 | 6-Cl | 3-OCF$_3$ |
| B1-296 | 6-Cl | 4-OCF$_3$ |
| B1-297 | 6-Cl | 2-OCHF$_2$ |
| B1-298 | 6-Cl | 3-OCHF$_2$ |
| B1-299 | 6-Cl | 4-OCHF$_2$ |
| B1-300 | 6-Cl | 2,4,6-(CH$_3$)$_3$ |
| B1-301 | 6-Cl | 2,3-Cl$_2$ |
| B1-302 | 6-Cl | 2,4-Cl$_2$ |
| B1-303 | 6-Cl | 2,5-Cl$_2$ |
| B1-304 | 6-Cl | 3,4-Cl$_2$ |
| B1-305 | 6-Cl | 3,5-Cl$_2$ |
| B1-306 | 6-Cl | 2,6-Cl$_2$ |
| B1-307 | 6-Cl | 2,3-F$_2$ |
| B1-308 | 6-Cl | 2,4-F$_2$ |
| B1-309 | 6-Cl | 2,5-F$_2$ |
| B1-310 | 6-Cl | 3,4-F$_2$ |
| B1-311 | 6-Cl | 3,5-F$_2$ |
| B1-312 | 6-Cl | 2,6-F$_2$ |
| B1-313 | 6-Cl | 2-CF$_3$-4-Cl |
| B1-314 | 6-Cl | 2-CF$_3$-4-F |
| B1-315 | 6-Cl | 2-Cl-4-CF$_3$ |
| B1-316 | 6-Cl | 2-F-4-CF$_3$ |
| B1-317 | 6-Cl | 2-CN-4-Cl |
| B1-318 | 6-Cl | 2-CN-4-F |
| B1-319 | 6-Cl | 2-Cl-4-CN |
| B1-320 | 6-Cl | 2-F-4-CN |
| B1-321 | 2-F | —* |
| B1-322 | 2-F | 2-Cl |
| B1-323 | 2-F | 3-Cl |
| B1-324 | 2-F | 4-Cl |
| B1-325 | 2-F | 2-F |
| B1-326 | 2-F | 3-F |
| B1-327 | 2-F | 4-F |
| B1-328 | 2-F | 2-CN |
| B1-329 | 2-F | 3-CN |
| B1-330 | 2-F | 4-CN |
| B1-331 | 2-F | 2-NO$_2$ |
| B1-332 | 2-F | 3-NO$_2$ |
| B1-333 | 2-F | 4-NO$_2$ |
| B1-334 | 2-F | 2-SCH$_3$ |
| B1-335 | 2-F | 3-SCH$_3$ |
| B1-336 | 2-F | 4-SCH$_3$ |
| B1-337 | 2-F | 2-SOCH$_3$ |
| B1-338 | 2-F | 3-SOCH$_3$ |
| B1-339 | 2-F | 4-SOCH$_3$ |
| B1-340 | 2-F | 2-SO$_2$CH$_3$ |
| B1-341 | 2-F | 3-SO$_2$CH$_3$ |
| B1-342 | 2-F | 4-SO$_2$CH$_3$ |
| B1-343 | 2-F | 2-CO$_2$CH$_3$ |
| B1-344 | 2-F | 3-CO$_2$CH$_3$ |
| B1-345 | 2-F | 4-CO$_2$CH$_3$ |
| B1-346 | 2-F | 2-CH$_3$ |
| B1-347 | 2-F | 3-CH$_3$ |
| B1-348 | 2-F | 4-CH$_3$ |
| B1-349 | 2-F | 2-CF$_3$ |
| B1-350 | 2-F | 3-CF$_3$ |
| B1-351 | 2-F | 4-CF$_3$ |
| B1-352 | 2-F | 2-CHF$_2$ |
| B1-353 | 2-F | 3-CHF$_2$ |
| B1-354 | 2-F | 4-CHF$_2$ |
| B1-355 | 2-F | 2-OCH$_3$ |
| B1-356 | 2-F | 3-OCH$_3$ |
| B1-357 | 2-F | 4-OCH$_3$ |
| B1-358 | 2-F | 2-OCF$_3$ |
| B1-359 | 2-F | 3-OCF$_3$ |
| B1-360 | 2-F | 4-OCF$_3$ |

TABLE B1-continued

For compounds where ZY is in meta-position. The position(s) of the substituent(s) $(R^4)_n$ is/are given in relation to the attachment of the isoxazole-unit. The position(s) of the substituent(s) $(R^5)_m$ is/are given in relation to the attachment of the phenyl to the O-phenyl-unit.

| line | $(R^4)_n$ | $(R^5)_m$ |
|---|---|---|
| B1-361 | 2-F | 2-OCHF$_2$ |
| B1-362 | 2-F | 3-OCHF$_2$ |
| B1-363 | 2-F | 4-OCHF$_2$ |
| B1-364 | 2-F | 2,4,6-(CH$_3$)$_3$ |
| B1-365 | 2-F | 2,3-Cl$_2$ |
| B1-366 | 2-F | 2,4-Cl$_2$ |
| B1-367 | 2-F | 2,5-Cl$_2$ |
| B1-368 | 2-F | 3,4-Cl$_2$ |
| B1-369 | 2-F | 3,5-Cl$_2$ |
| B1-370 | 2-F | 2,6-Cl$_2$ |
| B1-371 | 2-F | 2,3-F$_2$ |
| B1-372 | 2-F | 2,4-F$_2$ |
| B1-373 | 2-F | 2,5-F$_2$ |
| B1-374 | 2-F | 3,4-F$_2$ |
| B1-375 | 2-F | 3,5-F$_2$ |
| B1-376 | 2-F | 2,6-F$_2$ |
| B1-377 | 2-F | 2-CF$_3$-4-Cl |
| B1-378 | 2-F | 2-CF$_3$-4-F |
| B1-379 | 2-F | 2-Cl-4-CF$_3$ |
| B1-380 | 2-F | 2-F-4-CF$_3$ |
| B1-381 | 2-F | 2-CN-4-Cl |
| B1-382 | 2-F | 2-CN-4-F |
| B1-383 | 2-F | 2-Cl-4-CN |
| B1-384 | 2-F | 2-F-4-CN |
| B1-385 | 4-F | —* |
| B1-386 | 4-F | 2-Cl |
| B1-387 | 4-F | 3-Cl |
| B1-388 | 4-F | 4-Cl |
| B1-389 | 4-F | 2-F |
| B1-390 | 4-F | 3-F |
| B1-391 | 4-F | 4-F |
| B1-392 | 4-F | 2-CN |
| B1-393 | 4-F | 3-CN |
| B1-394 | 4-F | 4-CN |
| B1-395 | 4-F | 2-NO$_2$ |
| B1-396 | 4-F | 3-NO$_2$ |
| B1-397 | 4-F | 4-NO$_2$ |
| B1-398 | 4-F | 2-SCH$_3$ |
| B1-399 | 4-F | 3-SCH$_3$ |
| B1-400 | 4-F | 4-SCH$_3$ |
| B1-401 | 4-F | 2-SOCH$_3$ |
| B1-402 | 4-F | 3-SOCH$_3$ |
| B1-403 | 4-F | 4-SOCH$_3$ |
| B1-404 | 4-F | 2-SO$_2$CH$_3$ |
| B1-405 | 4-F | 3-SO$_2$CH$_3$ |
| B1-406 | 4-F | 4-SO$_2$CH$_3$ |
| B1-407 | 4-F | 2-CO$_2$CH$_3$ |
| B1-408 | 4-F | 3-CO$_2$CH$_3$ |
| B1-409 | 4-F | 4-CO$_2$CH$_3$ |
| B1-410 | 4-F | 2-CH$_3$ |
| B1-411 | 4-F | 3-CH$_3$ |
| B1-412 | 4-F | 4-CH$_3$ |
| B1-413 | 4-F | 2-CF$_3$ |
| B1-414 | 4-F | 3-CF$_3$ |
| B1-415 | 4-F | 4-CF$_3$ |
| B1-416 | 4-F | 2-CHF$_2$ |
| B1-417 | 4-F | 3-CHF$_2$ |
| B1-418 | 4-F | 4-CHF$_2$ |
| B1-419 | 4-F | 2-OCH$_3$ |
| B1-420 | 4-F | 3-OCH$_3$ |
| B1-421 | 4-F | 4-OCH$_3$ |
| B1-422 | 4-F | 2-OCF$_3$ |
| B1-423 | 4-F | 3-OCF$_3$ |
| B1-424 | 4-F | 4-OCF$_3$ |
| B1-425 | 4-F | 2-OCHF$_2$ |
| B1-426 | 4-F | 3-OCHF$_2$ |
| B1-427 | 4-F | 4-OCHF$_2$ |
| B1-428 | 4-F | 2,4,6-(CH$_3$)$_3$ |
| B1-429 | 4-F | 2,3-Cl$_2$ |
| B1-430 | 4-F | 2,4-Cl$_2$ |
| B1-431 | 4-F | 2,5-Cl$_2$ |
| B1-432 | 4-F | 3,4-Cl$_2$ |
| B1-433 | 4-F | 3,5-Cl$_2$ |
| B1-434 | 4-F | 2,6-Cl$_2$ |
| B1-435 | 4-F | 2,3-F$_2$ |
| B1-436 | 4-F | 2,4-F$_2$ |
| B1-437 | 4-F | 2,5-F$_2$ |
| B1-438 | 4-F | 3,4-F$_2$ |
| B1-439 | 4-F | 3,5-F$_2$ |
| B1-440 | 4-F | 2,6-F$_2$ |
| B1-441 | 4-F | 2-CF$_3$-4-Cl |
| B1-442 | 4-F | 2-CF$_3$-4-F |
| B1-443 | 4-F | 2-Cl-4-CF$_3$ |
| B1-444 | 4-F | 2-F-4-CF$_3$ |
| B1-445 | 4-F | 2-CN-4-Cl |
| B1-446 | 4-F | 2-CN-4-F |
| B1-447 | 4-F | 2-Cl-4-CN |
| B1-448 | 4-F | 2-F-4-CN |
| B1-449 | 5-F | —* |
| B1-450 | 5-F | 2-Cl |
| B1-451 | 5-F | 3-Cl |
| B1-452 | 5-F | 4-Cl |
| B1-453 | 5-F | 2-F |
| B1-454 | 5-F | 3-F |
| B1-455 | 5-F | 4-F |
| B1-456 | 5-F | 2-CN |
| B1-457 | 5-F | 3-CN |
| B1-458 | 5-F | 4-CN |
| B1-459 | 5-F | 2-NO$_2$ |
| B1-460 | 5-F | 3-NO$_2$ |
| B1-461 | 5-F | 4-NO$_2$ |
| B1-462 | 5-F | 2-SCH$_3$ |
| B1-463 | 5-F | 3-SCH$_3$ |
| B1-464 | 5-F | 4-SCH$_3$ |
| B1-465 | 5-F | 2-SOCH$_3$ |
| B1-466 | 5-F | 3-SOCH$_3$ |
| B1-467 | 5-F | 4-SOCH$_3$ |
| B1-468 | 5-F | 2-SO$_2$CH$_3$ |
| B1-469 | 5-F | 3-SO$_2$CH$_3$ |
| B1-470 | 5-F | 4-SO$_2$CH$_3$ |
| B1-471 | 5-F | 2-CO$_2$CH$_3$ |
| B1-472 | 5-F | 3-CO$_2$CH$_3$ |
| B1-473 | 5-F | 4-CO$_2$CH$_3$ |
| B1-474 | 5-F | 2-CH$_3$ |
| B1-475 | 5-F | 3-CH$_3$ |
| B1-476 | 5-F | 4-CH$_3$ |
| B1-477 | 5-F | 2-CF$_3$ |
| B1-478 | 5-F | 3-CF$_3$ |
| B1-479 | 5-F | 4-CF$_3$ |
| B1-480 | 5-F | 2-CHF$_2$ |
| B1-481 | 5-F | 3-CHF$_2$ |
| B1-482 | 5-F | 4-CHF$_2$ |
| B1-483 | 5-F | 2-OCH$_3$ |
| B1-484 | 5-F | 3-OCH$_3$ |
| B1-485 | 5-F | 4-OCH$_3$ |
| B1-486 | 5-F | 2-OCF$_3$ |
| B1-487 | 5-F | 3-OCF$_3$ |
| B1-488 | 5-F | 4-OCF$_3$ |
| B1-489 | 5-F | 2-OCHF$_2$ |
| B1-490 | 5-F | 3-OCHF$_2$ |
| B1-491 | 5-F | 4-OCHF$_2$ |
| B1-492 | 5-F | 2,4,6-(CH$_3$)$_3$ |
| B1-493 | 5-F | 2,3-Cl$_2$ |
| B1-494 | 5-F | 2,4-Cl$_2$ |
| B1-495 | 5-F | 2,5-Cl$_2$ |
| B1-496 | 5-F | 3,4-Cl$_2$ |
| B1-497 | 5-F | 3,5-Cl$_2$ |
| B1-498 | 5-F | 2,6-Cl$_2$ |
| B1-499 | 5-F | 2,3-F$_2$ |
| B1-500 | 5-F | 2,4-F$_2$ |
| B1-501 | 5-F | 2,5-F$_2$ |
| B1-502 | 5-F | 3,4-F$_2$ |
| B1-503 | 5-F | 3,5-F$_2$ |
| B1-504 | 5-F | 2,6-F$_2$ |

TABLE B1-continued

For compounds where ZY is in meta-position. The position(s) of the substituent(s) $(R^4)_n$ is/are given in relation to the attachment of the isoxazole-unit. The position(s) of the substituent(s) $(R^5)_m$ is/are given in relation to the attachment of the phenyl to the O-phenyl-unit.

| line | $(R^4)_n$ | $(R^5)_m$ |
|---|---|---|
| B1-505 | 5-F | 2-CF$_3$-4-Cl |
| B1-506 | 5-F | 2-CF$_3$-4-F |
| B1-507 | 5-F | 2-Cl-4-CF$_3$ |
| B1-508 | 5-F | 2-F-4-CF$_3$ |
| B1-509 | 5-F | 2-CN-4-Cl |
| B1-510 | 5-F | 2-CN-4-F |
| B1-511 | 5-F | 2-Cl-4-CN |
| B1-512 | 5-F | 2-F-4-CN |
| B1-513 | 6-F | —* |
| B1-514 | 6-F | 2-Cl |
| B1-515 | 6-F | 3-Cl |
| B1-516 | 6-F | 4-Cl |
| B1-517 | 6-F | 2-F |
| B1-518 | 6-F | 3-F |
| B1-519 | 6-F | 4-F |
| B1-520 | 6-F | 2-CN |
| B1-521 | 6-F | 3-CN |
| B1-522 | 6-F | 4-CN |
| B1-523 | 6-F | 2-NO$_2$ |
| B1-524 | 6-F | 3-NO$_2$ |
| B1-525 | 6-F | 4-NO$_2$ |
| B1-526 | 6-F | 2-SCH$_3$ |
| B1-527 | 6-F | 3-SCH$_3$ |
| B1-528 | 6-F | 4-SCH$_3$ |
| B1-529 | 6-F | 2-SOCH$_3$ |
| B1-530 | 6-F | 3-SOCH$_3$ |
| B1-531 | 6-F | 4-SOCH$_3$ |
| B1-532 | 6-F | 2-SO$_2$CH$_3$ |
| B1-533 | 6-F | 3-SO$_2$CH$_3$ |
| B1-534 | 6-F | 4-SO$_2$CH$_3$ |
| B1-535 | 6-F | 2-CO$_2$CH$_3$ |
| B1-536 | 6-F | 3-CO$_2$CH$_3$ |
| B1-537 | 6-F | 4-CO$_2$CH$_3$ |
| B1-538 | 6-F | 2-CH$_3$ |
| B1-539 | 6-F | 3-CH$_3$ |
| B1-540 | 6-F | 4-CH$_3$ |
| B1-541 | 6-F | 2-CF$_3$ |
| B1-542 | 6-F | 3-CF$_3$ |
| B1-543 | 6-F | 4-CF$_3$ |
| B1-544 | 6-F | 2-CHF$_2$ |
| B1-545 | 6-F | 3-CHF$_2$ |
| B1-546 | 6-F | 4-CHF$_2$ |
| B1-547 | 6-F | 2-OCH$_3$ |
| B1-548 | 6-F | 3-OCH$_3$ |
| B1-549 | 6-F | 4-OCH$_3$ |
| B1-550 | 6-F | 2-OCF$_3$ |
| B1-551 | 6-F | 3-OCF$_3$ |
| B1-552 | 6-F | 4-OCF$_3$ |
| B1-553 | 6-F | 2-OCHF$_2$ |
| B1-554 | 6-F | 3-OCHF$_2$ |
| B1-555 | 6-F | 4-OCHF$_2$ |
| B1-556 | 6-F | 2,4,6-(CH$_3$)$_3$ |
| B1-557 | 6-F | 2,3-Cl$_2$ |
| B1-558 | 6-F | 2,4-Cl$_2$ |
| B1-559 | 6-F | 2,5-Cl$_2$ |
| B1-560 | 6-F | 3,4-Cl$_2$ |
| B1-561 | 6-F | 3,5-Cl$_2$ |
| B1-562 | 6-F | 2,6-Cl$_2$ |
| B1-563 | 6-F | 2,3-F$_2$ |
| B1-564 | 6-F | 2,4-F$_2$ |
| B1-565 | 6-F | 2,5-F$_2$ |
| B1-566 | 6-F | 3,4-F$_2$ |
| B1-567 | 6-F | 3,5-F$_2$ |
| B1-568 | 6-F | 2,6-F$_2$ |
| B1-569 | 6-F | 2-CF$_3$-4-Cl |
| B1-570 | 6-F | 2-CF$_3$-4-F |
| B1-571 | 6-F | 2-Cl-4-CF$_3$ |
| B1-572 | 6-F | 2-F-4-CF$_3$ |
| B1-573 | 6-F | 2-CN-4-Cl |
| B1-574 | 6-F | 2-CN-4-F |
| B1-575 | 6-F | 2-Cl-4-CN |
| B1-576 | 6-F | 2-F-4-CN |
| B1-577 | 2-CN | —* |
| B1-578 | 2-CN | 2-Cl |
| B1-579 | 2-CN | 3-Cl |
| B1-580 | 2-CN | 4-Cl |
| B1-581 | 2-CN | 2-F |
| B1-582 | 2-CN | 3-F |
| B1-583 | 2-CN | 4-F |
| B1-584 | 2-CN | 2-CN |
| B1-585 | 2-CN | 3-CN |
| B1-586 | 2-CN | 4-CN |
| B1-587 | 2-CN | 2-NO$_2$ |
| B1-588 | 2-CN | 3-NO$_2$ |
| B1-589 | 2-CN | 4-NO$_2$ |
| B1-590 | 2-CN | 2-SCH$_3$ |
| B1-591 | 2-CN | 3-SCH$_3$ |
| B1-592 | 2-CN | 4-SCH$_3$ |
| B1-593 | 2-CN | 2-SOCH$_3$ |
| B1-594 | 2-CN | 3-SOCH$_3$ |
| B1-595 | 2-CN | 4-SOCH$_3$ |
| B1-596 | 2-CN | 2-SO$_2$CH$_3$ |
| B1-597 | 2-CN | 3-SO$_2$CH$_3$ |
| B1-598 | 2-CN | 4-SO$_2$CH$_3$ |
| B1-599 | 2-CN | 2-CO$_2$CH$_3$ |
| B1-600 | 2-CN | 3-CO$_2$CH$_3$ |
| B1-601 | 2-CN | 4-CO$_2$CH$_3$ |
| B1-602 | 2-CN | 2-CH$_3$ |
| B1-603 | 2-CN | 3-CH$_3$ |
| B1-604 | 2-CN | 4-CH$_3$ |
| B1-605 | 2-CN | 2-CF$_3$ |
| B1-606 | 2-CN | 3-CF$_3$ |
| B1-607 | 2-CN | 4-CF$_3$ |
| B1-608 | 2-CN | 2-CHF$_2$ |
| B1-609 | 2-CN | 3-CHF$_2$ |
| B1-610 | 2-CN | 4-CHF$_2$ |
| B1-611 | 2-CN | 2-OCH$_3$ |
| B1-612 | 2-CN | 3-OCH$_3$ |
| B1-613 | 2-CN | 4-OCH$_3$ |
| B1-614 | 2-CN | 2-OCF$_3$ |
| B1-615 | 2-CN | 3-OCF$_3$ |
| B1-616 | 2-CN | 4-OCF$_3$ |
| B1-617 | 2-CN | 2-OCHF$_2$ |
| B1-618 | 2-CN | 3-OCHF$_2$ |
| B1-619 | 2-CN | 4-OCHF$_2$ |
| B1-620 | 2-CN | 2,4,6-(CH$_3$)$_3$ |
| B1-621 | 2-CN | 2,3-Cl$_2$ |
| B1-622 | 2-CN | 2,4-Cl$_2$ |
| B1-623 | 2-CN | 2,5-Cl$_2$ |
| B1-624 | 2-CN | 3,4-Cl$_2$ |
| B1-625 | 2-CN | 3,5-Cl$_2$ |
| B1-626 | 2-CN | 2,6-Cl$_2$ |
| B1-627 | 2-CN | 2,3-F$_2$ |
| B1-628 | 2-CN | 2,4-F$_2$ |
| B1-629 | 2-CN | 2,5-F$_2$ |
| B1-630 | 2-CN | 3,4-F$_2$ |
| B1-631 | 2-CN | 3,5-F$_2$ |
| B1-632 | 2-CN | 2,6-F$_2$ |
| B1-633 | 2-CN | 2-CF$_3$-4-Cl |
| B1-634 | 2-CN | 2-CF$_3$-4-F |
| B1-635 | 2-CN | 2-Cl-4-CF$_3$ |
| B1-636 | 2-CN | 2-F-4-CF$_3$ |
| B1-637 | 2-CN | 2-CN-4-Cl |
| B1-638 | 2-CN | 2-CN-4-F |
| B1-639 | 2-CN | 2-Cl-4-CN |
| B1-640 | 2-CN | 2-F-4-CN |
| B1-641 | 4-CN | —* |
| B1-642 | 4-CN | 2-Cl |
| B1-643 | 4-CN | 3-Cl |
| B1-644 | 4-CN | 4-Cl |
| B1-645 | 4-CN | 2-F |
| B1-646 | 4-CN | 3-F |
| B1-647 | 4-CN | 4-F |
| B1-648 | 4-CN | 2-CN |

TABLE B1-continued

For compounds where ZY is in meta-position. The position(s) of the substituent(s) $(R^4)_n$ is/are given in relation to the attachment of the isoxazole-unit. The position(s) of the substituent(s) $(R^5)_m$ is/are given in relation to the attachment of the phenyl to the O-phenyl-unit.

| line | $(R^4)_n$ | $(R^5)_m$ |
|---|---|---|
| B1-649 | 4-CN | 3-CN |
| B1-650 | 4-CN | 4-CN |
| B1-651 | 4-CN | 2-$NO_2$ |
| B1-652 | 4-CN | 3-$NO_2$ |
| B1-653 | 4-CN | 4-$NO_2$ |
| B1-654 | 4-CN | 2-$SCH_3$ |
| B1-655 | 4-CN | 3-$SCH_3$ |
| B1-656 | 4-CN | 4-$SCH_3$ |
| B1-657 | 4-CN | 2-$SOCH_3$ |
| B1-658 | 4-CN | 3-$SOCH_3$ |
| B1-659 | 4-CN | 4-$SOCH_3$ |
| B1-660 | 4-CN | 2-$SO_2CH_3$ |
| B1-661 | 4-CN | 3-$SO_2CH_3$ |
| B1-662 | 4-CN | 4-$SO_2CH_3$ |
| B1-663 | 4-CN | 2-$CO_2CH_3$ |
| B1-664 | 4-CN | 3-$CO_2CH_3$ |
| B1-665 | 4-CN | 4-$CO_2CH_3$ |
| B1-666 | 4-CN | 2-$CH_3$ |
| B1-667 | 4-CN | 3-$CH_3$ |
| B1-668 | 4-CN | 4-$CH_3$ |
| B1-669 | 4-CN | 2-$CF_3$ |
| B1-670 | 4-CN | 3-$CF_3$ |
| B1-671 | 4-CN | 4-$CF_3$ |
| B1-672 | 4-CN | 2-$CHF_2$ |
| B1-673 | 4-CN | 3-$CHF_2$ |
| B1-674 | 4-CN | 4-$CHF_2$ |
| B1-675 | 4-CN | 2-$OCH_3$ |
| B1-676 | 4-CN | 3-$OCH_3$ |
| B1-677 | 4-CN | 4-$OCH_3$ |
| B1-678 | 4-CN | 2-$OCF_3$ |
| B1-679 | 4-CN | 3-$OCF_3$ |
| B1-680 | 4-CN | 4-$OCF_3$ |
| B1-681 | 4-CN | 2-$OCHF_2$ |
| B1-682 | 4-CN | 3-$OCHF_2$ |
| B1-683 | 4-CN | 4-$OCHF_2$ |
| B1-684 | 4-CN | 2,4,6-$(CH_3)_3$ |
| B1-685 | 4-CN | 2,3-$Cl_2$ |
| B1-686 | 4-CN | 2,4-$Cl_2$ |
| B1-687 | 4-CN | 2,5-$Cl_2$ |
| B1-688 | 4-CN | 3,4-$Cl_2$ |
| B1-689 | 4-CN | 3,5-$Cl_2$ |
| B1-690 | 4-CN | 2,6-$Cl_2$ |
| B1-691 | 4-CN | 2,3-$F_2$ |
| B1-692 | 4-CN | 2,4-$F_2$ |
| B1-693 | 4-CN | 2,5-$F_2$ |
| B1-694 | 4-CN | 3,4-$F_2$ |
| B1-695 | 4-CN | 3,5-$F_2$ |
| B1-696 | 4-CN | 2,6-$F_2$ |
| B1-697 | 4-CN | 2-$CF_3$-4-Cl |
| B1-698 | 4-CN | 2-$CF_3$-4-F |
| B1-699 | 4-CN | 2-Cl-4-$CF_3$ |
| B1-700 | 4-CN | 2-F-4-$CF_3$ |
| B1-701 | 4-CN | 2-CN-4-Cl |
| B1-702 | 4-CN | 2-CN-4-F |
| B1-703 | 4-CN | 2-Cl-4-CN |
| B1-704 | 4-CN | 2-F-4-CN |
| B1-705 | 5-CN | —* |
| B1-706 | 5-CN | 2-Cl |
| B1-707 | 5-CN | 3-Cl |
| B1-708 | 5-CN | 4-Cl |
| B1-709 | 5-CN | 2-F |
| B1-710 | 5-CN | 3-F |
| B1-711 | 5-CN | 4-F |
| B1-712 | 5-CN | 2-CN |
| B1-713 | 5-CN | 3-CN |
| B1-714 | 5-CN | 4-CN |
| B1-715 | 5-CN | 2-$NO_2$ |
| B1-716 | 5-CN | 3-$NO_2$ |
| B1-717 | 5-CN | 4-$NO_2$ |
| B1-718 | 5-CN | 2-$SCH_3$ |
| B1-719 | 5-CN | 3-$SCH_3$ |
| B1-720 | 5-CN | 4-$SCH_3$ |
| B1-721 | 5-CN | 2-$SOCH_3$ |
| B1-722 | 5-CN | 3-$SOCH_3$ |
| B1-723 | 5-CN | 4-$SOCH_3$ |
| B1-724 | 5-CN | 2-$SO_2CH_3$ |
| B1-725 | 5-CN | 3-$SO_2CH_3$ |
| B1-726 | 5-CN | 4-$SO_2CH_3$ |
| B1-727 | 5-CN | 2-$CO_2CH_3$ |
| B1-728 | 5-CN | 3-$CO_2CH_3$ |
| B1-729 | 5-CN | 4-$CO_2CH_3$ |
| B1-730 | 5-CN | 2-$CH_3$ |
| B1-731 | 5-CN | 3-$CH_3$ |
| B1-732 | 5-CN | 4-$CH_3$ |
| B1-733 | 5-CN | 2-$CF_3$ |
| B1-734 | 5-CN | 3-$CF_3$ |
| B1-735 | 5-CN | 4-$CF_3$ |
| B1-736 | 5-CN | 2-$CHF_2$ |
| B1-737 | 5-CN | 3-$CHF_2$ |
| B1-738 | 5-CN | 4-$CHF_2$ |
| B1-739 | 5-CN | 2-$OCH_3$ |
| B1-740 | 5-CN | 3-$OCH_3$ |
| B1-741 | 5-CN | 4-$OCH_3$ |
| B1-742 | 5-CN | 2-$OCF_3$ |
| B1-743 | 5-CN | 3-$OCF_3$ |
| B1-744 | 5-CN | 4-$OCF_3$ |
| B1-745 | 5-CN | 2-$OCHF_2$ |
| B1-746 | 5-CN | 3-$OCHF_2$ |
| B1-747 | 5-CN | 4-$OCHF_2$ |
| B1-748 | 5-CN | 2,4,6-$(CH_3)_3$ |
| B1-749 | 5-CN | 2,3-$Cl_2$ |
| B1-750 | 5-CN | 2,4-$Cl_2$ |
| B1-751 | 5-CN | 2,5-$Cl_2$ |
| B1-752 | 5-CN | 3,4-$Cl_2$ |
| B1-753 | 5-CN | 3,5-$Cl_2$ |
| B1-754 | 5-CN | 2,6-$Cl_2$ |
| B1-755 | 5-CN | 2,3-$F_2$ |
| B1-756 | 5-CN | 2,4-$F_2$ |
| B1-757 | 5-CN | 2,5-$F_2$ |
| B1-758 | 5-CN | 3,4-$F_2$ |
| B1-759 | 5-CN | 3,5-$F_2$ |
| B1-760 | 5-CN | 2,6-$F_2$ |
| B1-761 | 5-CN | 2-$CF_3$-4-Cl |
| B1-762 | 5-CN | 2-$CF_3$-4-F |
| B1-763 | 5-CN | 2-Cl-4-$CF_3$ |
| B1-764 | 5-CN | 2-F-4-$CF_3$ |
| B1-765 | 5-CN | 2-CN-4-Cl |
| B1-766 | 5-CN | 2-CN-4-F |
| B1-767 | 5-CN | 2-Cl-4-CN |
| B1-768 | 5-CN | 2-F-4-CN |
| B1-769 | 6-CN | —* |
| B1-770 | 6-CN | 2-Cl |
| B1-771 | 6-CN | 3-Cl |
| B1-772 | 6-CN | 4-Cl |
| B1-773 | 6-CN | 2-F |
| B1-774 | 6-CN | 3-F |
| B1-775 | 6-CN | 4-F |
| B1-776 | 6-CN | 2-CN |
| B1-777 | 6-CN | 3-CN |
| B1-778 | 6-CN | 4-CN |
| B1-779 | 6-CN | 2-$NO_2$ |
| B1-780 | 6-CN | 3-$NO_2$ |
| B1-781 | 6-CN | 4-$NO_2$ |
| B1-782 | 6-CN | 2-$SCH_3$ |
| B1-783 | 6-CN | 3-$SCH_3$ |
| B1-784 | 6-CN | 4-$SCH_3$ |
| B1-785 | 6-CN | 2-$SOCH_3$ |
| B1-786 | 6-CN | 3-$SOCH_3$ |
| B1-787 | 6-CN | 4-$SOCH_3$ |
| B1-788 | 6-CN | 2-$SO_2CH_3$ |
| B1-789 | 6-CN | 3-$SO_2CH_3$ |
| B1-790 | 6-CN | 4-$SO_2CH_3$ |
| B1-791 | 6-CN | 2-$CO_2CH_3$ |
| B1-792 | 6-CN | 3-$CO_2CH_3$ |

TABLE B1-continued

For compounds where ZY is in meta-position. The position(s) of the substituent(s) $(R^4)_n$ is/are given in relation to the attachment of the isoxazole-unit. The position(s) of the substituent(s) $(R^5)_m$ is/are given in relation to the attachment of the phenyl to the O-phenyl-unit.

| line | $(R^4)_n$ | $(R^5)_m$ |
|---|---|---|
| B1-793 | 6-CN | 4-CO$_2$CH$_3$ |
| B1-794 | 6-CN | 2-CH$_3$ |
| B1-795 | 6-CN | 3-CH$_3$ |
| B1-796 | 6-CN | 4-CH$_3$ |
| B1-797 | 6-CN | 2-CF$_3$ |
| B1-798 | 6-CN | 3-CF$_3$ |
| B1-799 | 6-CN | 4-CF$_3$ |
| B1-800 | 6-CN | 2-CHF$_2$ |
| B1-801 | 6-CN | 3-CHF$_2$ |
| B1-802 | 6-CN | 4-CHF$_2$ |
| B1-803 | 6-CN | 2-OCH$_3$ |
| B1-804 | 6-CN | 3-OCH$_3$ |
| B1-805 | 6-CN | 4-OCH$_3$ |
| B1-806 | 6-CN | 2-OCF$_3$ |
| B1-807 | 6-CN | 3-OCF$_3$ |
| B1-808 | 6-CN | 4-OCF$_3$ |
| B1-809 | 6-CN | 2-OCHF$_2$ |
| B1-810 | 6-CN | 3-OCHF$_2$ |
| B1-811 | 6-CN | 4-OCHF$_2$ |
| B1-812 | 6-CN | 2,4,6-(CH$_3$)$_3$ |
| B1-813 | 6-CN | 2,3-Cl$_2$ |
| B1-814 | 6-CN | 2,4-Cl$_2$ |
| B1-815 | 6-CN | 2,5-Cl$_2$ |
| B1-816 | 6-CN | 3,4-Cl$_2$ |
| B1-817 | 6-CN | 3,5-Cl$_2$ |
| B1-818 | 6-CN | 2,6-Cl$_2$ |
| B1-819 | 6-CN | 2,3-F$_2$ |
| B1-820 | 6-CN | 2,4-F$_2$ |
| B1-821 | 6-CN | 2,5-F$_2$ |
| B1-822 | 6-CN | 3,4-F$_2$ |
| B1-823 | 6-CN | 3,5-F$_2$ |
| B1-824 | 6-CN | 2,6-F$_2$ |
| B1-825 | 6-CN | 2-CF$_3$-4-Cl |
| B1-826 | 6-CN | 2-CF$_3$-4-F |
| B1-827 | 6-CN | 2-Cl-4-CF$_3$ |
| B1-828 | 6-CN | 2-F-4-CF$_3$ |
| B1-829 | 6-CN | 2-CN-4-Cl |
| B1-830 | 6-CN | 2-CN-4-F |
| B1-831 | 6-CN | 2-Cl-4-CN |
| B1-832 | 6-CN | 2-F-4-CN |
| B1-833 | 4,6-Cl$_2$ | —* |
| B1-834 | 4,6-Cl$_2$ | 2-Cl |
| B1-835 | 4,6-Cl$_2$ | 3-Cl |
| B1-836 | 4,6-Cl$_2$ | 4-Cl |
| B1-837 | 4,6-Cl$_2$ | 2-F |
| B1-838 | 4,6-Cl$_2$ | 3-F |
| B1-839 | 4,6-Cl$_2$ | 4-F |
| B1-840 | 4,6-Cl$_2$ | 2-CN |
| B1-841 | 4,6-Cl$_2$ | 3-CN |
| B1-842 | 4,6-Cl$_2$ | 4-CN |
| B1-843 | 4,6-Cl$_2$ | 2-NO$_2$ |
| B1-844 | 4,6-Cl$_2$ | 3-NO$_2$ |
| B1-845 | 4,6-Cl$_2$ | 4-NO$_2$ |
| B1-846 | 4,6-Cl$_2$ | 2-SCH$_3$ |
| B1-847 | 4,6-Cl$_2$ | 3-SCH$_3$ |
| B1-848 | 4,6-Cl$_2$ | 4-SCH$_3$ |
| B1-849 | 4,6-Cl$_2$ | 2-SOCH$_3$ |
| B1-850 | 4,6-Cl$_2$ | 3-SOCH$_3$ |
| B1-851 | 4,6-Cl$_2$ | 4-SOCH$_3$ |
| B1-852 | 4,6-Cl$_2$ | 2-SO$_2$CH$_3$ |
| B1-853 | 4,6-Cl$_2$ | 3-SO$_2$CH$_3$ |
| B1-854 | 4,6-Cl$_2$ | 4-SO$_2$CH$_3$ |
| B1-855 | 4,6-Cl$_2$ | 2-CO$_2$CH$_3$ |
| B1-856 | 4,6-Cl$_2$ | 3-CO$_2$CH$_3$ |
| B1-857 | 4,6-Cl$_2$ | 4-CO$_2$CH$_3$ |
| B1-858 | 4,6-Cl$_2$ | 2-CH$_3$ |
| B1-859 | 4,6-Cl$_2$ | 3-CH$_3$ |
| B1-860 | 4,6-Cl$_2$ | 4-CH$_3$ |
| B1-861 | 4,6-Cl$_2$ | 2-CF$_3$ |
| B1-862 | 4,6-Cl$_2$ | 3-CF$_3$ |
| B1-863 | 4,6-Cl$_2$ | 4-CF$_3$ |
| B1-864 | 4,6-Cl$_2$ | 2-CHF$_2$ |
| B1-865 | 4,6-Cl$_2$ | 3-CHF$_2$ |
| B1-866 | 4,6-Cl$_2$ | 4-CHF$_2$ |
| B1-867 | 4,6-Cl$_2$ | 2-OCH$_3$ |
| B1-868 | 4,6-Cl$_2$ | 3-OCH$_3$ |
| B1-869 | 4,6-Cl$_2$ | 4-OCH$_3$ |
| B1-870 | 4,6-Cl$_2$ | 2-OCF$_3$ |
| B1-871 | 4,6-Cl$_2$ | 3-OCF$_3$ |
| B1-872 | 4,6-Cl$_2$ | 4-OCF$_3$ |
| B1-873 | 4,6-Cl$_2$ | 2-OCHF$_2$ |
| B1-874 | 4,6-Cl$_2$ | 3-OCHF$_2$ |
| B1-875 | 4,6-Cl$_2$ | 4-OCHF$_2$ |
| B1-876 | 4,6-Cl$_2$ | 2,4,6-(CH$_3$)$_3$ |
| B1-877 | 4,6-Cl$_2$ | 2,3-Cl$_2$ |
| B1-878 | 4,6-Cl$_2$ | 2,4-Cl$_2$ |
| B1-879 | 4,6-Cl$_2$ | 2,5-Cl$_2$ |
| B1-880 | 4,6-Cl$_2$ | 3,4-Cl$_2$ |
| B1-881 | 4,6-Cl$_2$ | 3,5-Cl$_2$ |
| B1-882 | 4,6-Cl$_2$ | 2,6-Cl$_2$ |
| B1-883 | 4,6-Cl$_2$ | 2,3-F$_2$ |
| B1-884 | 4,6-Cl$_2$ | 2,4-F$_2$ |
| B1-885 | 4,6-Cl$_2$ | 2,5-F$_2$ |
| B1-886 | 4,6-Cl$_2$ | 3,4-F$_2$ |
| B1-887 | 4,6-Cl$_2$ | 3,5-F$_2$ |
| B1-888 | 4,6-Cl$_2$ | 2,6-F$_2$ |
| B1-889 | 4,6-Cl$_2$ | 2-CF$_3$-4-Cl |
| B1-890 | 4,6-Cl$_2$ | 2-CF$_3$-4-F |
| B1-891 | 4,6-Cl$_2$ | 2-Cl-4-CF$_3$ |
| B1-892 | 4,6-Cl$_2$ | 2-F-4-CF$_3$ |
| B1-893 | 4,6-Cl$_2$ | 2-CN-4-Cl |
| B1-894 | 4,6-Cl$_2$ | 2-CN-4-F |
| B1-895 | 4,6-Cl$_2$ | 2-Cl-4-CN |
| B1-896 | 4,6-Cl$_2$ | 2-F-4-CN |
| B1-897 | 4,6-F$_2$ | —* |
| B1-898 | 4,6-F$_2$ | 2-Cl |
| B1-899 | 4,6-F$_2$ | 3-Cl |
| B1-900 | 4,6-F$_2$ | 4-Cl |
| B1-901 | 4,6-F$_2$ | 2-F |
| B1-902 | 4,6-F$_2$ | 3-F |
| B1-903 | 4,6-F$_2$ | 4-F |
| B1-904 | 4,6-F$_2$ | 2-CN |
| B1-905 | 4,6-F$_2$ | 3-CN |
| B1-906 | 4,6-F$_2$ | 4-CN |
| B1-907 | 4,6-F$_2$ | 2-NO$_2$ |
| B1-908 | 4,6-F$_2$ | 3-NO$_2$ |
| B1-909 | 4,6-F$_2$ | 4-NO$_2$ |
| B1-910 | 4,6-F$_2$ | 2-SCH$_3$ |
| B1-911 | 4,6-F$_2$ | 3-SCH$_3$ |
| B1-912 | 4,6-F$_2$ | 4-SCH$_3$ |
| B1-913 | 4,6-F$_2$ | 2-SOCH$_3$ |
| B1-914 | 4,6-F$_2$ | 3-SOCH$_3$ |
| B1-915 | 4,6-F$_2$ | 4-SOCH$_3$ |
| B1-916 | 4,6-F$_2$ | 2-SO$_2$CH$_3$ |
| B1-917 | 4,6-F$_2$ | 3-SO$_2$CH$_3$ |
| B1-918 | 4,6-F$_2$ | 4-SO$_2$CH$_3$ |
| B1-919 | 4,6-F$_2$ | 2-CO$_2$CH$_3$ |
| B1-920 | 4,6-F$_2$ | 3-CO$_2$CH$_3$ |
| B1-921 | 4,6-F$_2$ | 4-CO$_2$CH$_3$ |
| B1-922 | 4,6-F$_2$ | 2-CH$_3$ |
| B1-923 | 4,6-F$_2$ | 3-CH$_3$ |
| B1-924 | 4,6-F$_2$ | 4-CH$_3$ |
| B1-925 | 4,6-F$_2$ | 2-CF$_3$ |
| B1-926 | 4,6-F$_2$ | 3-CF$_3$ |
| B1-927 | 4,6-F$_2$ | 4-CF$_3$ |
| B1-928 | 4,6-F$_2$ | 2-CHF$_2$ |
| B1-929 | 4,6-F$_2$ | 3-CHF$_2$ |
| B1-930 | 4,6-F$_2$ | 4-CHF$_2$ |
| B1-931 | 4,6-F$_2$ | 2-OCH$_3$ |
| B1-932 | 4,6-F$_2$ | 3-OCH$_3$ |
| B1-933 | 4,6-F$_2$ | 4-OCH$_3$ |
| B1-934 | 4,6-F$_2$ | 2-OCF$_3$ |
| B1-935 | 4,6-F$_2$ | 3-OCF$_3$ |
| B1-936 | 4,6-F$_2$ | 4-OCF$_3$ |

TABLE B1-continued

For compounds where ZY is in meta-position. The position(s) of the substituent(s) $(R^4)_n$ is/are given in relation to the attachment of the isoxazole-unit. The position(s) of the substituent(s) $(R^5)_m$ is/are given in relation to the attachment of the phenyl to the O-phenyl-unit.

| line | $(R^4)_n$ | $(R^5)_m$ |
|---|---|---|
| B1-937 | 4,6-F$_2$ | 2-OCHF$_2$ |
| B1-938 | 4,6-F$_2$ | 3-OCHF$_2$ |
| B1-939 | 4,6-F$_2$ | 4-OCHF$_2$ |
| B1-940 | 4,6-F$_2$ | 2,4,6-(CH$_3$)$_3$ |
| B1-941 | 4,6-F$_2$ | 2,3-Cl$_2$ |
| B1-942 | 4,6-F$_2$ | 2,4-Cl$_2$ |
| B1-943 | 4,6-F$_2$ | 2,5-Cl$_2$ |
| B1-944 | 4,6-F$_2$ | 3,4-Cl$_2$ |
| B1-945 | 4,6-F$_2$ | 3,5-Cl$_2$ |
| B1-946 | 4,6-F$_2$ | 2,6-Cl$_2$ |
| B1-947 | 4,6-F$_2$ | 2,3-F$_2$ |
| B1-948 | 4,6-F$_2$ | 2,4-F$_2$ |
| B1-949 | 4,6-F$_2$ | 2,5-F$_2$ |
| B1-950 | 4,6-F$_2$ | 3,4-F$_2$ |
| B1-951 | 4,6-F$_2$ | 3,5-F$_2$ |
| B1-952 | 4,6-F$_2$ | 2,6-F$_2$ |
| B1-953 | 4,6-F$_2$ | 2-CF$_3$-4-Cl |
| B1-954 | 4,6-F$_2$ | 2-CF$_3$-4-F |
| B1-955 | 4,6-F$_2$ | 2-Cl-4-CF$_3$ |
| B1-956 | 4,6-F$_2$ | 2-F-4-CF$_3$ |
| B1-957 | 4,6-F$_2$ | 2-CN-4-Cl |
| B1-958 | 4,6-F$_2$ | 2-CN-4-F |
| B1-959 | 4,6-F$_2$ | 2-Cl-4-CN |
| B1-960 | 4,6-F$_2$ | 2-F-4-CN |
| B1-961 | 4-Cl-6-F | —* |
| B1-962 | 4-Cl-6-F | 2-Cl |
| B1-963 | 4-Cl-6-F | 3-Cl |
| B1-964 | 4-Cl-6-F | 4-Cl |
| B1-965 | 4-Cl-6-F | 2-F |
| B1-966 | 4-Cl-6-F | 3-F |
| B1-967 | 4-Cl-6-F | 4-F |
| B1-968 | 4-Cl-6-F | 2-CN |
| B1-969 | 4-Cl-6-F | 3-CN |
| B1-970 | 4-Cl-6-F | 4-CN |
| B1-971 | 4-Cl-6-F | 2-NO$_2$ |
| B1-972 | 4-Cl-6-F | 3-NO$_2$ |
| B1-973 | 4-Cl-6-F | 4-NO$_2$ |
| B1-974 | 4-Cl-6-F | 2-SCH$_3$ |
| B1-975 | 4-Cl-6-F | 3-SCH$_3$ |
| B1-976 | 4-Cl-6-F | 4-SCH$_3$ |
| B1-977 | 4-Cl-6-F | 2-SOCH$_3$ |
| B1-978 | 4-Cl-6-F | 3-SOCH$_3$ |
| B1-979 | 4-Cl-6-F | 4-SOCH$_3$ |
| B1-980 | 4-Cl-6-F | 2-SO$_2$CH$_3$ |
| B1-981 | 4-Cl-6-F | 3-SO$_2$CH$_3$ |
| B1-982 | 4-Cl-6-F | 4-SO$_2$CH$_3$ |
| B1-983 | 4-Cl-6-F | 2-CO$_2$CH$_3$ |
| B1-984 | 4-Cl-6-F | 3-CO$_2$CH$_3$ |
| B1-985 | 4-Cl-6-F | 4-CO$_2$CH$_3$ |
| B1-986 | 4-Cl-6-F | 2-CH$_3$ |
| B1-987 | 4-Cl-6-F | 3-CH$_3$ |
| B1-988 | 4-Cl-6-F | 4-CH$_3$ |
| B1-989 | 4-Cl-6-F | 2-CF$_3$ |
| B1-990 | 4-Cl-6-F | 3-CF$_3$ |
| B1-991 | 4-Cl-6-F | 4-CF$_3$ |
| B1-992 | 4-Cl-6-F | 2-CHF$_2$ |
| B1-993 | 4-Cl-6-F | 3-CHF$_2$ |
| B1-994 | 4-Cl-6-F | 4-CHF$_2$ |
| B1-995 | 4-Cl-6-F | 2-OCH$_3$ |
| B1-996 | 4-Cl-6-F | 3-OCH$_3$ |
| B1-997 | 4-Cl-6-F | 4-OCH$_3$ |
| B1-998 | 4-Cl-6-F | 2-OCF$_3$ |
| B1-999 | 4-Cl-6-F | 3-OCF$_3$ |
| B1-1000 | 4-Cl-6-F | 4-OCF$_3$ |
| B1-1001 | 4-Cl-6-F | 2-OCHF$_2$ |
| B1-1002 | 4-Cl-6-F | 3-OCHF$_2$ |
| B1-1003 | 4-Cl-6-F | 4-OCHF$_2$ |
| B1-1004 | 4-Cl-6-F | 2,4,6-(CH$_3$)$_3$ |
| B1-1005 | 4-Cl-6-F | 2,3-Cl$_2$ |
| B1-1006 | 4-Cl-6-F | 2,4-Cl$_2$ |
| B1-1007 | 4-Cl-6-F | 2,5-Cl$_2$ |
| B1-1008 | 4-Cl-6-F | 3,4-Cl$_2$ |
| B1-1009 | 4-Cl-6-F | 3,5-Cl$_2$ |
| B1-1010 | 4-Cl-6-F | 2,6-Cl$_2$ |
| B1-1011 | 4-Cl-6-F | 2,3-F$_2$ |
| B1-1012 | 4-Cl-6-F | 2,4-F$_2$ |
| B1-1013 | 4-Cl-6-F | 2,5-F$_2$ |
| B1-1014 | 4-Cl-6-F | 3,4-F$_2$ |
| B1-1015 | 4-Cl-6-F | 3,5-F$_2$ |
| B1-1016 | 4-Cl-6-F | 2,6-F$_2$ |
| B1-1017 | 4-Cl-6-F | 2-CF$_3$-4-Cl |
| B1-1018 | 4-Cl-6-F | 2-CF$_3$-4-F |
| B1-1019 | 4-Cl-6-F | 2-Cl-4-CF$_3$ |
| B1-1020 | 4-Cl-6-F | 2-F-4-CF$_3$ |
| B1-1021 | 4-Cl-6-F | 2-CN-4-Cl |
| B1-1022 | 4-Cl-6-F | 2-CN-4-F |
| B1-1023 | 4-Cl-6-F | 2-Cl-4-CN |
| B1-1024 | 4-Cl-6-F | 2-F-4-CN |
| B1-1025 | 6-Cl-4-F | —* |
| B1-1026 | 6-Cl-4-F | 2-Cl |
| B1-1027 | 6-Cl-4-F | 3-Cl |
| B1-1028 | 6-Cl-4-F | 4-Cl |
| B1-1029 | 6-Cl-4-F | 2-F |
| B1-1030 | 6-Cl-4-F | 3-F |
| B1-1031 | 6-Cl-4-F | 4-F |
| B1-1032 | 6-Cl-4-F | 2-CN |
| B1-1033 | 6-Cl-4-F | 3-CN |
| B1-1034 | 6-Cl-4-F | 4-CN |
| B1-1035 | 6-Cl-4-F | 2-NO$_2$ |
| B1-1036 | 6-Cl-4-F | 3-NO$_2$ |
| B1-1037 | 6-Cl-4-F | 4-NO$_2$ |
| B1-1038 | 6-Cl-4-F | 2-SCH$_3$ |
| B1-1039 | 6-Cl-4-F | 3-SCH$_3$ |
| B1-1040 | 6-Cl-4-F | 4-SCH$_3$ |
| B1-1041 | 6-Cl-4-F | 2-SOCH$_3$ |
| B1-1042 | 6-Cl-4-F | 3-SOCH$_3$ |
| B1-1043 | 6-Cl-4-F | 4-SOCH$_3$ |
| B1-1044 | 6-Cl-4-F | 2-SO$_2$CH$_3$ |
| B1-1045 | 6-Cl-4-F | 3-SO$_2$CH$_3$ |
| B1-1046 | 6-Cl-4-F | 4-SO$_2$CH$_3$ |
| B1-1047 | 6-Cl-4-F | 2-CO$_2$CH$_3$ |
| B1-1048 | 6-Cl-4-F | 3-CO$_2$CH$_3$ |
| B1-1049 | 6-Cl-4-F | 4-CO$_2$CH$_3$ |
| B1-1050 | 6-Cl-4-F | 2-CH$_3$ |
| B1-1051 | 6-Cl-4-F | 3-CH$_3$ |
| B1-1052 | 6-Cl-4-F | 4-CH$_3$ |
| B1-1053 | 6-Cl-4-F | 2-CF$_3$ |
| B1-1054 | 6-Cl-4-F | 3-CF$_3$ |
| B1-1055 | 6-Cl-4-F | 4-CF$_3$ |
| B1-1056 | 6-Cl-4-F | 2-CHF$_2$ |
| B1-1057 | 6-Cl-4-F | 3-CHF$_2$ |
| B1-1058 | 6-Cl-4-F | 4-CHF$_2$ |
| B1-1059 | 6-Cl-4-F | 2-OCH$_3$ |
| B1-1060 | 6-Cl-4-F | 3-OCH$_3$ |
| B1-1061 | 6-Cl-4-F | 4-OCH$_3$ |
| B1-1062 | 6-Cl-4-F | 2-OCF$_3$ |
| B1-1063 | 6-Cl-4-F | 3-OCF$_3$ |
| B1-1064 | 6-Cl-4-F | 4-OCF$_3$ |
| B1-1065 | 6-Cl-4-F | 2-OCHF$_2$ |
| B1-1066 | 6-Cl-4-F | 3-OCHF$_2$ |
| B1-1067 | 6-Cl-4-F | 4-OCHF$_2$ |
| B1-1068 | 6-Cl-4-F | 2,4,6-(CH$_3$)$_3$ |
| B1-1069 | 6-Cl-4-F | 2,3-Cl$_2$ |
| B1-1070 | 6-Cl-4-F | 2,4-Cl$_2$ |
| B1-1071 | 6-Cl-4-F | 2,5-Cl$_2$ |
| B1-1072 | 6-Cl-4-F | 3,4-Cl$_2$ |
| B1-1073 | 6-Cl-4-F | 3,5-Cl$_2$ |
| B1-1074 | 6-Cl-4-F | 2,6-Cl$_2$ |
| B1-1075 | 6-Cl-4-F | 2,3-F$_2$ |
| B1-1076 | 6-Cl-4-F | 2,4-F$_2$ |
| B1-1077 | 6-Cl-4-F | 2,5-F$_2$ |
| B1-1078 | 6-Cl-4-F | 3,4-F$_2$ |
| B1-1079 | 6-Cl-4-F | 3,5-F$_2$ |
| B1-1080 | 6-Cl-4-F | 2,6-F$_2$ |

TABLE B1-continued

For compounds where ZY is in meta-position. The position(s) of the substituent(s) $(R^4)_n$ is/are given in relation to the attachment of the isoxazole-unit. The position(s) of the substituent(s) $(R^5)_m$ is/are given in relation to the attachment of the phenyl to the O-phenyl-unit.

| line | $(R^4)_n$ | $(R^5)_m$ |
| --- | --- | --- |
| B1-1081 | 6-Cl-4-F | 2-CF$_3$-4-Cl |
| B1-1082 | 6-Cl-4-F | 2-CF$_3$-4-F |
| B1-1083 | 6-Cl-4-F | 2-Cl-4-CF$_3$ |
| B1-1084 | 6-Cl-4-F | 2-F-4-CF$_3$ |
| B1-1085 | 6-Cl-4-F | 2-CN-4-Cl |
| B1-1086 | 6-Cl-4-F | 2-CN-4-F |
| B1-1087 | 6-Cl-4-F | 2-Cl-4-CN |
| B1-1088 | 6-Cl-4-F | 2-F-4-CN |
| B1-1089 | 2-CH$_3$ | —* |
| B1-1090 | 2-CH$_3$ | 2-Cl |
| B1-1091 | 2-CH$_3$ | 3-Cl |
| B1-1092 | 2-CH$_3$ | 4-Cl |
| B1-1093 | 2-CH$_3$ | 2-F |
| B1-1094 | 2-CH$_3$ | 3-F |
| B1-1095 | 2-CH$_3$ | 4-F |
| B1-1096 | 2-CH$_3$ | 2-CN |
| B1-1097 | 2-CH$_3$ | 3-CN |
| B1-1098 | 2-CH$_3$ | 4-CN |
| B1-1099 | 2-CH$_3$ | 2-NO$_2$ |
| B1-1100 | 2-CH$_3$ | 3-NO$_2$ |
| B1-1101 | 2-CH$_3$ | 4-NO$_2$ |
| B1-1102 | 2-CH$_3$ | 2-SCH$_3$ |
| B1-1103 | 2-CH$_3$ | 3-SCH$_3$ |
| B1-1104 | 2-CH$_3$ | 4-SCH$_3$ |
| B1-1105 | 2-CH$_3$ | 2-SOCH$_3$ |
| B1-1106 | 2-CH$_3$ | 3-SOCH$_3$ |
| B1-1107 | 2-CH$_3$ | 4-SOCH$_3$ |
| B1-1108 | 2-CH$_3$ | 2-SO$_2$CH$_3$ |
| B1-1109 | 2-CH$_3$ | 3-SO$_2$CH$_3$ |
| B1-1110 | 2-CH$_3$ | 4-SO$_2$CH$_3$ |
| B1-1111 | 2-CH$_3$ | 2-CO$_2$CH$_3$ |
| B1-1112 | 2-CH$_3$ | 3-CO$_2$CH$_3$ |
| B1-1113 | 2-CH$_3$ | 4-CO$_2$CH$_3$ |
| B1-1114 | 2-CH$_3$ | 2-CH$_3$ |
| B1-1115 | 2-CH$_3$ | 3-CH$_3$ |
| B1-1116 | 2-CH$_3$ | 4-CH$_3$ |
| B1-1117 | 2-CH$_3$ | 2-CF$_3$ |
| B1-1118 | 2-CH$_3$ | 3-CF$_3$ |
| B1-1119 | 2-CH$_3$ | 4-CF$_3$ |
| B1-1120 | 2-CH$_3$ | 2-CHF$_2$ |
| B1-1121 | 2-CH$_3$ | 3-CHF$_2$ |
| B1-1122 | 2-CH$_3$ | 4-CHF$_2$ |
| B1-1123 | 2-CH$_3$ | 2-OCH$_3$ |
| B1-1124 | 2-CH$_3$ | 3-OCH$_3$ |
| B1-1125 | 2-CH$_3$ | 4-OCH$_3$ |
| B1-1126 | 2-CH$_3$ | 2-OCF$_3$ |
| B1-1127 | 2-CH$_3$ | 3-OCF$_3$ |
| B1-1128 | 2-CH$_3$ | 4-OCF$_3$ |
| B1-1129 | 2-CH$_3$ | 2-OCHF$_2$ |
| B1-1130 | 2-CH$_3$ | 3-OCHF$_2$ |
| B1-1131 | 2-CH$_3$ | 4-OCHF$_2$ |
| B1-1132 | 2-CH$_3$ | 2,4,6-(CH$_3$)$_3$ |
| B1-1133 | 2-CH$_3$ | 2,3-Cl$_2$ |
| B1-1134 | 2-CH$_3$ | 2,4-Cl$_2$ |
| B1-1135 | 2-CH$_3$ | 2,5-Cl$_2$ |
| B1-1136 | 2-CH$_3$ | 3,4-Cl$_2$ |
| B1-1137 | 2-CH$_3$ | 3,5-Cl$_2$ |
| B1-1138 | 2-CH$_3$ | 2,6-Cl$_2$ |
| B1-1139 | 2-CH$_3$ | 2,3-F$_2$ |
| B1-1140 | 2-CH$_3$ | 2,4-F$_2$ |
| B1-1141 | 2-CH$_3$ | 2,5-F$_2$ |
| B1-1142 | 2-CH$_3$ | 3,4-F$_2$ |
| B1-1143 | 2-CH$_3$ | 3,5-F$_2$ |
| B1-1144 | 2-CH$_3$ | 2,6-F$_2$ |
| B1-1145 | 2-CH$_3$ | 2-CF$_3$-4-Cl |
| B1-1146 | 2-CH$_3$ | 2-CF$_3$-4-F |
| B1-1147 | 2-CH$_3$ | 2-Cl-4-CF$_3$ |
| B1-1148 | 2-CH$_3$ | 2-F-4-CF$_3$ |
| B1-1149 | 2-CH$_3$ | 2-CN-4-Cl |
| B1-1150 | 2-CH$_3$ | 2-CN-4-F |
| B1-1151 | 2-CH$_3$ | 2-Cl-4-CN |
| B1-1152 | 2-CH$_3$ | 2-F-4-CN |
| B1-1153 | 4-CH$_3$ | —* |
| B1-1154 | 4-CH$_3$ | 2-Cl |
| B1-1155 | 4-CH$_3$ | 3-Cl |
| B1-1156 | 4-CH$_3$ | 4-Cl |
| B1-1157 | 4-CH$_3$ | 2-F |
| B1-1158 | 4-CH$_3$ | 3-F |
| B1-1159 | 4-CH$_3$ | 4-F |
| B1-1160 | 4-CH$_3$ | 2-CN |
| B1-1161 | 4-CH$_3$ | 3-CN |
| B1-1162 | 4-CH$_3$ | 4-CN |
| B1-1163 | 4-CH$_3$ | 2-NO$_2$ |
| B1-1164 | 4-CH$_3$ | 3-NO$_2$ |
| B1-1165 | 4-CH$_3$ | 4-NO$_2$ |
| B1-1166 | 4-CH$_3$ | 2-SCH$_3$ |
| B1-1167 | 4-CH$_3$ | 3-SCH$_3$ |
| B1-1168 | 4-CH$_3$ | 4-SCH$_3$ |
| B1-1169 | 4-CH$_3$ | 2-SOCH$_3$ |
| B1-1170 | 4-CH$_3$ | 3-SOCH$_3$ |
| B1-1171 | 4-CH$_3$ | 4-SOCH$_3$ |
| B1-1172 | 4-CH$_3$ | 2-SO$_2$CH$_3$ |
| B1-1173 | 4-CH$_3$ | 3-SO$_2$CH$_3$ |
| B1-1174 | 4-CH$_3$ | 4-SO$_2$CH$_3$ |
| B1-1175 | 4-CH$_3$ | 2-CO$_2$CH$_3$ |
| B1-1176 | 4-CH$_3$ | 3-CO$_2$CH$_3$ |
| B1-1177 | 4-CH$_3$ | 4-CO$_2$CH$_3$ |
| B1-1178 | 4-CH$_3$ | 2-CH$_3$ |
| B1-1179 | 4-CH$_3$ | 3-CH$_3$ |
| B1-1180 | 4-CH$_3$ | 4-CH$_3$ |
| B1-1181 | 4-CH$_3$ | 2-CF$_3$ |
| B1-1182 | 4-CH$_3$ | 3-CF$_3$ |
| B1-1183 | 4-CH$_3$ | 4-CF$_3$ |
| B1-1184 | 4-CH$_3$ | 2-CHF$_2$ |
| B1-1185 | 4-CH$_3$ | 3-CHF$_2$ |
| B1-1186 | 4-CH$_3$ | 4-CHF$_2$ |
| B1-1187 | 4-CH$_3$ | 2-OCH$_3$ |
| B1-1188 | 4-CH$_3$ | 3-OCH$_3$ |
| B1-1189 | 4-CH$_3$ | 4-OCH$_3$ |
| B1-1190 | 4-CH$_3$ | 2-OCF$_3$ |
| B1-1191 | 4-CH$_3$ | 3-OCF$_3$ |
| B1-1192 | 4-CH$_3$ | 4-OCF$_3$ |
| B1-1193 | 4-CH$_3$ | 2-OCHF$_2$ |
| B1-1194 | 4-CH$_3$ | 3-OCHF$_2$ |
| B1-1195 | 4-CH$_3$ | 4-OCHF$_2$ |
| B1-1196 | 4-CH$_3$ | 2,4,6-(CH$_3$)$_3$ |
| B1-1197 | 4-CH$_3$ | 2,3-Cl$_2$ |
| B1-1198 | 4-CH$_3$ | 2,4-Cl$_2$ |
| B1-1199 | 4-CH$_3$ | 2,5-Cl$_2$ |
| B1-1200 | 4-CH$_3$ | 3,4-Cl$_2$ |
| B1-1201 | 4-CH$_3$ | 3,5-Cl$_2$ |
| B1-1202 | 4-CH$_3$ | 2,6-Cl$_2$ |
| B1-1203 | 4-CH$_3$ | 2,3-F$_2$ |
| B1-1204 | 4-CH$_3$ | 2,4-F$_2$ |
| B1-1205 | 4-CH$_3$ | 2,5-F$_2$ |
| B1-1206 | 4-CH$_3$ | 3,4-F$_2$ |
| B1-1207 | 4-CH$_3$ | 3,5-F$_2$ |
| B1-1208 | 4-CH$_3$ | 2,6-F$_2$ |
| B1-1209 | 4-CH$_3$ | 2-CF$_3$-4-Cl |
| B1-1210 | 4-CH$_3$ | 2-CF$_3$-4-F |
| B1-1211 | 4-CH$_3$ | 2-Cl-4-CF$_3$ |
| B1-1212 | 4-CH$_3$ | 2-F-4-CF$_3$ |
| B1-1213 | 4-CH$_3$ | 2-CN-4-Cl |
| B1-1214 | 4-CH$_3$ | 2-CN-4-F |
| B1-1215 | 4-CH$_3$ | 2-Cl-4-CN |
| B1-1216 | 4-CH$_3$ | 2-F-4-CN |
| B1-1217 | 5-CH$_3$ | —* |
| B1-1218 | 5-CH$_3$ | 2-Cl |
| B1-1219 | 5-CH$_3$ | 3-Cl |
| B1-1220 | 5-CH$_3$ | 4-Cl |
| B1-1221 | 5-CH$_3$ | 2-F |
| B1-1222 | 5-CH$_3$ | 3-F |
| B1-1223 | 5-CH$_3$ | 4-F |
| B1-1224 | 5-CH$_3$ | 2-CN |

TABLE B1-continued

For compounds where ZY is in meta-position. The position(s) of the substituent(s) $(R^4)_n$ is/are given in relation to the attachment of the isoxazole-unit. The position(s) of the substituent(s) $(R^5)_m$ is/are given in relation to the attachment of the phenyl to the O-phenyl-unit.

| line | $(R^4)_n$ | $(R^5)_m$ |
|---|---|---|
| B1-1225 | 5-CH$_3$ | 3-CN |
| B1-1226 | 5-CH$_3$ | 4-CN |
| B1-1227 | 5-CH$_3$ | 2-NO$_2$ |
| B1-1228 | 5-CH$_3$ | 3-NO$_2$ |
| B1-1229 | 5-CH$_3$ | 4-NO$_2$ |
| B1-1230 | 5-CH$_3$ | 2-SCH$_3$ |
| B1-1231 | 5-CH$_3$ | 3-SCH$_3$ |
| B1-1232 | 5-CH$_3$ | 4-SCH$_3$ |
| B1-1233 | 5-CH$_3$ | 2-SOCH$_3$ |
| B1-1234 | 5-CH$_3$ | 3-SOCH$_3$ |
| B1-1235 | 5-CH$_3$ | 4-SOCH$_3$ |
| B1-1236 | 5-CH$_3$ | 2-SO$_2$CH$_3$ |
| B1-1237 | 5-CH$_3$ | 3-SO$_2$CH$_3$ |
| B1-1238 | 5-CH$_3$ | 4-SO$_2$CH$_3$ |
| B1-1239 | 5-CH$_3$ | 2-CO$_2$CH$_3$ |
| B1-1240 | 5-CH$_3$ | 3-CO$_2$CH$_3$ |
| B1-1241 | 5-CH$_3$ | 4-CO$_2$CH$_3$ |
| B1-1242 | 5-CH$_3$ | 2-CH$_3$ |
| B1-1243 | 5-CH$_3$ | 3-CH$_3$ |
| B1-1244 | 5-CH$_3$ | 4-CH$_3$ |
| B1-1245 | 5-CH$_3$ | 2-CF$_3$ |
| B1-1246 | 5-CH$_3$ | 3-CF$_3$ |
| B1-1247 | 5-CH$_3$ | 4-CF$_3$ |
| B1-1248 | 5-CH$_3$ | 2-CHF$_2$ |
| B1-1249 | 5-CH$_3$ | 3-CHF$_2$ |
| B1-1250 | 5-CH$_3$ | 4-CHF$_2$ |
| B1-1251 | 5-CH$_3$ | 2-OCH$_3$ |
| B1-1252 | 5-CH$_3$ | 3-OCH$_3$ |
| B1-1253 | 5-CH$_3$ | 4-OCH$_3$ |
| B1-1254 | 5-CH$_3$ | 2-OCF$_3$ |
| B1-1255 | 5-CH$_3$ | 3-OCF$_3$ |
| B1-1256 | 5-CH$_3$ | 4-OCF$_3$ |
| B1-1257 | 5-CH$_3$ | 2-OCHF$_2$ |
| B1-1258 | 5-CH$_3$ | 3-OCHF$_2$ |
| B1-1259 | 5-CH$_3$ | 4-OCHF$_2$ |
| B1-1260 | 5-CH$_3$ | 2,4,6-(CH$_3$)$_3$ |
| B1-1261 | 5-CH$_3$ | 2,3-Cl$_2$ |
| B1-1262 | 5-CH$_3$ | 2,4-Cl$_2$ |
| B1-1263 | 5-CH$_3$ | 2,5-Cl$_2$ |
| B1-1264 | 5-CH$_3$ | 3,4-Cl$_2$ |
| B1-1265 | 5-CH$_3$ | 3,5-Cl$_2$ |
| B1-1266 | 5-CH$_3$ | 2,6-Cl$_2$ |
| B1-1267 | 5-CH$_3$ | 2,3-F$_2$ |
| B1-1268 | 5-CH$_3$ | 2,4-F$_2$ |
| B1-1269 | 5-CH$_3$ | 2,5-F$_2$ |
| B1-1270 | 5-CH$_3$ | 3,4-F$_2$ |
| B1-1271 | 5-CH$_3$ | 3,5-F$_2$ |
| B1-1272 | 5-CH$_3$ | 2,6-F$_2$ |
| B1-1273 | 5-CH$_3$ | 2-CF$_3$-4-Cl |
| B1-1274 | 5-CH$_3$ | 2-CF$_3$-4-F |
| B1-1275 | 5-CH$_3$ | 2-Cl-4-CF$_3$ |
| B1-1276 | 5-CH$_3$ | 2-F-4-CF$_3$ |
| B1-1277 | 5-CH$_3$ | 2-CN-4-Cl |
| B1-1278 | 5-CH$_3$ | 2-CN-4-F |
| B1-1279 | 5-CH$_3$ | 2-Cl-4-CN |
| B1-1280 | 5-CH$_3$ | 2-F-4-CN |
| B1-1281 | 6-CH$_3$ | —* |
| B1-1282 | 6-CH$_3$ | 2-Cl |
| B1-1283 | 6-CH$_3$ | 3-Cl |
| B1-1284 | 6-CH$_3$ | 4-Cl |
| B1-1285 | 6-CH$_3$ | 2-F |
| B1-1286 | 6-CH$_3$ | 3-F |
| B1-1287 | 6-CH$_3$ | 4-F |
| B1-1288 | 6-CH$_3$ | 2-CN |
| B1-1289 | 6-CH$_3$ | 3-CN |
| B1-1290 | 6-CH$_3$ | 4-CN |
| B1-1291 | 6-CH$_3$ | 2-NO$_2$ |
| B1-1292 | 6-CH$_3$ | 3-NO$_2$ |
| B1-1293 | 6-CH$_3$ | 4-NO$_2$ |
| B1-1294 | 6-CH$_3$ | 2-SCH$_3$ |
| B1-1295 | 6-CH$_3$ | 3-SCH$_3$ |
| B1-1296 | 6-CH$_3$ | 4-SCH$_3$ |
| B1-1297 | 6-CH$_3$ | 2-SOCH$_3$ |
| B1-1298 | 6-CH$_3$ | 3-SOCH$_3$ |
| B1-1299 | 6-CH$_3$ | 4-SOCH$_3$ |
| B1-1300 | 6-CH$_3$ | 2-SO$_2$CH$_3$ |
| B1-1301 | 6-CH$_3$ | 3-SO$_2$CH$_3$ |
| B1-1302 | 6-CH$_3$ | 4-SO$_2$CH$_3$ |
| B1-1303 | 6-CH$_3$ | 2-CO$_2$CH$_3$ |
| B1-1304 | 6-CH$_3$ | 3-CO$_2$CH$_3$ |
| B1-1305 | 6-CH$_3$ | 4-CO$_2$CH$_3$ |
| B1-1306 | 6-CH$_3$ | 2-CH$_3$ |
| B1-1307 | 6-CH$_3$ | 3-CH$_3$ |
| B1-1308 | 6-CH$_3$ | 4-CH$_3$ |
| B1-1309 | 6-CH$_3$ | 2-CF$_3$ |
| B1-1310 | 6-CH$_3$ | 3-CF$_3$ |
| B1-1311 | 6-CH$_3$ | 4-CF$_3$ |
| B1-1312 | 6-CH$_3$ | 2-CHF$_2$ |
| B1-1313 | 6-CH$_3$ | 3-CHF$_2$ |
| B1-1314 | 6-CH$_3$ | 4-CHF$_2$ |
| B1-1315 | 6-CH$_3$ | 2-OCH$_3$ |
| B1-1316 | 6-CH$_3$ | 3-OCH$_3$ |
| B1-1317 | 6-CH$_3$ | 4-OCH$_3$ |
| B1-1318 | 6-CH$_3$ | 2-OCF$_3$ |
| B1-1319 | 6-CH$_3$ | 3-OCF$_3$ |
| B1-1320 | 6-CH$_3$ | 4-OCF$_3$ |
| B1-1321 | 6-CH$_3$ | 2-OCHF$_2$ |
| B1-1322 | 6-CH$_3$ | 3-OCHF$_2$ |
| B1-1323 | 6-CH$_3$ | 4-OCHF$_2$ |
| B1-1324 | 6-CH$_3$ | 2,4,6-(CH$_3$)$_3$ |
| B1-1325 | 6-CH$_3$ | 2,3-Cl$_2$ |
| B1-1326 | 6-CH$_3$ | 2,4-Cl$_2$ |
| B1-1327 | 6-CH$_3$ | 2,5-Cl$_2$ |
| B1-1328 | 6-CH$_3$ | 3,4-Cl$_2$ |
| B1-1329 | 6-CH$_3$ | 3,5-Cl$_2$ |
| B1-1330 | 6-CH$_3$ | 2,6-Cl$_2$ |
| B1-1331 | 6-CH$_3$ | 2,3-F$_2$ |
| B1-1332 | 6-CH$_3$ | 2,4-F$_2$ |
| B1-1333 | 6-CH$_3$ | 2,5-F$_2$ |
| B1-1334 | 6-CH$_3$ | 3,4-F$_2$ |
| B1-1335 | 6-CH$_3$ | 3,5-F$_2$ |
| B1-1336 | 6-CH$_3$ | 2,6-F$_2$ |
| B1-1337 | 6-CH$_3$ | 2-CF$_3$-4-Cl |
| B1-1338 | 6-CH$_3$ | 2-CF$_3$-4-F |
| B1-1339 | 6-CH$_3$ | 2-Cl-4-CF$_3$ |
| B1-1340 | 6-CH$_3$ | 2-F-4-CF$_3$ |
| B1-1341 | 6-CH$_3$ | 2-CN-4-Cl |
| B1-1342 | 6-CH$_3$ | 2-CN-4-F |
| B1-1343 | 6-CH$_3$ | 2-Cl-4-CN |
| B1-1344 | 6-CH$_3$ | 2-F-4-CN |
| B1-1345 | 2-CF$_3$ | —* |
| B1-1346 | 2-CF$_3$ | 2-Cl |
| B1-1347 | 2-CF$_3$ | 3-Cl |
| B1-1348 | 2-CF$_3$ | 4-Cl |
| B1-1349 | 2-CF$_3$ | 2-F |
| B1-1350 | 2-CF$_3$ | 3-F |
| B1-1351 | 2-CF$_3$ | 4-F |
| B1-1352 | 2-CF$_3$ | 2-CN |
| B1-1353 | 2-CF$_3$ | 3-CN |
| B1-1354 | 2-CF$_3$ | 4-CN |
| B1-1355 | 2-CF$_3$ | 2-NO$_2$ |
| B1-1356 | 2-CF$_3$ | 3-NO$_2$ |
| B1-1357 | 2-CF$_3$ | 4-NO$_2$ |
| B1-1358 | 2-CF$_3$ | 2-SCH$_3$ |
| B1-1359 | 2-CF$_3$ | 3-SCH$_3$ |
| B1-1360 | 2-CF$_3$ | 4-SCH$_3$ |
| B1-1361 | 2-CF$_3$ | 2-SOCH$_3$ |
| B1-1362 | 2-CF$_3$ | 3-SOCH$_3$ |
| B1-1363 | 2-CF$_3$ | 4-SOCH$_3$ |
| B1-1364 | 2-CF$_3$ | 2-SO$_2$CH$_3$ |
| B1-1365 | 2-CF$_3$ | 3-SO$_2$CH$_3$ |
| B1-1366 | 2-CF$_3$ | 4-SO$_2$CH$_3$ |
| B1-1367 | 2-CF$_3$ | 2-CO$_2$CH$_3$ |
| B1-1368 | 2-CF$_3$ | 3-CO$_2$CH$_3$ |

TABLE B1-continued

For compounds where ZY is in meta-position. The position(s) of the substituent(s) $(R^4)_n$ is/are given in relation to the attachment of the isoxazole-unit. The position(s) of the substituent(s) $(R^5)_m$ is/are given in relation to the attachment of the phenyl to the O-phenyl-unit.

| line | $(R^4)_n$ | $(R^5)_m$ |
|---|---|---|
| B1-1369 | 2-CF$_3$ | 4-CO$_2$CH$_3$ |
| B1-1370 | 2-CF$_3$ | 2-CH$_3$ |
| B1-1371 | 2-CF$_3$ | 3-CH$_3$ |
| B1-1372 | 2-CF$_3$ | 4-CH$_3$ |
| B1-1373 | 2-CF$_3$ | 2-CF$_3$ |
| B1-1374 | 2-CF$_3$ | 3-CF$_3$ |
| B1-1375 | 2-CF$_3$ | 4-CF$_3$ |
| B1-1376 | 2-CF$_3$ | 2-CHF$_2$ |
| B1-1377 | 2-CF$_3$ | 3-CHF$_2$ |
| B1-1378 | 2-CF$_3$ | 4-CHF$_2$ |
| B1-1379 | 2-CF$_3$ | 2-OCH$_3$ |
| B1-1380 | 2-CF$_3$ | 3-OCH$_3$ |
| B1-1381 | 2-CF$_3$ | 4-OCH$_3$ |
| B1-1382 | 2-CF$_3$ | 2-OCF$_3$ |
| B1-1383 | 2-CF$_3$ | 3-OCF$_3$ |
| B1-1384 | 2-CF$_3$ | 4-OCF$_3$ |
| B1-1385 | 2-CF$_3$ | 2-OCHF$_2$ |
| B1-1386 | 2-CF$_3$ | 3-OCHF$_2$ |
| B1-1387 | 2-CF$_3$ | 4-OCHF$_2$ |
| B1-1388 | 2-CF$_3$ | 2,4,6-(CH$_3$)$_3$ |
| B1-1389 | 2-CF$_3$ | 2,3-Cl$_2$ |
| B1-1390 | 2-CF$_3$ | 2,4-Cl$_2$ |
| B1-1391 | 2-CF$_3$ | 2,5-Cl$_2$ |
| B1-1392 | 2-CF$_3$ | 3,4-Cl$_2$ |
| B1-1393 | 2-CF$_3$ | 3,5-Cl$_2$ |
| B1-1394 | 2-CF$_3$ | 2,6-Cl$_2$ |
| B1-1395 | 2-CF$_3$ | 2,3-F$_2$ |
| B1-1396 | 2-CF$_3$ | 2,4-F$_2$ |
| B1-1397 | 2-CF$_3$ | 2,5-F$_2$ |
| B1-1398 | 2-CF$_3$ | 3,4-F$_2$ |
| B1-1399 | 2-CF$_3$ | 3,5-F$_2$ |
| B1-1400 | 2-CF$_3$ | 2,6-F$_2$ |
| B1-1401 | 2-CF$_3$ | 2-CF$_3$-4-Cl |
| B1-1402 | 2-CF$_3$ | 2-CF$_3$-4-F |
| B1-1403 | 2-CF$_3$ | 2-Cl-4-CF$_3$ |
| B1-1404 | 2-CF$_3$ | 2-F-4-CF$_3$ |
| B1-1405 | 2-CF$_3$ | 2-CN-4-Cl |
| B1-1406 | 2-CF$_3$ | 2-CN-4-F |
| B1-1407 | 2-CF$_3$ | 2-Cl-4-CN |
| B1-1408 | 2-CF$_3$ | 2-F-4-CN |
| B1-1409 | 4-CF$_3$ | —* |
| B1-1410 | 4-CF$_3$ | 2-Cl |
| B1-1411 | 4-CF$_3$ | 3-Cl |
| B1-1412 | 4-CF$_3$ | 4-Cl |
| B1-1413 | 4-CF$_3$ | 2-F |
| B1-1414 | 4-CF$_3$ | 3-F |
| B1-1415 | 4-CF$_3$ | 4-F |
| B1-1416 | 4-CF$_3$ | 2-CN |
| B1-1417 | 4-CF$_3$ | 3-CN |
| B1-1418 | 4-CF$_3$ | 4-CN |
| B1-1419 | 4-CF$_3$ | 2-NO$_2$ |
| B1-1420 | 4-CF$_3$ | 3-NO$_2$ |
| B1-1421 | 4-CF$_3$ | 4-NO$_2$ |
| B1-1422 | 4-CF$_3$ | 2-SCH$_3$ |
| B1-1423 | 4-CF$_3$ | 3-SCH$_3$ |
| B1-1424 | 4-CF$_3$ | 4-SCH$_3$ |
| B1-1425 | 4-CF$_3$ | 2-SOCH$_3$ |
| B1-1426 | 4-CF$_3$ | 3-SOCH$_3$ |
| B1-1427 | 4-CF$_3$ | 4-SOCH$_3$ |
| B1-1428 | 4-CF$_3$ | 2-SO$_2$CH$_3$ |
| B1-1429 | 4-CF$_3$ | 3-SO$_2$CH$_3$ |
| B1-1430 | 4-CF$_3$ | 4-SO$_2$CH$_3$ |
| B1-1431 | 4-CF$_3$ | 2-CO$_2$CH$_3$ |
| B1-1432 | 4-CF$_3$ | 3-CO$_2$CH$_3$ |
| B1-1433 | 4-CF$_3$ | 4-CO$_2$CH$_3$ |
| B1-1434 | 4-CF$_3$ | 2-CH$_3$ |
| B1-1435 | 4-CF$_3$ | 3-CH$_3$ |
| B1-1436 | 4-CF$_3$ | 4-CH$_3$ |
| B1-1437 | 4-CF$_3$ | 2-CF$_3$ |
| B1-1438 | 4-CF$_3$ | 3-CF$_3$ |
| B1-1439 | 4-CF$_3$ | 4-CF$_3$ |
| B1-1440 | 4-CF$_3$ | 2-CHF$_2$ |
| B1-1441 | 4-CF$_3$ | 3-CHF$_2$ |
| B1-1442 | 4-CF$_3$ | 4-CHF$_2$ |
| B1-1443 | 4-CF$_3$ | 2-OCH$_3$ |
| B1-1444 | 4-CF$_3$ | 3-OCH$_3$ |
| B1-1445 | 4-CF$_3$ | 4-OCH$_3$ |
| B1-1446 | 4-CF$_3$ | 2-OCF$_3$ |
| B1-1447 | 4-CF$_3$ | 3-OCF$_3$ |
| B1-1448 | 4-CF$_3$ | 4-OCF$_3$ |
| B1-1449 | 4-CF$_3$ | 2-OCHF$_2$ |
| B1-1450 | 4-CF$_3$ | 3-OCHF$_2$ |
| B1-1451 | 4-CF$_3$ | 4-OCHF$_2$ |
| B1-1452 | 4-CF$_3$ | 2,4,6-(CH$_3$)$_3$ |
| B1-1453 | 4-CF$_3$ | 2,3-Cl$_2$ |
| B1-1454 | 4-CF$_3$ | 2,4-Cl$_2$ |
| B1-1455 | 4-CF$_3$ | 2,5-Cl$_2$ |
| B1-1456 | 4-CF$_3$ | 3,4-Cl$_2$ |
| B1-1457 | 4-CF$_3$ | 3,5-Cl$_2$ |
| B1-1458 | 4-CF$_3$ | 2,6-Cl$_2$ |
| B1-1459 | 4-CF$_3$ | 2,3-F$_2$ |
| B1-1460 | 4-CF$_3$ | 2,4-F$_2$ |
| B1-1461 | 4-CF$_3$ | 2,5-F$_2$ |
| B1-1462 | 4-CF$_3$ | 3,4-F$_2$ |
| B1-1463 | 4-CF$_3$ | 3,5-F$_2$ |
| B1-1464 | 4-CF$_3$ | 2,6-F$_2$ |
| B1-1465 | 4-CF$_3$ | 2-CF$_3$-4-Cl |
| B1-1466 | 4-CF$_3$ | 2-CF$_3$-4-F |
| B1-1467 | 4-CF$_3$ | 2-Cl-4-CF$_3$ |
| B1-1468 | 4-CF$_3$ | 2-F-4-CF$_3$ |
| B1-1469 | 4-CF$_3$ | 2-CN-4-Cl |
| B1-1470 | 4-CF$_3$ | 2-CN-4-F |
| B1-1471 | 4-CF$_3$ | 2-Cl-4-CN |
| B1-1472 | 4-CF$_3$ | 2-F-4-CN |
| B1-1473 | 5-CF$_3$ | —* |
| B1-1474 | 5-CF$_3$ | 2-Cl |
| B1-1475 | 5-CF$_3$ | 3-Cl |
| B1-1476 | 5-CF$_3$ | 4-Cl |
| B1-1477 | 5-CF$_3$ | 2-F |
| B1-1478 | 5-CF$_3$ | 3-F |
| B1-1479 | 5-CF$_3$ | 4-F |
| B1-1480 | 5-CF$_3$ | 2-CN |
| B1-1481 | 5-CF$_3$ | 3-CN |
| B1-1482 | 5-CF$_3$ | 4-CN |
| B1-1483 | 5-CF$_3$ | 2-NO$_2$ |
| B1-1484 | 5-CF$_3$ | 3-NO$_2$ |
| B1-1485 | 5-CF$_3$ | 4-NO$_2$ |
| B1-1486 | 5-CF$_3$ | 2-SCH$_3$ |
| B1-1487 | 5-CF$_3$ | 3-SCH$_3$ |
| B1-1488 | 5-CF$_3$ | 4-SCH$_3$ |
| B1-1489 | 5-CF$_3$ | 2-SOCH$_3$ |
| B1-1490 | 5-CF$_3$ | 3-SOCH$_3$ |
| B1-1491 | 5-CF$_3$ | 4-SOCH$_3$ |
| B1-1492 | 5-CF$_3$ | 2-SO$_2$CH$_3$ |
| B1-1493 | 5-CF$_3$ | 3-SO$_2$CH$_3$ |
| B1-1494 | 5-CF$_3$ | 4-SO$_2$CH$_3$ |
| B1-1495 | 5-CF$_3$ | 2-CO$_2$CH$_3$ |
| B1-1496 | 5-CF$_3$ | 3-CO$_2$CH$_3$ |
| B1-1497 | 5-CF$_3$ | 4-CO$_2$CH$_3$ |
| B1-1498 | 5-CF$_3$ | 2-CH$_3$ |
| B1-1499 | 5-CF$_3$ | 3-CH$_3$ |
| B1-1500 | 5-CF$_3$ | 4-CH$_3$ |
| B1-1501 | 5-CF$_3$ | 2-CF$_3$ |
| B1-1502 | 5-CF$_3$ | 3-CF$_3$ |
| B1-1503 | 5-CF$_3$ | 4-CF$_3$ |
| B1-1504 | 5-CF$_3$ | 2-CHF$_2$ |
| B1-1505 | 5-CF$_3$ | 3-CHF$_2$ |
| B1-1506 | 5-CF$_3$ | 4-CHF$_2$ |
| B1-1507 | 5-CF$_3$ | 2-OCH$_3$ |
| B1-1508 | 5-CF$_3$ | 3-OCH$_3$ |
| B1-1509 | 5-CF$_3$ | 4-OCH$_3$ |
| B1-1510 | 5-CF$_3$ | 2-OCF$_3$ |
| B1-1511 | 5-CF$_3$ | 3-OCF$_3$ |
| B1-1512 | 5-CF$_3$ | 4-OCF$_3$ |

TABLE B1-continued

For compounds where ZY is in meta-position. The position(s) of the substituent(s) $(R^4)_n$ is/are given in relation to the attachment of the isoxazole-unit. The position(s) of the substituent(s) $(R^5)_m$ is/are given in relation to the attachment of the phenyl to the O-phenyl-unit.

| line | $(R^4)_n$ | $(R^5)_m$ |
|---|---|---|
| B1-1513 | 5-$CF_3$ | 2-$OCHF_2$ |
| B1-1514 | 5-$CF_3$ | 3-$OCHF_2$ |
| B1-1515 | 5-$CF_3$ | 4-$OCHF_2$ |
| B1-1516 | 5-$CF_3$ | 2,4,6-$(CH_3)_3$ |
| B1-1517 | 5-$CF_3$ | 2,3-$Cl_2$ |
| B1-1518 | 5-$CF_3$ | 2,4-$Cl_2$ |
| B1-1519 | 5-$CF_3$ | 2,5-$Cl_2$ |
| B1-1520 | 5-$CF_3$ | 3,4-$Cl_2$ |
| B1-1521 | 5-$CF_3$ | 3,5-$Cl_2$ |
| B1-1522 | 5-$CF_3$ | 2,6-$Cl_2$ |
| B1-1523 | 5-$CF_3$ | 2,3-$F_2$ |
| B1-1524 | 5-$CF_3$ | 2,4-$F_2$ |
| B1-1525 | 5-$CF_3$ | 2,5-$F_2$ |
| B1-1526 | 5-$CF_3$ | 3,4-$F_2$ |
| B1-1527 | 5-$CF_3$ | 3,5-$F_2$ |
| B1-1528 | 5-$CF_3$ | 2,6-$F_2$ |
| B1-1529 | 5-$CF_3$ | 2-$CF_3$-4-Cl |
| B1-1530 | 5-$CF_3$ | 2-$CF_3$-4-F |
| B1-1531 | 5-$CF_3$ | 2-Cl-4-$CF_3$ |
| B1-1532 | 5-$CF_3$ | 2-F-4-$CF_3$ |
| B1-1533 | 5-$CF_3$ | 2-CN-4-Cl |
| B1-1534 | 5-$CF_3$ | 2-CN-4-F |
| B1-1535 | 5-$CF_3$ | 2-Cl-4-CN |
| B1-1536 | 5-$CF_3$ | 2-F-4-CN |
| B1-1537 | 6-$CF_3$ | —* |
| B1-1538 | 6-$CF_3$ | 2-Cl |
| B1-1539 | 6-$CF_3$ | 3-Cl |
| B1-1540 | 6-$CF_3$ | 4-Cl |
| B1-1541 | 6-$CF_3$ | 2-F |
| B1-1542 | 6-$CF_3$ | 3-F |
| B1-1543 | 6-$CF_3$ | 4-F |
| B1-1544 | 6-$CF_3$ | 2-CN |
| B1-1545 | 6-$CF_3$ | 3-CN |
| B1-1546 | 6-$CF_3$ | 4-CN |
| B1-1547 | 6-$CF_3$ | 2-$NO_2$ |
| B1-1548 | 6-$CF_3$ | 3-$NO_2$ |
| B1-1549 | 6-$CF_3$ | 4-$NO_2$ |
| B1-1550 | 6-$CF_3$ | 2-$SCH_3$ |
| B1-1551 | 6-$CF_3$ | 3-$SCH_3$ |
| B1-1552 | 6-$CF_3$ | 4-$SCH_3$ |
| B1-1553 | 6-$CF_3$ | 2-$SOCH_3$ |
| B1-1554 | 6-$CF_3$ | 3-$SOCH_3$ |
| B1-1555 | 6-$CF_3$ | 4-$SOCH_3$ |
| B1-1556 | 6-$CF_3$ | 2-$SO_2CH_3$ |
| B1-1557 | 6-$CF_3$ | 3-$SO_2CH_3$ |
| B1-1558 | 6-$CF_3$ | 4-$SO_2CH_3$ |
| B1-1559 | 6-$CF_3$ | 2-$CO_2CH_3$ |
| B1-1560 | 6-$CF_3$ | 3-$CO_2CH_3$ |
| B1-1561 | 6-$CF_3$ | 4-$CO_2CH_3$ |
| B1-1562 | 6-$CF_3$ | 2-$CH_3$ |
| B1-1563 | 6-$CF_3$ | 3-$CH_3$ |
| B1-1564 | 6-$CF_3$ | 4-$CH_3$ |
| B1-1565 | 6-$CF_3$ | 2-$CF_3$ |
| B1-1566 | 6-$CF_3$ | 3-$CF_3$ |
| B1-1567 | 6-$CF_3$ | 4-$CF_3$ |
| B1-1568 | 6-$CF_3$ | 2-$CHF_2$ |
| B1-1569 | 6-$CF_3$ | 3-$CHF_2$ |
| B1-1570 | 6-$CF_3$ | 4-$CHF_2$ |
| B1-1571 | 6-$CF_3$ | 2-$OCH_3$ |
| B1-1572 | 6-$CF_3$ | 3-$OCH_3$ |
| B1-1573 | 6-$CF_3$ | 4-$OCH_3$ |
| B1-1574 | 6-$CF_3$ | 2-$OCF_3$ |
| B1-1575 | 6-$CF_3$ | 3-$OCF_3$ |
| B1-1576 | 6-$CF_3$ | 4-$OCF_3$ |
| B1-1577 | 6-$CF_3$ | 2-$OCHF_2$ |
| B1-1578 | 6-$CF_3$ | 3-$OCHF_2$ |
| B1-1579 | 6-$CF_3$ | 4-$OCHF_2$ |
| B1-1580 | 6-$CF_3$ | 2,4,6-$(CH_3)_3$ |
| B1-1581 | 6-$CF_3$ | 2,3-$Cl_2$ |
| B1-1582 | 6-$CF_3$ | 2,4-$Cl_2$ |
| B1-1583 | 6-$CF_3$ | 2,5-$Cl_2$ |
| B1-1584 | 6-$CF_3$ | 3,4-$Cl_2$ |
| B1-1585 | 6-$CF_3$ | 3,5-$Cl_2$ |
| B1-1586 | 6-$CF_3$ | 2,6-$Cl_2$ |
| B1-1587 | 6-$CF_3$ | 2,3-$F_2$ |
| B1-1588 | 6-$CF_3$ | 2,4-$F_2$ |
| B1-1589 | 6-$CF_3$ | 2,5-$F_2$ |
| B1-1590 | 6-$CF_3$ | 3,4-$F_2$ |
| B1-1591 | 6-$CF_3$ | 3,5-$F_2$ |
| B1-1592 | 6-$CF_3$ | 2,6-$F_2$ |
| B1-1593 | 6-$CF_3$ | 2-$CF_3$-4-Cl |
| B1-1594 | 6-$CF_3$ | 2-$CF_3$-4-F |
| B1-1595 | 6-$CF_3$ | 2-Cl-4-$CF_3$ |
| B1-1596 | 6-$CF_3$ | 2-F-4-$CF_3$ |
| B1-1597 | 6-$CF_3$ | 2-CN-4-Cl |
| B1-1598 | 6-$CF_3$ | 2-CN-4-F |
| B1-1599 | 6-$CF_3$ | 2-Cl-4-CN |
| B1-1600 | 6-$CF_3$ | 2-F-4-CN |
| B1-1601 | 2-$CHF_2$ | —* |
| B1-1602 | 2-$CHF_2$ | 2-Cl |
| B1-1603 | 2-$CHF_2$ | 3-Cl |
| B1-1604 | 2-$CHF_2$ | 4-Cl |
| B1-1605 | 2-$CHF_2$ | 2-F |
| B1-1606 | 2-$CHF_2$ | 3-F |
| B1-1607 | 2-$CHF_2$ | 4-F |
| B1-1608 | 2-$CHF_2$ | 2-CN |
| B1-1609 | 2-$CHF_2$ | 3-CN |
| B1-1610 | 2-$CHF_2$ | 4-CN |
| B1-1611 | 2-$CHF_2$ | 2-$NO_2$ |
| B1-1612 | 2-$CHF_2$ | 3-$NO_2$ |
| B1-1613 | 2-$CHF_2$ | 4-$NO_2$ |
| B1-1614 | 2-$CHF_2$ | 2-$SCH_3$ |
| B1-1615 | 2-$CHF_2$ | 3-$SCH_3$ |
| B1-1616 | 2-$CHF_2$ | 4-$SCH_3$ |
| B1-1617 | 2-$CHF_2$ | 2-$SOCH_3$ |
| B1-1618 | 2-$CHF_2$ | 3-$SOCH_3$ |
| B1-1619 | 2-$CHF_2$ | 4-$SOCH_3$ |
| B1-1620 | 2-$CHF_2$ | 2-$SO_2CH_3$ |
| B1-1621 | 2-$CHF_2$ | 3-$SO_2CH_3$ |
| B1-1622 | 2-$CHF_2$ | 4-$SO_2CH_3$ |
| B1-1623 | 2-$CHF_2$ | 2-$CO_2CH_3$ |
| B1-1624 | 2-$CHF_2$ | 3-$CO_2CH_3$ |
| B1-1625 | 2-$CHF_2$ | 4-$CO_2CH_3$ |
| B1-1626 | 2-$CHF_2$ | 2-$CH_3$ |
| B1-1627 | 2-$CHF_2$ | 3-$CH_3$ |
| B1-1628 | 2-$CHF_2$ | 4-$CH_3$ |
| B1-1629 | 2-$CHF_2$ | 2-$CF_3$ |
| B1-1630 | 2-$CHF_2$ | 3-$CF_3$ |
| B1-1631 | 2-$CHF_2$ | 4-$CF_3$ |
| B1-1632 | 2-$CHF_2$ | 2-$CHF_2$ |
| B1-1633 | 2-$CHF_2$ | 3-$CHF_2$ |
| B1-1634 | 2-$CHF_2$ | 4-$CHF_2$ |
| B1-1635 | 2-$CHF_2$ | 2-$OCH_3$ |
| B1-1636 | 2-$CHF_2$ | 3-$OCH_3$ |
| B1-1637 | 2-$CHF_2$ | 4-$OCH_3$ |
| B1-1638 | 2-$CHF_2$ | 2-$OCF_3$ |
| B1-1639 | 2-$CHF_2$ | 3-$OCF_3$ |
| B1-1640 | 2-$CHF_2$ | 4-$OCF_3$ |
| B1-1641 | 2-$CHF_2$ | 2-$OCHF_2$ |
| B1-1642 | 2-$CHF_2$ | 3-$OCHF_2$ |
| B1-1643 | 2-$CHF_2$ | 4-$OCHF_2$ |
| B1-1644 | 2-$CHF_2$ | 2,4,6-$(CH_3)_3$ |
| B1-1645 | 2-$CHF_2$ | 2,3-$Cl_2$ |
| B1-1646 | 2-$CHF_2$ | 2,4-$Cl_2$ |
| B1-1647 | 2-$CHF_2$ | 2,5-$Cl_2$ |
| B1-1648 | 2-$CHF_2$ | 3,4-$Cl_2$ |
| B1-1649 | 2-$CHF_2$ | 3,5-$Cl_2$ |
| B1-1650 | 2-$CHF_2$ | 2,6-$Cl_2$ |
| B1-1651 | 2-$CHF_2$ | 2,3-$F_2$ |
| B1-1652 | 2-$CHF_2$ | 2,4-$F_2$ |
| B1-1653 | 2-$CHF_2$ | 2,5-$F_2$ |
| B1-1654 | 2-$CHF_2$ | 3,4-$F_2$ |
| B1-1655 | 2-$CHF_2$ | 3,5-$F_2$ |
| B1-1656 | 2-$CHF_2$ | 2,6-$F_2$ |

TABLE B1-continued

For compounds where ZY is in meta-position. The position(s) of the substituent(s) $(R^4)_n$ is/are given in relation to the attachment of the isoxazole-unit. The position(s) of the substituent(s) $(R^5)_m$ is/are given in relation to the attachment of the phenyl to the O-phenyl-unit.

| line | $(R^4)_n$ | $(R^5)_m$ |
|---|---|---|
| B1-1657 | 2-CHF$_2$ | 2-CF$_3$-4-Cl |
| B1-1658 | 2-CHF$_2$ | 2-CF$_3$-4-F |
| B1-1659 | 2-CHF$_2$ | 2-Cl-4-CF$_3$ |
| B1-1660 | 2-CHF$_2$ | 2-F-4-CF$_3$ |
| B1-1661 | 2-CHF$_2$ | 2-CN-4-Cl |
| B1-1662 | 2-CHF$_2$ | 2-CN-4-F |
| B1-1663 | 2-CHF$_2$ | 2-Cl-4-CN |
| B1-1664 | 2-CHF$_2$ | 2-F-4-CN |
| B1-1665 | 4-CHF$_2$ | —* |
| B1-1666 | 4-CHF$_2$ | 2-Cl |
| B1-1667 | 4-CHF$_2$ | 3-Cl |
| B1-1668 | 4-CHF$_2$ | 4-Cl |
| B1-1669 | 4-CHF$_2$ | 2-F |
| B1-1670 | 4-CHF$_2$ | 3-F |
| B1-1671 | 4-CHF$_2$ | 4-F |
| B1-1672 | 4-CHF$_2$ | 2-CN |
| B1-1673 | 4-CHF$_2$ | 3-CN |
| B1-1674 | 4-CHF$_2$ | 4-CN |
| B1-1675 | 4-CHF$_2$ | 2-NO$_2$ |
| B1-1676 | 4-CHF$_2$ | 3-NO$_2$ |
| B1-1677 | 4-CHF$_2$ | 4-NO$_2$ |
| B1-1678 | 4-CHF$_2$ | 2-SCH$_3$ |
| B1-1679 | 4-CHF$_2$ | 3-SCH$_3$ |
| B1-1680 | 4-CHF$_2$ | 4-SCH$_3$ |
| B1-1681 | 4-CHF$_2$ | 2-SOCH$_3$ |
| B1-1682 | 4-CHF$_2$ | 3-SOCH$_3$ |
| B1-1683 | 4-CHF$_2$ | 4-SOCH$_3$ |
| B1-1684 | 4-CHF$_2$ | 2-SO$_2$CH$_3$ |
| B1-1685 | 4-CHF$_2$ | 3-SO$_2$CH$_3$ |
| B1-1686 | 4-CHF$_2$ | 4-SO$_2$CH$_3$ |
| B1-1687 | 4-CHF$_2$ | 2-CO$_2$CH$_3$ |
| B1-1688 | 4-CHF$_2$ | 3-CO$_2$CH$_3$ |
| B1-1689 | 4-CHF$_2$ | 4-CO$_2$CH$_3$ |
| B1-1690 | 4-CHF$_2$ | 2-CH$_3$ |
| B1-1691 | 4-CHF$_2$ | 3-CH$_3$ |
| B1-1692 | 4-CHF$_2$ | 4-CH$_3$ |
| B1-1693 | 4-CHF$_2$ | 2-CF$_3$ |
| B1-1694 | 4-CHF$_2$ | 3-CF$_3$ |
| B1-1695 | 4-CHF$_2$ | 4-CF$_3$ |
| B1-1696 | 4-CHF$_2$ | 2-CHF$_2$ |
| B1-1697 | 4-CHF$_2$ | 3-CHF$_2$ |
| B1-1698 | 4-CHF$_2$ | 4-CHF$_2$ |
| B1-1699 | 4-CHF$_2$ | 2-OCH$_3$ |
| B1-1700 | 4-CHF$_2$ | 3-OCH$_3$ |
| B1-1701 | 4-CHF$_2$ | 4-OCH$_3$ |
| B1-1702 | 4-CHF$_2$ | 2-OCF$_3$ |
| B1-1703 | 4-CHF$_2$ | 3-OCF$_3$ |
| B1-1704 | 4-CHF$_2$ | 4-OCF$_3$ |
| B1-1705 | 4-CHF$_2$ | 2-OCHF$_2$ |
| B1-1706 | 4-CHF$_2$ | 3-OCHF$_2$ |
| B1-1707 | 4-CHF$_2$ | 4-OCHF$_2$ |
| B1-1708 | 4-CHF$_2$ | 2,4,6-(CH$_3$)$_3$ |
| B1-1709 | 4-CHF$_2$ | 2,3-Cl$_2$ |
| B1-1710 | 4-CHF$_2$ | 2,4-Cl$_2$ |
| B1-1711 | 4-CHF$_2$ | 2,5-Cl$_2$ |
| B1-1712 | 4-CHF$_2$ | 3,4-Cl$_2$ |
| B1-1713 | 4-CHF$_2$ | 3,5-Cl$_2$ |
| B1-1714 | 4-CHF$_2$ | 2,6-Cl$_2$ |
| B1-1715 | 4-CHF$_2$ | 2,3-F$_2$ |
| B1-1716 | 4-CHF$_2$ | 2,4-F$_2$ |
| B1-1717 | 4-CHF$_2$ | 2,5-F$_2$ |
| B1-1718 | 4-CHF$_2$ | 3,4-F$_2$ |
| B1-1719 | 4-CHF$_2$ | 3,5-F$_2$ |
| B1-1720 | 4-CHF$_2$ | 2,6-F$_2$ |
| B1-1721 | 4-CHF$_2$ | 2-CF$_3$-4-Cl |
| B1-1722 | 4-CHF$_2$ | 2-CF$_3$-4-F |
| B1-1723 | 4-CHF$_2$ | 2-Cl-4-CF$_3$ |
| B1-1724 | 4-CHF$_2$ | 2-F-4-CF$_3$ |
| B1-1725 | 4-CHF$_2$ | 2-CN-4-Cl |
| B1-1726 | 4-CHF$_2$ | 2-CN-4-F |
| B1-1727 | 4-CHF$_2$ | 2-Cl-4-CN |
| B1-1728 | 4-CHF$_2$ | 2-F-4-CN |
| B1-1729 | 5-CHF$_2$ | —* |
| B1-1730 | 5-CHF$_2$ | 2-Cl |
| B1-1731 | 5-CHF$_2$ | 3-Cl |
| B1-1732 | 5-CHF$_2$ | 4-Cl |
| B1-1733 | 5-CHF$_2$ | 2-F |
| B1-1734 | 5-CHF$_2$ | 3-F |
| B1-1735 | 5-CHF$_2$ | 4-F |
| B1-1736 | 5-CHF$_2$ | 2-CN |
| B1-1737 | 5-CHF$_2$ | 3-CN |
| B1-1738 | 5-CHF$_2$ | 4-CN |
| B1-1739 | 5-CHF$_2$ | 2-NO$_2$ |
| B1-1740 | 5-CHF$_2$ | 3-NO$_2$ |
| B1-1741 | 5-CHF$_2$ | 4-NO$_2$ |
| B1-1742 | 5-CHF$_2$ | 2-SCH$_3$ |
| B1-1743 | 5-CHF$_2$ | 3-SCH$_3$ |
| B1-1744 | 5-CHF$_2$ | 4-SCH$_3$ |
| B1-1745 | 5-CHF$_2$ | 2-SOCH$_3$ |
| B1-1746 | 5-CHF$_2$ | 3-SOCH$_3$ |
| B1-1747 | 5-CHF$_2$ | 4-SOCH$_3$ |
| B1-1748 | 5-CHF$_2$ | 2-SO$_2$CH$_3$ |
| B1-1749 | 5-CHF$_2$ | 3-SO$_2$CH$_3$ |
| B1-1750 | 5-CHF$_2$ | 4-SO$_2$CH$_3$ |
| B1-1751 | 5-CHF$_2$ | 2-CO$_2$CH$_3$ |
| B1-1752 | 5-CHF$_2$ | 3-CO$_2$CH$_3$ |
| B1-1753 | 5-CHF$_2$ | 4-CO$_2$CH$_3$ |
| B1-1754 | 5-CHF$_2$ | 2-CH$_3$ |
| B1-1755 | 5-CHF$_2$ | 3-CH$_3$ |
| B1-1756 | 5-CHF$_2$ | 4-CH$_3$ |
| B1-1757 | 5-CHF$_2$ | 2-CF$_3$ |
| B1-1758 | 5-CHF$_2$ | 3-CF$_3$ |
| B1-1759 | 5-CHF$_2$ | 4-CF$_3$ |
| B1-1760 | 5-CHF$_2$ | 2-CHF$_2$ |
| B1-1761 | 5-CHF$_2$ | 3-CHF$_2$ |
| B1-1762 | 5-CHF$_2$ | 4-CHF$_2$ |
| B1-1763 | 5-CHF$_2$ | 2-OCH$_3$ |
| B1-1764 | 5-CHF$_2$ | 3-OCH$_3$ |
| B1-1765 | 5-CHF$_2$ | 4-OCH$_3$ |
| B1-1766 | 5-CHF$_2$ | 2-OCF$_3$ |
| B1-1767 | 5-CHF$_2$ | 3-OCF$_3$ |
| B1-1768 | 5-CHF$_2$ | 4-OCF$_3$ |
| B1-1769 | 5-CHF$_2$ | 2-OCHF$_2$ |
| B1-1770 | 5-CHF$_2$ | 3-OCHF$_2$ |
| B1-1771 | 5-CHF$_2$ | 4-OCHF$_2$ |
| B1-1772 | 5-CHF$_2$ | 2,4,6-(CH$_3$)$_3$ |
| B1-1773 | 5-CHF$_2$ | 2,3-Cl$_2$ |
| B1-1774 | 5-CHF$_2$ | 2,4-Cl$_2$ |
| B1-1775 | 5-CHF$_2$ | 2,5-Cl$_2$ |
| B1-1776 | 5-CHF$_2$ | 3,4-Cl$_2$ |
| B1-1777 | 5-CHF$_2$ | 3,5-Cl$_2$ |
| B1-1778 | 5-CHF$_2$ | 2,6-Cl$_2$ |
| B1-1779 | 5-CHF$_2$ | 2,3-F$_2$ |
| B1-1780 | 5-CHF$_2$ | 2,4-F$_2$ |
| B1-1781 | 5-CHF$_2$ | 2,5-F$_2$ |
| B1-1782 | 5-CHF$_2$ | 3,4-F$_2$ |
| B1-1783 | 5-CHF$_2$ | 3,5-F$_2$ |
| B1-1784 | 5-CHF$_2$ | 2,6-F$_2$ |
| B1-1785 | 5-CHF$_2$ | 2-CF$_3$-4-Cl |
| B1-1786 | 5-CHF$_2$ | 2-CF$_3$-4-F |
| B1-1787 | 5-CHF$_2$ | 2-Cl-4-CF$_3$ |
| B1-1788 | 5-CHF$_2$ | 2-F-4-CF$_3$ |
| B1-1789 | 5-CHF$_2$ | 2-CN-4-Cl |
| B1-1790 | 5-CHF$_2$ | 2-CN-4-F |
| B1-1791 | 5-CHF$_2$ | 2-Cl-4-CN |
| B1-1792 | 5-CHF$_2$ | 2-F-4-CN |
| B1-1793 | 6-CHF$_2$ | —* |
| B1-1794 | 6-CHF$_2$ | 2-Cl |
| B1-1795 | 6-CHF$_2$ | 3-Cl |
| B1-1796 | 6-CHF$_2$ | 4-Cl |
| B1-1797 | 6-CHF$_2$ | 2-F |
| B1-1798 | 6-CHF$_2$ | 3-F |
| B1-1799 | 6-CHF$_2$ | 4-F |
| B1-1800 | 6-CHF$_2$ | 2-CN |

TABLE B1-continued

For compounds where ZY is in meta-position. The position(s) of the substituent(s) $(R^4)_n$ is/are given in relation to the attachment of the isoxazole-unit. The position(s) of the substituent(s) $(R^5)_m$ is/are given in relation to the attachment of the phenyl to the O-phenyl-unit.

| line | $(R^4)_n$ | $(R^5)_m$ |
|---|---|---|
| B1-1801 | 6-CHF$_2$ | 3-CN |
| B1-1802 | 6-CHF$_2$ | 4-CN |
| B1-1803 | 6-CHF$_2$ | 2-NO$_2$ |
| B1-1804 | 6-CHF$_2$ | 3-NO$_2$ |
| B1-1805 | 6-CHF$_2$ | 4-NO$_2$ |
| B1-1806 | 6-CHF$_2$ | 2-SCH$_3$ |
| B1-1807 | 6-CHF$_2$ | 3-SCH$_3$ |
| B1-1808 | 6-CHF$_2$ | 4-SCH$_3$ |
| B1-1809 | 6-CHF$_2$ | 2-SOCH$_3$ |
| B1-1810 | 6-CHF$_2$ | 3-SOCH$_3$ |
| B1-1811 | 6-CHF$_2$ | 4-SOCH$_3$ |
| B1-1812 | 6-CHF$_2$ | 2-SO$_2$CH$_3$ |
| B1-1813 | 6-CHF$_2$ | 3-SO$_2$CH$_3$ |
| B1-1814 | 6-CHF$_2$ | 4-SO$_2$CH$_3$ |
| B1-1815 | 6-CHF$_2$ | 2-CO$_2$CH$_3$ |
| B1-1816 | 6-CHF$_2$ | 3-CO$_2$CH$_3$ |
| B1-1817 | 6-CHF$_2$ | 4-CO$_2$CH$_3$ |
| B1-1818 | 6-CHF$_2$ | 2-CH$_3$ |
| B1-1819 | 6-CHF$_2$ | 3-CH$_3$ |
| B1-1820 | 6-CHF$_2$ | 4-CH$_3$ |
| B1-1821 | 6-CHF$_2$ | 2-CF$_3$ |
| B1-1822 | 6-CHF$_2$ | 3-CF$_3$ |
| B1-1823 | 6-CHF$_2$ | 4-CF$_3$ |
| B1-1824 | 6-CHF$_2$ | 2-CHF$_2$ |
| B1-1825 | 6-CHF$_2$ | 3-CHF$_2$ |
| B1-1826 | 6-CHF$_2$ | 4-CHF$_2$ |
| B1-1827 | 6-CHF$_2$ | 2-OCH$_3$ |
| B1-1828 | 6-CHF$_2$ | 3-OCH$_3$ |
| B1-1829 | 6-CHF$_2$ | 4-OCH$_3$ |
| B1-1830 | 6-CHF$_2$ | 2-OCF$_3$ |
| B1-1831 | 6-CHF$_2$ | 3-OCF$_3$ |
| B1-1832 | 6-CHF$_2$ | 4-OCF$_3$ |
| B1-1833 | 6-CHF$_2$ | 2-OCHF$_2$ |
| B1-1834 | 6-CHF$_2$ | 3-OCHF$_2$ |
| B1-1835 | 6-CHF$_2$ | 4-OCHF$_2$ |
| B1-1836 | 6-CHF$_2$ | 2,4,6-(CH$_3$)$_3$ |
| B1-1837 | 6-CHF$_2$ | 2,3-Cl$_2$ |
| B1-1838 | 6-CHF$_2$ | 2,4-Cl$_2$ |
| B1-1839 | 6-CHF$_2$ | 2,5-Cl$_2$ |
| B1-1840 | 6-CHF$_2$ | 3,4-Cl$_2$ |
| B1-1841 | 6-CHF$_2$ | 3,5-Cl$_2$ |
| B1-1842 | 6-CHF$_2$ | 2,6-Cl$_2$ |
| B1-1843 | 6-CHF$_2$ | 2,3-F$_2$ |
| B1-1844 | 6-CHF$_2$ | 2,4-F$_2$ |
| B1-1845 | 6-CHF$_2$ | 2,5-F$_2$ |
| B1-1846 | 6-CHF$_2$ | 3,4-F$_2$ |
| B1-1847 | 6-CHF$_2$ | 3,5-F$_2$ |
| B1-1848 | 6-CHF$_2$ | 2,6-F$_2$ |
| B1-1849 | 6-CHF$_2$ | 2-CF$_3$-4-Cl |
| B1-1850 | 6-CHF$_2$ | 2-CF$_3$-4-F |
| B1-1851 | 6-CHF$_2$ | 2-Cl-4-CF$_3$ |
| B1-1852 | 6-CHF$_2$ | 2-F-4-CF$_3$ |
| B1-1853 | 6-CHF$_2$ | 2-CN-4-Cl |
| B1-1854 | 6-CHF$_2$ | 2-CN-4-F |
| B1-1855 | 6-CHF$_2$ | 2-Cl-4-CN |
| B1-1856 | 6-CHF$_2$ | 2-F-4-CN |
| B1-1857 | 2-OCH$_3$ | —* |
| B1-1858 | 2-OCH$_3$ | 2-Cl |
| B1-1859 | 2-OCH$_3$ | 3-Cl |
| B1-1860 | 2-OCH$_3$ | 4-Cl |
| B1-1861 | 2-OCH$_3$ | 2-F |
| B1-1862 | 2-OCH$_3$ | 3-F |
| B1-1863 | 2-OCH$_3$ | 4-F |
| B1-1864 | 2-OCH$_3$ | 2-CN |
| B1-1865 | 2-OCH$_3$ | 3-CN |
| B1-1866 | 2-OCH$_3$ | 4-CN |
| B1-1867 | 2-OCH$_3$ | 2-NO$_2$ |
| B1-1868 | 2-OCH$_3$ | 3-NO$_2$ |
| B1-1869 | 2-OCH$_3$ | 4-NO$_2$ |
| B1-1870 | 2-OCH$_3$ | 2-SCH$_3$ |
| B1-1871 | 2-OCH$_3$ | 3-SCH$_3$ |
| B1-1872 | 2-OCH$_3$ | 4-SCH$_3$ |
| B1-1873 | 2-OCH$_3$ | 2-SOCH$_3$ |
| B1-1874 | 2-OCH$_3$ | 3-SOCH$_3$ |
| B1-1875 | 2-OCH$_3$ | 4-SOCH$_3$ |
| B1-1876 | 2-OCH$_3$ | 2-SO$_2$CH$_3$ |
| B1-1877 | 2-OCH$_3$ | 3-SO$_2$CH$_3$ |
| B1-1878 | 2-OCH$_3$ | 4-SO$_2$CH$_3$ |
| B1-1879 | 2-OCH$_3$ | 2-CO$_2$CH$_3$ |
| B1-1880 | 2-OCH$_3$ | 3-CO$_2$CH$_3$ |
| B1-1881 | 2-OCH$_3$ | 4-CO$_2$CH$_3$ |
| B1-1882 | 2-OCH$_3$ | 2-CH$_3$ |
| B1-1883 | 2-OCH$_3$ | 3-CH$_3$ |
| B1-1884 | 2-OCH$_3$ | 4-CH$_3$ |
| B1-1885 | 2-OCH$_3$ | 2-CF$_3$ |
| B1-1886 | 2-OCH$_3$ | 3-CF$_3$ |
| B1-1887 | 2-OCH$_3$ | 4-CF$_3$ |
| B1-1888 | 2-OCH$_3$ | 2-CHF$_2$ |
| B1-1889 | 2-OCH$_3$ | 3-CHF$_2$ |
| B1-1890 | 2-OCH$_3$ | 4-CHF$_2$ |
| B1-1891 | 2-OCH$_3$ | 2-OCH$_3$ |
| B1-1892 | 2-OCH$_3$ | 3-OCH$_3$ |
| B1-1893 | 2-OCH$_3$ | 4-OCH$_3$ |
| B1-1894 | 2-OCH$_3$ | 2-OCF$_3$ |
| B1-1895 | 2-OCH$_3$ | 3-OCF$_3$ |
| B1-1896 | 2-OCH$_3$ | 4-OCF$_3$ |
| B1-1897 | 2-OCH$_3$ | 2-OCHF$_2$ |
| B1-1898 | 2-OCH$_3$ | 3-OCHF$_2$ |
| B1-1899 | 2-OCH$_3$ | 4-OCHF$_2$ |
| B1-1900 | 2-OCH$_3$ | 2,4,6-(CH$_3$)$_3$ |
| B1-1901 | 2-OCH$_3$ | 2,3-Cl$_2$ |
| B1-1902 | 2-OCH$_3$ | 2,4-Cl$_2$ |
| B1-1903 | 2-OCH$_3$ | 2,5-Cl$_2$ |
| B1-1904 | 2-OCH$_3$ | 3,4-Cl$_2$ |
| B1-1905 | 2-OCH$_3$ | 3,5-Cl$_2$ |
| B1-1906 | 2-OCH$_3$ | 2,6-Cl$_2$ |
| B1-1907 | 2-OCH$_3$ | 2,3-F$_2$ |
| B1-1908 | 2-OCH$_3$ | 2,4-F$_2$ |
| B1-1909 | 2-OCH$_3$ | 2,5-F$_2$ |
| B1-1910 | 2-OCH$_3$ | 3,4-F$_2$ |
| B1-1911 | 2-OCH$_3$ | 3,5-F$_2$ |
| B1-1912 | 2-OCH$_3$ | 2,6-F$_2$ |
| B1-1913 | 2-OCH$_3$ | 2-CF$_3$-4-Cl |
| B1-1914 | 2-OCH$_3$ | 2-CF$_3$-4-F |
| B1-1915 | 2-OCH$_3$ | 2-Cl-4-CF$_3$ |
| B1-1916 | 2-OCH$_3$ | 2-F-4-CF$_3$ |
| B1-1917 | 2-OCH$_3$ | 2-CN-4-Cl |
| B1-1918 | 2-OCH$_3$ | 2-CN-4-F |
| B1-1919 | 2-OCH$_3$ | 2-Cl-4-CN |
| B1-1920 | 2-OCH$_3$ | 2-F-4-CN |
| B1-1921 | 4-OCH$_3$ | —* |
| B1-1922 | 4-OCH$_3$ | 2-Cl |
| B1-1923 | 4-OCH$_3$ | 3-Cl |
| B1-1924 | 4-OCH$_3$ | 4-Cl |
| B1-1925 | 4-OCH$_3$ | 2-F |
| B1-1926 | 4-OCH$_3$ | 3-F |
| B1-1927 | 4-OCH$_3$ | 4-F |
| B1-1928 | 4-OCH$_3$ | 2-CN |
| B1-1929 | 4-OCH$_3$ | 3-CN |
| B1-1930 | 4-OCH$_3$ | 4-CN |
| B1-1931 | 4-OCH$_3$ | 2-NO$_2$ |
| B1-1932 | 4-OCH$_3$ | 3-NO$_2$ |
| B1-1933 | 4-OCH$_3$ | 4-NO$_2$ |
| B1-1934 | 4-OCH$_3$ | 2-SCH$_3$ |
| B1-1935 | 4-OCH$_3$ | 3-SCH$_3$ |
| B1-1936 | 4-OCH$_3$ | 4-SCH$_3$ |
| B1-1937 | 4-OCH$_3$ | 2-SOCH$_3$ |
| B1-1938 | 4-OCH$_3$ | 3-SOCH$_3$ |
| B1-1939 | 4-OCH$_3$ | 4-SOCH$_3$ |
| B1-1940 | 4-OCH$_3$ | 2-SO$_2$CH$_3$ |
| B1-1941 | 4-OCH$_3$ | 3-SO$_2$CH$_3$ |
| B1-1942 | 4-OCH$_3$ | 4-SO$_2$CH$_3$ |
| B1-1943 | 4-OCH$_3$ | 2-CO$_2$CH$_3$ |
| B1-1944 | 4-OCH$_3$ | 3-CO$_2$CH$_3$ |

TABLE B1-continued

For compounds where ZY is in meta-position. The position(s) of the substituent(s) $(R^4)_n$ is/are given in relation to the attachment of the isoxazole-unit. The position(s) of the substituent(s) $(R^5)_m$ is/are given in relation to the attachment of the phenyl to the O-phenyl-unit.

| line | $(R^4)_n$ | $(R^5)_m$ |
|---|---|---|
| B1-1945 | 4-OCH$_3$ | 4-CO$_2$CH$_3$ |
| B1-1946 | 4-OCH$_3$ | 2-CH$_3$ |
| B1-1947 | 4-OCH$_3$ | 3-CH$_3$ |
| B1-1948 | 4-OCH$_3$ | 4-CH$_3$ |
| B1-1949 | 4-OCH$_3$ | 2-CF$_3$ |
| B1-1950 | 4-OCH$_3$ | 3-CF$_3$ |
| B1-1951 | 4-OCH$_3$ | 4-CF$_3$ |
| B1-1952 | 4-OCH$_3$ | 2-CHF$_2$ |
| B1-1953 | 4-OCH$_3$ | 3-CHF$_2$ |
| B1-1954 | 4-OCH$_3$ | 4-CHF$_2$ |
| B1-1955 | 4-OCH$_3$ | 2-OCH$_3$ |
| B1-1956 | 4-OCH$_3$ | 3-OCH$_3$ |
| B1-1957 | 4-OCH$_3$ | 4-OCH$_3$ |
| B1-1958 | 4-OCH$_3$ | 2-OCF$_3$ |
| B1-1959 | 4-OCH$_3$ | 3-OCF$_3$ |
| B1-1960 | 4-OCH$_3$ | 4-OCF$_3$ |
| B1-1961 | 4-OCH$_3$ | 2-OCHF$_2$ |
| B1-1962 | 4-OCH$_3$ | 3-OCHF$_2$ |
| B1-1963 | 4-OCH$_3$ | 4-OCHF$_2$ |
| B1-1964 | 4-OCH$_3$ | 2,4,6-(CH$_3$)$_3$ |
| B1-1965 | 4-OCH$_3$ | 2,3-Cl$_2$ |
| B1-1966 | 4-OCH$_3$ | 2,4-Cl$_2$ |
| B1-1967 | 4-OCH$_3$ | 2,5-Cl$_2$ |
| B1-1968 | 4-OCH$_3$ | 3,4-Cl$_2$ |
| B1-1969 | 4-OCH$_3$ | 3,5-Cl$_2$ |
| B1-1970 | 4-OCH$_3$ | 2,6-Cl$_2$ |
| B1-1971 | 4-OCH$_3$ | 2,3-F$_2$ |
| B1-1972 | 4-OCH$_3$ | 2,4-F$_2$ |
| B1-1973 | 4-OCH$_3$ | 2,5-F$_2$ |
| B1-1974 | 4-OCH$_3$ | 3,4-F$_2$ |
| B1-1975 | 4-OCH$_3$ | 3,5-F$_2$ |
| B1-1976 | 4-OCH$_3$ | 2,6-F$_2$ |
| B1-1977 | 4-OCH$_3$ | 2-CF$_3$-4-Cl |
| B1-1978 | 4-OCH$_3$ | 2-CF$_3$-4-F |
| B1-1979 | 4-OCH$_3$ | 2-Cl-4-CF$_3$ |
| B1-1980 | 4-OCH$_3$ | 2-F-4-CF$_3$ |
| B1-1981 | 4-OCH$_3$ | 2-CN-4-Cl |
| B1-1982 | 4-OCH$_3$ | 2-CN-4-F |
| B1-1983 | 4-OCH$_3$ | 2-Cl-4-CN |
| B1-1984 | 4-OCH$_3$ | 2-F-4-CN |
| B1-1985 | 5-OCH$_3$ | —* |
| B1-1986 | 5-OCH$_3$ | 2-Cl |
| B1-1987 | 5-OCH$_3$ | 3-Cl |
| B1-1988 | 5-OCH$_3$ | 4-Cl |
| B1-1989 | 5-OCH$_3$ | 2-F |
| B1-1990 | 5-OCH$_3$ | 3-F |
| B1-1991 | 5-OCH$_3$ | 4-F |
| B1-1992 | 5-OCH$_3$ | 2-CN |
| B1-1993 | 5-OCH$_3$ | 3-CN |
| B1-1994 | 5-OCH$_3$ | 4-CN |
| B1-1995 | 5-OCH$_3$ | 2-NO$_2$ |
| B1-1996 | 5-OCH$_3$ | 3-NO$_2$ |
| B1-1997 | 5-OCH$_3$ | 4-NO$_2$ |
| B1-1998 | 5-OCH$_3$ | 2-SCH$_3$ |
| B1-1999 | 5-OCH$_3$ | 3-SCH$_3$ |
| B1-2000 | 5-OCH$_3$ | 4-SCH$_3$ |
| B1-2001 | 5-OCH$_3$ | 2-SOCH$_3$ |
| B1-2002 | 5-OCH$_3$ | 3-SOCH$_3$ |
| B1-2003 | 5-OCH$_3$ | 4-SOCH$_3$ |
| B1-2004 | 5-OCH$_3$ | 2-SO$_2$CH$_3$ |
| B1-2005 | 5-OCH$_3$ | 3-SO$_2$CH$_3$ |
| B1-2006 | 5-OCH$_3$ | 4-SO$_2$CH$_3$ |
| B1-2007 | 5-OCH$_3$ | 2-CO$_2$CH$_3$ |
| B1-2008 | 5-OCH$_3$ | 3-CO$_2$CH$_3$ |
| B1-2009 | 5-OCH$_3$ | 4-CO$_2$CH$_3$ |
| B1-2010 | 5-OCH$_3$ | 2-CH$_3$ |
| B1-2011 | 5-OCH$_3$ | 3-CH$_3$ |
| B1-2012 | 5-OCH$_3$ | 4-CH$_3$ |
| B1-2013 | 5-OCH$_3$ | 2-CF$_3$ |
| B1-2014 | 5-OCH$_3$ | 3-CF$_3$ |
| B1-2015 | 5-OCH$_3$ | 4-CF$_3$ |
| B1-2016 | 5-OCH$_3$ | 2-CHF$_2$ |
| B1-2017 | 5-OCH$_3$ | 3-CHF$_2$ |
| B1-2018 | 5-OCH$_3$ | 4-CHF$_2$ |
| B1-2019 | 5-OCH$_3$ | 2-OCH$_3$ |
| B1-2020 | 5-OCH$_3$ | 3-OCH$_3$ |
| B1-2021 | 5-OCH$_3$ | 4-OCH$_3$ |
| B1-2022 | 5-OCH$_3$ | 2-OCF$_3$ |
| B1-2023 | 5-OCH$_3$ | 3-OCF$_3$ |
| B1-2024 | 5-OCH$_3$ | 4-OCF$_3$ |
| B1-2025 | 5-OCH$_3$ | 2-OCHF$_2$ |
| B1-2026 | 5-OCH$_3$ | 3-OCHF$_2$ |
| B1-2027 | 5-OCH$_3$ | 4-OCHF$_2$ |
| B1-2028 | 5-OCH$_3$ | 2,4,6-(CH$_3$)$_3$ |
| B1-2029 | 5-OCH$_3$ | 2,3-Cl$_2$ |
| B1-2030 | 5-OCH$_3$ | 2,4-Cl$_2$ |
| B1-2031 | 5-OCH$_3$ | 2,5-Cl$_2$ |
| B1-2032 | 5-OCH$_3$ | 3,4-Cl$_2$ |
| B1-2033 | 5-OCH$_3$ | 3,5-Cl$_2$ |
| B1-2034 | 5-OCH$_3$ | 2,6-Cl$_2$ |
| B1-2035 | 5-OCH$_3$ | 2,3-F$_2$ |
| B1-2036 | 5-OCH$_3$ | 2,4-F$_2$ |
| B1-2037 | 5-OCH$_3$ | 2,5-F$_2$ |
| B1-2038 | 5-OCH$_3$ | 3,4-F$_2$ |
| B1-2039 | 5-OCH$_3$ | 3,5-F$_2$ |
| B1-2040 | 5-OCH$_3$ | 2,6-F$_2$ |
| B1-2041 | 5-OCH$_3$ | 2-CF$_3$-4-Cl |
| B1-2042 | 5-OCH$_3$ | 2-CF$_3$-4-F |
| B1-2043 | 5-OCH$_3$ | 2-Cl-4-CF$_3$ |
| B1-2044 | 5-OCH$_3$ | 2-F-4-CF$_3$ |
| B1-2045 | 5-OCH$_3$ | 2-CN-4-Cl |
| B1-2046 | 5-OCH$_3$ | 2-CN-4-F |
| B1-2047 | 5-OCH$_3$ | 2-Cl-4-CN |
| B1-2048 | 5-OCH$_3$ | 2-F-4-CN |
| B1-2049 | 6-OCH$_3$ | —* |
| B1-2050 | 6-OCH$_3$ | 2-Cl |
| B1-2051 | 6-OCH$_3$ | 3-Cl |
| B1-2052 | 6-OCH$_3$ | 4-Cl |
| B1-2053 | 6-OCH$_3$ | 2-F |
| B1-2054 | 6-OCH$_3$ | 3-F |
| B1-2055 | 6-OCH$_3$ | 4-F |
| B1-2056 | 6-OCH$_3$ | 2-CN |
| B1-2057 | 6-OCH$_3$ | 3-CN |
| B1-2058 | 6-OCH$_3$ | 4-CN |
| B1-2059 | 6-OCH$_3$ | 2-NO$_2$ |
| B1-2060 | 6-OCH$_3$ | 3-NO$_2$ |
| B1-2061 | 6-OCH$_3$ | 4-NO$_2$ |
| B1-2062 | 6-OCH$_3$ | 2-SCH$_3$ |
| B1-2063 | 6-OCH$_3$ | 3-SCH$_3$ |
| B1-2064 | 6-OCH$_3$ | 4-SCH$_3$ |
| B1-2065 | 6-OCH$_3$ | 2-SOCH$_3$ |
| B1-2066 | 6-OCH$_3$ | 3-SOCH$_3$ |
| B1-2067 | 6-OCH$_3$ | 4-SOCH$_3$ |
| B1-2068 | 6-OCH$_3$ | 2-SO$_2$CH$_3$ |
| B1-2069 | 6-OCH$_3$ | 3-SO$_2$CH$_3$ |
| B1-2070 | 6-OCH$_3$ | 4-SO$_2$CH$_3$ |
| B1-2071 | 6-OCH$_3$ | 2-CO$_2$CH$_3$ |
| B1-2072 | 6-OCH$_3$ | 3-CO$_2$CH$_3$ |
| B1-2073 | 6-OCH$_3$ | 4-CO$_2$CH$_3$ |
| B1-2074 | 6-OCH$_3$ | 2-CH$_3$ |
| B1-2075 | 6-OCH$_3$ | 3-CH$_3$ |
| B1-2076 | 6-OCH$_3$ | 4-CH$_3$ |
| B1-2077 | 6-OCH$_3$ | 2-CF$_3$ |
| B1-2078 | 6-OCH$_3$ | 3-CF$_3$ |
| B1-2079 | 6-OCH$_3$ | 4-CF$_3$ |
| B1-2080 | 6-OCH$_3$ | 2-CHF$_2$ |
| B1-2081 | 6-OCH$_3$ | 3-CHF$_2$ |
| B1-2082 | 6-OCH$_3$ | 4-CHF$_2$ |
| B1-2083 | 6-OCH$_3$ | 2-OCH$_3$ |
| B1-2084 | 6-OCH$_3$ | 3-OCH$_3$ |
| B1-2085 | 6-OCH$_3$ | 4-OCH$_3$ |
| B1-2086 | 6-OCH$_3$ | 2-OCF$_3$ |
| B1-2087 | 6-OCH$_3$ | 3-OCF$_3$ |
| B1-2088 | 6-OCH$_3$ | 4-OCF$_3$ |

TABLE B1-continued

For compounds where ZY is in meta-position. The position(s) of the substituent(s) $(R^4)_n$ is/are given in relation to the attachment of the isoxazole-unit. The position(s) of the substituent (s) $(R^5)_m$ is/are given in relation to the attachment of the phenyl to the O-phenyl-unit.

| line | $(R^4)_n$ | $(R^5)_m$ |
| --- | --- | --- |
| B1-2089 | 6-OCH$_3$ | 2-OCHF$_2$ |
| B1-2090 | 6-OCH$_3$ | 3-OCHF$_2$ |
| B1-2091 | 6-OCH$_3$ | 4-OCHF$_2$ |
| B1-2092 | 6-OCH$_3$ | 2,4,6-(CH$_3$)$_3$ |
| B1-2093 | 6-OCH$_3$ | 2,3-Cl$_2$ |
| B1-2094 | 6-OCH$_3$ | 2,4-Cl$_2$ |
| B1-2095 | 6-OCH$_3$ | 2,5-Cl$_2$ |
| B1-2096 | 6-OCH$_3$ | 3,4-Cl$_2$ |
| B1-2097 | 6-OCH$_3$ | 3,5-Cl$_2$ |
| B1-2098 | 6-OCH$_3$ | 2,6-Cl$_2$ |
| B1-2099 | 6-OCH$_3$ | 2,3-F$_2$ |
| B1-2100 | 6-OCH$_3$ | 2,4-F$_2$ |
| B1-2101 | 6-OCH$_3$ | 2,5-F$_2$ |
| B1-2102 | 6-OCH$_3$ | 3,4-F$_2$ |
| B1-2103 | 6-OCH$_3$ | 3,5-F$_2$ |
| B1-2104 | 6-OCH$_3$ | 2,6-F$_2$ |
| B1-2105 | 6-OCH$_3$ | 2-CF$_3$-4-Cl |
| B1-2106 | 6-OCH$_3$ | 2-CF$_3$-4-F |
| B1-2107 | 6-OCH$_3$ | 2-Cl-4-CF$_3$ |
| B1-2108 | 6-OCH$_3$ | 2-F-4-CF$_3$ |
| B1-2109 | 6-OCH$_3$ | 2-CN-4-Cl |
| B1-2110 | 6-OCH$_3$ | 2-CN-4-F |
| B1-2111 | 6-OCH$_3$ | 2-Cl-4-CN |
| B1-2112 | 6-OCH$_3$ | 2-F-4-CN |

*means that m = 0

The compound I and the compositions according to the invention, respectively, are suitable as fungicides.

Consequently, according to a further aspect, the present invention relates to the use of compounds of formula I, the N-oxides and the agriculturally acceptable salts thereof or of the compositions of the invention for combating phytopathogenic fungi.

Accordingly, the present invention also encompasses a method for combating harmful fungi, comprising treating the fungi or the materials, plants, the soil or seeds to be protected against fungal attack with an effective amount of at least one compound of formula I or with a composition comprising according to the invention.

They are distinguished by an outstanding effectiveness against a broad spectrum of phytopathogenic fungi, including soil-borne fungi, which derive especially from the classes of the Plasmodiophoromycetes, Peronosporomycetes (syn. Oomycetes), Chytridio$_n$cetes, Zygo$_n$cetes, Ascomycetes, Basidio$_n$cetes and Deutero$_n$cetes (syn. Fungi imperfecti). Some are systemically effective and they can be used in crop protection as foliar fungicides, fungicides for seed dressing and soil fungicides. Moreover, they are suitable for controlling harmful fungi, which inter alia occur in wood or roots of plants.

The compound I and the compositions according to the invention are particularly important in the control of a multitude of phytopathogenic fungi on various cultivated plants, such as cereals, e. g. wheat, rye, barley, triticale, oats or rice; beet, e. g. sugar beet or fodder beet; fruits, such as pomes, stone fruits or soft fruits, e. g. apples, pears, plums, peaches, almonds, cherries, strawberries, raspberries, blackberries or gooseberries; leguminous plants, such as lentils, peas, alfalfa or soybeans; oil plants, such as rape, mustard, olives, sunflowers, coconut, cocoa beans, castor oil plants, oil palms, ground nuts or soybeans; cucurbits, such as squashes, cucumber or melons; fiber plants, such as cotton, flax, hemp or jute; citrus fruit, such as oranges, lemons, grapefruits or mandarins; vegetables, such as spinach, lettuce, asparagus, cabbages, carrots, onions, tomatoes, potatoes, cucurbits or paprika; lauraceous plants, such as avocados, cinnamon or camphor; energy and raw material plants, such as corn, soybean, rape, sugar cane or oil palm; corn; tobacco; nuts; coffee; tea; bananas; vines (table grapes and grape juice grape vines); hop; turf; sweet leaf (also called *Stevia*); natural rubber plants or ornamental and forestry plants, such as flowers, shrubs, broad-leaved trees or evergreens, e. g. conifers; and on the plant propagation material, such as seeds, and the crop material of these plants.

Preferably, compound I and compositions thereof, respectively are used for controlling a multitude of fungi on field crops, such as potatoes sugar beets, tobacco, wheat, rye, barley, oats, rice, corn, cotton, soybeans, rape, legumes, sunflowers, coffee or sugar cane; fruits; vines; ornamentals; or vegetables, such as cucumbers, tomatoes, beans or squashes.

The term "plant propagation material" is to be understood to denote all the generative parts of the plant such as seeds and vegetative plant material such as cuttings and tubers (e. g. potatoes), which can be used for the multiplication of the plant. This includes seeds, roots, fruits, tubers, bulbs, rhizomes, shoots, sprouts and other parts of plants, including seedlings and young plants, which are to be transplanted after germination or after emergence from soil. These young plants may also be protected before transplantation by a total or partial treatment by immersion or pouring.

Preferably, treatment of plant propagation materials with compound I and compositions thereof, respectively, is used for controlling a multitude of fungi on cereals, such as wheat, rye, barley and oats; rice, corn, cotton and soybeans.

The term "cultivated plants" is to be understood as including plants which have been modified by breeding, mutagenesis or genetic engineering including but not limiting to agricultural biotech products on the market or in development (cf. http://cera-gmc.org/, see GM crop database therein). Genetically modified plants are plants, which genetic material has been so modified by the use of recombinant DNA techniques that under natural circumstances cannot readily be obtained by cross breeding, mutations or natural recombination. Typically, one or more genes have been integrated into the genetic material of a genetically modified plant in order to improve certain properties of the plant. Such genetic modifications also include but are not limited to targeted post-translational modification of protein (s), oligo- or polypeptides e. g. by glycosylation or polymer additions such as prenlated, acetylated or farnesylated moieties or PEG moieties.

Plants that have been modified by breeding, mutagenesis or genetic engineering, e. g. have been rendered tolerant to applications of specific classes of herbicides, such as auxin herbicides such as dicamba or 2,4-D; bleacher herbicides such as hydroxylphenylpyruvate dioxygenase (HPPD) inhibitors or phytoene desaturase (PDS) inhibitors; acetolactate synthase (ALS) inhibitors such as sulfo$_n$l ureas or imidazolinones; enolpyruvylshikimate-3-phosphate synthase (EPSPS) inhibitors, such as glyphosate; glutamine synthetase (GS) inhibitors such as glufosinate; protoporphyrinogen-IX oxidase inhibitors; lipid biosynthesis inhibitors such as acetyl CoA carboxylase (ACCase) inhibitors; or oxynil (i. e. bromoxynil or ioxynil) herbicides as a result of conventional methods of breeding or genetic engineering. Furthermore, plants have been made resistant to multiple classes of herbicides through multiple genetic modifications, such as resistance to both glyphosate and glufosinate or to both glyphosate and a herbicide from another class such as ALS inhibitors, HPPD inhibitors, auxin herbicides, or ACCase inhibitors. These herbicide resistance technologies are e. g. described in Pest Managem. Sci. 61, 2005, 246; 61, 2005, 258; 61, 2005, 277; 61, 2005, 269; 61, 2005, 286; 64, 2008, 326; 64, 2008, 332; Weed Sci. 57, 2009, 108; Austral. J. Agricult. Res. 58, 2007, 708; Science 316, 2007, 1185; and references quoted therein. Several cultivated plants have been rendered tolerant to herbicides by conventional methods of breeding (mutagenesis), e. g. Clearfield® summer rape (Canola, BASF SE, Germany) being tolerant to imidazolinones, e. g. imazamox, or ExpressSun® sunflowers (DuPont, USA) being tolerant to sulfo$_n$l ureas, e. g. tribenuron. Genetic engineering methods have been used to render cultivated plants such as soybean, cotton, corn, beets and rape, tolerant to herbicides such as glyphosate and glufosinate, some of which are commercially available under the trade names RoundupReady® (glyphosate-tolerant, Monsanto, U.S.A.), Cultivance® (imidazolinone tolerant, BASF SE, Germany) and LibertyLink® (glufosinate-tolerant, Bayer CropScience, Germany).

Furthermore, plants are also covered that are by the use of recombinant DNA techniques capable to synthesize one or more insecticidal proteins, especially those known from the bacterial genus *Bacillus*, particularly from *Bacillus thuringiensis*, such as δ-endotoxins, e. g. CryIA(b), CryIA(c), CryIF, CryIF(a2), CryIIA(b), CryIIIA, CryIIIB(b1) or Cry9c; vegetative insecticidal proteins (VIP), e. g. VIP1, VIP2, VIP3 or VIP3A; insecticidal proteins of bacteria colonizing nematodes, e. g. *Photorhabdus* spp. or *Xenorhabdus* spp.; toxins produced by animals, such as scorpion toxins, arachnid toxins, wasp toxins, or other insect-specific neurotoxins; toxins produced by fungi, such as Strepto$_n$cetes toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxysteroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilben synthase, bibenzyl synthase, chitinases or glucanases. In the context of the present invention these insecticidal proteins or toxins are to be understood expressly also as pre-toxins, hybrid proteins, truncated or otherwise modified proteins. Hybrid proteins are characterized by a new combination of protein domains, (see, e. g. WO 02/015701). Further examples of such toxins or genetically modified plants capable of synthesizing such toxins are disclosed, e. g., in EP-A 374 753, WO 93/007278, WO 95/34656, EP-A 427 529, EP-A 451 878, WO 03/18810 and WO 03/52073. The methods for producing such genetically modified plants are generally known to the person skilled in the art and are described, e. g. in the publications mentioned above. These insecticidal proteins contained in the genetically modified plants impart to the plants producing these proteins tolerance to harmful pests from all taxonomic groups of athropods, especially to beetles (Coeloptera), two-winged insects (Diptera), and moths (Lepidoptera) and to nematodes (Nematoda). Genetically modified plants capable to synthesize one or more insecticidal proteins are, e. g., described in the publications mentioned above, and some of which are commercially available such as YieldGard® (corn cultivars producing the Cry1Ab toxin), YieldGard® Plus (corn cultivars producing Cry1Ab and Cry3Bb1 toxins), Starlink® (corn cultivars producing the Cry9c toxin), Herculex® RW (corn cultivars producing Cry34Ab1, Cry35Ab1 and the enzyme Phosphinothricin-N-Acetyltransferase [PAT]); NuCOTN® 33B (cotton cultivars producing the Cry1Ac toxin), Bollgard® I (cotton cultivars producing the Cry1Ac toxin), Bollgard® II (cotton cultivars producing Cry1Ac and Cry2Ab2 toxins); VIPCOT® (cotton cultivars producing a VIP-toxin); NewLeaf® (potato cultivars producing the Cry3A toxin); Bt-Xtra®, NatureGard®, KnockOut®, BiteGard®, Protecta®, Bt11 (e. g. Agrisure® CB) and Bt176 from Syngenta Seeds SAS, France, (corn cultivars producing the Cry1Ab toxin and PAT e$_n$zme), MIR604 from Syngenta Seeds SAS, France (corn cultivars producing a modified version of the Cry3A toxin, c.f. WO 03/018810), MON 863 from Monsanto Europe S.A., Belgium (corn cultivars producing the Cry3Bb1 toxin), IPC 531 from Monsanto Europe S.A., Belgium (cotton cultivars producing a modified version of the Cry1Ac toxin) and 1507 from Pioneer Overseas Corporation, Belgium (corn cultivars producing the Cry1F toxin and PAT enzyme).

Furthermore, plants are also covered that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, e. g. EP-A 392 225), plant disease resistance genes (e. g. potato cultivars, which express resistance genes acting against *Phytophthora infestans* derived from the mexican wild potato *Solanum bulbocastanum*) or T4-lysozym (e. g. potato cultivars capable of synthesizing these proteins with increased resistance against bacteria such as *Erwinia a$_n$lvora*). The methods for producing such genetically modified plants are generally known to the person skilled in the art and are described, e. g. in the publications mentioned above.

Furthermore, plants are also covered that are by the use of recombinant DNA techniques capable to synthesize one or more proteins to increase the productivity (e. g. bio mass production, grain yield, starch content, oil content or protein content), tolerance to drought, salinity or other growth-limiting environmental factors or tolerance to pests and fungal, bacterial or viral pathogens of those plants.

Furthermore, plants are also covered that contain by the use of recombinant DNA techniques a modified amount of substances of content or new substances of content, specifically to improve human or animal nutrition, e. g. oil crops that produce health-promoting long-chain omega-3 fatty acids or unsaturated omega-9 fatty acids (e. g. Nexera® rape, DOW Agro Sciences, Canada).

Furthermore, plants are also covered that contain by the use of recombinant DNA techniques a modified amount of substances of content or new substances of content, specifically to improve raw material production, e. g. potatoes that produce increased amounts of a$_n$lopectin (e. g. Amflora® potato, BASF SE, Germany).

The compound I and compositions thereof, respectively, are particularly suitable for controlling the following plant diseases:

*Albugo* spp. (white rust) on ornamentals, vegetables (e. g. *A. candida*) and sunflowers (e. g. *A. tragopogonis*); *Alternaria* spp. (*Alternaria* leaf spot) on vegetables, rape (*A. brassicola* or *brassicae*), sugar beets (*A. tenuis*), fruits, rice, soybeans, potatoes (e. g. *A. solani* or *A. alternata*), tomatoes (e. g. *A. solani* or *A. alternata*) and wheat; *Aphano$_n$ces* spp. on sugar beets and vegetables; *Ascochyta* spp. on cereals and vegetables, e. g. *A. tritici* (anthracnose) on wheat and *A. hordei* on barley; *Bipolaris* and *Drechslera* spp. (teleomorph: *Cochliobolus* spp.), e. g. Southern leaf blight (*D.*

*maydis*) or Northern leaf blight (*B. zeicola*) on corn, e. g. spot blotch (*B. sorokiniana*) on cereals and e.g. *B. oryzae* on rice and turfs; *Blumeria* (formerly *Erysiphe*) *graminis* (powdery mildew) on cereals (e. g. on wheat or barley); *Botrytis cinerea* (teleomorph: *Botryotinia fuckliana*: grey mold) on fruits and berries (e. g. strawberries), vegetables (e. g. lettuce, carrots, celery and cabbages), rape, flowers, vines, forestry plants and wheat; *Bremia lactucae* (down mildew) on lettuce; *Ceratocystis* (syn. *Ophiostoma*) spp. (rot or wilt) on broad-leaved trees and evergreens, e. g. *C. ulmi* (Dutch elm disease) on elms; *Cercospora* spp. (*Cercospora* leaf spots) on corn (e.g. Gray leaf spot: *C. zeae-maydis*), rice, sugar beets (e. g. *C. beticola*), sugar cane, vegetables, coffee, soybeans (e. g. *C. solina* or *C. kikuchii*) and rice; *Cladosporium* spp. on tomatoes (e. g. *C. fulvum*: leaf mold) and cereals, e. g. *C. herbarum* (black ear) on wheat; *Claviceps purpurea* (ergot) on cereals; *Cochliobolus* (anamorph: *Helminthosporium* of *Bipolaris*) spp. (leaf spots) on corn (*C. carbonum*), cereals (e. g. *C. sativus*, anamorph: *B. sorokiniana*) and rice (e. g. *C. miyabeanus*, anamorph: *H. oryzae*); *Colletotrichum* (teleomorph: *Glomerella*) spp. (anthracnose) on cotton (e. g. *C. gossypii*), corn (e. g. *C. graminicola*: Anthracnose stalk rot), soft fruits, potatoes (e. g. *C. coccodes*: black dot), beans (e. g. *C. lindemuthianum*) and soybeans (e. g. *C. truncatum* or *C. gloeosporiodes*); *Corticium* spp., e. g. *C. sasakii* (sheath blight) on rice; *Corynespora cassiicola* (leaf spots) on soybeans and ornamentals; *Cycloconium* spp., e. g. *C. oleaginum* on olive trees; *Cylindrocarpon* spp. (e. g. fruit tree canker or young vine decline, teleomorph: *Nectria* or *Neonectna* spp.) on fruit trees, vines (e. g. *C. liriodendri*, teleomorph: *Neonectria liriodendri*: Black Foot Disease) and ornamentals; *Dematophora* (teleomorph: *Rosellinia*) *necatrix* (root and stem rot) on soybeans; *Diaporthe* spp., e. g. *D. phaseolorum* (damping off) on soybeans; *Drechslera* (syn. *Helminthosporium*, teleomorph: *Pyrenophora*) spp. on corn, cereals, such as barley (e. g. *D. teres*, net blotch) and wheat (e. g. *D. tritici-repentis*: tan spot), rice and turf; Esca (dieback, apoplexy) on vines, caused by *Formitiporia* (syn. *Phellinus*) *punctata, F. mediterranea, Phaeomoniella chlandospora* (earlier *Phaeoacremonium chlandosporum*), *Phaeoacremonium aleophllum* and/or *Botryosphaeria obtusa*; *Elsinoe* spp. on pome fruits (*E. pyri*), soft fruits (*E. veneta*: anthracnose) and vines (*E. ampelina*: anthracnose); *Entyloma oryzae* (leaf smut) on rice; *Epicoccum* spp. (black mold) on wheat; *Erysiphe* spp. (powdery mildew) on sugar beets (*E. betae*), vegetables (e. g. *E. pisi*), such as cucurbits (e. g. *E. cichoracearum*), cabbages, rape (e. g. *E. cruciferarum*); *Eutypa lata* (Eutypa canker or dieback, anamorph: *Cytosporina lata*, syn. *Libertella blepharis*) on fruit trees, vines and ornamental woods; *Exserohllum* (syn. *Helminthosporium*) spp. on corn (e. g. *E. turcicum*); *Fusarium* (teleomorph: *Gibberella*) spp. (wilt, root or stem rot) on various plants, such as *F. graminearum* or *F. culmorum* (root rot, scab or head blight) on cereals (e. g. wheat or barley), *F. oxysporum* on tomatoes, *F. solani* (f. sp. glycines now syn. *F. virguliforme*) and *F. tucumaniae* and *F. brasiliense* each causing sudden death syndrome on soybeans and *F. verticilliodes* on corn; *Gaeumannoynces graminis* (take-all) on cereals (e. g. wheat or barley) and corn; *Gibberella* spp. on cereals (e. g. *G. zeae*) and rice (e. g. *G. fujikuroi*: Bakanae disease); *Glomerella angulata* on vines, pome fruits and other plants and *G. gossypii* on cotton; Grainstaining complex on rice; *Guignardia bidwellii* (black rot) on vines; *Gymnosporangium* spp. on rosaceous plants and junipers, e. g. *G. sabinae* (rust) on pears; *Helminthosporium* spp. (syn. *Drechslera*, teleomorph: *Cochliobolus*) on corn, cereals and rice; *Hemileia* spp., e. g. *H. vastataX* (coffee leaf rust) on coffee; *Isariopsis clavispora* (syn. *Cladosporium vitis*) on vines; *Macrophomina phaseolina* (syn. *phaseoli*) (root and stem rot) on soybeans and cotton; *Microdochium* (syn. *Fusarium*) *nivale* (pink snow mold) on cereals (e. g. wheat or barley); *Microsphaera diffusa* (powdery mildew) on soybeans; *Monilinia* spp., e. g. *M. laxa, M. fructicola* and *M. fructigena* (bloom and twig blight, brown rot) on stone fruits and other rosaceous plants; $_N$*cosphaerella* spp. on cereals, bananas, soft fruits and ground nuts, such as e. g. *M gram/n/cola* (anamorph: *Septoria Septoria* blotch) on wheat or *M. fijiensis* (black Sigatoka disease) on bananas; *Peronospora* spp. (down mildew) on cabbage (e. g. *P. brassicae*), rape (e. g. *P. parasitica*), onions (e. g. *P. destructor*), tobacco (*P. tabacina*) and soybeans (e. g. *P. manshurica*); *Phakopsora pachyrhizi* and *P. meibomiae* (soybean rust) on soybeans; *Phialophora* spp. e. g. on vines (e. g. *P. tracheiphila* and *P. tetraspora*) and soybeans (e. g. *P. gregata*: stem rot); *Phoma lingam* (root and stem rot) on rape and cabbage and *P. betae* (root rot, leaf spot and damping-off) on sugar beets; *Phomopsis* spp. on sunflowers, vines (e. g. *P. viticola*: can and leaf spot) and soybeans (e. g. stem rot: *P. phaseoli*, teleomorph: *Diaporthe phaseolorum*); *Physoderma maydis* (brown spots) on corn; *Phytophthora* spp. (wilt, root, leaf, fruit and stem root) on various plants, such as paprika and cucurbits (e. g. *P. capsici*), soybeans (e. g. *P. megasperma*, syn. *P. sojae*), potatoes and tomatoes (e. g. *P. infestans*: late blight) and broad-leaved trees (e. g. *P. ramorum*: sudden oak death); *Plasmodiophora brassicae* (club root) on cabbage, rape, radish and other plants; *Plasmopara* spp., e. g. *P. viticola* (grapevine down mildew) on vines and *P. halstedii* on sunflowers; *Podosphaera* spp. (powdery mildew) on rosaceous plants, hop, pome and soft fruits, e. g. *P. leucotricha* on apples; *Polynxa* spp., e. g. on cereals, such as barley and wheat (*P. graminis*) and sugar beets (*P. betae*) and thereby transmitted viral diseases; *Pseudocercosporella herpotrichoides* (eyespot, teleomorph: *Tapesia yallundae*) on cereals, e. g. wheat or barley; *Pseudoperonospora* (down mildew) on various plants, e. g. *P. cubensis* on cucurbits or *P. humili* on hop; *Pseudopezicula tracheiphila* (red fire disease or 'rotbrenner', anamorph: *Phialophora*) on vines; *Puccinia* spp. (rusts) on various plants, e. g. *P. triticina* (brown or leaf rust), *P. striiformis* (stripe or yellow rust), *P. hordei* (dwarf rust), *P. graminis* (stem or black rust) or *P. recondita* (brown or leaf rust) on cereals, such as e. g. wheat, barley or rye, *P. kuehnii* (orange rust) on sugar cane and *P. asparagi* on asparagus; *Pyrenophora* (anamorph: *Drechslera*) *tritici-repentis* (tan spot) on wheat or *P. teres* (net blotch) on barley; *Pyriculana* spp., e. g. *P. oryzae* (teleomorph: *Magnaporthe grisea*, rice blast) on rice and *P. grisea* on turf and cereals; *Pythium* spp. (damping-off) on turf, rice, corn, wheat, cotton, rape, sunflowers, soybeans, sugar beets, vegetables and various other plants (e. g. *P. ultimum* or *P. aphanidermatum*); *Ramularia* spp., e. g. *R. collo-cygni* (*Ramularia* leaf spots, Physiological leaf spots) on barley and *R. beticola* on sugar beets; *Rhizoctonia* spp. on cotton, rice, potatoes, turf, corn, rape, potatoes, sugar beets, vegetables and various other plants, e. g. *R. solani* (root and stem rot) on soybeans, *R. solani* (sheath blight) on rice or *R. cerealis* (*Rhizoctonia* spring blight) on wheat or barley; *Rhizopus stolonifer* (black mold, soft rot) on strawberries, carrots, cabbage, vines and tomatoes; *Rhynchosporium secalis* (scald) on barley, rye and triticale; *Sarocladium oryzae* and *S. attenuatum* (sheath rot) on rice; *Sclerotinia* spp. (stem rot or white mold) on vegetables and field crops, such as rape, sunflowers (e. g. *S. sclerotiorum*) and soybeans (e. g. *S. rolfsii* or *S. sclerotiorum*); *Septoria* spp. on various plants, e. g. *S. glycines* (brown spot) on soybeans, *S. tritici* (*Septoria* blotch) on wheat and S. (syn. *Stagonospora*) *nodorum* (*Stagonospora* blotch) on cereals; *Uncinula* (syn. *Erysiphe*) *necator* (powdery mildew, anamorph: *Oidium tuckeri*) on vines; *Setospaeria* spp. (leaf blight) on corn (e. g. *S. turcicum*, syn. *Helminthosporium turcicum*) and turf; *Sphacelotheca* spp. (smut) on corn, (e. g. *S. reiliana*: head smut), sorghum and sugar cane; *Sphaerotheca fuliginea* (powdery mildew) on cucurbits; *Spongospora subterranea* (powdery scab) on potatoes and thereby transmitted viral diseases; *Stagonospora* spp. on cereals, e. g. *S. nodorum* (*Stagonospora* blotch, teleomorph: *Leptosphaeria* [syn. *Phaeosphaeria*] *nodorum*) on wheat; *Synchytrium endobioticum* on potatoes (potato wart disease); *Taphrina* spp., e. g. *T. deformans* (leaf curl disease) on peaches and *T. pruni* (plum pocket) on plums; *Thielaviopsis* spp. (black root rot) on tobacco, pome fruits, vegetables, soybeans and cotton, e. g. *T. basicola* (syn. *Chalara elegans*); *Tilletia* spp. (common bunt or stinking smut) on cereals, such as e. g. *T. tritici* (syn. *T. caries*, wheat bunt) and *T. controversa* (dwarf bunt) on wheat; *Typhula incarnata* (grey snow mold) on barley or wheat; *Urocystis* spp., e. g. *U. occulta* (stem smut) on rye; *Uronces* spp. (rust) on vegetables, such as beans (e. g. *U. appendiculatus*, syn. *U. phaseoli*) and sugar beets (e. g. *U. betae*); *Ustilago* spp. (loose smut) on cereals (e. g. *U. nulla* and *U. avaenae*), corn (e. g. *U. maydis*: corn smut) and sugar cane; *Venturia* spp. (scab) on apples (e. g. *V. inaequalis*) and pears; and *Verticillium* spp. (wilt) on various plants, such as fruits and ornamentals, vines, soft fruits, vegetables and field crops, e. g. *V. dahliae* on strawberries, rape, potatoes and tomatoes.

The compound I and compositions thereof, respectively, are also suitable for controlling harmful fungi in the protection of stored products or harvest and in the protection of materials. The term "protection of materials" is to be understood to denote the protection of technical and non-living materials, such as adhesives, glues, wood, paper and paperboard, textiles, leather, paint dispersions, plastics, coiling lubricants, fiber or fabrics, against the infestation and destruction by harmful microorganisms, such as fungi and bacteria. As to the protection of wood and other materials, the particular attention is paid to the following harmful fungi: Asco$_n$cetes such as *Ophiostoma* spp., *Ceratocystis* spp., *Aureobasidium pullulans*, *Sclerophoma* spp., *Chaetomium* spp., *Humicola* spp., *Petriella* spp., *Trichurus* spp.; Basidio$_n$cetes such as *Coniophora* spp., *Corsolus*spp., *Gloeophyllum* spp., *Lentinus* spp., *Pleurotus* spp., *Poria* spp., *Serpula* spp. and *Tyro$_n$ces* spp., Deutero$_n$cetes such as *Aspergillus* spp., *Cladosporium* spp., *Penicillium* spp., *Tfichorma* spp., *Alternaria* spp., *Paecdo$_n$ces* spp. and Zygo$_n$-cetes such as *Mucor* spp., and in addition in the protection of stored products and harvest the following yeast fungi are worthy of note: *Candida* spp. and *Saccharo$_n$ces cerevisae*.

The compound I and compositions thereof, respectively, may be used for improving the health of a plant. The invention also relates to a method for improving plant health by treating a plant, its propagation material and/or the locus where the plant is growing or is to grow with an effective amount of compound I and compositions thereof, respectively.

The term "plant health" is to be understood to denote a condition of the plant and/or its products which is determined by several indicators alone or in combination with each other such as yield (e. g. increased biomass and/or increased content of valuable ingredients), plant vigor (e. g. improved plant growth and/or greener leaves ("greening effect")), quality (e. g. improved content or composition of certain ingredients) and tolerance to abiotic and/or biotic stress. The above identified indicators for the health condition of a plant may be interdependent or may result from each other.

The compounds of formula I, can be present in different crystal modifications whose biological activity may differ. They are likewise subject matter of the present invention.

The compound I are employed as such or in form of compositions by treating the fungi or the plants, plant propagation materials, such as seeds, soil, surfaces, materials or rooms to be protected from fungal attack with a fungicidally effective amount of the active substances. The application can be carried out both before and after the infection of the plants, plant propagation materials, such as seeds, soil, surfaces, materials or rooms by the fungi.

Plant propagation materials may be treated with compound I as such or a composition comprising at least one compound I prophylactically either at or before planting or transplanting.

The invention also relates to compositions comprising one compound I according to the invention. In particular, such composition further comprises an auxiliary as defined below.

The term "effective amount" used denotes an amount of the composition or of the compound I which is sufficient for controlling harmful fungi on cultivated plants or in the protection of materials and which does not result in a substantial damage to the treated plants. Such an amount can vary in a broad range and is dependent on various factors, such as the fungal species to be controlled, the treated cultivated plant or material, the climatic conditions and the specific compound I used.

The compound I, their N-oxides and salts, respectively can be converted into customary types of agrochemical compositions, e. g. solutions, emulsions, suspensions, dusts, powders, pastes, granules, pressings, capsules, and mixtures thereof. Examples for composition types are suspensions (e.g. SC, OD, FS), emulsifiable concentrates (e.g. EC), emulsions (e.g. EW, EO, ES, ME), capsules (e.g. CS, ZC), pastes, pastilles, wettable powders or dusts (e.g. WP, SP, WS, DP, DS), pressings (e.g. BR, TB, DT), granules (e.g. WG, SG, GR, FG, GG, MG), insecticidal articles (e.g. LN), as well as gel formulations for the treatment of plant propagation materials such as seeds (e.g. GF). These and further compositions types are defined in the "Catalogue of pesticide formulation types and international coding system", Technical Monograph No. 2, 6th Ed. May 2008, CropLife International.

The compositions are prepared in a known manner, such as described by Mollet and Grubemann, Formulation technology, Wiley VCH, Weinheim, 2001; or Knowles, New developments in crop protection product formulation, Agrow Reports DS243, T&F Informa, London, 2005.

Suitable auxiliaries are solvents, liquid carriers, solid carriers or fillers, surfactants, dispersants, emulsifiers, wetters, adjuvants, solubilizers, penetration enhancers, protective colloids, adhesion agents, thickeners, humectants, repellents, attractants, feeding stimulants, compatibilizers, bactericides, anti-freezing agents, anti-foaming agents, colorants, tackifiers and binders.

Suitable solvents and liquid carriers are water and organic solvents, such as mineral oil fractions of medium to high boiling point, e.g. kerosene, diesel oil; oils of vegetable or animal origin; aliphatic, cyclic and aromatic hydrocarbons, e. g. toluene, paraffin, tetrahydronaphthalene, alkylated naphthalenes; alcohols, e.g. ethanol, propanol, butanol, benzylalcohol, cyclohexanol; glycols; DMSO; ketones, e.g.

cyclohexanone; esters, e.g. lactates, carbonates, fatty acid esters, gamma-butyrolactone; fatty acids; phosphonates; amines; amides, e.g. N-methylpyrrolidone, fatty acid dimethylamides; and mixtures thereof.

Suitable solid carriers or fillers are mineral earths, e.g. silicates, silica gels, talc, kaolins, limestone, lime, chalk, clays, dolomite, diatomaceous earth, bentonite, calcium sulfate, magnesium sulfate, magnesium oxide; polysaccharides, e.g. cellulose, starch; fertilizers, e.g. ammonium sulfate, ammonium phosphate, ammonium nitrate, ureas; products of vegetable origin, e.g. cereal meal, tree bark meal, wood meal, nutshell meal, and mixtures thereof.

Suitable surfactants are surface-active compounds, such as anionic, cationic, nonionic and amphoteric surfactants, block polymers, polyelectrolytes, and mixtures thereof. Such surfactants can be used as emusifier, dispersant, solubilizer, wetter, penetration enhancer, protective colloid, or adjuvant. Examples of surfactants are listed in McCutcheon's, Vol. 1: Emulsifiers & Detergents, McCutcheon's Directories, Glen Rock, USA, 2008 (International Ed. or North American Ed.).

Suitable anionic surfactants are alkali, alkaline earth or ammonium salts of sulfonates, sulfates, phosphates, carboxylates, and mixtures thereof. Examples of sulfonates are alkylarylsulfonates, diphenylsulfonates, alpha-olefin sulfonates, lignine sulfonates, sulfonates of fatty acids and oils, sulfonates of ethoxylated alkylphenols, sulfonates of alkoxylated arylphenols, sulfonates of condensed naphthalenes, sulfonates of dodecyl- and tridecylbenzenes, sulfonates of naphthalenes and alkylnaphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Examples of carboxylates are alkyl carboxylates, and carboxylated alcohol or alkylphenol ethoxylates.

Suitable nonionic surfactants are alkoxylates, N-substituted fatty acid amides, amine oxides, esters, sugar-based surfactants, polymeric surfactants, and mixtures thereof. Examples of alkoxylates are compounds such as alcohols, alkylphenols, amines, amides, arylphenols, fatty acids or fatty acid esters which have been alkoxylated with 1 to 50 equivalents. Ethylene oxide and/or propylene oxide may be employed for the alkoxylation, preferably ethylene oxide. Examples of N-substituted fatty acid amides are fatty acid glucamides or fatty acid alkanolamides. Examples of esters are fatty acid esters, glycerol esters or monoglycerides. Examples of sugar-based surfactants are sorbitans, ethoxylated sorbitans, sucrose and glucose esters or alkylpolyglucosides. Examples of polymeric surfactants are home- or copolymers of vinylpyrrolidone, vinylalcohols, or vinylacetate.

Suitable cationic surfactants are quaternary surfactants, for example quaternary ammonium compounds with one or two hydrophobic groups, or salts of long-chain primary amines. Suitable amphoteric surfactants are alkylbetains and imidazolines. Suitable block polymers are block polymers of the A-B or A-B-A type comprising blocks of polyethylene oxide and polypropylene oxide, or of the A-B-C type comprising alkanol, polyethylene oxide and polypropylene oxide. Suitable polyelectrolytes are polyacids or polybases. Examples of polyacids are alkali salts of polyacrylic acid or polyacid comb polymers. Examples of polybases are polyvinylamines or polyethyleneamines.

Suitable adjuvants are compounds, which have a neglectable or even no pesticidal activity themselves, and which improve the biological performance of the compound I on the target. Examples are surfactants, mineral or vegetable oils, and other auxilaries. Further examples are listed by Knowles, Adjuvants and additives, Agrow Reports DS256, T&F Informa UK, 2006, chapter 5.

Suitable thickeners are polysaccharides (e.g. xanthan gum, carboxymethylcellulose), anorganic clays (organically modified or unmodified), polycarboxylates, and silicates.

Suitable bactericides are bronopol and isothiazolinone derivatives such as alkylisothiazolinones and benzisothiazolinones.

Suitable anti-freezing agents are ethylene glycol, propylene glycol, urea and glycerin.

Suitable anti-foaming agents are silicones, long chain alcohols, and salts of fatty acids.

Suitable colorants (e.g. in red, blue, or green) are pigments of low water solubility and water-soluble dyes. Examples are inorganic colorants (e.g. iron oxide, titan oxide, iron hexacyanoferrate) and organic colorants (e.g. alizarin-, azo- and phthalocyanine colorants).

Suitable tackifiers or binders are polyvinylpyrrolidons, polyvinylacetates, polyvinyl alcohols, polyacrylates, biological or synthetic waxes, and cellulose ethers.

Examples for composition types and their preparation are:

i) Water-Soluble Concentrates (SL, LS)

10-60 wt % of a compound I and 5-15 wt % wetting agent (e.g. alcohol alkoxylates) are dissolved in water and/or in a water-soluble solvent (e.g. alcohols) ad 100 wt %. The active substance dissolves upon dilution with water.

ii) Dispersible Concentrates (DC)

5-25 wt % of a compound I and 1-10 wt % dispersant (e.g. polyvinylpyrrolidone) are dissolved in organic solvent (e.g. cyclohexanone) ad 100 wt %. Dilution with water gives a dispersion.

iii) Emulsifiable Concentrates (EC)

15-70 wt % of a compound I and 5-10 wt % emulsifiers (e.g. calcium dodecylbenzenesulfonate and castor oil ethoxylate) are dissolved in water-insoluble organic solvent (e.g. aromatic hydrocarbon) ad 100 wt %. Dilution with water gives an emulsion.

iv) Emulsions (EW, EO, ES)

5-40 wt % of a compound I and 1-10 wt % emulsifiers (e.g. calcium dodecylbenzenesulfonate and castor oil ethoxylate) are dissolved in 20-40 wt % water-insoluble organic solvent (e.g. aromatic hydrocarbon). This mixture is introduced into water ad 100 wt % by means of an emulsifying machine and made into a homogeneous emulsion. Dilution with water gives an emulsion.

v) Suspensions (SC, OD, FS)

In an agitated ball mill, 20-60 wt % of a compound I are comminuted with addition of 2-10 wt % dispersants and wetting agents (e.g. sodium lignosulfonate and alcohol ethoxylate), 0.1-2 wt % thickener (e.g. xanthan gum) and water ad 100 wt % to give a fine active substance suspension. Dilution with water gives a stable suspension of the active substance. For FS type composition up to 40 wt % binder (e.g. polyvinylalcohol) is added.

vi) Water-Dispersible Granules and Water-Soluble Granules (WG, SG)

50-80 wt % of a compound I are ground finely with addition of dispersants and wetting agents (e.g. sodium lignosulfonate and alcohol ethoxylate) ad 100 wt % and prepared as water-dispersible or water-soluble granules by means of technical appliances (e. g. extrusion, spray tower, fluidized bed). Dilution with water gives a stable dispersion or solution of the active substance.

vii) Water-Dispersible Powders and Water-Soluble Powders (WP, SP, WS)

50-80 wt % of a compound I are ground in a rotor-stator mill with addition of 1-5 wt % dispersants (e.g. sodium lignosulfonate), 1-3 wt % wetting agents (e.g. alcohol ethoxylate) and solid carrier (e.g. silica gel) ad 100 wt %. Dilution with water gives a stable dispersion or solution of the active substance.

viii) Gel (GW, GF)

In an agitated ball mill, 5-25 wt % of a compound I are comminuted with addition of 3-10 wt % dispersants (e.g. sodium lignosulfonate), 1-5 wt % thickener (e.g. carboxymethylcellulose) and water ad 100 wt % to give a fine suspension of the active substance. Dilution with water gives a stable suspension of the active substance.

ix) Microemulsion (ME)

5-20 wt % of a compound I are added to 5-30 wt % organic solvent blend (e.g. fatty acid dimethylamide and cyclohexanone), 10-25 wt % surfactant blend (e.g. alcohol ethoxylate and arylphenol ethoxylate), and water ad 100%. This mixture is stirred for 1 h to produce spontaneously a thermodynamically stable microemulsion.

x) Microcapsules (CS)

An oil phase comprising 5-50 wt % of a compound I 0-40 wt % water insoluble organic solvent (e.g. aromatic hydrocarbon), 2-15 wt % acrylic monomers (e.g. methylmethacrylate, methacrylic acid and a di- or triacrylate) are dispersed into an aqueous solution of a protective colloid (e.g. polyvinyl alcohol). Radical polymerization initiated by a radical initiator results in the formation of poly(meth)acrylate microcapsules. Alternatively, an oil phase comprising 5-50 wt % of a compound I according to the invention, 0-40 wt % water insoluble organic solvent (e.g. aromatic hydrocarbon), and an isocyanate monomer (e.g. diphenylmethene-4, 4'-diisocyanatae) are dispersed into an aqueous solution of a protective colloid (e.g. polyvinyl alcohol). The addition of a polyamine (e.g. hexamethylenediamine) results in the formation of polyurea microcapsules. The monomers amount to 1-10 wt %. The wt % relate to the total CS composition.

xi) Dustable Powders (DP, DS)

1-10 wt % of a compound I are ground finely and mixed intimately with solid carrier (e.g. finely divided kaolin) ad 100 wt %.

xii) Granules (GR, FG)

0.5-30 wt % of a compound I is ground finely and associated with solid carrier (e.g. silicate) ad 100 wt %. Granulation is achieved by extrusion, spray-drying or fluidized bed.

xiii) Ultra-Low Volume Liquids (UL)

1-50 wt % of a compound I are dissolved in organic solvent (e.g. aromatic hydrocarbon) ad 100 wt %.

The compositions types i) to xiii) may optionally comprise further auxiliaries, such as 0.1-1 wt % bactericides, 5-15 wt % anti-freezing agents, 0.1-1 wt % anti-foaming agents, and 0.1-1 wt % colorants.

The agrochemical compositions generally comprise between 0.01 and 95%, preferably between 0.1 and 90%, and in particular between 0.5 and 75%, by weight of active substance. The active substances are employed in a purity of from 90% to 100%, preferably from 95% to 100% (according to NMR spectrum).

Solutions for seed treatment (LS), Suspoemulsions (SE), flowable concentrates (FS), powders for dry treatment (DS), water-dispersible powders for slurry treatment (WS), water-soluble powders (SS), emulsions (ES), emulsifiable concentrates (EC) and gels (GF) are usually employed for the purposes of treatment of plant propagation materials, particularly seeds. The compositions in question give, after two-to-tenfold dilution, active substance concentrations of from 0.01 to 60% by weight, preferably from 0.1 to 40%, in the ready-to-use preparations. Application can be carried out before or during sowing. Methods for applying compound I and compositions thereof, respectively, on to plant propagation material, especially seeds include dressing, coating, pelleting, dusting, soaking and in-furrow application methods of the propagation material. Preferably, compound I or the compositions thereof, respectively, are applied on to the plant propagation material by a method such that germination is not induced, e. g. by seed dressing, pelleting, coating and dusting.

When employed in plant protection, the amounts of active substances applied are, depending on the kind of effect desired, from 0.001 to 2 kg per ha, preferably from 0.005 to 2 kg per ha, more preferably from 0.05 to 0.9 kg per ha, and in particular from 0.1 to 0.75 kg per ha.

In treatment of plant propagation materials such as seeds, e. g. by dusting, coating or drenching seed, amounts of active substance of from 0.1 g to 10 kg, in particular 0.1 to 1000 g, more particularly from 1 to 1000 g, specifically from 1 to 100 g and most specifically from 5 to 100 g, per 100 kilogram of plant propagation material (preferably seeds) are generally required.

When used in the protection of materials or stored products, the amount of active substance applied depends on the kind of application area and on the desired effect. Amounts customarily applied in the protection of materials are 0.001 g to 2 kg, preferably 0.005 g to 1 kg, of active substance per cubic meter of treated material.

Various types of oils, wetters, adjuvants, fertilizer, or micronutrients, and further pesticides (e.g. herbicides, insecticides, fungicides, growth regulators, safeners) may be added to the active substances or the compositions comprising them as premix or, if appropriate not until immediately prior to use (tank mix). These agents can be admixed with the compositions according to the invention in a weight ratio of 1:100 to 100:1, preferably 1:10 to 10:1.

The user applies the composition according to the invention usually from a predosage device, a knapsack sprayer, a spray tank, a spray plane, or an irrigation system. Usually, the agrochemical composition is made up with water, buffer, and/or further auxiliaries to the desired application concentration and the ready-to-use spray liquor or the agrochemical composition according to the invention is thus obtained. Usually, 20 to 2000 liters, preferably 50 to 400 liters, of the ready-to-use spray liquor are applied per hectare of agricultural useful area.

According to one embodiment, individual components of the composition according to the invention such as parts of a kit or parts of a composition comprising two or three active ingredients, may be mixed by the user himself in a spray tank and further auxiliaries may be added, if appropriate.

Mixing the compound I or the compositions comprising them in the use form as fungicides with other fungicides results in many cases in an expansion of the fungicidal spectrum of activity being obtained or in a prevention of fungicide resistance development. Furthermore, in many cases, synergistic effects are obtained.

The following list of active substances, in conjunction with which the compounds I and II, respectively, can be used, is intended to illustrate the possible combinations but does not limit them:

A) Respiration Inhibitors

Inhibitors of complex III at $Q_o$ site (e.g. strobilurins):
azoxystrobin, coumethoxystrobin, coumoxystrobin, dimoxystrobin, enestroburin, fenaminstrobin, fenoxystrobin/flufenoxystrobin, fluoxastrobin, kresoximmethyl, metominostrobin, orysastrobin, picoxystrobin, pyraclostrobin, pyrametostrobin, pyraoxystrobin, trifloxystrobin, 2-[2-(2,5-dimethyl-phenoxymethyl)-phenyl]-3-methoxy-acrylic acid methyl ester and 2-(2-(3-(2,6-dichlorophenyl)-1-methyl-allylideneaminooxymethyl)-phenyl)-2-methoxyimino-N-methyl-acetamide, pyribencarb, triclopyricarb/chlorodincarb, famoxadone, fenamidone, (3S,6S,7R,8R)-3-[[(3-hydroxy-4-methoxy-2-pyridinyl)carbonyl]amino]-6-methyl-4,9-dioxo-8-(phenylmethyl)-1,5-dioxonan-7-yl 2-methylpropanoate;

inhibitors of complex III at $Q_i$ site: cyazofamid, amisulbrom, [(3S,6S,7R,8R)-8-benzyl-3-[(3-acetoxy-4-methoxy-pyridine-2-carbonyl)amino]-6-methyl-4,9-dioxo-1,5-dioxonan-7-yl]2-methylpropanoate, [(3S,6S,7R,8R)-8-benzyl-3-[[3-(acetoxymethoxy)-4-methoxy-pyridine-2-carbonyl]amino]-6-methyl-4,9-dioxo-1,5-dioxonan-7-yl]2-methylpropanoate, [(3S,6S,7R,8R)-8-benzyl-3-[(3-isobutoxycarbonyloxy-4-methoxy-pyridine-2-carbonyl)amino]-6-methyl-4,9-dioxo-1,5-dioxonan-7-yl]2-methylpropanoate, [(3S,6S,7R,8R)-8-benzyl-3-[[3-(1,3-benzodioxol-5-ylmethoxy)-4-methoxy-pyridine-2-carbonyl]amino]-6-methyl-4,9-dioxo-1,5-dioxonan-7-yl]2-methylpropanoate; (3S,6S,7R,8R)-3-[[(3-hydroxy-4-methoxy-2-pyridinyl)carbonyl]amino]-6-methyl-4,9-dioxo-8-(phenylmethyl)-1,5-dioxonan-7-yl 2-methylpropanoate;

inhibitors of complex II (e. g. carboxamides): benodanil, benzovindiflupyr, bixafen, boscalid, carboxin, fenfuram, fluopyram, flutolanil, fluxapyroxad, furametpyr, isofetamid, isopyrazam, mepronil, oxycarboxin, penflufen, penthiopyrad, sedaxane, tecloftalam, thifluzamide, N-(4'-trifluoromethylthiobiphenyl-2-yl)-3-difluoromethyl-1-methyl-1H-pyrazole-4-carboxamide, N-(2-(1,3,3-trimethyl-butyl)-phenyl)-1,3-dimethyl-5-fluoro-1H-pyrazole-4-carboxamide, 3-(difluoromethyl)-1-methyl-N-(1,1,3-trimethylindan-4-yl)pyrazole-4-carboxamide, 3-(trifluoromethyl)-1-methyl-N-(1,1,3-trimethylindan-4-yl)pyrazole-4-carboxamide, 1,3-dimethyl-N-(1,1,3-trimethylindan-4-yl)pyrazole-4-carboxamide, 3-(trifluoromethyl)-1,5-dimethyl-N-(1,1,3-trimethyl-indan-4-yl)pyrazole-4-carboxamide, 1,3,5-trimethyl-N-(1,1,3-trimethylindan-4-yl)pyrazole-4-carboxamide, N-(7-fluoro-1,1,3-trimethyl-indan-4-yl)-1,3-dimethyl-pyrazole-4-carboxamide, N-[2-(2,4-dichlorophenyl)-2-methoxy-1-methyl-ethyl]-3-(difluoromethyl)-1-methylpyrazole-4-carboxamide;

other respiration inhibitors (e.g. complex I, uncouplers): diflumetorim, (5,8-difluoroquinazolin-4-yl)-{2-[2-fluoro-4-(4-trifluoromethylpyridin-2-yloxy)-phenyl]-ethyl}-amine; nitrophenyl derivates: binapacryl, dinobuton, dinocap, fluazinam; ferimzone; organometal compounds: fentin salts, such as fentin-acetate, fentin chloride or fentin hydroxide; ametoctradin; and silthiofam;

B) Sterol Biosynthesis Inhibitors (SBI Fungicides)

C14 demethylase inhibitors (DMI fungicides): triazoles: azaconazole, bitertanol, bromuconazole, cyproconazole, difenoconazole, diniconazole, diniconazole-M, epoxiconazole, fenbuconazole, fluquinconazole, flusilazole, flutriafol, hexaconazole, imibenconazole, ipconazole, metconazole, myclobutanil, oxpoconazole, paclobutrazole, penconazole, propiconazole, prothioconazole, simeconazole, tebuconazole, tetraconazole, triadimefon, triadimenol, triticonazole, uniconazole, 1-[rel-(2S;3R)-3-(2-chlorophenyl)-2-(2,4-difluorophenyl)-oxiranylmethyl]-5-thiocyanato-1H[1,2,4]triazole, 2-[rel-(2S;3R)-3-(2-chlorophenyl)-2-(2,4-difluorophenyl)-oxiranylmethyl]-2H-[1,2,4]triazole-3-thiol, 2-[2-chloro-4-(4-chlorophenoxy)phenyl]-1-(1,2,4-triazol-1-yl)pentan-2-ol, 1-[4-(4-chlorophenoxy)-2-(trifluoromethyl)phenyl]-1-cyclopropyl-2-(1,2,4-triazol-1-yl)ethanol, 2-[4-(4-chlorophenoxy)-2-(trifluoromethyl)phenyl]-1-(1,2,4-triazol-1-yl)butan-2-ol, 2-[2-chloro-4-(4-chlorophenoxy)phenyl]-1-(1,2,4-triazol-1-yl)butan-2-ol, 2-[4-(4-chlorophenoxy)-2-(trifluoromethyl)phenyl]-3-methyl-1-(1,2,4-triazol-1-yl)butan-2-ol, 2-[4-(4-chlorophenoxy)-2-(trifluoromethyl)phenyl]-1-(1,2,4-triazol-1-yl)propan-2-ol, 2-[2-chloro-4-(4-chlorophenoxy)phenyl]-3-methyl-1-(1,2,4-triazol-1-yl)butan-2-ol, 2-[4-(4-chlorophenoxy)-2-(trifluoromethyl)phenyl]-1-(1,2,4-triazol-1-yl)pentan-2-ol, 2-[4-(4-fluorophenoxy)-2-(trifluoromethyl)phenyl]-1-(1,2,4-triazol-1-yl)propan-2-ol, 2-[2-chloro-4-(4-chlorophenoxy)phenyl]-1-(1,2,4-triazol-1-yl)pent-3-yn-2-ol; imidazoles: imazalil, pefurazoate, prochloraz, triflumizol; pyrimidines, pyridines and piperazines: fenarimol, nuarimol, pyrifenox, triforine, [3-(4-chloro-2-fluoro-phenyl)-5-(2,4-difluorophenyl)isoxazol-4-yl]-(3-pyridyl)methanol;

Delta14-reductase inhibitors: aldimorph, dodemorph, dodemorph-acetate, fenpropimorph, tridemorph, fenpropidin, piperalin, spiroxamine;

Inhibitors of 3-keto reductase: fenhexamid;

C) Nucleic Acid Synthesis Inhibitors phenylamides or acyl amino acid fungicides: benalaxyl, benalaxyl-M, kiralaxyl, metalaxyl, metalaxyl-M (mefenoxam), ofurace, oxadixyl;

others: hymexazole, octhilinone, oxolinic acid, bupirimate, 5-fluorocytosine, 5-fluoro-2-(ptolylmethoxy)pyrimidin-4-amine, 5-fluoro-2-(4-fluorophenylmethoxy)pyrimidin-4-amine;

D) Inhibitors of Cell Division and Cytoskeleton tubulin inhibitors, such as benzimidazoles, thiophanates: benonl, carbendazim, fuberidazole, thiabendazole, thiophanate-methyl; triazolopyrimidines: 5-chloro-7-(4-methylpiperidin-1-yl)-6-(2,4,6-trifluorophenyl)-[1,2,4]triazolo[1,5-a]pyrimidine other cell division inhibitors: diethofencarb, ethaboxam, pencycuron, fluopicolide, zoxamide, metrafenone, pyriofenone;

E) Inhibitors of Amino Acid and Protein Synthesis methionine synthesis inhibitors (anilino-pyrimidines): cyprodinil, mepanipyrim, pyrimethanil;

protein synthesis inhibitors: blasticidin-S, kasuga$_n$cin, kasuga$_n$cin hydrochloride-hydrate, mildio$_n$cin, strepto$_n$cin, oxytetracyclin, polyoxine, valida$_n$cin A;

F) Signal Transduction Inhibitors

MAP/histidine kinase inhibitors: fluoroimid, iprodione, procymidone, vinclozolin, fenpiclonil, fludioxonil;

G protein inhibitors: quinoxyfen;

G) Lipid and Membrane Synthesis Inhibitors

Phospholipid biosynthesis inhibitors: edifenphos, iprobenfos, pyrazophos, isoprothiolane;

lipid peroxidation: dicloran, quintozene, tecnazene, tolclofos-methyl, biphenyl, chloroneb, etridazole;

phospholipid biosynthesis and cell wall deposition: dimethomorph, flumorph, mandipropamid, pyrimorph, benthiavalicarb, iprovalicarb, valifenalate and N-(1-(1-(4-cyano-phenyl)ethanesulfo$_n$l)-but-2-yl) carbamic acid-(4-fluorophenyl) ester;

compounds affecting cell membrane permeability and fatty acides: propamocarb, propamocarb-hydrochlorid
fatty acid amide hydrolase inhibitors: 1-[4-[4-[5-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]ethanone; 2-{3-[2-(1-{[3,5-bis(difluoromethyl-1H-pyrazol-1-yl]acetyl}piperidin-4-yl)-1,3-thiazol-4-yl]-4,5-dihydro-1,2-oxazol-5-yl}phenyl methanesulfonate, 2-{3-[2-(1-{[3,5-bis(difluoromethyl)-1H-pyrazol-1-yl]acetyl}piperidin-4-yl) 1,3-thiazol-4-yl]-4,5-dihydro-1,2-oxazol-5-yl}-3-chlorophenyl methanesulfonate;
H) Inhibitors with Multi Site Action
inorganic active substances: Bordeaux mixture, copper acetate, copper hydroxide, copper oxychloride, basic copper sulfate, sulfur;
thio- and dithiocarbamates: ferbam, mancozeb, maneb, metam, metiram, propineb, thiram, zineb, ziram;
organochlorine compounds (e.g. phthalimides, sulfamides, chloronitriles): anilazine, chlorothalonil, captafol, captan, folpet, dichlofluanid, dichlorophen, hexachlorobenzene, pentachlorphenole and its salts, phthalide, tolylfluanid, N-(4-chloro-2-nitro-phenyl)-N-ethyl-4-methylbenzenesulfonamide;
guanidines and others: guanidine, dodine, dodine free base, guazatine, guazatineacetate, iminoctadine, iminoctadine-triacetate, iminoctadine-tris(albesilate), dithianon, 2,6-dimethyl-1H,5H-[1,4]dithiino[2,3-c:5,6-c]dipyrrole-1,3,5,7(2H,6H)-tetraone;
I) Cell Wall Synthesis Inhibitors
inhibitors of glucan synthesis: valida„cin, polyoxin B;
melanin synthesis inhibitors: pyroquilon, tricyclazole, carpropamid, dicyclomet, fenoxanil;
J) Plant Defence Inducers
acibenzolar-S-methyl, probenazole, isotianil, tiadinil, prohexadione-calcium; phosphonates: fosetyl, fosetyl-aluminum, phosphorous acid and its salts;
K) Unknown Mode of Action
bronopol, chinomethionat, cyflufenamid, cymoxanil, dazomet, debacarb, diclomezine, difenzoquat, difenzoquat-methylsulfate, diphenylamin, fenpyrazamine, flumetover, flusulfamide, flutianil, methasulfocarb, nitrapyrin, nitrothal-isopropyl, oxathiapiprolin, tolprocarb, 2-[3,5-bis(difluoromethyl)-1H-pyrazol-1-yl]-1-[4-(4-{5-[2-(prop-2-yn-1-yloxy)phenyl]-4,5-dihydro-1,2-oxazol-3-yl}-1,3-thiazol-2-yl)piperidin-1-yl]ethanone, 2-[3,5-bis(difluoromethyl)-1H-pyrazol-1-yl]-1-[4-(4-{5-[2-fluoro-6-(prop-2-yn-1-yloxy)phenyl]-4,5-dihydro-1,2-oxazol-3-yl}-1,3-thiazol-2-yl)piperidin-1-yl]ethanone, 2-[3,5-bis(difluoromethyl))-1H-pyrazol-1-yl]-1-[4-(4-{5-[2-chloro-6-(prop-2-yn-1-yloxy)phenyl]-4,5-dihydro-1,2-oxazol-3-yl}-1,3-thiazol-2-yl)piperidin-1-yl]ethanone, oxin-copper, proquinazid, tebufloquin, tecloftalam, triazoxide, 2-butoxy-6-iodo-3-propylchromen-4-one, N-(cyclopropylmethoxyimino-(6-difluoro-methoxy-2,3-difluoro-phenyl)-methyl)-2-phenyl acetamide, N'-(4-(4-chloro-3-trifluoromethyl-phenoxy)-2,5-dimethyl-phenyl)-N-ethyl-N-methyl formamidine, N'-(4-(4-fluoro-3-trifluoromethyl-phenoxy)-2,5-dimethyl-phenyl)-N-ethyl-N-methyl formamidine, N'-(2-methyl-5-trifluoromethyl-4-(3-trimethylsilanyl-propoxy)-phenyl)-N-ethyl-N-methyl formamidine, N'-(5-difluoromethyl-2-methyl-4-(3-trimethylsilanyl-propoxy)-phenyl)-N-ethyl-N-methyl formamidine, methoxy-acetic acid 6-tert-butyl-8-fluoro-2,3-dimethyl-quinolin-4-yl ester, 3-[5-(4-methylphenyl)-2,3-dimethyl-isoxazolidin-3-yl]-pyridine, 3-[5-(4-chlorophenyl)-2,3-dimethyl-isoxazolidin-3-yl]-pyridine (pyrisoxazole), N-(6-methoxy-pyridin-3-yl)cyclopropanecarboxylic acid amide, 5-chloro-1-(4,6-dimethoxypyrimidin-2-yl)-2-methyl-1H-benzoimidazole, 2-(4-chloro-phenyl)-N-[4-(3,4-dimethoxy-phenyl)-isoxazol-5-yl]-2-prop-2-ynyloxy-acetamide, ethyl (Z)-3-amino-2-cyano-3-phenyl-prop-2-enoate, tert-butyl N-[6-[[(Z)-[(1-methyltetrazol-5-yl)-phenylmethylene]amino]oxymethyl]-2-pyridyl]carbamate, 2-[2-[(7,8-difluoro-2-methyl-3-quinolyl)oxy]-6-fluoro-phenyl]propan-2-ol, 2-[2-fluoro-6-[(8-fluoro-2-methyl-3-quinolyl)oxy]phenyl]propan-2-ol, 3-(5-fluoro-3,3,4,4-tetramethyl-3,4-dihydroisoquinolin-1-yl)quinoline, 3-(4,4-difluoro-3,3-dimethyl-3,4-dihydroisoquinolin-1-yl)quinoline, 3-(4,4,5-trifluoro-3,3-dimethyl-3,4-dihydroisoquinolin-1-yl)quinolone, 9-fluoro-2,2-dimethyl-5-(3-quinolyl)-3H-1,4-benzoxazepine; picarbutrazox;
L) Biopesticides
L1) Microbial pesticides with fungicidal, bactericidal, viricidal and/or plant defense activator activity: *Ampelomyces quisqualis, Aspergillus flavus, Aureobasidium pullulans, Bacillus amyloliquefaciens, B. mojavensis, B. pumllus, B. simplex, B. solisalsi, B. subtilis, B. subtilis* var. *amyloliquefaciens, Candida oleophlla, C. saitoana, Clawbacter michiganensis* (bacteriophages), *Coniothyrium minitans, Cryphonectria parasitica, Cryptococcus albidus, Dilophosphora alopecuri, Fusarium oxysporum, Clonostachys rosea* f. *catenulate* (also named *Gliocladium catenulatum*), *Gliocladium roseum, Lysobacter antibioticus, L. enzymogenes, Metschnikowia fructicola, Microdochium dimerum, Microsphaeropsis ochracea, Muscodor albus, Paenibacillus polymyxa, Pantoea vagans, Phlebiopsis gigantea, Pseudomonas* sp., *Pseudomonas chloraphis, Pseudozyma flocculosa, Pichia anomala, Pythium oligandrum, Sphaerodes mycoparasitica, Streptomyces griseoviridis, S. lydicus, S. microflavus, S. violaceusniger, Talaromyces flavus, Trichoderma asperellum, T. atroviride, T. fertile, T. gamsii, T. harmatum, T. harzianum*; mixture of *T. harzianum* and *T. viride*; mixture of *T. polysporum* and *T. harzianum*; *T. stromaticum, T. virens* (also named *Gliocladium virens*), *T. viride, Typhula phacorrhiza, Ulocladium oudemansii, Verticillium dahlia*, zucchini yellow mosaic virus (avirulent strain);
L2) Biochemical pesticides with fungicidal, bactericidal, viricidal and/or plant defense activator activity: chitosan (hydrolysate), harpin protein, laminarin, Menhaden fish oil, natamycin, Plum pox virus coat protein, potassium or sodium bicarbonate, *Reynoutria sachlinensis* extract, salicylic acid, tea tree oil;
L3) Microbial pesticides with insecticidal, acaricidal, molluscidal and/or nematicidal activity: *Agrobacterium radiobacter, Bacillus cereus, B. firmus, B. thuringiensis, B. thuringiensis* ssp. *aizawai*, B. t. ssp. *israelensis*, B. t. ssp. *galleriae*, B. t. ssp. *kurstaki*, B. t. ssp. *tenebrionis, Beauveria bassiana, B. brongniartii Burkholderia* sp., *Chromobacterium subtsugae, Cydia pomonella granulosis virus, Cryptophiebia leucotreta granulovirus* (CrIeGV), *Flavobacterium* sp., *Helicoverpa armigera* nucleopolyhedrovirus (HearNPV), *Isaria fumosorosea, Heterorhabditis bacteriophora, Lecanicillium longisporum, L. muscarium* (formerly *Verticillium lecanii*), *Metarhizium anisopliae, M. anisopliae* var. *acridum, Nomuraea rileyi, Paecilomy-* ces *fumosoroseus*, *P. lilacinus*, *Paembacillus popaae*, *Pasteuria* sp., *P. nishizawae*, *P. penetrans*, *P. ramose*, *P. reneformis*, *P. thornea*, *P. usgae*, *Pseudomonas fluorescens*, *Spodoptera littoralis* nucleopolyhedrovirus (SpliNPV), *Steinernema carpocapsae*, *S. feltiae*, *S. kraussei*, *Streptomyces microflavus*;

L4) Biochemical pesticides with insecticidal, acaricidal, molluscidal, pheromone and/or nematicidal activity: L-carvone, citral, (E,Z)-7,9-dodecadien-1-ylacetate, ethyl formate, (E,Z)-2,4-ethyl decadienoate (pear ester), (Z,Z,E)-7,11,13-hexadecatrienal, heptyl butyrate, isopropyl myristate, lavanulyl senecioate, cis-jasmone, 2-methyl 1-butanol, methyl eugenol, methyl jasmonate, (E,Z)-2,13-octadecadien-1-ol, (E,Z)-2,13-octadecadien-1-ol acetate, (E,Z)-3,13-octadecadien-1-ol, R-1-octen-3-ol, pentatermanone, potassium silicate, sorbitol actanoate, (E,Z,Z)-3,8,11-tetradecatrienyl acetate, (Z,E)-9,12-tetradecadien-1-yl acetate, Z-7-tetradecen-2-one, Z-9-tetradecen-1-yl acetate, Z-11-tetradecenal, Z-11-tetradecen-1-ol, Acacia negra extract, extract of grapefruit seeds and pulp, extract of *Chenopodium ambrosioides*, Catnip oil, Neem oil, Quillay extract, Tagetes oil;

L5) Microbial pesticides with plant stress reducing, plant growth regulator, plant growth promoting and/or yield enhancing activity: *Azospirillum amazonense*, *A. brasilense*, *A. lipoferum*, *A. irakense*, *A. halopraeferens*, *Bradyrhizobium* sp., *B. elkanii*, *B. japonicum*, *B. liaoningense*, *B. lupini*, *Delftia acidovorans*, *Glomus intraradices*, *Mesorhizobium* sp., *Paembacillus alvei*, *Penicillium bilaiae*, *Rhizobium leguminosarum* bv. *phaseoli*, *R. I.* bv. *trifolii*, *R. I.* bv. *viciae*, *R. tropici*, *Sinorhizobium meliloti*, L6) Biochemical pesticides with plant stress reducing, plant growth regulator and/or plant yield enhancing activity: abscisic acid, aluminium silicate (kaolin), 3-decen-2-one, formononetin, genistein, hesperetin, homobrassinlide, humates, jasmonic acid or salts or derivatives thereof, lysophosphatidyl ethanolamine, naringenin, polymeric polyhydroxy acid, *Ascophyllum nodosum* (Norwegian kelp, Brown kelp) extract and *Ecklonia maxima* (kelp) extract;

M) Growth regulators abscisic acid, amidochlor, ancymidol, 6-benzylaminopurine, brassinolide, butralin, chlormequat (chlormequat chloride), choline chloride, cyclanilide, daminozide, dikegulac, dimethipin, 2,6-dimethylpuridine, ethephon, flumetralin, flurprimidol, fluthiacet, forchlorfenuron, gibberellic acid, inabenfide, indole-3-acetic acid, maleic hydrazide, mefluidide, mepiquat (mepiquat chloride), naphthaleneacetic acid, N-6-benzyladenine, paclobutrazol, prohexadione (prohexadione-calcium), prohydrojasmon, thidiazuron, triapenthenol, tributyl phosphorotrithioate, 2,3,5-tri-iodobenzoic acid, trinexapac-ethyl and uniconazole;

N) Herbicides acetamides: acetochlor, alachlor, butachlor, dimethachlor, dimethenamid, flufenacet, mefenacet, metolachlor, metazachlor, napropamide, naproanilide, pethoxamid, pretilachlor, propachlor, thenylchlor;

amino acid derivatives: bilanafos, glyphosate, glufosinate, sulfosate;

aryloxyphenoxypropionates: clodinafop, cyhalofop-butyl, fenoxaprop, fluazifop, haloxyfop, metamifop, propaquizafop, quizalofop, quizalofop-P-tefuryl;

Bipyridyls: diquat, paraquat;

(thio)carbamates: asulam, butylate, carbetamide, desmedipham, dimepiperate, eptam (EPTC), esprocarb, molinate, orbencarb, phenmedipham, prosulfocarb, pyributicarb, thiobencarb, triallate;

cyclohexanediones: butroxydim, clethodim, cycloxydim, profoxydim, sethoxydim, tepraloxydim, tralkoxydim;

dinitroanilines: benfluralin, ethalfluralin, oryzalin, pendimethalin, prodiamine, trifluralin;

diphenyl ethers: acifluorfen, aclonifen, bifenox, diclofop, ethoxyfen, fomesafen, lactofen, oxyfluorfen;

hydroxybenzonitriles: bomoxynil, dichlobenil, ioxynil;

imidazolinones: imazamethabenz, imazamox, imazapic, imazapyr, imazaquin, imazethapyr;

phenoxy acetic acids: clomeprop, 2,4-dichlorophenoxyacetic acid (2,4-D), 2,4-DB, dichlorprop, MCPA, MCPA-thioethyl, MCPB, Mecoprop;

pyrazines: chloridazon, flufenpyr-ethyl, fluthiacet, norflurazon, pyridate;

pyridines: aminopyralid, clopyralid, diflufenican, dithiopyr, fluridone, fluroxypyr, picloram, picolinafen, thiazopyr;

sulfo$_n$1 ureas: amidosulfuron, azimsulfuron, bensulfuron, chlorimuron-ethyl, chlorsulfuron, cinosulfuron, cyclosulfamuron, ethoxysulfuron, flazasulfuron, flucetosulfuron, flupyrsulfuron, foramsulfuron, halosulfuron, imazosulfuron, iodosulfuron, mesosulfuron, metazosulfuron, metsulfuron-methyl, nicosulfuron, oxasulfuron, primisulfuron, prosulfuron, pyrazosulfuron, rimsulfuron, sulfometuron, sulfosulfuron, thifensulfuron, triasulfuron, tribenuron, trifloxysulfuron, triflusulfuron, tritosulfuron, 1-((2-chloro-6-propyl-imidazo[1,2-b]pyridazin-3-yl)sulfo$_n$1)-3-(4,6-dimethoxypyrimidin-2-yl)urea;

triazines: ametryn, atrazine, cyanazine, dimethametryn, ethiozin, hexazinone, metamitron, metribuzin, prometryn, simazine, terbuthylazine, terbutryn, triaziflam;

ureas: chlorotoluron, daimuron, diuron, fluometuron, isoproturon, linuron, methabenzthiazuron, tebuthiuron;

other acetolactate synthase inhibitors: bispyribac-sodium, cloransulam-methyl, diclosulam, florasulam, flucarbazone, flumetsulam, metosulam, ortho-sulfamuron, penoxsulam, propoxycarbazone, pyribambenz-propyl, pyribenzoxim, pyriftalid, pyriminobac-methyl, pyrimisulfan, pyrithiobac, pyroxasulfone, pyroxsulam;

others: amicarbazone, aminotriazole, anilofos, beflubutamid, benazolin, bencarbazone, benfluresate, benzofenap, bentazone, benzobicyclon, bicyclopyrone, bromacil, bromobutide, butafenacil, butamifos, cafenstrole, carfentrazone, cinidon-ethyl, chlorthal, cinmethylin, clomazone, cu$_n$luron, cyprosulfamide, dicamba, difenzoquat, diflufenzopyr, *Drechslera monoceras*, endothal, ethofumesate, etobenzanid, fenoxasulfone, fentrazamide, flumiclorac-pentyl, flumioxazin, flupoxam, flurochloridone, flurtamone, indanofan, isoxaben, isoxaflutole, lenacil, propanil, propyzamide, quinclorac, quinmerac, mesotrione, methyl arsonic acid, naptalam, oxadiargyl, oxadiazon, oxaziclomefone, pentoxazone, pinoxaden, pyraclonil, pyraflufen-ethyl, pyrasulfotole, pyrazoxyfen, pyrazolynate, quinoclamine, saflufenacil, sulcotrione, sulfentrazone, terbacil, tefuryltrione, tembotrione, thiencarbazone, topramezone, (3-[2-chloro-4-fluoro-5-(3-methyl-2,6-dioxo-4-trifluoromethyl-3,6-dihydro-2H-pyrimidin-1-yl)-phenoxy]-pyridin-2-yloxy)acetic acid ethyl ester, 6-amino-5-chloro-2-cyclopropyl-pyrimidine-4-carboxylic acid methyl ester, 6-chloro-3-(2-cyclopropyl-6-methyl-phenoxy)-pyridazin-4-ol, 4-amino-3-chloro-6-(4-chloro-phenyl)-5-fluoro-pyridine-2-carboxylic acid, 4-amino-3-chloro-6-(4-chloro- 2-fluoro-3-methoxyphenyl)-pyridine-2-carboxylic acid methyl ester, and 4-amino-3-chloro-6-(4-chloro-3-dimethylamino-2-fluoro-phenyl)-pyridine-2-carboxylic acid methyl ester.

O) Insecticides organo(thio)phosphates: acephate, azamethiphos, azinphos-methyl, chlorpyrifos, chlorpyrifos-methyl, chlorfenvinphos, diazinon, dichlorvos, dicrotophos, dimethoate, disulfoton, ethion, fenitrothion, fenthion, isoxathion, malathion, methamidophos, methidathion, methylparathion, mevinphos, monocrotophos, oxydemeton-methyl, paraoxon, parathion, phenthoate, phosalone, phosmet, phosphamidon, phorate, phoxim, pirimiphos-methyl, profenofos, prothiofos, sulprophos, tetrachlorvinphos, terbufos, triazophos, trichlorfon;

carbamates: alancarb, aldicarb, bendiocarb, benfuracarb, carbaryl, carbofuran, carbosulfan, fenoxycarb, furathiocarb, methiocarb, metho$_n$l, oxa$_n$l, pirimicarb, propoxur, thiodicarb, triazamate;

pyrethroids: allethrin, bifenthrin, cyfluthrin, cyhalothrin, cyphenothrin, cypermethrin, alphacypermethrin, betacypermethrin, zeta-cypermethrin, deltamethrin, esfenvalerate, etofenprox, fenpropathrin, fenvalerate, imiprothrin, lambda-cyhalothrin, permethrin, prallethrin, pyrethrin I and II, resmethrin, silafluofen, tau-fluvalinate, tefluthrin, tetramethrin, tralomethrin, transfluthrin, profluthrin, dimefluthrin;

insect growth regulators: a) chitin synthesis inhibitors: benzoylureas: chlorfluazuron, cyramazin, diflubenzuron, flucycloxuron, flufenoxuron, hexaflumuron, lufenuron, novaluron, teflubenzuron, triflumuron; buprofezin, diofenolan, hexythiazox, etoxazole, clofentazine; b) ecdysone antagonists: halofenozide, methoxyfenozide, tebufenozide, azadirachtin; c) juvenoids: pyriproxyfen, methoprene, fenoxycarb; d) lipid biosynthesis inhibitors: spirodiclofen, spiromesifen, spirotetramat;

nicotinic receptor agonists/antagonists compounds: clothianidin, dinotefuran, flupyradifurone, imidacloprid, thiamethoxam, nitenpyram, acetamiprid, thiacloprid, 1-2-chloro-thiazol-5-ylmethyl)-2-nitrimino-3,5-dimethyl-[1,3,5]triazinane;

GABA antagonist compounds: endosulfan, ethiprole, fipronil, vaniliprole, pyrafluprole, pyriprole, 5-amino-1-(2,6-dichloro-4-methyl-phenyl)-4-sulfinamoyl-1H-pyrazole-3-carbothioic acid amide;

macrocyclic lactone insecticides: abamectin, emamectin, milbemectin, lepimectin, spinosad, spinetoram;

mitochondrial electron transport inhibitor (METI) I acaricides: fenazaquin, pyridaben, tebufenpyrad, tolfenpyrad, flufenerim;

METI II and III compounds: acequinocyl, fluacyprim, hydramethylnon;

Uncouplers: chlorfenapyr;

oxidative phosphorylation inhibitors: cyhexatin, diafenthiuron, fenbutatin oxide, propargite;

moulting disruptor compounds: cryomazine;

mixed function oxidase inhibitors: piperonl butoxide;

sodium channel blockers: indoxacarb, metaflumizone;

ryanodine receptor inhibitors: chlorantraniliprole, cyantraniliprole, flubendiamide, N-[4,6-dichloro-2-[(diethyl-lambda-4-sulfanylidene)carbamoyl]-phenyl]-2-(3-chloro-2-pyridyl)-5-(trifluoromethyl)pyrazole-3-carboxamide; N-[4-chloro-2-[(diethyl-lambda-4-sulfanylidene)carbamoyl]-6-methyl-phenyl]-2-(3-chloro-2-pyridyl)-5-(trifluoromethyl)pyrazole-3-carboxamide; N-[4-chloro-2-[(di-2-propyl-lambda-4-sulfanylidene)carbamoyl]-6-methyl-phenyl]-2-(3-chloro-2-pyridyl)-5-(trifluoromethyl)pyrazole-3-carboxamide; N-[4,6-dichloro-2-[(di-2-propyl-lambda-4-sulfanylidene)carbamoyl]-phenyl]-2-(3-chloro-2-pyridyl)-5-(trifluoromethyl)pyrazole-3-carboxamide; N-[4,6-dichloro-2-[(diethyl-lambda-4-sulfanylidene)carbamoyl]-phenyl]-2-(3-chloro-2-pyridyl)-5-(difluoromethyl)pyrazole-3-carboxamide; N-[4,6-dibromo-2-[(di-2-propyl-lambda-4-sulfanylidene)carbamoyl]-phenyl]-2-(3-chloro-2-pyridyl)-5-(trifluoromethyl)pyrazole-3-carboxamide; N-[4-chloro-2-[(di-2-propyl-lambda-4-sulfanylidene)carbamoyl]-6-cyano-phenyl]-2-(3-chloro-2-pyridyl)-5-(trifluoromethyl)pyrazole-3-carboxamide; N-[4,6-dibromo-2-[(diethyl-lambda-4-sulfanylidene)carbamoyl]-phenyl]-2-(3-chloro-2-pyridyl)-5-(trifluoromethyl)pyrazole-3-carboxamide;

others: benclothiaz, bifenazate, cartap, flonicamid, pyridalyl, pymetrozine, sulfur, thiocyclam, flubendiamide, chlorantraniliprole, cyazypyr (HGW86), cyenopyrafen, flupyrazofos, cyflumetofen, amidoflumet, imicyafos, bistrifluron, pyrifluquinazon and 1,1'-[(3S,4R,4aR,6S,6aS,12R,12aS,12bS)-4-[[(2-cyclopropylacetyl)oxy]methyl]-1,3,4,4a,5,6,6a,12,12a,12b-decahydro-12-hydroxy-4,6a,12b-trimethyl-11-oxo-9-(3-pyridinyl)$_2$H,11H-naphtho[2,1-b]pyrano[3,4-e]pyran-3,6-diyl]cyclopropaneacetic acid ester.

The present invention furthermore relates to compositions comprising a compound I (component 1) and at least one further active substance useful for plant protection, e. g. selected from the groups A) to O) (component 2), in particular one further fungicide, e. g. fungicide from the groups A) to L), as described above, and if desired one suitable solvent or solid carrier. Those compositions are of particular interest, since many of them at the same application rate show higher efficiencies against harmful fungi. Furthermore, combating harmful fungi with a compristion comprising a compound I and a fungicide from groups A) to L), as described above, is more efficient than combating those fungi with individual compounds I or individual fungicides from groups A) to L). By applying compound I together with at least one active substance from groups A) to O) a synergistic effect can be obtained, i.e. more then simple addition of the individual effects is obtained (synergistic compositions).

This can be obtained by applying the compounds I or II, respectively, and at least one further active substance simultaneously, either jointly (e. g. as tank-mix) or separately, or in succession, wherein the time interval between the individual applications is selected to ensure that the active substance applied first still occurs at the site of action in a sufficient amount at the time of application of the further active substance(s). The order of application is not essential for working of the present invention.

In compositions according to the invention comprising one compound I (component 1) and one further active substance (component 2), e. g. one active substance from groups A) to O), the weight ratio of component 1 and component 2 generally depends from the properties of the active substances used, usually it is in the range of from 1:100 to 100:1, regularly in the range of from 1:50 to 50:1, preferably in the range of from 1:20 to 20:1, more preferably in the range of from 1:10 to 10:1 and in particular in the range of from 1:3 to 3:1.

In compositions according to the invention comprising one compound I (component 1) and a first further active substance (component 2) and a second further active substance (component 3), e. g. two active substances from groups A) to O), the weight ratio of component 1 and component 2 depends from the properties of the active substances used, preferably it is in the range of from 1:50 to 50:1 and particularly in the range of from 1:10 to 10:1, and the weight ratio of component 1 and component 3 preferably is in the range of from 1:50 to 50:1 and particularly in the range of from 1:10 to 10:1.

Preference is also given to compositions comprising a compound I (component 1) and at least one active substance selected from group A) (component 2) and particularly selected from azoxystrobin, dimoxystrobin, fluoxastrobin, kresoxim-methyl, orysastrobin, picoxystrobin, pyraclostrobin, trifloxystrobin; famoxadone, fenamidone; benzovindiflupyr, bixafen, boscalid, fluopyram, fluxapyroxad, isopyrazam, penflufen, penthiopyrad, sedaxane; ametoctradin, cyazofamid, fluazinam, fentin salts, such as fentin acetate.

Preference is given to compositions comprising a compound of formula I, (component 1) and at least one active substance selected from group B) (component 2) and particularly selected from cyproconazole, difenoconazole, epoxiconazole, fluquinconazole, flusilazole, flutriafol, metconazole, „clobutanil, penconazole, propiconazole, prothioconazole, triadimefon, triadimenol, tebuconazole, tetraconazole, triticonazole, prochloraz, fenarimol, triforine; dodemorph, fenpropimorph, tridemorph, fenpropidin, spiroxamine; fenhexamid.

Preference is given to compositions comprising a compound of formula I, (component 1) and at least one active substance selected from group C) (component 2) and particularly selected from metalaxyl, (metalaxyl-M) mefenoxam, ofurace.

Preference is given to compositions comprising a compound of formula I, (component 1) and at least one active substance selected from group D) (component 2) and particularly selected from benomyl, carbendazim, thiophanate-methyl, ethaboxam, fluopicolide, zoxamide, metrafenone, pyriofenone.

Preference is also given to compositions comprising a compound I (component 1) and at least one active substance selected from group E) (component 2) and particularly selected from cyprodinil, mepanipyrim, pyrimethanil.

Preference is also given to compositions comprising a compound I (component 1) and at least one active substance selected from group F) (component 2) and particularly selected from iprodione, fludioxonil, vinclozolin, quinoxyfen.

Preference is also given to compositions comprising a compound I (component 1) and at least one active substance selected from group G) (component 2) and particularly selected from dimethomorph, flumorph, iprovalicarb, benthiavalicarb, mandipropamid, propamocarb.

Preference is also given to compositions comprising a compound I (component 1) and at least one active substance selected from group H) (component 2) and particularly selected from copper acetate, copper hydroxide, copper oxychloride, copper sulfate, sulfur, mancozeb, metiram, propineb, thiram, captafol, folpet, chlorothalonil, dichlofluanid, dithianon.

Preference is also given to compositions comprising a compound I (component 1) and at least one active substance selected from group I) (component 2) and particularly selected from carpropamid and fenoxanil.

Preference is also given to compositions comprising a compound I (component 1) and at least one active substance selected from group J) (component 2) and particularly selected from acibenzolar-S-methyl, probenazole, tiadinil, fosetyl, fosetyl-aluminium, $H_3PO_3$ and salts thereof.

Preference is also given to compositions comprising a compound I (component 1) and at least one active substance selected from group K) (component 2) and particularly selected from cymoxanil, proquinazid and N-methyl-2-{1-[(5-methyl-3-trifluoromethyl-1H-pyrazol-1-yl)-acetyl]-piperidin-4-yl}-N-[(1R)-1,2,3,4-tetrahydronaphthalen-1-yl]-4-thiazolecarboxamide.

Preference is also given to compositions comprising a compound I (component 1) and at least one active substance selected from group L) (component 2) and particularly selected from *Bacillus subtilis* strain NRRL No. B-21661, *Bacillus pumllus* strain NRRL No. B-30087 and *Ulocladium oudemansii*.

Accordingly, the present invention furthermore relates to compositions comprising one compound I (component 1) and one further active substance (component 2), which further active substance is selected from the column "Component 2" of the lines C-1 to C-402 of Table C.

A further embodiment relates to the compositions C-1 to C-402 listed in Table C, wherein one row of Table C corresponds in each case to a composition comprising one of the compounds I that are individualized compounds of formula I (component 1) and the respective further active substance from groups A) to 0) (component 2) stated in the respective row. According to a preferred embodiment, the "individualized compound I" is one of the compounds as individualized in Tables 1a to 142a, Tables 1b to 142b, Tables 1c to 142c and Tables 1d to 142d. Preferably, the compositions described comprise the active substances in synergistically effective amounts.

TABLE C

Composition comprising one individualized compound of the present invention and one further active substance from groups A) to O)

| Mixture | Component 1 | Component 2 |
| --- | --- | --- |
| C-1 | one individualized compound I | Azoxystrobin |
| C-2 | one individualized compound I | Coumethoxystrobin |
| C-3 | one individualized compound I | Coumoxystrobin |
| C-4 | one individualized compound I | Dimoxystrobin |
| C-5 | one individualized compound I | Enestroburin |
| C-6 | one individualized compound I | Fenaminstrobin |
| C-7 | one individualized compound I | Fenoxystrobin/Flufenoxystrobin |
| C-8 | one individualized compound I | Fluoxastrobin |
| C-9 | one individualized compound I | Kresoxim-methyl |
| C-10 | one individualized compound I | Metominostrobin |
| C-11 | one individualized compound I | Orysastrobin |
| C-12 | one individualized compound I | Picoxystrobin |
| C-13 | one individualized compound I | Pyraclostrobin |

TABLE C-continued

Composition comprising one individualized compound of the present invention and one further active substance from groups A) to O)

| Mixture | Component 1 | Component 2 |
|---|---|---|
| C-14 | one individualized compound I | Pyrametostrobin |
| C-15 | one individualized compound I | Pyraoxystrobin |
| C-16 | one individualized compound I | Pyribencarb |
| C-17 | one individualized compound I | Trifloxystrobin |
| C-18 | one individualized compound I | Triclopyricarb/Chlorodincarb |
| C-19 | one individualized compound I | 2-[2-(2,5-dimethyl-phenoxymethyl)-phenyl]-3-methoxy-acrylic acid methyl ester |
| C-20 | one individualized compound I | 2-(2-(3-(2,6-dichlorophenyl)-1-methyl-allylideneaminooxymethyl)-phenyl)-2-methoxyimino-N-methyl-acetamide |
| C-21 | one individualized compound I | Cyazofamid |
| C-22 | one individualized compound I | Amisulbrom |
| C-23 | one individualized compound I | Benalaxyl |
| C-24 | one individualized compound I | Benalaxyl-M |
| C-25 | one individualized compound I | Benodanil |
| C-26 | one individualized compound I | Benzovindiflupyr |
| C-27 | one individualized compound I | Bixafen |
| C-28 | one individualized compound I | Boscalid |
| C-29 | one individualized compound I | Carboxin |
| C-30 | one individualized compound I | Fenfuram |
| C-31 | one individualized compound I | Fenhexamid |
| C-32 | one individualized compound I | Flutolanil |
| C-33 | one individualized compound I | Fluxapyroxad |
| C-34 | one individualized compound I | Furametpyr |
| C-35 | one individualized compound I | Isofetamid |
| C-36 | one individualized compound I | Isopyrazam |
| C-37 | one individualized compound I | Isotianil |
| C-38 | one individualized compound I | Kiralaxyl |
| C-39 | one individualized compound I | Mepronil |
| C-40 | one individualized compound I | Metalaxyl |
| C-41 | one individualized compound I | Metalaxyl-M |
| C-42 | one individualized compound I | Ofurace |
| C-43 | one individualized compound I | Oxadixyl |
| C-44 | one individualized compound I | Oxycarboxin |
| C-45 | one individualized compound I | Penflufen |
| C-46 | one individualized compound I | Penthiopyrad |
| C-47 | one individualized compound I | Sedaxane |
| C-48 | one individualized compound I | Tecloftalam |
| C-49 | one individualized compound I | Thifluzamide |
| C-50 | one individualized compound I | Tiadinil |
| C-51 | one individualized compound I | 2-Amino-4-methyl-thiazole-5-carboxylic acid anilide |
| C-52 | one individualized compound I | N-(4'-trifluoromethylthiobiphenyl-2-yl)-3-difluoromethyl-1-methyl-1H-pyrazole-4-carboxamide |
| C-53 | one individualized compound I | N-(2-(1,3,3-trimethyl-butyl)-phenyl)-1,3-dimethyl-5-fluoro-1 H-pyrazole-4-carboxamide |
| C-54 | one individualized compound I | 3-(difluoromethyl)-1-methyl-N-(1,1,3-tri-methylindan-4-yl)pyrazole-4-carboxamide |
| C-55 | one individualized compound I | 3-(trifluoromethyl)-1-methyl-N-(1,1,3-tri-methylindan-4-yl)pyrazole-4-carboxamide |
| C-56 | one individualized compound I | 1,3-dimethyl-N-(1,1,3-trimethylindan-4-yl)pyrazole-4-carboxamide |
| C-57 | one individualized compound I | 3-(trifluoromethyl)-1,5-dimethyl-N-(1,1,3-trimethylindan-4-yl)pyrazole-4-carboxamide |
| C-58 | one individualized compound I | N-(7-fluoro-1,1,3-trimethyl-indan-4-yl)-1,3-dimethyl-pyrazole-4-carboxamide |
| C-59 | one individualized compound I | 1,3,5-trimethyl-N-(1,1,3-trimethylindan-4-yl)pyrazole-4-carboxamide |
| C-60 | one individualized compound I | N-[2-(2,4-dichlorophenyl)-2-methoxy-1-methyl-ethyl]-3-(difluoromethyl)-1-methyl-pyrazole-4-carboxamide |
| C-61 | one individualized compound I | Dimethomorph |
| C-62 | one individualized compound I | Flumorph |
| C-63 | one individualized compound I | Pyrimorph |
| C-64 | one individualized compound I | Flumetover |
| C-65 | one individualized compound I | Fluopicolide |
| C-66 | one individualized compound I | Fluopyram |
| C-67 | one individualized compound I | Zoxamide |
| C-68 | one individualized compound I | Carpropamid |
| C-69 | one individualized compound I | Diclocymet |
| C-70 | one individualized compound I | Mandipropamid |

TABLE C-continued

Composition comprising one individualized compound of the present invention and one further active substance from groups A) to O)

| Mixture | Component 1 | Component 2 |
|---|---|---|
| C-71 | one individualized compound I | Oxytetracyclin |
| C-72 | one individualized compound I | Silthiofam |
| C-73 | one individualized compound I | N-(6-methoxy-pyridin-3-yl) cyclopropanecarboxylic acid amide |
| C-74 | one individualized compound I | Azaconazole |
| C-75 | one individualized compound I | Bitertanol |
| C-76 | one individualized compound I | Bromuconazole |
| C-77 | one individualized compound I | Cyproconazole |
| C-78 | one individualized compound I | Difenoconazole |
| C-79 | one individualized compound I | Diniconazole |
| C-80 | one individualized compound I | Diniconazole-M |
| C-81 | one individualized compound I | Epoxiconazole |
| C-82 | one individualized compound I | Fenbuconazole |
| C-83 | one individualized compound I | Fluquinconazole |
| C-84 | one individualized compound I | Flusilazole |
| C-85 | one individualized compound I | Flutriafol |
| C-86 | one individualized compound I | Hexaconazol |
| C-87 | one individualized compound I | Imibenconazole |
| C-88 | one individualized compound I | Ipconazole |
| C-89 | one individualized compound I | Metconazole |
| C-90 | one individualized compound I | Myclobutanil |
| C-91 | one individualized compound I | Oxpoconazol |
| C-92 | one individualized compound I | Paclobutrazol |
| C-93 | one individualized compound I | Penconazole |
| C-94 | one individualized compound I | Propiconazole |
| C-95 | one individualized compound I | Prothioconazole |
| C-96 | one individualized compound I | Simeconazole |
| C-97 | one individualized compound I | Tebuconazole |
| C-98 | one individualized compound I | Tetraconazole |
| C-99 | one individualized compound I | Triadimefon |
| C-100 | one individualized compound I | Triadimenol |
| C-101 | one individualized compound I | Triticonazole |
| C-102 | one individualized compound I | Uniconazole |
| C-103 | one individualized compound I | 1-[rel-(2S;3R)-3-(2-chlorophenyl)-2-(2,4-difluorophenyl)-oxiranylmethyl]-5-thiocyanato-1H-[1,2,4]triazole, |
| C-104 | one individualized compound I | 2-[rel-(2S;3R)-3-(2-chlorophenyl)-2-(2,4-difluorophenyl)-oxiranylmethyl]-2H-[1,2,4]triazole-3-thiol |
| C-105 | one individualized compound I | 2-[2-chloro-4-(4-chlorophenoxy)phenyl]-1-(1,2,4-triazol-1-yl)pentan-2-ol |
| C-106 | one individualized compound I | 1-[4-(4-chlorophenoxy)-2-(trifluoromethyl)phenyl]-1-cyclopropyl-2-(1,2,4-triazol-1-yl)ethanol |
| C-107 | one individualized compound I | 2-[4-(4-chlorophenoxy)-2-(trifluoromethyl)phenyl]-1-(1,2,4-triazol-1-yl)butan-2-ol |
| C-108 | one individualized compound I | 2-[2-chloro-4-(4-chlorophenoxy)phenyl]-1-(1,2,4-triazol-1-yl)butan-2-ol |
| C-109 | one individualized compound I | 2-[4-(4-chlorophenoxy)-2-(trifluoromethyl)phenyl]-3-methyl-1-(1,2,4-triazol-1-yl)butan-2-ol |
| C-110 | one individualized compound I | 2-[4-(4-chlorophenoxy)-2-(trifluoromethyl)phenyl]-1-(1,2,4-triazol-1-yl)propan-2-ol |
| C-111 | one individualized compound I | 2-[2-chloro-4-(4-chlorophenoxy)phenyl]-3-methyl-1-(1,2,4-triazol-1-yl)butan-2-ol |
| C-112 | one individualized compound I | 2-[4-(4-chlorophenoxy)-2-(trifluoromethyl)phenyl]-1-(1,2,4-triazol-1-yl)pentan-2-ol; |
| C-113 | one individualized compound I | 2-[4-(4-fluorophenoxy)-2-(trifluoromethyl)phenyl]-1-(1,2,4-triazol-1-yl)propan-2-ol |
| C-114 | one individualized compound I | Amisulbrom |
| C-115 | one individualized compound I | Imazalil |
| C-116 | one individualized compound I | Imazalil-sulfate |
| C-117 | one individualized compound I | Pefurazoate |
| C-118 | one individualized compound I | Prochloraz |
| C-119 | one individualized compound I | Triflumizole |
| C-120 | one individualized compound I | Benomyl |
| C-121 | one individualized compound I | Carbendazim |
| C-122 | one individualized compound I | Fuberidazole |
| C-123 | one individualized compound I | Thiabendazole |
| C-124 | one individualized compound I | Ethaboxam |
| C-125 | one individualized compound I | Etridiazole |
| C-126 | one individualized compound I | Hymexazole |

TABLE C-continued

Composition comprising one individualized compound of the present
invention and one further active substance from groups A) to O)

| Mixture | Component 1 | Component 2 |
|---|---|---|
| C-127 | one individualized compound I | 2-(4-Chloro-phenyl)-N-[4-(3,4-dimethoxy-phenyl)-isoxazol-5-yl]-2-prop-2-yn-yloxy-acetamide |
| C-128 | one individualized compound I | Fluazinam |
| C-129 | one individualized compound I | Pyrifenox |
| C-130 | one individualized compound I | 3-[5-(4-Chloro-phenyl)-2,3-dimethyl-isoxazolidin-3-yl]-pyridine (Pyrisoxazole) |
| C-131 | one individualized compound I | 3-[5-(4-Methyl-phenyl)-2,3-dimethyl-isoxazolidin-3-yl]-pyridine |
| C-132 | one individualized compound I | Bupirimate |
| C-133 | one individualized compound I | Cyprodinil |
| C-134 | one individualized compound I | 5-Fluorocytosine |
| C-135 | one individualized compound I | 5-Fluoro-2-(p-tolylmethoxy)pyrimidin-4-amine |
| C-136 | one individualized compound I | 5-Fluoro-2-(4-fluorophenylmethoxy)-pyrimidin-4-amine |
| C-137 | one individualized compound I | Diflumetorim |
| C-138 | one individualized compound I | (5,8-Difluoroquinazolin-4-yl)-{2-[2-fluoro-4-(4-trifluoromethylpyridin-2-yloxy)-phenyl]-ethyl}-amine |
| C-139 | one individualized compound I | Fenarimol |
| C-140 | one individualized compound I | Ferimzone |
| C-141 | one individualized compound I | Mepanipyrim |
| C-142 | one individualized compound I | Nitrapyrin |
| C-143 | one individualized compound I | Nuarimol |
| C-144 | one individualized compound I | Pyrimethanil |
| C-145 | one individualized compound I | Triforine |
| C-146 | one individualized compound I | Fenpiclonil |
| C-147 | one individualized compound I | Fludioxonil |
| C-148 | one individualized compound I | Aldimorph |
| C-149 | one individualized compound I | Dodemorph |
| C-150 | one individualized compound I | Dodemorph-acetate |
| C-151 | one individualized compound I | Fenpropimorph |
| C-152 | one individualized compound I | Tridemorph |
| C-153 | one individualized compound I | Fenpropidin |
| C-154 | one individualized compound I | Fluoroimid |
| C-155 | one individualized compound I | Iprodione |
| C-156 | one individualized compound I | Procymidone |
| C-157 | one individualized compound I | Vinclozolin |
| C-158 | one individualized compound I | Famoxadone |
| C-159 | one individualized compound I | Fenamidone |
| C-160 | one individualized compound I | Flutianil |
| C-161 | one individualized compound I | Octhilinone |
| C-162 | one individualized compound I | Probenazole |
| C-163 | one individualized compound I | Fenpyrazamine |
| C-164 | one individualized compound I | Acibenzolar-S-methyl |
| C-165 | one individualized compound I | Ametoctradin |
| C-166 | one individualized compound I | Amisulbrom |
| C-167 | one individualized compound I | [(3S,6S,7R,8R)-8-benzyl-3-[(3-isobuty-ryloxymethoxy-4-methoxypyridine-2-carbonyl)amino]-6-methyl-4,9-dioxo-[1,5]dioxonan-7-yl] 2-methylpropanoate |
| C-168 | one individualized compound I | [(3S,6S,7R,8R)-8-benzyl-3-[(3-acetoxy-4-methoxy-pyridine-2-carbonyl)amino]-6-methyl-4,9-dioxo-1,5-dioxonan-7-yl] 2-methylpropanoate |
| C-169 | one individualized compound I | [(3S,6S,7R,8R)-8-benzyl-3-[[3-(acet-oxymethoxy)-4-methoxy-pyridine-2-carbonyl]amino]-6-methyl-4,9-dioxo-1,5-dioxonan-7-yl] 2-methylpropanoate |
| C-170 | one individualized compound I | [(3S,6S,7R,8R)-8-benzyl-3-[(3-isobut-oxycarbonyloxy-4-methoxy-pyridine-2-carbonyl)amino]-6-methyl-4,9-dioxo-1,5-dioxonan-7-yl] 2-methylpropanoate |
| C-171 | one individualized compound I | [(3S,6S,7R,8R)-8-benzyl-3-[[3-(1,3-benzodioxol-5-ylmethoxy)-4-methoxy-pyridine-2-carbonyl]amino]-6-methyl-4,9-dioxo-1,5-dioxonan-7-yl] 2-methylpropanoate |
| C-172 | one individualized compound I | (3S,6S,7R,8R)-3-[[(3-hydroxy-4-methoxy-2-pyridinyl)carbonyl]amino]-6-methyl-4,9-dioxo-8-(phenylmethyl)-1,5-dioxonan-7-yl 2-methylpropanoate |
| C-173 | one individualized compound I | Anilazin |
| C-174 | one individualized compound I | Blasticidin-S |
| C-175 | one individualized compound I | Captafol |

TABLE C-continued

Composition comprising one individualized compound of the present invention and one further active substance from groups A) to O)

| Mixture | Component 1 | Component 2 |
|---|---|---|
| C-176 | one individualized compound I | Captan |
| C-177 | one individualized compound I | Chinomethionat |
| C-178 | one individualized compound I | Dazomet |
| C-179 | one individualized compound I | Debacarb |
| C-180 | one individualized compound I | Diclomezine |
| C-181 | one individualized compound I | Difenzoquat, |
| C-182 | one individualized compound I | Difenzoquat-methylsulfate |
| C-183 | one individualized compound I | Fenoxanil |
| C-184 | one individualized compound I | Folpet |
| C-185 | one individualized compound I | Oxolinsäure |
| C-186 | one individualized compound I | Piperalin |
| C-187 | one individualized compound I | Proquinazid |
| C-188 | one individualized compound I | Pyroquilon |
| C-189 | one individualized compound I | Quinoxyfen |
| C-190 | one individualized compound I | Triazoxid |
| C-191 | one individualized compound I | Tricyclazole |
| C-192 | one individualized compound I | 2-Butoxy-6-iodo-3-propyl-chromen-4-one |
| C-193 | one individualized compound I | 5-Chloro-1-(4,6-dimethoxy-pyrimidin-2-yl)-2-methyl-1H-benzoimidazole |
| C-194 | one individualized compound I | 5-Chloro-7-(4-methyl-piperidin-1-yl)-6-(2,4,6-trifluoro-phenyl)-[1,2,4]triazolo[1,5-a]pyrimidine |
| C-195 | one individualized compound I | Ferbam |
| C-196 | one individualized compound I | Mancozeb |
| C-197 | one individualized compound I | Maneb |
| C-198 | one individualized compound I | Metam |
| C-199 | one individualized compound I | Methasulphocarb |
| C-200 | one individualized compound I | Metiram |
| C-201 | one individualized compound I | Propineb |
| C-202 | one individualized compound I | Thiram |
| C-203 | one individualized compound I | Zineb |
| C-204 | one individualized compound I | Ziram |
| C-205 | one individualized compound I | Diethofencarb |
| C-206 | one individualized compound I | Benthiavalicarb |
| C-207 | one individualized compound I | Iprovalicarb |
| C-208 | one individualized compound I | Propamocarb |
| C-209 | one individualized compound I | Propamocarb hydrochlorid |
| C-210 | one individualized compound I | Valifenalate |
| C-211 | one individualized compound I | N-(1-(1-(4-cyanophenyl)ethanesulfonyl)-but-2-yl) carbamic acid-(4-fluorophenyl) ester |
| C-212 | one individualized compound I | Dodine |
| C-213 | one individualized compound I | Dodine free base |
| C-214 | one individualized compound I | Guazatine |
| C-215 | one individualized compound I | Guazatine-acetate |
| C-216 | one individualized compound I | Iminoctadine |
| C-217 | one individualized compound I | Iminoctadine-triacetate |
| C-218 | one individualized compound I | Iminoctadine-tris(albesilate) |
| C-219 | one individualized compound I | Kasugamycin |
| C-220 | one individualized compound I | Kasugamycin-hydrochloride-hydrate |
| C-221 | one individualized compound I | Polyoxine |
| C-222 | one individualized compound I | Streptomycin |
| C-223 | one individualized compound I | Validamycin A |
| C-224 | one individualized compound I | Binapacryl |
| C-225 | one individualized compound I | Dicloran |
| C-226 | one individualized compound I | Dinobuton |
| C-227 | one individualized compound I | Dinocap |
| C-228 | one individualized compound I | Nitrothal-isopropyl |
| C-229 | one individualized compound I | Tecnazen |
| C-230 | one individualized compound I | Fentin salts |
| C-231 | one individualized compound I | Dithianon |
| C-232 | one individualized compound I | 2,6-dimethyl-1H,5H-[1,4]dithiino[2,3-c:5,6-c']dipyrrole-1,3,5,7(2H,6H)-tetraone |
| C-233 | one individualized compound I | Isoprothiolane |
| C-234 | one individualized compound I | Edifenphos |
| C-235 | one individualized compound I | Fosetyl, Fosetyl-aluminium |
| C-236 | one individualized compound I | Iprobenfos |
| C-237 | one individualized compound I | Phosphorous acid ($H_3PO_3$) and derivatives |
| C-238 | one individualized compound I | Pyrazophos |
| C-239 | one individualized compound I | Tolclofos-methyl |
| C-240 | one individualized compound I | Chlorothalonil |
| C-241 | one individualized compound I | Dichlofluanid |

TABLE C-continued

Composition comprising one individualized compound of the present invention and one further active substance from groups A) to O)

| Mixture | Component 1 | Component 2 |
|---|---|---|
| C-242 | one individualized compound I | Dichlorophen |
| C-243 | one individualized compound I | Flusulfamide |
| C-244 | one individualized compound I | Hexachlorbenzene |
| C-245 | one individualized compound I | Pencycuron |
| C-246 | one individualized compound I | Pentachlorophenol and salts |
| C-247 | one individualized compound I | Phthalide |
| C-248 | one individualized compound I | Quintozene |
| C-249 | one individualized compound I | Thiophanate Methyl |
| C-250 | one individualized compound I | Tolylfluanid |
| C-251 | one individualized compound I | N-(4-chloro-2-nitro-phenyl)-N-ethyl-4-methyl-benzenesulfonamide |
| C-252 | one individualized compound I | Bordeaux mixture |
| C-253 | one individualized compound I | Copper acetate |
| C-254 | one individualized compound I | Copper hydroxide |
| C-255 | one individualized compound I | Copper oxychloride |
| C-256 | one individualized compound I | basic Copper sulfate |
| C-257 | one individualized compound I | Sulfur |
| C-258 | one individualized compound I | Biphenyl |
| C-259 | one individualized compound I | Bronopol |
| C-260 | one individualized compound I | Cyflufenamid |
| C-261 | one individualized compound I | Cymoxanil |
| C-262 | one individualized compound I | Diphenylamin |
| C-263 | one individualized compound I | Metrafenone |
| C-264 | one individualized compound I | Pyriofenone |
| C-265 | one individualized compound I | Mildiomycin |
| C-266 | one individualized compound I | Oxin-copper |
| C-267 | one individualized compound I | Oxathiapiprolin |
| C-268 | one individualized compound I | Tolprocarb |
| C-269 | one individualized compound I | 2-[3,5-bis(difluoromethyl)-1H-pyrazol-1-yl]-1-[4-(4-{5-[2-(prop-2-yn-1-yloxy)phenyl]-4,5-dihydro-1,2-oxazol-3-yl}-1,3-thisazol-2-yl)piperidin-1-yl]ethanone |
| C-270 | one individualized compound I | 2-[3,5-bis(difluoromethyl)-1H-pyrazol-1-yl]-1-[4-(4-{5-[2-fluoro-6-(prop-2-yn-1-yloxy)phenyl]-4,5-dihydro-1,2-oxazol-3-yl}-1,3-thiazol-2-yl)piperidin-1-yl]-ethanone |
| C-271 | one individualized compound I | 2-[3,5-bis(difluoromethyl)-1H-pyrazol-1-yl]-1-[4-(4-{5-[2-chloro-6-(prop-2-yn-1-yloxy)phenyl]-4,5-dihydro-1,2-oxazol-3-yl}-1,3-thiazol-2-yl)piperidin-1-yl]-ethanone |
| C-272 | one individualized compound I | ethyl (Z)-3-amino-2-cyano-3-phenyl-prop-2-enoate |
| C-273 | one individualized compound I | tert-butyl N-[6-[[(Z)-[(1-methyltetrazol-5-yl)-phenyl-methylene]amino]oxy-methyl]-2-pyridyl]carbamate |
| C-274 | one individualized compound I | pentyl N-[6-[[(Z)-[(1-methyltetrazol-5-yl)-phenyl-methylene]amino]oxy-methyl]-2-pyridyl]carbamate |
| C-275 | one individualized compound I | 2-[2-[(7,8-difluoro-2-methyl-3-quinolyl)oxy]-6-fluoro-phenyl]propan-2-ol |
| C-276 | one individualized compound I | 2-[2-fluoro-6-[(8-fluoro-2-methyl-3-quinolyl)oxy]phenyl]propan-2-ol |
| C-277 | one individualized compound I | 3-(5-fluoro-3,3,4,4-tetramethyl-3,4-di-hydroisoquinolin-1-yl)quinoline |
| C-278 | one individualized compound I | 3-(4,4-difluoro-3,3-dimethyl-3,4-di-hydroisoquinolin-1-yl)quinoline |
| C-279 | one individualized compound I | 3-(4,4,5-trifluoro-3,3-dimethyl-3,4-di-hydroisoquinolin-1-yl)quinoline |
| C-280 | one individualized compound I | Prohexadione calcium |
| C-281 | one individualized compound I | Spiroxamine |
| C-282 | one individualized compound I | Tebufloquin |
| C-283 | one individualized compound I | Tolylfluanid |
| C-284 | one individualized compound I | N-(Cyclopropylmethoxyimino-(6-difluoromethoxy-2,3-difluoro-phenyl)-methyl)-2-phenyl acetamide |
| C-285 | one individualized compound I | N'-(4-(4-chloro-3-trifluoromethyl-phenoxy)-2,5-dimethyl-phenyl)-N-ethyl-N-methyl formamidine |
| C-286 | one individualized compound I | N'-(4-(4-fluoro-3-trifluoromethyl-phenoxy)-2,5-dimethyl-phenyl)-N-ethyl-N-methyl formamidine |
| C-287 | one individualized compound I | N'-(2-methyl-5-trifluoromethyl-4-(3-tri-methylsilanyl-propoxy)-phenyl)-N-ethyl-N-methyl formamidine |

TABLE C-continued

Composition comprising one individualized compound of the present invention and one further active substance from groups A) to O)

| Mixture | Component 1 | Component 2 |
|---|---|---|
| C-288 | one individualized compound I | N'-(5-difluoromethyl-2-methyl-4-(3-tri-methylsilanyl-propoxy)-phenyl)-N-ethyl-N-methyl formamidine |
| C-289 | one individualized compound I | Methoxy-acetic acid 6-tert-butyl-8-fluoro-2,3-dimethyl-quinolin-4-yl ester |
| C-290 | one individualized compound I | *Bacillus subtilis* NRRL No. B-21661 |
| C-291 | one individualized compound I | *Bacillus pumilus* NRRL No. B-30087 |
| C-292 | one individualized compound I | *Ulocladium oudemansii* |
| C-293 | one individualized compound I | Carbaryl |
| C-294 | one individualized compound I | Carbofuran |
| C-295 | one individualized compound I | Carbosulfan |
| C-296 | one individualized compound I | Methomylthiodicarb |
| C-297 | one individualized compound I | Bifenthrin |
| C-298 | one individualized compound I | Cyfluthrin |
| C-299 | one individualized compound I | Cypermethrin |
| C-300 | one individualized compound I | alpha-Cypermethrin |
| C-301 | one individualized compound I | zeta-Cypermethrin |
| C-302 | one individualized compound I | Deltamethrin |
| C-303 | one individualized compound I | Esfenvalerate |
| C-304 | one individualized compound I | Lambda-cyhalothrin |
| C-305 | one individualized compound I | Permethrin |
| C-306 | one individualized compound I | Tefluthrin |
| C-307 | one individualized compound I | Diflubenzuron |
| C-308 | one individualized compound I | Flufenoxuron |
| C-309 | one individualized compound I | Lufenuron |
| C-310 | one individualized compound I | Teflubenzuron |
| C-311 | one individualized compound I | Spirotetramate |
| C-312 | one individualized compound I | Clothianidin |
| C-313 | one individualized compound I | Dinotefuran |
| C-314 | one individualized compound I | Imidacloprid |
| C-315 | one individualized compound I | Thiamethoxam |
| C-316 | one individualized compound I | Flupyradifurone |
| C-317 | one individualized compound I | Acetamiprid |
| C-318 | one individualized compound I | Thiacloprid |
| C-319 | one individualized compound I | Endosulfan |
| C-320 | one individualized compound I | Fipronil |
| C-321 | one individualized compound I | Abamectin |
| C-322 | one individualized compound I | Emamectin |
| C-323 | one individualized compound I | Spinosad |
| C-324 | one individualized compound I | Spinetoram |
| C-325 | one individualized compound I | Hydramethylnon |
| C-326 | one individualized compound I | Chlorfenapyr |
| C-327 | one individualized compound I | Fenbutatin oxide |
| C-328 | one individualized compound I | Indoxacarb |
| C-329 | one individualized compound I | Metaflumizone |
| C-330 | one individualized compound I | Flonicamid |
| C-331 | one individualized compound I | Flubendiamide |
| C-332 | one individualized compound I | Chlorantraniliprole |
| C-333 | one individualized compound I | Cyantraniliprole |
| C-334 | one individualized compound I | N-[4,6-dichloro-2-[(diethyl-lambda-4-sulfanylidene)carbamoyl]-phenyl]-2-(3-chloro-2-pyridyl)-5-(trifluoromethyl)pyrazole-3-carboxamide |
| C-335 | one individualized compound I | N-[4-chloro-2-[(diethyl-lambda-4-sulfanylidene)carbamoyl]-6-methyl-phenyl]-2-(3-chloro-2-pyridyl)-5-(trifluoromethyl)pyrazole-3-carboxamide |
| C-336 | one individualized compound I | N-[4-chloro-2-[(di-2-propyl-lambda-4-sulfanylidene)carbamoyl]-6-methyl-phenyl]-2-(3-chloro-2-pyridyl)-5-(trifluoromethyl)pyrazole-3-carboxamide |
| C-337 | one individualized compound I | N-[4,6-dichloro-2-[(di-2-propyl-lambda-4-sulfanylidene)carbamoyl]-phenyl]-2-(3-chloro-2-pyridyl)-5-(trifluoromethyl)pyrazole-3-carboxamide |
| C-338 | one individualized compound I | N-[4,6-dichloro-2-[(diethyl-lambda-4-sulfanylidene)carbamoyl]-phenyl]-2-(3-chloro-2-pyridyl)-5-(difluoro-methyl)pyrazole-3-carboxamide |
| C-339 | one individualized compound I | N-[4,6-dibromo-2-[(di-2-propyl-lambda-4-sulfanylidene)carbamoyl]-phenyl]-2-(3-chloro-2-pyridyl)-5-(trifluoromethyl)-pyrazole-3-carboxamide |
| C-340 | one individualized compound I | N-[4-chloro-2-[(di-2-propyl-lambda-4-sulfanylidene)carbamoyl]-6-cyano-phenyl]-2-(3-chloro-2-pyridyl)-5-(trifluoromethyl)pyrazole-3-carboxamide |

TABLE C-continued

Composition comprising one individualized compound of the present invention and one further active substance from groups A) to O)

| Mixture | Component 1 | Component 2 |
|---|---|---|
| C-341 | one individualized compound I | N-[4,6-dibromo-2-[(diethyl-lambda-4-sulfanylidene)carbamoyl]-phenyl]-2-(3-chloro-2-pyridyl)-5-(trifluoromethyl)pyrazole-3-carboxamide |
| C-342 | one individualized compound I | Cyflumetofen |
| C-343 | one individualized compound I | Acetochlor |
| C-344 | one individualized compound I | Dimethenamid |
| C-345 | one individualized compound I | metolachlor |
| C-346 | one individualized compound I | Metazachlor |
| C-347 | one individualized compound I | Glyphosate |
| C-348 | one individualized compound I | Glufosinate |
| C-349 | one individualized compound I | Sulfosate |
| C-350 | one individualized compound I | Clodinafop |
| C-351 | one individualized compound I | Fenoxaprop |
| C-352 | one individualized compound I | Fluazifop |
| C-353 | one individualized compound I | Haloxyfop |
| C-354 | one individualized compound I | Paraquat |
| C-355 | one individualized compound I | Phenmedipham |
| C-356 | one individualized compound I | Clethodim |
| C-357 | one individualized compound I | Cycloxydim |
| C-358 | one individualized compound I | Profoxydim |
| C-359 | one individualized compound I | Sethoxydim |
| C-360 | one individualized compound I | Tepraloxydim |
| C-361 | one individualized compound I | Pendimethalin |
| C-362 | one individualized compound I | Prodiamine |
| C-363 | one individualized compound I | Trifluralin |
| C-364 | one individualized compound I | Acifluorfen |
| C-365 | one individualized compound I | Bromoxynil |
| C-366 | one individualized compound I | Imazamethabenz |
| C-367 | one individualized compound I | Imazamox |
| C-368 | one individualized compound I | Imazapic |
| C-369 | one individualized compound I | Imazapyr |
| C-370 | one individualized compound I | Imazaquin |
| C-371 | one individualized compound I | Imazethapyr |
| C-372 | one individualized compound I | 2,4-Dichlorophenoxyacetic acid (2,4-D) |
| C-373 | one individualized compound I | Chloridazon |
| C-374 | one individualized compound I | Clopyralid |
| C-375 | one individualized compound I | Fluroxypyr |
| C-376 | one individualized compound I | Picloram |
| C-377 | one individualized compound I | Picolinafen |
| C-378 | one individualized compound I | Bensulfuron |
| C-379 | one individualized compound I | Chlorimuron-ethyl |
| C-380 | one individualized compound I | Cyclosulfamuron |
| C-381 | one individualized compound I | Iodosulfuron |
| C-382 | one individualized compound I | Mesosulfuron |
| C-383 | one individualized compound I | Metsulfuron-methyl |
| C-384 | one individualized compound I | Nicosulfuron |
| C-385 | one individualized compound I | Rimsulfuron |
| C-386 | one individualized compound I | Triflusulfuron |
| C-387 | one individualized compound I | Atrazine |
| C-388 | one individualized compound I | Hexazinone |
| C-389 | one individualized compound I | Diuron |
| C-390 | one individualized compound I | Florasulam |
| C-391 | one individualized compound I | Pyroxasulfone |
| C-392 | one individualized compound I | Bentazone |
| C-393 | one individualized compound I | Cinidon-ethyl |
| C-394 | one individualized compound I | Cinmethylin |
| C-395 | one individualized compound I | Dicamba |
| C-396 | one individualized compound I | Diflufenzopyr |
| C-397 | one individualized compound I | Quinclorac |
| C-398 | one individualized compound I | Quinmerac |
| C-399 | one individualized compound I | Mesotrione |
| C-400 | one individualized compound I | Saflufenacil |
| C-401 | one individualized compound I | Topramezone |
| C-402 | one individualized compound I | 1,1'-[(3S,4R,4aR,6S,6aS,12R,12aS,12bS)-4-[[(2-cyclopropylacetyl)oxy]methyl]-1,3,4,4a,5,6,6a,12,12a,12b-deca-hydro-12-hydroxy-4,6a,12b-trimethyl-11-oxo-9-(3-pyridinyl)-2H,11H-naphtho[2,1-b]pyrano[3,4-e]pyran-3,6-diyl] cyclopropaneacetic acid ester |

The active substances referred to as component 2, their preparation and their activity against harmful fungi is known (cf.: http://www.alanwood.net/pesticides/); these substances are commercially available. The compounds described by IUPAC nomenclature, their preparation and their fungicidal activity are also known (cf. Can. J. Plant Sci. 48(6), 587-94, 1968; EP-A 141 317; EP-A 152 031; EP-A 226 917; EP-A 243 970; EP-A 256 503; EP-A 428 941; EPA 532 022; EP-A 1 028 125; EP-A 1 035 122; EP-A 1 201 648; EP-A 1 122 244, JP 2002316902; DE 19650197; DE 10021412; DE 102005009458; U.S. Pat. No. 3,296,272; U.S. Pat. No. 3,325,503; WO 98/46608; WO 99/14187; WO 99/24413; WO 99/27783; WO 00/29404; WO 00/46148; WO 00/65913; WO 01/54501; WO 01/56358; WO 02/22583; WO 02/40431; WO 03/10149; WO 03/11853; WO 03/14103; WO 03/16286; WO 03/53145; WO 03/61388; WO 03/66609; WO 03/74491; WO 04/49804; WO 04/83193; WO 05/120234; WO 05/123689; WO 05/123690; WO 05/63721; WO 05/87772; WO 05/87773; WO 06/15866; WO 06/87325; WO 06/87343; WO 07/82098; WO 07/90624, WO 11/028657, WO2012/168188, WO 2007/006670, WO 2011/77514; WO13/047749, WO 10/069882, WO 13/047441, WO 03/16303, WO 09/90181, WO 13/010862, WO 13/007767, PCT/EP2012/065650, PCT/EP2012/065651). The composition of active substances can be prepared as compositions comprising besides the active ingredients at least one inert ingredient by usual means, e. g. by the means given for the compositions of compounds I.

Concerning usual ingredients of such compositions reference is made to the explanations given for the compositions containing compounds I.

The compositions of active substances according to the present invention are suitable as fungicides, as are the compounds of formula I or II. They are distinguished by an outstanding effectiveness against a broad spectrum of phytopathogenic fungi, especially from the classes of the Asco$_n$-cetes, Basidio$_n$cetes, Deutero$_n$cetes and Peronosporo$_n$cetes (syn. Oo$_n$cetes). In addition, it is referred to the explanations regarding the fungicidal activity of the compounds and the compositions containing compounds I.

I. SYNTHESIS EXAMPLES

With due modification of the starting compounds, the procedures shown in the synthesis examples below were used to obtain further compounds I. The resulting compounds, together with physical data, are listed in Table I below.

The compounds I listed in Table I have been prepared in an analogous manner.

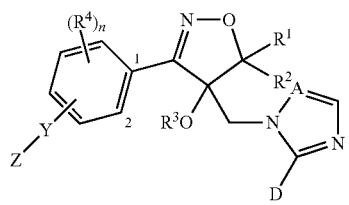

I

TABLE I

| No. | D | A | R$^1$ | R$^2$ | R$^3$ | (R$^4$)$_n$ | Y-Z | HPLC* R$_t$ (min) |
|---|---|---|---|---|---|---|---|---|
| I-1 | H | N | cyclohexyl | H | | n = 0 | 4-(4-Cl-phenoxy) | 1.22 |

TABLE I-continued

| No. | D | A | R$^1$ | R$^2$ | R$^3$ | (R$^4$)$_n$ | Y-Z | HPLC* R$_t$ (min) |
|---|---|---|---|---|---|---|---|---|
| I-2 | H | N | cyclohexyl | CH$_3$ | | n = 0 | 4-(4-Cl-phenoxy) | 1.36 |
| I-3 | H | N | CH$_3$ | CH$_3$ | H | n = 1 2-Cl | 4-(4-Cl-phenoxy) | 1.17 |
| I-4 | H | N | CH$_3$ | CH$_3$ | CH$_3$ | n = 1 2-Cl | 4-(4-Cl-phenoxy) | 1.28 |
| I-5 | H | N | cyclohexyl | H | | n = 1 2-Cl | 4-(4-Cl-phenoxy) | 1.28 |
| I-6 | H | N | CH$_3$ | CH$_3$ | H | n = 0 | 4-(4-Cl-phenoxy) | 1.10 |
| I-7 | H | N | cyclohexyl | CH$_3$ | | n = 1 2-Cl | 4-(4-Cl-phenoxy) | 1.39 |
| I-8 | H | N | CH$_3$ | CH$_3$ | CH$_3$ | n = 0 | 4-(4-Cl-phenoxy) | 1.24 |
| I-9 | H | CH | CH$_3$ | CH$_3$ | H | n = 0 | 4-(4-Cl-phenoxy) | 0.937 |

*HPLC methode Data:

Mobile Phase: A: Water+0.1% TFA, B: acetonitrile; Gradient: 5% B to 100% B in 1.5 min; Temperature: 60° C.; MS method: ESI positive; mass area (m/z): 10-700; Flow: 0.8 ml/min to 1.0 ml/min in 1.5 min; Column: Kinetex XB C18 1.7μ 50×2.1 mm; Aparatus: Shimadzu Nexera LC-30 LCMS-2020

Example 1

Synthesis of 2-[4-(4-chlorophenoxy)phenyl]-1-(1,2,4-triazol-1-ylmethyl)-4-oxa-3-azaspiro[4.5]dec-2-en-1-ol (I-1)

Step 1:

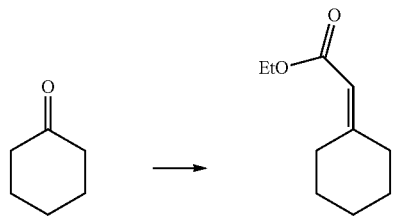 [SMILES: O=C1CCCCC1 ; CCOC(=O)C=C1CCCCC1]

Ethyl 2-diethoxyphosphorylacetate (235.0 g, 1.0 mol) was dissolved in THF (1500 ml) and cooled at 0° C. NaH (50.0 g, 1.2 mol) was added in portions and the solution was stirred at this temperature for 0.5 h. Then a solution of cyclohexanone (98.0 g, 1.0 mol) in THF (200 ml) was added dropwise and the solution was stirred overnight. NH$_4$Cl aq. was added, extracted with MTBE (1000 mL×2), washed with brine, dried over Na$_2$SO$_4$ and concentrated, then purified by chromatogram on silica gel (PE: EA=1000:1~100:1) to afford ethyl 2-cyclohexylideneacetate (70.0 g, 43%). $^1$H NMR: CDCl$_3$ 400 MHz: 5.56 (m, 1H), 4.15 (q, 2H J=11 Hz), 2.95 (s, 1H), 2.02 (m, 3H), 1.48-1.55 (m, 5H), 1.28 (t, 3H J=10 Hz), 0.87 (m, 3H).

Step 2:

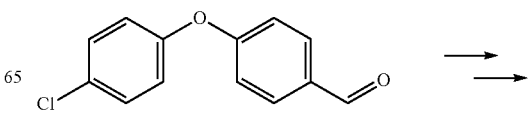

223

-continued

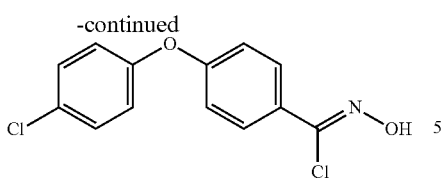

To 4-(4-chlorophenoxy)benzaldehyde (40.0 g, 0.17 mol) and NH$_2$OH.HCl (14.8 g, 0.20 mol) dissolved in DCM (1000 ml) was added pyridine (33.0 mL, 020 mol) and the solution was stirred at RT for overnight. 2M HCl (150 ml) was added, extracted with DCM (300 mL×2), washed with brine, dried over Na$_2$SO$_4$ and concentrated to give (1Z)-4-(4-chlorophenoxy)benzaldehyde oxime (40.0 g, 92%). The crude compound (36.0 g, 0.14 mol) was then dissolved in THF (300 ml) cooled at 0° C. was added conc. HCl (74 mL) slowly, then added NaClO (8%) (202 ml) dropwise and keep the reaction temperature below 5° C. and stirred another 1 h. The resulting solution was extracted with DCM (300 mL×2), washed with brine, dried over Na$_2$SO$_4$ and concentrated to give 4-(4-chlorophenoxy)-N-hydroxy-benzimidoyl chloride (36 g, 82%).

Step 3:

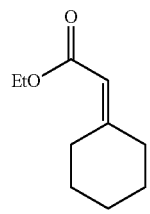 

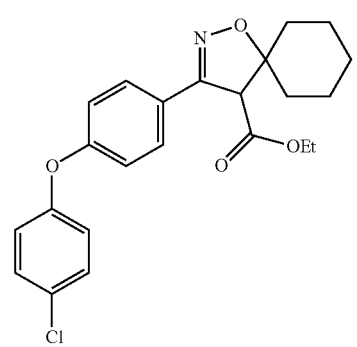

To 4-(4-chlorophenoxy)-N-hydroxy-benzimidoyl chloride (20.0 g, 0.07 mol) and ethyl 2-cyclohexylideneacetate (30.0 g, 0.17 mol) dissolved in THF (400 ml) was added NaHCO$_3$ (12.0 g, 0.14 mol) and the solution was refluxed overnight. The resulting solution was extracted with MTBE (200 mL×2), washed with brine, dried over Na$_2$SO$_4$ and concentrated then purified by chromatogram on silica gel (PE: EA=500:1~100:1) to afford ethyl 2-[4-(4-chlorophenoxy)phenyl]-4-oxa-3-azaspiro[4.5]dec-2-ene-1-carboxylate (3.0 g, 10%) $^1$H NMR: CDCl$_3$ 400 MHz: 7.58 (d, 2H J=12 Hz), 7.30 (d, 2H J=8 Hz), 6.95 (m, 4H), 4.17 (t, 2H J=14 Hz), 3.92 (s, 1H), 1.53-1.88 (m, 9H), 1.35 (m, 1H), 1.19 (q, 3H J=4 Hz).

224

Step 4:

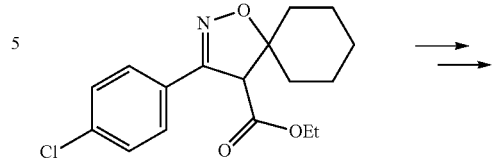

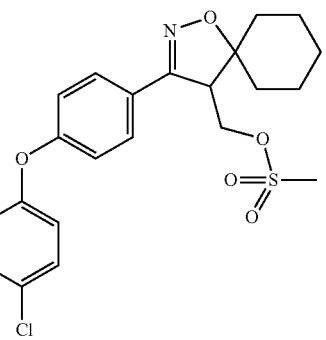 

To ethyl 2-[4-(4-chlorophenoxy)phenyl]-4-oxa-3-azaspiro[4.5]dec-2-ene-1-carboxylate (2.7 g, 6.0 mmol) dissolved in THF (100 ml) cooled at −20° C. was added LiAlH$_4$ (0.25 g, 6.0 mol) in portion and the solution was stirred at this temperature for 1 h. H$_2$O (0.3 g) was added slowly, dried over Na$_2$SO$_4$ and filtered, then the filtrate was concentrated to give [2-[4-(4-chlorophenoxy)phenyl]-4-oxa-3-azaspiro[4.5]dec-2-en-1-yl]methanol (2.0 g, 83%). To the crude [2-[4-(4-chlorophenoxy)phenyl]-4-oxa-3-azaspiro[4.5]dec-2-en-1-yl]methanol (2.0 g, 5.3 mmol) and triethylamine (0.9 g, 8.0 mmol) dissolved in DCM (70 ml) cooled at 0° C. was added MsCl (0.9 g, 8.0 mmol) dropwise over 5 min and the solution was stirred at this temperature for 1 h. Water was added, extracted with DCM (150 mL×2), washed with brine, dried over Na$_2$SO$_4$ and concentrated to give [2-[4-(4-chlorophenoxy)phenyl]-4-oxa-3-azaspiro[4.5]dec-2-en-1-yl] methyl methanesulfonate (2.5 g, 93%). $^1$H NMR: CDCl$_3$ 400 MHz: 7.71 (d, 2H J=8 Hz), 7.35 (d, 2H 8 Hz), 7.02 (m, 4H), 4.35 (m, 2H), 3.53 (s, 1H), 2.97 (s, 3H), 2.07 (m, 1H), 1.71-1.89 (m, 5H), 1.21-1.41 (m, 3H).

Step 5:

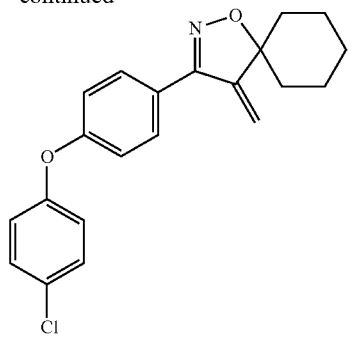

A mixture of [2-[4-(4-chlorophenoxy)phenyl]-4-oxa-3-azaspiro[4.5]dec-2-en-1-yl]methyl methanesulfonate (2.7 g, 6.0 mmol) and Cs$_2$CO$_3$ (1.5 g, 9.0 mmol) in MeCN (70 ml) was heated at 80° C. for overnight. The resulting solution was extracted with MTBE (200 mL×2), washed with brine, dried over Na$_2$SO$_4$ and concentrated to afford 2-[4-(4-chlorophenoxy)phenyl]-1-methylene-4-oxa-3-azaspiro[4.5]dec-2-ene (1.7 g, 81%). $^1$H NMR: CDCl$_3$ 400 MHz: 7.51 (d, 2H J=8 Hz), 7.24 (d, 2H J=8 Hz), 6.90-6.98 (m, 4H), 5.35 (s, 1H), 5.01 (s, 1H), 1.65-1.84 (m, 7H), 1.18-1.36 (m, 3H).

Step 6:

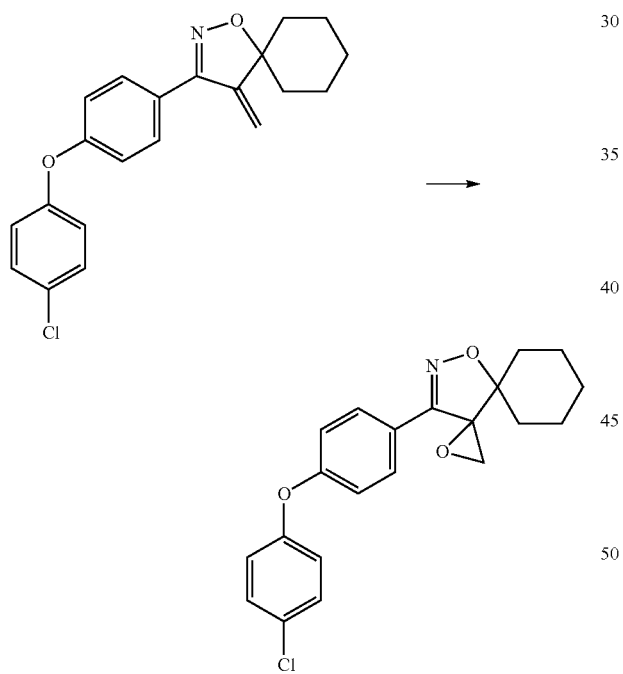

A solution of 2-[4-(4-chlorophenoxy)phenyl]-1-methylene-4-oxa-3-azaspiro[4.5]dec-2-ene (1.6 g, 4.5 mmol) and m-CPBA (1.6 g, 6.7 mmol) in DCM (70 ml) was heated at 40° C. for overnight. The resulting solution was extracted with DCM (100 mL×2), washed with NaHCO$_3$ and Na$_2$SO$_3$ aq., dried over Na$_2$SO$_4$ and concentrated to afford 12-[4-(4-chlorophenoxy)phenyl]-2,10-dioxa-11-azadispiro[2.0.5^{4}0.3^{3}]dodec-11-ene (1.4 g, crude). $^1$H NMR: CDCl$_3$ 400 MHz: 7.62 (d, 2H J=8 Hz), 7.33 (d, 2H J=8 Hz), 6.97-7.03 (m, 4H), 3.26 (s, 1H), 3.11 (s, 1H), 1.73-1.93 (m, 4H), 1.28-1.35 (m, 5H), 0.89 (m, 1H).

Step 7:

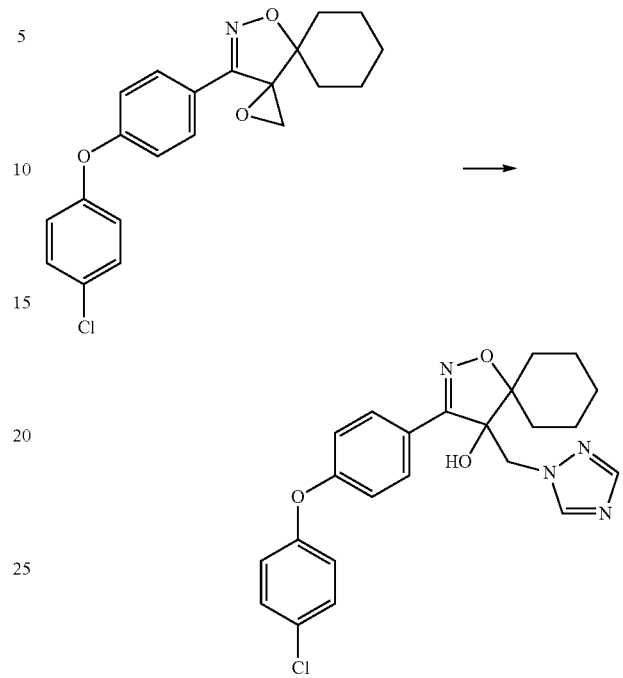

To a solution of 12-[4-(4-chlorophenoxy)phenyl]-2,10-dioxa-11-azadispiro [2.0.5^{4}0.3^{3}]dodec-11-ene (1.5 g, 4.0 mmol), 1,2,4-triazole (80 mg, 4.8 mmol) and K$_2$CO$_3$ (0.33 mg, 4.8 mmol) in DMF (25 mL) was irradiated in the microwave on a Biotage Smith Synthesis at 70° C. for 0.5 hr. Water was added, extracted with EtOAc, dried and concentrated, purified by prepare HPLC to give 2-[4-(4-chlorophenoxy)phenyl]-1-(1,2,4-triazol-1-ylmethyl)-4-oxa-3-azaspiro[4.5]dec-2-en-1-ol (0.45 g, 26%). $^1$H NMR: CDCl$_3$ 400 MHz: 8.01 (s, 1H), 7.89 (s, 1H), 7.65 (d, 2H J=8 Hz), 7.34 (d, 2H J=8 Hz), 6.91-6.98 (m, 4H), 4.53 (d, 1H J=12 Hz), 4.46 (d, 1H J=12 Hz), 1.52-1.91 (m, 8H), 1.20-1.21 (m, 2H).

Example 2

Synthesis of 2-[4-(4-chlorophenoxy)phenyl]-1-methoxy-1-(1,2,4-triazol-1-ylmethyl)-4-oxa-3-azaspiro[4.5]dec-2-ene (1-2)

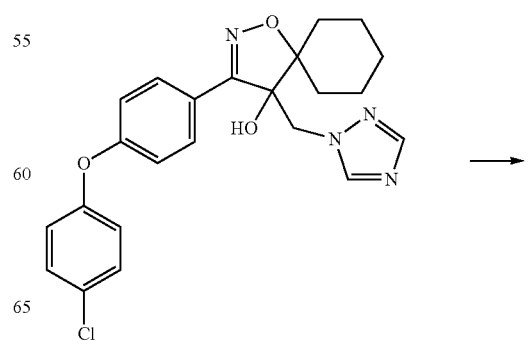

-continued

The 2-[4-(4-chlorophenoxy)phenyl]-1-(1,2,4-triazol-1-yl-methyl)-4-oxa-3-azaspiro[4.5]dec-2-en-1-ol (0.14 g, 0.4 mmol) dissolved in THF (100 ml) cooled at 0° C. was added NaH (30 mg, 0.6 mmol) and the solution was stirred at this temperature for 0.5 h. Then MeI (80 mg, 0.8 mmol) was added and the solution was stirred for overnight. NH$_4$Cl aq. was added, extracted with EtOAc (50 mL×2), washed with brine, dried over Na$_2$SO$_4$ and concentrated then purified by Pre-HPLC to afford 2-[4-(4-chlorophenoxy)phenyl]-1-methoxy-1-(1,2,4-triazol-1-ylmethyl)-4-oxa-3-azaspiro[4.5] dec-2-ene (80 mg, 57%). $^1$H NMR: CDCl$_3$ 400 MHz: 8.27 (s, 1H), 7.82 (s, 1H), 7.51 (d, 2H Hz), 7.27 (d, 2H J=8 Hz), 6.91-6.98 (m, 4H), 4.46 (m, 2H), 1.53-1.87 (m, 8H), 1.03 (m, 1H), 0.55 (m, 1H).

II. EXAMPLES OF THE ACTION AGAINST HARMFUL FUNGI

The fungicidal action of the compounds of the formula I was demonstrated by the following experiments:

Green House

The spray solutions were prepared in several steps:

The stock solution were prepared: a mixture of acetone and/or dimethylsulfoxide and the wetting agent/emulsifier Wettol, which is based on ethoxylated alkylphenoles, in a relation (volume) solvent-emulsifier of 99 to 1 was added to 25 mg of the compound to give a total of 5 ml. Water was then added to total volume of 100 ml. This stock solution was diluted with the described solvent-emulsifier-water mixture to the given concentration.

G1 Preventative Control of Brown Rust on Wheat Caused by *Pucania recondita* (Puccrt P7)

The first two developed leaves of pot-grown wheat seedling were sprayed to run-off with an aqueous suspension, containing the concentration of active ingredient or their mixture as described below. Seven days later the plants were inoculated with spores of *Puccinia recondita*. To ensure the success the artificial inoculation, the plants were transferred to a humid chamber without light and a relative humidity of 95 to 99% and 20 to 24° C. for 24 h. Then the trial plants were cultivated for 6 days in a greenhouse chamber at 20-24° C. and a relative humidity between 65 and 70%. The extent of fungal attack on the leaves was visually assessed as % diseased leaf area. In this test, the plants which had been treated with 250 ppm of the active substance I-3, I-1, I-5, I-7 or I-8, respectively, showed an infection of at most 1%, whereas the untreated plants were 90% infected.

G2 Preventative Control of Leaf Blotch on Wheat Caused by *Septoria tritici* (Septtr P1)

Leaves of pot-grown wheat seedling were sprayed to run-off with an aqueous suspension of the active compound or their mixture, prepared as described. The plants were allowed to air-dry. At the following day the plants were inoculated with an aqueous spore suspension of *Septoria tritici*. Then the trial plants were immediately transferred to a humid chamber at 18-22° C. and a relative humidity close to 100%. After 4 days the plants were transferred to a chamber with 18-22° C. and a relative humidity close to 70%. After 4 weeks the extent of fungal attack on the leaves was visually assessed as % diseased leaf area. In this test, the plants which had been treated with 150 ppm of the active substance I-3, I-1, I-4, I-5, I-6, I-2, I-7 or I-8, respectively, showed an infection of at most 10%, whereas the untreated plants were 100% infected.

G3 Protective Control of Soy Bean Rust on Soy Beans Caused by *Phakopsora pachyrhizi* (Phakpa P1)

Leaves of pot-grown soy bean seedlings were sprayed to run-off with an aqueous suspension, containing the concentration of active ingredient or their mixture as described below. The plants were allowed to air-dry. The trial plants were cultivated for 1 day in a greenhouse chamber at 23-27° C. and a relative humidity between 60 and 80%. Then the plants were inoculated with spores of *Phakopsora pachyrhizi* To ensure the success the artificial inoculation, the plants were transferred to a humid chamber with a relative humidity of about 95% and 20 to 24° C. for 24 h. The trial plants were cultivated for fourteen days in a greenhouse chamber at 23-27° C. and a relative humidity between 60 and 80%. The extent of fungal attack on the leaves was visually assessed as % diseased leaf area. In this test, the plants which had been treated with 150 ppm of the active substance I-1, I-5, I-6 or I-8, respectively, showed an infection of at most 10%, whereas the untreated plants were 90% infected.

Microtest

The active compounds were formulated separately as a stock solution having a concentration of 10000 ppm in dimethyl sulfoxide.

M1 Activity Against the Grey Mold *Botrytis cinerea* in the Microtiterplate Test (*Botrci*)

The stock solutions were mixed according to the ratio, pipetted onto a micro titer plate (MTP) and diluted with water to the stated concentrations. A spore suspension of *Botrci cinerea* in an aqueous biomalt or yeast-bactopeptone-sodiumacetate solution was then added. The plates were placed in a water vapor-saturated chamber at a temperature of 18° C. Using an absorption photometer, the MTPs were measured at 405 nm 7 days after the inoculation. Compounds I-3, I-1, I-4, I-5, I-6 and I-8, respectively, showed a growth of 12% or less at 31 ppm.

M2 Activity Against Rice Blast *Pyricularia oryzae* in the Microtiterplate Test (Pyrior)

The stock solutions were mixed according to the ratio, pipetted onto a micro titer plate (MTP) and diluted with water to the stated concentrations. A spore suspension of *Pyricularia oryzae* in an aqueous biomalt or yeast-bacto-peptone-glycerine solution was then added. The plates were placed in a water vapor-saturated chamber at a temperature of 18° C. Using an absorption photometer, the MTPs were measured at 405 nm 7 days after the inoculation. Compounds I-3, I-1, I-4, I-5, I-6, I-2, I-7, I-9 and I-8, respectively, showed a growth of 9% or less at 31 ppm.

M3 Activity Against Leaf Blotch on Wheat Caused by *Septona tritici* (Septtr)

The stock solutions were mixed according to the ratio, pipetted onto a micro titer plate (MTP) and diluted with water to the stated concentrations. A spore suspension of *Septoria tritici* in an aqueous biomalt or yeast-bactopeptone-glycerine solution was then added. The plates were placed in a water vapor-saturated chamber at a temperature of 18° C. Using an absorption photometer, the MTPs were measured at 405 nm 7 days after the inoculation. Compounds I-3, I-1, I-4, I-6, I-2, I-9 and I-8, respectively, showed a growth of 11% or less at 31 ppm.

The measured parameters were compared to the growth of the active compound-free control variant (100%) and the fungus-free and active compound-free blank value to determine the relative growth in % of the pathogens in the respective active compounds.

The invention claimed is:
1. A compound of the formula I

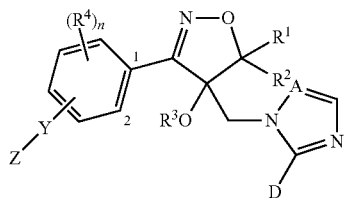

wherein
A is CH or N;
D is selected from the group consisting of H, halogen and $SR^D$, wherein $R^D$ is selected from the group consisting of hydrogen, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl and CN;
$R^1$ is selected from the group consisting of hydrogen, $C_1$-$C_8$-alkyl, $C_1$-$C_8$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, $C_1$-$C_6$-alkoxy, $C_1$-$C_6$-haloalkoxy, $C_1$-$C_6$-alkoxy-$C_1$-$C_6$-alkyl, $C_1$-$C_6$-alkylthio, and $C_1$-$C_6$-haloalkylthio;
wherein the aliphatic and/or alicyclic moieties of $R^1$ are not further substituted or carry one, two, three, four or five identical or different groups $R^{1a}$; wherein
each $R^{1a}$ is independently selected from the group consisting of halogen, OH, CN, nitro, $C_1$-$C_8$-alkoxy, $C_1$-$C_8$-haloalkoxy, $C_1$-$C_8$-alkylthio, $C_1$-$C_8$-haloalkylthio, $C_1$-$C_8$-alkylsulfinyl, $C_1$-$C_8$-haloalkylsulfinyl, $C_1$-$C_8$-alkylsulfonyl, $C_1$-$C_8$-haloalkylsulfonyl, $C_1$-$C_8$-alkylcarbonyl, $C_1$-$C_8$-alkoxycarbonyl, unsubstituted aryl, aryl, that is substituted by one, two, three, four or five independently selected $R^{1b}$, unsubstituted saturated, partially unsaturated or aromatic heterocyclyl and saturated, partially unsaturated or aromatic heterocyclyl, that is substituted by one, two, three, four or five independently selected $R^{1b}$;
each $R^{1b}$ is independently selected from the group consisting of halogen, OH, CN, nitro, $NH_2$, $C_1$-$C_4$-alkyl, $C_1$-$C_4$-haloalkyl, $C_2$-$C_4$-alkenyl, $C_2$-$C_4$-haloalkenyl, $C_2$-$C_4$-alkynyl, $C_2$-$C_4$-haloalkynyl, $C_3$-$C_6$-cycloalkyl, $C_3$-$C_6$-halocycloalkyl, $C_1$-$C_3$-alkoxy, $C_1$-$C_3$-haloalkoxy, $C_1$-$C_3$-alkylthio, $C_1$-$C_3$-haloalkylthio, $C_1$-$C_3$-alkylsulfinyl, $C_1$-$C_3$-haloalkylsulfinyl, $C_1$-$C_3$-alkylsulfonyl, $C_1$-$C_3$-haloalkylsulfonyl, $C_1$-$C_4$-alkylamino, di-($C_1$-$C_4$-alkyl)-amino, $C_1$-$C_4$-alkylcarbonyl, $C_1$-$C_4$-alkylcarbonyloxy, $C_1$-$C_4$-alkoxycarbonyl, and $C_1$-$C_4$-alkylcarbonylamino;
$R^2$ is independently selected from the substituents as given for $R^1$;

or $R^1$ and $R^2$ together with the carbon atom to which they are bound form a saturated or partially unsaturated three-, four-, five-, six-, seven-, eight-, nine-, ten-, eleven-, twelve-, thirteen- or fourteen-membered carbocycle, which may be monocyclic or polycyclic or spirocyclic, or saturated or partially unsaturated three-, four-, five-, six-, seven-, eight-, nine-, ten-, eleven-, twelve-, thirteen- or fourteen-membered heterocycle, which may be monocyclic or polycyclic or spirocyclic, wherein the heterocycle contains one, two, three or four heteroatoms selected from the group consisting of N, O and S, or wherein the heterocycle contains one of S=O and $SO_2$ as ring members, and wherein the carbo- or heterocycle is unsubstituted or carries one, two, three, four or five substituents $R^{12a}$ independently selected from the group consisting of halogen, CN, $NO_2$, OH, SH, $NH_2$, $C_1$-$C_6$-alkyl, $C_1$-$C_6$-haloalkyl, $C_1$-$C_4$-alkoxy-$C_1$-$C_4$-alkyl, $C_1$-$C_8$-alkoxy, $C_1$-$C_8$-haloalkoxy, $C_1$-$C_8$-alkylthio, $C_1$-$C_8$-haloalkylthio, $C_1$-$C_8$-alkylsulfinyl, $C_1$-$C_8$-haloalkylsulfinyl, $C_1$-$C_8$-alkylsulfonyl, $C_1$-$C_8$-haloalkylsulfonyl, $C_1$-$C_8$-alkylcarbonyl, $C_1$-$C_8$-alkoxycarbonyl, phenyl and phenyl that is substituted by one, two, three, four or five independently selected $R^{1b}$; and wherein one or two $CH_2$ groups of the carbo- or heterocycle may be replaced by a group independently selected from the group consisting of $C=CH_2$, $C(=O)$ and $C(=S)$;
$R^3$ is selected from the group consisting of hydrogen, $C_1$-$C_6$-alkyl, $C_2$-$C_6$-alkenyl, $C_2$-$C_6$-alkynyl, $C_3$-$C_8$-cycloalkyl, $C_3$-$C_8$-cycloalkyl-$C_1$-$C_6$-alkyl, phenyl, phenyl-$C_1$-$C_4$-alkyl, phenyl-$C_2$-$C_4$-alkenyl and phenyl-$C_2$-$C_4$-alkynyl;
wherein the aliphatic moieties of $R^3$ are not further substituted or carry one, two, three or up to the maximum possible number of identical or different groups $R^{3a}$ which independently of one another are selected from:
$R^{3a}$ is selected from the group consisting of halogen, OH, CN, nitro, $C_1$-$C_4$-alkoxy, $C_3$-$C_8$-cycloalkyl, $C_3$-$C_8$-halocycloalkyl and $C_1$-$C_4$-haloalkoxy;
wherein the cycloalkyl and/or phenyl moieties of $R^3$ are not further substituted or carry one, two, three, four, five or up to the maximum number of identical or different groups $R^{3b}$ which independently of one another are selected from:
$R^{3b}$ is selected from the group consisting of halogen, OH, CN, nitro, $C_1$-$C_4$-alkyl, $C_1$-$C_4$-alkoxy, $C_1$-$C_4$-haloalkyl, $C_3$-$C_8$-cycloalkyl, $C_3$-$C_8$-halocycloalkyl and $C_1$-$C_4$-haloalkoxy;
n is 0, 1, 2, 3 or 4;
each $R^4$ is independently selected from the group consisting of halogen, CN, $NO_2$, OH, SH, $C_1$-$C_6$-alkyl, $C_1$-$C_6$-alkoxy, $C_2$-$C_6$-alkenyl, $C_2$-$C_6$-alkynyl, $C_3$-$C_8$-cycloalkyl, $C_3$-$C_8$-cycloalkyloxy, $NH_2$, $NH(C_1$-$C_4$-alkyl), $N(C_1$-$C_4$-alkyl)$_2$, $NH(C_3$-$C_6$-cycloalkyl),$N(C_3$-$C_6$-cycloalkyl)$_2$, $S(O)_p(C_1$-$C_4$-alkyl), $C(=O)(C_1$-$C_4$-alkyl), $C(=O)(OH)$, $C(=O)(O-C_1$-$C_4$-alkyl), $C(=O)(NH(C_1$-$C_4$-alkyl))$, $C(=O)(N(C_1$-$C_4$-alkyl)$_2$), $C(=O)(NH(C_3$-$C_6$-cycloalkyl))$ and $C(=O)-(N(C_3$-$C_6$-cycloalkyl)$_2$); wherein each of $R^4$ is unsubstituted or further substituted by one, two, three or four $R^{4a}$;
wherein
each $R^{4a}$ is independently selected from the group consisting of halogen, CN, $NO_2$, OH, $C_1$-$C_4$-alkyl, $C_1$-$C_4$-haloalkyl, $C_3$-$C_8$-cycloalkyl, $C_3$-$C_8$-halocycloalkyl, $C_1$-$C_4$-alkoxy and $C_1$-$C_4$-halogenalkoxy;

Y is a divalent group selected from the group consisting of —O—, —S—, SO—, —SO$_2$—, —NH—, —N(C$_1$-C$_4$-alkyl)-, CR$^6$R$^7$—, —CR$^8$R$^9$—CR$^{10}$—R$^{11}$—, —CR$^{12}$=CR$^{13}$ and —C≡C—;
wherein
R$^6$,R$^7$,R$^8$,R$^9$,R$^{10}$,R$^{11}$,R$^{12}$,R$^{13}$ are independently selected from the group consisting of hydrogen, halogen, CN, nitro, OH, C$_1$-C$_4$-alkyl, C$_1$-C$_4$-halogenalkyl, C$_1$-C$_4$-alkoxy and C$_1$-C$_4$-halogenalkoxy;
Z is phenyl or five or six-membered heteroaryl, wherein the heteroaryl contains 1, 2, 3 or 4 heteroatoms selected from the group consisting of O, N and S, wherein the phenyl and the heteroaryl is unsubstituted (m=0) or substituted by (R$^5$)$_m$;
wherein
m is 0, 1, 2, 3, 4 or 5; and
each R$^5$ is independently selected from the group consisting of halogen, CN, NO$_2$, OH, SH, C$_1$-C$_6$-alkyl, C$_1$-C$_6$-alkoxy, C$_2$-C$_6$-alkenyl, C$_2$-C$_6$-alkynyl, C$_3$-C$_8$-cycloalkyl, C$_3$-C$_8$-cycloalkyloxy, NH$_2$, NH(C$_1$-C$_4$-alkyl), N(C$_1$-C$_4$-alkyl)$_2$, NH(C$_3$-C$_6$-cycloalkyl),N(C$_3$-C$_6$-cycloalkyl)$_2$, S(O)$_p$(C$_1$-C$_4$-alkyl), C(=O)(C$_1$-C$_4$-alkyl), C(=O)(OH), C(=O)(O—C$_1$-C$_4$-alkyl), C(=O)(NH(C$_1$-C$_4$-alkyl)), C(=O)(N(C$_1$-C$_4$-alkyl)$_2$), C(=O)(NH(C$_3$-C$_6$-cycloalkyl)) and C(=O)—(N(C$_3$-C$_6$-cycloalkyl)$_2$); wherein each of R$^5$ is unsubstituted or further substituted by one, two, three or four R$^{5a}$
wherein
each R$^{5a}$ is independently selected from the group consisting of halogen, CN, NO$_2$, OH, C$_1$-C$_4$-alkyl, C$_1$-C$_4$-haloalkyl, C$_3$-C$_8$-cycloalkyl, C$_3$-C$_8$-halocycloalkyl, C$_1$-C$_4$-alkoxy and C$_1$-C$_4$-haloalkoxy;
p is 0, 1 or 2;
and the N-oxides and the agriculturally acceptable salts thereof.

2. The compound of claim 1, wherein Y is —O—.

3. The compound of claim 1, wherein Z—Y is bound in para-(4-)-position to the phenyl, in relation to the attachment of the isoxazole ring.

4. The compound of claim 1, wherein Z—Y is bound in meta-(3-)-position to the phenyl, in relation to the attachment of the isoxazole ring.

5. The compound of claim 1, wherein Z is phenyl or substituted phenyl.

6. The compound of claim 5, wherein m is at least 1.

7. The compound of claim 1, wherein n is at least 1.

8. The compound of claim 1, wherein one of the respective R$^4$ is in para-(4-)position.

9. The compound of claim 1, wherein A is N.

10. A compound of claim 1 selected from the group consisting of
compound I, wherein D is H, A is N, R$^1$ and R$^2$ together form cyclohexyl, R$^3$ is H, n in (R$^4$)$_n$ is 0 and Y—Z is 4-(4-Cl-phenoxy);
compound I, wherein D is H, A is N, R$^1$ and R$^2$ together form cyclohexyl, R$^3$ is CH$_3$, n in (R$^4$)$_n$ is 0 and Y—Z is 4-(4-Cl-phenoxy);
compound I, wherein D is H, A is N, R$^1$ and R$^2$ both are CH$_3$, R$^3$ is H, (R$^4$)$_n$ is 2-Cl (n=1) and Y—Z is 4-(4-Cl-phenoxy);
compound I, wherein D is H, A is N, R$^1$ and R$^2$ both are CH$_3$, R$^3$ is CH$_3$, (R$^4$)$_n$ is 2-Cl (n=1) and Y—Z is 4-(4-Cl-phenoxy);
compound I, wherein D is H, A is N, R$^1$ and R$^2$ together form cyclohexyl, R$^3$ is H, (R$^4$)$_n$ is 2-Cl (n=1) and Y—Z is 4-(4-Cl-phenoxy);
compound I, wherein D is H, A is N, R$^1$ and R$^2$ both are CH$_3$, R$^3$ is H, n in (R$^4$)$_n$ is 0 and Y—Z is 4-(4-Cl-phenoxy);
compound I, wherein D is H, A is N, R$^1$ and R$^2$ together form cyclohexyl, R$^3$ is CH$_3$, (R$^4$)$_n$ is 2-Cl (n=1) and Y—Z is 4-(4-Cl-phenoxy);
compound I, wherein D is H, A is N, R$^1$ and R$^2$ both are CH$_3$, R$^3$ is CH$_3$, n in (R$^4$)$_n$ is 0 and Y—Z is 4-(4-Cl-phenoxy); and
compound I, wherein D is H, A is CH, R$^1$ and R$^2$ both are CH$_3$, R$^3$ is H, n in (R$^4$)$_n$ is 0 and Y—Z is 4-(4-Cl-phenoxy).

11. A composition comprising one compound of formula I, as defined in claim 1, an N-oxide or an agriculturally acceptable salt thereof.

12. The composition of claim 11, comprising additionally a further active substance.

13. A method for combating phytopathogenic fungi, comprising treating the fungi or the materials, plants, the soil or seeds to be protected against fungal attack with an effective amount of at least one compound of formula I, as defined in claim 1.

14. A method for combating phytopathogenic fungi, comprising treating the fungi or the materials, plants, the soil or seeds to be protected against fungal attack with an effective amount of the composition of claim 11.

15. A seed, coated with at least one compound of the formula I, as defined in claim 1, and/or an agriculturally acceptable salt thereof, in an amount of from 0.1 to 10 kg per 100 kg of seed.

16. A seed coated with the composition of claim 11, in an amount of from 0.1 to 10 kg per 100 kg of seed.

* * * * *